(12) United States Patent
Triebel et al.

(10) Patent No.: US 12,252,535 B2
(45) Date of Patent: *Mar. 18, 2025

(54) ANTIBODY MOLECULES TO LAG-3 AND USES THEREOF

(71) Applicants: NOVARTIS AG, Basel (CH); Immutep S.A.S., Orsay (FR)

(72) Inventors: Frédéric Triebel, Versailles (FR); Chrystelle Brignone, Chatenay-Malabry (FR); Walter A. Blattler, Brookline, MA (US); Jennifer Marie Mataraza, Cambridge, MA (US); Catherine Anne Sabatos-Peyton, Cambridge, MA (US); Hwai Wen Chang, San Marcos, CA (US); Gerhard Johann Frey, San Diego, CA (US)

(73) Assignees: Novartis AG, Basel (CH); Immutep S.A.S., Orsay (FR)

( * ) Notice: Subject to any disclaimer, the term of this patent is extended or adjusted under 35 U.S.C. 154(b) by 712 days.

This patent is subject to a terminal disclaimer.

(21) Appl. No.: 16/897,238

(22) Filed: Jun. 9, 2020

(65) Prior Publication Data

US 2021/0009687 A1 Jan. 14, 2021

Related U.S. Application Data

(62) Division of application No. 15/829,284, filed on Dec. 1, 2017, now Pat. No. 10,711,060, which is a division of application No. 14/657,260, filed on Mar. 13, 2015, now abandoned.

(60) Provisional application No. 62/094,889, filed on Dec. 19, 2014, provisional application No. 62/059,690, filed on Oct. 3, 2014, provisional application No. 61/953,536, filed on Mar. 14, 2014.

(51) Int. Cl.
C07K 16/28 (2006.01)
A61K 39/395 (2006.01)
A61K 45/06 (2006.01)

(52) U.S. Cl.
CPC .... *C07K 16/2803* (2013.01); *A61K 39/39558* (2013.01); *A61K 45/06* (2013.01); *C07K 2317/24* (2013.01); *C07K 2317/51* (2013.01); *C07K 2317/515* (2013.01); *C07K 2317/56* (2013.01); *C07K 2317/565* (2013.01); *C07K 2317/70* (2013.01); *C07K 2317/76* (2013.01); *G01N 2333/70596* (2013.01)

(58) Field of Classification Search
CPC ............ C07K 2317/60; C07K 2317/31; C07K 16/468
USPC ...................................................... 424/136.1
See application file for complete search history.

(56) References Cited

U.S. PATENT DOCUMENTS

| | | | |
|---|---|---|---|
| 5,324,514 A | 6/1994 | Sipos | |
| 5,434,131 A | 7/1995 | Linsley et al. | |
| 5,629,204 A | 5/1997 | Honjo et al. | |
| 5,698,520 A | 12/1997 | Honjo et al. | |
| 5,773,578 A | 6/1998 | Hercend et al. | |
| 5,811,097 A | 9/1998 | Allison et al. | |
| 5,874,250 A | 2/1999 | Hercend et al. | |
| 5,897,862 A | 4/1999 | Hardy et al. | |
| 5,968,511 A | 10/1999 | Akita et al. | |
| 5,976,877 A | 11/1999 | Hercend et al. | |
| 6,051,227 A | 4/2000 | Allison et al. | |
| 6,084,083 A | 7/2000 | Levinson | |
| 6,143,273 A | 11/2000 | Faure et al. | |
| 6,197,524 B1 | 3/2001 | Romagnani | |
| 6,204,371 B1 | 3/2001 | Levinson | |
| 6,288,218 B1 | 9/2001 | Levinson | |
| 6,414,117 B1 | 7/2002 | Levinson | |
| 6,482,925 B1 | 11/2002 | El Tayar et al. | |
| 6,562,343 B1 | 5/2003 | Levinson | |
| 6,596,536 B1 | 7/2003 | Hercend et al. | |
| 6,632,927 B2 | 10/2003 | Adair et al. | |
| 6,632,976 B1 | 10/2003 | Tomizuka et al. | |
| RE38,313 E | 11/2003 | Faure et al. | |
| 6,803,192 B1 | 10/2004 | Chen | |
| 6,808,710 B1 | 10/2004 | Wood et al. | |
| 6,936,704 B1 | 8/2005 | Freeman et al. | |
| 7,029,674 B2 | 4/2006 | Carreno et al. | |
| 7,038,013 B2 | 5/2006 | Freeman et al. | |
| 7,041,474 B2 | 5/2006 | Kingsbury | |
| 7,101,550 B2 | 9/2006 | Wood et al. | |
| 7,105,328 B2 | 9/2006 | Wood et al. | |
| 7,122,372 B2 | 10/2006 | Hardy et al. | |

(Continued)

FOREIGN PATENT DOCUMENTS

AU 774391 B2 6/2004
CN 102492038 A 6/2012

(Continued)

OTHER PUBLICATIONS

Schöffski et al (J Immunother Cancer 2022;10:e003776. doi:10.1136/jitc-2021-003776).*
Agrawal, S., et al., "Clinical pharmacokinetics (PK) of BMS-936558, a fully human anti-PD-1 monoclonal antibody," 012 ASCO Annual Meeting, Website, 1 page (2012).
Amin et al: "Nivolumab (anti-PD-1; BMS-936558, ONO-4538) in combination with sunitinib or pazopanib in patients (pts) with metastatic renal cell carcinoma (mRCC)" Journal of Clinical Oncology (2014) vol. 32, No. 15 suppl, Abstract 5010.

(Continued)

*Primary Examiner* — Lynn A Bristol
(74) *Attorney, Agent, or Firm* — K&L Gates LLP

(57) ABSTRACT

Antibody molecules that specifically bind to LAG-3 and bispecific antibody molecules with a first binding specificity for LAG-3 and a second binding specificity for one of PD-1, TIM-3, CEACAM-1, CEACAM-5, PD-L1, or PD-L2, are disclosed. The anti-LAG-3 antibody molecules can be used to treat, prevent and/or diagnose cancerous or infectious disorders.

10 Claims, 15 Drawing Sheets

Specification includes a Sequence Listing.

(56) References Cited

U.S. PATENT DOCUMENTS

| | | |
|---|---|---|
| 7,138,501 B2 | 11/2006 | Ruben et al. |
| 7,169,791 B2 | 1/2007 | Breitenstein et al. |
| 7,172,750 B2 | 2/2007 | Levinson |
| 7,306,906 B2 | 12/2007 | Maruyama et al. |
| 7,329,639 B2 | 2/2008 | Hardy et al. |
| 7,329,737 B2 | 2/2008 | Sexton et al. |
| 7,332,582 B2 | 2/2008 | Hardy et al. |
| 7,414,171 B2 | 8/2008 | Honjo et al. |
| 7,423,128 B2 | 9/2008 | Gazit-Bornstein et al. |
| 7,449,300 B2 | 11/2008 | Chen et al. |
| 7,470,428 B2 | 12/2008 | Kuchroo et al. |
| 7,488,802 B2 | 2/2009 | Collins et al. |
| 7,521,051 B2 | 4/2009 | Collins et al. |
| 7,524,498 B2 | 4/2009 | Hardy et al. |
| 7,553,939 B2 | 6/2009 | McIntire et al. |
| 7,563,441 B2 | 7/2009 | Graus et al. |
| 7,563,869 B2 | 7/2009 | Honjo et al. |
| 7,595,048 B2 | 9/2009 | Honjo et al. |
| 7,598,257 B2 | 10/2009 | Rodgers et al. |
| 7,605,238 B2 | 10/2009 | Korman et al. |
| 7,635,757 B2 | 12/2009 | Freeman et al. |
| 7,695,715 B2 | 4/2010 | Hardy et al. |
| 7,722,868 B2 | 5/2010 | Freeman et al. |
| 7,767,675 B2 | 8/2010 | Zhuo et al. |
| 7,790,160 B2 | 9/2010 | Von Strandmann et al. |
| 7,794,710 B2 | 9/2010 | Chen et al. |
| 7,838,220 B2 | 11/2010 | McIntire et al. |
| 7,850,965 B2 | 12/2010 | Jensen et al. |
| 7,858,746 B2 | 12/2010 | Honjo et al. |
| 7,943,743 B2 | 5/2011 | Korman et al. |
| 8,008,449 B2 | 8/2011 | Korman et al. |
| 8,039,273 B2 | 10/2011 | Jeffrey |
| 8,039,479 B2 | 10/2011 | Michellys et al. |
| 8,088,905 B2 | 1/2012 | Collins et al. |
| 8,101,176 B2 | 1/2012 | Kuchroo et al. |
| 8,168,179 B2 | 5/2012 | Honjo et al. |
| 8,168,757 B2 | 5/2012 | Finnefrock et al. |
| 8,217,149 B2 | 7/2012 | Irving et al. |
| 8,287,856 B2 | 10/2012 | Li et al. |
| 8,329,660 B2 | 12/2012 | Kuchroo et al. |
| 8,354,509 B2 | 1/2013 | Carven et al. |
| 8,361,736 B2 | 1/2013 | Majeti et al. |
| 8,415,355 B2 | 4/2013 | Brain et al. |
| 8,460,886 B2 | 6/2013 | Shibayama et al. |
| 8,460,927 B2 | 6/2013 | Chen |
| 8,461,330 B2 | 6/2013 | Zhuo et al. |
| 8,501,758 B2 | 8/2013 | Huang et al. |
| 8,546,336 B2 | 10/2013 | Chen et al. |
| 8,551,481 B2 | 10/2013 | Pardoll et al. |
| 8,552,002 B2 | 10/2013 | Ding et al. |
| 8,552,154 B2 | 10/2013 | Freeman et al. |
| 8,552,156 B2 | 10/2013 | Takayanagi et al. |
| 8,568,728 B2 | 10/2013 | Jeffrey |
| 8,580,247 B2 | 11/2013 | Li et al. |
| 8,609,089 B2 | 12/2013 | Langermann et al. |
| 8,617,546 B2 | 12/2013 | Kang et al. |
| 8,647,623 B2 | 2/2014 | Takayanagi et al. |
| 8,685,980 B2 | 4/2014 | Besong et al. |
| 8,697,069 B2 | 4/2014 | Kuchroo et al. |
| 8,709,412 B2 | 4/2014 | Jones et al. |
| 8,709,416 B2 | 4/2014 | Langermann et al. |
| 8,709,429 B2 | 4/2014 | Majeti et al. |
| 8,715,619 B2 | 5/2014 | Karsunky |
| 8,728,474 B2 | 5/2014 | Honjo et al. |
| 8,735,551 B2 | 5/2014 | Garner et al. |
| 8,735,553 B1 | 5/2014 | Li et al. |
| 8,779,105 B2 | 7/2014 | Korman et al. |
| 8,779,108 B2 | 7/2014 | Queva et al. |
| 8,841,418 B2 | 9/2014 | Karsunky et al. |
| 8,900,587 B2 | 12/2014 | Carven et al. |
| 8,927,697 B2 | 1/2015 | Davis et al. |
| 8,952,136 B2 | 2/2015 | Carven et al. |
| 9,005,629 B2 | 4/2015 | Pardoll et al. |
| 9,045,545 B1 | 6/2015 | Clube |
| 9,067,999 B1 | 6/2015 | Honjo et al. |
| 9,073,994 B2 | 7/2015 | Honjo et al. |
| 9,084,776 B2 | 7/2015 | Korman et al. |
| 9,102,727 B2 | 8/2015 | Freeman et al. |
| 9,103,832 B2 | 8/2015 | Takayanagi et al. |
| 9,109,034 B1 | 8/2015 | Clube |
| 9,132,281 B2 | 9/2015 | Zeng et al. |
| 9,175,082 B2 | 11/2015 | Zhou et al. |
| 9,333,256 B2 | 5/2016 | Kuchroo et al. |
| 9,358,289 B2 | 6/2016 | Korman et al. |
| 9,387,247 B2 | 7/2016 | Korman et al. |
| 9,409,970 B2 | 8/2016 | Mikesell et al. |
| 9,457,080 B2 | 10/2016 | Freeman et al. |
| 9,492,539 B2 | 11/2016 | Korman et al. |
| 9,492,540 B2 | 11/2016 | Korman et al. |
| 9,505,839 B2 | 11/2016 | Lonberg et al. |
| 9,605,070 B2 | 3/2017 | Sabatos-Peyton et al. |
| 9,683,048 B2 * | 6/2017 | Freeman ................. A61P 37/04 |
| 9,815,898 B2 * | 11/2017 | Freeman ............ A61K 39/3955 |
| 9,815,901 B2 | 11/2017 | Brogdon et al. |
| 9,834,605 B2 | 12/2017 | Carven et al. |
| 9,884,913 B2 | 2/2018 | Sabatos-Peyton et al. |
| 9,908,936 B2 * | 3/2018 | Triebel .................... A61P 17/00 |
| 9,944,645 B2 | 4/2018 | Zhuo et al. |
| 9,988,452 B2 * | 6/2018 | Freeman ................. A61P 35/00 |
| 10,005,832 B2 | 6/2018 | Yoshida et al. |
| 10,253,086 B2 | 4/2019 | Bitter et al. |
| 10,472,419 B2 | 11/2019 | Sabatos-Peyton et al. |
| 10,513,558 B2 | 12/2019 | Tipton et al. |
| 10,561,653 B2 | 2/2020 | Bilic et al. |
| 10,570,204 B2 | 2/2020 | Johnson et al. |
| 10,711,060 B2 * | 7/2020 | Triebel .................... A61P 37/02 |
| 10,752,687 B2 * | 8/2020 | Freeman .................. A61P 1/18 |
| 10,851,165 B2 * | 12/2020 | Freeman ......... G01N 33/57492 |
| 10,981,990 B2 | 4/2021 | Sabatos-Peyton et al. |
| 11,155,620 B2 | 10/2021 | Sabatos-Peyton et al. |
| 11,312,783 B2 | 4/2022 | Prinz et al. |
| 11,344,620 B2 | 5/2022 | Lebwohl et al. |
| 11,708,412 B2 | 7/2023 | Johnson et al. |
| 11,827,704 B2 | 11/2023 | Freeman et al. |
| 2002/0086014 A1 | 7/2002 | Korman et al. |
| 2002/0146753 A1 | 10/2002 | Ditzel et al. |
| 2002/0164660 A1 | 11/2002 | Spaulding et al. |
| 2003/0039653 A1 | 2/2003 | Chen et al. |
| 2003/0059937 A1 | 3/2003 | Ruben et al. |
| 2003/0129601 A1 | 7/2003 | Cole |
| 2003/0232323 A1 | 12/2003 | Freeman et al. |
| 2004/0072164 A1 | 4/2004 | Maruyama et al. |
| 2004/0073957 A1 | 4/2004 | Tomizuka et al. |
| 2004/0171551 A1 | 9/2004 | Triebel |
| 2004/0241745 A1 | 12/2004 | Honjo et al. |
| 2005/0009136 A1 | 1/2005 | Nixon et al. |
| 2005/0191721 A1 | 9/2005 | Kuchroo et al. |
| 2005/0226876 A1 | 10/2005 | Graus et al. |
| 2005/0276756 A1 | 12/2005 | Hoo et al. |
| 2006/0110383 A1 | 5/2006 | Honjo et al. |
| 2006/0177442 A1 | 8/2006 | Von Strandmann et al. |
| 2006/0210567 A1 | 9/2006 | Collins et al. |
| 2006/0240024 A1 | 10/2006 | Pardoll et al. |
| 2007/0004910 A1 | 1/2007 | Sexton et al. |
| 2007/0041982 A1 | 2/2007 | Ponath et al. |
| 2007/0065427 A1 | 3/2007 | Freeman et al. |
| 2007/0071675 A1 | 3/2007 | Wu et al. |
| 2007/0122378 A1 | 5/2007 | Freeman et al. |
| 2007/0160598 A1 | 7/2007 | Dennis et al. |
| 2007/0202100 A1 | 8/2007 | Wood et al. |
| 2008/0025979 A1 | 1/2008 | Honjo et al. |
| 2008/0038264 A1 | 2/2008 | Bodary et al. |
| 2008/0069822 A1 | 3/2008 | Jensen et al. |
| 2008/0167287 A1 | 7/2008 | Zhuo et al. |
| 2008/0311117 A1 | 12/2008 | Collins et al. |
| 2009/0055944 A1 | 2/2009 | Korman et al. |
| 2009/0076250 A1 | 3/2009 | Honjo et al. |
| 2009/0155275 A1 | 6/2009 | Wu et al. |
| 2009/0304693 A1 | 12/2009 | Ghayur et al. |
| 2009/0311253 A1 | 12/2009 | Ghayur et al. |
| 2010/0028330 A1 | 2/2010 | Collins et al. |
| 2010/0056576 A1 | 3/2010 | Burger et al. |
| 2010/0061992 A1 | 3/2010 | Anderson et al. |
| 2010/0074900 A1 | 3/2010 | Ghayur et al. |

(56) References Cited

U.S. PATENT DOCUMENTS

| | | |
|---|---|---|
| 2010/0076178 A1 | 3/2010 | Ghayur et al. |
| 2010/0105667 A1 | 4/2010 | Furet et al. |
| 2010/0136009 A1 | 6/2010 | Papkoff et al. |
| 2010/0203056 A1 | 8/2010 | Irving et al. |
| 2010/0233079 A1 | 9/2010 | Jakob et al. |
| 2010/0233183 A1 | 9/2010 | Triebel et al. |
| 2010/0260668 A1 | 10/2010 | Ghayur et al. |
| 2010/0266531 A1 | 10/2010 | Hsieh et al. |
| 2010/0266617 A1 | 10/2010 | Carven et al. |
| 2011/0008766 A1 | 1/2011 | Ghayur et al. |
| 2011/0044894 A1 | 2/2011 | Karsunky |
| 2011/0044980 A1 | 2/2011 | Ghayur et al. |
| 2011/0054151 A1 | 3/2011 | Lazar et al. |
| 2011/0059106 A1 | 3/2011 | Kuchroo et al. |
| 2011/0070238 A1 | 3/2011 | Triebel et al. |
| 2011/0081341 A1 | 4/2011 | Honjo et al. |
| 2011/0091372 A1 | 4/2011 | Ghayur et al. |
| 2011/0091463 A1 | 4/2011 | Ghayur et al. |
| 2011/0110852 A1 | 5/2011 | Miller et al. |
| 2011/0123550 A1 | 5/2011 | Shibayama et al. |
| 2011/0136781 A1 | 6/2011 | Zhuo et al. |
| 2011/0150892 A1 | 6/2011 | Thudium et al. |
| 2011/0171220 A1 | 7/2011 | Davis |
| 2011/0177088 A1 | 7/2011 | Olive et al. |
| 2011/0195068 A1 | 8/2011 | Langermann et al. |
| 2011/0209230 A1 | 8/2011 | Korman et al. |
| 2011/0212094 A1 | 9/2011 | Ghayur et al. |
| 2011/0229461 A1 | 9/2011 | Tyson |
| 2011/0236375 A1 | 9/2011 | Lazar et al. |
| 2011/0263827 A1 | 10/2011 | Ghayur et al. |
| 2011/0271358 A1 | 11/2011 | Freeman et al. |
| 2011/0280800 A1 | 11/2011 | Wu et al. |
| 2011/0280877 A1 | 11/2011 | Tamada |
| 2011/0287009 A1 | 11/2011 | Scheer et al. |
| 2012/0014957 A1 | 1/2012 | Ghayur et al. |
| 2012/0034160 A1 | 2/2012 | Ghayur et al. |
| 2012/0039870 A9 | 2/2012 | Dolk et al. |
| 2012/0039906 A1 | 2/2012 | Olive |
| 2012/0070450 A1 | 3/2012 | Ishikawa et al. |
| 2012/0076805 A1 | 3/2012 | Sharpe et al. |
| 2012/0087858 A1 | 4/2012 | Ghayur et al. |
| 2012/0100131 A1 | 4/2012 | Takayanagi et al. |
| 2012/0107234 A1 | 5/2012 | Pedersen et al. |
| 2012/0114649 A1 | 5/2012 | Langermann et al. |
| 2012/0141501 A1 | 6/2012 | Yoshida et al. |
| 2012/0195900 A1 | 8/2012 | Ghayur et al. |
| 2012/0201746 A1 | 8/2012 | Liu et al. |
| 2012/0201824 A1 | 8/2012 | Wasik |
| 2012/0258108 A1 | 10/2012 | Ghayur et al. |
| 2012/0263722 A1 | 10/2012 | Ghayur et al. |
| 2013/0005216 A1 | 1/2013 | Rittberger |
| 2013/0017199 A1 | 1/2013 | Langermann |
| 2013/0022623 A1 | 1/2013 | Karsunky et al. |
| 2013/0039911 A1 | 2/2013 | Bedi et al. |
| 2013/0058947 A1 | 3/2013 | Stull et al. |
| 2013/0095098 A1 | 4/2013 | Tyson |
| 2013/0109843 A1 | 5/2013 | Carven et al. |
| 2013/0133091 A1 | 5/2013 | Korman et al. |
| 2013/0156774 A1 | 6/2013 | Kuchroo et al. |
| 2013/0183688 A1 | 7/2013 | Kuchroo et al. |
| 2013/0202623 A1 | 8/2013 | Chomont et al. |
| 2013/0230514 A1 | 9/2013 | Langermann et al. |
| 2013/0324515 A1 | 12/2013 | Zhuo et al. |
| 2014/0044728 A1 | 2/2014 | Takayanagi et al. |
| 2014/0044738 A1 | 2/2014 | Langermann et al. |
| 2014/0065142 A1 | 3/2014 | Roschke et al. |
| 2014/0093511 A1 | 4/2014 | Lonberg et al. |
| 2014/0127226 A1 | 5/2014 | Pardoll et al. |
| 2014/0155678 A1 | 6/2014 | Zeng et al. |
| 2014/0178370 A1 | 6/2014 | Freeman et al. |
| 2014/0212422 A1 | 7/2014 | Korman et al. |
| 2014/0234320 A1 | 8/2014 | Croft et al. |
| 2014/0242094 A1 | 8/2014 | Kuchroo et al. |
| 2014/0274788 A1 | 9/2014 | Ishikawa et al. |
| 2014/0294852 A1 | 10/2014 | Korman et al. |
| 2014/0314714 A1 | 10/2014 | Honjo et al. |
| 2014/0328833 A1 | 11/2014 | Korman et al. |
| 2014/0341902 A1 | 11/2014 | Maecker et al. |
| 2014/0348743 A1 | 11/2014 | Korman et al. |
| 2015/0017185 A1 | 1/2015 | Akbar et al. |
| 2015/0023986 A1 | 1/2015 | Jones et al. |
| 2015/0079109 A1 | 3/2015 | Li et al. |
| 2015/0086574 A1 | 3/2015 | Karsunky et al. |
| 2015/0093380 A1 | 4/2015 | Honjo et al. |
| 2015/0210769 A1 | 7/2015 | Freeman et al. |
| 2015/0218274 A1* | 8/2015 | Sabatos-Peyton ........................ A61K 39/3955 435/254.2 |
| 2015/0232555 A1 | 8/2015 | Carven et al. |
| 2015/0259420 A1 | 9/2015 | Triebel et al. |
| 2015/0290316 A1 | 10/2015 | Graziano et al. |
| 2015/0307609 A1 | 10/2015 | Lonberg et al. |
| 2016/0002334 A1 | 1/2016 | Kuchroo et al. |
| 2016/0068601 A1 | 3/2016 | Brogdon et al. |
| 2016/0108123 A1 | 4/2016 | Freeman et al. |
| 2016/0159905 A1 | 6/2016 | Abdiche et al. |
| 2016/0222121 A1 | 8/2016 | Johnson et al. |
| 2016/0326178 A1 | 11/2016 | Zhuo et al. |
| 2016/0362472 A1 | 12/2016 | Bitter et al. |
| 2017/0044259 A1 | 2/2017 | Tipton et al. |
| 2017/0088615 A1 | 3/2017 | Korman et al. |
| 2017/0137514 A1 | 5/2017 | Lonberg et al. |
| 2017/0190777 A1 | 7/2017 | Sabatos-Peyton et al. |
| 2017/0198041 A1 | 7/2017 | Sabatos-Peyton et al. |
| 2017/0209574 A1 | 7/2017 | Cao et al. |
| 2017/0210804 A1 | 7/2017 | Triebel et al. |
| 2017/0247456 A1 | 8/2017 | Freeman et al. |
| 2017/0281624 A1 | 10/2017 | Peters et al. |
| 2017/0296659 A1 | 10/2017 | Lebwohl et al. |
| 2017/0304443 A1 | 10/2017 | Lebwohl et al. |
| 2017/0340733 A1 | 11/2017 | Cao |
| 2018/0066054 A1 | 3/2018 | Thudium et al. |
| 2018/0086830 A1 | 3/2018 | Triebel et al. |
| 2018/0155427 A1 | 6/2018 | Freeman et al. |
| 2018/0186882 A1 | 7/2018 | Freeman et al. |
| 2018/0207273 A1 | 7/2018 | Dranoff et al. |
| 2018/0222982 A1 | 8/2018 | Dranoff et al. |
| 2018/0282340 A1 | 10/2018 | Zhuo et al. |
| 2018/0340025 A1* | 11/2018 | Dranoff .............. C07K 16/2803 |
| 2018/0371093 A1 | 12/2018 | Bilic et al. |
| 2019/0000944 A1 | 1/2019 | Brogdon et al. |
| 2019/0016797 A1 | 1/2019 | Arenas-Ramirez et al. |
| 2019/0031766 A1* | 1/2019 | Prinz ...................... A61P 35/00 |
| 2019/0062365 A1 | 2/2019 | Katibah et al. |
| 2019/0113513 A1 | 4/2019 | Shaked |
| 2019/0151365 A1 | 5/2019 | Anak et al. |
| 2019/0185511 A1 | 6/2019 | Kanne et al. |
| 2019/0202917 A1 | 7/2019 | Campbell et al. |
| 2020/0030442 A1 | 6/2020 | Cao |
| 2020/0172617 A1* | 6/2020 | Stein ...................... A61K 45/06 |
| 2020/0223917 A1 | 7/2020 | Sabatos-Peyton et al. |
| 2020/0223924 A1* | 7/2020 | Stein .................. C07K 16/2896 |
| 2020/0277378 A1* | 9/2020 | Sabatos-Peyton ........................ A61K 39/39541 |
| 2020/0308277 A1 | 10/2020 | Sabatos-Peyton et al. |
| 2020/0339689 A1 | 10/2020 | Freeman et al. |
| 2020/0369762 A1 | 11/2020 | Bruederle et al. |
| 2020/0377600 A1 | 12/2020 | Johnson et al. |
| 2021/0000951 A1 | 1/2021 | Cao et al. |
| 2021/0009687 A1 | 1/2021 | Triebel et al. |
| 2021/0284737 A1* | 9/2021 | Freeman ............ C07K 16/2827 |
| 2021/0371529 A1* | 12/2021 | Miao .................. C07K 16/2803 |
| 2022/0133889 A1 | 5/2022 | Dranoff et al. |
| 2022/0153835 A1* | 5/2022 | Dranoff .............. C07K 16/2803 |
| 2022/0185819 A1 | 6/2022 | Sabatos-Peyton et al. |
| 2022/0306737 A1 | 9/2022 | Eliasson et al. |
| 2023/0013364 A1 | 1/2023 | Dranoff et al. |
| 2023/0057071 A1 | 2/2023 | Vanasse et al. |
| 2023/0058489 A1 | 2/2023 | Menssen et al. |
| 2023/0088070 A1 | 3/2023 | Bruederle et al. |
| 2024/0043541 A1 | 2/2024 | Johnson et al. |
| 2024/0075136 A1 | 3/2024 | Lebwohl et al. |

(56) References Cited

U.S. PATENT DOCUMENTS

| | | |
|---|---|---|
| 2024/0301053 A1 | 9/2024 | Menssen et al. |
| 2024/0301054 A1 | 9/2024 | Vanasse et al. |

FOREIGN PATENT DOCUMENTS

| | | |
|---|---|---|
| CN | 103079644 A | 5/2013 |
| CN | 103242448 A | 8/2013 |
| EP | 0510079 A1 | 10/1992 |
| EP | 0670369 A2 | 9/1995 |
| EP | 0742795 A1 | 11/1996 |
| EP | 0758383 A1 | 2/1997 |
| EP | 0843557 A1 | 5/1998 |
| EP | 1165616 A1 | 1/2002 |
| EP | 1210424 A1 | 6/2002 |
| EP | 1334659 A1 | 8/2003 |
| EP | 1385533 A1 | 2/2004 |
| EP | 1445264 A1 | 8/2004 |
| EP | 1537878 A1 | 6/2005 |
| EP | 1576014 A1 | 9/2005 |
| EP | 1591527 A1 | 11/2005 |
| EP | 1870399 A1 | 12/2007 |
| EP | 1896582 A1 | 3/2008 |
| EP | 1897548 A1 | 3/2008 |
| EP | 2142210 A1 | 1/2010 |
| EP | 2161336 A1 | 3/2010 |
| EP | 2206517 A1 | 7/2010 |
| EP | 2243493 A1 | 10/2010 |
| EP | 2270051 A2 | 1/2011 |
| EP | 2320940 A2 | 5/2011 |
| EP | 2360254 A1 | 8/2011 |
| EP | 2412825 A1 | 2/2012 |
| EP | 2417984 A1 | 2/2012 |
| EP | 2418278 A2 | 2/2012 |
| EP | 2439272 A2 | 4/2012 |
| EP | 2439273 A2 | 4/2012 |
| EP | 2482849 B1 | 8/2012 |
| EP | 2504364 B1 | 10/2012 |
| EP | 2099447 B1 | 11/2012 |
| EP | 2535354 A1 | 12/2012 |
| EP | 2051990 B1 | 2/2013 |
| EP | 2581113 A1 | 4/2013 |
| EP | 2170959 B1 | 10/2013 |
| EP | 2659893 A2 | 11/2013 |
| EP | 2691112 B1 | 2/2014 |
| EP | 2699264 B1 | 2/2014 |
| EP | 2723381 A2 | 4/2014 |
| EP | 2867258 A1 | 5/2015 |
| EP | 2905030 A1 | 8/2015 |
| EP | 2344474 B1 | 9/2015 |
| EP | 2927240 A1 | 10/2015 |
| EP | 2417984 B1 | 3/2016 |
| EP | 2474545 B1 | 11/2016 |
| EP | 3222634 A1 | 9/2017 |
| JP | H07291996 A | 11/1995 |
| JP | 2002194491 A | 7/2002 |
| JP | 2003029846 A | 1/2003 |
| JP | 2004512005 A | 4/2004 |
| RU | 2494107 C2 | 9/2013 |
| WO | 1990003394 A2 | 4/1990 |
| WO | 9110682 A1 | 7/1991 |
| WO | 1991010682 A1 | 7/1991 |
| WO | 1992013949 A1 | 8/1992 |
| WO | 1992013950 A2 | 8/1992 |
| WO | 9530750 A2 | 11/1995 |
| WO | 1995030750 A2 | 11/1995 |
| WO | 1996027603 A1 | 9/1996 |
| WO | 9703695 A1 | 2/1997 |
| WO | 1997003695 A1 | 2/1997 |
| WO | 9713852 A1 | 4/1997 |
| WO | 1997013852 A1 | 4/1997 |
| WO | 1998023741 A1 | 6/1998 |
| WO | 9858059 A1 | 12/1998 |
| WO | 1998058059 A1 | 12/1998 |
| WO | 1999004810 A2 | 2/1999 |
| WO | 32231 A1 | 6/2000 |
| WO | 0058363 A1 | 10/2000 |
| WO | 0069914 A2 | 11/2000 |
| WO | 0071078 A2 | 11/2000 |
| WO | 0073498 A1 | 12/2000 |
| WO | 0114424 A2 | 3/2001 |
| WO | 0114556 A1 | 3/2001 |
| WO | 0114557 A1 | 3/2001 |
| WO | 0139722 A2 | 6/2001 |
| WO | 01077342 A1 | 10/2001 |
| WO | 01083750 A2 | 11/2001 |
| WO | 200194413 A2 | 12/2001 |
| WO | 0200692 A2 | 1/2002 |
| WO | 0200730 A2 | 1/2002 |
| WO | 0224891 A2 | 3/2002 |
| WO | 2002022577 A2 | 3/2002 |
| WO | 0234205 A2 | 5/2002 |
| WO | 0239813 A1 | 5/2002 |
| WO | 02078731 A1 | 10/2002 |
| WO | 02079499 A1 | 10/2002 |
| WO | 02086083 A2 | 10/2002 |
| WO | 03000066 A1 | 1/2003 |
| WO | 03002722 A2 | 1/2003 |
| WO | 03011911 A1 | 2/2003 |
| WO | 03033644 A2 | 4/2003 |
| WO | 03042402 A2 | 5/2003 |
| WO | 03063792 A2 | 8/2003 |
| WO | 03077914 A1 | 9/2003 |
| WO | 03088808 A2 | 10/2003 |
| WO | 03099196 A2 | 12/2003 |
| WO | 2004004771 A1 | 1/2004 |
| WO | 2004005281 A1 | 1/2004 |
| WO | 2004007679 A2 | 1/2004 |
| WO | 2004008218 A1 | 1/2004 |
| WO | 2004/039956 A2 | 5/2004 |
| WO | 2004056875 A1 | 7/2004 |
| WO | 2004072286 A1 | 8/2004 |
| WO | 2004078928 A2 | 9/2004 |
| WO | 2005027854 A2 | 3/2005 |
| WO | 2005033144 A2 | 4/2005 |
| WO | 2005034733 A2 | 4/2005 |
| WO | 2005097211 A2 | 10/2005 |
| WO | 2006004988 A2 | 1/2006 |
| WO | 2006007850 A1 | 1/2006 |
| WO | 2006021955 A2 | 3/2006 |
| WO | 2006042237 A2 | 4/2006 |
| WO | 2006121168 A1 | 11/2006 |
| WO | 2006124269 A2 | 11/2006 |
| WO | 2006133396 A2 | 12/2006 |
| WO | 2007005874 A2 | 1/2007 |
| WO | 2007011968 A2 | 1/2007 |
| WO | 2007024705 A2 | 3/2007 |
| WO | 2007024715 A2 | 3/2007 |
| WO | 2007070514 A1 | 6/2007 |
| WO | 2007082154 A2 | 7/2007 |
| WO | 2007084786 A1 | 7/2007 |
| WO | 2007113648 A2 | 10/2007 |
| WO | 2007146968 A2 | 12/2007 |
| WO | 2008007648 A1 | 1/2008 |
| WO | 2008008218 A1 | 1/2008 |
| WO | 2008016893 A1 | 2/2008 |
| WO | 2008060617 A2 | 5/2008 |
| WO | 2008064157 A1 | 5/2008 |
| WO | 2008071447 A2 | 6/2008 |
| WO | 2008073160 A2 | 6/2008 |
| WO | 2008073687 A2 | 6/2008 |
| WO | 2008083174 A2 | 7/2008 |
| WO | 2008085562 A2 | 7/2008 |
| WO | 2008132601 A1 | 11/2008 |
| WO | 2008156712 A1 | 12/2008 |
| WO | 2009014708 A2 | 1/2009 |
| WO | 2009024531 A1 | 2/2009 |
| WO | 2009029342 A1 | 3/2009 |
| WO | 2009032256 A2 | 3/2009 |
| WO | 2009044273 A2 | 4/2009 |
| WO | 2009091547 A1 | 7/2009 |
| WO | 2009097394 A2 | 8/2009 |
| WO | 2009101611 A1 | 8/2009 |
| WO | 2009114335 A2 | 9/2009 |
| WO | 2009120905 A2 | 10/2009 |

(56) References Cited

FOREIGN PATENT DOCUMENTS

| | | |
|---|---|---|
| WO | 2009141386 A1 | 11/2009 |
| WO | 2010001617 A1 | 1/2010 |
| WO | 2010019570 A1 | 2/2010 |
| WO | 2010019570 A2 | 2/2010 |
| WO | 2010019571 A2 | 2/2010 |
| WO | 2010026124 A1 | 3/2010 |
| WO | 2010027423 A2 | 3/2010 |
| WO | 2010027827 A2 | 3/2010 |
| WO | 2010027828 A2 | 3/2010 |
| WO | 2010029082 A1 | 3/2010 |
| WO | 2010029434 A1 | 3/2010 |
| WO | 2010029435 A1 | 3/2010 |
| WO | 2010036959 A2 | 4/2010 |
| WO | 2010051502 A2 | 5/2010 |
| WO | 2010063011 A2 | 6/2010 |
| WO | 2010077634 A1 | 7/2010 |
| WO | 2010084999 A1 | 7/2010 |
| WO | 2010089411 A2 | 8/2010 |
| WO | 2010098788 A2 | 9/2010 |
| WO | 2010102278 A1 | 9/2010 |
| WO | 2010110346 A1 | 9/2010 |
| WO | 2010117057 A1 | 10/2010 |
| WO | 2011005481 A1 | 1/2011 |
| WO | 2011011027 A1 | 1/2011 |
| WO | 2011025927 A1 | 3/2011 |
| WO | 2011034605 A2 | 3/2011 |
| WO | 2011041613 A2 | 4/2011 |
| WO | 2011066342 A2 | 6/2011 |
| WO | 2011066389 A1 | 6/2011 |
| WO | 2011069104 A2 | 6/2011 |
| WO | 2011076786 A1 | 6/2011 |
| WO | 2011100841 A1 | 8/2011 |
| WO | 2011110604 A1 | 9/2011 |
| WO | 2011110621 A1 | 9/2011 |
| WO | 2011131472 A1 | 10/2011 |
| WO | 2011155607 A1 | 12/2011 |
| WO | 2011159877 A2 | 12/2011 |
| WO | 2012018538 A2 | 2/2012 |
| WO | 2012022814 A1 | 2/2012 |
| WO | 2012054438 A1 | 4/2012 |
| WO | 2012064733 A2 | 5/2012 |
| WO | 2012079000 A1 | 6/2012 |
| WO | 2012106587 A1 | 8/2012 |
| WO | 2012135408 A1 | 10/2012 |
| WO | 2012145493 A1 | 10/2012 |
| WO | 2012177624 A2 | 12/2012 |
| WO | 2012177788 A1 | 12/2012 |
| WO | 201306490 A2 | 1/2013 |
| WO | 2013003761 A1 | 1/2013 |
| WO | 2013006727 A1 | 1/2013 |
| WO | 2013019906 A1 | 2/2013 |
| WO | 2013043647 A1 | 3/2013 |
| WO | 2013079174 A1 | 6/2013 |
| WO | 2013079945 A1 | 6/2013 |
| WO | 2013169693 A1 | 11/2013 |
| WO | 2013173223 A1 | 11/2013 |
| WO | 2013181452 A1 | 12/2013 |
| WO | 2013181634 A2 | 12/2013 |
| WO | 2013184757 A1 | 12/2013 |
| WO | 2014008218 A1 | 1/2014 |
| WO | 2014018632 A1 | 1/2014 |
| WO | 2014022138 A2 | 2/2014 |
| WO | 2014022332 A1 | 2/2014 |
| WO | 2014022758 A1 | 2/2014 |
| WO | 2014028502 A1 | 2/2014 |
| WO | 2014047350 A1 | 3/2014 |
| WO | 2014055648 A1 | 4/2014 |
| WO | 2014055897 A2 | 4/2014 |
| WO | 2014072493 A1 | 5/2014 |
| WO | 2014085318 A1 | 6/2014 |
| WO | 2014100079 A1 | 6/2014 |
| WO | 2014140180 A1 | 9/2014 |
| WO | 2014165082 A2 | 10/2014 |
| WO | 2014165422 A1 | 10/2014 |
| WO | 2014179664 A2 | 11/2014 |
| WO | 2014189805 A1 | 11/2014 |
| WO | 2014195852 A1 | 12/2014 |
| WO | 2015009856 A2 | 1/2015 |
| WO | 2015026634 A1 | 2/2015 |
| WO | 2015026684 A1 | 2/2015 |
| WO | 2015035606 A1 | 3/2015 |
| WO | 2015036394 A1 | 3/2015 |
| WO | 2015036499 A1 | 3/2015 |
| WO | 2015036511 A1 | 3/2015 |
| WO | 2015042246 A1 | 3/2015 |
| WO | 2015048312 A1 | 4/2015 |
| WO | 2015048520 A1 | 4/2015 |
| WO | 2015061668 A1 | 4/2015 |
| WO | 2015070060 A1 | 5/2015 |
| WO | 2015081158 A1 | 6/2015 |
| WO | 2015085847 A1 | 6/2015 |
| WO | 2015088847 A1 | 6/2015 |
| WO | 2015095423 A2 | 6/2015 |
| WO | 2015095811 A2 | 6/2015 |
| WO | 2015103602 A1 | 7/2015 |
| WO | 2015109124 A2 | 7/2015 |
| WO | 2015109391 A1 | 7/2015 |
| WO | 2015112800 A1 | 7/2015 |
| WO | 2015112805 A1 | 7/2015 |
| WO | 2015112900 A1 | 7/2015 |
| WO | 2015116539 A1 | 8/2015 |
| WO | 2015117002 A1 | 8/2015 |
| WO | 2015118175 A2 | 8/2015 |
| WO | 2015119944 A1 | 8/2015 |
| WO | 2015120198 A1 | 8/2015 |
| WO | 2015134605 A1 | 9/2015 |
| WO | 2015138920 A1 | 9/2015 |
| WO | 2015176033 A1 | 11/2015 |
| WO | 2015181342 A1 | 12/2015 |
| WO | 2015195163 A1 | 12/2015 |
| WO | 2015200119 A1 | 12/2015 |
| WO | 2016000619 A1 | 1/2016 |
| WO | 2016028672 A1 | 2/2016 |
| WO | 2016040880 A1 | 3/2016 |
| WO | 2016040882 A1 | 3/2016 |
| WO | 2016040892 A1 | 3/2016 |
| WO | 2016054555 A2 | 4/2016 |
| WO | WO 2016061142 A1 * | 4/2016 |
| WO | 2016069727 A1 | 5/2016 |
| WO | 2016079049 A1 | 5/2016 |
| WO | 2016100882 A1 | 6/2016 |
| WO | 2016161239 A1 | 10/2016 |
| WO | 2016161270 A1 | 10/2016 |
| WO | 2017017623 A1 | 2/2017 |
| WO | 2017017624 A1 | 2/2017 |
| WO | 2017019894 A1 | 2/2017 |
| WO | 2017019896 A1 | 2/2017 |
| WO | 2017019897 A1 | 2/2017 |
| WO | 2017034916 A1 | 3/2017 |
| WO | 2017097407 A1 | 6/2017 |
| WO | 2017106656 A1 | 6/2017 |
| WO | 2017189433 A1 | 11/2017 |
| WO | 2018222718 A1 | 12/2018 |
| WO | 2019006007 A1 | 1/2019 |
| WO | 2019018640 A1 | 1/2019 |
| WO | 2019018730 A1 | 1/2019 |
| WO | 2019099838 A1 | 5/2019 |
| WO | 2019200229 A1 | 10/2019 |
| WO | 2020128636 A1 | 6/2020 |
| WO | 2021053490 A1 | 3/2021 |
| WO | 2021079188 A1 | 4/2021 |
| WO | 2021079195 A1 | 4/2021 |
| WO | 2021123902 A1 | 6/2021 |
| WO | 2021144657 A1 | 7/2021 |
| WO | 2022195551 A1 | 9/2021 |

OTHER PUBLICATIONS

Anderson et al. "Lag-3, Tim-3, and TIGIT: Co-inhibitory Receptors with Specialized Functions in Immune Regulation" Immunity (2016) vol. 44, pp. 989-1004.

Andrews et al., "LAG3 (CD223) as a Cancer Immunotherapy Target," Immunol Rev. Mar. 2017 ; 276(1): 80-96.

(56) References Cited

OTHER PUBLICATIONS

Angevin et al., Analysis of T-Cell Imune Response in Renal Cell Carcinoma: Polarization to Type 1-Like Differentiation Pattern, Clonal T-Cell Expansion and Tumor-Specific Cytotoxicity Int. J. Cancer (1997) vol. 72 pp. 431-440.
Ashworth et al. "Management of a Patient With Advanced BRAF-Mutant Melanoma" Journal of the National Comprehensive Cancer Network (2014) vol. 12, No. 3, pp. 315-319.
Avice et al., "Lymphocyte Activation Gene-3, a MHC Class II Ligand Expressed on Activated T Cells, Stimulates TNF-a and IL-12 Production by Monocytes and Dendritic Cells" The Journal of Immunology (1999) vol. 162 pp. 2748-2753.
Hemon et al,. "MHC Class II Engagement by Its Ligand LAG-3 (CD223) Contributes to Melanoma Resistance to Apoptosis" J Immunol (2011) vol. 186 pp. 5173-5183.
Batus et al. "Optimal Management of Metastatic Melanoma: Current Strategies and Future Directions" Am. J. Clin. Dermatol. (2013) vol. 14, No. 3, pp. 179-194.
Beckman et al. "Antibody Constructs in Cancer Therapy" Cancer (2007) vol. 109, No. 2.
Bellucci et al: "JAKI and JAK2 Modulate Tumor Cell Susceptibility To Natural Killer (NK) Cells Through Regulation Of PDLI Expression", Blood (Nov. 15, 2013), Retrieved from the Internet: URL:http://www.bloodjournal.orgjcontent/122/21/3472.full.pdf [retrieved on Apr. 14, 2016].
Benson et al. "The PD-1/PD-L1 axis modulates the natural killer cell versus multiple myeloma effect: a therapeutic target for CT-011, a novel monoclonal anti-PD-1 antibody" Blood (2010) vol. 116, No. 13, pp. 2286-2294.
Grygielewicz Paulina et al: "Epithelial-mesenchymal transition confers resistance to selective FGFR inhibitors in SNU-16 gastric cancer cells". Gastric Cancer. Springer Japan. Tokyo. vol. 19. No. 1., Nov. 19, 2014 (Nov. 19, 2014). pp. 53-62.
Blackburn, Shawn D. et al., "Coregulation of CD8+ T cell exhaustion by multiple inhibitory receptors during chronic viral infection," Nature Immunology, vol. 10(1):29-37 (2009).
Blank et al "Combination of targeted therapy and immunotherapy in melanoma" Cancer Immunol Immunother (2011) vol. 60, pp. 1359-1371.
Brignone et al., "First-line chemoimmunotherapy in metastatic breast carcinoma: combination of paclitaxel and IMP321 (LAG-3Ig) enhances immune responses and antitumor activity" Journal of Translational Medicine (2010) vol. 8 No. 71 pp. 1-11.
Camisaschi et al. "LAG-3 Expression Defines a Subset of CD4+ CD25highFoxp3+ Regulatory T Cells That Are Expanded at Tumor Sites" The Journal of Immunology (2010) doi: 10.4049/jimmunol. 0903879, pp. 6545-6551.
Camisaschi et al., "Alternative Activation of Human Plasmacytoid DCs In Vitro and in Melanoma Lesions: Involvement of LAG-3" Journal of Investigative Dermatology (2014) vol. 134 pp. 1893-1902.
Casati, Chiara et al., "Soluble Human LAG-3 Molecule Amplifies the In vitro Generation of Type 1 Tumor-Specific Immunity," Cancer Res., vol. 66(8):4450-4460 (2006).
Castelli et al., "Lymphocyte activation gene-3 (LAG-3, CD223) in plasmacytoid dendritic cells (pDCs): a colecular target for the restoration of active antitumor immunity" OncoImmunology (2014) vol. 3 No. 11.
Cespedes "Mouse models in ocogenesis and cancer therapy" Clin. Tranl. Oncol. (2006) vol. 8, No. 5, pp. 318-329.
Chelius, Dirk et al., "Identification and Characterization of Deamidation Sites in the Conserved Regions of Human Immunoglobulin Gamma Antibiodies," Anal. Chemn., American Chemical Society, vol. 77(18): 6004-6011 (2005).
Chen & Flies, "Molecular mechanisms of T cell co-stimulation and co-inhibition" Nat Rev Immunol (2013) vol. 13 No. 4 pp. 227-242.
Chervontseva A M et al: "Effect of cytarabine on expression of cell adhesion molecules and on endothelium-leukocyte interaction in vitro.", Terapeuticheskii Arkhiv 2006, vol. 78, No. 7, 2006, pp. 67-72.

Christiansen et al: "Eradication of solid tumors using histone deacetylase inhibitors combined with immune-stimulating antibodies", Proceedings of the National Academy of Sciences, vol. 108 No. 10, Feb. 22, 2011 (Feb. 22, 2011), pp. 4141-4146.
Christiansson Lisa et al: "The tyrosine kinase inhibitors imatinib and dasatinib reduce myeloid suppressor cells and release effector lymphocyte responses.", Molecular Cancer Therapeutics, vol. 14, No. 5, May 2015 (May 2015), pp. 1181-1191.
ClincalTrials.gov Identifier: NCT01988896 "A Phase 1 b Study of MPDL3280A (an Engineered Anti-PDL1 Antibody) in Combination With Cobimetinib in Patients With Locally Advanced or Metastatic Solid Tumors" Clinicaltrials.gov, last updated Dec. 1, 2014.
Clinicaltrials.gov (search terms "Novartis" and "LAG3", p. 1: Mar. 30, 2017).
Giraldo et al., "Orchestration and Prognostic Significance of Immune Checkpoints in the Microenvironment of Primary Metastatic Renal Cell Cancer" Clinical Cancer Research (2015) vol. 21 No. 13 pp. 3031-3040.
ClinicalTrials.gov Identifier: NCT02040064 "Tolerability and Efficacy of Tremelimumab in Combination With Gefitinib in NSCLC Patients", ClinicalTrials.gov; last updated Jan. 17, 2014.
Dennis "Off by a whisker" Nature (2006) vol. 442, pp. 739-741.
Dey et al: "Nutl in-3 inhibits the NF[kappa]B Pathway in a p53 Dependent Manner: Implications in Lung Cancer Therapy". Cell Cycle, vol. 6, No. 17, Sep. 1, 2007 (Sep. 1, 2007), pp. 2178-2185.
Gettinger et al. "Safety and Response 1-98 With Nivolumab (Anti-PD-1; BMS-936558, ONO-4538) Plus Erlotinib in Patients (Pts) With Epidermal Growth Factor Receptor Mutant (EGFR MT) Advanced Non-Small Cell Lung Cancer (NSCLC} Metastatic Non-Small Cell Lung Cancer" International Journal of Radiation: Oncology Biology Physics (2014) vol. 90, No. 5, pp. S34-S35.
El Mir, Samir et al., "A Soluble Lymphocyte Activation Gene-3 Molecule Used as a Vaccine Adjuvant Elicits Greater Humoral and Cellular Immune Responses to Both Particulate and Soluble Antigens," The Journal of Immunology, vol. 164:5583-5589 (2000).
Fishwild, D.M. et al., "High-avidity human IgG kappa monoclonal antibodies from a novel strain of minilocus transgenic mice.," Nature Biotechnol., vol. 14, pp. 845-851 (1996).
Fujimori et al. "A Modeling Analysis of Monoclonal Antibody Percolation Through Tumors: A Binding-Site Barrier" J Mucl Med (1990) vol. 31, pp. 1191-1198.
Gagliani et al., "Coexpression of CD49b and LAG-3 identifies human and mouse T regulatory type 1 cells" Nature Medicine (2013) vol. 19 No. 6 pp. 739-746.
Garcia et al: "The Pan-PIM Kinase Inhibitor LGH447 Shows Activity In PIM2-Dependent Multiple Myeloma and In AML Models", Blood (2013) Retrieved from the Internet: URL:http://www.bloodjournal.orgjcontent/12 2/21/1666 [retrieved on Apr. 14, 2016].
Garrison K et al: "The small molecule TGF-[beta] signaling inhibitor SM16 synergizes with agonistic OX40 antibody to suppress established mammary tumors and reduce spontaneous metastasis" Cancer Immunology, Immunotherapy (2012) vol. 61 No. 4 pp. 511-521.
Hu et al., "Essential role of AKT in tumor cells addicted to FGFR", Anti-Cancer Drugs, 25(2):183-188 (2014).
Huang, "Role of LAG-3 in Regulatory T Cells", Immunity, 21:503-513 (2004).
Huard et al., "Cellular expression and tissue distribution of the human LAG-3-encoded protein, an MHC class II ligand", Immunogenetics, 39(3):213-217 (1994).
Huard, "Characterization of the major histocompatibility complex class II binding site on LAG-3 protein", Proc. Natl. Acad. Sci. USA, 94:5744-5749 (1997).
Huard et al., "Lymphocyte-activation gene 3/major histocompatibility complex class II interaction modulates the antigenic response of CD4+ T lymphocytes", Eur. J. Immunol., 24(12):3216-3221 (1994).
Huard et al., "T cell major histocompatibility complex class II molecules down-regulate CD4+ T cell clone responses following LAG-3 binding", Eur. J. Immunol., 26:1180-1186 (1996).
International Search Report and Written Opinion for International Application No. PCT/US2016/044545 dated Oct. 28, 2016.

(56) References Cited

OTHER PUBLICATIONS

International Search Report and Written Opinion for International Application No. PCT/US2015/049826 dated Dec. 16, 2015.
International Search Report and Written Opinion for International Application No. PCT/US2015/053799 dated May 17, 2016.
International Search Report and Written Opinion for International Application No. PCT/US2015/066812 dated Mar. 23, 2016.
International Search Report and Written Opinion for PCT/US2014/057491 dated Jan. 7, 2015.
International Search Report and Written Opinion for PCT/US2015/020474 mailed Jun. 15, 2015.
Iouzalen et al., "LAP, a lymphocyte activation gene-3 (LAG-3)-associated protein that binds to a repeated EP motif in the intracellular region of LAG-3, may participate in the down-regulation of the CD3/TCR activation pathway", Eur. J. Immunol., 31:2885-2891.
Acquaviva et al., "FGFR3 Translocations in Bladder Cancer: Differential Sensitivity to HsP90 Inhibition Based on Drug Metabolism", Molecular Cancer Research, 12(7):1042-1054 (2014).
Song et al., "3681 Phenotypic and Functional Effects of Novel HDAC Inhibitor LBH589 On Human Lymphocyte Populations", 51st ASH Annual Meeting and Exposition (2009) Retrieved from the Internet: URL:https:jash.confex.comjash/2889/webprogramjpaper22684.html [retrieved on 2816-84-14].
Song et al., "HDAC inhibition by LBH589 affects the phenotype and function of human myeloid dendritic cells", Leukemia Jan 2811, 25(1):161-168 (2011).
Subramanyam et al., "soluble human lymphocyte activation gene-3 modulates allospecific T cell responses", International Immunology, 10(4):679-689 (1998).
Supplementary European Search Report for European Application No. EP 1484888 mailed May 31, 2017.
Supplementary European Search Report for European Application No. EP 1484888 mailed Mar. 1, 2017.
Talmadge et al., "Murine Models to Evaluate Novel and Conventional Therapeutic Strategies for Cancer", The Americal Journal of Pathology, 170(3):793-804 (2007).
Thurber et al., "Antibody tumor penetration: Transport opposed by systemic and antigen-mediated clearance", Advanced Drug Delivery Reviews, 60:1421-1434 (2008).
Triebel et al., "LAG-3, A Novel Lymphocyte Activation Gene Closely Related to CD4", J. Exp. Med., 171:1393-1405 (1990).
Triebel et al., "LAG-3: a regulator T-cell and DC responses and its use in therapeutic vaccination", Trends in Immunology, 24(12):619-622 (2003).
Tsai et al., "Origin of the Isoelectric Heterogeneity of Monoclonal Immunoglobulin h1B4", Pharmaceutical Research, 10(11):1580-1586 (1993).
Turnis et al., "Combinatorial immunotherapy: PD-1 may not be LAG-in behind any more", OncoImmunology, 7:1172-1174 (2012).
Vanneman et al., "Combining immunotherapy and targeted therapies in cancer treatment", Nature Reviews Cancer, 12(4):237-251 (2012).
Verbrugge et al., "The curative outcome of radioimmunotherapy in a mouse breast cancer model relies on mTOR signaling", Radiation Research, Radiation Research Society, GB, 182(2):219-229.
Voskoglou-Nomikos et al., "Clinical Predictive Value of the in Vitro Cell Line, Human Xenograft, and Mouse Allograft Preclinical Cancer Models", Clinical Cancer Research, 9:4227-4239 (2003).
Wang et al., "In Vitro Characterization of te Anti-PD-1 Antibody Nivolumab, BMS-936558, and In Vivo Toxicology in Non-Human Primates", Cancer Immunol. Res., 2(9):846-856 (2014).
Wang et al., "The Mdm2 inhibitor, NvP-CGM097, in combination with the BRAF inhibitor NVP-LGX818 elicits synergistic antitumor effects in melanoma", Cancer Research, retrieved from the Internet: URL:http://cancerres.aacrjournals.orgjcontent/74/19 Supplement/5466 [retrieved on Apr. 14, 2016] (2014).
Wang et al., "Abstract 2929: The Mdm2 inhibitor NVP-CGM097 enhances the anti-tumor activity of NVP-LDK378 in ALK mutant neuroblastomamodels", Cancer Research retrieved from the Internet: URL:http:jjcancerres.aacrjournals.orgjcontent/74/19 Suppment/2929 [retrieved on Apr. 14, 2016] (2014).
Woo et al., "Immune inhibitory Molecules LAG-3 and PD-1 Synergistically Regulate T-cell Function to Promote Tumoral Immune Escape", Cancer Research, 72(4):917-927 (2011).
Woods et al., "HDAC Inhibition Upregulates PD-1 Ligands in Melanoma and Augments Immunotherapy with PD-1 Blockade", Cancer Immunology Research, 3(12):1375-1385 (2015).
Woods et al., "The antimelanoma activity of the histone deacetylase inhibitor panobinostat (LBH589) is mediated by direct tumor cytotoxicity and increased tumor immunogenicity", Melanoma Research, 23(5):341-348 (2013).
Woods et al., "Abstract 4090: Inhibition of class I histone deacetylases promotes robust and durable enhancement of PDL 1 expression in melanoma: Rationale for combination therapy", Cancer Research retrieved from the Internet: URL: http://cancerres.aacrjournals.orgjcont ent/74/19 Supplement/4090.short [retrieved on Apr. 14, 2016] (2014).
Workman et al., "LA-3 Regulates Plasmacytoid Dendritic Cell Homeostatis", The Journal of Immunology, 182:1885-1891 (2009).
Workman et al., "Phenotypic analysis of the murine CD4-related glycoprotein, CD223 (LAG-3)", Eur. J. Immunol., 32(8):2255-2263 (2002).
Workman et al., "Negative Regulation of T Cell Homeostatis by Lymphohocyte Activation Gene-3 (CD223)", The Journal of Immunology, 174:688-695 (2005).
Xu et al., "LSECtin Expressed on Melanoma Cells Promotoes Tumor Progression by Inhibiting Antitumor T-cell Responses", Cancer Research, 74(14):3418-3428 (2014).
Yervoy (ipilimumab) Drug Label, Initial U.S. Approval: 2011, Revised Oct. 2015.
Yuan et al., "Blockade of inhibitors of apoptosis (IAPs) in combination with tumor-targeted delivery of tumor necrosis factor-[alpha] leads to synergistic antitumor activity", Cancer Gene Theapy, 20(1):46-56 (2013).
Zamarin et al., "Immune checkpoint modulation: Rational design of combindation strategies", Pharmacology & Therapeutics, 150:23-32 (2015).
Zhou et al., "Coexpression of Tim-3 and PD-1 identifies a CD8 T-cell exhaustion phenotype in mice with disseminated acute myelogenous leukemia", Blood, 117(17:4501-4510 (2011).
Zhuang et al., "Selective IAP inhibition results in sensitization of unstimulated but not CD40-stimulated chronic lymphocytic leukemia cells to Trail-inducted apoptosis", Pharmacology Research & Perspectives, John Wiley & Songs Ltd, GB, 2(6)1-14.
Anderson et al. "Tim-3, a negative regulator of anti-tumor immunity" Current Opinion in Immunology (2012) vol. 24, No. 2, pp. 213-216.
Berrien-Elliott et al., "Durable Adoptive Immunotherapy for Leukemia Produced by Manipulation of Multiple Regulatory Pathways of CD8+ T-Cell Tolerance," Cancer Research (2012) vol. 73, pp. 605-616.
Hallett et al., "Immunosuppressive Effects of Multiple Myeloma Are Oversome by PD-L1 Blockade" Biol Blood Marrow Transplant (2011) vol. 17, No. 8, pp. 1133-1145.
Kearl et al., "Programmed Death Receptor-1/Programmed Death Receptor Ligand-1 Blockage after transient Lymphodepletion to Treat Myeloma," J Immunol (2013) vol. 190, pp. 5620-5628.
Khalil et al. "The New Era of Cancer Immunotherapy: Manipulating T-Cell Activity to Overcome Malignancy" Immunotherapy of Cancer in: Advances in Cancer Research (2015) vol. 128, pp. 1-68.
Li et al., "Contribution of PD-L1 to oncogenesis of lymphoma and its RNAi-based targeting therapy" Leukemia & Lymphoma (2012) vol. 53, No. 10, pp. 2015-2023.
Miska et al., "Autoimmunity-mediated antitumor immunity: Tumor as an immunoprivileged self," Eur J Immunol (2012) vol. 42, pp. 2584-2596.
Pardoll et al. "The blockade of immune checkpoints in cancer immunotherapy" Nature Reviews Cancer (2012) vol. 12, pp. 252-264.
Clinicaltrials.gov : A Phase 1 Dose Escalation and Cohort Expansion Study of the Safety, Tolerability, and Efficacy of Anti-LAG-3

(56) References Cited

OTHER PUBLICATIONS

Antibody (BMS-986016) in Relapsed or Refractory Chronic Lymphocytic Leukemia and Lymphomas. 2014.
Clinicaltrials.gov : A Phase 1 Dose Escalation and Cohort Expansion Study of the Safety, Tolerability, and Efficacy of Anti-LAG-3 Monoclonal Antibody (BMS-986016) Administered Alone and in Combination With Anti-PD-1 Monoclonal Antibody (Nivolumab, BMS-936558) in Advanced Solid Tumors. 2013.
Macon-Lemaitre L et al: "The negative regulatory function of the lymphocyteactivation gene-3 co-receptor (CD223) on human T cells", Immunology, Blackwell Publishing, Oxford, GB, vol. 115, No. 2, Jun. 1, 2005 (Jun. 1, 2005), pp. 170-178, KP002453818, ISSN: 0019-2805, DOI: 10.1111/J.1365-2567.2005.02145.X DOI: http://dx.doi.org/10.1111/j.1365-2567.2005.02145.x.
Goding SR, et al: "Restoring immune function of tumor-specific CD4+ T cells during recurrence of melanoma". J Immunol. May 1, 2013;190(9):4899-909. doi: 10.4049/jimmunol.1300271. Epub Mar. 27, 2013.
Grosso, et al: "LAG-3 regulates CD8+ T cell accumulation and effector function in murine selfand tumor-tolerance systems". J Clin Invest. Nov. 2007;117(11):3383-92.
Drake C G et al: "Blocking the regulatory T cell molecule LAG-3 augments in vivo anti-tumor immunity in an autochthonous model of prostate cancer", Journal of Clinical Oncology, American Society of Clinical Oncology, US, vol. 24, No. 18, suppl, Jun. 20, 2006 (Jun. 20, 2006), p. 2573, XP009138507, ISSN: 0732-183X.
Baixeras E et al: "Characterization of the Lymphocyte Activation Gene 3-Encoded Protein. A New Ligand for Human Leukocyte Antigen Class II Antigens", The Journal of Experimental Medicine, Rockefeller University Press, US, vol. 176, Aug. 1, 1992 (Aug. 1, 1992), pp. 327-337, XP000672152, ISSN: 0022-1007, DOI: 10.1084/JEM.176.2.327.
Goding S., et al., "Combination of adoptive cell transfer, anti-PD-L 1 and anti-LAG-3 antibodies for the treatment of recurrent tumors Better with More," OncoImmunology, vol. 2 (8), 4 pages (2013).
Rothe et al. "Enhancing dendritic cell-induced T-cell responses by immunomodulating molecules" 13th CIMT Annual Meeting (2015) p. 74.
Hu Yi et al: "Essential role of AKT in tumor cells addicted to FGFR.", Anti-Cancer Drugs, vol. 25, No. 2, Feb. 2014 (Feb. 2014), pp. 183-188.
Huang, Ching-Tai et al., "Role of LAG-3 in Regulatory T Cells," Immunity, vol. 21:503-513 (2004).
Huard, B. et al., "Cellular expression and tissue distribution of the human LAG-3-encoded protein, an MHC class II ligand," Immunogenetics, vol. 39(3), pp. 213-217 (1994).
Huard, Bertrand et al., "Characterization of the major histocompatibility complex class II binding site on LAG-3 protein," Proc. Natl. Acad. Sci. USA, vol. 94:5744-5749 (1997).
Huard, Bertrand et al., "Lymphocyte-activation gene 3/major histocompatibility complex class II interaction modulates the antigenic response of CD4+ T lymphocytes," Eur. J. Immunol., vol. 24(12):3216-3221 (1994).
Huard, Bertrand et al., "T cell major histocompatibility complex class II molecules down-regulate CD4+ T cell clone responses following LAG-3 binding," Eur. J. Immunol., vol. 26:1180-1186 (1996).
International Search Report and Written Opinion for International Appliaction No. PCT/US2016/044545 dated Oct. 28, 2016.
Iouzalen, Nathalie et al., "LAP, a lymphocyte activation gene-3 (LAG-3)-associated protein that binds to a repeated EP motif in the intracellular region of LAG-3, may participate in the downregulation of the CD3/TCR activation pathway," Eur. J. Immunol., vol. 31:2885-2891.
J . Acquaviva et al: "FGFR3 Translocations in Bladder Cancer: Differential Sensitivity to HSP90 Inhibition Based on Drug Metabolism". Molecular Cancer Research. vol. 12. No. 7. Jul. 1, 2014 (Jul. 1, 2014). pp. 1042-1054.

Jiang et al, "mTOR Kinase Inhibitor AZD8855 Enhances the Inmunotherapeutic Activity of an Agonist CD40 Antibody in Cancer Treatment" Cancer Research (2011) vol. 71 No. 12.
Jiang X et al: "The activation of MAPK in melanoma cells resistant to BRAF inhibition promotes PD-L1 expression that is reversible by MEK and PI3K inhibition", Clinical Cancer Research, the American Association for Cancer Research, US, vol. 19, No. 3, Feb. 1, 2013 (Feb. 1, 2013). pp. 598-609.
Jing et al. "Combined immune checkpoint protein blockade and low dose whole body irradiation as immunotherapy for myeloma" Journal for Immuno Therapy of Cancer (2015) vol. 3, No. 2, pp. 1-15.
Search Report and Written Opinion issued in Singapore Application No. 11201605951Y, mailed Oct. 16, 2017.
Keytruda (pembrolizumab) Drug Label, Initial U.S. Approval: 2014, Revised Oct. 2016.
Scurr et al., "Highly prevalent colorectal cancer-infiltrating LAP+ Foxp3− T cells exhibit more potent immunosuppressive activity than Foxp3+ regulatory T cells" Nature Publishing Group (2014) vol. 7 No. 2 pp. 428-439.
Kim et al: "Eradication of metastatic mouse cancers resistant to irrmune checkpoint blockade by suppression of myeloid-derived cells. (Includes Supporting Information)", Proceedings of the National Academy of Sciences of the United States of America, vol. 111, No. 32, Aug. 12, 2014 (Aug. 12, 2014), pp. 11774-11777.
Klein Jan M et al: "The histone deacetylase inhibitor LBH589 (panobinostat) modulates the crosstalk of lymphocytes with Hodgkin lymphoma cell lines.", PLoS One, vol. 8, No. 11, E79582, 2813, pp. 1-6.
Knight et al. " Host immunity contributes to the antimelanoma activity of BRAE inhibitors" The Journal of Clinical Investigation (2013) vol. 123, No. 3, pp. 1371-1381.
Knights et al., "Inhibitor of apoptosis protein (IAP) antagonists demonstrate divergent immunomodulatory properties in human immune subsets with implications for combination therapy" Cancer Immunology and Immunotherapy (2013) vol. 62 No. 2 pp. 321-335.
Kocak, Ergun et al., "Combination Therapy with Anti-CTL Antigen-4 and Anti-4-1 BB Antibodies Enhances Cancer Immunity and Reduces Autoimmunity," Cancer Res., vol. 66(14):7276-7284 (2006).
Kroon D. et al., "Identification of Sites of Degradation in a Therapeutic Monoclonal Antibody by Peptide Mapping," Pharmaceutical Research, vol. 9(11 ): 1386-1393 (1992).
Scurr et al. "Highly prevalent colorectal cancer-infiltrating LAP+ Foxp3− T cells exhibit more potent immunosuppressive activity than Foxp3+ regulatory T cells" Mucosal Immunology (2013) doi:10.1038/mi.2013.62, pp. 1-12.
Lipson et al. "Initial Experience Administering BMS-986016, a Monoclonal Antibody That Targets Lymphocyte Activation Gene (LAG)-3, Alone and in Combination With Nivolumab to Patients With Hematologic and Solid Malignancies" Presented at the Society for Immunotherapy of Cancer Annual Meeting; Nov. 9-13, 2016, National Harbor, MD.
List of anti-LAG-3 clinical trials identified in ClinicalTrials.gov as of Jan. 20, 2017.
Rudnick et al. "Affinity and Avidity in Antibody-Based Tumor Targeting" Cancer Biotherapy and Radiopharmaceuticals (2009) vol. 24, No. 2, pp. 155-160.
Masters et al., "Abstract 5016: Antitumor activity of anti-PD-1 in combination with tyrosine kinase inhibitors in a preclinical renal cell carcinoma model" AACR Annual Meeting (2014) vol. 74, No. 5016.
Menzies et al. "Recent advances in melanoma systemic therapy. BRAF inhibitors, CTLA4 antibodies and beyond" European Journal of Cancer (2013) vol. 49, pp. 3229-3241.
Menzies et al. "Systemic treatment for BRAF-mutant melanoma: where do we go next?" The Lancet (2014) vol. 15, pp. e371-e381.
Quintarelli et al: "Selective strong synergism of Ruxolitinib and second generation tyrosine kinase inhibitors to overcome bone marrow stroma related drug resistance in chronic myelogenous leukemia", Leukemia Research, New York, NY, US, vol. 38, No. 2, Nov. 15, 2013 (Nov. 15, 2013), pp. 236-242.

(56) References Cited

OTHER PUBLICATIONS

Mittendorf Elizabeth A et al: "PD-L1 expression in triple-negative breast cancer." Cancer Immunology Research. vol. 2. No. 4. Apr. 2014 (Apr. 2014). pp. 361-370.
Moreira Da Silva, "Nivolumab Anti-PD-1 monoclonal antibody cancer immunotherapy" Drugs of the Future (2014) vol. 39 No. 1 pp. 15-24.
Nakae et al., "Mast cells enhance T cell activation: importance of mast cell costimulatory molecules and secreted TNF" The Journal of Immunology (2006) vol. 176 No. 4 pp. 2238-2248.
Oki Y et al: "Immune regulatory effects of panobinostat in patients with Hodgkin lymphoma through modulation of serum cytokine levels and T-cell PD1 expression .", Blood Cancer Journal, vol. 4, E236, 2014, pp. 1-4.
Opdivo (nivolumab) Drug Label, Initial U.S. Approval: 2014, Revised Nov. 2016.
Prigent, Philippe et al., "Lymphocyte activation gene-3 induces tumor regression and antitumor immune responses," Eur. J. Immunol., vol. 29:3867-3876 (1999).
Pardoll, D. et al., "Dendritic Cells and Coregulatory Signals: Immune Checkpoint Blockade to Stimulate Immunotherapy," Cancer Immunotherapy, vol. 86(5) pp. 257-275 (2007).
Perez-Gracia et al, "Orchestrating immune check-point blockade for cancer inmunotherapy in combinations", Current Opinion in Immunology. vol. 27 pp. 89-97.
Pinzon-Ortiz et al: "S710: The combination of JAK inhibitor, ruxolitinib, pan-PIM inhibitor, LGH447, and CDK4/6 inhibitor, LEE011, in a preclinical mouse model of myeloproliferative neoplasia", Haematologica, the Hematology Journal: Official Organ of the European Hematology Association, vol. 99. No. Supp 1 (2014) p. 252.
Song et al: "3681 Phenotypic and Functional Effects of Novel HDAC Inhibitor LBH589 On Human Lymphocyte Populations", 51st ASH Annual Meeting and Exposition (2009) Retrieved from the Internet: URL:https:jjash.confex.comjash/2889/webpro gramjPaper22684.html [retrieved on 2816-84-14].
Song W et al: "HDAC inhibition by LBH589 affects the phenotype and function of human myeloid dendritic cells.", Leukemia Jan. 2811, vol. 25, No. 1, Jan. 2011 (Jan. 2011), pp. 161-168.
Subramanyam, Meena et al., "Soluble human lymphocyte activation gene-3 modulates allospecific T cell responses," International Immunology, vol. 10(4):679-689 (1998).
Supplementary Partial European Search Report for European Application No. EP 1484888, mailed Mar. 1, 2017.
Talmadge et al. "Murine Models to Evaluate Novel and Conventional Therapeutic Strategies for Cancer" The American Journal of Pathology (2007) vol. 170, No. 3, pp. 793-804.
Thurber et al. "Antibody tumor penetration: Transport opposed by systemic and antigen-mediated clearance" Advanced Drug Delivery Reviews (2008) vol. 60, pp. 1421-1434.
Triebel, Frederic et al., "LAG-3, A Novel Lymphocyte Activation Gene Closely Related to CD4," J. Exp. Med., vol. 171:1393-1405 (1990).
Triebel, Frederic et al., "LAG-3: a regulator T-cell and DC responses and its use in therapeutic vaccination," Trends In Immunology, vol. 24(12):619-622 (2003).
Tsai P.K. et al., "Origin of the Isoelectric Heterogeneity of Monoclonal Immunoglobulin h1B4," Pharmaceutical Research, vol. 10(11): 1580-1586 (1993).
Turnis M. et al., "Combinatorial immunotherapy: PD-1 may not be LAG-ing behind any more," Oncolmmunolgy, vol. (7), pp. 1172-1174 (2012).
Vanneman et al: "Combining immunotherapy and targeted therapies in cancer treatment" Nature Reviews Cancer (2012) vol. 12 No. 4 pp. 237-251.
Verbrugge et al: "The curative outcome of radioinmunotherapy in a mouse breast cancer model relies on mTOR signaling", Radiation Research. Radiation Research Society, GB, vol. 182 No. 2 pp. 219-229.

Voskoglou-Nomikos et al. "Clinical Predictive Value of the in Vitro Cell Line, Human Xenograft, and Mouse Allograft Preclinical Cancer Models" Clinical Cancer Research (2003) vol. 9, pp. 4227-4239.
Wang et al. "In Vitro Characterization of the Anti-PD-1 Antibody Nivolumab, BMS-936558, and In Vivo Toxicology in Non-Human Primates" Cancer Immunol Res. (2014) vol. 2, No. 9, pp. 846-856.
Wang et al., "The Mdm2 inhibitor, NVP-CGM097, in combination with the BRAF inhibitor NVP-LGX818 elicits synergistic antitumor effects in melanoma" Cancer Research (2014) Retrieved from the Internet: URL:http://cancerres.aacrjournals.orgjcontent/74/19 Supplement/5466 [retrieved on Apr. 14, 2016].
Wang et al: "Abstract 2929: The Mdm2 inhibitor NVP-CGM097 enhances the anti-tumor activityof NVP-LDK378 in ALK mutant neuroblastomamodels", Cancer Research (2014) Retrieved from the Internet: URL:http:jjcancerres.aacrjournals.orgjcontent/74/19 Supplement/2929 [retrieved on Apr. 14, 2016].
Woo et al. "Immune Inhibitory Molecules LAG-3 and PD-1 Synergistically Regulate T-cell Function to Promote Tumoral Immune Escape" Cancer Research (2011) vol. 72, No. 4, pp. 917-927.
Woods David M et al: "HDAC Inhibition Upregulates PD-1 Ligands in Melanoma and Augments Immunotherapy with PD-1 Blockade.",Cancer Immunology Research, vol. 3, No. 12, Dec. 2015 (Dec. 2015), pp. 1375-1385.
Woods David M et al: "The antimelanoma activity of the histone deacetylase inhibitor panobinostat (LBH589) is mediated by direct tumor cytotoxicity and increased tumor immunogenicity.", Melanoma Research, vol. 23, No. 5, Oct. 2013 (Oct. 2013), pp. 341-348.
Woods et al: "Abstract 4090: Inhibition of class I histone deacetylases promotes robust and durable enhancement of PDL 1 expression in melanoma: Rationale for combination therapy", Cancer Research (2014)Retrieved from the Internet: URL:http://cancerres.aacrjournals. orgjcont ent/74/19 Supplement/4090.short [retrieved on Apr. 14, 2016].
Workman et al., "LAG-3 Regulates Plasmacytoid Dendritic Cell Homeostatis" The Journal of Immunology (2009) vol. 182 pp. 1885-1891.
Workman, C.J. et al., "Phenotypic analysis of the murine CD4-related glycoprotein, CD223 (LAG-3).," Eur. J. Immunol., vol. 32(8): 2255-2263 (2002).
Workman, Creg J. et al., "Negative Regulation of T Cell Homeostasis by Lympohocyte Activation Gene-3 (CD223)," The Journal of Immunology, vol. 174:688-695 (2005).
Xu et al., "LSECtin Expressed on Melanoma Cells Promotoes Tumor Progression by Inhibiting Antitumor T-cell Responses" Cancer Research (2014) vol. 74 No. 14 pp. 3418-3428.
Yuan Z et al, "Blockade of inhibitors of apoptosis (IAPs) in combination with tumor-targeted delivery of tumor necrosis factor-[alpha] leads to synergistic antitumor activity" Cancer Gene Therapy (2013) vol. 20 No. 1 pp. 46-56.
Zamarin et al. "Immune checkpoint modulation: Rational design of combindation strategies" Pharmacology & Therapeutics (2015) vol. 150, pp. 23-32.
Zhou et al., "Coexpression of Tim-3 and PD-1 identifies a CD8 T-cell exhaustion phenotype in mice with disseminated acute myelogenous leukemia" Blood (2011) vol. 117 No. 17 pp. 4501-4510.
Zhuang J et al: "Selective IAP inhibition results in sensitization of unstimulated but not CD40-stimulated chronic lymphocytic leukaemia cells to Trail-induced apoptosis" Pharmacology Research & Perspectives. John Wiley & Sons Ltd, GB, vol. 2 No. 6 pp. 1-14.
Agoram et al., "Use of pharmacokinetic/pharmacodynamic modelling for starting dose selection in first-in-human trials of high-risk biologics," Br. J. Clin. Pharm., 67(2):153-160 (2009).
Grimwood et al., "Target site occupancy: Emerging generalizations from clinical and preclinical studies," Pharm. Therapeutics, 122(3):281-301 (2009).
Hong et al., "Phase I/II study of LAG525 +− spartalizumab (PDR001) in patients (pts) with advanced malignancies," J. Clin. Onc., ASCO Annual Meeting (2018) 36 (Suppl): abstract 301.
Tiwari et al., "Optimal Affinity of a Monoclonal Antibody: Guiding Principles Using Mechanistic Modeling" J. AAPS, 19(2):510-519 (2017).

(56) References Cited

OTHER PUBLICATIONS

Ngiow et al., "Anti-Tim3 Antibody Promotes T Cell IFN-γ-Mediated Antitumor Immunity and Suppresses Established Tumors" Cancer Research (2011) vol. 71 No. 10 pp. 3540-3551.
Nicholson et al., "An Altered Peptide Ligand Mediates Immune Deviation and Prevents Autoimmune Encephalomyelitis" Immunity (1995) vol. 3 pp. 397-405.
Nielsen, C., et al., "A putative regulatory polymorphism in PD-1 is associated with nephropathy in a population-based cohort of systemic lupus erythematosus patients," Lupus 13(7):510-516, SAGE, England (2004).
Nirschl et al., "Molecular Pathways: Coexpression of Immune Checkpoint Molecules: Signaling Pathways and Implications for Cancer Immunotherapy," Cancer Res (2013) vol. 19, No. 18, pp. 4917-4924.
Nishimura et al., "Developmentally regulated expression of the PD-1 protein on the surface of double-negative (CD4-CD8-) thymocytes," Int Immunol (1996) vol. 8, No. 5, pp. 773-780.
Nishimura, H., et al., "Autoimmune dilated cardiomyopathy Science in PD-1 receptor-deficient mice," Science 291(5502):319-322, American Association for the Advancement of Science, United States (2001).
Nishimura, H., et al., "Development of lupus-like autoimmune diseases by disruption of the PD-1gene encoding an ITIM motif-carrying immunoreceptor," Immunity 11(2):141-151, Cell Press, United States (1999).
Nishimura, H., et al., "Immunological studies on PD-1 deficient mice: implication of PD-1 as a negative regulator for B cell responses," International Immunology 10(10):1563-1572, Oxford University Press, England (1998).
Nomi, T., et al., "Clinical significance and therapeutic potential of the programmed death-1 ligand/programmed death-1 pathway in human pancreatic cancer," Clinical Cancer Research 13(7):2151-2157, The Association, United States (2007).
Ohigashi et al, "Clinical Significance of Programmed Death-1 Ligand-1 and Programmed Death-1 Ligand-2 Expression in Human Esophageal Cancer" Clin Cancer Research (2005) vol. 11, pp. 2947-2953.
Ohno et al., "Antigen-binding specificities of antibodies are primarily determined by seven residues of VH," PNAS (1985) vol. 82, pp. 2945-2949.
Okamoto et al., "T-Helper Type 1/T-Helper Type 2 Balance in Malignant Pleural Effusions Compared to Tuberculous Pleural Effusions" Chest (2005) vol. 128 pp. 4030-4035.
Okazaki et al, "PD-1 and PD-1 ligands: from discovery to clinical application" Intern. Immun. (2007) vol. 19, pp. 813-824.
Okazaki, T., et al., "New regulatory co-receptors: inducible co-stimulator and PD-1," Current Opinion in Immunology 14(6):779-782, Elsevier, England (2002).
Okazaki, T., et al., "PD-1 immunoreceptor inhibits B cell receptor-mediated signaling by recruiting src homology 2-domain-containing tyrosine phosphatase 2 to phophotyrosine," Proceeding of the National Academy of Sciences 98(24):13866-13871,National Academy of Sciences, United States (2001).
Okudaira et al., "A modified version of galectin-9 suppresses cell growth and induces apoptosis of human T-cell leukemia virus type 1-infected T-cell lines" Int. J. Cancer (2007) vol. 120 pp. 2251-2261.
Opdivo (nivolumab) Drug Label, Initial U.S. Approval: 2014, Revised Oct. 2016.
Opdivo (nivolumab) Drug Label, Initial U.S. Approval: 2014, Revised May 2016.
Opposition filed by Laboratorios Legrand S.A. in corresponding Colombian Application No. NC2017/0003490 on Dec. 7, 2017, admitted Dec. 19, 2017, published Dec. 20, 2017.
Opposition filed in Colombian Application No. NC2016/0001001, filed Feb. 15, 2017.
Ozaki, S., et al., "Immunotherapy of Multiple Myeloma with a Monoclonal Antibody Directed Against a Plasma Cell-specific Antigen, HM1.24," Blood 90(8):3179-3186, American Society of Hematology, United States (1997).
Ozkaynak, E., et al., "Programmed death-1 targeting can promote allograft survival," The Journal of Immunology 169(11):6546-6553, The American Association of Immunologists, United States (2002).
Pal et al., "Programmed Death-1 Inhibition in Renal Cell Carcinoma: Clinical Insights and Future Directions," Clinical Adv Hem Onc (2014) vol. 12, Issue 2, pp. 90-99.
Panka, et al.; "Variable region framework differences result in decreased or increased affinity of variant anti-digoxin antibodies"; Proc. Natl. Acad. Sci. USA; 85:3080-3084 (1988).
Park, J.W. and Smolen, J., "Monoclonal antibody therapy," Advances in Protein Chemistry 56:369-421, Academic Press, United States (2001).
Parry, Richard V., et al.; "CTLA-4 and PD-1 Receptors Inhibit T-Cell Activation by Distinct Mechanisms"; Molecular and Cellular Biology; 25(21):9543-9553 (2005).
Partial European Search Report issued in European Patent Application No. 19206634.8, mailed Apr. 30, 2020.
Patel et al., "Taming dendritic cells with Tim-3: another immunosuppressive strategy used by tumors" Immunotherapy (2012) vol. 4 No. 12 pp. 1795-1798.
Paterson et al., "The Programmed Death-1 Ligand 1:B7-1 Pathway Restrains Diabetogenic Effector T Cells In Vivo," J Immunol (2011) vol. 187, pp. 1097-1105.
Patsoukis, N., et al., "PD-1 Increases PTEN Phosphatase Activity While Decreasing PTEN Protein Stability by Inhibiting Casein Kinase 2," Molecular and Cellular Biology 33(16):3091-3098, American Society for Microbiology, United States (Aug. 2013).
Patsoukis, N., et al., "PD-1 inhibits T cell proliferation by upregulating p. 27 and p. 15 and suppressing Cdc25A," Cell Cycle 11(23):1-5, Landes Bioscience, United States (Dec. 2012).
Patsoukis, N., et al., "Selective Effects of PD-1 on Akt and Ras Pathways Regulate Molecular Components of the Cell Cycle and Inhibit T Cell Proliferation," Science Signaling 5(230): ra46, pp. 1-14, American Association for the Advancement ofScience, United States (Jun. 2012).
Phong et al., "Tim-3 enhances Fc[epsilon]RI-proximal signaling to modulate mast cell activation," J Experimental Medicine (2015) vol. 212, No. 13, pp. 2289-2304.
Polyak, M.J. and Deans, J.P., "Alanine-170 and proline-172 are critical determinants for extracellular CD20 epitopes; heterogeneity in the fine specificity of CD20 monoclonal antibodies is defined by additional requirements imposed by both aminoacid sequence and quaternary structure," Blood 99(9):3256-3262, American Society of Hematology, United States (2002).
Post Grant Opposition filed in Colombian Patent Application No. NC2016/0001001, dated Jul. 31, 2018.
Postel-Vinay et al. "Challenges of phase 1 clinical trials evaluating immune checkpoint-targeted antibodies" Annals of Oncology (2016) vol. 27, pp. 214-224.
Powles et al., "MPDL3280A (anti-PD-L1) treatment leads to clinical activity in metastatic bladder cancer," Nature (2014) vol. 515, pp. 558-562.
Prokunina, L. and Alarcon-Riquelme, M., "The genetic basis of systemic lupus erythematosus—knowledge of today and thoughts for tomorrow," Human Molecular Genetics 13(1):R143-R148, Oxford University Press, England (2004).
Raziorrouh et al. "The Immunoregulatory Role of CD244 in Chronic Hepatitis B Infection and its Inhibitory Potential on Virus-Specific CD8+ T-cell Function" Hepatology (2010) vol. 52 pp. 1934-1947.
Richter et al., "On the role of the inhibitory receptor LAG-3 in acute and chronic LCMV infection," Int Immunol (2009) vol. 22, No. 1, pp. 13-23.
Riley, J.L. and June, C.H., "The CD28 family: a T-cell rheostat for therapeutic control of T-cell activation," Blood 105(1):13-21, American Society of Hematology, United States (Jan. 2005).
Rowe et al., "Innate IFN-gamma is essential for programmed death ligand-1-mediated T cell stimulation following Listeria monocytogenes infection," J Immunol (2012) vol. 189, No. 2, pp. 876-884.
Rudikoff, et al.; "Single Amino Acid Substitution Altering Antigen-binding Specificity"; Proc. Natl. Acad. Sci. USA; 79:1979-1983 (1982).

(56) References Cited

OTHER PUBLICATIONS

Sabatos et al. "Interaction of Tim-3 and Tim-3 ligand regulates T helper type 1 responses and induction of peripheral tolerance" Nature Immunology (2003) vol. 4, pp. 1102-1110.
Sabatos-Peyton et al., "Blockade of Tim-3 binding to phosphatidylserine and CEACAM1 is a shared feature of anti-Tim-3 antibodies that have functional efficacy," Oncoimmunology (2018) vol. 7, No. 2, Article e1385690, 9 pages.
Sachdev et al., "Phase 1/2a study of double immune suppression blockade by combining a CSF1R inhibitor (pexidartinib/PLX3397) with an anti-PD-1 antibody (pembrolizumab) to treat advanced melanoma and other solid tumors," Gynecologic Oncology (2016) vol. 141, pp. 147-148.
Sakuishi et al., "Emerging Tim-3 functions in anti-microbial and tumor immunity" Trends Immunol (2011) vol. 32 No. 8 pp. 345-349.
Sakuishi et al., "Targeting Tim-3 and PD-1 pathways to reverse T cell exhaustion and restore anti-tumor immunity," J Experimental Medicine (2010) vol. 207, No. 10, pp. 2187-2194.
Sakuishi et al., "Tim3+FOXP3+ regulatory T cells are tissue-specific promoters of T-cell dysfunction in cancer" OncoImmunology (2013) vol. 2 No. 4 pp. e23849-1-e23849-9.
Salama, A.D., et al., "Critical role of the programmed death-I (PD-1) pathway in regulation of experimental autoimmune encephalomyelitis," The Journal of Experimental Medicine 198(1):71-78, The Rockefeller University Press, United States (2003).
Chesi et al., "IAP antagonists induce anti-tumor immunity in multiple myeloma," Nat Med (2016) vol. 22, No. 12, pp. 1411-1420.
Christensen et al., "c-Met as a target for human cancer and characterization of inhibitors for therapeutic intervention," Cancer Letters (2005) vol. 225, pp. 1-26.
ClincalTrials.gov Identifier: NCT02323126 "Study of Efficacy and Safety of Nivolumab in Combination With EGF816 and of Nivolumab in Combination With INC280 in Patients With Previously Treated Non-small Cell Lung Cancer (EGF816)," Clinicaltrials.gov, last updated Jun. 6, 2018.
ClinicalTrials.gov "History of Changes for Study NCT01454102," ClinicalTrials.Gov, latest version submitted on Nov. 3, 2017.
ClinicalTrials.gov Identifier: NCT02263508 "A Phase 1 b/3, Multicenter, Open-label Trial of Tafimogene Laherparepvec in Combination With Pembrolizumab (MK-3475) for Treatment of Unresected, Stage IIIB to IVM1c Melanoma (Masterkey-265)", ClinicalTrials.gov; last updated Jun. 22, 2015.
ClinicalTrials.gov Identifier: NCT02339571 "Randomized Phase II/III Study of Nivolumab Plus Ipilimumab Plus Sargramostim Versus Nivolumab Plus Ipilimumab in Patients With Unresectable Stage III or Stage IV Melanoma", ClinicalTrials.gov; last updated Apr. 9, 2015.
ClinicalTrials.gov Identifier: NCT02608268, Safety and Efficacy of MBG453 as Single Agent and in Combination With PDR001 in Patients With Advanced Malignancies, Information provided by Novartis (Novartis Pharmaceuticals), last updated Oct. 13, 2016.
ClinicalTrials.gov Identifier: NCT02817633, A Phase 1 Study of TSR-022, an Anti-Tim-3 Monoclonal Antibody, in Patients With Advanced Solid Tumors, Information provided by Tesaro, Inc., last updated Aug. 26, 2016.
Cloeckaert, A., et al., "O-Polysaccharide epitopic heterogeneity at the surface of *Brucella* spp.studied by enzyme-linked immunosorbent assay and flow cytometry," Clinical and Diagnostic Laboratory Immunology 5(6):862-870, American Society forMicrobiology, United States (1998).
Cohen et al., "Image Cytometry of Estrogen Receptors in Breast Carcinomas" Cytometry (1988) vol. 9 pp. 579-587.
Collins et al., "The B7 family of immune-regulatory ligands" Genome Biology (2005) vol. 6 No. 223.
Cragg, M.S. et al., "Complement-mediated lysis by anti-CD20 mAb correlated with segregation into lipid rafts," Blood 101(3):1045-1052, American Society of Hematology, United States (2003).

Creelan, B.C., "Update on Immune Checkpoint Inhibitors in Lung Cancer," Journal of the Moffitt Cancer Center 21(1):80-89, H. Lee Moffitt Cancer Center and Research Institute, United States (2014).
Cruse, J.M. and Lewis, R.E., "Antigens and Immunogens," in Atlas of Immunology, 2nd ed., pp. 105-126, CRC Press, United States (Dec. 29, 2003).
Curigliano et al., "Abstract CT183: Phase (Ph) I/II study of MBG453 +/- spartalizumab (PDR001) in patients (pts) ith advanced malignancies," AACR Annual Meeting 2019, Cancer Research, vol. 79, Issue 13, Supplement, 2 pages.
Davies, D.R. and Cohen, G.H., "Interactions of protein antigens with antibodies," Proceedings of the National Academy of Sciences USA 93(1):7-12, National Academy of Sciences, United States (1996).
Davies, Julian, et al.; "Affinity improvement of single antibody VH domains: residues in all three hypervariable regions affect antigen binding"; ; 2:169-179 (1996).
Dekruyff et al., "T Cell/Transmembrane, Ig, and Mucin-3 Allelic Variants Differentially Recognize Phosphatidylserine and MEdiate Phagocytosis of Apoptotic Cells" The Journal of Immunology (2010) vol. 184 pp. 1918-1930.
Del-Rio, Maria-Luisa, et al.; "Antibody-mediated signaling through PD-1 costimulates T cells and enhances CD28-dependent proliferation"; Eur. J. Immunol.; 35(12):3545-3560 (2005).
DeMaria et al., "Immune-mediated inhibition of Metastases after Treatment with Local Radiation and CTLA-4 Blockade in a Mouse Model of Breast Cancer," Clinical Cancer Research (2005) vol. 11, pp. 728-734.
Dong et al., "Tumor-associated B7-H1 promotes T-cell apoptosis: A potential mechanism of immune evasion", Nat Med (2002) vol. 8 pp. 793-800.
Dong, H. and Chen, L., "B7-H1 pathway and its role in the evasion of tumor immunity," Journal of Molecular Medicine 81(5):281-287, Springer, Germany (2003).
Dorfman et al., "The phosphatidylserine receptors, T cell immunoglobulin mucin proteins 3 and 4, are markers of histiocytic sarcoma and other histiocytic and decdritic cell neoplasms" Hum Pathol (2010) vol. 41 No. 10 pp. 1486-1494.
Dougan et al., "Regulation of innate and adaptive antitumor immunity by IAP antagonists," Immunotherapy (2018) vol. 10, No. 9, pp. 787-796.
Dougan, D.A., et al., "Effects of subsitutions in the binding surface of an antibody on antigen affinity," Protein Engineering 11(1):65-74, Oxford University Press, England (1998).
Du Manoir et al., "Ki-67 Labeling in Postmitotic Cells Defines Different Ki-67 Pathways Within the 2c Compartment" Cytometry (1991) vol. 12 pp. 455-463.
Entzminger et al., "De novo design of antibody complementarity determining regions binding a FLAG tetrapeptide," Sci Rep (2017), retrived from www.nature.com/ articles/s41598-017-10737-9.pdf?origin=ppub, last accessed Jan. 12, 2018.
Extended European Search Report for European Application No. EP 1484888.5, mailed May 31, 2017.
Extended European Search Report issued in European Application No. 19199437.5, mailed Mar. 12, 2020, 8 pages.
Extended European Search Report issued in European Patent Application No. 18211373.8, mailed Jun. 25, 2019.
Fessas et al., "A molecular and preclinical comparison of the PD-1-targeted T-cell checkpoint inhibitors nivolumab and pembrolizumab," Seminars in Oncology (2017) vol. 44, pp. 136-140.
Finger, L.R., et al., "The human PD-1 gene: complete cDNA, genomic organization, and developmentally regulated expression in B cell progenitors," Gene 197(1-2):177-187, Elsevier, United States (1997).
Fivash, M., et al., "BIAcore for macromolecular interaction," Current Opinion in Biotechnology 9(1):97-101, Current Biology, England (1998).
Fleischer, Bernhard, et al.; "T cell stimulation by staphylococcal enterotoxins"; J. Exp. Medicine; 167(5):1697-1707 (1988).

(56) References Cited

OTHER PUBLICATIONS

Fourcade et al., "Upregulation of Tim-3 and PD-1 expression is associated with tumor antigen-specific CD8+ T cell dysfunction in melanoma patients" The Journal of Experimental Medicine (2010) vol. 207 No. 10 pp. 2175-2186.
Franklin, M.C., et al., "Insights into ErbB signaling from the structure of the ErbB2-pertuzumab complex," Cancer Cell 5(4):317-328, Cell Press, United States (Apr. 2004).
Freeman et al., "Cloning of B7-2: a CTLA-4 counter-receptor that costimulates human T cell proliferation," Science (1993) vol. 262, pp. 909-911.
Freeman et al., "Engagement of the PD-1 immunoinhibitory receptor by a novel B7 family member leads to negative regulation of lymphocyte activation", J Exp Med. (2000) vol. 192, No. 7, pp. 1027-1034.
Freeman et al., "Tim genes: a family of cell surface phosphatidylserine receptors that regulate innate and adaptive immunity" Immunol Rev (2010) vol. 235 No. 1 pp. 172-189.
Fukushima et al., "Antibodies to T-cell Ig and mucin domain-containing proteins (Tim)-1 and -3 suppress the Induction and progression of murine allergic conjunctivitis" Biochemical and Biophysical Research Communications (2006) vol. 353 No. 1 p. 211-16.
Fulda, "Molecular Pathways: Targeting Inhibitor of Apoptosis Proteins in Cancer—From Molecular Mechanism to Therapeutic Application," Clin Cancer Res (2013) vol. 20, No. 2, pp. 289-295.
Gao et al., "Tim-3 Expression Characterizes Regulatory T Cells in Tumor Tissues and Is Associated with Lung Cancer Progression" PLoS One (2012) vol. 7 No. 2 e30676.
Ge, X., et al., "CD134-Allodepletion Allows Selective Elimination of Alloreactive Human T Cells without Loss of Virus-Specific and Leukemia-Specific Effectors," Biology of Blood and Marrow Transplantation 14(5):518-530, American Society for Bloodand Marrow Transplantation, United States (2008).
Geng et al., "Soluble Form of T Cell Ig Mucin 3 Is an Inhibitory Molecule in T Cell-Mediated Immune Response" The Journal of Immunology (2006) vol. 176 pp. 1411-1420.
Ghebeh et al., "Doxorubicin downregulates cell surface B7-H1 expression and upregulates its nuclear expression in breast cancer cells: role of B7-H1 as an anti-apoptotic molecule," Breast Cancer Research (2010) vol. 12, No. 4, Article R48, 12 pages.
Goldberg et al. "LAG-3 in Cancer Immunology" Current Topics in Microbiology and Immunology (2010) vol. 344, pp. 269-278.
Golden-Mason et al., "Negative Immune Regulator Tim-3 Is Overexpressed on T Cells in Hepatitis C Virus Infection and Its Blockade Rescues Dysfunctional CD4+ and CD8+ T Cells," J Virol (2009) vol. 83, No. 18, pp. 9122-9130.
Greenspan, N.S., "Epitopes, paratopes and other topes: do immunologists know what they are talking about?" Bulletin de l'Institut Pasteur 90(4):267-279, Elsevier, France (1992).
Grosso, Joseph F et al., "LAG-3 regulates CD8+ T cell accumulation and effector function in murine self- and tumor-tolerance systems," J. Clin. Invest., vol. 117(11 ):3383-3392 (2007).
Haitov, "Immunology: Structure and Functions of the Immune System," Geotar-Media Publishing Group, Moscow (2013) p. 110. Russian.
Wiener et al., "Tim-3 Is Expressed in Melanoma Cells and Is Upregulated in TGF-Beta Stimulated Mast Cells" Journal of Investigative Dermatology (2007) vol. 127 pp. 906-914.
Wilson, I.A. and Stanfield, R.L., "Antibody-antigen interactions," Current Opinion in Sturctural Biology 3:113-118, Current Biology, United States (1993).
Winslow, R., "New Cancer Drugs Harness Power of Immune System", The Wall Street Journal, May 15, 2013, accessed at http://www.wsj.com/articles/SB10001424127887323398204578485401089823868, accessed on Jun. 1, 2016, 4 pages.
Wolchok et al., "Nivolumab plus Ipilimumab in Advanced Melanoma," N Engl J Med (2013) vol. 369, pp. 122-133.

Wong, R.M., et al., "Programmed death-1 blockade enhances expansion and functional capacity of human melanoma antigen-specific CTLs," International Immunology 19(10):1223-1234, Oxford University Press, England (2007).
Workman et al., "Negative Regulation of T Cell Homeostasis by Lymphocyte Activation Gene-3 (CD223)," J Immunol (2005) vol. 174, pp. 688-695.
Wu et al., "Endothelial cell-expressed Tim-3 facilitates metastasis of melanoma cells by activating the NF-kB pathway" Oncology Reports (2010) vol. 24 pp. 693-699.
Wu et al., "Immunotherapies: The Blockade of Inhibitory Signals," Int J Biol Sci (2012) vol. 8, No. 10, pp. 1420-1430.
Wu, K-P., et al., "Structural Basis of a Flavivirus Recognized by Its Neutralizing Antibody: Solution Structure of the Domain III of the Japanese Encephalitis Virus Envelope Protein," The Journal of Biological Chemistry 278(46):46007-46013, AmericanSociety for Biochemistry and Molecular Biology, Inc., United States (Nov. 2003).
Yamazaki, T., et al., "Expression of programmed death 1 ligands by murine T cells and APC," The Journal of Immunology 169(10):5538-5545, The American Association of Immunologists, United States (2002).
Yan et al., "Tim-3 Expression Defines Regulatory T Cells in Human Tumors" PLoS One (2013) vol. 8 No. 3 e58006.
Yang et al., "Lack of Tim-3 Immunoregulation in Multiple Sclerosis" The Journal of Immunology (2008) vol. 180 No. 7 pp. 4409-4414.
Yi, J., et al., "Mapping the Epitope of an Inhibitory Monoclonal Antibody to the C-terminal DNA-binding Domain of HIV-1 Integrase," The Journal of Biological Chemistry 277(14):12164-12174, American Society for Biochemistry and Molecular Biology, Inc., United States (2002).
Youngnak, Pornpan, et al.; "Differential binding properties of B7-H1 and B7-DC to programmed death-1"; Biochem. Biophys. Res. Commun.; 307:672-677 (2003).
Zehavi-Willner, Tova, et al.; "The mitogenic activity of staphylococcal enterotoxin B (Seb): a monovalent T cell mitogen that stimulates cytolytic T lymphocytes but cannot mediate their lytic interaction"; J. Immunol.; 137(8):2682-2687 (1986).
Zhang et al., "Tim-3 regulates pro-and anti-inflammatory cytokine expression in human CD14+ monocytes" Journal of Leukocyte Biology (2012) vol. 91 pp. 189-196.
Zhang, "P2.01—Poster Session/Treatment of Advanced Diseases—NSCLC (ID207) A Phase 3 Study of Pembrolizumab vs Platinum-Based Chemotherapy for PD-L1 ," (NSCLC ID 2182) Abstract from Poster Presentation from International Association for the Study of Lung Cancer, Aug. 9, 2015, retrieved from library.iaslc.org/search-speaker?search_speaker=30076.
Zhang, Xuewu, et al.; "Structural and Functional Ana ysis of the Costimulatory Receptor Programmed Death-1"; Immunity; 20:337-347 (2004).
Zhu et al., "CSF1/CSF1R Blockade Reprograms Tumor-Infiltrating Macrophages and Improves Response to T-cell Checkpoint Immunotherapy in Pancreatic Cancer Models," Cancer Research (2014) vol. 74, No. 18, pp. 5057-5069.
Zou, W. and Chen, L., "Inhibitory B7-family Molecules in the Tumour Microenvironment," Nature Reviews Immunology 8(6):467-477, Nature Publishing Group, England (2008).
Zuberek, K., "The role of in vivo PD-1/PD-L1 interactions in syngeneic and allogeneic antitumor responses in murine tumor models," Blood 98(11):42B (2001).
Zuberek, Krystyna, et al.; "In vitro and in vivo expression regulation of PD-1 and PD-L1 in murine tumor models"; Blood; 98(11 Part 1):25a (2001).
Hamid et al., "Safety and Tumor Responses with Lambrolizumab (Anti-PD-1) in Melanoma" New England Journal of Medicine (2013) vol. 369 No. 2 pp. 134-144.
Hansen, J.A., et al., "Monoclonal Antibodies Identifying a Novel T-Cell Antigen and Ia Antigens of Human Lymphocytes," Immunogenetics 10:247-260, Springer-Verlag (1980).
Harlow, E. and Lane, D., "Using Antibodies: A Laboratory Manual," Cold Spring Harbor Laboratory Press, Cold Spring Harbor, United States various pages (1999).

(56) References Cited

OTHER PUBLICATIONS

Hastings et al., "Tim-3 is Expressed on Activated Human CD4+ T Cells and Regulates Th1 and Th17 Cytokines" Eur J Immunol (2009) vol. 39 No. 9 pp. 2492-2501.
He, Y-F., et al., "Blocking programmed death-1 ligand-PD-1 interactions by local gene therapy results in enhancement of antitumor effect of secondary lymphoid tissue chemokine," The Journal of Immunology 173(8):4919-4928, The American Association of Immunologists, United States (2004).
Henry et al., "Structure and evolution of the extended B7 family," Immunol Today (1999) vol. 20, No. 6, pp. 285-288.
Herbst et al., "A study of MPDL3280A, an engineered PD-L1 antibody in patients with locally advanced or metastatic tumors," J Clin Oncol (2013) vol. 31, No. 15 (Supp), Abstract 3000.
Highfill et al., "Disruption of CXCR2-Mediated MDSC Tumor Trafficking Enhances Anti-PD1 Efficacy," Science Translational Medicine (2014) vol. 6, Issue 237, Article 237ra67, 15 pages.
Hirano, F., et al., "Blockade of B7-H1 and PD-1 by monoclonal antibodies potentiates cancer therapeutic immunity," Cancer Research 65(3):1089-1096, American Association for Cancer Research, United States (2005).
Hofstra et al., "Prevention of Th2-like cell responses by coadministration of IL-12 and IL-18 is associated with inhibition of antigen-induced airway hyperresponsiveness, eosinophilia, and serum IgE levels." Journal of Immunology (1998) vol. 161 No. 9 pp. 5054-5060.
Hogenesch et al. "Challenges in pre-clinical testing of anti-cancer drugs in cell culture and in animal models" Journal of Controlled Release (2012) vol. 164, No. 2, pp. 183-186.
Huang et al., "Lymphoma endothelium preferentially expresses Tim-3 and facilitates the progression of lymphoma by mediating immune evasion" The Journal of Experimental Medicine (2010) vol. 207 No. 3 pp. 505-520.
Huang, Z., "Structural chemistry and therapeutic intervention of protein-protein interactions in immune response, human immunodeficiency virus entry, and apoptosis," Pharmacology & Therapeutics 86(3):201-215, Pergamon Press, England (2000).
Hutloff, A., et al., "ICOS is an inducible T-cell co-stimulator structurally and functionally related to CD28," Nature 397(6716):263-266, Nature Publishing Group, England (1999).
International Search Report and Written Opinion for International Application No. PCT/US2015/055390, dated Dec. 17, 2015.
International Search Report and Written Opinion for International Application No. PCT/US2016/044547 dated Oct. 18, 2016.
International Search Report and Written Opinion for International Application No. PCT/US2016/044549 dated Oct. 14, 2016.
International Search Report and Written Opinion for PCT/US2015/012754 dated May 20, 2015.
International Search Report and Written Opinion for PCT/US2015/013913 mailed May 4, 2015.
International Search Report and Written Opinion issued in International Application No. PCT/US2016/067200, mailed Apr. 10, 2017.
International Search Report and Written Opinion issued in International Application No. PCT/US2018/039825, mailed Oct. 4, 2018.
International Search Report and Written Opinion issued in PCT/US2007/085100, mailed Apr. 28, 2008, 11 pages.
International Search Report and Written Opinion issued in PCT/US2018/061534, mailed Apr. 1, 2019, 9 pages.
Ishida et al., "Induced expression of PD-1, a novel member of the immunoglobulin gene superfamily, upon programmed cell death," The EMBO Journal (1992) vol. 11, No. 11, pp. 3887-3895.
Ishima, R. and Torchia, D.A., "Protein Dynamics from NMR," Nature Structural Biology 7(9):740-743, Nature Publishing Company, United States (2000).
Iwai et al, "Involvement of PD-L1 on tumor cells in the escape from host immune system and tumor immunotherapy by PD-L1 blockade" PNAS (2002) vol. 99, pp. 12293-12297.
Iwai et al, "PD-1 blockade inhibits hematogenous spread of poorly immunogenic tumor cells by enhanced recruitment of effector T cells", International Immunology (2005) vol. 17, No. 2, pp. 133-144.
Iwai, Y., et al., "Microanatomical localization of PD-1 in human tonsils," Immunology Letters 83(3):215-220, Elsevier, Netherlands (2002).
Iwai, Y., et al., "PD-1 inhibits antiviral immunity at the effector phase in the liver," The Journal of Experimental Medicine 198(1):39-50, The Rockefeller University Press, United States (2003).
Jan et al., "Prospective separation of normal and leukemic stem cells based on differential expression of Tim3, a human acute myeloid leukemia stem cell marker" PNAS (2011) vol. 108 No. 12 pp. 5009-5014.
Jason-Moller, L., et al., "Overview of Biacore Systems and Their Applications," Current Protocols in Protein Science S45:19.13.1-19.13.14, John Wiley & Sons, Inc., United States (2006).
Jin et al. " Cooperation of Tim-3 and PD-1 in CD8 T-cell exhaustion during chronic viral infection" PNAS (2010) vol. 107, Issue 33, pp. 14733-14738.
Johne, B., "Protocol: Epitope Mapping by Surface Plasmon Resonance in the BIAcore," Molecular Biotechnology 9(1):65-71, Humana Press, United States (1998).
Jones et al., "Tim-3 expression defines a novel population of dysfunctional T cells with highly elevated frequencies in progressive HIV-1 infection," J Exp Med (2008) vol. 205, No. 12, pp. 2763-2779.
Ju et al., "T cell immunoglobulin-and mucin-domain-containing molecule-3 (Tim-3) mediates natural killer cell suppression in chronic hepatitis B" Journal of Hepatology (2010) vol. 52 No. 3 pp. 322-329.
Kanai, T., et al., "Blockade of B7-H1 Suppresses the Development of Chronic Intestinal Inflammation," The Journal of Immunology 171(8):4156-4163, American Association of Immunologists, Inc., United States (2003).
Karu et al., "Recombinant Antibody Technology," ILAR Journal, vol. 37, No. 3, pp. 132-141 (1995).
Kasagi, S., et al., "Anti-programmed cell death 1 antibody reduces CD4+PD-1+ T cells and relieves the lupus-like hephritis of NZB/W FI mice," The Journal Immunology 184(5):2337-2347, The American Association of Immunologists, United States (2010).
Kaveri, S., "Epitope and idiotope mapping using monoclonal antibodies," Medthods in Molecular Biology 51:171-181, Humana Press, United States (1995).
Kearl et al., "PD-1/PD-L1 Blockade after Transient Lymphodepletion to Treat Myeloma," Presentation from Society for Immunotherapy of Cancer Conference, Oct. 27, 2012, North Bethesda, Maryland, 19 pages.
Kearley et al., "Th-2 driven, allergen-induced airway inflammation is reduced after treatment with anti-Tim-3 antibody in vivo" The Journal of Experimental Medicine (2007) vol. 204 No. 6 pp. 1289-1294.
Keytruda (pembrolizumab) Drug Label, Initial U.S. Approval: 2014, Revised Aug. 2016.
Kier et al., "PD-1 and its ligands in tolerance and immunity" Annu. Rev. Immunol. (2008) vol. 26 pp. 677-704.
Kikushige et al. "Tim-3 as a therapeutic target for malignant stem cells in acute myelogenous leukemia" New York Academy of Sciences (2012) vol. 1266, pp. 118-123.
Kikushige et al., "Tim-3 Is a Promising Target to Selectively Kill Acute Myeloid Leukemia Stem Cells" Cell Stem Cell (2010) vol. 7 pp. 708-717.
Kirkwood et al, "Immunotherapy of cancer in 2012" CA: A Cancer Journal for Clinicians (2012) vol. 62 No. 5 pp. 309-335.
Klibi et al. "Blood diffusion and Th1-suppressive effects of galectin-9-containing exosomes released by Epstein-Barr virus-infected nasopharyngeal carcinoma cells" Blood (2009) vol. 113 No. 9 pp. 1957-1966.
Koga et al., "Blockade of the Interaction Between PD-1 and PD-L1 Accelerates Graft Arterial Disease in Cardiac Allografts," Arterioscler Thromb Vasc Biol (2004) vol. 24, pp. 2057-2062.
Konishi, J., et al., "B7-H1 expression on non-small cell lung cancer cells and its relationship with tumor-infiltrating lymphocytes and

(56) References Cited

OTHER PUBLICATIONS their PD-1 expression," Clinical Cancer Research 10(15):5094-5100, American Association for Cancer Research, United States (2004).
Korman et al, "Checkpoint Blockade in Cancer Immunotherapy" Adv Immunol (2006) vol. 90 pp. 297-339.
Koya et al., "BRAF Inhibitor Vemurafenib Improves the Antitumor Activity of Adoptive Cell Immunotherapy," Cancer Res (2012) vol. 72, No. 16, pp. 3928-3937.
Kuchroo et al. "The Tim Gene Family: Emerging Roles in Immunity and Disease" Nature Reviews Immunology (2003) vol. 3, pp. 454-462.
Kuchroo et al., "B7-1 and B7-2 Costimulatory Molecules Activate Differentially the Th1/Th2 Developmental Pathways: Application to Autoimmune Disease Therapy" Cell (1995) vol. 80 No. 707-18.
Kwong et al., "Molecular Analysis of Tumor-Promoting CD8+ Cells in Two-Stage Cutaneous Chemical Carcinogenesis" J Invest Dermatol (2010) vol. 130 No. 6 pp. 1726-1736.
Lack et al. "Nebulized but not parenteral IFN-gamma decreases IgE production and normalizes airways function in a murine model of allergen sensitization" Journal of Immunology (1994) vol. 152, pp. 2546-2554.
Ladner, R.C., "Mapping the epitopes of Antibodies," Biotechnology and Genetic Engineering Reviews 24(1):1-30, Taylor & Francis, England (2007).
Laricchia, Robbio, L., et al., "Mapping of Monoclonal Antibody- and Receptor-Binding Domains on Human Granulocyte-Macrophage Colony-Stimulation Factor (hGM-CSF) Using a Surface Plasmon Resonance-Based Biosensor," Hybridoma 15(5):343-350, Mary AnnLiebert, Inc. United States (1996).
Latchman et al., "PD-L2 is a second ligand for PD-1 and inhibits T cell activation," Nature Immunol (2001) vol. 2, No. 3, pp. 261-268.
Leach, D.R., et al., "Enhancement of antitumor immunity by CTLA-4 blockade," Science 271(5256):1734-1736, American Association for the Advancement of Science, United States (1996).
Lee et al. "The inhibition of the T-cell immunoglobulin and mucin domain 3 (Tim3) pathway enhances the efficacy of tumor vaccine" Biochemical and Biophysical Reseach Communications (2010) vol. 402, pp. 88-93.
Lehmann et al, "Identification of human triple-negative breast cancer subtypes and preclinical models for selection of targeted therapies", J Clin Invest. (2011) 121(7): 2750-2767.
Lenschow et al., "Expression and functional significance of an additional ligand for CTLA-2," PNAS (1993) vol. 90, pp. 11054-11058.
Lenschow et al., "Long-term survival of xenogeneic pancreatic islet grafts induced by CTLA4Ig," Science (1992) vol. 257, Issue 5071, pp. 789-792.
Lesokhin, A.M., et al., "291 Preliminary Results of a Phase I Study of Nivolumab (BMS-936558) in Patients with Relapsed of Refractory Lymphoid Malignancies," 56th ASH Annual Meeting and Exposition, Abstracts & Program, San Francisco, CA, UnitedStates, Dec. 6-9, 2014.
Lewis, D.E., et al., "Tumor Necrosis Factor-alpha and CD80 Modulate CD28 Expression through a Similar Mechanism of T-cell Receptor-Independent of Transcription," The Journal of Biological Chemistry 279(28):29130-29138, The American Society forBiochemistry and Molecular Biology, Inc., United States (2004).
Li, L., et al., "A pathway regulated by cell cycle inhibitor p27Kip1 and checkpoint inhibitor Smad3 is involved in the induction of T cell tolerance," Nature Immunology 7(11):1157-1165, Nature Publishing, United States (2006).
Li, L., et al., "CD4+CD25+ regulatory T-cell lines from human cord blood have functional and molecular properties and T-cell anergy," Blood 106(9):3068-3073, American Society of Hematology, United States (Nov. 2005).
Li, L., et al., "IL-1beta-Mediated Signals Preferentially Drive Conversion of Regulatory T Cells but Not Coventional T Cells into IL-17-Producing Cells," The Journal of Immunology 185(7):4148-4153, American Association of Immunologists, Inc., UnitedStates (2010).
Li, L., et al., "Rap1-GTP is a Negative Regulator of Th Cell Function and Promotes the Generation of CD4+CD103+ Regulatory T Cells In Vivo," The Journal of Immunology 175(5):3133-3139, American Association of Immunologists, Inc., United States (Sep. 2005).
Li, L., et al., "The cyclin dependent kinase inhibitor (R)-roscovitine prevents alloreactive T cell clonal expansion and protects against acute GvHD," Cell Cycle 8(11):1794-1802, Landes Bioscience, United States (2009).
Liblau et al. "Th1 and Th2 CD4+ T cells in the pathogenesis of organ-specific autoimune diseases" Immunology Today (1995) vol. 16, Issue 1, pp. 34-38.
Lin, David Yin-Wei, et al.; "The PD-1/PD-L1 complex resembles the antigen-binding Fv domains of antibodies and T cell receptors"; Proc. Natl. Acad. Sci. USA 105(8):3011-3016 (2008).
Linsley et al., "CTLA-4 Is a Second Receptor for the B Cell Activation Antigen B7," J Exp Med (1991) vol. 174, pp. 561-569.
Linsley et al., "Immunosuppression in Vivo by a Soluble Form of the CTLA-4 T Cell Activation Molecule," Science (1992) vol. 257, pp. 792-795.
Linsley et al., "Intracellular Trafficking of CTLA-4 and Focal Localization Towards Sites of TCR Engagement" Immunity (1996) vol. 4 pp. 535-543.
Liu et al., "A Novel Kinase Inhibitor, INC28060, Blocks c-MET-Dependent Signaling, Neoplastic Activities, and Cross-Talk with EGFR and HER-3," Clin Cancer Res (2011) vol. 17, No. 22, pp. 7127-7138.
Liu et al., "The BRAF and MEK Inhibitors Dabrafenib and Trametinib: Effects on Immune Function and in Combination with Immunomodulatory Antibodies Targeting PD-1, PD-L1, and CTLA-4," Clin Cancer Res (2015) vol. 21, No. 7, pp. 1639-1651.
Lonberg, N., et al., "Antigen-specific human antibodies from mice comprising four distinct genetic modifications," Nature 368(6474):856-859, Nature Publishing Group, United States (1994).
Loser et al., "IL-10 Controls Ultraviolet-Induced Carcinogenesis in Mice" The Journal of Immunology (2007) vol. 179 pp. 365-371.
Lu et al., "Everolimus enhances the cytotoxicity of bendamustine in multiple myeloma cells through a network of pro-apoptotic and cell-cycle-progression regulatory proteins," Acta Biochim Biophys Sin (2013) vol. 45, pp. 683-691.
Lute, K.D., et al., "Human CTLA4 knock-in mice unravel the quantitative link between tumor immunity and autoimmunity induced by anti-CTLA-4 antibodies," Blood 106(9):3127-3133, American Society of Hematology, United States (2005).
Mach et al., "Phase (PH) II Study of MBG453 + Spartalizumab in Patients (PTS) with Non-Small Cell Lung Cancer (NSCLC) and Melanoma Pretreated with Anti-PD-1/L1 Therapy," Poster Display Session 3 from ESMO Congress, Sep. 30, 2019, 3 pages.
Mahoney et al. "The Next Immune-Checkpoint Inhibitors: PD-1/PDD-L1 Blockade in Melanoma" Clinical Therapeutics (2015) vol. 37, No. 4, pp. 764-782.
Maier et al., "PD-1: PD-L1 Interactions Contribute to the Functional Suppression of Virus-Specific CD8+ T Lymphocytes in the Liver," J Immunol (2007) vol. 178, pp. 2714-2720.
Makishi et al. "Retracted: A modified version of galectin-9 induces cell cycle arrest and apoptosis of Burkitt and Hodgkin lymphoma cells" British Journal of Hematology (2008) vol. 142 pp. 583-594.
Manning et al., "A model of multiple myeloma: culture of 5T33 murine myeloma cells and evaluation of tumorigenicity in the C57BL/KaLwRij mouse.", Br J Cancer., 66(6): 1088-1093 (1992).
Marri et al., "Human Biochemistry" Mir Publishing, Moscow (1993) vol. 1, p. 34. Russian.
May, K.F., Jr., et al., "Anti-human CTLA-4 monoclonal antibody promotes T-cell expansion and immunity it a hu-PBL-SCID model: a new method for preclinical screening of costimulatory monoclonal antibodies," Blood 105(3):1114-1120, American Society ofHematology, United States (2005).
Miko et al., "Involvement of Galectin-9/Tim-3 Pathway in the Systemic Inflammatory Response in Early-Onset Preeclampsia," PLoS One (2013) vol. 8, No. 8, Article e71811, 9 pages.

(56) References Cited

OTHER PUBLICATIONS

Mocellin et al., "CTLA-4 blockade and the renaissance of cancer immunotherapy," Biochim Biophys Acta (2013) vol. 1836, pp. 187-196.
Monney et al. "Th1-specific cell surface protein Tim-3 regulates macrophage activation and severity of an autoimmune disease" Nature (2002) vol. 415, pp. 536-541.
Mosmann et al. "The expanding universe of T-cell subsets: Th1, Th2 and more" Immunology Today (1996) vol. 17, Issue 3, pp. 138-146.
Mossman et al. "Two Types of Murine Helper T Cell Clone" Journal of Immunology (1986) vol. 136, Issue 7, pp. 2348-2357).
Mou et al., "Association Between Tim-1 Gene Polymorphisms and Allergic Rhinitis in a Han Chinese Population" J Investig Allergol Clin Immunol (2010) vol. 20 No. 1 pp. 3-8.
Nagahara et al., "Galectin-9 Increases Tim-3+ Dendritic Cells and CD+ T Cells and Enhances Antitumor Immunity via Galectin-9-Tim-3 Interactions" The Journal of Immunology (2008) vol. 181 pp. 7660-7669.
Naing et al. "A first-in-human phase I study of the anti-PD-1 antibody PDR001 in patients with advanced solid tumors" 2016 ASCO Annual Meeting, J Clin Oncol 34, 2016 (suppl; abstr 3060).
Najjar et al., "Myeloid-Derived Suppressor Cell Subset Accumulation in Renal Cell Carcinoma Parenchyma Is Associated with Intratumoral Expression of IL 1beta, IL8, CXCL5, and Mip-1alpha," Clinical Cancer Research (2016) vol. 23, No. 9, pp. 2346-2355.
Nellore, A., et al., "The cyclin dependent kinase inhibitor (R)-roscovitine mediates selective suppression of alloreactive human T cells but preserves pathogen-specific and leukemia-specific effectors," Clinical Immunology 152(1-2):48-57 (May-Jun. 2014; Epub Mar. 12, 2014).
Neubert et al., "T cell-induced CSF1 promotes melanoma resistance to PD1 blockade," Science Translational Medicine (2018) vol. 10, No. 436, Article eaan3311, 14 pages.
Ngiow et al. "Prospects for Tim3-Targeted Antitumor Immunotherapy" Cancer Research (2011) vol. 71, Issue 21, pp. 6567-6571.
[No Author Listed] "Crean un ADN sintético capaz de evolucionar," retrieved from www.nationalgeographic.es/ciencia/crean-un-adn-sintetico-capaz-de-evolucionar, Apr. 25, 2012, last accessed Oct. 18, 2019.
[No Author Listed] Press Release: "Bristol-Myers Squibb Announces Collaboration to Evaluate Opdivo (nivolumab) in Combination with Targeted Therapies from Novartis to Treat Non-Small Cell Lung Cancer (NSCLC)," dated Oct. 6, 2014.
Abbas et al. "Functional diversity of helper T lymphocytes" Nature (1996) vol. 383, pp. 787-793.
Abbas, A.K., et al., Cellular and Molecular Immunobiology, 2nd ed., pp. 8, 47-50, W.B. Saunders Company, United States (1991).
Adams, G.P. and Weiner, L.M., "Monoclonal antibody therapy of cancer," Nature Biotechnology 23(9):1147-1157, Nature Publishing Group, United States (2005).
Agata, Y., et al., "Expression of the PD-1 antigen on the surface of stimulated mouse T and B lymphocytes," International Immunology 8(5):765-772, Oxford University Press, England (1996).
Allard et al. "Targeting CD73 Enhances the Antitumor Activity of Anti-FD-1 and Anti-CTLA-4 mAbs" Clinical Cancer Research (2013) vol. 19, No. 20, pp. 5626-5635.
Allison, J.P. and Krummel, M.F., "The Yin and Yang of T Cell Costimulation," Science 270(5238):932-933, American Association for the Advancement of Science, United States (1995).
Almagro et al. "Humanization of Antibodies" Frontiers in Bioscience (2008) vol. 13, pp. 1619-1633.
Anderson "Tim-3 as a therapeutic target in human inflammatory diseases" Expert Opinion on Therapeutic Targets (2007) vol. 11, issue 8, pp. 1005-1009.
Anderson et al. "Promotion of Tissue Inflammation by the Immune Receptor Tim-3 Expressed on Innate Immune Cells" Science (2007) vol. 318, pp. 1141-1143.
Anderson, "Tim-3: An Emerging Target in the Cancer Immunotherapy Landscape" Cancer Immunology Research (2014) vol. 2 No. 5 pp. 393-398.
Andre, E., et al., "Precise Characterization of the Epitope Recognized by a Monoclonal Antibody Against *Escherichia coli* RNA Polymerase," Hybridoma 24(1):1-5, Mary Ann Liebert, Inc., United States (Feb. 2005).
Ansari, M.J., et al., "The programmed death-1 (PD-1) pathway regulates autoimmune diabetes in nonobese diabetic (NOD) mice," The Journal of Experimental Medicine 198(1):63-69, The Rockefeller University Press, United States (2003).
Ansell, S.M., et al., "PD-1 Blockade with Nivolumab in Relapsed or Refractory Hodgkin's Lymphoma," The New England Journal of Medicine 372(4):311-319, Massachusetts Medical Society, United States (Jan. 22, 2015).
Armand, P., et al., "289 Nivolumab in Patients with relapsed or Refractory Hodgkin Lymphoma—Preliminary Safety, Efficacy and Biomarker Results of a Phase I Study," 56th ASH Annual Meeting and Exposition, Abstracts & Program, San Francisco, CA, Dec. 6-9, 2014.
Ascierto et al. "Future perspectives in melanoma research" meeting report from the "Melanoma Bridge", Napoli, Dec. 5-8, 2013 Journal of Translational Medicine (2014) vol. 12, No. 277, pp. 1-29.
Aspeslagh et al. "Rationale for anti-OX40 cancer immunotherapy" European Journal of Cancer (2016) vol. 52, pp. 50-66.
Barber, Daniel L., et al.; "Restoring function in exhausted CD8 T cells during chronic viral infection"; Nature 439:682-687 (2006).
Bennett, F., et al., "Program death-1 engagement upon TCR activation has distinct effects on costimulation and cytokine-driven proliferation: attenuation of ICOS, IL-4, and IL-21, but not CD28, IL-7, and IL-15 responses," The Journal of Immunology170(2):711-718, The American Association of Immunologists, United States (2003).
Berg, J.M., et al., "The Immune System," in Biochemistry 5th ed., pp. 921-950, W.H. Freeman and Company, United States (2002).
Berger, R., et al., "Phase I safety and pharmacokinetic study of CT-011, a humanized antibody interacting with PD-1, in patients with advanced hematologic malignancies," Clinical Cancer Research 14(10):3044-3051, American Association for CancerResearch, United States (2008).
Bigras, et al. "Spatial distribution of DNA ploidy in colorectal carcinoma" Analytic Cellular Pathology (1994) vol. 7, pp. 289-300.
Blank, C., et al., "Interaction of PD-L1 on tumor cells with PD-1 on tumor-specific T cells as a mechanism of immune evasion: implications for tumor immunotherapy," Cancer Immunology Immunotherapy 54(4):307-314, Springer-Verlag, Germany (2005).
Blank, C., et al., "PD-L1/B7H-1 inhibits the effector phase of tumor rejection by T cell receptor (TCR) transgenic CD8+ T cells," Cancer Research 64(3):1140-1145, American Association for Cancer Research, United States (2004).
Blank, Christian, et al.; "Contribution of the PD-L1/PD-1 pathway to T-cell exhaustion: an update on implications for chronic infections and tumor evasion"; Cancer Immunol. Immunotherapy; 56(5):739-745 (2007).
Blazar, B.R., et al., "Infusion of anti-B7.1 (CD80) and anti-B7.2 (CD86) monoclenal antibodies inhibits murine graft-versus-host disease lethality in part via direct effects on CD4+ and CD8+ T cells," The Journal of Immunology 157(8):3250-3259, TheAmerican Association of Immunologists, United States (1996).
Borate et al., "Phase Ib Study of the Anti-Tim-3 Antibody MBG453 in Combination with Decitabine in Patients with High-Risk Myelodysplastic Syndrome (MDS) and Acute Myeloid Leukemia (AML)," Blood (2019) vol. 134, Supp. 1, Abstract 637, 5 pages.
Brahmer et al., "Safety and Activity of Anti-PD-L1 Antibody in Patients with Advanced Cancer," N Engl J Med (2012) vol. 366, pp. 2455-2465.
Brahmer, J.R., et al., "Safety and activity of MDX-1106 (ONO-4538) anti-PD-1 monoclonal antibody in patients with selected refractory or relapsed malignancies," Journal of Clinical Oncology 26:Abstract No. 3006, American Society of ClinicalOncology, United States (2008).
Brahmer., J.R., et al., "Phase I study of single-agent anti-programmed death-1 (MDX-1106) in refractory solid tumors: Safety,

(56) References Cited

OTHER PUBLICATIONS clinical activity, pharmacodynamics, and immunologic correlates," Journal of Clinical Oncology 28(19):3167-3175, AmericanSociety of Clinical Oncology, United States (2005).
Brand et al., "Prospect for Anti-HER2 Receptor Therapy in Breast Cancer," Anticancer Research (2006) vol. 26, pp. 463-470.
Brown et al, "Blockade of Programmed Death-1 Ligands on Dendritic Cells Enhances T Cell Activation and Cytokine Production", J. Immunol. (2003) vol. 170, pp. 1257-1266.
Brown et al., "Tolerance to Single, but Not Multiple, Amino Acid Replacements in Antibody VH CDR2: A Means of Minimizing B Cell Wastage from Somatic Hypermutation?" J Immunol (1996) vol. 156, pp. 3285-3291.
Brown, J.A., et al., "Expression and functional consequences PD-1 ligands on natural APCS and tumors," The FASEB Journal 15(4):A345 (abstract No. 275.23), Federation of American Societies for Experimental Biology, United States (2001).
Brunet et al., "A new member of the immunoglobin superfamily CTLA-4," Nature (1987) vol. 328, pp. 267-270.
Butte et al, "Interaction of human PD-L1 and B7-1", Mol Immunol (2008) vol. 45, pp. 3567-3572.
Butte et al., "Programmed Death-1 Ligand 1 Interacts Specifically with the B7-1 Costimulatory Molecule to Inhibit T Cell Responses," Immunity (2007) vol. 27, pp. 111-122.
Campbell, A.M., "Characterisation of monoclonal antibodies," in Laboratory Techniques in Biochemistry and Molecular Biology, Monoclonal Antibody Technology: The Production and Characterization of Rodent and Human Hybridomas, vol. 13, pp. 186-215, Elsevier, the Netherlands (1984).
Cao et al. "Genetic variations and haplotypes in Tim-3 gene and the risk pf gastric cancer" Cancer Immunol Immunother (2010) vol. 59 pp. 1851-1857.
Carreno, B,M, and Collins, M., "The B7 family of ligands and its receptors: new pathways for costimulation and inhibition of immune responses," Annual Review of Immunology 20:29-53, Annual Reviews, United States (2002).
Carreno, B.M., "BTLA: a new inhibitory receptor with a B7-like ligand," Trends in Immunology 24(10):524-527, Elsevier, England (2003).
Carter, L.L. and Carreno, B.M., et al., "Cytotoxic T-lymphocyte antigen-4 and programmed death-1 function as negative regulators of lymphocyte activation," Immunologic Research 28(1):49-59, Humana Press, United States (2003).
Carter, L.L., et al., "PD-1:PD-L inhibitory pathway affects both CD4(+) and CD8(+) T cells and is overcome by IL-2," European Journal of Immunology 32(3):634-643, Wiley-VCH Verlag GmbH, Germany (2002).
Carvalho et al., "Doxorubicin: the good, the bad and the ugly effect," Current Medicinal Chemistry (2009) vol. 16, No. 25, pp. 3267-3285.
Catherine Sabatos-Peyton, MBG453: A high affinity, ligand-blocking anti-Tim-3 monoclonal Ab. American Association for Cancer Research (AACR) Annual Meeting, Apr. 17, 2016, New Orleans, Louisiana.
Ceeraz et al., "B7 family checkpoint regulators in immune regulation and disease," Trends Immunol (2013) vol. 34, No. 11, pp. 556-563.
Chan et al. "Therapeutic antibodies for autoimmunity and inflammation" Nature Reviews Immunology (2010) vol. 10, pp. 301-316.
Chen, L., "Co-inhibitory molecules of the B7-CD28 family in the control of T-cell immunity," Nature Reviews Immunology 4(5):336-347, Nature Publishing Group, England (2004).
Chen, Y., et al., "Selection and Analysis of an Optimized Anti-VEGF Antibody: Crystal Structure of an Affinity-matured Fab in Complex with Antigen," Journal of Molecular Biology 293(4):865-881, Academic Press, England (1999).
Sanmamed et al. "Agonists of Co-stimulation in Cancer Immunotherapy Directed Against CD137, OX40, GITR, CD27, CD28, and ICOS" Seminars in Oncology (2015) vol. 42, No. 4, pp. 640-655.

Santiago et al., "Structures of T Cell Immunoglobulin Mucin Receptors 1 and 2 Reveal Mechanisms for Regulation of Immune Responses by the Tim Receptor Family" Immunity (2007) vol. 26 pp. 299-310.
Schroll, A. et al., "Tim3 Is Upregulated and Protective in Nephrotoxic Serum Nephritis", The American Journal of Pathology, vol. 176, No. 4, pp. 1716-1742, Apr. 2010.
Search Report and Written Opinion issued in Singapore Application No. 11201605627T dated Aug. 15, 2017.
Search Report and Written Opinion issued in Singapore Application No. 11201702401R, completed Mar. 29, 2018.
Shakhov et al., "Smuckler/Tim4 is a distinct member of Tim family expressed by stromal cells of secondary ymphoid tissues and associated with lymphotoxin signaling" Eur. J. Immunol (2004) vol. 34 pp. 494-503.
Sher et al. "Regulation of Immunity to Parasited by T cells and T Cell-derived Cytokines" Annual Review Immunol (1992) vol. 10, pp. 385-409.
Shinohara, T., et al., "Structure and chromosomal localization of the human PD-1 gene (PDCD1)," Genomics 23(3):704-706, Academic Press, United States (1994).
Simeone et al., "Immunomodulating antibodies in the treatment of metastatic melanoma: The experience with anti-CTLA-4, anti-CD137, and anti-PD1," Journal of Immunotoxicology (2012) vol. 9, No. 3, pp. 241-247.
Simmons et al., "Tim-3+ T-bet+ Tumor-Specific Th1 Cells Colocalize with and Inhibit Development and Growth of Murine Neoplasms" The Journal of Immunology (2005) vol. 174 pp. 1405-1415.
Soares et al. "Recombinant Himan Tumor Antigen MUC1 Expressed in Insect Cells: Structure and Immunogenicity" Protein Expression and Purification (2001) vol. 22, pp. 92-100.
Soh, E.Y., et al., "Neutralizing vascular endothelial growth factor activity inhibits thyroid cancer growth in vivo," Surgery 128(6):1059-1066, Mosby, United States (2000).
Steele et al., "CXCR2 Inhibition Profoundly Suppresses Metastases and Augments Immunotherapy in Pancreatic Ductal Adenocarcinoma," Cancel Cell (2016) vol. 29, pp. 832-845.
Strome et al., "A Mechanistic Perspective of Monoclonal Antibodies in Cancer Therapy Beyond Target-Related Effects," The Oncologist (2007) vol. 12, pp. 1084-1095.
Stromnes et al., "Pancreatic Cancer: Planning Ahead for Metastatic Spread," Cancel Cell (2016) vol. 29, No. 6, pp. 774-776.
Swallow et al., "B7h, a Novel Costimulatory Homolog of B7.1 and B7.2, Is Induced by TNFa," Immunity (1999) vol. 11, pp. 423-432.
Sánchez-Fueyo et al., "Tim-3 inhibits T helper type 1-mediated auto- and alloimmune responses and promotes immunological tolerance," Nat Immunol (2003) vol. 4, No. 11, pp. 1093-1101.
Takamura et al., "Premature Terminal Exhaustion of Friend Virus-Specific Effector CD8+ T Cells by Rapid Induction of Multiple Inhibitory Receptors" J Immunol (2010) vol. 184 pp. 4696-4707.
Tamura, H., et al., "B7-H1 costimulation preferentially enhances CD28-independent T-helper cell function," Blood 97(6):1809-1816, The American Society of Hematology, United States (2001).
Tang et al. "Immunotherapy and tumor microenvironment" Cancer Letters (2016) vol. 370, pp. 85-90.
Teeling, J.L., et al., "Characterization of new human CD20 monoclonal antibodies with potent cytolytic activity against non-Hodgkin Lymphomas," Blood 104(6):1793-1800, American Society of Hematology, United States (2004).
Thangamathesvaran et al., "Immune checkpoint inhibitors and radiotherapy—concept and review of current literature," Ann Transl Med (2018) vol. 6, No. 8, Article 155, 11 pages.
Thomas et al "Combined Effects of RU486 and Tamoxifen on the Growth and Cell Cycle Phases of the MCF-7 Cell Line" Journal of Clinical Endocrinology and Metabolism (1992) vol. 75, Issue 3, pp. 865-870.
Thomas et al. "Effects of Gossypol on the Cell Cycle Phases in T-47D Human Breast Cancer Cells" Anticancer Research (1991) vol. 11, No. 4, pp. 1469-1476.
Thomas, M.L., "Of ITAMs and ITIMs: turning on and off the B cell antigen receptor," The Journal of Experimental Medicine 181(6):1953-1956, The Rockefeller University Press, United States (1995).

(56) References Cited

OTHER PUBLICATIONS

Thompson et al, "Tumor B7-H1 Is Associated with Poor Prognosis in Renal Cell Carcinoma Patients with Long-term Follow-up" Cancer Res. (2006) vol. 66, pp. 3381-3385.
Thompson, R. Houston, et al.; "PD-1 is expressed by tumor-infiltrating immune cells and is associated with poor outcome for patients with renal cell carcinoma"; Clin. Cancer Res. 13(6):1757-1761 (2007).
Tomlinson, I.M., et al., "The repertoire of human germline VH sequences reveals about fifty groups of VH segments with different hypervariable loops," Journal of Molecular Biology 227(3):776-798, Elsevier, Netherlands (1992).
Topalian et al., "Safety, Activity, and Immune Correlates of Anti-PD-1 Antibody in Cancer," N Engl J Med (2012) vol. 366, No. 26, pp. 2443-2454.
Topalian, S., "Q & A: Suzanne Topalian on Immune Therapies", Cancer Discovery 3(7):712, American Association for Cancer Research, United States, published online Jun. 27, 2013.
Topalian, S., et al., "Nivolumab (anti-PD-1; BMS-936558; ONO-4538) in patients with advanced solid tumors: Survival and long-term safety in a phase I trial," accessed at http://meetinglibrary.asco.org/content/113543-132, accessed on Jun. 1, 2016, 2pages.
Trautmann, Lydie, et al.; "Upregulation of PD-1 expression on HIV-specific CD8+ T cells leads to reversible immune dysfunction"; Nat. Med.; 12(10):1198-1202 (2006).
Triebel, "LAG-3: a regulator of T-cell and DC responses and its use in therapeutc vaccination," Trends Immunol (2003) vol. 24, No. 12, pp. 619-622.
Tsai, C-J., et al., "Protein Allostery, signal transmission and dynamics: a classification scheme of allosteric mechanisms," Molecular BioSystems 5(3):207-216, Royal Society of Chemistry, England (2009).
Tsushima, Fumihiko, et al.; "Predominant expression of B7-H1 and its immunoregulatory roles in oral squamous cell carcinoma"; Oral Oncology; 42:268-274 (2006).
Tuskan et al., "Real-time PCR analysis of candidate imprinted genes on mouse chromosome 11 shows balanced expression from the maternal and paternal chromosomes and strain-specific variation in expression levels" Epigenetics (2008) vol. 3 No. 1 pp. 43-50.
UniProtKB/Swiss-Prot Database entry, PDCD1.sub.—Human, accessed at http://www.uniprot.org/uniprot/Q15116.txt, accessed on Jun. 1, 2016, 5 pages.
Van De Weyer et al. "A highly conserved tyosine of Tim-3 is phosphorylated upon stimulation by its ligand galectin-9" Biochemical and Biophysical Research Communications (2006) vol. 351, pp. 571-576.
Van Regenmortel, M.H.V., "The recognition of Proteins and Peptides by Antibodies," Journal of Immunoassay 21(2-3):85-108, Taylor & Francis, England (2000).
Vietta et al. "Considering Therapeutic Antibodies" Science (2006) vol. 313, pp. 308-309.
Villalobos, "Primer organismo con ADN artificial logra reproducirse," retrieved from www.fayerwayer.com/2014/05/primer-organismo-con-adn-artificial-logra-reproducirse (2014) last accessed Oct. 18, 2019.
Vivier et al., "Immunoreceptor tyrosine-based inhibition motifs," Immunol Today (1997) vol. 18, No. 6, pp. 286-291.
Waldmann, Thomas A.; "Effective cancer therapy through immunomodulation"; Annual Rev.; 57(1):65-81 (2006).
Walunas et al., "CTLA-4 can function as a negative regulator of T cell activation," Immunity (1994) vol. 1, No. 5, pp. 405-413.
Wang et al., "Fixed Dosing Versus Body Size-Based Dosing of Monoclonal Antibodies in Adult Clinical Trials," J Clin Pharmacology (2009) vol. 49, pp. 1012-1024.
Wang et al., "Vista, a novel mouse Ig superfamily ligand that negatively regulates T cell responses" The Journal of Experimental Medicine (2011) vol. 208 No. 3 pp. 577-592.
Wang, "Interaction of Tim4-Tim1 Modulates the Function of CD4+ CD25+Treg in Food Allergic Mice," Master's Thesis submitted at Zhengzhou University (2010) 65 pages, Chinese with English Abstract.
Watanabe et al., "Current approaches for the treatment of multiple myeloma," Int J Hematol (2013) vol. 97, pp. 333-344.
Weber, J.S., et al., "Safety, Efficacy, and Biomarkers of Nivolumab with Vaccine in Ipilimumab-Refractory or -Naive Melanoma," Journal of Clinical Oncology 31 (34):4311-4318, American Society of Clinical Oncology, United States (2013).
Weisberg et al., "Smac mimetics: implications for enhancement of targeted therapies in leukemia: Treating leukemia with Smac mimetics," Leukemia (2010) vol. 24, No. 12, pp. 2100-2109.
Ji et al., "Challenges and Opportunities in Dose Finding in Oncology and Immuno-oncology," Clin Transl Sci (2018) vol. 11, pp. 345-351.
Stagg et al., "Immunotherapeutic approaches in triple-negative breast cancer: latest research and clinical prospects," Ther Adv Med Oncol (2013) vol. 5, No. 3, pp. 169-181.

\* cited by examiner

Light chain (murine κ)

```
     FWL1                    CDRL1              FWL2              CDRL2              FWL3
DIQMTQTTSS LSASLGDRVT ISCSSSQDIS NYLNWYQQKP DGTVKVLIY Y TSTLHLGVPS RFSGSGSGTD

CDRL3      FWL4
YSLTISNLEL EDIATYYCQQ YYNLPWTFGG GTKLEIK
```

Heavy Chain (murine IgG1)

```
     FWH1                    CDRH1              FWH2                     CDRH2
QIQLVQSGPE LKKPGETVKI SCKASGFTLT NYGMNWVRQT PGKGLKWMGW INTDTGEPTY ADDFKGRFAF

FWH3                              CDRH3              FWH4
SLETSASTAS LQINNLKNAD TATYFCARNP PYYYGTNNAE AMDYWGQGTA VTVSS
```

FIGURE 1

Light chain

```
GL     DIQMTQTTSS LSASLGDRVT ISCSASQGIS NYLNWYQQKP DGTVKLLIYY TSSLHSGVPS
Mu mAb ---------- ---------- ----S--D-- ---------- -----V---- ---T--L---

GL     RFSGSGSGTD YSLTISNLEP EDIATYYCQQ YSKLP
Mu mAb ---------- --------L- ---------- -YN--WTFGG GTKLEIK
```

Heavy chain

```
GL     QIQLVQSGPE LKKPGETVKI SCKASGYTFT NYGMNWVKQA PGKGLKWMGW INTYTGEPTY
Mu mAb ---------- ---------- -------F-L ------R-T- ---------- -----D----

GL     ADDFKGRFAF SLETSASTAY LQINNLKNED TATYFCAR          NP PYYYGTNWAE AMDYWGQGTA
Mu mAb ---------- ---S------ ---------- --------- ---------- ---------- ----------

GL     VTVSS
Mu mAb
```

FIGURE 2

| Clone No. | μg/mL | Sequence | | | | | |
|---|---|---|---|---|---|---|---|
| | | HC | | | LC | | |
| | | FW1 | FW2 | FW3 | FW1 | FW2 | FW3 |
| chimera | 31.7 | 6 unique HC | | | 12 unique LC | | |
| 1 | 35.4 | a | a | a | a | a | a |
| 2 | 25.2 | a | a | a | a | a | b |
| 3 | 3.2 | a | a | a | b | b | a |
| 4 | 26 | a | a | a | a | c | c |
| 5 | 16.9 | a | a | a | c | a | a |
| 6 | 9.1 | a | a | a | d | b | d |
| 7 | 35.8 | a | a | a | a | d | d |
| 8 | 24.7 | a | a | a | e | b | e |
| 9 | 19.9 | b | b | a | a | a | b |
| 10 | 7.7 | b | b | a | b | b | a |
| 11 | 34.9 | b | b | a | a | d | d |
| 12 | 17.9 | b | b | a | e | b | e |
| 13 | 24.9 | b | a | a | a | a | b |
| 14 | 7.5 | a | c | a | b | b | a |
| 15 | 21.9 | a | c | a | e | b | e |
| 16 | 17.7 | c | d | b | e | b | e |
| 17 | 21.2 | d | a | c | a | a | f |
| 18 | 8.1 | a | a | a | f | b | e |
| 19 | 7.5 | a | a | a | e | b | a |
| 20 | 3.2 | b | b | a | d | b | g |

FIGURE 4

| Clone No. | Conc. µg/mL | Sequence | | | | | | Ranking | | Structure |
|---|---|---|---|---|---|---|---|---|---|---|
| | | HC | | | LC | | | Binding data | Compet. data * | |
| | | FW1 | FW2 | FW3 | FW1 | FW2 | FW3 | | | |
| | | 6 unique HC | | | 12 unique LC | | | | | |
| 1 | 35.4 | a | a | a | a | a | a | 1 | 2 | D |
| 2 | 25.2 | a | a | a | a | a | b | 5 | 1 | B |
| 3 | 3.2 | a | a | a | b | b | a | 7 | 1 | E |
| 4 | 26 | a | a | a | a | c | c | 8 | 2 | E |
| 5 | 16.9 | a | a | a | c | a | a | 6 | | E |
| 6 | 9.1 | a | a | a | d | b | d | 9 | 1 | E |
| 7 | 35.8 | a | a | a | a | d | d | 8 | | C |
| 8 | 24.7 | a | a | a | e | b | e | 4 | | E |
| 9 | 19.9 | b | b | a | a | a | b | 8 | 2 | B |
| 10 | 7.7 | b | b | a | b | b | a | 9 | 2 | E |
| 11 | 34.9 | b | b | a | a | d | d | 2 | 2 | C |
| 12 | 17.9 | b | b | a | e | b | e | 3 | 2 | E |
| 13 | 24.9 | b | a | a | a | a | b | 9 | 3 | A |
| 14 | 7.5 | a | c | a | b | b | a | 9 | | F |
| 15 | 21.9 | a | c | a | e | b | e | 20 | 20 | F |
| 16 | 17.7 | c | d | b | e | b | e | 20 | 20 | D |
| 17 | 21.2 | d | a | c | a | a | f | 9 | | E |
| 18 | 8.1 | a | a | a | f | b | e | 8 | | C |
| 19 | 7.5 | a | a | a | e | b | a | 9 | | D |
| 20 | 3.2 | b | b | a | d | b | g | 9 | 3 | C |

*empty boxes means worse than 3.

FIGURE 6

```
                              10        20        30        40        50        60
                     ....|....|....|....|....|....|....|....|....|....|....|....|
BAP050-chi-HC        QIQLVQSGPELKKPGETVKISCKASGFTLTNYGMNWVRQTPGKGLKWMGWINTDTGEPTY
BAP050-hum01-HC      EVQLVQSGAEVKKPGATVKISCKVSGFTLTNYGMNWVRQAPGQGLEWMGWINTDTGEPTY
BAP050-hum02-HC      EVQLVQSGAEVKKPGATVKISCKVSGFTLTNYGMNWVRQAPGQGLEWMGWINTDTGEPTY
BAP050-hum03-HC      EVQLVQSGAEVKKPGATVKISCKVSGFTLTNYGMNWVRQAPGQGLEWMGWINTDTGEPTY
BAP050-hum04-HC      EVQLVQSGAEVKKPGATVKISCKVSGFTLTNYGMNWVRQAPGQGLEWMGWINTDTGEPTY
BAP050-hum05-HC      EVQLVQSGAEVKKPGATVKISCKVSGFTLTNYGMNWVRQAPGQGLEWMGWINTDTGEPTY
BAP050-hum06-HC      EVQLVQSGAEVKKPGATVKISCKVSGFTLTNYGMNWVRQAPGQGLEWMGWINTDTGEPTY
BAP050-hum07-HC      EVQLVQSGAEVKKPGATVKISCKVSGFTLTNYGMNWVRQAPGQGLEWMGWINTDTGEPTY
BAP050-hum08-HC      EVQLVQSGAEVKKPGATVKISCKVSGFTLTNYGMNWVRQAPGQGLEWMGWINTDTGEPTY
BAP050-hum18-HC      EVQLVQSGAEVKKPGATVKISCKVSGFTLTNYGMNWVRQAPGQGLEWMGWINTDTGEPTY
BAP050-hum19-HC      EVQLVQSGAEVKKPGATVKISCKVSGFTLTNYGMNWVRQAPGQGLEWMGWINTDTGEPTY
BAP050-hum09-HC      QVQLVQSGAEVKKPGASVKVSCKASGFTLTNYGMNWVRQARGQRLEWIGWINTDTGEPTY
BAP050-hum10-HC      QVQLVQSGAEVKKPGASVKVSCKASGFTLTNYGMNWVRQARGQRLEWIGWINTDTGEPTY
BAP050-hum11-HC      QVQLVQSGAEVKKPGASVKVSCKASGFTLTNYGMNWVRQARGQRLEWIGWINTDTGEPTY
BAP050-hum12-HC      QVQLVQSGAEVKKPGASVKVSCKASGFTLTNYGMNWVRQARGQRLEWIGWINTDTGEPTY
BAP050-hum20-HC      QVQLVQSGAEVKKPGASVKVSCKASGFTLTNYGMNWVRQARGQRLEWIGWINTDTGEPTY
BAP050-hum13-HC      QVQLVQSGAEVKKPGASVKVSCKASGFTLTNYGMNWVRQAPGQGLEWMGWINTDTGEPTY
BAP050-hum14-HC      EVQLVQSGAEVKKPGATVKISCKVSGFTLTNYGMNWIRQSPSRGLEWLGWINTDTGEPTY
BAP050-hum15-HC      EVQLVQSGAEVKKPGATVKISCKVSGFTLTNYGMNWIRQSPSRGLEWLGWINTDTGEPTY
BAP050-hum16-HC      EVQLVQSGAEVKKPGESLRISCKGSGFTLTNYGMNWVRQATGQGLEWMGWINTDTGEPTY
BAP050-hum17-HC      QVQLVQSGSELKKPGASVKVSCKASGFTLTNYGMNWVRQAPGQGLEWMGWINTDTGEPTY 70        80        90       100       110       120
                     ....|....|....|....|....|....|....|....|....|....|....|....|
BAP050-chi-HC        ADDFKGRPAFSLETSASTASLQINNLKNADTATYFCARNPPYYYGTNNAEAMDYWGQGTTVTVSS
BAP050-hum01-HC      ADDFKGRFVFSLDTSVSTAYLQICSLKAEDTAVYYCARNPPYYYGTNNAEAMDYWGQGTTVTVSS
BAP050-hum02-HC      ADDFKGRFVFSLDTSVSTAYLQICSLKAEDTAVYYCARNPPYYYGTNNAEAMDYWGQGTTVTVSS
BAP050-hum03-HC      ADDFKGRFVFSLDTSVSTAYLQICSLKAEDTAVYYCARNPPYYYGTNNAEAMDYWGQGTTVTVSS
BAP050-hum04-HC      ADDFKGRFVFSLDTSVSTAYLQICSLKAEDTAVYYCARNPPYYYGTNNAEAMDYWGQGTTVTVSS
BAP050-hum05-HC      ADDFKGRFVFSLDTSVSTAYLQICSLKAEDTAVYYCARNPPYYYGTNNAEAMDYWGQGTTVTVSS
BAP050-hum06-HC      ADDFKGRFVFSLDTSVSTAYLQICSLKAEDTAVYYCARNPPYYYGTNNAEAMDYWGQGTTVTVSS
BAP050-hum07-HC      ADDFKGRFVFSLDTSVSTAYLQICSLKAEDTAVYYCARNPPYYYGTNNAEAMDYWGQGTTVTVSS
BAP050-hum08-HC      ADDFKGRFVFSLDTSVSTAYLQICSLKAEDTAVYYCARNPPYYYGTNNAEAMDYWGQGTTVTVSS
BAP050-hum18-HC      ADDFKGRFVFSLDTSVSTAYLQICSLKAEDTAVYYCARNPPYYYGTNNAEAMDYWGQGTTVTVSS
BAP050-hum19-HC      ADDFKGRFVFSLDTSVSTAYLQICSLKAEDTAVYYCARNPPYYYGTNNAEAMDYWGQGTTVTVSS
BAP050-hum09-HC      ADDFKGRFVFSLDTSVSTAYLQICSLKAEDTAVYYCARNPPYYYGTNNAEAMDYWGQGTTVTVSS
BAP050-hum10-HC      ADDFKGRFVFSLDTSVSTAYLQICSLKAEDTAVYYCARNPPYYYGTNNAEAMDYWGQGTTVTVSS
BAP050-hum11-HC      ADDFKGRFVFSLDTSVSTAYLQICSLKAEDTAVYYCARNPPYYYGTNNAEAMDYWGQGTTVTVSS
BAP050-hum12-HC      ADDFKGRFVFSLDTSVSTAYLQICSLKAEDTAVYYCARNPPYYYGTNNAEAMDYWGQGTTVTVSS
BAP050-hum20-HC      ADDFKGRFVFSLDTSVSTAYLQICSLKAEDTAVYYCARNPPYYYGTNNAEAMDYWGQGTTVTVSS
BAP050-hum13-HC      ADDFKGRFVFSLDTSVSTAYLQICSLKAEDTAVYYCARNPPYYYGTNNAEAMDYWGQGTTVTVSS
BAP050-hum14-HC      ADDFKGRFVFSLDTSVSTAYLQICSLKAEDTAVYYCARNPPYYYGTNNAEAMDYWGQGTTVTVSS
BAP050-hum15-HC      ADDFKGRFVFSLDTSVSTAYLQICSLKAEDTAVYYCARNPPYYYGTNNAEAMDYWGQGTTVTVSS
BAP050-hum16-HC      ADDFKGRVTISADKSISTAYLQWSSLKASDTAMYYCARNPPYYYGTNNAEAMDYWGQGTTVTVSS
BAP050-hum17-HC      ADDFKGRFVFSLDTSVSTAYLQISTLKAEDTATYFCARNPPYYYGTNNAEAMDYWGQGTTVTVSS
```

FIGURE 9A

```
                        10        20        30        40        50        60
                ....|....|....|....|....|....|....|....|....|....|....|....|
BAP050-chi-HC   QIQLVQSGPELKKPGETVKISCKASGFTLTNYGMNWVRQTPGKGLKWMGWINTDTGEPTY
BAP050-hum01-HC EV......A.V....A........V.............A..Q..E...............
BAP050-hum02-HC EV......A.V....A........V.............A..Q..E...............
BAP050-hum03-HC EV......A.V....A........V.............A..Q..E...............
BAP050-hum04-HC EV......A.V....A........V.............A..Q..E...............
BAP050-hum05-HC EV......A.V....A........V.............A..Q..E...............
BAP050-hum06-HC EV......A.V....A........V.............A..Q..E...............
BAP050-hum07-HC EV......A.V....A........V.............A..Q..E...............
BAP050-hum08-HC EV......A.V....A........V.............A..Q..E...............
BAP050-hum18-HC EV......A.V....A........V.............A..Q..E...............
BAP050-hum19-HC EV......A.V....A........V.............A..Q..E...............
BAP050-hum09-HC .V......A.V....AS..V.................AR.QR.E.I..............
BAP050-hum10-HC .V......A.V....AS..V.................AR.QR.E.I..............
BAP050-hum11-HC .V......A.V....AS..V.................AR.QR.E.I..............
BAP050-hum12-HC .V......A.V....AS..V.................AR.QR.E.I..............
BAP050-hum20-HC .V......A.V....AS..V.................AR.QR.E.I..............
BAP050-hum13-HC .V......A.V....AS..V.................A..Q..E...............
BAP050-hum14-HC EV......A.V....A........V.............I..S.SR..E.L...........
BAP050-hum15-HC EV......A.V....A........V.............I..S.SR..E.L...........
BAP050-hum16-HC EV......A.V.....SLR....G..............AT.Q..E...............
BAP050-hum17-HC .V......S......AS..V..................A..Q..E...............

70        80        90       100       110       120
                ....|....|....|....|....|....|....|....|....|....|....|....|
BAP050-chi-HC   ADDFKGRFAFSLETSASTASLQINNLKNADTATYFCARNPPYYYGTNNAEAMDYWGQGTTVTVSS
BAP050-hum01-HC ........V...D..V...Y...CS..AE...V.Y..............................
BAP050-hum02-HC ........V...D..V...Y...CS..AE...V.Y..............................
BAP050-hum03-HC ........V...D..V...Y...CS..AE...V.Y..............................
BAP050-hum04-HC ........V...D..V...Y...CS..AE...V.Y..............................
BAP050-hum05-HC ........V...D..V...Y...CS..AE...V.Y..............................
BAP050-hum06-HC ........V...D..V...Y...CS..AE...V.Y..............................
BAP050-hum07-HC ........V...D..V...Y...CS..AE...V.Y..............................
BAP050-hum08-HC ........V...D..V...Y...CS..AE...V.Y..............................
BAP050-hum18-HC ........V...D..V...Y...CS..AE...V.Y..............................
BAP050-hum19-HC ........V...D..V...Y...CS..AE...V.Y..............................
BAP050-hum09-HC ........V...D..V...Y...CS..AE...V.Y..............................
BAP050-hum10-HC ........V...D..V...Y...CS..AE...V.Y..............................
BAP050-hum11-HC ........V...D..V...Y...CS..AE...V.Y..............................
BAP050-hum12-HC ........V...D..V...Y...CS..AE...V.Y..............................
BAP050-hum20-HC ........V...D..V...Y...CS..AE...V.Y..............................
BAP050-hum13-HC ........V...D..V...Y...CS..AE...V.Y..............................
BAP050-hum14-HC ........V...D..V...Y...CS..AE...V.Y..............................
BAP050-hum15-HC ........V...D..V...Y...CS..AE...V.Y..............................
BAP050-hum16-HC ........VTI.ADK.I...Y..WSS..AS...M.Y..............................
BAP050-hum17-HC ........V...D..V...Y...ST..AE.....................................
```

FIGURE 9B

```
                        10        20        30        40        50        60
                ....|....|....|....|....|....|....|....|....|....|....|....|
BAP050-chi-LC   DIQMTQTTSSLSASLGDRVTISCSSSQDISNYLNWYQQKPDGTVKVLIYYTSTLHLGVPS
BAP050-hum01-LC DIQMTQSPSSLSASVGDRVTITCSSSQDISNYLNWYQQKPGKAPKLLIYYTSTLHLGVPS
BAP050-hum02-LC DIQMTQSPSSLSASVGDRVTITCSSSQDISNYLNWYQQKPGKAPKLLIYYTSTLHLGIPP
BAP050-hum13-LC DIQMTQSPSSLSASVGDRVTITCSSSQDISNYLNWYQQKPGKAPKLLIYYTSTLHLGIPP
BAP050-hum09-LC DIQMTQSPSSLSASVGDRVTITCSSSQDISNYLNWYQQKPGKAPKLLIYYTSTLHLGIPP
BAP050-hum03-LC EIVLTQSPATLPVSLGQTASISCSSSQDISNYLNWYQQKPGQAPRLLIYYTSTLHLGVPS
BAP050-hum10-LC EIVLTQSPATLPVSLGQTASISCSSSQDISNYLNWYQQKPGQAPRLLIYYTSTLHLGVPS
BAP050-hum14-LC EIVLTQSPATLPVSLGQTASISCSSSQDISNYLNWYQQKPGQAPRLLIYYTSTLHLGVPS
BAP050-hum04-LC DIQMTQSPSSLSASVGDRVTITCSSSQDISNYLNWYLQKPGQSPQLLIYYTSTLHLGIPD
BAP050-hum05-LC EIVLTQSPATLSLSPGERATLSCSSSQDISNYLNWYQQKPGKAPKLLIYYTSTLHLGVPS
BAP050-hum06-LC DIVMTQTPLSLPVTPGEPASISCSSSQDISNYLNWYQQKPGQAPRLLIYYTSTLHLGVPS
BAP050-hum07-LC DIQMTQSPSSLSASVGDRVTITCSSSQDISNYLNWYLQKPGQSPQLLIYYTSTLHLGVPS
BAP050-hum11-LC DIQMTQSPSSLSASVGDRVTITCSSSQDISNYLNWYLQKPGQSPQLLIYYTSTLHLGVPS
BAP050-hum08-LC EIVLTQSPDFQSVTPKEKVTITCSSSQDISNYLNWYQQKPGQAPRLLIYYTSTLHLGVPS
BAP050-hum12-LC EIVLTQSPDFQSVTPKEKVTITCSSSQDISNYLNWYQQKPGQAPRLLIYYTSTLHLGVPS
BAP050-hum15-LC EIVLTQSPDFQSVTPKEKVTITCSSSQDISNYLNWYQQKPGQAPRLLIYYTSTLHLGVPS
BAP050-hum16-LC EIVLTQSPDFQSVTPKEKVTITCSSSQDISNYLNWYQQKPGQAPRLLIYYTSTLHLGVPS
BAP050-hum17-LC DIQMTQSPSSLSASVGDRVTITCSSSQDISNYLNWYQQKPGKAPKLLIYYTSTLHLGVPS
BAP050-hum18-LC AIQLTQSPSSLSASVGDRVTITCSSSQDISNYLNWYQQKPGQAPRLLIYYTSTLHLGVPS
BAP050-hum19-LC EIVLTQSPDFQSVTPKEKVTITCSSSQDISNYLNWYQQKPGQAPRLLIYYTSTLHLGVPS
BAP050-hum20-LC DIVMTQTPLSLPVTPGEPASISCSSSQDISNYLNWYQQKPGQAPRLLIYYTSTLHLGIPD 70        80        90        100
                ....|....|....|....|....|....|....|....|....|....|..
BAP050-chi-LC   RFSGSGSGTDYSLTISNLELEDIATYYCQQYYNLPWTFGQGTKVEIK
BAP050-hum01-LC RFSGSGSGTDFTFTISSLEAEDAATYYCQQYYNLPWTFGQGTKVEIK
BAP050-hum02-LC RFSGSGYGTDFTLTINNIESEDAAYYFCQQYYNLPWTFGQGTKVEIK
BAP050-hum13-LC RFSGSGYGTDFTLTINNIESEDAAYYFCQQYYNLPWTFGQGTKVEIK
BAP050-hum09-LC RFSGSGYGTDFTLTINNIESEDAAYYFCQQYYNLPWTFGQGTKVEIK
BAP050-hum03-LC RFSGSGSGTDFTFTISSLEAEDAATYYCQQYYNLPWTFGQGTKVEIK
BAP050-hum10-LC RFSGSGSGTDFTFTISSLEAEDAATYYCQQYYNLPWTFGQGTKVEIK
BAP050-hum14-LC RFSGSGSGTDFTFTISSLEAEDAATYYCQQYYNLPWTFGQGTKVEIK
BAP050-hum04-LC RFSGSGSGTDFTLTISRLEPEDFAVYYCQQYYNLPWTFGQGTKVEIK
BAP050-hum05-LC RFSGSGSGTDFTFTISSLEAEDAATYYCQQYYNLPWTFGQGTKVEIK
BAP050-hum06-LC RFSGSGSGTEFTLTISSLQPDDFATYYCQQYYNLPWTFGQGTKVEIK
BAP050-hum07-LC RFSGSGSGTEFTLTISSLQPDDFATYYCQQYYNLPWTFGQGTKVEIK
BAP050-hum11-LC RFSGSGSGTEFTLTISSLQPDDFATYYCQQYYNLPWTFGQGTKVEIK
BAP050-hum08-LC RFSGSGSGTDFTLTISSLQPEDFATYYCQQYYNLPWTFGQGTKVEIK
BAP050-hum12-LC RFSGSGSGTDFTLTISSLQPEDFATYYCQQYYNLPWTFGQGTKVEIK
BAP050-hum15-LC RFSGSGSGTDFTLTISSLQPEDFATYYCQQYYNLPWTFGQGTKVEIK
BAP050-hum16-LC RFSGSGSGTDFTLTISSLQPEDFATYYCQQYYNLPWTFGQGTKVEIK
BAP050-hum17-LC RFSGSGSGTDFTFTISSLQPEDIATYYCQQYYNLPWTFGQGTKVEIK
BAP050-hum18-LC RFSGSGSGTDFTLTISSLQPEDFATYYCQQYYNLPWTFGQGTKVEIK
BAP050-hum19-LC RFSGSGSGTDFTFTISSLEAEDAATYYCQQYYNLPWTFGQGTKVEIK
BAP050-hum20-LC RFSGSGSGTDFTLTISRLEPEDFAVYYCQQYYNLPWTFGQGTKVEIK
```

FIGURE 10A

```
                         10        20        30        40        50        60
                ....|....|....|....|....|....|....|....|....|....|....|....|
BAP050-chi-LC   DIQMTQTTSSLSASLGDRVTISCSSSQDISNYLNWYQQKPDGTVKVLIYYTSTLHLGVPS
BAP050-hum01-LC ......SP......V......T....................GKAP.L..............
BAP050-hum02-LC ......SP......V......T....................GKAP.L...........I.P
BAP050-hum13-LC ......SP......V......T....................GKAP.L...........I.P
BAP050-hum09-LC ......SP......V......T....................GKAP.L...........I.P
BAP050-hum03-LC E.VL..SPAT.PV...QTAS.......................GQAPRL.............
BAP050-hum10-LC E.VL..SPAT.PV...QTAS.......................GQAPRL.............
BAP050-hum14-LC E.VL..SPAT.PV...QTAS.......................GQAPRL.............
BAP050-hum04-LC ......SP......V......T............L...GQSPQL...........I.D
BAP050-hum05-LC E.VL..SPAT..L.P.E.A.L..................GKAP.L.................
BAP050-hum06-LC ..V....PL..PVTP.EPAS.......................GQAPRL.............
BAP050-hum07-LC ......SP......V......T............L...GQSPQL...............
BAP050-hum11-LC ......SP......V......T............L...GQSPQL...............
BAP050-hum08-LC E.VL..SPDFQ.VTPKEK...T......................GQAPRL.............
BAP050-hum12-LC E.VL..SPDFQ.VTPKEK...T......................GQAPRL.............
BAP050-hum15-LC E.VL..SPDFQ.VTPKEK...T......................GQAPRL.............
BAP050-hum16-LC E.VL..SPDFQ.VTPKEK...T......................GQAPRL.............
BAP050-hum17-LC ......SP......V......T....................GKAP.L..............
BAP050-hum18-LC A..L..SP......V......T.....................GQAPRL.............
BAP050-hum19-LC E.VL..SPDFQ.VTPKEK...T......................GQAPRL.............
BAP050-hum20-LC ..V....PL..PVTP.EPAS.......................GQAPRL...........I.D 70        80        90       100
                ....|....|....|....|....|....|....|....|....|....|..
BAP050-chi-LC   RFSGSGSGTDYSLTISNLELEDIATYYCQQYYNLPWTFGQGTKVEIK
BAP050-hum01-LC ..........FTF...S..A..A........................
BAP050-hum02-LC .......Y...FT...N.I.S..A.Y.F...................
BAP050-hum13-LC .......Y...FT...N.I.S..A.Y.F...................
BAP050-hum09-LC .......Y...FT...N.I.S..A.Y.F...................
BAP050-hum03-LC ..........FTF...S..A..A........................
BAP050-hum10-LC ..........FTF...S..A..A........................
BAP050-hum14-LC ..........FTF...S..A..A........................
BAP050-hum04-LC ..........FT....R..P..F.V......................
BAP050-hum05-LC ..........FTF...S..A..A........................
BAP050-hum06-LC .........EFT....S.QPD.F........................
BAP050-hum07-LC .........EFT....S.QPD.F........................
BAP050-hum11-LC .........EFT....S.QPD.F........................
BAP050-hum08-LC ..........FT....S.QP..F........................
BAP050-hum12-LC ..........FT....S.QP..F........................
BAP050-hum15-LC ..........FT....S.QP..F........................
BAP050-hum16-LC ..........FT....S.QP..F........................
BAP050-hum17-LC ..........FTF...S.QP...........................
BAP050-hum18-LC ..........FT....S.QP..F........................
BAP050-hum19-LC ..........FTF...S..A..A........................
BAP050-hum20-LC ..........FT....R..P..F.V......................
```

FIGURE 10B

```
                          SEQUENCE LISTING

<160> NUMBER OF SEQ ID NOS: 293

<210> SEQ ID NO 1
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Asn Tyr Gly Met Asn
1               5

<210> SEQ ID NO 2
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Trp Ile Asn Thr Asp Thr Gly Glu Pro Thr Tyr Ala Asp Asp Phe Lys
1               5                   10                  15

Gly

<210> SEQ ID NO 3
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Asn Pro Pro Tyr Tyr Gly Thr Asn Asn Ala Glu Ala Met Asp Tyr
1               5                   10                  15

<210> SEQ ID NO 4
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 4

Gly Phe Thr Leu Thr Asn Tyr
1               5

<210> SEQ ID NO 5
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Asn Thr Asp Thr Gly Glu
1               5

<210> SEQ ID NO 6
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Gln Ile Gln Leu Val Gln Ser Gly Pro Glu Leu Lys Lys Pro Gly Glu
1               5                   10                  15

Thr Val Lys Ile Ser Cys Lys Ala Ser Gly Phe Thr Leu Thr Asn Tyr
            20                  25                  30

Gly Met Asn Trp Val Arg Gln Thr Pro Gly Lys Gly Leu Lys Trp Met
        35                  40                  45

Gly Trp Ile Asn Thr Asp Thr Gly Glu Pro Thr Tyr Ala Asp Asp Phe
    50                  55                  60

Lys Gly Arg Phe Ala Phe Ser Leu Glu Thr Ser Ala Ser Thr Ala Ser
65                  70                  75                  80

Leu Gln Ile Asn Asn Leu Lys Asn Ala Asp Thr Ala Thr Tyr Phe Cys
                85                  90                  95

Ala Arg Asn Pro Pro Tyr Tyr Tyr Gly Thr Asn Asn Ala Glu Ala Met
            100                 105                 110

Asp Tyr Trp Gly Gln Gly Thr Ala Val Thr Val Ser Ser
        115                 120                 125

<210> SEQ ID NO 7
<211> LENGTH: 375
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 7
cagatccagt tggtgcagtc tggacctgag ctgaagaagc ctggagagac agtcaagatc      60
tcctgcaagg cttctggatt taccctcaca aactatggaa tgaactgggt gaggcagact     120
ccaggaaagg gtttaaagtg gatgggctgg ataaacaccg acactggaga gccaacatat     180
gctgatgact tcaagggacg gtttgccttc tctttggaga cctctgccag cactgcctct     240
ttgcagatca acaacctcaa aaatgcggac acggctacat atttctgtgc aagaaacccc     300
ccttattact acggtactaa taacgcggag gctatggact actggggtca aggaaccgca     360
gtcaccgtct cctca                                                      375

<210> SEQ ID NO 8
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Glu Val Gln Leu Val Gln Ser Gly Ala Glu Val Lys Lys Pro Gly Ala
1               5                   10                  15

Thr Val Lys Ile Ser Cys Lys Val Ser Gly Phe Thr Leu Thr Asn Tyr
            20                  25                  30

Gly Met Asn Trp Ile Arg Gln Ser Pro Ser Arg Gly Leu Glu Trp Leu
        35                  40                  45

Gly Trp Ile Asn Thr Asp Thr Gly Glu Pro Thr Tyr Ala Asp Asp Phe
    50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Arg Asn Pro Pro Tyr Tyr Tyr Gly Thr Asn Asn Ala Glu Ala Met
            100                 105                 110

Asp Tyr Trp Gly Gln Gly Thr Thr Val Thr Val Ser Ser
        115                 120                 125

<210> SEQ ID NO 9
<211> LENGTH: 375
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 9
gaggtccagc tggtacagtc tggggctgag gtgaagaagc ctggggctac agtgaaaatc      60
tcctgcaagg tttctggatt taccctcaca actatggaa tgaactggat caggcagtcc     120
ccatcgagag gccttgagtg gctgggttgg ataaacaccg acactggaga gccaacatat    180
gctgatgact caagggaag atttgtcttc tccttgaca cctctgtcag cacggcatat      240
ctgcagatca gcagcctaaa ggctgaggac actgccgtgt attactgtgc aagaaaccct    300
ccctattact acggtactaa taacgcggag gctatggact actggggcca gggcaccacc    360
gtgaccgtgt cctcc                                                     375

<210> SEQ ID NO 10
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Ser Ser Ser Gln Asp Ile Ser Asn Tyr Leu Asn
1               5                   10

<210> SEQ ID NO 11
<211> LENGTH: 7
<212> TYPE: PRT

```
<213> ORGANISM: Artificial Sequence
<220> FEATURE:
<223> OTHER INFORMATION: Description of Artificial Sequence: Synthetic
      peptide

<400> SEQUENCE: 11

Tyr Thr Ser Thr Leu His Leu
1               5

<210> SEQ ID NO 12
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Gln Gln Tyr Tyr Asn Leu Pro Trp Thr
1               5

<210> SEQ ID NO 13
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Ser Gln Asp Ile Ser Asn Tyr
1               5

<210> SEQ ID NO 14
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Tyr Thr Ser
1

<210> SEQ ID NO 15
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Tyr Tyr Asn Leu Pro Trp
1               5

<210> SEQ ID NO 16
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Asp Ile Gln Met Thr Gln Thr Thr Ser Ser Leu Ser Ala Ser Leu Gly
1               5                   10                  15
```

```
Asp Arg Val Thr Ile Ser Cys Ser Ser Gln Asp Ile Ser Asn Tyr
            20                  25                  30

Leu Asn Trp Tyr Gln Gln Lys Pro Asp Gly Thr Val Lys Val Leu Ile
        35                  40                  45

Tyr Tyr Thr Ser Thr Leu His Leu Gly Val Pro Ser Arg Phe Ser Gly
 50                  55                  60

Ser Gly Ser Gly Thr Asp Tyr Ser Leu Thr Ile Ser Asn Leu Glu Leu
 65                  70                  75                  80

Glu Asp Ile Ala Thr Tyr Tyr Cys Gln Gln Tyr Tyr Asn Leu Pro Trp
                85                  90                  95

Thr Phe Gly Gly Gly Thr Lys Leu Glu Ile Lys
            100                 105

<210> SEQ ID NO 17
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 17
gatatccaga tgacacagac tacatcctcc ctgtctgcct ctctgggaga cagagtcacc      60
atcagttgca gttcaagtca ggacatcagc aattatttaa actggtatca gcagaaacca    120
gatggaactg ttaaagtcct gatctattac acatcaacct acacttagg agtcccatca     180 aggttcagtg gcagtgggtc tgggacagat tattctctca ccatcagcaa cctggaactc    240
gaagatattg ccacatacta ttgtcagcag tattataacc ttccgtggac gttcggtgga    300
ggcaccaagt tggaaatcaa a                                              321

<210> SEQ ID NO 18
<211> LENGTH: 452
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Glu Val Gln Leu Val Gln Ser Gly Ala Glu Val Lys Lys Pro Gly Ala
 1               5                  10                  15

Thr Val Lys Ile Ser Cys Lys Val Ser Gly Phe Thr Leu Thr Asn Tyr
            20                  25                  30

Gly Met Asn Trp Ile Arg Gln Ser Pro Ser Arg Gly Leu Glu Trp Leu
        35                  40                  45

Gly Trp Ile Asn Thr Asp Thr Gly Glu Pro Thr Tyr Ala Asp Asp Phe
 50                  55                  60

Lys Gly Arg Phe Val Phe Ser Leu Asp Thr Ser Val Ser Thr Ala Tyr
 65                  70                  75                  80

Leu Gln Ile Ser Ser Leu Lys Ala Glu Asp Thr Ala Val Tyr Tyr Cys
                85                  90                  95

Ala Arg Asn Pro Pro Tyr Tyr Gly Thr Asn Asn Ala Glu Ala Met
            100                 105                 110

Asp Tyr Trp Gly Gln Gly Thr Thr Val Thr Val Ser Ser Ala Ser Thr
        115                 120                 125

Lys Gly Pro Ser Val Phe Pro Leu Ala Pro Cys Ser Arg Ser Thr Ser
130                 135                 140
```

Glu Ser Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
            165                 170                 175

Thr Phe Pro Ala Val Leu Gln Ser Ser Gly Leu Tyr Ser Leu Ser Ser
        180                 185                 190

Val Val Thr Val Pro Ser Ser Ser Leu Gly Thr Lys Thr Tyr Thr Cys
            195                 200                 205

Asn Val Asp His Lys Pro Ser Asn Thr Lys Val Asp Lys Arg Val Glu
    210                 215                 220

Ser Lys Tyr Gly Pro Pro Cys Pro Pro Cys Pro Ala Pro Glu Phe Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

Gln Glu Asp Pro Glu Val Gln Phe Asn Trp Tyr Val Asp Gly Val Glu
        275                 280                 285

Val His Asn Ala Lys Thr Lys Pro Arg Glu Glu Gln Phe Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Gly Leu Pro Ser Ser
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Gln Glu Glu Met Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Arg Leu Thr
                405                 410                 415

Val Asp Lys Ser Arg Trp Gln Glu Gly Asn Val Phe Ser Cys Ser Val
            420                 425                 430

Met His Glu Ala Leu His Asn His Tyr Thr Gln Lys Ser Leu Ser Leu
        435                 440                 445

Ser Leu Gly Lys
    450

<210> SEQ ID NO 19
<211> LENGTH: 1356
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 19
gaggtccagc tggtacagtc tgggctgag gtgaagaagc ctggggctac agtgaaaatc     60
tcctgcaagg tttctggatt taccctcaca aactatggaa tgaactggat caggcagtcc    120
ccatcgagag gccttgagtg gctgggttgg ataaacaccg acactggaga gccaacatat    180
gctgatgact tcaagggaag atttgtcttc tccttggaca cctctgtcag cacggcatat    240

```
ctgcagatca gcagcctaaa ggctgaggac actgccgtgt attactgtgc aagaaaccct      300
ccctattact acggtactaa taacgcggag gctatggact actggggcca gggcaccacc      360
gtgaccgtgt cctccgcttc caccaagggc ccatccgtct tccccctggc gccctgctcc      420
aggagcacct ccgagagcac agccgccctg ggctgcctgg tcaaggacta cttccccgaa      480
ccggtgacgg tgtcgtggaa ctcaggcgcc ctgaccagcg gcgtgcacac cttcccggct      540
gtcctacagt cctcaggact ctactccctc agcagcgtgg tgaccgtgcc ctccagcagc      600
ttgggcacga agacctacac ctgcaacgta gatcacaagc ccagcaacac caaggtggac      660
aagagagttg agtccaaata tggtccccca tgcccaccgt gcccagcacc tgagttcctg      720
gggggaccat cagtcttcct gttcccccca aaacccaagg acactctcat gatctcccgg      780
acccctgagg tcacgtgcgt ggtggtggac gtgagccagg aagaccccga ggtccagttc      840
aactggtacg tggatggcgt ggaggtgcat aatgccaaga caaagccgcg ggaggagcag      900
ttcaacagca cgtaccgtgt ggtcagcgtc ctcaccgtcc tgcaccagga ctggctgaac      960
ggcaaggagt acaagtgcaa ggtgtccaac aaaggcctcc cgtcctccat cgagaaaacc     1020
atctccaaag ccaaagggca gccccgagag ccacaggtgt acaccctgcc cccatcccag     1080
gaggagatga ccaagaacca ggtcagcctg acctgcctgg tcaaaggctt ctaccccagc     1140
gacatcgccg tggagtggga gagcaatggg cagccggaga acaactacaa gaccacgcct     1200
cccgtgctgg actccgacgg ctccttcttc ctctacagca ggctaaccgt ggacaagagc     1260
aggtggcagg aggggaatgt cttctcatgc tccgtgatgc atgaggctct gcacaaccac     1320
tacacacaga agagcctctc cctgtctctg ggtaaa                                1356
```

<210> SEQ ID NO 20
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Gln Ile Gln Leu Val Gln Ser Gly Pro Glu Leu Lys Lys Pro Gly Glu
1               5                   10                  15

Thr Val Lys Ile Ser Cys Lys Ala Ser Gly Phe Thr Leu Thr Asn Tyr
            20                  25                  30

Gly Met Asn Trp Val Arg Gln Thr Pro Gly Lys Gly Leu Lys Trp Met
        35                  40                  45

Gly Trp Ile Asn Thr Asp Thr Gly Glu Pro Thr Tyr Ala Asp Asp Phe
    50                  55                  60

Lys Gly Arg Phe Ala Phe Ser Leu Glu Thr Ser Ala Ser Thr Ala Ser
65                  70                  75                  80

Leu Gln Ile Asn Asn Leu Lys Asn Ala Asp Thr Ala Thr Tyr Phe Cys
                85                  90                  95

Ala Arg Asn Pro Pro Tyr Tyr Gly Thr Asn Asn Ala Glu Ala Met
            100                 105                 110

Asp Tyr Trp Gly Gln Gly Thr Thr Val Thr Val Ser Ser
        115                 120                 125

<210> SEQ ID NO 21
<211> LENGTH: 375
<212> TYPE: DNA
<213> ORGANISM: Artificial Sequence

```
<220> FEATURE:
<223> OTHER INFORMATION: Description of Artificial Sequence: Synthetic
      polynucleotide

<400> SEQUENCE: 21
cagatccagt tggtgcagtc tggacctgag ctgaagaagc ctggagagac agtcaagatc      60
tcctgcaagg cttctggatt taccctcaca aactatggaa tgaactgggt gaggcagact     120
ccaggaaagg gtttaaagtg gatgggctgg ataaacaccg acactggaga gccaacatat     180
gctgatgact tcaagggacg gtttgccttc tctttggaga cctctgccag cactgcctct     240
ttgcagatca acaacctcaa aaatgcggac acggctacat atttctgtgc aagaaacccc     300
ccttattact acggtactaa taacgcggag gctatggact actggggcca gggcaccacc     360
gtgaccgtgt cctcc                                                      375

<210> SEQ ID NO 22
<211> LENGTH: 452
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Gln Ile Gln Leu Val Gln Ser Gly Pro Glu Leu Lys Lys Pro Gly Glu
1               5                   10                  15

Thr Val Lys Ile Ser Cys Lys Ala Ser Gly Phe Thr Leu Thr Asn Tyr
            20                  25                  30

Gly Met Asn Trp Val Arg Gln Thr Pro Gly Lys Gly Leu Lys Trp Met
        35                  40                  45

Gly Trp Ile Asn Thr Asp Thr Gly Glu Pro Thr Tyr Ala Asp Asp Phe
    50                  55                  60

Lys Gly Arg Phe Ala Phe Ser Leu Glu Thr Ser Ala Ser Thr Ala Ser
65                  70                  75                  80

Leu Gln Ile Asn Asn Leu Lys Asn Ala Asp Thr Ala Thr Tyr Phe Cys
                85                  90                  95

Ala Arg Asn Pro Pro Tyr Tyr Tyr Gly Thr Asn Asn Ala Glu Ala Met
            100                 105                 110

Asp Tyr Trp Gly Gln Gly Thr Thr Val Thr Val Ser Ser Ala Ser Thr
        115                 120                 125

Lys Gly Pro Ser Val Phe Pro Leu Ala Pro Cys Ser Arg Ser Thr Ser
    130                 135                 140

Glu Ser Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Lys Thr Tyr Thr Cys
        195                 200                 205

Asn Val Asp His Lys Pro Ser Asn Thr Lys Val Asp Lys Arg Val Glu
    210                 215                 220

Ser Lys Tyr Gly Pro Pro Cys Pro Pro Cys Pro Ala Pro Glu Phe Leu
225                 230                 235                 240

Gly Gly Pro Ser Val Phe Leu Phe Pro Pro Lys Pro Lys Asp Thr Leu
                245                 250                 255
```

Met Ile Ser Arg Thr Pro Glu Val Thr Cys Val Val Asp Val Ser
        260                 265                 270

Gln Glu Asp Pro Glu Val Gln Phe Asn Trp Tyr Val Asp Gly Val Glu
    275                 280                 285

Val His Asn Ala Lys Thr Lys Pro Arg Glu Glu Gln Phe Asn Ser Thr
290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Gly Leu Pro Ser Ser
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Gln Glu Glu Met Thr Lys Asn Gln Val
        355                 360                 365

Ser Leu Thr Cys Leu Val Lys Gly Phe Tyr Pro Ser Asp Ile Ala Val
370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Arg Leu Thr
                405                 410                 415

Val Asp Lys Ser Arg Trp Gln Glu Gly Asn Val Phe Ser Cys Ser Val
            420                 425                 430

Met His Glu Ala Leu His Asn His Tyr Thr Gln Lys Ser Leu Ser Leu
        435                 440                 445

Ser Leu Gly Lys
    450

<210> SEQ ID NO 23
<211> LENGTH: 1356
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 23
cagatccagt tggtgcagtc tggacctgag ctgaagaagc tggagagaca gtcaagatc      60 tcctgcaagg cttctggatt taccctcaca aactatggaa tgaactgggt gaggcagact    120
ccaggaaagg gtttaaagtg gatgggctgg ataaacaccg acactggaga gccaacatat    180
gctgatgact caagggacg gtttgccttc tctttggaga cctctgccag cactgcctct    240
ttgcagatca caacctcaa aaatgcggac acggctacat atttctgtgc aagaaacccc    300
ccttattact acggtactaa taacgcggag gctatggact actggggcca gggcaccacc    360
gtgaccgtgt cctccgcttc caccaagggc ccatccgtct tccccctggc gccctgctcc    420
aggagcacct ccgagagcac agccgccctg ggctgcctgg tcaaggacta cttccccgaa    480
ccggtgacgg tgtcgtggaa ctcaggcgcc ctgaccagcg gcgtgcacac cttcccggct    540
gtcctacagt cctcaggact ctactccctc agcagcgtgg tgaccgtgcc ctccagcagc    600
ttgggcacga agacctacac ctgcaacgta gatcacaagc ccagcaacac caaggtggac    660
aagagagttg agtccaaata tggtccccca tgcccaccgt gcccagcacc tgagttcctg    720
gggggaccat cagtcttcct gttccccca aaacccaagg acactctcat gatctcccgg    780
acccctgagg tcacgtgcgt ggtggtggac gtgagccagg aagaccccga ggtccagttc    840
aactggtacg tggatggcgt ggaggtgcat aatgccaaga caaagccgcg ggaggagcag    900

```
ttcaacagca cgtaccgtgt ggtcagcgtc ctcaccgtcc tgcaccagga ctggctgaac    960
ggcaaggagt acaagtgcaa ggtgtccaac aaaggcctcc cgtcctccat cgagaaaacc   1020
atctccaaag ccaaagggca gccccgagag ccacaggtgt acaccctgcc cccatcccag   1080
gaggagatga ccaagaacca ggtcagcctg acctgcctgg tcaaaggctt ctaccccagc   1140
gacatcgccg tggagtggga gagcaatggg cagccggaga caactacaa gaccacgcct    1200 cccgtgctgg actccgacgg ctccttcttc ctctacagca ggctaaccgt ggacaagagc   1260
aggtggcagg aggggaatgt cttctcatgc tccgtgatgc atgaggctct gcacaaccac   1320
tacacacaga gagcctctc cctgtctctg ggtaaa                             1356
```

<210> SEQ ID NO 24
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Asp Ile Gln Met Thr Gln Thr Thr Ser Ser Leu Ser Ala Ser Leu Gly
1               5                   10                  15

Asp Arg Val Thr Ile Ser Cys Ser Ser Ser Gln Asp Ile Ser Asn Tyr
            20                  25                  30

Leu Asn Trp Tyr Gln Gln Lys Pro Asp Gly Thr Val Lys Val Leu Ile
        35                  40                  45

Tyr Tyr Thr Ser Thr Leu His Leu Gly Val Pro Ser Arg Phe Ser Gly
    50                  55                  60

Ser Gly Ser Gly Thr Asp Tyr Ser Leu Thr Ile Ser Asn Leu Glu Leu
65                  70                  75                  80

Glu Asp Ile Ala Thr Tyr Tyr Cys Gln Gln Tyr Tyr Asn Leu Pro Trp
                85                  90                  95

Thr Phe Gly Gln Gly Thr Lys Val Glu Ile Lys
            100                 105

<210> SEQ ID NO 25
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 25

```
gatatccaga tgacacagac tacatcctcc ctgtctgcct ctctgggaga cagagtcacc     60
atcagttgca gttcaagtca ggacatcagc aattatttaa actggtatca gcagaaacca    120
gatggaactg ttaaagtcct gatctattac acatcaacct acacttagg agtcccatca     180 aggttcagtg gcagtgggtc tgggacagat tattctctca ccatcagcaa cctggaactc    240
gaagatattg ccacatacta ttgtcagcag tattataacc ttccgtggac gttcggccaa    300
gggaccaagg tggaaatcaa a                                              321
```

<210> SEQ ID NO 26
<211> LENGTH: 214
<212> TYPE: PRT
<213> ORGANISM: Artificial Sequence
<220> FEATURE:
<223> OTHER INFORMATION: Description of Artificial Sequence: Synthetic

```
                              polypeptide

<400> SEQUENCE: 26

Asp Ile Gln Met Thr Gln Thr Thr Ser Ser Leu Ser Ala Ser Leu Gly
1               5                   10                  15

Asp Arg Val Thr Ile Ser Cys Ser Ser Ser Gln Asp Ile Ser Asn Tyr
            20                  25                  30

Leu Asn Trp Tyr Gln Gln Lys Pro Asp Gly Thr Val Lys Val Leu Ile
        35                  40                  45

Tyr Tyr Thr Ser Thr Leu His Leu Gly Val Pro Ser Arg Phe Ser Gly
    50                  55                  60

Ser Gly Ser Gly Thr Asp Tyr Ser Leu Thr Ile Ser Asn Leu Glu Leu
65                  70                  75                  80

Glu Asp Ile Ala Thr Tyr Tyr Cys Gln Gln Tyr Tyr Asn Leu Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 27
<211> LENGTH: 642
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 27
gatatccaga tgacacagac tacatcctcc ctgtctgcct ctctgggaga cagagtcacc       60
atcagttgca gttcaagtca ggacatcagc aattatttaa actggtatca gcagaaacca     120
gatggaactg ttaaagtcct gatctattac acatcaacct acacttagg agtcccatca      180 aggttcagtg gcagtgggtc tgggacagat tattctctca ccatcagcaa cctggaactc     240
gaagatattg ccacatacta ttgtcagcag tattataacc ttccgtggac gttcggccaa     300
gggaccaagg tggaaatcaa acgtacggtg gctgcaccat ctgtcttcat cttcccgcca     360
tctgatgagc agttgaaatc tggaactgcc tctgttgtgt gcctgctgaa taacttctat     420
cccagagagg ccaaagtaca gtggaaggtg gataacgccc tccaatcggg taactcccag     480
gagagtgtca cagagcagga cagcaaggac agcacctaca gcctcagcag caccctgacg     540
ctgagcaaag cagactacga gaaacacaaa gtctacgcct gcgaagtcac ccatcagggc     600
ctgagctcgc ccgtcacaaa gagcttcaac aggggagagt gt                        642
```

<210> SEQ ID NO 28
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Glu Val Gln Leu Val Gln Ser Gly Ala Glu Val Lys Lys Pro Gly Ala
1               5                   10                  15

Thr Val Lys Ile Ser Cys Lys Val Ser Gly Phe Thr Leu Thr Asn Tyr
            20                  25                  30

Gly Met Asn Trp Val Arg Gln Ala Pro Gly Gln Gly Leu Glu Trp Met
        35                  40                  45

Gly Trp Ile Asn Thr Asp Thr Gly Glu Pro Thr Tyr Ala Asp Asp Phe
    50                  55                  60

Lys Gly Arg Phe Val Phe Ser Leu Asp Thr Ser Val Ser Thr Ala Tyr
65                  70                  75                  80

Leu Gln Ile Cys Ser Leu Lys Ala Glu Asp Thr Ala Val Tyr Tyr Cys
                85                  90                  95

Ala Arg Asn Pro Pro Tyr Tyr Gly Thr Asn Asn Ala Glu Ala Met
            100                 105                 110

Asp Tyr Trp Gly Gln Gly Thr Thr Val Thr Val Ser Ser
        115                 120                 125

<210> SEQ ID NO 29
<211> LENGTH: 375
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 29
gaggtccagc tggtacagtc tggggctgag gtgaagaagc ctggggctac agtgaaaatc      60
tcctgcaagg tttctggatt taccctcaca aactatggaa tgaactgggt gcgacaggcc    120
cctggacaag ggcttgagtg gatgggttgg ataaacaccg acactggaga gccaacatat    180
gctgatgact tcaagggaag atttgtcttc tccttggaca cctctgtcag cacggcatat    240
ctgcagatct gcagcctaaa ggctgaggac actgccgtgt attactgtgc aagaaaccct    300
ccctattact acggtactaa taacgcggag gctatggact actggggcca gggcaccacc    360
gtgaccgtgt cctcc                                                      375

<210> SEQ ID NO 30
<211> LENGTH: 452
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

Glu Val Gln Leu Val Gln Ser Gly Ala Glu Val Lys Lys Pro Gly Ala
1               5                   10                  15

Thr Val Lys Ile Ser Cys Lys Val Ser Gly Phe Thr Leu Thr Asn Tyr
            20                  25                  30

Gly Met Asn Trp Val Arg Gln Ala Pro Gly Gln Gly Leu Glu Trp Met
        35                  40                  45

```
Gly Trp Ile Asn Thr Asp Thr Gly Glu Pro Thr Tyr Ala Asp Asp Phe
 50                  55                  60

Lys Gly Arg Phe Val Phe Ser Leu Asp Thr Ser Val Ser Thr Ala Tyr
 65                  70                  75                  80

Leu Gln Ile Cys Ser Leu Lys Ala Glu Asp Thr Ala Val Tyr Tyr Cys
                 85                  90                  95

Ala Arg Asn Pro Pro Tyr Tyr Gly Thr Asn Asn Ala Glu Ala Met
             100                 105                 110

Asp Tyr Trp Gly Gln Gly Thr Thr Val Thr Val Ser Ser Ala Ser Thr
             115                 120                 125

Lys Gly Pro Ser Val Phe Pro Leu Ala Pro Cys Ser Arg Ser Thr Ser
130                 135                 140

Glu Ser Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
             180                 185                 190

Val Val Thr Val Pro Ser Ser Leu Gly Thr Lys Thr Tyr Thr Cys
             195                 200                 205

Asn Val Asp His Lys Pro Ser Asn Thr Lys Val Asp Lys Arg Val Glu
210                 215                 220

Ser Lys Tyr Gly Pro Pro Cys Pro Pro Cys Pro Ala Pro Glu Phe Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
             260                 265                 270

Gln Glu Asp Pro Glu Val Gln Phe Asn Trp Tyr Val Asp Gly Val Glu
             275                 280                 285

Val His Asn Ala Lys Thr Lys Pro Arg Glu Glu Gln Phe Asn Ser Thr
290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Gly Leu Pro Ser Ser
                325                 330                 335

Ile Glu Lys Thr Ile Ser Lys Ala Lys Gly Gln Pro Arg Glu Pro Gln
             340                 345                 350

Val Tyr Thr Leu Pro Pro Ser Gln Glu Glu Met Thr Lys Asn Gln Val
             355                 360                 365

Ser Leu Thr Cys Leu Val Lys Gly Phe Tyr Pro Ser Asp Ile Ala Val
370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Arg Leu Thr
                405                 410                 415

Val Asp Lys Ser Arg Trp Gln Glu Gly Asn Val Phe Ser Cys Ser Val
             420                 425                 430

Met His Glu Ala Leu His Asn His Tyr Thr Gln Lys Ser Leu Ser Leu
             435                 440                 445

Ser Leu Gly Lys
    450
```

<210> SEQ ID NO 31
<211> LENGTH: 1356
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 31

```
gaggtccagc tggtacagtc tggggctgag gtgaagaagc ctggggctac agtgaaaatc      60
tcctgcaagg tttctggatt taccctcaca aactatggaa tgaactgggt gcgacaggcc     120
cctggacaag gcttgagtg gatgggttgg ataaacaccg acactggaga gccaacatat     180
gctgatgact tcaagggaag atttgtcttc tccttggaca cctctgtcag cacggcatat     240
ctgcagatct gcagcctaaa ggctgaggac actgccgtgt attactgtgc aagaaaccct     300
ccctattact acggtactaa taacgcggag gctatggact actggggcca gggcaccacc     360
gtgaccgtgt cctccgcttc caccaagggc ccatccgtct tccccctggc gccctgctcc     420
aggagcacct ccgagagcac agccgccctg gctgcctgg tcaaggacta cttccccgaa     480
ccggtgacgg tgtcgtggaa ctcaggcgcc ctgaccagcg gcgtgcacac cttcccggct     540
gtcctacagt cctcaggact ctactccctc agcagcgtgg tgaccgtgcc ctccagcagc     600
ttgggcacga gacctacac ctgcaacgta gatcacaagc ccagcaacac caaggtggac     660
aagagagttg agtccaaata tggtccccca tgcccaccgt gcccagcacc tgagttcctg     720
ggggggaccat cagtcttcct gttccccca aacccaagg acactctcat gatctcccgg     780
accctgagg tcacgtgcgt ggtggtggac gtgagccagg aagaccccga ggtccagttc     840
aactggtacg tggatggcgt ggaggtgcat aatgccaaga caaagccgcg ggaggagcag     900
ttcaacagca cgtaccgtgt ggtcagcgtc ctcaccgtcc tgcaccagga ctggctgaac     960
ggcaaggagt acaagtgcaa ggtgtccaac aaaggcctcc cgtcctccat cgagaaaacc    1020
atctccaaag ccaaagggca gccccgagag ccacaggtgt acaccctgcc cccatcccag    1080
gaggagatga ccaagaacca ggtcagcctg acctgcctgg tcaaaggctt ctaccccagc    1140
gacatcgccg tggagtggga gagcaatggg cagccggaga caactacaa gaccacgcct    1200
cccgtgctgg actccgacgg ctccttcttc ctctacagca ggctaaccgt ggacaagagc    1260
aggtggcagg aggggaatgt cttctcatgc tccgtgatgc atgaggctct gcacaaccac    1320
tacacacaga gagcctctc cctgtctctg ggtaaa                              1356
```

<210> SEQ ID NO 32
<211> LENGTH: 107
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 32

Asp Ile Gln Met Thr Gln Ser Pro Ser Ser Leu Ser Ala Ser Val Gly
1               5                   10                  15

Asp Arg Val Thr Ile Thr Cys Ser Ser Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Thr Leu His Leu Gly Val Pro Ser Arg Phe Ser Gly
    50                  55                  60

```
Ser Gly Ser Gly Thr Asp Phe Thr Phe Thr Ile Ser Ser Leu Glu Ala
65                  70                  75                  80

Glu Asp Ala Ala Thr Tyr Tyr Cys Gln Gln Tyr Tyr Asn Leu Pro Trp
                85                  90                  95

Thr Phe Gly Gln Gly Thr Lys Val Glu Ile Lys
            100                 105

<210> SEQ ID NO 33
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 33
gacatccaga tgacccagtc tccatcctcc ctgtctgcat ctgtaggaga cagagtcacc      60
atcacttgca gttcaagtca ggacatcagc aattatttaa actggtatca gcagaaacca    120
gggaaagctc ctaagctcct gatctattac acatcaacct tacacttagg ggtcccctcg    180
aggttcagtg gcagtggatc tgggacagat ttcaccttta ccatcagtag cctggaagct    240
gaagatgctg caacatatta ctgtcagcag tattataacc ttccgtggac gttcggccaa    300
gggaccaagg tggaaatcaa a                                              321

<210> SEQ ID NO 34
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

Asp Ile Gln Met Thr Gln Ser Pro Ser Ser Leu Ser Ala Ser Val Gly
1               5                   10                  15

Asp Arg Val Thr Ile Thr Cys Ser Ser Ser Gln Asp Ile Ser Asn Tyr
                20                  25                  30

Leu Asn Trp Tyr Gln Gln Lys Pro Gly Lys Ala Pro Lys Leu Leu Ile
        35                  40                  45

Tyr Tyr Thr Ser Thr Leu His Leu Gly Val Pro Ser Arg Phe Ser Gly
    50                  55                  60

Ser Gly Ser Gly Thr Asp Phe Thr Phe Thr Ile Ser Ser Leu Glu Ala
65                  70                  75                  80

Glu Asp Ala Ala Thr Tyr Tyr Cys Gln Gln Tyr Tyr Asn Leu Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190
```

Ala Cys Glu Val Thr His Gln Gly Leu Ser Ser Pro Val Thr Lys Ser
         195                 200                 205

Phe Asn Arg Gly Glu Cys
    210

<210> SEQ ID NO 35
<211> LENGTH: 642
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 35
gacatccaga tgacccagtc tccatcctcc ctgtctgcat ctgtaggaga cagagtcacc      60
atcacttgca gttcaagtca ggacatcagc aattatttaa actggtatca gcagaaacca    120
gggaaagctc ctaagctcct gatctattac acatcaacct tacacttagg ggtcccctcg    180
aggttcagtg gcagtggatc tgggacagat ttcaccttta ccatcagtag cctggaagct    240
gaagatgctg caacatatta ctgtcagcag tattataacc ttccgtggac gttcggccaa    300
gggaccaagg tggaaatcaa acgtacggtg gctgcaccat ctgtcttcat cttcccgcca    360
tctgatgagc agttgaaatc tggaactgcc tctgttgtgt gcctgctgaa taacttctat    420
cccagagagg ccaaagtaca gtggaaggtg gataacgccc tccaatcggg taactcccag    480
gagagtgtca cagagcagga cagcaaggac agcacctaca gcctcagcag caccctgacg    540
ctgagcaaag cagactacga aaacacaaa gtctacgcct gcgaagtcac ccatcagggc    600
ctgagctcgc ccgtcacaaa gagcttcaac aggggagagt gt                       642

<210> SEQ ID NO 36
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

Asp Ile Gln Met Thr Gln Ser Pro Ser Ser Leu Ser Ala Ser Val Gly
1               5                   10                  15

Asp Arg Val Thr Ile Thr Cys Ser Ser Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Thr Leu His Leu Gly Ile Pro Pro Arg Phe Ser Gly
    50                  55                  60

Ser Gly Tyr Gly Thr Asp Phe Thr Leu Thr Ile Asn Asn Ile Glu Ser
65                  70                  75                  80

Glu Asp Ala Ala Tyr Tyr Phe Cys Gln Gln Tyr Tyr Asn Leu Pro Trp
                85                  90                  95

Thr Phe Gly Gln Gly Thr Lys Val Glu Ile Lys
            100                 105

<210> SEQ ID NO 37
<211> LENGTH: 321
<212> TYPE: DNA
<213> ORGANISM: Artificial Sequence
<220> FEATURE:
<223> OTHER INFORMATION: Description of Artificial Sequence: Synthetic -continued polynucleotide

<400> SEQUENCE: 37

```
gacatccaga tgacccagtc tccatcctcc ctgtctgcat ctgtaggaga cagagtcacc      60
atcacttgca gttcaagtca ggacatcagc aattatttaa actggtatca gcagaaacca     120
gggaaagctc ctaagctcct gatctattac acatcaacct tacacttagg gatcccacct     180
cgattcagtg gcagcgggta tggaacagat tttacccctca caattaataa catagaatct    240
gaggatgctg catattactt ctgtcagcag tattataacc ttccgtggac gttcggccaa     300
gggaccaagg tggaaatcaa a                                                321
```

<210> SEQ ID NO 38
<211> LENGTH: 214
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 38

Asp Ile Gln Met Thr Gln Ser Pro Ser Ser Leu Ser Ala Ser Val Gly
1               5                   10                  15

Asp Arg Val Thr Ile Thr Cys Ser Ser Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Thr Leu His Leu Gly Ile Pro Pro Arg Phe Ser Gly
    50                  55                  60

Ser Gly Tyr Gly Thr Asp Phe Thr Leu Thr Ile Asn Asn Ile Glu Ser
65                  70                  75                  80

Glu Asp Ala Ala Tyr Tyr Phe Cys Gln Gln Tyr Tyr Asn Leu Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 39
<211> LENGTH: 642
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 39

```
gacatccaga tgacccagtc tccatcctcc ctgtctgcat ctgtaggaga cagagtcacc      60
atcacttgca gttcaagtca ggacatcagc aattatttaa actggtatca gcagaaacca     120
gggaaagctc ctaagctcct gatctattac acatcaacct tacacttagg gatcccacct     180
cgattcagtg gcagcgggta tggaacagat tttacccctca caattaataa catagaatct    240
gaggatgctg catattactt ctgtcagcag tattataacc ttccgtggac gttcggccaa     300
gggaccaagg tggaaatcaa acgtacggtg gctgcaccat ctgtcttcat cttcccgcca     360
tctgatgagc agttgaaatc tggaactgcc tctgttgtgt gcctgctgaa taacttctat     420
cccagagagg ccaaagtaca gtggaaggtg gataacgccc tccaatcggg taactcccag     480
gagagtgtca cagagcagga cagcaaggac agcacctaca gcctcagcag caccctgacg     540
ctgagcaaag cagactacga gaaacacaaa gtctacgcct gcgaagtcac ccatcagggc     600
ctgagctcgc ccgtcacaaa gagcttcaac aggggagagt gt                        642
```

<210> SEQ ID NO 40
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40

```
Glu Ile Val Leu Thr Gln Ser Pro Ala Thr Leu Pro Val Thr Leu Gly
1               5                   10                  15

Gln Pro Ala Ser Ile Ser Cys Ser Ser Ser Gln Asp Ile Ser Asn Tyr
            20                  25                  30

Leu Asn Trp Tyr Gln Gln Lys Pro Gly Gln Ala Pro Arg Leu Leu Ile
        35                  40                  45

Tyr Tyr Thr Ser Thr Leu His Leu Gly Val Pro Ser Arg Phe Ser Gly
    50                  55                  60

Ser Gly Ser Gly Thr Asp Phe Thr Phe Thr Ile Ser Ser Leu Glu Ala
65                  70                  75                  80

Glu Asp Ala Ala Thr Tyr Tyr Cys Gln Gln Tyr Tyr Asn Leu Pro Trp
                85                  90                  95

Thr Phe Gly Gln Gly Thr Lys Val Glu Ile Lys
            100                 105
```

<210> SEQ ID NO 41
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 41

```
gaaattgtgt tgacacagtc tccagccacc ctgcccgtca cccttggaca gccggcctcc      60
atctcctgca gttcaagtca ggacatcagc aattatttaa actggtacca gcagaaacct     120
ggccaggctc ccaggctcct catctattac acatcaacct tacacttagg ggtcccctcg     180
aggttcagtg gcagtggatc tgggacagat ttcacctta ccatcagtag cctggaagct     240
gaagatgctg caacatatta ctgtcagcag tattataacc ttccgtggac gttcggccaa     300
gggaccaagg tggaaatcaa a                                               321
```

```
<210> SEQ ID NO 42
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 42

Glu Ile Val Leu Thr Gln Ser Pro Ala Thr Leu Pro Val Thr Leu Gly
1               5                   10                  15

Gln Pro Ala Ser Ile Ser Cys Ser Ser Ser Gln Asp Ile Ser Asn Tyr
            20                  25                  30

Leu Asn Trp Tyr Gln Gln Lys Pro Gly Gln Ala Pro Arg Leu Leu Ile
        35                  40                  45

Tyr Tyr Thr Ser Thr Leu His Leu Gly Val Pro Ser Arg Phe Ser Gly
50                  55                  60

Ser Gly Ser Gly Thr Asp Phe Thr Phe Thr Ile Ser Ser Leu Glu Ala
65                  70                  75                  80

Glu Asp Ala Ala Thr Tyr Tyr Cys Gln Gln Tyr Tyr Asn Leu Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 43
<211> LENGTH: 642
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 43
gaaattgtgt tgacacagtc tccagccacc ctgcccgtca cccttggaca gccggcctcc      60
atctcctgca gttcaagtca ggacatcagc aattatttaa actggtacca gcagaaacct     120
ggccaggctc ccaggctcct catctattac acatcaacct tacacttagg ggtcccctcg     180
aggttcagtg gcagtggatc tgggacagat ttcaccttta ccatcagtag cctggaagct     240
gaagatgctg caacatatta ctgtcagcag tattataacc ttccgtggac gttcggccaa     300
gggaccaagg tggaaatcaa acgtacggtg gctgcaccat ctgtcttcat cttcccgcca     360
tctgatgagc agttgaaatc tggaactgcc tctgttgtgt gcctgctgaa taacttctat     420
cccagagagg ccaaagtaca gtggaaggtg gataacgccc tccaatcggg taactcccag     480
```

```
gagagtgtca cagagcagga cagcaaggac agcacctaca gcctcagcag caccctgacg       540
ctgagcaaag cagactacga gaaacacaaa gtctacgcct gcgaagtcac ccatcagggc       600
ctgagctcgc ccgtcacaaa gagcttcaac aggggagagt gt                         642
```

<210> SEQ ID NO 44
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44

```
Asp Ile Gln Met Thr Gln Ser Pro Ser Ser Leu Ser Ala Ser Val Gly
1               5                   10                  15

Asp Arg Val Thr Ile Thr Cys Ser Ser Ser Gln Asp Ile Ser Asn Tyr
            20                  25                  30

Leu Asn Trp Tyr Leu Gln Lys Pro Gly Gln Ser Pro Gln Leu Leu Ile
        35                  40                  45

Tyr Tyr Thr Ser Thr Leu His Leu Gly Ile Pro Asp Arg Phe Ser Gly
    50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln Tyr Tyr Asn Leu Pro Trp
                85                  90                  95

Thr Phe Gly Gln Gly Thr Lys Val Glu Ile Lys
            100                 105
```

<210> SEQ ID NO 45
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 45

```
gacatccaga tgacccagtc tccatcctcc ctgtctgcat ctgtaggaga cagagtcacc       60
atcacttgca gttcaagtca ggacatcagc aattatttaa actggtacct gcagaagcca      120
gggcagtctc cacagctcct gatctattac acatcaacct acacttagg gatcccagac       180 aggttcagtg gcagtgggtc tgggacagac ttcactctca ccatcagcag actggagcct      240
gaagattttg cagtgtatta ctgtcagcag tattataacc ttccgtggac gttcggccaa      300
gggaccaagg tggaaatcaa a                                                 321
```

<210> SEQ ID NO 46
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 46

```
Asp Ile Gln Met Thr Gln Ser Pro Ser Ser Leu Ser Ala Ser Val Gly
1               5                   10                  15

Asp Arg Val Thr Ile Thr Cys Ser Ser Ser Gln Asp Ile Ser Asn Tyr
            20                  25                  30

Leu Asn Trp Tyr Leu Gln Lys Pro Gly Gln Ser Pro Gln Leu Leu Ile
```

```
                    35                  40                  45
Tyr Tyr Thr Ser Thr Leu His Leu Gly Ile Pro Asp Arg Phe Ser Gly
 50                  55                  60

Ser Gly Ser Gly Thr Asp Phe Thr Leu Thr Ile Ser Arg Leu Glu Pro
 65                  70                  75                  80

Glu Asp Phe Ala Val Tyr Tyr Cys Gln Gln Tyr Tyr Asn Leu Pro Trp
                 85                  90                  95

Thr Phe Gly Gln Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
                115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
                195                 200                 205

Phe Asn Arg Gly Glu Cys
    210

<210> SEQ ID NO 47
<211> LENGTH: 642
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 47
gacatccaga tgacccagtc tccatcctcc ctgtctgcat ctgtaggaga cagagtcacc      60
atcacttgca gttcaagtca ggacatcagc aattatttaa actggtacct gcagaagcca     120
gggcagtctc cacagctcct gatctattac acatcaacct acacttagg gatcccagac      180 aggttcagtg gcagtgggtc tgggacagac ttcactctca ccatcagcag actggagcct     240
gaagattttg cagtgtatta ctgtcagcag tattataacc ttccgtggac gttcggccaa     300
gggaccaagg tggaaatcaa acgtacggtg gctgcaccat ctgtcttcat cttcccgcca     360
tctgatgagc agttgaaatc tggaactgcc tctgttgtgt gcctgctgaa taacttctat     420
cccagagagg ccaaagtaca gtggaaggtg gataacgccc tccaatcggg taactcccag     480
gagagtgtca cagagcagga cagcaaggac agcacctaca gcctcagcag caccctgacg     540
ctgagcaaag cagactacga gaaacacaaa gtctacgcct gcgaagtcac ccatcagggc     600
ctgagctcgc ccgtcacaaa gagcttcaac agggagagt gt                        642

<210> SEQ ID NO 48
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 48
```

```
Glu Ile Val Leu Thr Gln Ser Pro Ala Thr Leu Ser Leu Ser Pro Gly
1               5                  10                  15

Glu Arg Ala Thr Leu Ser Cys Ser Ser Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Thr Leu His Leu Gly Val Pro Ser Arg Phe Ser Gly
    50                  55                  60

Ser Gly Ser Gly Thr Asp Phe Thr Phe Thr Ile Ser Ser Leu Glu Ala
65                  70                  75                  80

Glu Asp Ala Ala Thr Tyr Tyr Cys Gln Gln Tyr Tyr Asn Leu Pro Trp
                85                  90                  95

Thr Phe Gly Gln Gly Thr Lys Val Glu Ile Lys
            100                 105

<210> SEQ ID NO 49
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 49
gaaattgtgt tgacacagtc tccagccacc ctgtctttgt ctccagggga aagagccacc    60
ctctcctgca gttcaagtca ggacatcagc aattatttaa actggtatca gcagaaacca   120
gggaaagctc ctaagctcct gatctattac acatcaacct tacacttagg ggtcccctcg   180
aggttcagtg gcagtggatc tgggacagat ttcaccttta ccatcagtag cctggaagct   240
gaagatgctg caacatatta ctgtcagcag tattataacc ttccgtggac gttcggccaa   300
gggaccaagg tggaaatcaa a                                              321

<210> SEQ ID NO 50
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 50

Glu Ile Val Leu Thr Gln Ser Pro Ala Thr Leu Ser Leu Ser Pro Gly
1               5                  10                  15

Glu Arg Ala Thr Leu Ser Cys Ser Ser Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Thr Leu His Leu Gly Val Pro Ser Arg Phe Ser Gly
    50                  55                  60

Ser Gly Ser Gly Thr Asp Phe Thr Phe Thr Ile Ser Ser Leu Glu Ala
65                  70                  75                  80

Glu Asp Ala Ala Thr Tyr Tyr Cys Gln Gln Tyr Tyr Asn Leu Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125
```

Thr Ala Ser Val Val Cys Leu Leu Asn Asn Phe Tyr Pro Arg Glu Ala
            130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 51
<211> LENGTH: 642
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 51
gaaattgtgt tgacacagtc tccagccacc ctgtctttgt ctccagggga aagagccacc      60
ctctcctgca gttcaagtca ggacatcagc aattatttaa actggtatca gcagaaacca     120
gggaaagctc ctaagctcct gatctattac acatcaacct tacacttagg ggtcccctcg     180
aggttcagtg gcagtggatc tgggacagat ttcaccttta ccatcagtag cctggaagct     240
gaagatgctg caacatatta ctgtcagcag tattataacc ttccgtggac gttcggccaa     300
gggaccaagg tggaaatcaa acgtacggtg gctgcaccat ctgtcttcat cttcccgcca     360
tctgatgagc agttgaaatc tggaactgcc tctgttgtgt gcctgctgaa taacttctat     420
cccagagagg ccaaagtaca gtggaaggtg gataacgccc tccaatcggg taactcccag     480
gagagtgtca cagagcagga cagcaaggac agcacctaca gcctcagcag caccctgacg     540
ctgagcaaag cagactacga gaaacacaaa gtctacgcct gcgaagtcac ccatcagggc     600
ctgagctcgc ccgtcacaaa gagcttcaac aggggagagt gt                        642

<210> SEQ ID NO 52
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 52

Asp Ile Val Met Thr Gln Thr Pro Leu Ser Leu Pro Val Thr Pro Gly
1               5                   10                  15

Glu Pro Ala Ser Ile Ser Cys Ser Ser Ser Gln Asp Ile Ser Asn Tyr
            20                  25                  30

Leu Asn Trp Tyr Gln Gln Lys Pro Gly Gln Ala Pro Arg Leu Leu Ile
        35                  40                  45

Tyr Tyr Thr Ser Thr Leu His Leu Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Tyr Asn Leu Pro Trp
                85                  90                  95

Thr Phe Gly Gln Gly Thr Lys Val Glu Ile Lys
            100                 105

<210> SEQ ID NO 53
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 53
gatattgtga tgacccagac tccactctcc ctgcccgtca cccctggaga gccggcctcc      60
atctcctgca gttcaagtca ggacatcagc aattatttaa actggtacca gcagaaacct     120
ggccaggctc ccaggctcct catctattac acatcaacct tacacttagg ggtcccatca     180
aggttcagcg gcagtggatc tgggacagaa ttcactctca ccatcagcag cctgcagcct     240
gatgattttg caacttatta ctgtcagcag tattataacc ttccgtggac gttcggccaa     300
gggaccaagg tggaaatcaa a                                                321

<210> SEQ ID NO 54
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 54

Asp Ile Val Met Thr Gln Thr Pro Leu Ser Leu Pro Val Thr Pro Gly
1               5                   10                  15

Glu Pro Ala Ser Ile Ser Cys Ser Ser Ser Gln Asp Ile Ser Asn Tyr
            20                  25                  30

Leu Asn Trp Tyr Gln Gln Lys Pro Gly Gln Ala Pro Arg Leu Leu Ile
        35                  40                  45

Tyr Tyr Thr Ser Thr Leu His Leu Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Tyr Asn Leu Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 55
<211> LENGTH: 642
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 55
gatattgtga tgacccagac tccactctcc ctgcccgtca cccctggaga gccggcctcc      60
atctcctgca gttcaagtca ggacatcagc aattatttaa actggtacca gcagaaacct    120
ggccaggctc ccaggctcct catctattac acatcaacct tacacttagg ggtcccatca    180
aggttcagcg gcagtggatc tgggacagaa ttcactctca ccatcagcag cctgcagcct    240
gatgattttg caacttatta ctgtcagcag tattataacc ttccgtggac gttcggccaa    300
gggaccaagg tggaaatcaa acgtacggtg gctgcaccat ctgtcttcat cttcccgcca    360
tctgatgagc agttgaaatc tggaactgcc tctgttgtgt gcctgctgaa taacttctat    420
cccagagagg ccaaagtaca gtggaaggtg gataacgccc tccaatcggg taactcccag    480
gagagtgtca cagagcagga cagcaaggac agcacctaca gcctcagcag cacccctgacg    540 ctgagcaaag cagactacga gaaacacaaa gtctacgcct gcgaagtcac ccatcagggc    600
ctgagctcgc ccgtcacaaa gagcttcaac aggggagagt gt                        642

<210> SEQ ID NO 56
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 56

Asp Ile Gln Met Thr Gln Ser Pro Ser Ser Leu Ser Ala Ser Val Gly
1               5                   10                  15

Asp Arg Val Thr Ile Thr Cys Ser Ser Ser Gln Asp Ile Ser Asn Tyr
            20                  25                  30

Leu Asn Trp Tyr Leu Gln Lys Pro Gly Gln Ser Pro Gln Leu Leu Ile
        35                  40                  45

Tyr Tyr Thr Ser Thr Leu His Leu Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Tyr Asn Leu Pro Trp
                85                  90                  95

Thr Phe Gly Gln Gly Thr Lys Val Glu Ile Lys
            100                 105

<210> SEQ ID NO 57
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 57
gacatccaga tgacccagtc tccatcctcc ctgtctgcat ctgtaggaga cagagtcact      60

```
atcacttgca gttcaagtca ggacatcagc aattatttaa actggtacct gcagaagcca      120
gggcagtctc cacagctcct gatctattac acatcaacct tacacttagg ggtcccatca      180
aggttcagcg gcagtggatc tgggacagaa ttcactctca ccatcagcag cctgcagcct      240
gatgattttg caacttatta ctgtcagcag tattataacc ttccgtggac gttcggccaa      300
gggaccaagg tggaaatcaa a                                                321
```

<210> SEQ ID NO 58
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 58

```
Asp Ile Gln Met Thr Gln Ser Pro Ser Ser Leu Ser Ala Ser Val Gly
1               5                   10                  15

Asp Arg Val Thr Ile Thr Cys Ser Ser Ser Gln Asp Ile Ser Asn Tyr
            20                  25                  30

Leu Asn Trp Tyr Leu Gln Lys Pro Gly Gln Ser Pro Gln Leu Leu Ile
        35                  40                  45

Tyr Tyr Thr Ser Thr Leu His Leu Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Tyr Asn Leu Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 59
<211> LENGTH: 642
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 59

```
gacatccaga tgacccagtc tccatcctcc ctgtctgcat ctgtaggaga cagagtcact      60
atcacttgca gttcaagtca ggacatcagc aattatttaa actggtacct gcagaagcca      120
gggcagtctc cacagctcct gatctattac acatcaacct tacacttagg ggtcccatca      180
```

```
aggttcagcg gcagtggatc tgggacagaa ttcactctca ccatcagcag cctgcagcct    240
gatgattttg caacttatta ctgtcagcag tattataacc ttccgtggac gttcggccaa    300
gggaccaagg tggaaatcaa acgtacggtg ctgcaccat ctgtcttcat cttcccgcca    360
tctgatgagc agttgaaatc tggaactgcc tctgttgtgt gcctgctgaa taacttctat    420
cccagagagg ccaaagtaca gtggaaggtg gataacgccc tccaatcggg taactcccag    480
gagagtgtca cagagcagga cagcaaggac agcacctaca gcctcagcag caccctgacg    540
ctgagcaaag cagactacga gaaacacaaa gtctacgcct gcgaagtcac ccatcagggc    600
ctgagctcgc ccgtcacaaa gagcttcaac aggggagagt gt                       642
```

<210> SEQ ID NO 60
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 60

Glu Ile Val Leu Thr Gln Ser Pro Asp Phe Gln Ser Val Thr Pro Lys
1               5                   10                  15

Glu Lys Val Thr Ile Thr Cys Ser Ser Ser Gln Asp Ile Ser Asn Tyr
            20                  25                  30

Leu Asn Trp Tyr Gln Gln Lys Pro Gly Gln Ala Pro Arg Leu Leu Ile
        35                  40                  45

Tyr Tyr Thr Ser Thr Leu His Leu Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Asn Leu Pro Trp
                85                  90                  95

Thr Phe Gly Gln Gly Thr Lys Val Glu Ile Lys
            100                 105

<210> SEQ ID NO 61
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 61

```
gaaattgtgc tgactcagtc tccagacttt cagtctgtga ctccaaagga gaaagtcacc    60
atcacctgca gttcaagtca ggacatcagc aattatttaa actggtacca gcagaaacct    120
ggccaggctc ccaggctcct catctattac acatcaacct tacacttagg ggtcccatca    180
aggttcagcg gcagtggatc tgggacagat ttcactctca ccatcagcag cctgcagcct    240
gaagattttg caacttatta ctgtcagcag tattataacc ttccgtggac gttcggccaa    300
gggaccaagg tggaaatcaa a                                              321
```

<210> SEQ ID NO 62
<211> LENGTH: 214
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 62

```
Glu Ile Val Leu Thr Gln Ser Pro Asp Phe Gln Ser Val Thr Pro Lys
1               5                   10                  15
Glu Lys Val Thr Ile Thr Cys Ser Ser Ser Gln Asp Ile Ser Asn Tyr
            20                  25                  30
Leu Asn Trp Tyr Gln Gln Lys Pro Gly Gln Ala Pro Arg Leu Leu Ile
        35                  40                  45
Tyr Tyr Thr Ser Thr Leu His Leu Gly Val Pro Ser Arg Phe Ser Gly
    50                  55                  60
Ser Gly Ser Gly Thr Asp Phe Thr Leu Thr Ile Ser Ser Leu Gln Pro
65                  70                  75                  80
Glu Asp Phe Ala Thr Tyr Tyr Cys Gln Gln Tyr Tyr Asn Leu Pro Trp
                85                  90                  95
Thr Phe Gly Gln Gly Thr Lys Val Glu Ile Lys Arg Thr Val Ala Ala
            100                 105                 110
Pro Ser Val Phe Ile Phe Pro Pro Ser Asp Glu Gln Leu Lys Ser Gly
        115                 120                 125
Thr Ala Ser Val Val Cys Leu Leu Asn Asn Phe Tyr Pro Arg Glu Ala
    130                 135                 140
Lys Val Gln Trp Lys Val Asp Asn Ala Leu Gln Ser Gly Asn Ser Gln
145                 150                 155                 160
Glu Ser Val Thr Glu Gln Asp Ser Lys Asp Ser Thr Tyr Ser Leu Ser
                165                 170                 175
Ser Thr Leu Thr Leu Ser Lys Ala Asp Tyr Glu Lys His Lys Val Tyr
            180                 185                 190
Ala Cys Glu Val Thr His Gln Gly Leu Ser Ser Pro Val Thr Lys Ser
        195                 200                 205
Phe Asn Arg Gly Glu Cys
    210
```

<210> SEQ ID NO 63
<211> LENGTH: 642
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 63

```
gaaattgtgc tgactcagtc tccagacttt cagtctgtga ctccaaagga gaaagtcacc      60
atcacctgca gttcaagtca ggacatcagc aattatttaa actggtacca gcagaaacct     120
ggccaggctc ccaggctcct catctattac acatcaacct acacttaggg gtcccatca      180
aggttcagcg gcagtggatc tgggacagat tcactctca ccatcagcag cctgcagcct     240
gaagattttg caacttatta ctgtcagcag tattataacc ttccgtggac gttcggccaa     300
gggaccaagg tggaaatcaa acgtacggtg gctgcaccat ctgtcttcat cttcccgcca     360
tctgatgagc agttgaaatc tggaactgcc tctgttgtgt gcctgctgaa taacttctat     420
cccagagagg ccaaagtaca gtggaaggtg gataacgccc tccaatcggg taactcccag     480
gagagtgtca cagagcagga cagcaaggac agcacctaca gcctcagcag caccctgacg     540
ctgagcaaag cagactacga gaaacacaaa gtctacgcct gcgaagtcac ccatcagggc     600
ctgagctcgc ccgtcacaaa gagcttcaac aggggagagt gt                       642
```

<210> SEQ ID NO 64
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 64

Gln Val Gln Leu Val Gln Ser Gly Ala Glu Val Lys Lys Pro Gly Ala
1               5                   10                  15

Ser Val Lys Val Ser Cys Lys Ala Ser Gly Phe Thr Leu Thr Asn Tyr
            20                  25                  30

Gly Met Asn Trp Val Arg Gln Ala Arg Gly Gln Arg Leu Glu Trp Ile
        35                  40                  45

Gly Trp Ile Asn Thr Asp Thr Gly Glu Pro Thr Tyr Ala Asp Asp Phe
    50                  55                  60

Lys Gly Arg Phe Val Phe Ser Leu Asp Thr Ser Val Ser Thr Ala Tyr
65                  70                  75                  80

Leu Gln Ile Cys Ser Leu Lys Ala Glu Asp Thr Ala Val Tyr Tyr Cys
                85                  90                  95

Ala Arg Asn Pro Pro Tyr Tyr Gly Thr Asn Asn Ala Glu Ala Met
            100                 105                 110

Asp Tyr Trp Gly Gln Gly Thr Thr Val Thr Val Ser Ser
        115                 120                 125

<210> SEQ ID NO 65
<211> LENGTH: 375
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 65
caggttcagc tggtgcagtc tggagctgag gtgaagaagc ctggggcctc agtgaaggtc     60
tcctgcaagg cttctggatt taccctcaca aactatggaa tgaactgggt gcgacaggct    120
cgtggacaac gccttgagtg gataggttgg ataaacaccg acactggaga gccaacatat    180
gctgatgact caagggaag atttgtcttc tccttggaca cctctgtcag cacggcatat    240
ctgcagatct gcagcctaaa ggctgaggac actgccgtgt attactgtgc aagaaaccct    300
ccctattact acggtactaa taacgcggag gctatggact actggggcca gggcaccacc    360
gtgaccgtgt cctcc                                                    375

<210> SEQ ID NO 66
<211> LENGTH: 452
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 66

Gln Val Gln Leu Val Gln Ser Gly Ala Glu Val Lys Lys Pro Gly Ala
1               5                   10                  15

Ser Val Lys Val Ser Cys Lys Ala Ser Gly Phe Thr Leu Thr Asn Tyr
            20                  25                  30

Gly Met Asn Trp Val Arg Gln Ala Arg Gly Gln Arg Leu Glu Trp Ile
        35                  40                  45

-continued

```
Gly Trp Ile Asn Thr Asp Thr Gly Glu Pro Thr Tyr Ala Asp Asp Phe
        50                  55                  60

Lys Gly Arg Phe Val Phe Ser Leu Asp Thr Ser Val Ser Thr Ala Tyr
 65                  70                  75                  80

Leu Gln Ile Cys Ser Leu Lys Ala Glu Asp Thr Ala Val Tyr Tyr Cys
                     85                  90                  95

Ala Arg Asn Pro Pro Tyr Tyr Tyr Gly Thr Asn Asn Ala Glu Ala Met
                100                 105                 110

Asp Tyr Trp Gly Gln Gly Thr Thr Val Thr Val Ser Ser Ala Ser Thr
            115                 120                 125

Lys Gly Pro Ser Val Phe Pro Leu Ala Pro Cys Ser Arg Ser Thr Ser
130                 135                 140

Glu Ser Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
                180                 185                 190

Val Val Thr Val Pro Ser Ser Ser Leu Gly Thr Lys Thr Tyr Thr Cys
                195                 200                 205

Asn Val Asp His Lys Pro Ser Asn Thr Lys Val Asp Lys Arg Val Glu
210                 215                 220

Ser Lys Tyr Gly Pro Pro Cys Pro Pro Cys Pro Ala Pro Glu Phe Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
                260                 265                 270

Gln Glu Asp Pro Glu Val Gln Phe Asn Trp Tyr Val Asp Gly Val Glu
            275                 280                 285

Val His Asn Ala Lys Thr Lys Pro Arg Glu Glu Gln Phe Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Gly Leu Pro Ser Ser
                325                 330                 335

Ile Glu Lys Thr Ile Ser Lys Ala Lys Gly Gln Pro Arg Glu Pro Gln
                340                 345                 350

Val Tyr Thr Leu Pro Pro Ser Gln Glu Glu Met Thr Lys Asn Gln Val
            355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Arg Leu Thr
                405                 410                 415

Val Asp Lys Ser Arg Trp Gln Glu Gly Asn Val Phe Ser Cys Ser Val
                420                 425                 430

Met His Glu Ala Leu His Asn His Tyr Thr Gln Lys Ser Leu Ser Leu
                435                 440                 445

Ser Leu Gly Lys
    450
```

<210> SEQ ID NO 67
<211> LENGTH: 1356
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 67

```
caggttcagc tggtgcagtc tggagctgag gtgaagaagc tggggcctc agtgaaggtc      60
tcctgcaagg cttctggatt taccctcaca aactatggaa tgaactgggt gcgacaggct    120
cgtggacaac gccttgagtg gataggttgg ataaacaccg acactggaga gccaacatat   180
gctgatgact tcaagggaag atttgtcttc tccttggaca cctctgtcag cacggcatat   240
ctgcagatct gcagcctaaa ggctgaggac actgccgtgt attactgtgc aagaaaccct   300
ccctattact acggtactaa taacgcggag gctatggact actggggcca gggcaccacc   360
gtgaccgtgt cctccgcttc caccaagggc ccatccgtct tccccctggc gccctgctcc   420
aggagcacct ccgagagcac agccgccctg gctgcctgg tcaaggacta cttccccgaa    480
ccggtgacgg tgtcgtggaa ctcaggcgcc ctgaccagcg gcgtgcacac cttcccggct   540
gtcctacagt cctcaggact ctactccctc agcagcgtgg tgaccgtgcc ctccagcagc   600
ttgggcacga agacctacac ctgcaacgta gatcacaagc ccagcaacac caaggtggac   660
aagagagttg agtccaaata tggtcccca tgcccaccgt gcccagcacc tgagttcctg    720
gggggaccat cagtcttcct gttccccca aacccaagg acactctcat gatctcccgg    780
acccctgagg tcacgtgcgt ggtggtggac gtgagccagg aagaccccga ggtccagttc    840
aactggtacg tggatggcgt ggaggtgcat aatgccaaga caaagccgcg ggaggagcag   900
ttcaacagca cgtaccgtgt ggtcagcgtc ctcaccgtcc tgcaccagga ctggctgaac   960
ggcaaggagt acaagtgcaa ggtgtccaac aaaggcctcc cgtcctccat cgagaaaacc  1020
atctccaaag ccaaagggca gccccgagag ccacaggtgt acaccctgcc cccatcccag  1080
gaggagatga ccaagaacca ggtcagcctg acctgcctgg tcaaaggctt ctaccccagc  1140
gacatcgccg tggagtggga gagcaatggg cagccggaga caactacaa gaccacgcct   1200
cccgtgctgg actccgacgg ctccttcttc ctctacagca ggctaaccgt ggacaagagc  1260
aggtggcagg aggggaatgt cttctcatgc tccgtgatgc atgaggctct gcacaaccac  1320
tacacacaga gagcctctc cctgtctctg ggtaaa                              1356
```

<210> SEQ ID NO 68
<211> LENGTH: 125
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 68

```
Gln Val Gln Leu Val Gln Ser Gly Ala Glu Val Lys Lys Pro Gly Ala
1               5                   10                  15

Ser Val Lys Val Ser Cys Lys Ala Ser Gly Phe Thr Leu Thr Asn Tyr
            20                  25                  30

Gly Met Asn Trp Val Arg Gln Ala Pro Gly Gln Gly Leu Glu Trp Met
        35                  40                  45

Gly Trp Ile Asn Thr Asp Thr Gly Glu Pro Thr Tyr Ala Asp Asp Phe
    50                  55                  60
```

Lys Gly Arg Phe Val Phe Ser Leu Asp Thr Ser Val Ser Thr Ala Tyr
65                  70                  75                  80

Leu Gln Ile Cys Ser Leu Lys Ala Glu Asp Thr Ala Val Tyr Tyr Cys
                85                  90                  95

Ala Arg Asn Pro Pro Tyr Tyr Tyr Gly Thr Asn Asn Ala Glu Ala Met
            100                 105                 110

Asp Tyr Trp Gly Gln Gly Thr Thr Val Thr Val Ser Ser
        115                 120                 125

<210> SEQ ID NO 69
<211> LENGTH: 375
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 69
caggttcagc tggtgcagtc cggagctgag gtgaagaagc ctggggcctc agtgaaggtc      60
tcctgcaagg cttctggatt taccctcaca aactatggaa tgaactgggt gcgacaggcc    120
cctggacaag ggcttgagtg gatgggttgg ataaacaccg acactggaga gccaacatat    180
gctgatgact tcaagggaag atttgtcttc tccttggaca cctctgtcag cacggcatat    240
ctgcagatct gcagcctaaa ggctgaggac actgccgtgt attactgtgc aagaaaccct    300
ccctattact acggtactaa taacgcggag gctatggact actggggcca gggcaccacc    360
gtgaccgtgt cctcc                                                     375

<210> SEQ ID NO 70
<211> LENGTH: 452
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 70

Gln Val Gln Leu Val Gln Ser Gly Ala Glu Val Lys Lys Pro Gly Ala
1               5                   10                  15

Ser Val Lys Val Ser Cys Lys Ala Ser Gly Phe Thr Leu Thr Asn Tyr
            20                  25                  30

Gly Met Asn Trp Val Arg Gln Ala Pro Gly Gln Gly Leu Glu Trp Met
        35                  40                  45

Gly Trp Ile Asn Thr Asp Thr Gly Glu Pro Thr Tyr Ala Asp Asp Phe
    50                  55                  60

Lys Gly Arg Phe Val Phe Ser Leu Asp Thr Ser Val Ser Thr Ala Tyr
65                  70                  75                  80

Leu Gln Ile Cys Ser Leu Lys Ala Glu Asp Thr Ala Val Tyr Tyr Cys
                85                  90                  95

Ala Arg Asn Pro Pro Tyr Tyr Tyr Gly Thr Asn Asn Ala Glu Ala Met
            100                 105                 110

Asp Tyr Trp Gly Gln Gly Thr Thr Val Thr Val Ser Ser Ala Ser Thr
        115                 120                 125

Lys Gly Pro Ser Val Phe Pro Leu Ala Pro Cys Ser Arg Ser Thr Ser
    130                 135                 140

Glu Ser Thr Ala Ala Leu Gly Cys Leu Val Lys Asp Tyr Phe Pro Glu
145                 150                 155                 160

```
Pro Val Thr Val Ser Trp Asn Ser Gly Ala Leu Thr Ser Gly Val His
            165                 170                 175

Thr Phe Pro Ala Val Leu Gln Ser Ser Gly Leu Tyr Ser Leu Ser Ser
        180                 185                 190

Val Val Thr Val Pro Ser Ser Ser Leu Gly Thr Lys Thr Tyr Thr Cys
        195                 200                 205

Asn Val Asp His Lys Pro Ser Asn Thr Lys Val Asp Lys Arg Val Glu
    210                 215                 220

Ser Lys Tyr Gly Pro Pro Cys Pro Pro Cys Pro Ala Pro Glu Phe Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

Gln Glu Asp Pro Glu Val Gln Phe Asn Trp Tyr Val Asp Gly Val Glu
        275                 280                 285

Val His Asn Ala Lys Thr Lys Pro Arg Glu Glu Gln Phe Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Gly Leu Pro Ser Ser
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Gln Glu Glu Met Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Arg Leu Thr
                405                 410                 415

Val Asp Lys Ser Arg Trp Gln Glu Gly Asn Val Phe Ser Cys Ser Val
            420                 425                 430

Met His Glu Ala Leu His Asn His Tyr Thr Gln Lys Ser Leu Ser Leu
        435                 440                 445

Ser Leu Gly Lys
    450

<210> SEQ ID NO 71
<211> LENGTH: 1356
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 71
caggttcagc tggtgcagtc cggagctgag gtgaagaagc ctggggcctc agtgaaggtc     60
tcctgcaagg cttctggatt taccctcaca aactatggaa tgaactgggt gcgacaggcc    120
cctggacaag ggcttgagtg gatgggttgg ataaacaccg acactggaga gccaacatat    180
gctgatgact tcaagggaag atttgtcttc tccttggaca cctctgtcag cacggcatat    240
ctgcagatct gcagcctaaa ggctgaggac actgccgtgt attactgtgc aagaaaccct    300
ccctattact acggtactaa taacgcggag gctatggact actggggcca gggcaccacc    360
```

```
gtgaccgtgt cctccgcttc caccaagggc ccatccgtct tcccctggc gccctgctcc        420 aggagcacct ccgagagcac agccgccctg ggctgcctgg tcaaggacta cttcccgaa        480 ccggtgacgg tgtcgtggaa ctcaggcgcc ctgaccagcg gcgtgcacac cttcccggct       540
gtcctacagt cctcaggact ctactccctc agcagcgtgg tgaccgtgcc ctccagcagc       600
ttgggcacga agacctacac ctgcaacgta gatcacaagc ccagcaacac caaggtggac       660
aagagagttg agtccaaata tggtccccca tgcccaccgt gcccagcacc tgagttcctg       720
gggggaccat cagtcttcct gttcccccca aaacccaagg acactctcat gatctcccgg       780
acccctgagg tcacgtgcgt ggtggtggac gtgagccagg aagaccccga ggtccagttc       840
aactggtacg tggatggcgt ggaggtgcat aatgccaaga caaagccgcg ggaggagcag       900
ttcaacagca cgtaccgtgt ggtcagcgtc ctcaccgtcc tgcaccagga ctggctgaac       960
ggcaaggagt acaagtgcaa ggtgtccaac aaaggcctcc cgtcctccat cgagaaaacc      1020
atctccaaag ccaaagggca gccccgagag ccacaggtgt acaccctgcc cccatcccag      1080
gaggagatga ccaagaacca ggtcagcctg acctgcctgg tcaaaggctt ctaccccagc      1140
gacatcgccg tggagtggga gagcaatggg cagccggaga acaactacaa gaccacgcct      1200
cccgtgctgg actccgacgg ctccttcttc ctctacagca ggctaaccgt ggacaagagc      1260
aggtggcagg aggggaatgt cttctcatgc tccgtgatgc atgaggctct gcacaaccac      1320
tacacacaga agagcctctc cctgtctctg ggtaaa                                1356
```

<210> SEQ ID NO 72
<211> LENGTH: 125
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 72

```
Glu Val Gln Leu Val Gln Ser Gly Ala Glu Val Lys Lys Pro Gly Ala
1               5                   10                  15

Thr Val Lys Ile Ser Cys Lys Val Ser Gly Phe Thr Leu Thr Asn Tyr
            20                  25                  30

Gly Met Asn Trp Ile Arg Gln Ser Pro Ser Arg Gly Leu Glu Trp Leu
        35                  40                  45

Gly Trp Ile Asn Thr Asp Thr Gly Glu Pro Thr Tyr Ala Asp Asp Phe
    50                  55                  60

Lys Gly Arg Phe Val Phe Ser Leu Asp Thr Ser Val Ser Thr Ala Tyr
65                  70                  75                  80

Leu Gln Ile Cys Ser Leu Lys Ala Glu Asp Thr Ala Val Tyr Tyr Cys
                85                  90                  95

Ala Arg Asn Pro Pro Tyr Tyr Tyr Gly Thr Asn Asn Ala Glu Ala Met
            100                 105                 110

Asp Tyr Trp Gly Gln Gly Thr Thr Val Thr Val Ser Ser
        115                 120                 125
```

<210> SEQ ID NO 73
<211> LENGTH: 375
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 73

```
gaggtccagc tggtacagtc tggggctgag gtgaagaagc ctggggctac agtgaaaatc    60
tcctgcaagg tttctggatt taccctcaca aactatggaa tgaactggat caggcagtcc   120
ccatcgagag gccttgagtg gctgggttgg ataaacaccg acactggaga gccaacatat   180
gctgatgact tcaagggaag atttgtcttc tccttggaca cctctgtcag cacggcatat   240
ctgcagatct gcagcctaaa ggctgaggac actgccgtgt attactgtgc aagaaaccct   300
ccctattact acggtactaa taacgcggag gctatggact actggggcca gggcaccacc   360
gtgaccgtgt cctcc                                                    375
```

<210> SEQ ID NO 74
<211> LENGTH: 452
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 74

```
Glu Val Gln Leu Val Gln Ser Gly Ala Glu Val Lys Lys Pro Gly Ala
1               5                   10                  15

Thr Val Lys Ile Ser Cys Lys Val Ser Gly Phe Thr Leu Thr Asn Tyr
            20                  25                  30

Gly Met Asn Trp Ile Arg Gln Ser Pro Ser Arg Gly Leu Glu Trp Leu
        35                  40                  45

Gly Trp Ile Asn Thr Asp Thr Gly Glu Pro Thr Tyr Ala Asp Asp Phe
    50                  55                  60

Lys Gly Arg Phe Val Phe Ser Leu Asp Thr Ser Val Ser Thr Ala Tyr
65                  70                  75                  80

Leu Gln Ile Cys Ser Leu Lys Ala Glu Asp Thr Ala Val Tyr Tyr Cys
                85                  90                  95

Ala Arg Asn Pro Pro Tyr Tyr Gly Thr Asn Asn Ala Glu Ala Met
            100                 105                 110

Asp Tyr Trp Gly Gln Gly Thr Thr Val Thr Val Ser Ser Ala Ser Thr
        115                 120                 125

Lys Gly Pro Ser Val Phe Pro Leu Ala Pro Cys Ser Arg Ser Thr Ser
    130                 135                 140

Glu Ser Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Lys Thr Tyr Thr Cys
        195                 200                 205

Asn Val Asp His Lys Pro Ser Asn Thr Lys Val Asp Lys Arg Val Glu
    210                 215                 220

Ser Lys Tyr Gly Pro Pro Cys Pro Pro Cys Pro Ala Pro Glu Phe Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

Gln Glu Asp Pro Glu Val Gln Phe Asn Trp Tyr Val Asp Gly Val Glu
```

```
               275                 280                 285
Val His Asn Ala Lys Thr Lys Pro Arg Glu Glu Gln Phe Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Gly Leu Pro Ser Ser
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Gln Glu Glu Met Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Arg Leu Thr
                405                 410                 415

Val Asp Lys Ser Arg Trp Gln Glu Gly Asn Val Phe Ser Cys Ser Val
            420                 425                 430

Met His Glu Ala Leu His Asn His Tyr Thr Gln Lys Ser Leu Ser Leu
        435                 440                 445

Ser Leu Gly Lys
    450

<210> SEQ ID NO 75
<211> LENGTH: 1356
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 75
gaggtccagc tggtacagtc tggggctgag gtgaagaagc ctggggctac agtgaaaatc      60
tcctgcaagg tttctggatt taccctcaca aactatggaa tgaactggat caggcagtcc     120
ccatcgagag gccttgagtg gctgggttgg ataaacaccg acactggaga gccaacatat     180
gctgatgact caagggaag atttgtcttc tccttggaca cctctgtcag cacggcatat     240
ctgcagatct gcagcctaaa ggctgaggac actgccgtgt attactgtgc aagaaaccct     300
ccctattact acggtactaa taacgcggag gctatggact actggggcca gggcaccacc     360
gtgaccgtgt cctccgcttc caccaagggc ccatccgtct tcccctggc gccctgctcc     420 aggagcacct ccgagagcac agccgccctg gctgcctgg tcaaggacta cttccccgaa     480
ccggtgacgg tgtcgtggaa ctcaggcgcc ctgaccagcg gcgtgcacac cttcccggct     540
gtcctacagt cctcaggact ctactccctc agcagcgtgg tgaccgtgcc ctccagcagc     600
ttgggcacga agacctacac ctgcaacgta gatcacaagc ccagcaacac caaggtggac     660
aagagagttg agtccaaata tggtccccca tgcccaccgt gcccagcacc tgagttcctg     720
gggggaccat cagtcttcct gttcccccca aaacccaagg acactctcat gatctcccgg     780
acccctgagg tcacgtgcgt ggtggtggac gtgagccagg aagaccccga ggtccagttc     840
aactggtacg tggatggcgt ggaggtgcat aatgccaaga caaagccgcg ggaggagcag     900
ttcaacagca cgtaccgtgt ggtcagcgtc ctcaccgtcc tgcaccagga ctggctgaac     960
ggcaaggagt acaagtgcaa ggtgtccaac aaaggcctcc cgtcctccat cgagaaaacc    1020
```

```
atctccaaag ccaaagggca gccccgagag ccacaggtgt acaccctgcc cccatcccag    1080
gaggagatga ccaagaacca ggtcagcctg acctgcctgg tcaaaggctt ctaccccagc    1140
gacatcgccg tggagtggga gagcaatggg cagccggaga caactacaa gaccacgcct     1200 cccgtgctgg actccgacgg ctccttcttc ctctacagca ggctaaccgt ggacaagagc    1260
aggtggcagg aggggaatgt cttctcatgc tccgtgatgc atgaggctct gcacaaccac    1320
tacacacaga gagcctctc cctgtctctg ggtaaa                                1356

<210> SEQ ID NO 76
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 76

Glu Val Gln Leu Val Gln Ser Gly Ala Glu Val Lys Lys Pro Gly Glu
1               5                   10                  15

Ser Leu Arg Ile Ser Cys Lys Gly Ser Gly Phe Thr Leu Thr Asn Tyr
            20                  25                  30

Gly Met Asn Trp Val Arg Gln Ala Thr Gly Gln Gly Leu Glu Trp Met
        35                  40                  45

Gly Trp Ile Asn Thr Asp Thr Gly Glu Pro Thr Tyr Ala Asp Asp Phe
    50                  55                  60

Lys Gly Arg Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Asn Pro Pro Tyr Tyr Tyr Gly Thr Asn Asn Ala Glu Ala Met
            100                 105                 110

Asp Tyr Trp Gly Gln Gly Thr Thr Val Thr Val Ser Ser
        115                 120                 125

<210> SEQ ID NO 77
<211> LENGTH: 375
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 77
gaagtgcagc tggtgcagtc tggagcagag gtgaaaaagc ccggggagtc tctgaggatc    60
tcctgtaagg gttctggatt taccctcaca aactatggaa tgaactgggt gcgacaggcc    120
actggacaag gcttgagtg gatgggttgg ataaacaccg acactggaga gccaacatat     180
gctgatgact caagggaag agtcaccatc tcagccgaca gtccatcag caccgcctac     240 ctgcagtgga gcagcctgaa ggcctcggac accgccatgt attactgtgc aagaaaccct    300
ccctattact acggtactaa taacgcggag gctatggact actggggcca gggcaccacc    360
gtgaccgtgt cctcc                                                      375

<210> SEQ ID NO 78
<211> LENGTH: 452
<212> TYPE: PRT
<213> ORGANISM: Artificial Sequence
<220> FEATURE:
```

<223> OTHER INFORMATION: Description of Artificial Sequence: Synthetic polypeptide

<400> SEQUENCE: 78

```
Glu Val Gln Leu Val Gln Ser Gly Ala Glu Val Lys Pro Gly Glu
1               5                   10                  15

Ser Leu Arg Ile Ser Cys Lys Gly Ser Gly Phe Thr Leu Thr Asn Tyr
            20                  25                  30

Gly Met Asn Trp Val Arg Gln Ala Thr Gly Gln Gly Leu Glu Trp Met
        35                  40                  45

Gly Trp Ile Asn Thr Asp Thr Gly Glu Pro Thr Tyr Ala Asp Asp Phe
    50                  55                  60

Lys Gly Arg Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Asn Pro Pro Tyr Tyr Tyr Gly Thr Asn Asn Ala Glu Ala Met
            100                 105                 110

Asp Tyr Trp Gly Gln Gly Thr Thr Val Thr Val Ser Ser Ala Ser Thr
        115                 120                 125

Lys Gly Pro Ser Val Phe Pro Leu Ala Pro Cys Ser Arg Ser Thr Ser
    130                 135                 140

Glu Ser Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Lys Thr Tyr Thr Cys
        195                 200                 205

Asn Val Asp His Lys Pro Ser Asn Thr Lys Val Asp Lys Arg Val Glu
    210                 215                 220

Ser Lys Tyr Gly Pro Pro Cys Pro Pro Cys Pro Ala Pro Glu Phe Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

Gln Glu Asp Pro Glu Val Gln Phe Asn Trp Tyr Val Asp Gly Val Glu
        275                 280                 285

Val His Asn Ala Lys Thr Lys Pro Arg Glu Glu Gln Phe Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Gly Leu Pro Ser Ser
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Gln Glu Glu Met Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400
```

Pro Val Leu Asp Ser Asp Gly Ser Phe Phe Leu Tyr Ser Arg Leu Thr
            405                 410                 415

Val Asp Lys Ser Arg Trp Gln Glu Gly Asn Val Phe Ser Cys Ser Val
        420                 425                 430

Met His Glu Ala Leu His Asn His Tyr Thr Gln Lys Ser Leu Ser Leu
        435                 440                 445

Ser Leu Gly Lys
    450

<210> SEQ ID NO 79
<211> LENGTH: 1356
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 79

| | | | | | |
|---|---|---|---|---|---|
| gaagtgcagc | tggtgcagtc | tggagcagag | gtgaaaaagc | ccggggagtc | tctgaggatc | 60 |
| tcctgtaagg | gttctggatt | taccctcaca | aactatggaa | tgaactgggt | gcgacaggcc | 120 |
| actggacaag | ggcttgagtg | gatgggttgg | ataaacaccg | acactggaga | gccaacatat | 180 |
| gctgatgact | tcaagggaag | agtcaccatc | tcagccgaca | agtccatcag | caccgcctac | 240 |
| ctgcagtgga | gcagcctgaa | ggcctcggac | accgccatgt | attactgtgc | aagaaaccct | 300 |
| ccctattact | acggtactaa | taacgcggag | gctatggact | actggggcca | gggcaccacc | 360 |
| gtgaccgtgt | cctccgcttc | caccaagggc | ccatccgtct | tccccctggc | gccctgctcc | 420 |
| aggagcacct | ccgagagcac | agccgccctg | ggctgcctgg | tcaaggacta | cttccccgaa | 480 |
| ccggtgacgg | tgtcgtggaa | ctcaggcgcc | ctgaccagcg | gcgtgcacac | cttcccggct | 540 |
| gtcctacagt | cctcaggact | ctactccctc | agcagcgtgg | tgaccgtgcc | ctccagcagc | 600 |
| ttgggcacga | agacctacac | ctgcaacgta | gatcacaagc | ccagcaacac | caaggtggac | 660 |
| aagagagttg | agtccaaata | tggtccccca | tgcccaccgt | gcccagcacc | tgagttcctg | 720 |
| gggggaccat | cagtcttcct | gttccccccca | aaacccaagg | acactctcat | gatctcccgg | 780 |
| acccctgagg | tcacgtgcgt | ggtggtggac | gtgagccagg | aagacccccga | ggtccagttc | 840 |
| aactggtacg | tggatggcgt | ggaggtgcat | aatgccaaga | caaagccgcg | ggaggagcag | 900 |
| ttcaacagca | cgtaccgtgt | ggtcagcgtc | ctcaccgtcc | tgcaccagga | ctggctgaac | 960 |
| ggcaaggagt | acaagtgcaa | ggtgtccaac | aaaggcctcc | cgtcctccat | cgagaaaacc | 1020 |
| atctccaaag | ccaaagggca | gccccgagag | ccacaggtgt | acaccctgcc | cccatcccag | 1080 |
| gaggagatga | ccaagaacca | ggtcagcctg | acctgcctgg | tcaaaggctt | ctaccccagc | 1140 |
| gacatcgccg | tggagtggga | gagcaatggg | cagccggaga | acaactacaa | gaccacgcct | 1200 |
| cccgtgctgg | actccgacgg | ctccttcttc | ctctacagca | ggctaaccgt | ggacaagagc | 1260 |
| aggtggcagc | aggggaatgt | cttctcatgc | tccgtgatgc | atgaggctct | gcacaaccac | 1320 |
| tacacacaga | agagcctctc | cctgtctctg | ggtaaa | | | 1356 |

<210> SEQ ID NO 80
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 80

Gln Val Gln Leu Val Gln Ser Gly Ser Glu Leu Lys Lys Pro Gly Ala
1               5                   10                  15

Ser Val Lys Val Ser Cys Lys Ala Ser Gly Phe Thr Leu Thr Asn Tyr
            20                  25                  30

Gly Met Asn Trp Val Arg Gln Ala Pro Gly Gln Gly Leu Glu Trp Met
        35                  40                  45

Gly Trp Ile Asn Thr Asp Thr Gly Glu Pro Thr Tyr Ala Asp Asp Phe
    50                  55                  60

Lys Gly Arg Phe Val Phe Ser Leu Asp Thr Ser Val Ser Thr Ala Tyr
65                  70                  75                  80

Leu Gln Ile Ser Thr Leu Lys Ala Glu Asp Thr Ala Thr Tyr Phe Cys
                85                  90                  95

Ala Arg Asn Pro Pro Tyr Tyr Tyr Gly Thr Asn Asn Ala Glu Ala Met
            100                 105                 110

Asp Tyr Trp Gly Gln Gly Thr Thr Val Thr Val Ser Ser
        115                 120                 125

<210> SEQ ID NO 81
<211> LENGTH: 375
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 81
caggtgcagc tggtgcaatc tgggtctgag ttgaagaagc ctggggcctc agtgaaggtt      60
tcctgcaagg cttctggatt caccctgact aactatggca tgaattgggt gcgacaggcc     120
cctggacaag ggcttgagtg gatgggatgg atcaacaccg acactgggga gccaacgtat     180
gccgatgact tcaagggacg gtttgtcttc tccttggaca cctctgtcag cacggcatat     240
ctgcagatca gcacgctaaa ggctgaggac actgctacat atttctgtgc aagaaacccc     300
ccttattact acggtactaa taacgcggag gctatggact actggggcca gggcaccacc     360
gtgaccgtgt cctcc                                                      375

<210> SEQ ID NO 82
<211> LENGTH: 452
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 82

Gln Val Gln Leu Val Gln Ser Gly Ser Glu Leu Lys Lys Pro Gly Ala
1               5                   10                  15

Ser Val Lys Val Ser Cys Lys Ala Ser Gly Phe Thr Leu Thr Asn Tyr
            20                  25                  30

Gly Met Asn Trp Val Arg Gln Ala Pro Gly Gln Gly Leu Glu Trp Met
        35                  40                  45

Gly Trp Ile Asn Thr Asp Thr Gly Glu Pro Thr Tyr Ala Asp Asp Phe
    50                  55                  60

Lys Gly Arg Phe Val Phe Ser Leu Asp Thr Ser Val Ser Thr Ala Tyr
65                  70                  75                  80

Leu Gln Ile Ser Thr Leu Lys Ala Glu Asp Thr Ala Thr Tyr Phe Cys
                85                  90                  95

Ala Arg Asn Pro Pro Tyr Tyr Gly Thr Asn Asn Ala Glu Ala Met
            100                 105                 110

Asp Tyr Trp Gly Gln Gly Thr Thr Val Thr Val Ser Ser Ala Ser Thr
        115                 120                 125

Lys Gly Pro Ser Val Phe Pro Leu Ala Pro Cys Ser Arg Ser Thr Ser
130                 135                 140

Glu Ser Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Lys Thr Tyr Thr Cys
        195                 200                 205

Asn Val Asp His Lys Pro Ser Asn Thr Lys Val Asp Lys Arg Val Glu
210                 215                 220

Ser Lys Tyr Gly Pro Pro Cys Pro Pro Cys Pro Ala Pro Glu Phe Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

Gln Glu Asp Pro Glu Val Gln Phe Asn Trp Tyr Val Asp Gly Val Glu
        275                 280                 285

Val His Asn Ala Lys Thr Lys Pro Arg Glu Glu Gln Phe Asn Ser Thr
290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Gly Leu Pro Ser Ser
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Gln Glu Glu Met Thr Lys Asn Gln Val
        355                 360                 365

Ser Leu Thr Cys Leu Val Lys Gly Phe Tyr Pro Ser Asp Ile Ala Val
370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Arg Leu Thr
                405                 410                 415

Val Asp Lys Ser Arg Trp Gln Glu Gly Asn Val Phe Ser Cys Ser Val
            420                 425                 430

Met His Glu Ala Leu His Asn His Tyr Thr Gln Lys Ser Leu Ser Leu
        435                 440                 445

Ser Leu Gly Lys
    450

<210> SEQ ID NO 83
<211> LENGTH: 1356
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 83

```
caggtgcagc tggtgcaatc tgggtctgag ttgaagaagc ctggggcctc agtgaaggtt      60
tcctgcaagg cttctggatt caccctgact aactatggca tgaattgggt gcgacaggcc     120
cctggacaag ggcttgagtg gatgggatgg atcaacaccg acactgggga gccaacgtat     180
gccgatgact tcaagggacg gtttgtcttc tccttggaca cctctgtcag cacggcatat     240
ctgcagatca gcacgctaaa ggctgaggac actgctacat atttctgtgc aagaaacccc     300
ccttattact acggtactaa taacgcggag gctatggact actggggcca gggcaccacc     360
gtgaccgtgt cctccgcttc caccaagggc ccatccgtct tccccctggc gccctgctcc     420
aggagcacct ccgagagcac agccgccctg ggctgcctgg tcaaggacta cttccccgaa     480
ccggtgacgg tgtcgtggaa ctcaggcgcc ctgaccagcg gcgtgcacac cttcccggct     540
gtcctacagt cctcaggact ctactccctc agcagcgtgg tgaccgtgcc ctccagcagc     600
ttgggcacga agacctacac ctgcaacgta gaccacaagc ccagcaacac caaggtggac     660
aagagagttg agtccaaata tggtccccca tgcccaccgt gcccagcacc tgagttcctg     720
gggggaccat cagtcttcct gttcccccca aaacccaagg acactctcat gatctcccgg     780
acccctgagg tcacgtgcgt ggtggtggac gtgagccagg aagaccccga ggtccagttc     840
aactggtacg tggatggcgt ggaggtgcat aatgccaaga caaagccgcg ggaggagcag     900
ttcaacagca cgtaccgtgt ggtcagcgtc ctcaccgtcc tgcaccagga ctggctgaac     960
ggcaaggagt acaagtgcaa ggtgtccaac aaaggcctcc cgtcctccat cgagaaaacc    1020
atctccaaag ccaaagggca gccccgagag ccacaggtgt acaccctgcc cccatcccag    1080
gaggagatga ccaagaacca ggtcagcctg acctgcctgg tcaaaggctt ctaccccagc    1140
gacatcgccg tggagtggga gagcaatggg cagccggaga acaactacaa gaccacgcct    1200
cccgtgctgg actccgacgg ctccttcttc ctctacagca ggctaaccgt ggacaagagc    1260
aggtggcagg aggggaatgt cttctcatgc tccgtgatgc atgaggctct gcacaaccac    1320
tacacacaga agagcctctc cctgtctctg ggtaaa                              1356
```

<210> SEQ ID NO 84
<211> LENGTH: 107
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 84

```
Asp Ile Gln Met Thr Gln Ser Pro Ser Ser Leu Ser Ala Ser Val Gly
1               5                   10                  15

Asp Arg Val Thr Ile Thr Cys Ser Ser Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Thr Leu His Leu Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Tyr Tyr Asn Leu Pro Trp
                85                  90                  95

Thr Phe Gly Gln Gly Thr Lys Val Glu Ile Lys
            100                 105
```

<210> SEQ ID NO 85
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 85
gacatccaga tgacccagtc tccatcctcc ctgtctgcat ctgtaggaga cagagtcacc    60
atcacttgct cctctagtca ggacattagc aactatttaa attggtatca gcagaaacca   120
gggaaagccc ctaagctcct gatctactat acatccactt tgcacctggg ggtcccatca   180
aggttcagtg gaagtggatc tgggacagat tttactttca ccatcagcag cctgcagcct   240
gaagatattg caacatatta ctgtcaacag tattataatc tcccttggac gttcggccaa   300
gggaccaagg tggaaatcaa a                                             321

<210> SEQ ID NO 86
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 86

Asp Ile Gln Met Thr Gln Ser Pro Ser Ser Leu Ser Ala Ser Val Gly
1               5                   10                  15

Asp Arg Val Thr Ile Thr Cys Ser Ser Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Thr Leu His Leu Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Tyr Tyr Asn Leu Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 87

```
<211> LENGTH: 642
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 87
gacatccaga tgacccagtc tccatcctcc ctgtctgcat ctgtaggaga cagagtcacc      60
atcacttgct cctctagtca ggacattagc aactatttaa attggtatca gcagaaacca     120
gggaaagccc ctaagctcct gatctactat acatccactt tgcacctggg ggtcccatca     180
aggttcagtg gaagtggatc tgggacagat tttactttca ccatcagcag cctgcagcct     240
gaagatattg caacatatta ctgtcaacag tattataatc tcccttggac gttcggccaa     300
gggaccaagg tggaaatcaa acgtacggtg gctgcaccat ctgtcttcat cttcccgcca     360
tctgatgagc agttgaaatc tggaactgcc tctgttgtgt gcctgctgaa taacttctat     420
cccagagagg ccaaagtaca gtggaaggtg gataacgccc tccaatcggg taactcccag     480
gagagtgtca cagagcagga cagcaaggac agcacctaca gcctcagcag cacctgacg      540 ctgagcaaag cagactacga gaaacacaaa gtctacgcct gcgaagtcac ccatcagggc     600
ctgagctcgc ccgtcacaaa gagcttcaac aggggagagt gt                        642

<210> SEQ ID NO 88
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 88

Ala Ile Gln Leu Thr Gln Ser Pro Ser Ser Leu Ser Ala Ser Val Gly
1               5                   10                  15

Asp Arg Val Thr Ile Thr Cys Ser Ser Ser Gln Asp Ile Ser Asn Tyr
            20                  25                  30

Leu Asn Trp Tyr Gln Gln Lys Pro Gly Gln Ala Pro Arg Leu Leu Ile
        35                  40                  45

Tyr Tyr Thr Ser Thr Leu His Leu Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Asn Leu Pro Trp
                85                  90                  95

Thr Phe Gly Gln Gly Thr Lys Val Glu Ile Lys
            100                 105

<210> SEQ ID NO 89
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 89
gccatccagt tgacccagtc tccatcctcc ctgtctgcat ctgtaggaga cagagtcacc      60
atcacttgca gttcaagtca ggacatcagc aattatttaa actggtacca gcagaaacct     120
ggccaggctc ccaggctcct catctattac acatcaacct acacttaggg gtcccatca      180
```

```
aggttcagcg gcagtggatc tgggacagat ttcactctca ccatcagcag cctgcagcct    240
gaagattttg caacttatta ctgtcagcag tattataacc ttccgtggac gttcggccaa    300
gggaccaagg tggaaatcaa a                                              321
```

```
<210> SEQ ID NO 90
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 90
```

Ala Ile Gln Leu Thr Gln Ser Pro Ser Ser Leu Ser Ala Ser Val Gly
1               5                   10                  15

Asp Arg Val Thr Ile Thr Cys Ser Ser Ser Gln Asp Ile Ser Asn Tyr
            20                  25                  30

Leu Asn Trp Tyr Gln Gln Lys Pro Gly Gln Ala Pro Arg Leu Leu Ile
        35                  40                  45

Tyr Tyr Thr Ser Thr Leu His Leu Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Asn Leu Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

```
<210> SEQ ID NO 91
<211> LENGTH: 642
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 91
gccatccagt tgacccagtc tccatcctcc ctgtctgcat ctgtaggaga cagagtcacc    60
atcacttgca gttcaagtca ggacatcagc aattatttaa actggtacca gcagaaacct    120
ggccaggctc ccaggctcct catctattac acatcaacct tacacttagg gtcccatca    180 aggttcagcg gcagtggatc tgggacagat ttcactctca ccatcagcag cctgcagcct    240
```

```
gaagattttg caacttatta ctgtcagcag tattataacc ttccgtggac gttcggccaa    300
gggaccaagg tggaaatcaa acgtacggtg ctgcaccat  ctgtcttcat cttcccgcca    360
tctgatgagc agttgaaatc tggaactgcc tctgttgtgt gcctgctgaa taacttctat    420
cccagagagg ccaaagtaca gtggaaggtg gataacgccc tccaatcggg taactcccag    480
gagagtgtca cagagcagga cagcaaggac agcacctaca gcctcagcag caccctgacg    540
ctgagcaaag cagactacga gaaacacaaa gtctacgcct gcgaagtcac ccatcagggc    600
ctgagctcgc ccgtcacaaa gagcttcaac aggggagagt gt                      642
```

<210> SEQ ID NO 92
<211> LENGTH: 107
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 92

```
Glu Ile Val Leu Thr Gln Ser Pro Asp Phe Gln Ser Val Thr Pro Lys
1               5                   10                  15

Glu Lys Val Thr Ile Thr Cys Ser Ser Ser Gln Asp Ile Ser Asn Tyr
            20                  25                  30

Leu Asn Trp Tyr Gln Gln Lys Pro Gly Gln Ala Pro Arg Leu Leu Ile
        35                  40                  45

Tyr Tyr Thr Ser Thr Leu His Leu Gly Val Pro Ser Arg Phe Ser Gly
    50                  55                  60

Ser Gly Ser Gly Thr Asp Phe Thr Phe Thr Ile Ser Ser Leu Glu Ala
65                  70                  75                  80

Glu Asp Ala Ala Thr Tyr Tyr Cys Gln Gln Tyr Tyr Asn Leu Pro Trp
                85                  90                  95

Thr Phe Gly Gln Gly Thr Lys Val Glu Ile Lys
            100                 105
```

<210> SEQ ID NO 93
<211> LENGTH: 321
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 93

```
gaaattgtgc tgactcagtc tccagacttt cagtctgtga ctccaaagga gaaagtcacc    60
atcacctgca gttcaagtca ggacatcagc aattatttaa actggtacca gcagaaacct    120
ggccaggctc ccaggctcct catctattac acatcaacct acacttaggg gtcccctcg    180 aggttcagtg gcagtggatc tgggacagat ttcacctta ccatcagtag cctggaagct    240
gaagatgctg caacatatta ctgtcagcag tattataacc ttccgtggac gttcggccaa    300
gggaccaagg tggaaatcaa a                                              321
```

<210> SEQ ID NO 94
<211> LENGTH: 214
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 94

Glu Ile Val Leu Thr Gln Ser Pro Asp Phe Gln Ser Val Thr Pro Lys
1               5                   10                  15

Glu Lys Val Thr Ile Thr Cys Ser Ser Ser Gln Asp Ile Ser Asn Tyr
            20                  25                  30

Leu Asn Trp Tyr Gln Gln Lys Pro Gly Gln Ala Pro Arg Leu Leu Ile
        35                  40                  45

Tyr Tyr Thr Ser Thr Leu His Leu Gly Val Pro Ser Arg Phe Ser Gly
    50                  55                  60

Ser Gly Ser Gly Thr Asp Phe Thr Phe Thr Ile Ser Ser Leu Glu Ala
65              70                  75                  80

Glu Asp Ala Ala Thr Tyr Tyr Cys Gln Gln Tyr Tyr Asn Leu Pro Trp
            85                  90                  95

Thr Phe Gly Gln Gly Thr Lys Val Glu Ile Lys Arg Thr Val Ala Ala
        100                 105                 110

Pro Ser Val Phe Ile Phe Pro Pro Ser Asp Glu Gln Leu Lys Ser Gly
    115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
            165                 170                 175

Ser Thr Leu Thr Leu Ser Lys Ala Asp Tyr Glu Lys His Lys Val Tyr
        180                 185                 190

Ala Cys Glu Val Thr His Gln Gly Leu Ser Ser Pro Val Thr Lys Ser
            195                 200                 205

Phe Asn Arg Gly Glu Cys
        210

<210> SEQ ID NO 95
<211> LENGTH: 642
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 95
gaaattgtgc tgactcagtc tccagacttt cagtctgtga ctccaaagga gaaagtcacc    60
atcacctgca gttcaagtca ggacatcagc aattatttaa actggtacca gcagaaacct   120
ggccaggctc ccaggctcct catctattac acatcaacct tacacttagg ggtcccctcg   180
aggttcagtg gcagtggatc tgggacagat ttcaccttta ccatcagtag cctggaagct   240
gaagatgctg caacatatta ctgtcagcag tattataacc ttccgtggac gttcggccaa   300
gggaccaagg tggaaatcaa acgtacggtg gctgcaccat ctgtcttcat cttcccgcca   360
tctgatgagc agttgaaatc tggaactgcc tctgttgtgt gcctgctgaa taacttctat   420
cccagagagg ccaaagtaca gtggaaggtg gataacgccc tccaatcggg taactcccag   480
gagagtgtca cagagcagga cagcaaggac agcacctaca gcctcagcag cacccctgacg   540 ctgagcaaag cagactacga aaacacaaa gtctacgcct gcgaagtcac ccatcagggc   600
ctgagctcgc cgtcacaaa gagcttcaac aggggagagt gt                       642

<210> SEQ ID NO 96
<211> LENGTH: 107

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 96

Asp Ile Val Met Thr Gln Thr Pro Leu Ser Leu Pro Val Thr Pro Gly
1               5                   10                  15

Glu Pro Ala Ser Ile Ser Cys Ser Ser Ser Gln Asp Ile Ser Asn Tyr
            20                  25                  30

Leu Asn Trp Tyr Gln Gln Lys Pro Gly Gln Ala Pro Arg Leu Leu Ile
        35                  40                  45

Tyr Tyr Thr Ser Thr Leu His Leu Gly Ile Pro Asp Arg Phe Ser Gly
    50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln Tyr Tyr Asn Leu Pro Trp
                85                  90                  95

Thr Phe Gly Gln Gly Thr Lys Val Glu Ile Lys
            100                 105

<210> SEQ ID NO 97
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 97
gatattgtga tgacccagac tccactctcc ctgcccgtca cccctggaga gccggcctcc      60
atctcctgca gttcaagtca ggacatcagc aattatttaa actggtacca gcagaaacct    120
ggccaggctc ccaggctcct catctattac acatcaacct tacacttagg gatcccagac    180
aggttcagtg gcagtgggtc tgggacagac ttcactctca ccatcagcag actggagcct    240
gaagattttg cagtgtatta ctgtcagcag tattataacc ttccgtggac gttcggccaa    300
gggaccaagg tggaaatcaa a                                              321

<210> SEQ ID NO 98
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 98

Asp Ile Val Met Thr Gln Thr Pro Leu Ser Leu Pro Val Thr Pro Gly
1               5                   10                  15

Glu Pro Ala Ser Ile Ser Cys Ser Ser Ser Gln Asp Ile Ser Asn Tyr
            20                  25                  30

Leu Asn Trp Tyr Gln Gln Lys Pro Gly Gln Ala Pro Arg Leu Leu Ile
        35                  40                  45

Tyr Tyr Thr Ser Thr Leu His Leu Gly Ile Pro Asp Arg Phe Ser Gly
    50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln Tyr Tyr Asn Leu Pro Trp
```

```
                85                  90                  95
Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 99
<211> LENGTH: 642
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 99

```
gatattgtga tgacccagac tccactctcc ctgcccgtca cccctggaga gccggcctcc      60
atctcctgca gttcaagtca ggacatcagc aattatttaa actggtacca gcagaaacct    120
ggccaggctc ccaggctcct catctattac acatcaacct tacacttagg gatcccagac    180
aggttcagtg gcagtgggtc tgggacagac ttcactctca ccatcagcag actggagcct    240
gaagattttg cagtgtatta ctgtcagcag tattataacc ttccgtggac gttcggccaa    300
gggaccaagg tggaaatcaa acgtacggtg gctgcaccat ctgtcttcat cttcccgcca    360
tctgatgagc agttgaaatc tggaactgcc tctgttgtgt gcctgctgaa taacttctat    420
cccagagagg ccaaagtaca gtggaaggtg gataacgccc tccaatcggg taactcccag    480
gagagtgtca cagagcagga cagcaaggac agcacctaca gcctcagcag caccctgacg    540
ctgagcaaag cagactacga gaaacacaaa gtctacgcct gcgaagtcac ccatcagggc    600
ctgagctcgc ccgtcacaaa gagcttcaac aggggagagt gt                        642
```

<210> SEQ ID NO 100
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 100

```
Glu Val Gln Leu Val Gln Ser Gly Ala Glu Val Lys Lys Pro Gly Ala
1               5                   10                  15

Thr Val Lys Ile Ser Cys Lys Val Ser Gly Phe Thr Leu Thr Asn Tyr
            20                  25                  30

Gly Met Asn Trp Val Arg Gln Ala Pro Gly Gln Gly Leu Glu Trp Met
        35                  40                  45
```

```
Gly Trp Ile Asn Thr Asp Thr Gly Glu Pro Thr Tyr Ala Asp Asp Phe
            50                  55                  60

Lys Gly Arg Phe Val Phe Ser Leu Asp Thr Ser Val Ser Thr Ala Tyr
 65                  70                  75                  80

Leu Gln Ile Ser Ser Leu Lys Ala Glu Asp Thr Ala Val Tyr Tyr Cys
                    85                  90                  95

Ala Arg Asn Pro Pro Tyr Tyr Tyr Gly Thr Asn Asn Ala Glu Ala Met
                100                 105                 110

Asp Tyr Trp Gly Gln Gly Thr Thr Val Thr Val Ser Ser
            115                 120                 125

<210> SEQ ID NO 101
<211> LENGTH: 375
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 101
gaggtccagc tggtacagtc tggggctgag gtgaagaagc ctggggctac agtgaaaatc     60
tcctgcaagg tttctggatt taccctcaca aactatggaa tgaactgggt gcgacaggcc    120
cctggacaag ggcttgagtg gatgggttgg ataaacaccg acactggaga gccaacatat    180
gctgatgact caaggggaag atttgtcttc tccttggaca cctctgtcag cacggcatat    240
ctgcagatca gcagcctaaa ggctgaggac actgccgtgt attactgtgc aagaaaccct    300
ccctattact acggtactaa taacgcggag gctatggact actggggcca gggcaccacc    360
gtgaccgtgt cctcc                                                    375

<210> SEQ ID NO 102
<211> LENGTH: 452
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 102

Glu Val Gln Leu Val Gln Ser Gly Ala Glu Val Lys Lys Pro Gly Ala
 1               5                  10                  15

Thr Val Lys Ile Ser Cys Lys Val Ser Gly Phe Thr Leu Thr Asn Tyr
                20                  25                  30

Gly Met Asn Trp Val Arg Gln Ala Pro Gly Gln Gly Leu Glu Trp Met
            35                  40                  45

Gly Trp Ile Asn Thr Asp Thr Gly Glu Pro Thr Tyr Ala Asp Asp Phe
            50                  55                  60

Lys Gly Arg Phe Val Phe Ser Leu Asp Thr Ser Val Ser Thr Ala Tyr
 65                  70                  75                  80

Leu Gln Ile Ser Ser Leu Lys Ala Glu Asp Thr Ala Val Tyr Tyr Cys
                    85                  90                  95

Ala Arg Asn Pro Pro Tyr Tyr Tyr Gly Thr Asn Asn Ala Glu Ala Met
                100                 105                 110

Asp Tyr Trp Gly Gln Gly Thr Thr Val Thr Val Ser Ser Ala Ser Thr
            115                 120                 125

Lys Gly Pro Ser Val Phe Pro Leu Ala Pro Cys Ser Arg Ser Thr Ser
        130                 135                 140

Glu Ser Thr Ala Ala Leu Gly Cys Leu Val Lys Asp Tyr Phe Pro Glu
```

```
            145                 150                 155                 160
Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
                180                 185                 190

Val Val Thr Val Pro Ser Ser Leu Gly Thr Lys Thr Tyr Thr Cys
                195                 200                 205

Asn Val Asp His Lys Pro Ser Asn Thr Lys Val Asp Lys Arg Val Glu
210                 215                 220

Ser Lys Tyr Gly Pro Pro Cys Pro Pro Cys Pro Ala Pro Glu Phe Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
                260                 265                 270

Gln Glu Asp Pro Glu Val Gln Phe Asn Trp Tyr Val Asp Gly Val Glu
                275                 280                 285

Val His Asn Ala Lys Thr Lys Pro Arg Glu Glu Gln Phe Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Gly Leu Pro Ser Ser
                325                 330                 335

Ile Glu Lys Thr Ile Ser Lys Ala Lys Gly Gln Pro Arg Glu Pro Gln
                340                 345                 350

Val Tyr Thr Leu Pro Pro Ser Gln Glu Glu Met Thr Lys Asn Gln Val
                355                 360                 365

Ser Leu Thr Cys Leu Val Lys Gly Phe Tyr Pro Ser Asp Ile Ala Val
            370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Arg Leu Thr
                405                 410                 415

Val Asp Lys Ser Arg Trp Gln Glu Gly Asn Val Phe Ser Cys Ser Val
                420                 425                 430

Met His Glu Ala Leu His Asn His Tyr Thr Gln Lys Ser Leu Ser Leu
                435                 440                 445

Ser Leu Gly Lys
    450

<210> SEQ ID NO 103
<211> LENGTH: 1356
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 103
gaggtccagc tggtacagtc tggggctgag gtgaagaagc ctggggctac agtgaaaatc      60
tcctgcaagg tttctggatt taccctcaca aactatggaa tgaactgggt gcgacaggcc     120
cctggacaag ggcttgagtg gatgggttgg ataaacaccg acactggaga gccaacatat     180
gctgatgact caaggggaag atttgtcttc tccttggaca cctctgtcag cacggcatat     240
ctgcagatca gcagcctaaa ggctgaggac actgccgtgt attactgtgc aagaaaccct     300
```

```
cctattact acggtactaa taacgcggag ctatggact actggggcca gggcaccacc        360
gtgaccgtgt cctccgcttc caccaagggc ccatccgtct ccccctggc gccctgctcc        420
aggagcacct ccgagagcac agccgccctg gctgcctgg tcaaggacta cttccccgaa        480
ccggtgacgg tgtcgtggaa ctcaggcgcc ctgaccagcg gcgtgcacac cttcccggct        540
gtcctacagt cctcaggact ctactccctc agcagcgtgg tgaccgtgcc ctccagcagc        600
ttgggcacga gacctacac ctgcaacgta gatcacaagc ccagcaacac caaggtggac        660
aagagagttg agtccaaata tggtccccca tgcccaccgt gcccagcacc tgagttcctg        720
gggggaccat cagtcttcct gttccccca aacccaagg acactctcat gatctcccgg        780
acccctgagg tcacgtgcgt ggtggtggac gtgagccagg aagaccccga ggtccagttc        840
aactggtacg tggatggcgt ggaggtgcat aatgccaaga caaagccgcg ggaggagcag        900
ttcaacagca cgtaccgtgt ggtcagcgtc ctcaccgtcc tgcaccagga ctggctgaac        960
ggcaaggagt acaagtgcaa ggtgtccaac aaaggcctcc cgtcctccat cgagaaaacc       1020
atctccaaag ccaaagggca gccccgagag ccacaggtgt acaccctgcc cccatcccag       1080
gaggagatga ccaagaacca ggtcagcctg acctgcctgg tcaaaggctt ctaccccagc       1140
gacatcgccg tggagtggga gagcaatggg cagccggaga caactacaa gaccacgcct       1200
cccgtgctgg actccgacgg ctccttcttc ctctacagca ggctaaccgt ggacaagagc       1260
aggtggcagg aggggaatgt cttctcatgc tccgtgatgc atgaggctct gcacaaccac       1320
tacacacaga agagcctctc cctgtctctg ggtaaa                                 1356

<210> SEQ ID NO 104
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 104

Gln Val Gln Leu Val Gln Ser Gly Ala Glu Val Lys Lys Pro Gly Ala
1               5                   10                  15

Ser Val Lys Val Ser Cys Lys Ala Ser Gly Phe Thr Leu Thr Asn Tyr
            20                  25                  30

Gly Met Asn Trp Val Arg Gln Ala Arg Gly Gln Arg Leu Glu Trp Ile
        35                  40                  45

Gly Trp Ile Asn Thr Asp Thr Gly Glu Pro Thr Tyr Ala Asp Asp Phe
    50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Arg Asn Pro Pro Tyr Tyr Gly Thr Asn Asn Ala Glu Ala Met
            100                 105                 110

Asp Tyr Trp Gly Gln Gly Thr Thr Val Thr Val Ser Ser
        115                 120                 125

<210> SEQ ID NO 105
<211> LENGTH: 375
<212> TYPE: DNA
<213> ORGANISM: Artificial Sequence
<220> FEATURE:
<223> OTHER INFORMATION: Description of Artificial Sequence: Synthetic
``` polynucleotide

<400> SEQUENCE: 105

```
caggttcagc tggtgcagtc tggagctgag gtgaagaagc tggggcctc agtgaaggtc      60
tcctgcaagg cttctggatt taccctcaca aactatggaa tgaactgggt gcgacaggct    120
cgtggacaac gccttgagtg gataggttgg ataaacaccg acactggaga gccaacatat    180
gctgatgact tcaagggaag atttgtcttc tccttggaca cctctgtcag cacggcatat    240
ctgcagatca gcagcctaaa ggctgaggac actgccgtgt attactgtgc aagaaaccct    300
ccctattact acggtactaa taacgcggag gctatggact actggggcca gggcaccacc    360
gtgaccgtgt cctcc                                                     375
```

<210> SEQ ID NO 106
<211> LENGTH: 452
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 106

```
Gln Val Gln Leu Val Gln Ser Gly Ala Glu Val Lys Lys Pro Gly Ala
1               5                   10                  15

Ser Val Lys Val Ser Cys Lys Ala Ser Gly Phe Thr Leu Thr Asn Tyr
            20                  25                  30

Gly Met Asn Trp Val Arg Gln Ala Arg Gly Gln Arg Leu Glu Trp Ile
        35                  40                  45

Gly Trp Ile Asn Thr Asp Thr Gly Glu Pro Thr Tyr Ala Asp Asp Phe
    50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Arg Asn Pro Pro Tyr Tyr Tyr Gly Thr Asn Asn Ala Glu Ala Met
            100                 105                 110

Asp Tyr Trp Gly Gln Gly Thr Thr Val Thr Val Ser Ser Ala Ser Thr
        115                 120                 125

Lys Gly Pro Ser Val Phe Pro Leu Ala Pro Cys Ser Arg Ser Thr Ser
    130                 135                 140

Glu Ser Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Lys Thr Tyr Thr Cys
        195                 200                 205

Asn Val Asp His Lys Pro Ser Asn Thr Lys Val Asp Lys Arg Val Glu
    210                 215                 220

Ser Lys Tyr Gly Pro Pro Cys Pro Pro Cys Pro Ala Pro Glu Phe Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270
```

```
Gln Glu Asp Pro Glu Val Gln Phe Asn Trp Tyr Val Asp Gly Val Glu
            275                 280                 285

Val His Asn Ala Lys Thr Lys Pro Arg Glu Glu Gln Phe Asn Ser Thr
        290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Gly Leu Pro Ser Ser
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Gln Glu Glu Met Thr Lys Asn Gln Val
        355                 360                 365

Ser Leu Thr Cys Leu Val Lys Gly Phe Tyr Pro Ser Asp Ile Ala Val
370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Arg Leu Thr
                405                 410                 415

Val Asp Lys Ser Arg Trp Gln Glu Gly Asn Val Phe Ser Cys Ser Val
            420                 425                 430

Met His Glu Ala Leu His Asn His Tyr Thr Gln Lys Ser Leu Ser Leu
        435                 440                 445

Ser Leu Gly Lys
    450

<210> SEQ ID NO 107
<211> LENGTH: 1356
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 107
caggttcagc tggtgcagtc tggagctgag gtgaagaagc tggggcctc agtgaaggtc      60 tcctgcaagg cttctggatt taccctcaca aactatggaa tgaactgggt gcgacaggct     120
cgtggacaac gccttgagtg gataggttgg ataaacaccg acactggaga gccaacatat     180
gctgatgact tcaagggaag atttgtcttc tccttggaca cctctgtcag cacggcatat     240
ctgcagatca gcagcctaaa ggctgaggac actgccgtgt attactgtgc aagaaaccct     300
ccctattact acggtactaa taacgcggag gctatggact actggggcca gggcaccacc     360
gtgaccgtgt cctccgcttc caccaagggc ccatccgtct tccccctggc cctgctcc      420 aggagcacct ccgagagcac agccgccctg gctgcctgg tcaaggacta cttccccgaa     480
ccggtgacgg tgtcgtggaa ctcaggcgcc ctgaccagcg gcgtgcacac cttcccggct     540
gtcctacagt cctcaggact ctactccctc agcagcgtgg tgaccgtgcc ctccagcagc     600
ttgggcacga agacctacac ctgcaacgta gatcacaagc ccagcaacac caaggtggac     660
aagagagttg agtccaaata tggtccccca tgcccaccgt gcccagcacc tgagttcctg     720
gggggaccat cagtcttcct gttcccccca aaacccaagg acactctcat gatctcccgg     780
acccctgagg tcacgtgcgt ggtggtggac gtgagccagg aagacccga ggtccagttc     840 aactggtacg tggatggcgt ggaggtgcat aatgccaaga caaagccgcg ggaggagcag     900
ttcaacagca cgtaccgtgt ggtcagcgtc ctcaccgtcc tgcaccagga ctggctgaac     960
```

```
ggcaaggagt acaagtgcaa ggtgtccaac aaaggcctcc cgtcctccat cgagaaaacc    1020
atctccaaag ccaaagggca gccccgagag ccacaggtgt acaccctgcc cccatcccag    1080
gaggagatga ccaagaacca ggtcagcctg acctgcctgg tcaaaggctt ctaccccagc    1140
gacatcgccg tggagtggga gagcaatggg cagccggaga acaactacaa gaccacgcct    1200
cccgtgctgg actccgacgg ctccttcttc ctctacagca ggctaaccgt ggacaagagc    1260
aggtggcagg aggggaatgt cttctcatgc tccgtgatgc atgaggctct gcacaaccac    1320
tacacacaga gagcctctc cctgtctctg ggtaaa    1356
```

<210> SEQ ID NO 108
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 108

```
Gln Val Gln Leu Val Gln Ser Gly Ala Glu Val Lys Lys Pro Gly Ala
1               5                   10                  15

Ser Val Lys Val Ser Cys Lys Ala Ser Gly Phe Thr Leu Thr Asn Tyr
            20                  25                  30

Gly Met Asn Trp Val Arg Gln Ala Pro Gly Gln Gly Leu Glu Trp Met
        35                  40                  45

Gly Trp Ile Asn Thr Asp Thr Gly Glu Pro Thr Tyr Ala Asp Asp Phe
    50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Arg Asn Pro Pro Tyr Tyr Tyr Gly Thr Asn Asn Ala Glu Ala Met
            100                 105                 110

Asp Tyr Trp Gly Gln Gly Thr Thr Val Thr Val Ser Ser
        115                 120                 125
```

<210> SEQ ID NO 109
<211> LENGTH: 375
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 109

```
caggttcagc tggtgcagtc cggagctgag gtgaagaagc tggggcctc agtgaaggtc    60 tcctgcaagg cttctggatt taccctcaca aactatggaa tgaactgggt gcgacaggcc    120
cctggacaag gcttgagtg gatgggttgg ataaacaccg acactggaga gccaacatat    180
gctgatgact caagggaag atttgtcttc tccttggaca cctctgtcag cacggcatat    240
ctgcagatca gcagcctaaa ggctgaggac actgccgtgt attactgtgc aagaaaccct    300
ccctattact acggtactaa taacgcggag gctatggact actggggcca gggcaccacc    360
gtgaccgtgt cctcc    375
```

<210> SEQ ID NO 110
<211> LENGTH: 452
<212> TYPE: PRT

<213> ORGANISM: Artificial Sequence
<220> FEATURE:
<223> OTHER INFORMATION: Description of Artificial Sequence: Synthetic polypeptide

<400> SEQUENCE: 110

Gln Val Gln Leu Val Gln Ser Gly Ala Glu Val Lys Lys Pro Gly Ala
1               5                   10                  15

Ser Val Lys Val Ser Cys Lys Ala Ser Gly Phe Thr Leu Thr Asn Tyr
            20                  25                  30

Gly Met Asn Trp Val Arg Gln Ala Pro Gly Gln Gly Leu Glu Trp Met
        35                  40                  45

Gly Trp Ile Asn Thr Asp Thr Gly Glu Pro Thr Tyr Ala Asp Asp Phe
    50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Arg Asn Pro Pro Tyr Tyr Gly Thr Asn Asn Ala Glu Ala Met
            100                 105                 110

Asp Tyr Trp Gly Gln Gly Thr Thr Val Thr Val Ser Ser Ala Ser Thr
            115                 120                 125

Lys Gly Pro Ser Val Phe Pro Leu Ala Pro Cys Ser Arg Ser Thr Ser
        130                 135                 140

Glu Ser Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Lys Thr Tyr Thr Cys
        195                 200                 205

Asn Val Asp His Lys Pro Ser Asn Thr Lys Val Asp Lys Arg Val Glu
210                 215                 220

Ser Lys Tyr Gly Pro Pro Cys Pro Pro Cys Pro Ala Pro Glu Phe Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

Gln Glu Asp Pro Glu Val Gln Phe Asn Trp Tyr Val Asp Gly Val Glu
        275                 280                 285

Val His Asn Ala Lys Thr Lys Pro Arg Glu Glu Gln Phe Asn Ser Thr
290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Gly Leu Pro Ser Ser
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Gln Glu Glu Met Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Arg Leu Thr
            405                 410                 415

Val Asp Lys Ser Arg Trp Gln Glu Gly Asn Val Phe Ser Cys Ser Val
        420                 425                 430

Met His Glu Ala Leu His Asn His Tyr Thr Gln Lys Ser Leu Ser Leu
        435                 440                 445

Ser Leu Gly Lys
    450

<210> SEQ ID NO 111
<211> LENGTH: 1356
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 111
caggttcagc tggtgcagtc cggagctgag gtgaagaagc ctggggcctc agtgaaggtc     60
tcctgcaagg cttctggatt taccctcaca aactatggaa tgaactgggt gcgacaggcc    120
cctggacaag ggcttgagtg gatgggttgg ataaacaccg acactggaga gccaacatat    180
gctgatgact tcaagggaag atttgtcttc tccttggaca cctctgtcag cacggcatat    240
ctgcagatca gcagcctaaa ggctgaggac actgccgtgt attactgtgc aagaaaccct    300
ccctattact acggtactaa taacgcggag gctatggact actggggcca gggcaccacc    360
gtgaccgtgt cctccgcttc caccaagggc ccatccgtct tccccctggc gccctgctcc    420
aggagcacct ccgagagcac agccgccctg ggctgcctgg tcaaggacta cttccccgaa    480
ccggtgacgg tgtcgtggaa ctcaggcgcc ctgaccagcg gcgtgcacac cttcccggct    540
gtcctacagt cctcaggact ctactccctc agcagcgtgg tgaccgtgcc ctccagcagc    600
ttgggcacga agacctacac ctgcaacgta gatcacaagc ccagcaacac caaggtggac    660
aagagagttg agtccaaata tggtccccca tgcccaccgt gcccagcacc tgagttcctg    720
gggggaccat cagtcttcct gttccccccca aaacccaagg acactctcat gatctcccgg    780
acccctgagg tcacgtgcgt ggtggtggac gtgagccagg aagaccccga ggtccagttc    840
aactggtacg tggatggcgt ggaggtgcat aatgccaaga caaagccgcg ggaggagcag    900
ttcaacagca cgtaccgtgt ggtcagcgtc ctcaccgtcc tgcaccagga ctggctgaac    960
ggcaaggagt acaagtgcaa ggtgtccaac aaaggcctcc cgtcctccat cgagaaaacc   1020
atctccaaag ccaaagggca gccccgagag ccacaggtgt acaccctgcc cccatcccag   1080
gaggagatga ccaagaacca ggtcagcctg acctgcctgg tcaaaggctt ctaccccagc   1140
gacatcgccg tggagtggga gagcaatggg cagccggaga acaactacaa gaccacgcct   1200
cccgtgctgg actccgacgg ctccttcttc ctctacagca ggctaaccgt ggacaagagc   1260
aggtggcagg aggggaatgt cttctcatgc tccgtgatgc atgaggctct gcacaaccac   1320
tacacacaga gagcctctc cctgtctctg ggtaaa                              1356

<210> SEQ ID NO 112
<211> LENGTH: 375
<212> TYPE: DNA
<213> ORGANISM: Artificial Sequence
<220> FEATURE:
<223> OTHER INFORMATION: Description of Artificial Sequence: Synthetic -continued polynucleotide

<400> SEQUENCE: 112

```
gaagtgcagc tggtgcagtc tggcgccgaa gtgaagaaac ccggcgctac cgtgaagatc      60
tcctgcaagg tgtccggctt caccctgacc aactacggca tgaactgggt gcgacaggcc     120
cctggacagg gcctggaatg gatgggctgg atcaacaccg acaccggcga gcctacctac     180
gccgacgact tcaagggcag attcgtgttc tccctggaca cctccgtgtc caccgcctac     240
ctgcagatct ccagcctgaa ggccgaggat accgccgtgt actactgcgc ccggaacccc     300
ccttactact acggcaccaa caacgccgag gccatggact attggggcca gggcaccacc     360
gtgaccgtgt cctct                                                      375
```

<210> SEQ ID NO 113
<211> LENGTH: 451
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 113

```
Glu Val Gln Leu Val Gln Ser Gly Ala Glu Val Lys Lys Pro Gly Ala
1               5                   10                  15

Thr Val Lys Ile Ser Cys Lys Val Ser Gly Phe Thr Leu Thr Asn Tyr
            20                  25                  30

Gly Met Asn Trp Val Arg Gln Ala Pro Gly Gln Gly Leu Glu Trp Met
        35                  40                  45

Gly Trp Ile Asn Thr Asp Thr Gly Glu Pro Thr Tyr Ala Asp Asp Phe
    50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Arg Asn Pro Pro Tyr Tyr Tyr Gly Thr Asn Asn Ala Glu Ala Met
            100                 105                 110

Asp Tyr Trp Gly Gln Gly Thr Thr Val Thr Val Ser Ser Ala Ser Thr
        115                 120                 125

Lys Gly Pro Ser Val Phe Pro Leu Ala Pro Cys Ser Arg Ser Thr Ser
    130                 135                 140

Glu Ser Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Lys Thr Tyr Thr Cys
        195                 200                 205

Asn Val Asp His Lys Pro Ser Asn Thr Lys Val Asp Lys Arg Val Glu
    210                 215                 220

Ser Lys Tyr Gly Pro Pro Cys Pro Pro Cys Pro Ala Pro Glu Phe Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270
```

```
Gln Glu Asp Pro Glu Val Gln Phe Asn Trp Tyr Val Asp Gly Val Glu
            275                 280                 285

Val His Asn Ala Lys Thr Lys Pro Arg Glu Glu Gln Phe Asn Ser Thr
        290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Gly Leu Pro Ser Ser
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Gln Glu Glu Met Thr Lys Asn Gln Val
        355                 360                 365

Ser Leu Thr Cys Leu Val Lys Gly Phe Tyr Pro Ser Asp Ile Ala Val
370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Arg Leu Thr
                405                 410                 415

Val Asp Lys Ser Arg Trp Gln Glu Gly Asn Val Phe Ser Cys Ser Val
            420                 425                 430

Met His Glu Ala Leu His Asn His Tyr Thr Gln Lys Ser Leu Ser Leu
        435                 440                 445

Ser Leu Gly
    450

<210> SEQ ID NO 114
<211> LENGTH: 1353
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 114
gaagtgcagc tggtgcagtc tggcgccgaa gtgaagaaac ccggcgctac cgtgaagatc      60
tcctgcaagg tgtccggctt caccctgacc aactacggca tgaactgggt gcgacaggcc     120
cctggacagg gcctggaatg gatgggctgg atcaacaccg acaccggcga gcctacctac     180
gccgacgact tcaagggcag attcgtgttc tccctggaca cctccgtgtc caccgcctac     240
ctgcagatct ccagcctgaa ggccgaggat accgccgtgt actactgcgc ccggaacccc     300
ccttactact acggcaccaa caacgccgag gccatggact attggggcca gggcaccacc     360
gtgaccgtgt cctctgcttc taccaagggg ccaagcgtgt tccccctggc ccctgctcc      420 agaagcacca gcgagagcac agccgccctg ggctgcctgg tgaaggacta cttccccgag     480
cccgtgaccg tgtcctggaa cagcggagcc ctgaccagcg gcgtgcacac cttccccgcc     540
gtgctgcaga gcagcggcct gtacagcctg agcagcgtgg tgaccgtgcc cagcagcagc     600
ctgggcacca agacctacac ctgtaacgtg gaccacaagc ccagcaacac caaggtggac     660
aagagggtgg agagcaagta cggcccaccc tgccccccct gcccagcccc cgagttcctg     720
ggcggaccca gcgtgttcct gttccccccc aagcccaagg acaccctgat gatcagcaga     780
acccccgagg tgacctgtgt ggtggtggac gtgtcccagg aggaccccga ggtccagttc     840
aactggtacg tggacggcgt ggaggtgcac aacgccaaga ccaagcccag agaggagcag     900
tttaacagca cctaccgggt ggtgtccgtg ctgaccgtgc tgcaccagga ctggctgaac     960
```

```
ggcaaagagt acaagtgtaa ggtctccaac aagggcctgc caagcagcat cgaaaagacc    1020
atcagcaagg ccaagggcca gcctagagag ccccaggtct acaccctgcc acccagccaa    1080
gaggagatga ccaagaacca ggtgtccctg acctgtctgg tgaagggctt ctacccaagc    1140
gacatcgccg tggagtggga gagcaacggc cagcccgaga caactacaa gaccaccccc    1200 ccagtgctgg acagcgacgg cagcttcttc ctgtacagca ggctgaccgt ggacaagtcc    1260
agatggcagg agggcaacgt ctttagctgc tccgtgatgc acgaggccct gcacaaccac    1320
tacacccaga gagcctgag cctgtccctg ggc                                  1353
```

<210> SEQ ID NO 115
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 115

```
gacatccaga tgacccagtc cccctccagc ctgtctgctt ccgtgggcga cagagtgacc      60
atcacctgtt cctccagcca ggacatctcc aactacctga actggtatca gcagaagccc     120
ggcaaggccc ccaagctgct gatctactac acctccaccc tgcacctggg cgtgccctcc     180
agattttccg gctctggctc tggcaccgac tttaccttca ccatcagctc cctggaagcc     240
gaggacgccg ccacctacta ctgccagcag tactacaacc tgccctggac cttcggccag     300
ggcaccaagg tggaaatcaa g                                               321
```

<210> SEQ ID NO 116

<400> SEQUENCE: 116

000

<210> SEQ ID NO 117
<211> LENGTH: 642
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 117

```
gacatccaga tgacccagtc cccctccagc ctgtctgctt ccgtgggcga cagagtgacc      60
atcacctgtt cctccagcca ggacatctcc aactacctga actggtatca gcagaagccc     120
ggcaaggccc ccaagctgct gatctactac acctccaccc tgcacctggg cgtgccctcc     180
agattttccg gctctggctc tggcaccgac tttaccttca ccatcagctc cctggaagcc     240
gaggacgccg ccacctacta ctgccagcag tactacaacc tgccctggac cttcggccag     300
ggcaccaagg tggaaatcaa gcgtacggtg gccgctccca gcgtgttcat cttcccccca     360
agcgacgagc agctgaagag cggcaccgcc agcgtggtgt gtctgctgaa caacttctac     420
cccagggagg ccaaggtgca gtggaaggtg acaacgccc tgcagagcgg caacagccag     480
gagagcgtca ccgagcagga cagcaaggac tccacctaca gcctgagcag caccctgacc     540
ctgagcaagg ccgactacga gaagcacaag gtgtacgcct gtgaggtgac ccaccagggc     600
ctgtccagcc ccgtgaccaa gagcttcaac aggggcgagt gc                        642
```

```
<210> SEQ ID NO 118
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 118
gacatccaga tgacccagtc cccctccagc ctgtctgctt ccgtgggcga cagagtgacc      60
atcacctgtt cctccagcca ggacatctcc aactacctga actggtatca gcagaagccc     120
ggcaaggccc ccaagctgct gatctactac acctccaccc tgcacctggg catccccct     180 agattctccg gctctggcta cggcaccgac ttcaccctga ccatcaacaa catcgagtcc    240
gaggacgccg cctactactt ctgccagcag tactacaacc tgccctggac cttcggccag    300
ggcaccaagg tggaaatcaa g                                              321

<210> SEQ ID NO 119

<400> SEQUENCE: 119

000

<210> SEQ ID NO 120
<211> LENGTH: 652
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 120
gacatccaga tgacccagtc cccctccagc ctgtctgctt ccgtgggcga cagagtgacc      60
atcacctgtt cctccagcca ggacatctcc aactacctga actggtatca gcagaagccc     120
ggcaaggccc ccaagctgct gatctactac acctccaccc tgcacctggg catccccct     180 agattctccg gctctggcta cggcaccgac ttcaccctga ccatcaacaa catcgagtcc    240
gaggacgccg cctactactt ctgccagcag tactacaacc tgccctggac cttcggccag    300
ggcaccaagg tggaaatcaa gcgtacggtg ccgctccca gcgtgttcat cttcccccca    360
agcgacgagc agctgaagag cggcaccgcc agcgtggtgt gtctgctgaa caacttctac    420
cccagggagg ccaaggtgca gtggaaggtg gacaacgccc tgcagagcgg caacagccag    480
gagagcgtca ccgagcagga cagcaaggac tccacctaca gcctgagcag caccctgacc    540
ctgagcaagg ccgactacga aagcacaag gtgtacgcct gtgaggtgac ccaccagggc    600
ctgtccagcc ccgtgaccaa gagcttcaac aggggcgagt gctgatgaat tc           652

<210> SEQ ID NO 121
<211> LENGTH: 375
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 121
caggtgcagc tggtgcagtc tggcgccgaa gtgaagaaac ctggcgcctc cgtgaaggtg      60
tcctgcaagg cctctggctt caccctgacc aactacggca tgaactgggt gcgacaggcc    120
aggggccagc ggctggaatg gatcggctgg atcaacaccg acaccggcga gcctacctac    180
```

```
gccgacgact tcaagggcag attcgtgttc tccctggaca cctccgtgtc caccgcctac    240
ctgcagatct ccagcctgaa ggccgaggat accgccgtgt actactgcgc ccggaacccc    300
ccttactact acggcaccaa caacgccgag gccatggact attggggcca gggcaccacc    360
gtgaccgtgt cctct                                                    375
```

<210> SEQ ID NO 122
<211> LENGTH: 451
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 122

```
Gln Val Gln Leu Val Gln Ser Gly Ala Glu Val Lys Lys Pro Gly Ala
1               5                   10                  15

Ser Val Lys Val Ser Cys Lys Ala Ser Gly Phe Thr Leu Thr Asn Tyr
            20                  25                  30

Gly Met Asn Trp Val Arg Gln Ala Arg Gly Gln Arg Leu Glu Trp Ile
        35                  40                  45

Gly Trp Ile Asn Thr Asp Thr Gly Glu Pro Thr Tyr Ala Asp Asp Phe
    50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Arg Asn Pro Pro Tyr Tyr Gly Thr Asn Asn Ala Glu Ala Met Asp
            100                 105                 110

Asp Tyr Trp Gly Gln Gly Thr Thr Val Thr Val Ser Ser Ala Ser Thr
        115                 120                 125

Lys Gly Pro Ser Val Phe Pro Leu Ala Pro Cys Ser Arg Ser Thr Ser
    130                 135                 140

Glu Ser Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Lys Thr Tyr Thr Cys
        195                 200                 205

Asn Val Asp His Lys Pro Ser Asn Thr Lys Val Asp Lys Arg Val Glu
    210                 215                 220

Ser Lys Tyr Gly Pro Pro Cys Pro Pro Cys Pro Ala Pro Glu Phe Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

Gln Glu Asp Pro Glu Val Gln Phe Asn Trp Tyr Val Asp Gly Val Glu
        275                 280                 285

Val His Asn Ala Lys Thr Lys Pro Arg Glu Glu Gln Phe Asn Ser Thr
    290                 295                 300

Tyr Arg Val Val Ser Val Leu Thr Val Leu His Gln Asp Trp Leu Asn
305                 310                 315                 320
```

```
Gly Lys Glu Tyr Lys Cys Lys Val Ser Asn Lys Gly Leu Pro Ser Ser
                325                 330                 335
Ile Glu Lys Thr Ile Ser Lys Ala Lys Gly Gln Pro Arg Glu Pro Gln
            340                 345                 350
Val Tyr Thr Leu Pro Pro Ser Gln Glu Glu Met Thr Lys Asn Gln Val
        355                 360                 365
Ser Leu Thr Cys Leu Val Lys Gly Phe Tyr Pro Ser Asp Ile Ala Val
    370                 375                 380
Glu Trp Glu Ser Asn Gly Gln Pro Glu Asn Asn Tyr Lys Thr Thr Pro
385                 390                 395                 400
Pro Val Leu Asp Ser Asp Gly Ser Phe Phe Leu Tyr Ser Arg Leu Thr
                405                 410                 415
Val Asp Lys Ser Arg Trp Gln Glu Gly Asn Val Phe Ser Cys Ser Val
            420                 425                 430
Met His Glu Ala Leu His Asn His Tyr Thr Gln Lys Ser Leu Ser Leu
        435                 440                 445
Ser Leu Gly
    450

<210> SEQ ID NO 123
<211> LENGTH: 1353
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 123
caggtgcagc tggtgcagtc tggcgccgaa gtgaagaaac ctggcgcctc cgtgaaggtg      60
tcctgcaagg cctctggctt caccctgacc aactacggca tgaactgggt gcgacaggcc    120
aggggccagc ggctggaatg gatcggctgg atcaacaccg acaccggcga gcctacctac    180
gccgacgact tcaagggcag attcgtgttc tccctggaca cctccgtgtc caccgcctac    240
ctgcagatct ccagcctgaa ggccgaggat accgccgtgt actactgcgc ccggaacccc    300
ccttactact acggcaccaa caacgccgag gccatggact attggggcca gggcaccacc    360
gtgaccgtgt cctctgcttc taccaagggg cccagcgtgt tccccctggc ccctgctcc    420 agaagcacca gcgagagcac agccgccctg ggctgcctgg tgaaggacta cttccccgag    480
cccgtgaccg tgtcctggaa cagcggagcc ctgaccagcg gcgtgcacac cttccccgcc    540
gtgctgcaga gcagcggcct gtacagcctg agcagcgtgg tgaccgtgcc agcagcagc    600 ctgggcacca agacctacac ctgtaacgtg gaccacaagc ccagcaacac caaggtggac    660
aagagggtgg agagcaagta cggcccaccc tgcccccct gcccagcccc cgagttcctg    720
ggcggaccca gcgtgttcct gttcccccc aagcccaagg acaccctgat gatcagcaga    780
acccccgagg tgacctgtgt ggtggtggac gtgtcccagg aggaccccga ggtccagttc    840
aactggtacg tggacggcgt ggaggtgcac aacgccaaga ccaagcccag agaggagcag    900
tttaacagca cctaccgggt ggtgtccgtg ctgaccgtgc tgcaccagga ctggctgaac    960
ggcaaagagt acaagtgtaa ggtctccaac aagggcctgc caagcagcat cgaaaagacc   1020
atcagcaagg ccaagggcca gcctagagag ccccaggtct acaccctgcc acccagccaa   1080
gaggagatga ccaagaacca ggtgtccctg acctgtctgg tgaagggctt ctacccaagc   1140
gacatcgccg tggagtggga gagcaacggc cagcccgaga acaactacaa gaccaccccc   1200
ccagtgctgg acagcgacgg cagcttcttc ctgtacagca ggctgaccgt ggacaagtcc   1260
```

| | |
|---|---|
| agatggcagg agggcaacgt ctttagctgc tccgtgatgc acgaggccct gcacaaccac | 1320 |
| tacacccaga agagcctgag cctgtccctg ggc | 1353 |

<210> SEQ ID NO 124
<211> LENGTH: 375
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 124

| | |
|---|---|
| caagtgcagc tggtgcagtc gggagccgaa gtgaagaagc tggagcctc ggtgaaggtg | 60 |
| tcgtgcaagg catccggatt caccctcacc aattacggga tgaactgggt cagacaggcc | 120 |
| cggggtcaac ggctggagtg gatcggatgg attaacaccg acaccgggga gcctacctac | 180 |
| gcggacgatt tcaagggacg gttcgtgttc tccctcgaca cctccgtgtc caccgcctac | 240 |
| ctccaaatct cctcactgaa agcggaggac accgccgtgt actattgcgc gaggaacccg | 300 |
| ccctactact acggaaccaa caacgccgaa gccatggact actggggcca gggcaccact | 360 |
| gtgactgtgt ccagc | 375 |

<210> SEQ ID NO 125
<211> LENGTH: 375
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 125

| | |
|---|---|
| caggtgcagc tggtgcagtc tggcgccgaa gtgaagaaac tggcgcctc cgtgaaggtg | 60 |
| tcctgcaagg cctctggctt caccctgacc aactacggca tgaactgggt gcgacaggcc | 120 |
| aggggccagc ggctggaatg gatcggctgg atcaacaccg acaccggcga gcctacctac | 180 |
| gccgacgact tcaagggcag attcgtgttc tccctggaca cctccgtgtc caccgcctac | 240 |
| ctgcagatct ccagcctgaa ggccgaggat accgccgtgt actactgcgc ccggaacccc | 300 |
| ccttactact acggcaccaa caacgccgag gccatggact attggggcca gggcaccacc | 360 |
| gtgaccgtgt cctct | 375 |

<210> SEQ ID NO 126
<211> LENGTH: 1353
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 126

| | |
|---|---|
| caagtgcagc tggtgcagtc gggagccgaa gtgaagaagc tggagcctc ggtgaaggtg | 60 |
| tcgtgcaagg catccggatt caccctcacc aattacggga tgaactgggt cagacaggcc | 120 |
| cggggtcaac ggctggagtg gatcggatgg attaacaccg acaccgggga gcctacctac | 180 |
| gcggacgatt tcaagggacg gttcgtgttc tccctcgaca cctccgtgtc caccgcctac | 240 |
| ctccaaatct cctcactgaa agcggaggac accgccgtgt actattgcgc gaggaacccg | 300 |
| ccctactact acggaaccaa caacgccgaa gccatggact actggggcca gggcaccact | 360 |
| gtgactgtgt ccagcgcgtc cactaagggc ccgtccgtgt tccccctggc accttgtagc | 420 |

```
cggagcacta gcgaatccac cgctgccctc ggctgcctgg tcaaggatta cttcccggag      480
cccgtgaccg tgtcctggaa cagcggagcc ctgacctccg gagtgcacac cttccccgct      540
gtgctgcaga gctccgggct gtactcgctg tcgtcggtgg tcacggtgcc ttcatctagc      600
ctgggtacca agacctacac ttgcaacgtg gaccacaagc cttccaacac taaggtggac      660
aagcgcgtcg aatcgaagta cggcccaccg tgcccgcctt gtcccgcgcc ggagttcctc      720
ggcggtccct cggtctttct gttcccaccg aagcccaagg acactttgat gatttcccgc      780 accccctgaag tgacatgcgt ggtcgtggac gtgtcacagg aagatccgga ggtgcagttc      840
aattggtacg tggatggcgt cgaggtgcac aacgccaaaa ccaagccgag ggaggagcag      900
ttcaactcca cttaccgcgt cgtgtccgtg ctgacggtgc tgcatcagga ctggctgaac      960
gggaaggagt acaagtgcaa agtgtccaac aagggacttc ctagctcaat cgaaaagacc     1020
atctcgaaag ccaagggaca gccccgggaa ccccaagtgt ataccctgcc accgagccag     1080
gaagaaatga ctaagaacca agtctcattg acttgccttg tgaagggctt ctacccatcg     1140
gatatcgccg tggaatggga gtccaacggc cagccggaaa acaactacaa gaccaccccct    1200 ccggtgctgg actcagacgg atccttcttc ctctactcgc ggctgaccgt ggataagagc     1260
agatggcagg agggaaatgt gttcagctgt tctgtgatgc atgaagccct gcacaaccac     1320
tacactcaga gtccctgtc cctctccctg gga                                   1353
```

<210> SEQ ID NO 127
<211> LENGTH: 1353
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 127

```
caggtgcagc tggtgcagtc tggcgccgaa gtgaagaaac ctggcgcctc cgtgaaggtg       60
tcctgcaagg cctctggctt caccctgacc aactacggca tgaactgggt gcgacaggcc      120
aggggccagc ggctggaatg gatcggctgg atcaacaccg acaccggcga gcctacctac      180
gccgacgact tcaagggcag attcgtgttc tccctggaca cctccgtgtc caccgcctac      240
ctgcagatct ccagcctgaa ggccgaggat accgccgtgt actactgcgc ccggaacccc      300
ccttactact acggcaccaa caacgccgag gccatggact attggggcca gggcaccacc      360
gtgaccgtgt cctctgcttc taccaagggg ccagcgtgt tccccctggc ccctgctcc        420 agaagcacca gcgagagcac agccgccctg ggctgcctgg tgaaggacta cttccccgag      480
cccgtgaccg tgtcctggaa cagcggagcc ctgaccagcg gcgtgcacac cttccccgcc      540
gtgctgcaga gcagcggcct gtacagcctg agcagcgtgg tgaccgtgcc cagcagcagc      600
ctgggcacca gacctacac ctgtaacgtg gaccacaagc ccagcaacac caaggtggac       660
aagagggtgg agagcaagta cggcccaccc tgcccccct gcccagcccc cgagttcctg       720
ggcggaccca gcgtgttcct gttccccccc aagcccaagg acaccctgat gatcagcaga      780 accccccgagg tgacctgtgt ggtggtggac gtgtcccagg aggaccccga ggtccagttc      840
aactggtacg tggacggcgt ggaggtgcac aacgccaaga ccaagcccag agaggagcag      900
tttaacagca cctaccgggt ggtgtccgtg ctgaccgtgc tgcaccagga ctggctgaac      960
ggcaaagagt acaagtgtaa ggtctccaac aagggcctgc caagcagcat cgaaaagacc     1020
atcagcaagg ccaagggcca gcctagagag ccccaggtct acaccctgcc acccagccaa     1080
```

```
gaggagatga ccaagaacca ggtgtccctg acctgtctgg tgaagggctt ctacccaagc    1140
gacatcgccg tggagtggga gagcaacggc cagcccgaga caactacaa gaccaccccc     1200 ccagtgctgg acagcgacgg cagcttcttc ctgtacagca ggctgaccgt ggacaagtcc    1260
agatggcagg agggcaacgt ctttagctgc tccgtgatgc acgaggccct gcacaaccac    1320
tacacccaga agagcctgag cctgtccctg ggc                                 1353
```

<210> SEQ ID NO 128
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 128

```
gatattcaga tgactcagtc acctagtagc ctgagcgcta gtgtgggcga tagagtgact    60
atcacctgta gctctagtca ggatatctct aactacctga actggtatct gcagaagccc    120
ggtcaatcac ctcagctgct gatctactac actagcaccc tgcacctggg cgtgccctct    180
aggtttagcg gtagcggtag tggcaccgag ttcaccctga ctatctctag cctgcagccc    240
gacgacttcg ctacctacta ctgtcagcag tactataacc tgccctggac cttcggtcaa    300
ggcactaagg tcgagattaa g                                              321
```

<210> SEQ ID NO 129
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 129

```
gacatccaga tgacccagtc cccctccagc ctgtctgctt ccgtgggcga cagagtgacc    60
atcacctgtt cctccagcca ggacatctcc aactacctga actggtatct gcagaagccc    120
ggccagtccc ctcagctgct gatctactac acctccaccc tgcacctggg cgtgccctcc    180
agattttccg gctctggctc tggcaccgag tttaccctga ccatcagctc cctgcagccc    240
gacgacttcg ccacctacta ctgccagcag tactacaacc tgccctggac cttcggccag    300
ggcaccaagg tggaaatcaa g                                              321
```

<210> SEQ ID NO 130
<211> LENGTH: 642
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 130

```
gatattcaga tgactcagtc acctagtagc ctgagcgcta gtgtgggcga tagagtgact    60
atcacctgta gctctagtca ggatatctct aactacctga actggtatct gcagaagccc    120
ggtcaatcac ctcagctgct gatctactac actagcaccc tgcacctggg cgtgccctct    180
aggtttagcg gtagcggtag tggcaccgag ttcaccctga ctatctctag cctgcagccc    240
gacgacttcg ctacctacta ctgtcagcag tactataacc tgccctggac cttcggtcaa    300
ggcactaagg tcgagattaa gcgtacggtg gccgctccca gcgtgttcat cttccccccc    360
```

```
agcgacgagc agctgaagag cggcaccgcc agcgtggtgt gcctgctgaa caacttctac    420
ccccgggagg ccaaggtgca gtggaaggtg acaacgccc tgcagagcgg caacagccag     480
gagagcgtca ccgagcagga cagcaaggac tccacctaca gcctgagcag caccctgacc   540
ctgagcaagg ccgactacga aagcataag gtgtacgcct gcgaggtgac ccaccagggc    600
ctgtccagcc ccgtgaccaa gagcttcaac aggggcgagt gc                      642
```

<210> SEQ ID NO 131
<211> LENGTH: 642
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 131

```
gacatccaga tgacccagtc cccctccagc ctgtctgctt ccgtgggcga cagagtgacc   60
atcacctgtt cctccagcca ggacatctcc aactacctga actggtatct gcagaagccc   120
ggccagtccc ctcagctgct gatctactac acctccaccc tgcacctggg cgtgccctcc   180
agattttccg gctctggctc tggcaccgag tttacccctga ccatcagctc cctgcagccc   240
gacgacttcg ccacctacta ctgccagcag tactacaacc tgccctggac cttcggccag   300
ggcaccaagg tggaaatcaa gcgtacggtg gccgctccca gcgtgttcat cttccccca    360 agcgacgagc agctgaagag cggcaccgcc agcgtggtgt gtctgctgaa caacttctac   420
cccagggagg ccaaggtgca gtggaaggtg acaacgccc tgcagagcgg caacagccag    480
gagagcgtca ccgagcagga cagcaaggac tccacctaca gcctgagcag caccctgacc   540
ctgagcaagg ccgactacga aagcacaag gtgtacgcct gtgaggtgac ccaccagggc    600
ctgtccagcc ccgtgaccaa gagcttcaac aggggcgagt gc                      642
```

<210> SEQ ID NO 132
<211> LENGTH: 375
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 132

```
caggtgcagc tggtgcagtc aggcgccgaa gtgaagaaac ccggcgctag tgtgaaagtc   60
agctgtaaag ctagtggctt caccctgact aactacggga tgaactgggt ccgccaggcc   120
ccaggtcaag gcctcgagtg gatgggctgg attaacaccg acaccggcga gcctacctac   180
gccgacgact ttaagggcag attcgtgttt agcctggaca ctagtgtgtc taccgcctac   240
ctgcagatct ctagcctgaa ggccgaggac accgccgtct actactgcgc tagaaacccc   300
ccctactact acggcactaa caacgccgag gctatggact actggggtca aggcactacc   360
gtgaccgtgt ctagc                                                    375
```

<210> SEQ ID NO 133
<211> LENGTH: 375
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 133

```
caggtgcagc tggtgcagtc tggcgccgaa gtgaagaaac ctggcgcctc cgtgaaggtg     60
tcctgcaagg cctctggctt caccctgacc aactacggca tgaactgggt gcgacaggcc    120
cctggacagg gcctggaatg gatgggctgg atcaacaccg acaccggcga gcctacctac    180
gccgacgact tcaagggcag attcgtgttc tccctggaca cctccgtgtc caccgcctac    240
ctgcagatct ccagcctgaa ggccgaggat accgccgtgt actactgcgc ccggaacccc    300
ccttactact acggcaccaa caacgccgag gccatggact attggggcca gggcaccacc    360
gtgaccgtgt cctct                                                     375

<210> SEQ ID NO 134
<211> LENGTH: 451
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 134

Gln Val Gln Leu Val Gln Ser Gly Ala Glu Val Lys Lys Pro Gly Ala
1               5                   10                  15

Ser Val Lys Val Ser Cys Lys Ala Ser Gly Phe Thr Leu Thr Asn Tyr
            20                  25                  30

Gly Met Asn Trp Val Arg Gln Ala Pro Gly Gln Gly Leu Glu Trp Met
        35                  40                  45

Gly Trp Ile Asn Thr Asp Thr Gly Glu Pro Thr Tyr Ala Asp Asp Phe
    50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Arg Asn Pro Pro Tyr Tyr Tyr Gly Thr Asn Asn Ala Glu Ala Met
            100                 105                 110

Asp Tyr Trp Gly Gln Gly Thr Thr Val Thr Val Ser Ser Ala Ser Thr
        115                 120                 125

Lys Gly Pro Ser Val Phe Pro Leu Ala Pro Cys Ser Arg Ser Thr Ser
    130                 135                 140

Glu Ser Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Leu Gly Thr Lys Thr Tyr Thr Cys
        195                 200                 205

Asn Val Asp His Lys Pro Ser Asn Thr Lys Val Asp Lys Arg Val Glu
    210                 215                 220

Ser Lys Tyr Gly Pro Pro Cys Pro Pro Cys Pro Ala Pro Glu Phe Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

Gln Glu Asp Pro Glu Val Gln Phe Asn Trp Tyr Val Asp Gly Val Glu
        275                 280                 285
```

Val His Asn Ala Lys Thr Lys Pro Arg Glu Glu Gln Phe Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Gly Leu Pro Ser Ser
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Gln Glu Glu Met Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Arg Leu Thr
                405                 410                 415

Val Asp Lys Ser Arg Trp Gln Glu Gly Asn Val Phe Ser Cys Ser Val
            420                 425                 430

Met His Glu Ala Leu His Asn His Tyr Thr Gln Lys Ser Leu Ser Leu
        435                 440                 445

Ser Leu Gly
    450

<210> SEQ ID NO 135
<211> LENGTH: 1353
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 135
caggtgcagc tggtgcagtc aggcgccgaa gtgaagaaac ccggcgctag tgtgaaagtc      60
agctgtaaag ctagtggctt caccctgact aactacggga tgaactgggt ccgccaggcc     120
ccaggtcaag gcctcgagtg gatgggctgg attaacaccg acaccggcga gcctacctac     180
gccgacgact ttaagggcag attcgtgttt agcctggaca ctagtgtgtc taccgcctac     240
ctgcagatct ctagcctgaa ggccgaggac accgccgtct actactgcgc tagaaacccc     300
ccctactact acggcactaa caacgccgag ctatggact actggggtca aggcactacc      360
gtgaccgtgt ctagcgctag cactaagggc ccgtccgtgt tccccctggc accttgtagc     420
cggagcacta gcgaatccac cgctgccctc ggctgcctgg tcaaggatta cttcccggag     480
cccgtgaccg tgtcctggaa cagcggagcc ctgacctccg gagtgcacac cttcccgcgt     540
gtgctgcaga gctccgggct gtactcgctg tcgtcggtgg tcacggtgcc ttcatctagc     600
ctgggtacca agacctacac ttgcaacgtg gaccacaagc cttccaacac taaggtggac     660
aagcgcgtcg aatcgaagta cggcccaccg tgcccgcctt gtcccgcgcc ggagttcctc     720
ggcggtccct cggtctttct gttcccaccg aagcccaagg acactttgat gatttcccgc     780 accccctgaag tgacatgcgt ggtcgtggac gtgtcacagg aagatccgga ggtgcagttc     840
aattggtacg tggatggcgt cgaggtgcac aacgccaaaa ccaagccgag ggaggagcag     900
ttcaactcca cttaccgcgt cgtgtccgtg ctgacggtgc tgcatcagga ctggctgaac     960
gggaaggagt acaagtgcaa agtgtccaac aagggacttc ctagctcaat cgaaaagacc    1020

```
atctcgaaag ccaagggaca gccccgggaa ccccaagtgt ataccctgcc accgagccag    1080
gaagaaatga ctaagaacca agtctcattg acttgccttg tgaagggctt ctacccatcg    1140
gatatcgccg tggaatggga gtccaacggc cagccggaaa acaactacaa gaccacccct    1200
ccggtgctgg actcagacgg atccttcttc ctctactcgc ggctgaccgt ggataagagc    1260
agatggcagg agggaaatgt gttcagctgt tctgtgatgc atgaagccct gcacaaccac    1320
tacactcaga agtccctgtc cctctccctg gga                                 1353
```

<210> SEQ ID NO 136
<211> LENGTH: 1353
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 136

```
caggtgcagc tggtgcagtc tggcgccgaa gtgaagaaac ctggcgcctc cgtgaaggtg     60
tcctgcaagg cctctggctt caccctgacc aactacggca tgaactgggt gcgacaggcc    120
cctggacagg gcctggaatg gatgggctgg atcaacaccg acaccggcga gcctacctac    180
gccgacgact tcaagggcag attcgtgttc tccctggaca cctccgtgtc caccgcctac    240
ctgcagatct ccagcctgaa ggccgaggat accgccgtgt actactgcgc cggaaacccc    300
ccttactact acggcaccaa caacgccgag gccatggact attggggcca gggcaccacc    360
gtgaccgtgt cctctgcttc taccaagggg cccagcgtgt tcccctggc cccctgctcc    420 agaagcacca gcgagagcac agccgccctg gctgcctgg tgaaggacta cttccccgag    480
cccgtgaccg tgtcctggaa cagcggagcc ctgaccagcg gcgtgcacac cttccccgcc    540
gtgctgcaga gcagcggcct gtacagcctg agcagcgtgg tgaccgtgcc cagcagcagc    600
ctgggcacca gacctacac ctgtaacgtg gaccacaagc ccagcaacac caaggtggac    660
aagagggtgg agagcaagta cggcccaccc tgccccccct gcccagcccc cgagttcctg    720
ggcggaccca gcgtgttcct gttccccccc aagcccaagg acaccctgat gatcagcaga    780
acccccgagg tgacctgtgt ggtggtggac gtgcccagg aggaccccga ggtccagttc    840
aactggtacg tggacggcgt ggaggtgcac aacgccaaga ccaagccag agaggagcag    900 tttaacagca cctaccgggt ggtgtccgtg ctgaccgtgc tgcaccagga ctggctgaac    960
ggcaaagagt acaagtgtaa ggtctccaac aagggcctgc caagcagcat cgaaaagacc   1020
atcagcaagg ccagggcca gcctagagag cccaggtct acccctgcc acccagcaa    1080 gaggagatga ccaagaacca ggtgtccctg acctgtctgg tgaagggctt ctacccaagc   1140
gacatcgccg tggagtggga gagcaacggc cagcccgaga caactacaa gaccaccccc    1200 ccagtgctgg acagcgacgg cagcttcttc ctgtacagca ggctgaccgt ggacaagtcc    1260
agatggcagg agggcaacgt ctttagctgc tccgtgatgc acgaggccct gcacaaccac   1320
tacacccaga agagcctgag cctgtccctg ggc                                1353
```

<210> SEQ ID NO 137
<211> LENGTH: 321
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 137

```
gatattcaga tgactcagtc acctagtagc ctgagcgcta gtgtgggcga tagagtgact      60
atcacctgta gctctagtca ggatatctct aactacctga actggtatca gcagaagccc     120
ggtaaagccc ctaagctgct gatctactac actagcaccc tgcacctggg aatccccct     180 aggtttagcg gtagcggcta cggcaccgac ttcaccctga ctattaacaa tatcgagtca     240
gaggacgccg cctactactt ctgtcagcag tactataacc tgccctggac cttcggtcaa     300
ggcactaagg tcgagattaa g                                               321
```

<210> SEQ ID NO 138
<211> LENGTH: 642
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 138

```
gatattcaga tgactcagtc acctagtagc ctgagcgcta gtgtgggcga tagagtgact      60
atcacctgta gctctagtca ggatatctct aactacctga actggtatca gcagaagccc     120
ggtaaagccc ctaagctgct gatctactac actagcaccc tgcacctggg aatccccct     180 aggtttagcg gtagcggcta cggcaccgac ttcaccctga ctattaacaa tatcgagtca     240
gaggacgccg cctactactt ctgtcagcag tactataacc tgccctggac cttcggtcaa     300
ggcactaagg tcgagattaa gcgtacggtg gccgctccca gcgtgttcat cttccccccc     360
agcgacgagc agctgaagag cggcaccgcc agcgtggtgt gcctgctgaa caacttctac     420
ccccgggagg ccaaggtgca gtggaaggtg acaacgccc tgcagagcgg caacagccag     480
gagagcgtca ccgagcagga cagcaaggac tccacctaca gcctgagcag caccctgacc     540
ctgagcaagg ccgactacga aagcataag gtgtacgcct gcgaggtgac ccaccagggc     600
ctgtccagcc ccgtgaccaa gagcttcaac aggggcgagt gc                        642
```

<210> SEQ ID NO 139
<211> LENGTH: 642
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 139

```
gacatccaga tgacccagtc cccctccagc ctgtctgctt ccgtgggcga cagagtgacc      60
atcacctgtt cctccagcca ggacatctcc aactacctga actggtatca gcagaagccc     120
ggcaaggccc ccaagctgct gatctactac acctccaccc tgcacctggg catccccct     180 agattctccg gctctggcta cggcaccgac ttcaccctga ccatcaacaa catcgagtcc     240
gaggacgccg cctactactt ctgccagcag tactacaacc tgccctggac cttcggccag     300
ggcaccaagg tggaaatcaa gcgtacggtg gccgctccca gcgtgttcat cttccccccca    360 agcgacgagc agctgaagag cggcaccgcc agcgtggtgt gtctgctgaa caacttctac     420
cccagggagg ccaaggtgca gtggaaggtg acaacgccc tgcagagcgg caacagccag     480
gagagcgtca ccgagcagga cagcaaggac tccacctaca gcctgagcag caccctgacc     540
ctgagcaagg ccgactacga aagcacaag gtgtacgcct gtgaggtgac ccaccagggc     600
ctgtccagcc ccgtgaccaa gagcttcaac aggggcgagt gc                        642
```

```
<210> SEQ ID NO 140
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 140
aactatggaa tgaac                                                          15

<210> SEQ ID NO 141
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 141
tggataaaca ccgacactgg agagccaaca tatgctgatg acttcaaggg a                  51

<210> SEQ ID NO 142
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 142 aaccccccctt attactacgg tactaataac gcggaggcta tggactac                     48

<210> SEQ ID NO 143
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 143
ggatttaccc tcacaaacta t                                                   21

<210> SEQ ID NO 144
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 144
aacaccgaca ctggagag                                                       18

<210> SEQ ID NO 145
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 145
agttcaagtc aggacatcag caattattta aac                                      33
```

```
<210> SEQ ID NO 146
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 146
tacacatcaa ccttacactt a                                              21

<210> SEQ ID NO 147
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 147
cagcagtatt ataaccttcc gtggacg                                        27

<210> SEQ ID NO 148
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 148
agtcaggaca tcagcaatta t                                              21

<210> SEQ ID NO 149
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 149 tacacatca                                                             9

<210> SEQ ID NO 150
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 150
tattataacc ttccgtgg                                                  18

<210> SEQ ID NO 151
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 151
aaccctccct attactacgg tactaataac gcggaggcta tggactac                 48

<210> SEQ ID NO 152
```

<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 152
aactatggca tgaat                                                        15

<210> SEQ ID NO 153
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 153
tggatcaaca ccgacactgg ggagccaacg tatgccgatg acttcaaggg a                51

<210> SEQ ID NO 154
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 154
ggattcaccc tgactaacta t                                                 21

<210> SEQ ID NO 155
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 155
aacaccgaca ctggggag                                                     18

<210> SEQ ID NO 156
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 156
tcctctagtc aggacattag caactattta aat                                    33

<210> SEQ ID NO 157
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 157
tatacatcca ctttgcacct g                                                 21

<210> SEQ ID NO 158
<211> LENGTH: 27

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 158
caacagtatt ataatctccc ttggacg                                          27

<210> SEQ ID NO 159
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 159
agtcaggaca ttagcaacta t                                                21

<210> SEQ ID NO 160
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 160 tatacatcc                                                               9

<210> SEQ ID NO 161
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 161
tattataatc tcccttgg                                                    18

<210> SEQ ID NO 162
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 162
aactacggca tgaac                                                       15

<210> SEQ ID NO 163
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 163
tggatcaaca ccgacaccgg cgagcctacc tacgccgacg acttcaaggg c                51

<210> SEQ ID NO 164
<211> LENGTH: 48
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 164 aaccccccctt actactacgg caccaacaac gccgaggcca tggactat            48

<210> SEQ ID NO 165
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 165
ggcttcaccc tgaccaacta c                                          21

<210> SEQ ID NO 166
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 166
aacaccgaca ccggcgag                                              18

<210> SEQ ID NO 167
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 167
tcctccagcc aggacatctc caactacctg aac                             33

<210> SEQ ID NO 168
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 168
tacacctcca ccctgcacct g                                          21

<210> SEQ ID NO 169
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 169
cagcagtact acaacctgcc ctggacc                                    27

<210> SEQ ID NO 170
<211> LENGTH: 21
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 170
agccaggaca tctccaacta c                                              21

<210> SEQ ID NO 171
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 171 tacacctcc                                                             9

<210> SEQ ID NO 172
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 172
tactacaacc tgccctgg                                                  18

<210> SEQ ID NO 173
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 173
aattacggga tgaac                                                     15

<210> SEQ ID NO 174
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 174
tggattaaca ccgacaccgg ggagcctacc tacgcggacg atttcaaggg a              51

<210> SEQ ID NO 175
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 175
aacccgccct actactacgg aaccaacaac gccgaagcca tggactac                 48

<210> SEQ ID NO 176
<211> LENGTH: 21
<212> TYPE: DNA
<213> ORGANISM: Artificial Sequence
<220> FEATURE:
```

```
<223> OTHER INFORMATION: Description of Artificial Sequence: Synthetic
      oligonucleotide

<400> SEQUENCE: 176
ggattcaccc tcaccaatta c                                              21

<210> SEQ ID NO 177
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 177
aacaccgaca ccgggggag                                                 18

<210> SEQ ID NO 178
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 178
agctctagtc aggatatctc taactacctg aac                                 33

<210> SEQ ID NO 179
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 179
tacactagca ccctgcacct g                                              21

<210> SEQ ID NO 180
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 180
cagcagtact ataacctgcc ctggacc                                        27

<210> SEQ ID NO 181
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 181
agtcaggata tctctaacta c                                              21

<210> SEQ ID NO 182
<211> LENGTH: 9
<212> TYPE: DNA
<213> ORGANISM: Artificial Sequence
<220> FEATURE:
<223> OTHER INFORMATION: Description of Artificial Sequence: Synthetic
```

-continued

```
      oligonucleotide

<400> SEQUENCE: 182 tacactagc                                                                9

<210> SEQ ID NO 183
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 183
tactataacc tgccctgg                                                     18

<210> SEQ ID NO 184
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 184
aactacggga tgaac                                                        15

<210> SEQ ID NO 185
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 185
tggattaaca ccgacaccgg cgagcctacc tacgccgacg actttaaggg c                 51

<210> SEQ ID NO 186
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 186
aaccccccct actactacgg cactaacaac gccgaggcta tggactac                    48

<210> SEQ ID NO 187
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 187

Glu Val Gln Leu Val Gln Ser Gly Ala Glu Val Lys Lys Pro Gly Ala
1               5                   10                  15

Thr Val Lys Ile Ser Cys Lys Val Ser
            20                  25

<210> SEQ ID NO 188
<211> LENGTH: 75
<212> TYPE: DNA
```

<213> ORGANISM: Artificial Sequence
<220> FEATURE:
<223> OTHER INFORMATION: Description of Artificial Sequence: Synthetic
      oligonucleotide

<400> SEQUENCE: 188
gaagtgcagc tggtgcagtc tggcgccgaa gtgaagaaac ccggcgctac cgtgaagatc    60
tcctgcaagg tgtcc                                                     75

<210> SEQ ID NO 189
<211> LENGTH: 75
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 189
gaggtccagc tggtacagtc tggggctgag gtgaagaagc tggggctac agtgaaaatc     60 tcctgcaagg tttct                                                     75

<210> SEQ ID NO 190
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 190

Gln Val Gln Leu Val Gln Ser Gly Ala Glu Val Lys Lys Pro Gly Ala
1               5                   10                  15

Ser Val Lys Val Ser Cys Lys Ala Ser
            20                  25

<210> SEQ ID NO 191
<211> LENGTH: 75
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 191
caagtgcagc tggtgcagtc gggagccgaa gtgaagaagc tggagcctc ggtgaaggtg     60 tcgtgcaagg catcc                                                     75

<210> SEQ ID NO 192
<211> LENGTH: 75
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 192
caggtgcagc tggtgcagtc tggcgccgaa gtgaagaaac ctggcgcctc cgtgaaggtg    60
tcctgcaagg cctct                                                     75

<210> SEQ ID NO 193
<211> LENGTH: 75
<212> TYPE: DNA
<213> ORGANISM: Artificial Sequence
<220> FEATURE:

```
<223> OTHER INFORMATION: Description of Artificial Sequence: Synthetic
      oligonucleotide

<400> SEQUENCE: 193
caggttcagc tggtgcagtc cggagctgag gtgaagaagc ctggggcctc agtgaaggtc    60
tcctgcaagg cttct                                                    75

<210> SEQ ID NO 194
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 194

Glu Val Gln Leu Val Gln Ser Gly Ala Glu Val Lys Lys Pro Gly Glu
1               5                   10                  15

Ser Leu Arg Ile Ser Cys Lys Gly Ser
            20                  25

<210> SEQ ID NO 195
<211> LENGTH: 75
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 195
gaagtgcagc tggtgcagtc tggagcagag gtgaaaaagc ccggggagtc tctgaggatc    60
tcctgtaagg gttct                                                    75

<210> SEQ ID NO 196
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 196

Gln Val Gln Leu Val Gln Ser Gly Ser Glu Leu Lys Lys Pro Gly Ala
1               5                   10                  15

Ser Val Lys Val Ser Cys Lys Ala Ser
            20                  25

<210> SEQ ID NO 197
<211> LENGTH: 75
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 197
caggtgcagc tggtgcaatc tgggtctgag ttgaagaagc ctggggcctc agtgaaggtt    60
tcctgcaagg cttct                                                    75

<210> SEQ ID NO 198
<211> LENGTH: 14
<212> TYPE: PRT
<213> ORGANISM: Artificial Sequence
<220> FEATURE:
```

<223> OTHER INFORMATION: Description of Artificial Sequence: Synthetic
      peptide

<400> SEQUENCE: 198

Trp Val Arg Gln Ala Pro Gly Gln Gly Leu Glu Trp Met Gly
1               5                   10

<210> SEQ ID NO 199
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 199
tgggtccgcc aggccccagg tcaaggcctc gagtggatgg gc                        42

<210> SEQ ID NO 200
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 200
tgggtgcgac aggcccctgg acagggcctg gaatggatgg gc                        42

<210> SEQ ID NO 201
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 201
tgggtgcgac aggcccctgg acaagggctt gagtggatgg gt                        42

<210> SEQ ID NO 202
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 202

Trp Val Arg Gln Ala Arg Gly Gln Arg Leu Glu Trp Ile Gly
1               5                   10

<210> SEQ ID NO 203
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 203
tgggtcagac aggcccgggg tcaacggctg gagtggatcg ga                        42

<210> SEQ ID NO 204
<211> LENGTH: 42
<212> TYPE: DNA
<213> ORGANISM: Artificial Sequence

```
<220> FEATURE:
<223> OTHER INFORMATION: Description of Artificial Sequence: Synthetic
      oligonucleotide

<400> SEQUENCE: 204
tgggtgcgac aggccagggg ccagcggctg gaatggatcg gc                              42

<210> SEQ ID NO 205
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 205
tgggtgcgac aggctcgtgg acaacgcctt gagtggatag gt                              42

<210> SEQ ID NO 206
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 206

Trp Ile Arg Gln Ser Pro Ser Arg Gly Leu Glu Trp Leu Gly
1               5                   10

<210> SEQ ID NO 207
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 207
tggatcaggc agtccccatc gagaggcctt gagtggctgg gt                              42

<210> SEQ ID NO 208
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 208

Trp Val Arg Gln Ala Thr Gly Gln Gly Leu Glu Trp Met Gly
1               5                   10

<210> SEQ ID NO 209
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 209
tgggtgcgac aggccactgg acaagggctt gagtggatgg gt                              42

<210> SEQ ID NO 210
<211> LENGTH: 32
<212> TYPE: PRT
```

```
<213> ORGANISM: Artificial Sequence
<220> FEATURE:
<223> OTHER INFORMATION: Description of Artificial Sequence: Synthetic
      polypeptide

<400> SEQUENCE: 210

Arg Phe Val Phe Ser Leu Asp Thr Ser Val Ser Thr Ala Tyr Leu Gln
1               5                   10                  15

Ile Cys Ser Leu Lys Ala Glu Asp Thr Ala Val Tyr Tyr Cys Ala Arg
            20                  25                  30

<210> SEQ ID NO 211
<211> LENGTH: 96
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 211
agatttgtct tctccttgga cacctctgtc agcacggcat atctgcagat ctgcagccta      60
aaggctgagg acactgccgt gtattactgt gcaaga                               96

<210> SEQ ID NO 212
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 212

Arg Phe Val Phe Ser Leu Asp Thr Ser Val Ser Thr Ala Tyr Leu Gln
1               5                   10                  15

Ile Ser Ser Leu Lys Ala Glu Asp Thr Ala Val Tyr Tyr Cys Ala Arg
            20                  25                  30

<210> SEQ ID NO 213
<211> LENGTH: 96
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 213
cggttcgtgt tctccctcga cacctccgtg tccaccgcct acctccaaat ctcctcactg      60
aaagcggagg acaccgccgt gtactattgc gcgagg                               96

<210> SEQ ID NO 214
<211> LENGTH: 96
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 214
agattcgtgt ttagcctgga cactagtgtg tctaccgcct acctgcagat ctctagcctg      60
aaggccgagg acaccgccgt ctactactgc gctaga                               96

<210> SEQ ID NO 215
<211> LENGTH: 96
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 215
agattcgtgt tctccctgga cacctccgtg tccaccgcct acctgcagat ctccagcctg    60
aaggccgagg ataccgccgt gtactactgc gcccgg                              96

<210> SEQ ID NO 216
<211> LENGTH: 96
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 216
agatttgtct tctccttgga cacctctgtc agcacggcat atctgcagat cagcagccta    60
aaggctgagg acactgccgt gtattactgt gcaaga                              96

<210> SEQ ID NO 217
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 217

Arg Val Thr Ile Ser Ala Asp Lys Ser Ile Ser Thr Ala Tyr Leu Gln
1               5                   10                  15

Trp Ser Ser Leu Lys Ala Ser Asp Thr Ala Met Tyr Tyr Cys Ala Arg
            20                  25                  30

<210> SEQ ID NO 218
<211> LENGTH: 96
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 218
agagtcacca tctcagccga caagtccatc agcaccgcct acctgcagtg gagcagcctg    60
aaggcctcgg acaccgccat gtattactgt gcaaga                              96

<210> SEQ ID NO 219
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 219

Arg Phe Val Phe Ser Leu Asp Thr Ser Val Ser Thr Ala Tyr Leu Gln
1               5                   10                  15

Ile Ser Thr Leu Lys Ala Glu Asp Thr Ala Thr Tyr Phe Cys Ala Arg
            20                  25                  30

<210> SEQ ID NO 220
<211> LENGTH: 96
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 220
cggtttgtct tctccttgga cacctctgtc agcacggcat atctgcagat cagcacgcta    60
aaggctgagg acactgctac atatttctgt gcaaga                              96

<210> SEQ ID NO 221
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 221

Trp Gly Gln Gly Thr Thr Val Thr Val Ser Ser
1               5                   10

<210> SEQ ID NO 222
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 222
tggggccagg gcaccactgt gactgtgtcc agc                                 33

<210> SEQ ID NO 223
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 223
tggggtcaag gcactaccgt gaccgtgtct agc                                 33

<210> SEQ ID NO 224
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 224
tggggccagg gcaccaccgt gaccgtgtcc tct                                 33

<210> SEQ ID NO 225
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 225
tggggccagg gcaccaccgt gaccgtgtcc tcc                                 33

<210> SEQ ID NO 226
```

```
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 226

Asp Ile Gln Met Thr Gln Ser Pro Ser Ser Leu Ser Ala Ser Val Gly
1               5                   10                  15

Asp Arg Val Thr Ile Thr Cys
            20

<210> SEQ ID NO 227
<211> LENGTH: 69
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 227
gatattcaga tgactcagtc acctagtagc ctgagcgcta gtgtgggcga tagagtgact      60
atcacctgt                                                             69

<210> SEQ ID NO 228
<211> LENGTH: 69
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 228
gacatccaga tgacccagtc cccctccagc ctgtctgctt ccgtgggcga cagagtgacc      60
atcacctgt                                                             69

<210> SEQ ID NO 229
<211> LENGTH: 69
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 229
gacatccaga tgacccagtc tccatcctcc ctgtctgcat ctgtaggaga cagagtcacc      60
atcacttgc                                                             69

<210> SEQ ID NO 230
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 230

Glu Ile Val Leu Thr Gln Ser Pro Ala Thr Leu Pro Val Thr Leu Gly
1               5                   10                  15

Gln Pro Ala Ser Ile Ser Cys
            20

<210> SEQ ID NO 231
```

```
<211> LENGTH: 69
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 231
gaaattgtgt tgacacagtc tccagccacc ctgcccgtca cccttggaca gccggcctcc        60
atctcctgc                                                                69

<210> SEQ ID NO 232
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 232

Glu Ile Val Leu Thr Gln Ser Pro Ala Thr Leu Ser Leu Ser Pro Gly
1               5                   10                  15

Glu Arg Ala Thr Leu Ser Cys
            20

<210> SEQ ID NO 233
<211> LENGTH: 69
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 233
gaaattgtgt tgacacagtc tccagccacc ctgtctttgt ctccagggga aagagccacc        60
ctctcctgc                                                                69

<210> SEQ ID NO 234
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 234

Asp Ile Val Met Thr Gln Thr Pro Leu Ser Leu Pro Val Thr Pro Gly
1               5                   10                  15

Glu Pro Ala Ser Ile Ser Cys
            20

<210> SEQ ID NO 235
<211> LENGTH: 69
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 235
gatattgtga tgacccagac tccactctcc ctgcccgtca cccctggaga gccggcctcc        60
atctcctgc                                                                69

<210> SEQ ID NO 236
```

<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 236

Glu Ile Val Leu Thr Gln Ser Pro Asp Phe Gln Ser Val Thr Pro Lys
1               5                   10                  15

Glu Lys Val Thr Ile Thr Cys
            20

<210> SEQ ID NO 237
<211> LENGTH: 69
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 237
gaaattgtgc tgactcagtc tccagacttt cagtctgtga ctccaaagga gaaagtcacc    60
atcacctgc                                                           69

<210> SEQ ID NO 238
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 238

Ala Ile Gln Leu Thr Gln Ser Pro Ser Ser Leu Ser Ala Ser Val Gly
1               5                   10                  15

Asp Arg Val Thr Ile Thr Cys
            20

<210> SEQ ID NO 239
<211> LENGTH: 69
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 239
gccatccagt tgacccagtc tccatcctcc ctgtctgcat ctgtaggaga cagagtcacc    60
atcacttgc                                                           69

<210> SEQ ID NO 240
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 240

Trp Tyr Gln Gln Lys Pro Gly Lys Ala Pro Lys Leu Leu Ile Tyr
1               5                   10                  15

<210> SEQ ID NO 241
<211> LENGTH: 45

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 241
tggtatcagc agaagcccgg taaagcccct aagctgctga tctac            45

<210> SEQ ID NO 242
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 242
tggtatcagc agaagcccgg caaggccccc aagctgctga tctac            45

<210> SEQ ID NO 243
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 243
tggtatcagc agaaaccagg gaaagctcct aagctcctga tctat            45

<210> SEQ ID NO 244
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 244

Trp Tyr Gln Gln Lys Pro Gly Gln Ala Pro Arg Leu Leu Ile Tyr
1               5                   10                  15

<210> SEQ ID NO 245
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 245
tggtaccagc agaaacctgg ccaggctccc aggctcctca tctat            45

<210> SEQ ID NO 246
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 246

Trp Tyr Leu Gln Lys Pro Gly Gln Ser Pro Gln Leu Leu Ile Tyr
1               5                   10                  15

<210> SEQ ID NO 247
```

```
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 247
tggtacctgc agaagccagg gcagtctcca cagctcctga tctat          45

<210> SEQ ID NO 248
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 248

Trp Tyr Leu Gln Lys Pro Gly Gln Ser Pro Gln Leu Leu Ile Tyr
1               5                   10                  15

<210> SEQ ID NO 249
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 249
tggtatctgc agaagcccgg tcaatcacct cagctgctga tctac          45

<210> SEQ ID NO 250
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 250
tggtatctgc agaagcccgg ccagtcccct cagctgctga tctac          45

<210> SEQ ID NO 251
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 251
tggtacctgc agaagccagg gcagtctcca cagctcctga tctat          45

<210> SEQ ID NO 252
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 252

Gly Val Pro Ser Arg Phe Ser Gly Ser Gly Ser Gly Thr Asp Phe Thr
1               5                   10                  15

Phe Thr Ile Ser Ser Leu Glu Ala Glu Asp Ala Ala Thr Tyr Tyr Cys
```

<210> SEQ ID NO 253
<211> LENGTH: 96
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 253

```
ggcgtgccct ccagattttc cggctctggc tctggcaccg actttacctt caccatcagc    60
tccctggaag ccgaggacgc cgccacctac tactgc                              96
```

<210> SEQ ID NO 254
<211> LENGTH: 96
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 254

```
ggggtcccct cgaggttcag tggcagtgga tctgggacag atttcacctt taccatcagt    60
agcctggaag ctgaagatgc tgcaacatat tactgt                              96
```

<210> SEQ ID NO 255
<211> LENGTH: 32
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 255

Gly Ile Pro Pro Arg Phe Ser Gly Ser Gly Tyr Gly Thr Asp Phe Thr
1               5                   10                  15
Leu Thr Ile Asn Asn Ile Glu Ser Glu Asp Ala Ala Tyr Tyr Phe Cys
            20                  25                  30

<210> SEQ ID NO 256
<211> LENGTH: 96
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 256

```
ggaatccccc ctaggtttag cggtagcggc tacggcaccg acttcaccct gactattaac    60
aatatcgagt cagaggacgc cgcctactac ttctgt                              96
```

<210> SEQ ID NO 257
<211> LENGTH: 96
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 257

```
ggcatccccc ctagattctc cggctctggc tacggcaccg acttcaccct gaccatcaac    60
aacatcgagt ccgaggacgc cgcctactac ttctgc                              96
```

<210> SEQ ID NO 258
<211> LENGTH: 96
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 258
gggatcccac ctcgattcag tggcagcggg tatggaacag attttaccct cacaattaat    60
aacatagaat ctgaggatgc tgcatattac ttctgt    96

<210> SEQ ID NO 259
<211> LENGTH: 32
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 259

Gly Ile Pro Asp Arg Phe Ser Gly Ser Gly Ser Gly Thr Asp Phe Thr
1               5                   10                  15

Leu Thr Ile Ser Arg Leu Glu Pro Glu Asp Phe Ala Val Tyr Tyr Cys
            20                  25                  30

<210> SEQ ID NO 260
<211> LENGTH: 96
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 260
gggatcccag acaggttcag tggcagtggg tctgggacag acttcactct caccatcagc    60
agactggagc ctgaagattt tgcagtgtat tactgt    96

<210> SEQ ID NO 261
<211> LENGTH: 32
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 261

Gly Val Pro Ser Arg Phe Ser Gly Ser Gly Ser Gly Thr Glu Phe Thr
1               5                   10                  15

Leu Thr Ile Ser Ser Leu Gln Pro Asp Asp Phe Ala Thr Tyr Tyr Cys
            20                  25                  30

<210> SEQ ID NO 262
<211> LENGTH: 96
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 262
ggcgtgccct ctaggtttag cggtagcggt agtggcaccg agttcaccct gactatctct    60
agcctgcagc ccgacgactt cgctacctac tactgt    96

<210> SEQ ID NO 263
<211> LENGTH: 96
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 263
ggcgtgccct ccagattttc cggctctggc tctggcaccg agtttaccct gaccatcagc        60
tccctgcagc ccgacgactt cgccacctac tactgc                                 96

<210> SEQ ID NO 264
<211> LENGTH: 96
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 264
ggggtcccat caaggttcag cggcagtgga tctgggacag aattcactct caccatcagc        60
agcctgcagc ctgatgattt tgcaacttat tactgt                                  96

<210> SEQ ID NO 265
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 265

Gly Val Pro Ser Arg Phe Ser Gly Ser Gly Ser Gly Thr Asp Phe Thr
1               5                   10                  15

Leu Thr Ile Ser Ser Leu Gln Pro Glu Asp Phe Ala Thr Tyr Tyr Cys
            20                  25                  30

<210> SEQ ID NO 266
<211> LENGTH: 96
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 266
ggggtcccat caaggttcag cggcagtgga tctgggacag atttcactct caccatcagc        60
agcctgcagc ctgaagattt tgcaacttat tactgt                                  96

<210> SEQ ID NO 267
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 267

Gly Val Pro Ser Arg Phe Ser Gly Ser Gly Ser Gly Thr Asp Phe Thr
1               5                   10                  15

Phe Thr Ile Ser Ser Leu Gln Pro Glu Asp Ile Ala Thr Tyr Tyr Cys
            20                  25                  30

```
<210> SEQ ID NO 268
<211> LENGTH: 96
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 268
ggggtcccat caaggttcag tggaagtgga tctgggacag attttacttt caccatcagc    60
agcctgcagc ctgaagatat tgcaacatat tactgt                              96

<210> SEQ ID NO 269
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 269

Gly Ile Pro Asp Arg Phe Ser Gly Ser Gly Ser Gly Thr Asp Phe Thr
1               5                   10                  15

Leu Thr Ile Ser Arg Leu Glu Pro Glu Asp Phe Ala Val Tyr Tyr Cys
            20                  25                  30

<210> SEQ ID NO 270
<211> LENGTH: 96
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 270
gggatcccag acaggttcag tggcagtggg tctgggacag acttcactct caccatcagc    60
agactggagc ctgaagattt tgcagtgtat tactgt                              96

<210> SEQ ID NO 271
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 271

Phe Gly Gln Gly Thr Lys Val Glu Ile Lys
1               5                   10

<210> SEQ ID NO 272
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 272
ttcggtcaag gcactaaggt cgagattaag                                     30

<210> SEQ ID NO 273
<211> LENGTH: 30
<212> TYPE: DNA
<213> ORGANISM: Artificial Sequence
```

-continued

```
<220> FEATURE:
<223> OTHER INFORMATION: Description of Artificial Sequence: Synthetic
      oligonucleotide

<400> SEQUENCE: 273
ttcggccagg gcaccaaggt ggaaatcaag                                          30

<210> SEQ ID NO 274
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 274
ttcggccaag ggaccaaggt ggaaatcaaa                                          30

<210> SEQ ID NO 275
<211> LENGTH: 327
<212> TYPE: PRT
<213> ORGANISM: Homo sapiens

<400> SEQUENCE: 275
```

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

```
Thr Thr Pro Pro Val Leu Asp Ser Asp Gly Ser Phe Phe Leu Tyr Ser
            275                 280                 285

Arg Leu Thr Val Asp Lys Ser Arg Trp Gln Glu Gly Asn Val Phe Ser
            290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 276
<211> LENGTH: 107
<212> TYPE: PRT
<213> ORGANISM: Homo sapiens

<400> SEQUENCE: 276

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 277
<211> LENGTH: 326
<212> TYPE: PRT
<213> ORGANISM: Homo sapiens

<400> SEQUENCE: 277

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
130                 135                 140

Asp Val Ser Gln Glu Asp Pro Glu Val Gln Phe Asn Trp Tyr Val Asp
145                 150                 155                 160
```

```
Gly Val Glu Val His Asn Ala Lys Thr Lys Pro Arg Glu Glu Gln Phe
            165                 170                 175

Asn Ser Thr Tyr Arg Val Val Ser Val Leu Thr Val Leu His Gln Asp
        180                 185                 190

Trp Leu Asn Gly Lys Glu Tyr Lys Cys Lys Val Ser Asn Lys Gly Leu
    195                 200                 205

Pro Ser Ser Ile Glu Lys Thr Ile Ser Lys Ala Lys Gly Gln Pro Arg
210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly
                325

<210> SEQ ID NO 278
<211> LENGTH: 330
<212> TYPE: PRT
<213> ORGANISM: Homo sapiens

<400> SEQUENCE: 278

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
```

```
            195                 200                 205
Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                    245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                    325                 330

<210> SEQ ID NO 279
<211> LENGTH: 330
<212> TYPE: PRT
<213> ORGANISM: Homo sapiens

<400> SEQUENCE: 279

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
                100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
        130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Ala Ser Thr Tyr Arg Val Val Ser Val Leu Thr Val Leu
                180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
        210                 215                 220

Gln Pro Arg Glu Pro Gln Val Tyr Thr Leu Pro Pro Ser Arg Glu Glu
225                 230                 235                 240
```

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 280
<211> LENGTH: 330
<212> TYPE: PRT
<213> ORGANISM: Homo sapiens

<400> SEQUENCE: 280

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Ala Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Ala Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

```
Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 281
<211> LENGTH: 330
<212> TYPE: PRT
<213> ORGANISM: Homo sapiens

<400> SEQUENCE: 281

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Ala Ala Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
```

<210> SEQ ID NO 282
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 282

Met Glu Trp Ser Trp Val Phe Leu Phe Phe Leu Ser Val Thr Thr Gly
1               5                   10                  15

Val His Ser

<210> SEQ ID NO 283
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 283

Met Ser Val Pro Thr Gln Val Leu Gly Leu Leu Leu Leu Trp Leu Thr
1               5                   10                  15

Asp Ala Arg Cys
            20

<210> SEQ ID NO 284
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 284

Met Ala Trp Val Trp Thr Leu Pro Phe Leu Met Ala Ala Ala Gln Ser
1               5                   10                  15

Val Gln Ala

<210> SEQ ID NO 285
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 285

Met Ser Val Leu Thr Gln Val Leu Ala Leu Leu Leu Leu Trp Leu Thr
1               5                   10                  15

Gly Thr Arg Cys
            20

<210> SEQ ID NO 286
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 286

Gly Phe Thr Leu Thr Asn Tyr Gly Met Asn
1               5                   10

<210> SEQ ID NO 287
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 287
ggcttcaccc tgactaacta c                                              21

<210> SEQ ID NO 288
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 288
gctgacagac taacagactg ttcc                                           24

<210> SEQ ID NO 289
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 289
caaatgtggt atggctga                                                  18

<210> SEQ ID NO 290
<211> LENGTH: 95
<212> TYPE: PRT
<213> ORGANISM: Mus musculus

<400> SEQUENCE: 290

Asp Ile Gln Met Thr Gln Thr Thr Ser Ser Leu Ser Ala Ser Leu Gly
1               5                   10                  15

Asp Arg Val Thr Ile Ser Cys Ser Ala Ser Gln Gly Ile Ser Asn Tyr
                20                  25                  30

Leu Asn Trp Tyr Gln Gln Lys Pro Asp Gly Thr Val Lys Leu Leu Ile
            35                  40                  45

Tyr Tyr Thr Ser Ser Leu His Ser Gly Val Pro Ser Arg Phe Ser Gly
        50                  55                  60

Ser Gly Ser Gly Thr Asp Tyr Ser Leu Thr Ile Ser Asn Leu Glu Pro
65                  70                  75                  80

Glu Asp Ile Ala Thr Tyr Tyr Cys Gln Gln Tyr Ser Lys Leu Pro
                85                  90                  95

<210> SEQ ID NO 291
<211> LENGTH: 98
<212> TYPE: PRT
<213> ORGANISM: Mus musculus

<400> SEQUENCE: 291

Gln Ile Gln Leu Val Gln Ser Gly Pro Glu Leu Lys Lys Pro Gly Glu
1               5                   10                  15

```
Thr Val Lys Ile Ser Cys Lys Ala Ser Gly Tyr Thr Phe Thr Asn Tyr
            20                  25                  30

Gly Met Asn Trp Val Lys Gln Ala Pro Gly Lys Gly Leu Lys Trp Met
            35                  40                  45

Gly Trp Ile Asn Thr Tyr Thr Gly Glu Pro Thr Tyr Ala Asp Asp Phe
        50                  55                  60

Lys Gly Arg Phe Ala Phe Ser Leu Glu Thr Ser Ala Ser Thr Ala Tyr
 65              70                  75                  80

Leu Gln Ile Asn Asn Leu Lys Asn Glu Asp Thr Ala Thr Tyr Phe Cys
                85                  90                  95

Ala Arg

<210> SEQ ID NO 292
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 292

Glu Ile Val Leu Thr Gln Ser Pro Ala Thr Leu Pro Val Ser Leu Gly
 1               5                  10                  15

Gln Thr Ala Ser Ile Ser Cys Ser Ser Ser Gln Asp Ile Ser Asn Tyr
            20                  25                  30

Leu Asn Trp Tyr Gln Gln Lys Pro Gly Gln Ala Pro Arg Leu Leu Ile
        35                  40                  45

Tyr Tyr Thr Ser Thr Leu His Leu Gly Val Pro Ser Arg Phe Ser Gly
    50                  55                  60

Ser Gly Ser Gly Thr Asp Phe Thr Phe Thr Ile Ser Ser Leu Glu Ala
 65              70                  75                  80

Glu Asp Ala Ala Thr Tyr Tyr Cys Gln Gln Tyr Tyr Asn Leu Pro Trp
                85                  90                  95

Thr Phe Gly Gln Gly Thr Lys Val Glu Ile Lys
            100                 105

<210> SEQ ID NO 293
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 293

Cys Asn Gly Arg Cys
 1               5
```

ANTIBODY MOLECULES TO LAG-3 AND USES THEREOF

CROSS REFERENCE TO RELATED APPLICATIONS

This application is a divisional of Ser. No. 15/829,284, filed Dec. 1, 2017 which is a divisional of Ser. No. 14/657,260, filed Mar. 13, 2015, which claims the benefit of U.S. Provisional Application No. 61/953,536, filed Mar. 14, 2014, U.S. Provisional Application No. 62/059,690, filed Oct. 3, 2014, and U.S. Provisional Application No. 62/094,889, filed Dec. 19, 2014, the contents of the aforementioned applications are hereby incorporated by reference in their entirety.

SEQUENCE LISTING

The instant application contains a Sequence Listing which has been submitted electronically in ASCII format and is hereby incorporated by reference in its entirety. Said ASCII copy, created on Mar. 10, 2015, is named C2160-700110_SL.txt and is 252,850 bytes in size.

BACKGROUND

Lymphocyte Activation Gene-3, or LAG-3 (also known as CD223), is a member of the immunoglobulin supergene family, and is expressed on activated T cells (Huard et al. (1994) *Immunogenetics* 39:213), NK cells (Triebel et al. (1990) *J. Exp. Med.* 171:1393-1405), regulatory T cells (Huang et al. (2004) *Immunity* 21:503-513; Camisaschi et al. (2010) *J Immunol.* 184:6545-6551; Gagliani et al. (2013) *Nat Med* 19:739-746), and plasmacytoid dendritic cells (DCs) (Workman et al. (2009) *J Immunol* 182:1885-1891). LAG-3 is a membrane protein encoded by a gene located on chromosome 12, and is structurally and genetically related to CD4.

Similar to CD4, LAG-3 can interact with MHC class II molecules on the cell surface (Baixeras et al. (1992) *J. Exp. Med.* 176:327-337; Huard et al. (1996) *Eur. J. Immunol.* 26:1180-1186). It has been suggested that the direct binding of LAG-3 to MHC class II plays a role in down-regulating antigen-dependent stimulation of CD4+T lymphocytes (Huard et al. (1994) *Eur. J. Immunol.* 24:3216-3221) and LAG-3 blockade has also been shown to reinvigorate CD8+ lymphocytes in both tumor or self-antigen (Gross et al. (2007) *J Clin Invest.* 117:3383-3392) and viral models (Blackburn et al. (2009) *Nat. Immunol.* 10:29-37). Further, the intra-cytoplasmic region of LAG-3 can interact with LAP (LAG-3-associated protein), which is a signal transduction molecule involved in the downregulation of the CD3/TCR activation pathway (Iouzalen et al. (2001) *Eur. J. Immunol.* 31:2885-2891). Moreover, CD4+CD25+ regulatory T cells ($T_{reg}$) have been shown to express LAG-3 upon activation, which contributes to the suppressor activity of $T_{reg}$ cells (Huang, C. et al. (2004) *Immunity* 21:503-513). LAG-3 can also negatively regulate T cell homeostasis by $T_{reg}$ cells in both T cell-dependent and independent mechanisms (Workman, C. J. and Vignali, D. A. (2005) *J. Immunol.* 174:688-695).

Given the importance of LAG-3 in downregulating an immune response, the need exists for developing novel agents that modulate its activity to activate the immune system. Such agents can be used, e.g., for cancer immunotherapy and treatment of other conditions, such as chronic infection.

SUMMARY

Disclosed herein are antibody molecules (e.g., humanized antibody molecules) that bind to Lymphocyte Activation Gene-3 (LAG-3) with high affinity and specificity. In one embodiment, the anti-LAG-3 antibody molecules include a novel combination of framework regions (e.g., FW1, FW2, FW3 and/or FW4), e.g., novel combinations of a heavy chain framework regions and/or light chain framework regions. Nucleic acid molecules encoding the antibody molecules, expression vectors, host cells and methods for making the antibody molecules are also provided. Immunoconjugates, multi- or bispecific antibody molecules and pharmaceutical compositions comprising the antibody molecules are also provided. The anti-LAG-3 antibody molecules disclosed herein can be used (alone or in combination with other agents or therapeutic modalities) to treat, prevent and/or diagnose cancerous disorders (e.g., solid and soft-tissue tumors), as well as infectious diseases. Thus, compositions and methods for detecting LAG-3, as well as methods for treating various disorders, including cancer and/or infectious diseases using the anti-LAG-3 antibody molecules are disclosed herein.

Accordingly, in one aspect, the invention features an antibody molecule (e.g., an isolated or recombinant antibody molecule) having one or more of the following properties:
  (i) binds to LAG-3, e.g., human LAG-3, with high affinity, e.g., with an affinity constant of at least about $10^7$ $M^{-1}$, typically about $10^8$ $M^{-1}$, and more typically, about $10^9$ $M^{-1}$ to $10^{10}$ $M^{-1}$ or stronger;
  (ii) binds to LAG-3, e.g., a LAG-3-CHO transfectant, with a $K_D$ of less than: 5 nM. 4 nM, 3 nM, 2 nM, 1 nM, e.g., 1 to 3 nM (e.g., about 1.92 nM or about 2.3 nM);
  (iii) does not substantially bind to CD4;
  (iv) inhibits binding of LAG-3 to a major histocompatibility (MHC) class II molecule, e.g., shows an $IC_{50}$ of about 1 to 20 nM, 5 to 15 nM, e.g., 5.5 nM;
  (v) binds to the D1 domain of LAG-3 (e.g., human LAG-3), e.g., binds to the D1 domain, but does not bind to the extra loop region of the D1 domain;
  (vi) modulates (e.g., stimulates, enhances, or restores) an immune response, e.g., an antigen-specific T cell response or anti-tumor response;
  (vii) binds specifically to an epitope on LAG-3, e.g., the same or similar epitope as the epitope recognized by murine monoclonal antibody BAP050 or chimeric antibody BAP050-chi;
  (viii) binds to a different epitope on LAG-3 than the one recognized by antibody BMS-986016;
  (ix) shows the same or similar binding affinity or specificity, or both, as any of BAP050-hum01, BAP050-hum02, BAP050-hum03, BAP050-hum04, BAP050-hum05, BAP050-hum06, BAP050-hum07, BAP050-hum08, BAP050-hum09, BAP050-hum10, BAP050-hum11, BAP050-hum12, BAP050-hum13, BAP050-hum14, BAP050-hum15, BAP050-hum16, BAP050-hum17, BAP050-hum18, BAP050-hum19, BAP050-hum20, huBAP050 (Ser) (e.g., BAP050-hum01-Ser, BAP050-hum02-Ser, BAP050-hum03-Ser, BAP050-hum04-Ser, BAP050-hum05-Ser, BAP050-hum06-Ser, BAP050-hum07-Ser, BAP050-hum08-Ser, BAP050-hum09-Ser, BAP050-hum10-Ser, BAP050-hum11-Ser, BAP050-hum12-Ser, BAP050-hum13-Ser, BAP050-hum14-Ser, BAP050-hum15-Ser, BAP050-hum18-Ser, BAP050-hum19-Ser, or BAP050-hum20-Ser), BAP050-Clone-F. BAP050-Clone-G, BAP050-Clone-H, BAP050-Clone-I, or BAP050-Clone-J.

(x) shows the same or similar binding affinity or specificity, or both, as an antibody molecule (e.g., an heavy chain variable region and light chain variable region) described in Table 1;
(xi) shows the same or similar binding affinity or specificity, or both, as an antibody molecule (e.g., an heavy chain variable region and light chain variable region) having an amino acid sequence shown in Table 1;
(xii) shows the same or similar binding affinity or specificity, or both, as an antibody molecule (e.g., an heavy chain variable region and light chain variable region) encoded by the nucleotide sequence shown in Table 1;
(xiii) inhibits, e.g., competitively inhibits, the binding of a second antibody molecule to LAG-3, wherein the second antibody molecule is an antibody molecule described herein, e.g., an antibody molecule chosen from, e.g., any of BAP050-hum01, BAP050-hum02, BAP050-hum03, BAP050-hum04, BAP050-hum05, BAP050-hum06, BAP050-hum07, BAP050-hum08, BAP050-hum09, BAP050-hum10, BAP050-hum11, BAP050-hum12, BAP050-hum13, BAP050-hum14, BAP050-hum15, BAP050-hum16, BAP050-hum17, BAP050-hum18, BAP050-hum19, BAP050-hum20, huBAP050 (Ser) (e.g., BAP050-hum01-Ser, BAP050-hum02-Ser, BAP050-hum03-Ser, BAP050-hum04-Ser, BAP050-hum05-Ser, BAP050-hum06-Ser, BAP050-hum07-Ser, BAP050-hum08-Ser, BAP050-hum09-Ser, BAP050-hum10-Ser, BAP050-hum11-Ser, BAP050-hum12-Ser, BAP050-hum13-Ser, BAP050-hum14-Ser, BAP050-hum15-Ser, BAP050-hum18-Ser, BAP050-hum19-Ser, or BAP050-hum20-Ser), BAP050-Clone-F. BAP050-Clone-G, BAP050-Clone-H, BAP050-Clone-I, or BAP050-Clone-J;
(xiv) binds the same or an overlapping epitope with a second antibody molecule to LAG-3, wherein the second antibody molecule is an antibody molecule described herein, e.g., an antibody molecule chosen from, e.g., any of BAP050-hum01, BAP050-hum02, BAP050-hum03, BAP050-hum04, BAP050-hum05, BAP050-hum06, BAP050-hum07, BAP050-hum08, BAP050-hum09, BAP050-hum10, BAP050-hum11, BAP050-hum12, BAP050-hum13, BAP050-hum14, BAP050-hum15, BAP050-hum16, BAP050-hum17, BAP050-hum18, BAP050-hum19, BAP050-hum20, huBAP050 (Ser) (e.g., BAP050-hum01-Ser, BAP050-hum02-Ser, BAP050-hum03-Ser, BAP050-hum04-Ser, BAP050-hum05-Ser, BAP050-hum06-Ser, BAP050-hum07-Ser, BAP050-hum08-Ser, BAP050-hum09-Ser, BAP050-hum10-Ser, BAP050-hum11-Ser, BAP050-hum12-Ser, BAP050-hum13-Ser, BAP050-hum14-Ser, BAP050-hum15-Ser, BAP050-hum18-Ser, BAP050-hum19-Ser, or BAP050-hum20-Ser), BAP050-Clone-F. BAP050-Clone-G, BAP050-Clone-H, BAP050-Clone-I, or BAP050-Clone-J;
(xv) competes for binding, and/or binds the same epitope, with a second antibody molecule to LAG-3, e.g., as measured by a BIACORE™ method, a FACS method, or both, wherein the second antibody molecule is an antibody molecule described herein, e.g., an antibody molecule chosen from, e.g., any of BAP050-hum01, BAP050-hum02, BAP050-hum03, BAP050-hum04, BAP050-hum05, BAP050-hum06, BAP050-hum07, BAP050-hum08, BAP050-hum09, BAP050-hum10, BAP050-hum11, BAP050-hum12, BAP050-hum13, BAP050-hum14, BAP050-hum15, BAP050-hum16, BAP050-hum17, BAP050-hum18, BAP050-hum19, BAP050-hum20, huBAP050 (Ser) (e.g., BAP050-hum01-Ser, BAP050-hum02-Ser, BAP050-hum03-Ser, BAP050-hum04-Ser, BAP050-hum05-Ser, BAP050-hum06-Ser, BAP050-hum07-Ser, BAP050-hum08-Ser, BAP050-hum09-Ser, BAP050-hum10-Ser, BAP050-hum11-Ser, BAP050-hum12-Ser, BAP050-hum13-Ser, BAP050-hum14-Ser, BAP050-hum15-Ser, BAP050-hum18-Ser, BAP050-hum19-Ser, or BAP050-hum20-Ser), BAP050-Clone-F. BAP050-Clone-G, BAP050-Clone-H, BAP050-Clone-I, or BAP050-Clone-J;
(xvi) has one or more biological properties of an antibody molecule described herein, e.g., an antibody molecule chosen from, e.g., any of BAP050-hum01, BAP050-hum02, BAP050-hum03, BAP050-hum04, BAP050-hum05, BAP050-hum06, BAP050-hum07, BAP050-hum08, BAP050-hum09, BAP050-hum10, BAP050-hum11, BAP050-hum12, BAP050-hum13, BAP050-hum14, BAP050-hum15, BAP050-hum16, BAP050-hum17, BAP050-hum18, BAP050-hum19, BAP050-hum20, huBAP050 (Ser) (e.g., BAP050-hum01-Ser, BAP050-hum02-Ser, BAP050-hum03-Ser, BAP050-hum04-Ser, BAP050-hum05-Ser, BAP050-hum06-Ser, BAP050-hum07-Ser, BAP050-hum08-Ser, BAP050-hum09-Ser, BAP050-hum10-Ser, BAP050-hum11-Ser, BAP050-hum12-Ser, BAP050-hum13-Ser, BAP050-hum14-Ser, BAP050-hum15-Ser, BAP050-hum18-Ser, BAP050-hum19-Ser, or BAP050-hum20-Ser), BAP050-Clone-F, BAP050-Clone-G, BAP050-Clone-H, BAP050-Clone-I, or BAP050-Clone-J;
(xvii) has one or more pharmacokinetic properties of an antibody molecule described herein, e.g., an antibody molecule chosen from, e.g., any of BAP050-hum01, BAP050-hum02, BAP050-hum03, BAP050-hum04, BAP050-hum05, BAP050-hum06, BAP050-hum07, BAP050-hum08, BAP050-hum09, BAP050-hum10, BAP050-hum11, BAP050-hum12, BAP050-hum13, BAP050-hum14, BAP050-hum15, BAP050-hum16, BAP050-hum17. BAP050-hum18, BAP050-hum19, BAP050-hum20, huBAP050 (Ser) (e.g., BAP050-hum01-Ser, BAP050-hum02-Ser, BAP050-hum03-Ser, BAP050-hum04-Ser, BAP050-hum05-Ser, BAP050-hum06-Ser, BAP050-hum07-Ser, BAP050-hum08-Ser, BAP050-hum09-Ser, BAP050-hum10-Ser, BAP050-hum11-Ser, BAP050-hum12-Ser, BAP050-hum13-Ser, BAP050-hum14-Ser, BAP050-hum15-Ser, BAP050-hum18-Ser, BAP050-hum19-Ser, or BAP050-hum20-Ser), BAP050-Clone-F, BAP050-Clone-G, BAP050-Clone-H, BAP050-Clone-I, or BAP050-Clone-J; or
(xviii) inhibits one or more activities of LAG-3, e.g., results in one or more of: an increase in antigen-dependent stimulation of CD4+T lymphocytes; an increase in T cell proliferation; an increase in expression of an activation antigen, e.g., CD25; an increase in expression of a cytokine, e.g., interferon-gamma (IFN-γ), interleukin-2 (IL-2), or interleukin-4 (IL-4); an increase in expression of a chemokine, e.g., CCL3, CCL4, or CCL5; a decrease in the suppressor activity of $T_{reg}$ cells; an increase in T cell homeostasis; an increase in tumor infiltrating lymphocytes; or a decrease in immune evasion by the cancerous cells.

As used herein, "huBAP050 (Ser)" refers to a humanized BAP050 antibody molecule, e.g., any of the humanized BAP050 antibody molecule described herein, e.g., as described in Table 1, that has a Cys to Ser substitution at position 84 of the heavy chain framework region 3 (VHFW3). In some embodiments, the huBAP050 (Ser) antibody molecule is chosen from BAP050-hum01-Ser, BAP050-hum02-Ser, BAP050-hum03-Ser, BAP050- hum04-Ser, BAP050-hum05-Ser, BAP050-hum06-Ser, BAP050-hum07-Ser, BAP050-hum08-Ser, BAP050-hum09-Ser, BAP050-hum10-Ser, BAP050-hum11-Ser, BAP050-hum12-Ser, BAP050-hum13-Ser, BAP050-hum14-Ser, BAP050-hum15-Ser, BAP050-hum18-Ser, BAP050-hum19-Ser, or BAP050-hum20-Ser.

In some embodiments, the anti-LAG-3 antibody molecule binds to LAG-3 with high affinity, e.g., with a dissociation equilibrium constant ($K_D$) that is about the same, or at least about 10%, 20%, 30%, 40%, 50%, 60%, 70%, 80% or 90% higher or lower than the $K_D$ of a murine or chimeric anti-LAG-3 antibody molecule, e.g., a murine or chimeric anti-LAG-3 antibody molecule described herein. In one embodiment, the anti-LAG-3 antibody molecule binds to LAG-3, e.g., a LAG-3-CHO transfectant, with a $K_D$ of less than: 5 nM, 4 nM, 3 nM, 2 nM, e.g., 1 to 3 nM (e.g., about 1.92 nM or about 2.3 nM).

In some embodiments, the expression level of the anti-LAG-3 antibody molecule is about the same, higher or lower, e.g., at least about 0.5, 1, 2, 3, 4, 5, 6, 7, 8, 9 or 10-fold higher or lower, than the expression level of a murine or chimeric antibody molecule, e.g., a murine or chimeric anti-LAG-3 antibody molecule described herein. In some embodiments, the antibody molecule is expressed in CHO cells.

In some embodiments, the anti-LAG-3 antibody molecule reduces one or more LAG-3-associated activities with an $IC_{50}$ (concentration at 50% inhibition) that is about the same, higher or lower, e.g., at least about 10%, 20%, 30%, 40%, 50%, 60%, 70%, 80% or 90% higher or lower, than the $IC_{50}$ of a murine or chimeric anti-LAG-3 antibody molecule, e.g., a murine or chimeric anti-LAG-3 antibody molecule described herein. In some embodiments, the LAG-3-associated activity is the binding of an MHC class II molecule to LAG-3. In some embodiments, the LAG-3-associated activity is the binding of L-SECtin to LAG-3. In one embodiment, the anti-LAG-3 antibody has an $IC_{50}$ of about 1 to 20 nM, 5 to 15 nM, 5.5 nM (e.g., detected by inhibition of MHC class II or L-SECtin binding).

In some embodiments, the anti-LAG-3 antibody molecule has about the same or improved stability, e.g., at least about 0.5, 1, 2, 3, 4, 5, 6, 7, 8, 9 or 10-fold more stable in vivo or in vitro, than a murine or chimeric anti-LAG-3 antibody molecule, e.g., a murine or chimeric anti-LAG-3 antibody molecule described herein.

In one embodiment, the anti-LAG-3 antibody molecule is a humanized antibody molecule and has a risk score based on T cell epitope analysis of 800 to 1200, 850 to 1150, 900 to 1100, 950 to 1050, or a risk score as described herein.

In another embodiment, the anti-LAG-3 antibody molecule comprises at least one antigen-binding region, e.g., a variable region or an antigen-binding fragment thereof, from an antibody described herein, e.g., an antibody chosen from any of BAP050-hum01, BAP050-hum02, BAP050-hum03, BAP050-hum04, BAP050-hum05, BAP050-hum06, BAP050-hum07, BAP050-hum08, BAP050-hum09, BAP050-hum10, BAP050-hum11, BAP050-hum12, BAP050-hum13, BAP050-hum14, BAP050-hum15, BAP050-hum16, BAP050-hum17, BAP050-hum18, BAP050-hum19, BAP050-hum20, huBAP050 (Ser) (e.g., BAP050-hum01-Ser, BAP050-hum02-Ser, BAP050-hum03-Ser, BAP050-hum04-Ser, BAP050-hum05-Ser, BAP050-hum06-Ser, BAP050-hum07-Ser, BAP050-hum08-Ser, BAP050-hum09-Ser, BAP050-hum10-Ser, BAP050-hum11-Ser, BAP050-hum12-Ser, BAP050-hum13-Ser, BAP050-hum14-Ser, BAP050-hum15-Ser, BAP050-hum18-Ser, BAP050-hum19-Ser, or BAP050-hum20-Ser), BAP050-Clone-F, BAP050-Clone-G, BAP050-Clone-H, BAP050-Clone-I, or BAP050-Clone-J; or as described in Table 1, or encoded by the nucleotide sequence in Table 1; or a sequence substantially identical (e.g., at least 80%, 85%, 90%, 92%, 95%, 97%, 98%, 99% or higher identical) to any of the aforesaid sequences.

In yet another embodiment, the anti-LAG-3 antibody molecule comprises at least one, two, three or four variable regions from an antibody described herein, e.g., an antibody chosen from any of BAP050-hum01, BAP050-hum02, BAP050-hum03, BAP050-hum04, BAP050-hum05, BAP050-hum06, BAP050-hum07, BAP050-hum08, BAP050-hum09, BAP050-hum10, BAP050-hum11, BAP050-hum12, BAP050-hum13, BAP050-hum14, BAP050-hum15, BAP050-hum16, BAP050-hum17, BAP050-hum18, BAP050-hum19, BAP050-hum20, huBAP050 (Ser) (e.g., BAP050-hum01-Ser, BAP050-hum02-Ser, BAP050-hum03-Ser, BAP050-hum04-Ser, BAP050-hum05-Ser, BAP050-hum06-Ser, BAP050-hum07-Ser, BAP050-hum08-Ser, BAP050-hum09-Ser, BAP050-hum10-Ser, BAP050-hum11-Ser, BAP050-hum12-Ser, BAP050-hum13-Ser, BAP050-hum14-Ser, BAP050-hum15-Ser, BAP050-hum18-Ser, BAP050-hum19-Ser, or BAP050-hum20-Ser), BAP050-Clone-F, BAP050-Clone-G, BAP050-Clone-H, BAP050-Clone-I, or BAP050-Clone-J; or as described in Table 1, or encoded by the nucleotide sequence in Table 1; or a sequence substantially identical (e.g., at least 80%, 85%, 90%, 92%, 95%, 97%, 98%, 99% or higher identical) to any of the aforesaid sequences. In one embodiment, the antibody molecule includes a substitution (e.g., a Cys to Ser substitution at position 84) in the heavy chain framework region 3 (VHFW3) (e.g., as shown in Tables 1 and 2).

In yet another embodiment, the anti-LAG-3 antibody molecule comprises at least one or two heavy chain variable regions from an antibody described herein, e.g., an antibody chosen from any of BAP050-hum01, BAP050-hum02, BAP050-hum03, BAP050-hum04, BAP050-hum05, BAP050-hum06, BAP050-hum07, BAP050-hum08, BAP050-hum09, BAP050-hum10, BAP050-hum11, BAP050-hum12, BAP050-hum13, BAP050-hum14, BAP050-hum15, BAP050-hum16, BAP050-hum17, BAP050-hum18, BAP050-hum19, BAP050-hum20, huBAP050 (Ser) (e.g., BAP050-hum01-Ser, BAP050-hum02-Ser, BAP050-hum03-Ser, BAP050-hum04-Ser, BAP050-hum05-Ser, BAP050-hum06-Ser, BAP050-hum07-Ser, BAP050-hum08-Ser, BAP050-hum09-Ser, BAP050-hum10-Ser, BAP050-hum11-Ser, BAP050-hum12-Ser, BAP050-hum13-Ser, BAP050-hum14-Ser, BAP050-hum15-Ser, BAP050-hum18-Ser, BAP050-hum 19-Ser, or BAP050-hum20-Ser), BAP050-Clone-F, BAP050-Clone-G, BAP050-Clone-H, BAP050-Clone-I, or BAP050-Clone-J; or as described in Table 1, or encoded by the nucleotide sequence in Table 1; or a sequence substantially identical (e.g., at least 80%, 85%, 90%, 92%, 95%, 97%, 98%, 99% or higher identical) to any of the aforesaid sequences.

In yet another embodiment, the anti-LAG-3 antibody molecule comprises at least one or two light chain variable regions from an antibody described herein, e.g., an antibody chosen from any of BAP050-hum01, BAP050-hum02, BAP050-hum03, BAP050-hum04, BAP050-hum05, BAP050-hum06, BAP050-hum07, BAP050-hum08, BAP050-hum09, BAP050-hum10, BAP050-hum11, BAP050-hum12, BAP050-hum13, BAP050-hum14, BAP050-hum15, BAP050-hum16, BAP050-hum17, BAP050-hum18, BAP050-hum19, BAP050-hum20, huBAP050 (Ser) (e.g., BAP050-hum01-Ser, BAP050-hum02-Ser, BAP050-hum03-Ser, BAP050-hum04-Ser, BAP050-hum05-Ser, BAP050-hum06-Ser, BAP050-hum07-Ser, BAP050-hum08-Ser, BAP050-hum09-Ser, BAP050-hum10-Ser, BAP050-hum11-Ser, BAP050-hum12-Ser, BAP050-hum13-Ser, BAP050-hum14-Ser, BAP050-hum15-Ser, BAP050-hum18-Ser, BAP050-hum19-Ser, or BAP050-hum20-Ser), BAP050-Clone-F, BAP050-Clone-G, BAP050-Clone-H, BAP050-Clone-I, or BAP050-Clone-J; or as described in Table 1, or encoded by the nucleotide sequence in Table 1; or a sequence substantially identical (e.g., at least 80%, 85%, 90%, 92%, 95%, 97%, 98%, 99% or higher identical) to any of the aforesaid sequences.

In yet another embodiment, the anti-LAG-3 antibody molecule includes a heavy chain constant region for an IgG4, e.g., a human IgG4. In one embodiment, the human IgG4 includes a substitution at position 228 (e.g., a Ser to Pro substitution). In still another embodiment, the anti-LAG-3 antibody molecule includes a heavy chain constant region for an IgG1, e.g., a human IgG1. In one embodiment, the human IgG1 includes a substitution at position 297 (e.g., an Asn to Ala substitution). In one embodiment, the human IgG1 includes a substitution at position 265, a substitution at position 329, or both (e.g., an Asp to Ala substitution at position 265 and/or a Pro to Ala substitution at position 329). In one embodiment, the human IgG1 includes a substitution at position 234, a substitution at position 235, or both (e.g., a Leu to Ala substitution at position 234 and/or a Leu to Ala substitution at position 235). In one embodiment, the heavy chain constant region comprises an amino sequence set forth in Table 3, or a sequence substantially identical (e.g., at least 80%, 85%, 90%, 92%, 95%, 97%, 98%, 99% or higher identical) thereto.

In yet another embodiment, the anti-LAG-3 antibody molecule includes a kappa light chain constant region, e.g., a human kappa light chain constant region. In one embodiment, the light chain constant region comprises an amino sequence set forth in Table 3, or a sequence substantially identical (e.g., at least 80%, 85%, 90%, 92%, 95%, 97%, 98%, 99% or higher identical) thereto.

In another embodiment, the anti-LAG-3 antibody molecule includes a heavy chain constant region for an IgG4, e.g., a human IgG4, and a kappa light chain constant region, e.g., a human kappa light chain constant region, e.g., a heavy and light chain constant region comprising an amino sequence set forth in Table 3, or a sequence substantially identical (e.g., at least 80%, 85%, 90%, 92%, 95%, 97%, 98%, 99% or higher identical) thereto. In one embodiment, the constant region is a mutated IgG4, e.g., a mutated human IgG4 (e.g., has a mutation at position 228 (e.g., a S228P mutation). In yet another embodiment, the anti-LAG-3 antibody molecule includes a heavy chain constant region for an IgG1, e.g., a human IgG1, and a kappa light chain constant region, e.g., a human kappa light chain constant region, e.g., a heavy and light chain constant region comprising an amino sequence set forth in Table 3, or a sequence substantially identical (e.g., at least 80%, 85%, 90%, 92%, 95%, 97%, 98%, 99% or higher identical) thereto. In one embodiment, the human IgG1 includes a substitution at position 297 (e.g., an Asn to Ala substitution). In one embodiment, the human IgG1 includes a substitution at position 265, a substitution at position 329, or both (e.g., an Asp to Ala substitution at position 265 and/or a Pro to Ala substitution at position 329). In one embodiment, the human IgG1 includes a substitution at position 234, a substitution at position 235, or both (e.g., a Leu to Ala substitution at position 234 and/or a Leu to Ala substitution at position 235).

In another embodiment, the anti-LAG-3 antibody molecule includes a heavy chain variable domain and a constant region, a light chain variable domain and a constant region, or both, comprising the amino acid sequence of BAP050-hum01, BAP050-hum02, BAP050-hum03, BAP050-hum04, BAP050-hum05, BAP050-hum06, BAP050-hum07, BAP050-hum08, BAP050-hum09, BAP050-hum10, BAP050-hum11, BAP050-hum12, BAP050-hum13, BAP050-hum14, BAP050-hum15, BAP050-hum16, BAP050-hum17, BAP050-hum18, BAP050-hum19, BAP050-hum20, huBAP050 (Ser) (e.g., BAP050-hum01-Ser, BAP050-hum02-Ser, BAP050-hum03-Ser, BAP050-hum04-Ser, BAP050-hum05-Ser, BAP050-hum06-Ser, BAP050-hum07-Ser, BAP050-hum08-Ser, BAP050-hum09-Ser, BAP050-hum10-Ser, BAP050-hum11-Ser, BAP050-hum12-Ser, BAP050-hum13-Ser, BAP050-hum14-Ser, BAP050-hum15-Ser, BAP050-hum18-Ser, BAP050-hum19-Ser, or BAP050-hum20-Ser), BAP050-Clone-F. BAP050-Clone-G, BAP050-Clone-H, BAP050-Clone-I, or BAP050-Clone-J; or as described in Table 1, or encoded by the nucleotide sequence in Table 1; or a sequence substantially identical (e.g., at least 80%, 85%, 90%, 92%, 95%, 97%, 98%, 99% or higher identical) to any of the aforesaid sequences. The anti-LAG-3 antibody molecule, optionally, comprises a leader sequence from a heavy chain, a light chain, or both, as shown in Table 4; or a sequence substantially identical thereto.

In yet another embodiment, the anti-LAG-3 antibody molecule includes at least one, two, or three complementarity determining regions (CDRs) from a heavy chain variable region of an antibody described herein, e.g., an antibody chosen from any of BAP050-hum01, BAP050-hum02, BAP050-hum03, BAP050-hum04, BAP050-hum05, BAP050-hum06, BAP050-hum07, BAP050-hum08, BAP050-hum09, BAP050-hum10, BAP050-hum11, BAP050-hum12, BAP050-hum13, BAP050-hum14, BAP050-hum15, BAP050-hum16, BAP050-hum17, BAP050-hum18, BAP050-hum19, BAP050-hum20, huBAP050 (Ser) (e.g., BAP050-hum01-Ser, BAP050-hum02-Ser, BAP050-hum03-Ser, BAP050-hum04-Ser, BAP050-hum05-Ser, BAP050-hum06-Ser, BAP050-hum07-Ser, BAP050-hum08-Ser, BAP050-hum09-Ser, BAP050-hum10-Ser, BAP050-hum11-Ser, BAP050-hum12-Ser, BAP050-hum13-Ser, BAP050-hum14-Ser, BAP050-hum15-Ser, BAP050-hum18-Ser, BAP050-hum19-Ser, or BAP050-hum20-Ser), BAP050-Clone-F, BAP050-Clone-G, BAP050-Clone-H, BAP050-Clone-I, or BAP050-Clone-J; or as described in Table 1; or encoded by the nucleotide sequence in Table 1; or a sequence substantially identical (e.g., at least 80%, 85%, 90%, 92%, 95%, 97%, 98%, 99% or higher identical) to any of the aforesaid sequences; or which have at least one amino acid alteration, but not more than two, three or four alterations (e.g., substitutions, deletions, or insertions, e.g., conservative substitutions) relative to one, two, or three CDRs shown in Table 1.

In one embodiment, the anti-LAG-3 antibody molecule includes at least one, two or three CDRs (or collectively all of the CDRs) from a heavy chain variable region comprising an amino acid sequence shown in Table 1, or encoded by a nucleotide sequence shown in Table 1. In one embodiment, one or more of the CDRs (or collectively all of the CDRs) have one, two, three, four, five, six or more changes, e.g., amino acid substitutions or deletions, relative to the amino acid sequence shown in Table 1, or encoded by a nucleotide sequence shown in Table 1.

In yet another embodiment, the anti-LAG-3 antibody molecule includes at least one, two, or three complementarity determining regions (CDRs) from a light chain variable region of an antibody described herein, e.g., an antibody chosen from any of BAP050-hum01, BAP050-hum02, BAP050-hum03, BAP050-hum04, BAP050-hum05, BAP050-hum06, BAP050-hum07, BAP050-hum08, BAP050-hum09, BAP050-hum10, BAP050-hum11, BAP050-hum12, BAP050-hum13, BAP050-hum14, BAP050-hum15, BAP050-hum16, BAP050-hum17, BAP050-hum18, BAP050-hum19, BAP050-hum20, huBAP050 (Ser) (e.g., BAP050-hum01-Ser, BAP050-hum02-Ser, BAP050-hum03-Ser, BAP050-hum04-Ser, BAP050-hum05-Ser, BAP050-hum06-Ser, BAP050-hum07-Ser, BAP050-hum08-Ser, BAP050-hum09-Ser, BAP050-hum10-Ser, BAP050-hum11-Ser, BAP050-hum12-Ser, BAP050-hum13-Ser, BAP050-hum14-Ser, BAP050-hum15-Ser, BAP050-hum18-Ser, BAP050-hum19-Ser, or BAP050-hum20-Ser), BAP050-Clone-F, BAP050-Clone-G, BAP050-Clone-H, BAP050-Clone-I, or BAP050-Clone-J; or as described in Table 1; or encoded by the nucleotide sequence in Table 1; or a sequence substantially identical (e.g., at least 80%, 85%, 90%, 92%, 95%, 97%, 98%, 99% or higher identical) to any of the aforesaid sequences; or which have at least one amino acid alteration, but not more than two, three or four alterations (e.g., substitutions, deletions, or insertions, e.g., conservative substitutions) relative to one, two, or three CDRs shown in Table 1.

In yet another embodiment, the anti-LAG-3 antibody molecule includes at least one, two, or three CDRs (or collectively all of the CDRs) from a light chain variable region comprising an amino acid sequence shown in Table 1, or encoded by a nucleotide sequence shown in Table 1. In one embodiment, one or more of the CDRs (or collectively all of the CDRs) have one, two, three, four, five, six or more changes, e.g., amino acid substitutions or deletions, relative to the amino acid shown in Table 1, or encoded by a nucleotide sequence shown in Table 1. In another embodiment, the anti-LAG-3 antibody molecule includes at least one, two, three, four, five or six CDRs (or collectively all of the CDRs) from a heavy and light chain variable region comprising an amino acid shown in Table 1, or encoded by a nucleotide sequence shown in Table 1. In one embodiment, one or more of the CDRs (or collectively all of the CDRs) have one, two, three, four, five, six or more changes, e.g., amino acid substitutions or deletions, relative to the amino acid shown in Table 1, or encoded by a nucleotide sequence shown in Table 1; or a sequence substantially identical (e.g., at least 80%, 85%, 90%, 92%, 95%, 97%, 98%, 99% or higher identical) to any of the aforesaid sequences; or which have at least one amino acid alteration, but not more than two, three or four alterations (e.g., substitutions, deletions, or insertions, e.g., conservative substitutions) relative to one, two, three, four, five, or six CDRs shown in Table 1.

In another embodiment, the anti-LAG-3 antibody molecule includes at least one, two, three, four, five or six CDRs (or collectively all of the CDRs) from a heavy and light chain variable region comprising an amino acid sequence shown in Table 1, or encoded by a nucleotide sequence shown in Table 1. In one embodiment, one or more of the CDRs (or collectively all of the CDRs) have one, two, three, four, five, six or more changes, e.g., amino acid substitutions or deletions, relative to the amino acid sequence shown in Table 1, or encoded by a nucleotide sequence shown in Table 1.

In one embodiment, the anti-LAG-3 antibody molecule includes all six CDRs from an antibody described herein, e.g., an antibody chosen from any of BAP050-hum01, BAP050-hum02, BAP050-hum03, BAP050-hum04, BAP050-hum05, BAP050-hum06, BAP050-hum07, BAP050-hum08, BAP050-hum09, BAP050-hum10, BAP050-hum11, BAP050-hum12, BAP050-hum13, BAP050-hum14, BAP050-hum15, BAP050-hum16, BAP050-hum17, BAP050-hum18, BAP050-hum19, BAP050-hum20, huBAP050 (Ser) (e.g., BAP050-hum01-Ser, BAP050-hum02-Ser, BAP050-hum03-Ser, BAP050-hum04-Ser, BAP050-hum05-Ser, BAP050-hum06-Ser, BAP050-hum07-Ser, BAP050-hum08-Ser, BAP050-hum09-Ser, BAP050-hum10-Ser, BAP050-hum11-Ser, BAP050-hum12-Ser, BAP050-hum13-Ser, BAP050-hum14-Ser, BAP050-hum15-Ser, BAP050-hum18-Ser, BAP050-hum19-Ser, or BAP050-hum20-Ser), BAP050-Clone-F, BAP050-Clone-G, BAP050-Clone-H, BAP050-Clone-I, or BAP050-Clone-J; or as described in Table 1, or encoded by the nucleotide sequence in Table 1, or closely related CDRs, e.g., CDRs which are identical or which have at least one amino acid alteration, but not more than two, three or four alterations (e.g., substitutions, deletions, or insertions, e.g., conservative substitutions) relative to one, two, three, four, five, or six CDRs shown in Table 1.

In one embodiment, the anti-LAG-3 antibody molecule may include any CDR described herein. In one embodiment, the anti-LAG-3 antibody molecule includes at least one, two or three CDRs according to Kabat (e.g., at least one, two, or three CDRs according to the Kabat definition as set out in Table 1) from a heavy chain variable region of an antibody described herein, e.g., an antibody chosen from any of BAP050-hum01, BAP050-hum02, BAP050-hum03, BAP050-hum04, BAP050-hum05, BAP050-hum06, BAP050-hum07, BAP050-hum08, BAP050-hum09, BAP050-hum10, BAP050-hum11, BAP050-hum12, BAP050-hum13, BAP050-hum14, BAP050-hum15, BAP050-hum16, BAP050-hum17, BAP050-hum18, BAP050-hum19, BAP050-hum20, huBAP050 (Ser) (e.g., BAP050-hum01-Ser, BAP050-hum02-Ser, BAP050-hum03-Ser, BAP050-hum04-Ser, BAP050-hum05-Ser, BAP050-hum06-Ser, BAP050-hum07-Ser, BAP050-hum08-Ser, BAP050-hum09-Ser, BAP050-hum10-Ser, BAP050-hum11-Ser, BAP050-hum12-Ser, BAP050-hum13-Ser, BAP050-hum14-Ser, BAP050-hum15-Ser, BAP050-hum18-Ser, BAP050-hum19-Ser, or BAP050-hum20-Ser), BAP050-Clone-F, BAP050-Clone-G, BAP050-Clone-H, BAP050-Clone-I, or BAP050-Clone-J, or as described in Table 1; or encoded by the nucleotide sequence in Table 1; or a sequence substantially identical (e.g., at least 80%, 85%, 90%, 92%, 95%, 97%, 98%, 99% or higher identical) to any of the aforesaid sequences; or which have at least one amino acid alteration, but not more than two, three or four alterations (e.g., substitutions, deletions, or insertions, e.g., conservative substitutions) relative to one, two, or three CDRs according to Kabat shown in Table 1.

In one embodiment, the anti-LAG-3 antibody molecule includes at least one, two or three CDRs according to Kabat (e.g., at least one, two, or three CDRs according to the Kabat definition as set out in Table 1) from a light chain variable region of an antibody described herein, e.g., an antibody chosen from any of BAP050-hum01, BAP050-hum02, BAP050-hum03, BAP050-hum04, BAP050-hum05, BAP050-hum06, BAP050-hum07, BAP050-hum08, BAP050-hum09, BAP050-hum10, BAP050-hum11, BAP050-hum12, BAP050-hum13, BAP050-hum14, BAP050-hum15, BAP050-hum16, BAP050-hum17, BAP050-hum18, BAP050-hum19, BAP050-hum20, huBAP050 (Ser) (e.g., BAP050-hum01-Ser, BAP050-hum02-Ser, BAP050-hum03-Ser, BAP050-hum04-Ser, BAP050-hum05-Ser, BAP050-hum06-Ser, BAP050-hum07-Ser, BAP050-hum08-Ser, BAP050-hum09-Ser, BAP050-hum10-Ser, BAP050-hum11-Ser, BAP050-hum12-Ser, BAP050-hum13-Ser, BAP050-hum14-Ser, BAP050-hum15-Ser, BAP050-hum18-Ser, BAP050-hum19-Ser, or BAP050-hum20-Ser), BAP050-Clone-F. BAP050-Clone-G, BAP050-Clone-H, BAP050-Clone-I, or BAP050-Clone-J; or as described in Table 1; or encoded by the nucleotide sequence in Table 1; or a sequence substantially identical (e.g., at least 80%, 85%, 90%, 92%, 95%, 97%, 98%, 99% or higher identical) to any of the aforesaid sequences; or which have at least one amino acid alteration, but not more than two, three or four alterations (e.g., substitutions, deletions, or insertions, e.g., conservative substitutions) relative to one, two, or three CDRs according to Kabat shown in Table 1.

In yet another embodiment, the anti-LAG-3 antibody molecule includes at least one, two, three, four, five, or six CDRs according to Kabat (e.g., at least one, two, three, four, five, or six CDRs according to the Kabat definition as set out in Table 1) from the heavy and light chain variable regions of an antibody described herein, e.g., an antibody chosen from any of BAP050-hum01, BAP050-hum02, BAP050-hum03, BAP050-hum04, BAP050-hum05, BAP050-hum06, BAP050-hum07, BAP050-hum08, BAP050-hum09, BAP050-hum10, BAP050-hum11, BAP050-hum12, BAP050-hum13, BAP050-hum14, BAP050-hum15, BAP050-hum16, BAP050-hum17, BAP050-hum18, BAP050-hum19, BAP050-hum20, huBAP050 (Ser) (e.g., BAP050-hum01-Ser, BAP050-hum02-Ser, BAP050-hum03-Ser, BAP050-hum04-Ser, BAP050-hum05-Ser, BAP050-hum06-Ser, BAP050-hum07-Ser, BAP050-hum08-Ser, BAP050-hum09-Ser, BAP050-hum10-Ser, BAP050-hum11-Ser, BAP050-hum12-Ser, BAP050-hum13-Ser, BAP050-hum14-Ser, BAP050-hum15-Ser, BAP050-hum18-Ser, BAP050-hum19-Ser, or BAP050-hum20-Ser), BAP050-Clone-F, BAP050-Clone-G, BAP050-Clone-H, BAP050-Clone-I, or BAP050-Clone-J; or as described in Table 1; or encoded by the nucleotide sequence in Table 1; or a sequence substantially identical (e.g., at least 80%, 85%, 90%, 92%, 95%, 97%, 98%, 99% or higher identical) to any of the aforesaid sequences; or which have at least one amino acid alteration, but not more than two, three or four alterations (e.g., substitutions, deletions, or insertions, e.g., conservative substitutions) relative to at least one, two, three, four, five, or six CDRs according to Kabat et al. shown in Table 1. In one embodiment, the anti-LAG-3 antibody molecule may include any CDR described herein.

In yet another embodiment, the anti-LAG-3 antibody molecule includes all six CDRs according to Kabat (e.g., all six CDRs according to the Kabat definition as set out in Table 1) from the heavy and light chain variable regions of an antibody described herein, e.g., an antibody chosen from any of BAP050-hum01, BAP050-hum02, BAP050-hum03, BAP050-hum04, BAP050-hum05, BAP050-hum06, BAP050-hum07, BAP050-hum08, BAP050-hum09, BAP050-hum10, BAP050-hum11, BAP050-hum12, BAP050-hum13, BAP050-hum14, BAP050-hum15, BAP050-hum16, BAP050-hum17, BAP050-hum18, BAP050-hum19, BAP050-hum20, huBAP050 (Ser) (e.g., BAP050-hum01-Ser, BAP050-hum02-Ser, BAP050-hum03-Ser, BAP050-hum04-Ser, BAP050-hum05-Ser, BAP050-hum06-Ser, BAP050-hum07-Ser, BAP050-hum08-Ser, BAP050-hum09-Ser, BAP050-hum10-Ser, BAP050-hum11-Ser, BAP050-hum12-Ser, BAP050-hum13-Ser, BAP050-hum14-Ser, BAP050-hum15-Ser, BAP050-hum18-Ser, BAP050-hum19-Ser, or BAP050-hum20-Ser), BAP050-Clone-F. BAP050-Clone-G, BAP050-Clone-H, BAP050-Clone-I, or BAP050-Clone-J; or as described in Table 1; or encoded by the nucleotide sequence in Table 1; or a sequence substantially identical (e.g., at least 80%, 85%, 90%, 92%, 95%, 97%, 98%, 99% or higher identical) to any of the aforesaid sequences; or which have at least one amino acid alteration, but not more than two, three or four alterations (e.g., substitutions, deletions, or insertions, e.g., conservative substitutions) relative to all six CDRs according to Kabat et al. shown in Table 1. In one embodiment, the anti-LAG-3 antibody molecule may include any CDR described herein.

In another embodiment, the anti-LAG-3 antibody molecule includes at least one, two or three hypervariable loops (e.g., at least one, two, or three hypervariable loops according to the Chothia definition as set out in Table 1) from a heavy chain variable region of an antibody described herein, e.g., an antibody chosen from any of BAP050-hum01, BAP050-hum02, BAP050-hum03, BAP050-hum04, BAP050-hum05, BAP050-hum06, BAP050-hum07, BAP050-hum08, BAP050-hum09, BAP050-hum10, BAP050-hum11, BAP050-hum12, BAP050-hum13, BAP050-hum14, BAP050-hum15, BAP050-hum16, BAP050-hum17, BAP050-hum18, BAP050-hum19, BAP050-hum20, huBAP050 (Ser) (e.g., BAP050-hum01-Ser, BAP050-hum02-Ser, BAP050-hum03-Ser, BAP050-hum04-Ser, BAP050-hum05-Ser, BAP050-hum06-Ser, BAP050-hum07-Ser, BAP050-hum08-Ser, BAP050-hum09-Ser, BAP050-hum10-Ser, BAP050-hum11-Ser, BAP050-hum12-Ser, BAP050-hum13-Ser, BAP050-hum14-Ser, BAP050-hum15-Ser, BAP050-hum18-Ser, BAP050-hum19-Ser, or BAP050-hum20-Ser), BAP050-Clone-F, BAP050-Clone-G, BAP050-Clone-H, BAP050-Clone-I, or BAP050-Clone-J, according to Chothia (e.g., at least one, two, or three hypervariable loops according to the Chothia definition as set out in Table 1); or encoded by the nucleotide sequence in Table 1; or a sequence substantially identical (e.g., at least 80%, 85%, 90%, 92%, 95%, 97%, 98%, 99% or higher identical) to any of the aforesaid sequences; or which have at least one amino acid alteration, but not more than two, three or four alterations (e.g., substitutions, deletions, or insertions, e.g., conservative substitutions) relative to one, two, or three hypervariable loops according to Chothia shown in Table 1.

In another embodiment, the anti-LAG-3 antibody molecule includes at least one, two or three hypervariable loops according to Chothia (e.g., at least one, two, or three CDRs according to the Chothia definition as set out in Table 1) from a light chain variable region of an antibody described herein, e.g., an antibody chosen from any of BAP050-hum01, BAP050-hum02, BAP050-hum03, BAP050-hum04, BAP050-hum05, BAP050-hum06, BAP050-hum07, BAP050-hum08, BAP050-hum09, BAP050-hum10, BAP050-hum11, BAP050-hum12, BAP050-hum13, BAP050-hum14, BAP050-hum15, BAP050-hum16, BAP050-hum17, BAP050-hum18, BAP050-hum19, BAP050-hum20, huBAP050 (Ser) (e.g., BAP050-hum01-Ser, BAP050-hum02-Ser, BAP050-hum03-Ser, BAP050-hum04-Ser, BAP050-hum05-Ser, BAP050- hum06-Ser, BAP050-hum07-Ser, BAP050-hum08-Ser, BAP050-hum09-Ser, BAP050-hum10-Ser, BAP050-hum11-Ser, BAP050-hum12-Ser, BAP050-hum13-Ser, BAP050-hum14-Ser, BAP050-hum15-Ser, BAP050-hum18-Ser, BAP050-hum19-Ser, or BAP050-hum20-Ser), BAP050-Clone-F. BAP050-Clone-G, BAP050-Clone-H, BAP050-Clone-I, or BAP050-Clone-J.; or encoded by the nucleotide sequence in Table 1; or a sequence substantially identical (e.g., at least 80%, 85%, 90%, 92%, 95%, 97%, 98%, 99% or higher identical) to any of the aforesaid sequences; or which have at least one amino acid alteration, but not more than two, three or four alterations (e.g., substitutions, deletions, or insertions, e.g., conservative substitutions) relative to one, two, or three hypervariable loops according to Chothia shown in Table 1.

In yet another embodiment, the anti-LAG-3 antibody molecule includes at least one, two, three, four, five, or six hypervariable loops (e.g., at least one, two, three, four, five, or six hypervariable loops according to the Chothia definition as set out in Table 1) from the heavy and light chain variable regions of an antibody described herein, e.g., an antibody chosen from any of BAP050-hum01, BAP050-hum02, BAP050-hum03, BAP050-hum04, BAP050-hum05, BAP050-hum06, BAP050-hum07, BAP050-hum08, BAP050-hum09, BAP050-hum10, BAP050-hum11, BAP050-hum12, BAP050-hum13, BAP050-hum14, BAP050-hum15, BAP050-hum16, BAP050-hum17, BAP050-hum18, BAP050-hum19, BAP050-hum20, huBAP050 (Ser) (e.g., BAP050-hum01-Ser, BAP050-hum02-Ser, BAP050-hum03-Ser, BAP050-hum04-Ser, BAP050-hum05-Ser, BAP050-hum06-Ser, BAP050-hum07-Ser, BAP050-hum08-Ser, BAP050-hum09-Ser, BAP050-hum10-Ser, BAP050-hum11-Ser, BAP050-hum12-Ser, BAP050-hum13-Ser, BAP050-hum14-Ser, BAP050-hum15-Ser, BAP050-hum18-Ser, BAP050-hum 19-Ser, or BAP050-hum20-Ser), BAP050-Clone-F, BAP050-Clone-G, BAP050-Clone-H, BAP050-Clone-I, or BAP050-Clone-J; or as described in Table 1; or encoded by the nucleotide sequence in Table 1; or at least the amino acids from those hypervariable loops that contact LAG-3. In one embodiment, the anti-LAG-3 antibody molecule includes at least one, two, three, four, five, or six Chothia hypervariable loops of Table 1.

In one embodiment, the anti-LAG-3 antibody molecule includes all six hypervariable loops (e.g., all six hypervariable loops according to the Chothia definition as set out in Table 1) of an antibody described herein, e.g., an antibody chosen from any of BAP050-hum01, BAP050-hum02, BAP050-hum03, BAP050-hum04, BAP050-hum05, BAP050-hum06, BAP050-hum07, BAP050-hum08, BAP050-hum09, BAP050-hum10, BAP050-hum11, BAP050-hum12, BAP050-hum13, BAP050-hum14, BAP050-hum15, BAP050-hum16, BAP050-hum17, BAP050-hum18, BAP050-hum19, BAP050-hum20, huBAP050 (Ser) (e.g., BAP050-hum01-Ser, BAP050-hum02-Ser, BAP050-hum03-Ser, BAP050-hum04-Ser, BAP050-hum05-Ser, BAP050-hum06-Ser, BAP050-hum07-Ser, BAP050-hum08-Ser, BAP050-hum09-Ser, BAP050-hum10-Ser, BAP050-hum11-Ser, BAP050-hum12-Ser, BAP050-hum13-Ser, BAP050-hum14-Ser, BAP050-hum15-Ser, BAP050-hum18-Ser, BAP050-hum19-Ser, or BAP050-hum20-Ser), BAP050-Clone-F. BAP050-Clone-G, BAP050-Clone-H, BAP050-Clone-I, or BAP050-Clone-J, or closely related hypervariable loops, e.g., hypervariable loops which are identical or which have at least one amino acid alteration, but not more than two, three or four alterations (e.g., substitutions, deletions, or insertions, e.g., conservative substitutions) relative to all six hypervariable loops shown in Table 1. In one embodiment, the anti-LAG-3 antibody molecule may include any hypervariable loop described herein.

In still another embodiment, the anti-LAG-3 antibody molecule includes at least one, two, or three hypervariable loops that have the same canonical structures as the corresponding hypervariable loop of an antibody described herein, e.g., an antibody chosen from any of BAP050-hum01, BAP050-hum02, BAP050-hum03, BAP050-hum04, BAP050-hum05, BAP050-hum06, BAP050-hum07, BAP050-hum08, BAP050-hum09, BAP050-hum10, BAP050-hum11, BAP050-hum12, BAP050-hum13, BAP050-hum14, BAP050-hum15, BAP050-hum16, BAP050-hum17, BAP050-hum18, BAP050-hum19, BAP050-hum20, huBAP050 (Ser) (e.g., BAP050-hum01-Ser, BAP050-hum02-Ser, BAP050-hum03-Ser, BAP050-hum04-Ser, BAP050-hum05-Ser, BAP050-hum06-Ser, BAP050-hum07-Ser, BAP050-hum08-Ser, BAP050-hum09-Ser, BAP050-hum10-Ser, BAP050-hum11-Ser, BAP050-hum12-Ser, BAP050-hum13-Ser, BAP050-hum14-Ser, BAP050-hum15-Ser, BAP050-hum18-Ser, BAP050-hum 19-Ser, or BAP050-hum20-Ser), BAP050-Clone-F, BAP050-Clone-G, BAP050-Clone-H, BAP050-Clone-I, or BAP050-Clone-J, e.g., the same canonical structures as at least loop 1 and/or loop 2 of the heavy and/or light chain variable domains of an antibody described herein. See, e.g., Chothia et al., (1992) *J. Mol. Biol.* 227:799-817; Tomlinson et al., (1992) *J. Mol. Biol.* 227:776-798 for descriptions of hypervariable loop canonical structures. These structures can be determined by inspection of the tables described in these references.

In certain embodiments, the anti-LAG-3 antibody molecule includes a combination of CDRs or hypervariable loops defined according to the Kabat et al. and Chothia et al.

In one embodiment, the anti-LAG-3 antibody molecule includes at least one, two or three CDRs or hypervariable loops from a heavy chain variable region of an antibody described herein, e.g., an antibody chosen from any of BAP050-hum01, BAP050-hum02, BAP050-hum03, BAP050-hum04, BAP050-hum05, BAP050-hum06, BAP050-hum07, BAP050-hum08, BAP050-hum09, BAP050-hum10, BAP050-hum11, BAP050-hum12, BAP050-hum13, BAP050-hum14, BAP050-hum15, BAP050-hum16, BAP050-hum17, BAP050-hum18, BAP050-hum19, BAP050-hum20, huBAP050 (Ser) (e.g., BAP050-hum01-Ser, BAP050-hum02-Ser, BAP050-hum03-Ser, BAP050-hum04-Ser, BAP050-hum05-Ser, BAP050-hum06-Ser, BAP050-hum07-Ser, BAP050-hum08-Ser, BAP050-hum09-Ser, BAP050-hum10-Ser, BAP050-hum11-Ser, BAP050-hum12-Ser, BAP050-hum13-Ser, BAP050-hum14-Ser, BAP050-hum15-Ser, BAP050-hum18-Ser, BAP050-hum19-Ser, or BAP050-hum20-Ser), BAP050-Clone-F. BAP050-Clone-G, BAP050-Clone-H, BAP050-Clone-I, or BAP050-Clone-J, according to the Kabat and Chothia definition (e.g., at least one, two, or three CDRs or hypervariable loops according to the Kabat and Chothia definition as set out in Table 1); or encoded by the nucleotide sequence in Table 1; or a sequence substantially identical (e.g., at least 80%, 85%, 90%, 92%, 95%, 97%, 98%, 99% or higher identical) to any of the aforesaid sequences; or which have at least one amino acid alteration, but not more than two, three or four alterations (e.g., substitutions, deletions, or insertions, e.g., conservative substitutions) relative to one, two, or three CDRs or hypervariable loops according to Kabat and/or Chothia shown in Table 1.

For example, the anti-LAG-3 antibody molecule can include VH CDR1 according to Kabat et al. or VH hypervariable loop 1 according to Chothia et al., or a combination thereof, e.g., as shown in Table 1. In one embodiment, the combination of Kabat and Chothia CDR of VH CDR1 comprises the amino acid sequence GFTLTNYGMN (SEQ ID NO: 286), or an amino acid sequence substantially identical thereto (e.g., having at least one amino acid alteration, but not more than two, three or four alterations (e.g., substitutions, deletions, or insertions, e.g., conservative substitutions)). The anti-LAG-3 antibody molecule can further include, e.g., VH CDRs 2-3 according to Kabat et al. and VL CDRs 1-3 according to Kabat et al., e.g., as shown in Table 1. Accordingly, in some embodiments, framework regions are defined based on a combination of CDRs defined according to Kabat et al. and hypervariable loops defined according to Chothia et al. For example, the anti-LAG-3 antibody molecule can include VH FR1 defined based on VH hypervariable loop 1 according to Chothia et al. and VH FR2 defined based on VH CDRs 1-2 according to Kabat et al., e.g., as shown in Table 1. The anti-LAG-3 antibody molecule can further include, e.g., VH FRs 3-4 defined based on VH CDRs 2-3 according to Kabat et al. and VL FRs 1-4 defined based on VL CDRs 1-3 according to Kabat et al.

The anti-LAG-3 antibody molecule can contain any combination of CDRs or hypervariable loops according to the Kabat and Chothia definitions. In one embodiment, the anti-LAG-3 antibody molecule includes at least one, two or three CDRs from a light chain variable region of an antibody described herein, e.g., an antibody chosen from any of BAP050-hum01, BAP050-hum02, BAP050-hum03, BAP050-hum04, BAP050-hum05, BAP050-hum06, BAP050-hum07, BAP050-hum08, BAP050-hum09, BAP050-hum10, BAP050-hum11, BAP050-hum12, BAP050-hum13, BAP050-hum14, BAP050-hum15, BAP050-hum16, BAP050-hum17, BAP050-hum18, BAP050-hum19, BAP050-hum20, huBAP050 (Ser) (e.g., BAP050-hum01-Ser, BAP050-hum02-Ser, BAP050-hum03-Ser, BAP050-hum04-Ser, BAP050-hum05-Ser, BAP050-hum06-Ser, BAP050-hum07-Ser, BAP050-hum08-Ser, BAP050-hum09-Ser, BAP050-hum10-Ser, BAP050-hum11-Ser, BAP050-hum12-Ser, BAP050-hum13-Ser, BAP050-hum14-Ser, BAP050-hum15-Ser, BAP050-hum18-Ser, BAP050-hum19-Ser, or BAP050-hum20-Ser), BAP050-Clone-F, BAP050-Clone-G, BAP050-Clone-H, BAP050-Clone-I, or BAP050-Clone-J, according to the Kabat and Chothia definition (e.g., at least one, two, or three CDRs according to the Kabat and Chothia definition as set out in Table 1).

In an embodiment, e.g., an embodiment comprising a variable region, CDR (e.g., CDR or Kabat CDR), or other sequence referred to herein, e.g., in Table 1, the antibody molecule is a monospecific antibody molecule, a bispecific antibody molecule, or is an antibody molecule that comprises an antigen binding fragment of an antibody, e.g., a half antibody or antigen binding fragment of a half antibody. In certain embodiments, the antibody molecule is a bispecific antibody molecule having a first binding specificity for LAG-3 and a second binding specifity for PD-1, TIM-3, CEACAM (e.g., CEACAM-1 and/or CEACAM-5), PD-L1 or PD-L2.

In one embodiment, the anti-LAG-3 antibody includes:
(i) a heavy chain variable region (VH) including a VHCDR1 amino acid sequence chosen from SEQ ID NO: 1, SEQ ID NO: 4 or SEQ ID NO: 286; a VHCDR2 amino acid sequence of SEQ ID NO: 2; and a VHCDR3 amino acid sequence of SEQ ID NO: 3; and
(ii) a light chain variable region (VL) including a VLCDR1 amino acid sequence of SEQ ID NO: 10, a VLCDR2 amino acid sequence of SEQ ID NO: 11, and a VLCDR3 amino acid sequence of SEQ ID NO: 12.

In another embodiment, the anti-LAG-3 antibody molecule includes:
(i) a heavy chain variable region (VH) including a VHCDR1 amino acid sequence chosen from SEQ ID NO: 1, SEQ ID NO: 4 or SEQ ID NO: 286; a VHCDR2 amino acid sequence of SEQ ID NO: 5, and a VHCDR3 amino acid sequence of SEQ ID NO: 3; and
(ii) a light chain variable region (VL) including a VLCDR1 amino acid sequence of SEQ ID NO: 13, a VLCDR2 amino acid sequence of SEQ ID NO: 14, and a VLCDR3 amino acid sequence of SEQ ID NO: 15.

In one embodiment, the anti-LAG-3 antibody molecule comprises the VHCDR1 amino acid sequence of SEQ ID NO: 1. In another embodiment, the anti-LAG-3 antibody molecule comprises the VHCDR1 amino acid sequence of SEQ ID NO: 4. In yet another embodiment, the anti-LAG-3 antibody molecule comprises the VHCDR1 amino acid sequence of SEQ ID NO: 286.

In one embodiment, the light or the heavy chain variable framework (e.g., the region encompassing at least FR1, FR2, FR3, and optionally FR4) of the anti-LAG-3 antibody molecule can be chosen from: (a) a light or heavy chain variable framework including at least 80%, 85%, 87% 90%, 92%, 93%, 95%, 97%, 98%, or preferably 100% of the amino acid residues from a human light or heavy chain variable framework, e.g., a light or heavy chain variable framework residue from a human mature antibody, a human germline sequence, or a human consensus sequence; (b) a light or heavy chain variable framework including from 20% to 80%, 40% to 60%, 60% to 90%, or 70% to 95% of the amino acid residues from a human light or heavy chain variable framework, e.g., a light or heavy chain variable framework residue from a human mature antibody, a human germline sequence, or a human consensus sequence; (c) a non-human framework (e.g., a rodent framework); or (d) a non-human framework that has been modified, e.g., to remove antigenic or cytotoxic determinants, e.g., deimmunized, or partially humanized. In one embodiment, the light or heavy chain variable framework region (particularly FR1, FR2 and/or FR3) includes a light or heavy chain variable framework sequence at least 70, 75, 80, 85, 87, 88, 90, 92, 94, 95, 96, 97, 98, 99% identical or identical to the frameworks of a VL or VH segment of a human germline gene.

In certain embodiments, the anti-LAG-3 antibody molecule comprises a heavy chain variable domain having at least one, two, three, four, five, six, seven, ten, fifteen, twenty or more changes, e.g., amino acid substitutions or deletions, from an amino acid sequence of BAP050-chi-HC, e.g., the amino acid sequence of the FR region in the entire variable region, e.g., shown in FIGS. 9A-9B, or SEQ ID NO: 20 or 22. In one embodiment, the anti-LAG-3 antibody molecule comprises a heavy chain variable domain having one or more of: E at position 1, V at position 2, A at position 9, V at position 11, A at position 16, S at position 17, L at position 18, R at position 19, V at position 20, V or G at position 24, I at position 37, A or S at position 40, R or T at position 41, S at position 42, Q or R at position 43, R at position 44, E at position 46, I or L at position 48, V at position 68, V or T at position 69, I at position 70, A at position 72, D at position 73, K at position 74, V or I at position 76, Y at position 80, W at position 83, C or S at position 84, S or T at position 85, A at position 88, E or S at position 89, V or M at position 93, or Y at position 95 of amino acid sequence of BAP050-chi-HC, e.g., the amino acid sequence of the FR in the entire variable region, e.g., shown in FIGS. 9A-9B, or SEQ ID NO: 20 or 22. In one embodiment, the antibody molecule includes a substitution (e.g., a Cys to Ser substitution at position 84) in the heavy chain framework region 3 (VHFW3) (e.g., as shown in Table 2).

Alternatively, or in combination with the heavy chain substitutions of BAP050-chi-HC described herein, the anti-LAG-3 antibody molecule comprises a light chain variable domain having at least one, two, three, four, five, six, seven, ten, fifteen, twenty or more amino acid changes, e.g., amino acid substitutions or deletions, from an amino acid sequence of BAP050-chi-LC, e.g., the amino acid sequence shown in FIGS. 10A-10B, or SEQ ID NO: 24 or 26. In one embodiment, the anti-LAG-3 antibody molecule comprises a heavy chain variable domain having one or more of: E or A at position 1, V at position 3, L at position 4, S at position 7, P at position 8, A or L or D at position 9, T or F at position 10, Q at position 11, P at position 12, V or L at position 13, T at position 14, V or P at position 15, K at position 16, Q or E at position 17, T or P or K at position 18, A at position 19, S at position 20, L at position 21, T at position 22, L at position 37, G at position 41, K or Q at position 42, A or S at position 43, P at position 44, R or Q at position 45, L at position 46, I at position 58, P or D at position 60, Y at position 67, E at position 70, F at position 71, T at position 72, F at position 73, N at position 76, S or R at position 77, I at position 78, Q at position 79, A or S or P at position 80, D at position 81, A or F at position 83, Y or V at position 85, or F at position 87 of the amino acid sequence of BAP050-chi-LC, e.g., the amino acid sequence shown in FIGS. 10A-10B, or SEQ ID NO: 24 or 26.

In other embodiments, the anti-LAG-3 antibody molecule includes one, two, three, or four heavy chain framework regions (e.g., a VHFW amino acid or nucleotide sequence shown in Table 2, or encoded by the nucleotide sequence shown in Table 2), or a sequence substantially identical thereto (e.g., a sequence at least about 85%, 90%, 95%, 99% or more identical thereto, and/or having one, two, three or more substitutions, insertions or deletions, e.g., conserved substitutions). In one embodiment, the antibody molecule includes a substitution (e.g., a Cys to Ser substitution at position 84) in the heavy chain framework region 3 (VHFW3) (e.g., as shown in Table 2).

In yet other embodiments, the anti-LAG-3 antibody molecule includes one, two, three, or four light chain framework regions (e.g., a VLFW amino acid sequence shown in Table 2, or encoded by the nucleotide sequence shown in Table 2), or a sequence substantially identical thereto (e.g., a sequence at least about 85%, 90%, 95%, 99% or more identical thereto, and/or having one, two, three or more substitutions, insertions or deletions, e.g., conserved substitutions).

In other embodiments, the anti-LAG-3 antibody molecule includes one, two, three, or four heavy chain framework regions (e.g., a VHFW amino acid sequence shown in Table 2, or encoded by the nucleotide sequence shown in Table 2), or a sequence substantially identical thereto; and one, two, three, or four light chain framework regions (e.g., a VLFW amino acid sequence shown in Table 2, or encoded by the nucleotide sequence shown in Table 2), or a sequence substantially identical thereto.

In some embodiments, the anti-LAG-3 antibody molecule comprises the heavy chain framework region 1 (VHFW1) of BAP050-hum01, BAP050-hum02, BAP050-hum03, BAP050-hum04, BAP050-hum05, BAP050-hum06, BAP050-hum07, BAP050-hum08, BAP050-hum14, BAP050-hum15, BAP050-hum18, BAP050-hum19, BAP050-hum01-Ser, BAP050-hum02-Ser, BAP050-hum03-Ser, BAP050-hum04-Ser, BAP050-hum05-Ser, BAP050-hum06-Ser, BAP050-hum07-Ser, BAP050-hum08-Ser, BAP050-hum14-Ser, BAP050-hum15-Ser, BAP050-hum18-Ser, BAP050-hum19-Ser, BAP050-Clone-F, or BAP050-Clone-G (e.g., SEQ ID NO: 187). In some embodiments, the antibody molecule comprises the heavy chain framework region 1 (VHFW1) of BAP050-hum09, BAP050-hum10, BAP050-hum11, BAP050-hum12, BAP050-hum13, or BAP050-hum20, BAP050-hum09-Ser, BAP050-hum10-Ser, BAP050-hum11-Ser, BAP050-hum12-Ser, BAP050-hum13-Ser, BAP050-Clone-H, BAP050-Clone-I, or BAP050-Clone J (e.g., SEQ ID NO: 190). In some embodiments, the antibody molecule comprises the heavy chain framework region 1 (VHFW1) of BAP050-hum16 (e.g., SEQ ID NO: 194). In some embodiments, the antibody molecule comprises the heavy chain framework region 1 (VHFW1) of BAP050-hum17 (e.g., SEQ ID NO: 196). In other embodiments, the antibody molecule comprises a heavy chain framework region 1 (VHFW1) having a sequence, or encoded by a sequence, substantially identical (e.g., a sequence at least about 85%, 90%, 95%, 99% or more identical) to any of the aforesaid sequences, and/or having one, two, three or more substitutions, insertions or deletions, e.g., conserved substitutions).

In some embodiments, the anti-LAG-3 antibody molecule comprises the heavy chain framework region 2 (VHFW2) of BAP050-hum01, BAP050-hum02, BAP050-hum03, BAP050-hum04, BAP050-hum05, BAP050-hum06, BAP050-hum07, BAP050-hum08, BAP050-hum13, BAP050-hum17, BAP050-hum18, BAP050-hum19, BAP050-hum01-Ser, BAP050-hum02-Ser, BAP050-hum03-Ser, BAP050-hum04-Ser, BAP050-hum05-Ser, BAP050-hum06-Ser, BAP050-hum07-Ser, BAP050-hum08-Ser, BAP050-hum13-Ser, BAP050-hum18-Ser, BAP050-hum19-Ser, BAP050-Clone-F, BAP050-Clone-G, or BAP050-Clone-J (e.g., SEQ ID NO: 198). In some embodiments, the antibody molecule comprises the heavy chain framework region 2 (VHFW2) of BAP050-hum09, BAP050-hum10, BAP050-hum11, BAP050-hum12, BAP050-hum20, BAP050-hum09-Ser, BAP050-hum10-Ser, BAP050-hum11-Ser, BAP050-hum12-Ser, BAP050-hum20-Ser, or BAP050-Clone-I (e.g., SEQ ID NO: 202). In some embodiments, the antibody molecule comprises the heavy chain framework region 2 (VHFW2) of BAP050-hum14, BAP050-hum15, BAP050-hum14-Ser, or BAP050-hum15-Ser (e.g., SEQ ID NO: 206). In some embodiments, the antibody molecule comprises the heavy chain framework region 2 (VHFW2) of BAP050-hum16 (e.g., SEQ ID NO: 208). In other embodiments, the antibody molecule comprises a heavy chain framework region 2 (VHFW2) having a sequence, or encoded by a sequence, substantially identical (e.g., a sequence at least about 85%, 90%, 95%, 99% or more identical) to any of the aforesaid sequences, and/or having one, two, three or more substitutions, insertions or deletions, e.g., conserved substitutions).

In some embodiments, the anti-LAG-3 antibody molecule comprises the heavy chain framework region 3 (VHFW3) of BAP050-hum01, BAP050-hum02, BAP050-hum03, BAP050-hum04, BAP050-hum05, BAP050-hum06, BAP050-hum07, BAP050-hum08, BAP050-hum09, BAP050-hum10, BAP050-hum11, BAP050-hum12, BAP050-hum13, BAP050-hum14, BAP050-hum15, BAP050-hum18, BAP050-hum19, or BAP050-hum20 (e.g., SEQ ID NO: 210). In some embodiments, the antibody molecule comprises the heavy chain framework region 3

(VHFW3) of BAP050-hum01-Ser, BAP050-hum02-Ser, BAP050-hum03-Ser, BAP050-hum04-Ser, BAP050-hum05-Ser, BAP050-hum06-Ser, BAP050-hum07-Ser, BAP050-hum08-Ser, BAP050-hum09-Ser, BAP050-hum10-Ser, BAP050-hum11-Ser, BAP050-hum12-Ser, BAP050-hum13-Ser, BAP050-hum14-Ser, BAP050-hum15-Ser, BAP050-hum18-Ser, BAP050-hum19-Ser, BAP050-hum20-Ser, BAP050-Clone-F. BAP050-Clone-G, BAP050-Clone-H, BAP050-Clone-I, or BAP050-Clone-J (e.g., SEQ ID NO: 212). In some embodiments, the antibody molecule comprises the heavy chain framework region 3 (VHFW3) of BAP050-hum16 (e.g., SEQ ID NO: 217). In some embodiments, the antibody molecule comprises the heavy chain framework region 3 (VHFW3) of BAP050-hum17 (e.g., SEQ ID NO: 219). In other embodiments, the antibody molecule comprises a heavy chain framework region 3 (VHFW3) having a sequence, or encoded by a sequence, substantially identical (e.g., a sequence at least about 85%, 90%, 95%, 99% or more identical) to any of the aforesaid sequences, and/or having one, two, three or more substitutions, insertions or deletions, e.g., conserved substitutions).

In some embodiments, the anti-LAG-3 antibody molecule comprises the heavy chain framework region 4 (VHFW4) of BAP050-hum01, BAP050-hum02, BAP050-hum03, BAP050-hum04, BAP050-hum05, BAP050-hum06, BAP050-hum07, BAP050-hum08, BAP050-hum09, BAP050-hum10, BAP050-hum11, BAP050-hum12, BAP050-hum13, BAP050-hum14, BAP050-hum15, BAP050-hum16, BAP050-hum17, BAP050-hum18, BAP050-hum19, or BAP050-hum20, BAP050-hum01-Ser, BAP050-hum02-Ser, BAP050-hum03-Ser, BAP050-hum04-Ser, BAP050-hum05-Ser, BAP050-hum06-Ser, BAP050-hum07-Ser, BAP050-hum08-Ser, BAP050-hum09-Ser, BAP050-hum10-Ser, BAP050-hum11-Ser, BAP050-hum12-Ser, BAP050-hum13-Ser, BAP050-hum14-Ser, BAP050-hum15-Ser, BAP050-hum18-Ser, BAP050-hum19-Ser, BAP050-hum20-Ser, BAP050-Clone-F, BAP050-Clone-G, BAP050-Clone-H, BAP050-Clone-I, or BAP050-Clone-J (e.g., SEQ ID NO: 221). In other embodiments, the antibody molecule comprises a heavy chain framework region 4 (VHFW4) having a sequence, or encoded by a sequence, substantially identical (e.g., a sequence at least about 85%, 90%, 95%, 99% or more identical) to any of the aforesaid sequences, and/or having one, two, three or more substitutions, insertions or deletions, e.g., conserved substitutions).

In some embodiments, the anti-LAG-3 antibody molecule comprises the light chain framework region 1 (VLFW1) of BAP050-hum01, BAP050-hum02, BAP050-hum04, BAP050-hum07, BAP050-hum09, BAP050-hum11, BAP050-hum13, BAP050-hum17, BAP050-hum01-Ser, BAP050-hum02-Ser, BAP050-hum04-Ser, BAP050-hum07-Ser, BAP050-hum09-Ser, BAP050-hum11-Ser, BAP050-hum13-Ser, BAP050-Clone-F, BAP050-Clone-G, BAP050-Clone-H, BAP050-Clone-I, or BAP050-Clone-J (e.g., SEQ ID NO: 226). In some embodiments, the antibody molecule comprises the light chain framework region 1 (VLFW1) of BAP050-hum03, BAP050-hum10, BAP050-hum14, BAP050-hum03-Ser, BAP050-hum10-Ser, or BAP050-hum14-Ser (e.g., SEQ ID NO: 230). In some embodiments, the antibody molecule comprises the light chain framework region 1 (VLFW1) of BAP050-hum05 or BAP050-hum05-Ser (e.g., SEQ ID NO: 232). In some embodiments, the antibody molecule comprises the light chain framework region 1 (VLFW1) of BAP050-hum06, BAP050-hum20, BAP050-hum06-Ser, or BAP050-hum20-Ser (e.g., SEQ ID NO: 234). In some embodiments, the antibody molecule comprises the light chain framework region 1 (VLFW1) of BAP050-hum08, BAP050-hum12, BAP050-hum15, BAP050-hum16, BAP050-hum19, BAP050-hum08-Ser, BAP050-hum12-Ser, BAP050-hum15-Ser, or BAP050-hum19-Ser (e.g., SEQ ID NO: 236). In some embodiments, the antibody molecule comprises the light chain framework region 1 (VLFW1) of BAP050-hum18 or BAP050-hum18-Ser (e.g., SEQ ID NO: 238). In other embodiments, the antibody molecule comprises a light chain framework region 1 (VLFW1) having a sequence, or encoded by a sequence, substantially identical (e.g., a sequence at least about 85%, 90%, 95%, 99% or more identical) to any of the aforesaid sequences, and/or having one, two, three or more substitutions, insertions or deletions, e.g., conserved substitutions).

In some embodiments, the anti-LAG-3 antibody molecule comprises the light chain framework region 2 (VLFW2) of BAP050-hum01, BAP050-hum02, BAP050-hum05, BAP050-hum09, BAP050-hum13, BAP050-hum17, BAP050-hum01-Ser, BAP050-hum02-Ser, BAP050-hum05-Ser, BAP050-hum09-Ser, BAP050-hum13-Ser, BAP050-hum17-Ser, BAP050-Clone-F. BAP050-Clone-G, BAP050-Clone-H, BAP050-Clone-I, or BAP050-Clone-J (e.g., SEQ ID NO: 240). In some embodiments, the antibody molecule comprises the light chain framework region 2 (VLFW2) of BAP050-hum03, BAP050-hum06, BAP050-hum08, BAP050-hum10, BAP050-hum12, BAP050-hum14, BAP050-hum15, BAP050-hum16, BAP050-hum18, BAP050-hum19. BAP050-hum20, BAP050-hum03-Ser, BAP050-hum06-Ser, BAP050-hum08-Ser, BAP050-hum10-Ser, BAP050-hum12-Ser, BAP050-hum14-Ser, BAP050-hum15-Ser, BAP050-hum18-Ser, BAP050-hum19-Ser, or BAP050-hum20-Ser (e.g., SEQ ID NO: 244). In some embodiments, the antibody molecule comprises the light chain framework region 2 (VLFW2) of BAP050-hum04 or BAP050-hum04-Ser (e.g., SEQ ID NO: 246). In some embodiments, the antibody molecule comprises the light chain framework region 2 (VLFW2) of BAP050-hum07, BAP050-hum11, BAP050-hum07-Ser, or BAP050-hum11-Ser (e.g., SEQ ID NO: 248). In other embodiments, the antibody molecule comprises a light chain framework region 2 (VLFW2) having a sequence, or encoded by a sequence, substantially identical (e.g., a sequence at least about 85%, 90%, 95%, 99% or more identical) to any of the aforesaid sequences, and/or having one, two, three or more substitutions, insertions or deletions, e.g., conserved substitutions).

In some embodiments, the anti-LAG-3 antibody molecule comprises the light chain framework region 3 (VLFW3) of BAP050-hum01, BAP050-hum03, BAP050-hum05, BAP050-hum10, BAP050-hum14, BAP050-hum19, BAP050-hum01-Ser, BAP050-hum03-Ser, BAP050-hum05-Ser, BAP050-hum10-Ser, BAP050-hum14-Ser, BAP050-hum19-Ser, or BAP050-Clone-F (e.g., SEQ ID NO: 252). In some embodiments, the antibody molecule comprises the light chain framework region 3 (VLFW3) of BAP050-hum02, BAP050-hum09, BAP050-hum13, BAP050-hum02-Ser. BAP050-hum09-Ser, BAP050-hum13-Ser, BAP050-Clone-G, BAP050-Clone-H, or BAP050-Clone-J (e.g., SEQ ID NO: 255). In some embodiments, the antibody molecule comprises the light chain framework region 3 (VLFW3) of BAP050-hum04 or BAP050-hum04-Ser (e.g., SEQ ID NO: 259). In some embodiments, the antibody molecule comprises the light chain framework region 3 (VLFW3) of BAP050-hum06, BAP050-hum07. BAP050-hum11, BAP050-hum06-Ser.

BAP050-hum07-Ser, BAP050-hum11-Ser, or BAP050-Clone-I (e.g., SEQ ID NO: 261). In some embodiments, the antibody molecule comprises the light chain framework region 3 (VLFW3) of BAP050-hum08, BAP050-hum12, BAP050-hum15, BAP050-hum16, BAP050-hum18, BAP050-hum08-Ser, BAP050-hum12-Ser, BAP050-hum15-Ser, or BAP050-hum18-Ser (e.g., SEQ ID NO: 265). In some embodiments, the antibody molecule comprises the light chain framework region 3 (VLFW3) of BAP050-hum17 (e.g., SEQ ID NO: 267). In some embodiments, the antibody molecule comprises the light chain framework region 3 (VLFW3) of BAP050-hum20 or BAP050-hum20-Ser (e.g., SEQ ID NO: 269). In other embodiments, the antibody molecule comprises a light chain framework region 3 (VHLW3) having a sequence, or encoded by a sequence, substantially identical (e.g., a sequence at least about 85%, 90%, 95%, 99% or more identical) to any of the aforesaid sequences, and/or having one, two, three or more substitutions, insertions or deletions, e.g., conserved substitutions).

In some embodiments, the anti-LAG-3 antibody molecule comprises the light chain framework region 4 (VLFW4) of BAP050-hum01, BAP050-hum02, BAP050-hum03, BAP050-hum04, BAP050-hum05, BAP050-hum06, BAP050-hum07, BAP050-hum08, BAP050-hum09, BAP050-hum10, BAP050-hum11, BAP050-hum12, BAP050-hum13, BAP050-hum14, BAP050-hum15, BAP050-hum16, BAP050-hum17, BAP050-hum18, BAP050-hum19, BAP050-hum20, BAP050-hum01-Ser, BAP050-hum02-Ser, BAP050-hum03-Ser, BAP050-hum04-Ser, BAP050-hum05-Ser, BAP050-hum06-Ser, BAP050-hum07-Ser, BAP050-hum08-Ser, BAP050-hum09-Ser, BAP050-hum10-Ser, BAP050-hum11-Ser, BAP050-hum12-Ser, BAP050-hum13-Ser, BAP050-hum14-Ser, BAP050-hum15-Ser, BAP050-hum18-Ser, BAP050-hum19-Ser, BAP050-hum20-Ser, BAP050-Clone-F, BAP050-Clone-G, BAP050-Clone-H, BAP050-Clone-I, or BAP050-Clone-J (e.g., SEQ ID NO: 271). In other embodiments, the antibody molecule comprises a light chain framework region 4 (VLFW4) having a sequence, or encoded by a sequence, substantially identical (e.g., a sequence at least about 85%, 90%, 95%, 99% or more identical) to any of the aforesaid sequences, and/or having one, two, three or more substitutions, insertions or deletions, e.g., conserved substitutions).

In some embodiments, the anti-LAG-3 antibody molecule comprises the heavy chain framework regions 1-3 of BAP050-hum01, BAP050-hum02, BAP050-hum03, BAP050-hum04, BAP050-hum05, BAP050-hum06, BAP050-hum07, BAP050-hum08, BAP050-hum18, BAP050-hum19 (e.g., SEQ ID NO: 187 (VHFW1), SEQ ID NO: 198 (VHFW2), and SEQ ID NO: 210 (VHFW3)). In some embodiments, the antibody molecule comprises the heavy chain framework regions 1-3 of BAP050-hum09, BAP050-hum10, BAP050-hum11, BAP050-hum12, BAP050-hum20 (e.g., SEQ ID NO: 190 (VHFW1), SEQ ID NO: 202 (VHFW2), and SEQ ID NO: 210 (VHFW3)). In some embodiments, the antibody molecule comprises the heavy chain framework regions 1-3 of BAP050-hum13 (e.g., SEQ ID NO: 190 (VHFW1), SEQ ID NO: 198 (VHFW2), and SEQ ID NO: 210 (VHFW3)). In some embodiments, the antibody molecule comprises the heavy chain framework regions 1-3 of BAP050-hum14 or BAP050-hum15 (e.g., SEQ ID NO: 187 (VHFW1), SEQ ID NO: 206 (VHFW2), and SEQ ID NO: 210 (VHFW3)). In some embodiments, the antibody molecule comprises the heavy chain framework regions 1-3 of BAP050-hum16 (e.g., SEQ ID NO: 194 (VHFW1), SEQ ID NO: 208 (VHFW2), and SEQ ID NO: 217 (VHFW3)). In some embodiments, the antibody molecule comprises the heavy chain framework regions 1-3 of BAP050-hum17 (e.g., SEQ ID NO: 196 (VHFW1), SEQ ID NO: 198 (VHFW2), and SEQ ID NO: 219 (VHFW3)). In some embodiments, the antibody molecule comprises the heavy chain framework regions 1-3 of BAP050-hum01-Ser, BAP050-hum02-Ser, BAP050-hum03-Ser, BAP050-hum04-Ser, BAP050-hum05-Ser, BAP050-hum06-Ser, BAP050-hum07-Ser, BAP050-hum08-Ser, BAP050-hum18-Ser, BAP050-hum19-Ser, BAP050-Clone-F. or BAP050-Clone-G (e.g., SEQ ID NO: 187 (VHFW1), SEQ ID NO: 198 (VHFW2), and SEQ ID NO: 212 (VHFW3)). In some embodiments, the antibody molecule comprises the heavy chain framework regions 1-3 of BAP050-hum09-Ser, BAP050-hum10-Ser, BAP050-hum11-Ser, BAP050-hum12-Ser, BAP050-hum20-Ser, BAP050-Clone-H, or BAP050-Clone I (e.g., SEQ ID NO: 190 (VHFW1), SEQ ID NO: 202 (VHFW2), and SEQ ID NO: 212 (VHFW3)). In some embodiments, the antibody molecule comprises the heavy chain framework regions 1-3 of BAP050-hum13-Ser or BAP050-Clone-J (e.g., SEQ ID NO: 190 (VHFW1), SEQ ID NO: 198 (VHFW2), and SEQ ID NO: 212 (VHFW3)). In some embodiments, the antibody molecule comprises the heavy chain framework regions 1-3 of BAP050-hum14-Ser or BAP050-hum15-Ser (e.g., SEQ ID NO: 187 (VHFW1), SEQ ID NO: 206 (VHFW2), and SEQ ID NO: 212 (VHFW3)). In some embodiments, the antibody molecule further comprises the heavy chain framework region 4 of BAP050-hum01, BAP050-hum02, BAP050-hum03, BAP050-hum04, BAP050-hum05, BAP050-hum06, BAP050-hum07, BAP050-hum08, BAP050-hum09, BAP050-hum10, BAP050-hum11, BAP050-hum12, BAP050-hum13, BAP050-hum14, BAP050-hum15, BAP050-hum16, BAP050-hum17, BAP050-hum18, BAP050-hum19, BAP050-hum20, BAP050-hum01-Ser, BAP050-hum02-Ser, BAP050-hum05-Ser, BAP050-hum09-Ser, BAP050-hum11-Ser, BAP050-hum13-Ser, BAP050-Clone-F, BAP050-Clone-G. BAP050-Clone-H. BAP050-Clone-I, or BAP050-Clone-J (e.g., SEQ ID NO: 221). In other embodiments, the antibody molecule comprises a heavy chain framework region having a sequence, or encoded by a sequence, substantially identical (e.g., a sequence at least about 85%, 90%, 95%, 99% or more identical) to any of the aforesaid sequences, and/or having one, two, three or more substitutions, insertions or deletions, e.g., conserved substitutions).

In some embodiments, the anti-LAG-3 antibody molecule comprises the light chain framework regions 1-3 of BAP050-hum01, BAP050-hum01-Ser, or BAP050-Clone-F (e.g., SEQ ID NO: 226 (VLFW1), SEQ ID NO: 240 (VLFW2), and SEQ ID NO: 252 (VLFW3)). In some embodiments, the antibody molecule comprises the light chain framework regions 1-3 of BAP050-hum02, BAP050-hum09, BAP050-hum13, BAP050-hum02-Ser, BAP050-hum09-Ser, BAP050-hum13-Ser, BAP050-Clone-G, BAP050-Clone-H, or BAP050-Clone-J (e.g., SEQ ID NO: 226 (VLFW1), SEQ ID NO: 240 (VLFW2), and SEQ ID NO: 255 (VLFW3)). In some embodiments, the antibody molecule comprises the light chain framework regions 1-3 of BAP050-hum03, BAP050-hum10, BAP050-hum14, BAP050-hum03-Ser, BAP050-hum10-Ser, or BAP050-hum14-Ser (e.g., SEQ ID NO: 230 (VLFW1), SEQ ID NO: 244 (VLFW2), and SEQ ID NO: 252 (VLFW3)). In some embodiments, the antibody molecule comprises the light chain framework regions 1-3 of BAP050-hum04 or BAP050-hum04-Ser (e.g., SEQ ID NO: 226 (VLFW1), SEQ ID NO: 246 (VLFW2), and SEQ ID NO: 259 (VLFW3)). In some embodiments, the antibody molecule comprises the light chain framework regions 1-3 of BAP050-hum05 or BAP050-hum05-Ser (e.g., SEQ ID NO: 232 (VLFW1), SEQ ID NO: 240 (VLFW2), and SEQ ID NO: 252 (VLFW3)). In some embodiments, the antibody molecule comprises the light chain framework regions 1-3 of BAP050-hum06 or BAP050-hum06-Ser (e.g., SEQ ID NO: 234 (VLFW1), SEQ ID NO: 244 (VLFW2), and SEQ ID NO: 261 (VLFW3)). In some embodiments, the antibody molecule comprises the light chain framework regions 1-3 of BAP050-hum07, BAP050-hum11, BAP050-hum07-Ser, BAP050-hum11-Ser, or BAP050-Clone-I (e.g., SEQ ID NO: 226 (VLFW1), SEQ ID NO: 248 (VLFW2), and SEQ ID NO: 261 (VLFW3)). In some embodiments, the antibody molecule comprises the light chain framework regions 1-3 of BAP050-hum08, BAP050-hum12, BAP050-hum15, BAP050-hum16, BAP050-hum08-Ser, BAP050-hum12-Ser, or BAP050-hum15-Ser (e.g., SEQ ID NO: 236 (VLFW1), SEQ ID NO: 244 (VLFW2), and SEQ ID NO: 265 (VLFW3)). In some embodiments, the antibody molecule comprises the light chain framework regions 1-3 of BAP050-hum17 (e.g., SEQ ID NO: 226 (VLFW1), SEQ ID NO: 240 (VLFW2), and SEQ ID NO: 267 (VLFW3)). In some embodiments, the antibody molecule comprises the light chain framework regions 1-3 of BAP050-hum18 or BAP050-hum18-Ser (e.g., SEQ ID NO: 238 (VLFW1), SEQ ID NO: 244 (VLFW2), and SEQ ID NO: 265 (VLFW3)). In some embodiments, the antibody molecule comprises the light chain framework regions 1-3 of BAP050-hum19 or BAP050-hum19-Ser (e.g., SEQ ID NO: 236 (VLFW1), SEQ ID NO: 244 (VLFW2), and SEQ ID NO: 252 (VLFW3)). In some embodiments, the antibody molecule comprises the light chain framework regions 1-3 of BAP050-hum20 or BAP050-hum20-Ser (e.g., SEQ ID NO: 234 (VLFW1), SEQ ID NO: 244 (VLFW2), and SEQ ID NO: 269 (VLFW3)). In some embodiments, the antibody molecule further comprises the heavy chain framework region 4 of BAP050-hum01, BAP050-hum02, BAP050-hum03, BAP050-hum04, BAP050-hum05, BAP050-hum06, BAP050-hum07, BAP050-hum08, BAP050-hum09, BAP050-hum10, BAP050-hum11, BAP050-hum12, BAP050-hum13, BAP050-hum14, BAP050-hum15, BAP050-hum16, BAP050-hum17, BAP050-hum18, BAP050-hum19, BAP050-hum20, BAP050-hum01-Ser, BAP050-hum02-Ser, BAP050-hum03-Ser, BAP050-hum04-Ser, BAP050-hum05-Ser, BAP050-hum06-Ser, BAP050-hum07-Ser, BAP050-hum08-Ser, BAP050-hum09-Ser, BAP050-hum10-Ser, BAP050-hum11-Ser, BAP050-hum12-Ser, BAP050-hum13-Ser, BAP050-hum14-Ser, BAP050-hum15-Ser, BAP050-hum18-Ser, BAP050-hum19-Ser, BAP050-hum20-Ser, BAP050-Clone-F, BAP050-Clone-G, BAP050-Clone-H, BAP050-Clone-I, or BAP050-Clone-J (e.g., SEQ ID NO: 271). In other embodiments, the antibody molecule comprises a light chain framework region having a sequence, or encoded by a sequence, substantially identical (e.g., a sequence at least about 85%, 90%, 95%, 99% or more identical) to any of the aforesaid sequences, and/or having one, two, three or more substitutions, insertions or deletions, e.g., conserved substitutions).

In some embodiments, the anti-LAG-3 antibody molecule comprises the heavy chain framework regions 1-3 of BAP050-hum01 (e.g., SEQ ID NO: 187 (VHFW1), SEQ ID NO: 198 (VHFW2), and SEQ ID NO: 210 (VHFW3)), or the heavy chain framework regions 1-3 of BAP050-hum01-Ser or BAP050-Clone-F (e.g., SEQ ID NO: 187 (VHFW1), SEQ ID NO: 198 (VHFW2), and SEQ ID NO: 212 (VHFW3)); and the light chain framework regions 1-3 of BAP050-hum01, BAP050-hum01-Ser, or BAP050-Clone-F (e.g., SEQ ID NO: 226 (VLFW1), SEQ ID NO: 240 (VLFW2), and SEQ ID NO: 252 (VLFW3)). In other embodiments, the antibody molecule comprises a heavy chain and a light chain framework region having a sequence, or encoded by a sequence, substantially identical (e.g., a sequence at least about 85%, 90%, 95%, 99% or more identical) to any of the aforesaid sequences, and/or having one, two, three or more substitutions, insertions or deletions, e.g., conserved substitutions).

In some embodiments, the anti-LAG-3 antibody molecule comprises the heavy chain framework regions 1-3 of BAP050-hum02 (e.g., SEQ ID NO: 187 (VHFW1), SEQ ID NO: 198 (VHFW2), and SEQ ID NO: 210 (VHFW3)), or the heavy chain framework regions 1-3 of BAP050-hum02-Ser or BAP050-Clone-G (e.g., SEQ ID NO: 187 (VHFW1), SEQ ID NO: 198 (VHFW2), and SEQ ID NO: 212 (VHFW3)); and the light chain framework regions 1-3 of BAP050-hum02, BAP050-hum02-Ser, or BAP050-Clone-G (e.g., SEQ ID NO: 226 (VLFW1), SEQ ID NO: 240 (VLFW2), and SEQ ID NO: 255 (VLFW3)). In other embodiments, the antibody molecule comprises a heavy chain and a light chain framework region having a sequence, or encoded by a sequence, substantially identical (e.g., a sequence at least about 85%, 90%, 95%, 99% or more identical) to any of the aforesaid sequences, and/or having one, two, three or more substitutions, insertions or deletions, e.g., conserved substitutions).

In some embodiments, the anti-LAG-3 antibody molecule comprises the heavy chain framework regions 1-3 of BAP050-hum03 (e.g., SEQ ID NO: 187 (VHFW1), SEQ ID NO: 198 (VHFW2), and SEQ ID NO: 210 (VHFW3)), or the heavy chain framework regions 1-3 of BAP050-hum03-Ser (e.g., SEQ ID NO: 187 (VHFW1), SEQ ID NO: 198 (VHFW2), and SEQ ID NO: 212 (VHFW3)); and the light chain framework regions 1-3 of BAP050-hum03 (e.g., SEQ ID NO: 230 (VLFW1), SEQ ID NO: 244 (VLFW2), and SEQ ID NO: 252 (VLFW3)). In other embodiments, the antibody molecule comprises a heavy chain and a light chain framework region having a sequence, or encoded by a sequence, substantially identical (e.g., a sequence at least about 85%, 90%, 95%, 99% or more identical) to any of the aforesaid sequences, and/or having one, two, three or more substitutions, insertions or deletions, e.g., conserved substitutions).

In some embodiments, the anti-LAG-3 antibody molecule comprises the heavy chain framework regions 1-3 of BAP050-hum04 (e.g., SEQ ID NO: 187 (VHFW1), SEQ ID NO: 198 (VHFW2), and SEQ ID NO: 210 (VHFW3)), or the heavy chain framework regions 1-3 of BAP050-hum04-Ser (e.g., SEQ ID NO: 187 (VHFW1), SEQ ID NO: 198 (VHFW2), and SEQ ID NO: 212 (VHFW3)); and the light chain framework regions 1-3 of BAP050-hum04 (e.g., SEQ ID NO: 226 (VLFW1), SEQ ID NO: 246 (VLFW2), and SEQ ID NO: 259 (VLFW3)). In other embodiments, the antibody molecule comprises a heavy chain and a light chain framework region having a sequence, or encoded by a sequence, substantially identical (e.g., a sequence at least about 85%, 90%, 95%, 99% or more identical) to any of the aforesaid sequences, and/or having one, two, three or more substitutions, insertions or deletions, e.g., conserved substitutions).

In some embodiments, the anti-LAG-3 antibody molecule comprises the heavy chain framework regions 1-3 of BAP050-hum05 (e.g., SEQ ID NO: 187 (VHFW1), SEQ ID NO: 198 (VHFW2), and SEQ ID NO: 210 (VHFW3)) or BAP050-hum05-Ser (e.g., SEQ ID NO: 187 (VHFW1), SEQ ID NO: 198 (VHFW2), and SEQ ID NO: 212 (VHFW3)); and the light chain framework regions 1-3 of BAP050-hum05 or BAP050-hum05-Ser (e.g., SEQ ID NO: 232 (VLFW1), SEQ ID NO: 240 (VLFW2), and SEQ ID NO: 252 (VLFW3)). In other embodiments, the antibody molecule comprises a heavy chain and a light chain framework region having a sequence, or encoded by a sequence, substantially identical (e.g., a sequence at least about 85%, 90%, 95%, 99% or more identical) to any of the aforesaid sequences, and/or having one, two, three or more substitutions, insertions or deletions, e.g., conserved substitutions).

In some embodiments, the anti-LAG-3 antibody molecule comprises the heavy chain framework regions 1-3 of BAP050-hum06 (e.g., SEQ ID NO: 187 (VHFW1), SEQ ID NO: 198 (VHFW2), and SEQ ID NO: 210 (VHFW3)), or the heavy chain framework regions 1-3 of BAP050-hum06-Ser (e.g., SEQ ID NO: 187 (VHFW1), SEQ ID NO: 198 (VHFW2), and SEQ ID NO: 212 (VHFW3)); and the light chain framework regions 1-3 of BAP050-hum06 (e.g., SEQ ID NO: 234 (VLFW1), SEQ ID NO: 244 (VLFW2), and SEQ ID NO: 261 (VLFW3)). In other embodiments, the antibody molecule comprises a heavy chain and a light chain framework region having a sequence, or encoded by a sequence, substantially identical (e.g., a sequence at least about 85%, 90%, 95%, 99% or more identical) to any of the aforesaid sequences, and/or having one, two, three or more substitutions, insertions or deletions, e.g., conserved substitutions).

In some embodiments, the anti-LAG-3 antibody molecule comprises the heavy chain framework regions 1-3 of BAP050-hum07 (e.g., SEQ ID NO: 187 (VHFW1), SEQ ID NO: 198 (VHFW2), and SEQ ID NO: 210 (VHFW3)), or the heavy chain framework regions 1-3 of BAP050-hum07-Ser (e.g., SEQ ID NO: 187 (VHFW1), SEQ ID NO: 198 (VHFW2), and SEQ ID NO: 212 (VHFW3)); and the light chain framework regions 1-3 of BAP050-hum07 (e.g., SEQ ID NO: 226 (VLFW1), SEQ ID NO: 248 (VLFW2), and SEQ ID NO: 261 (VLFW3)). In other embodiments, the antibody molecule comprises a heavy chain and a light chain framework region having a sequence, or encoded by a sequence, substantially identical (e.g., a sequence at least about 85%, 90%, 95%, 99% or more identical) to any of the aforesaid sequences, and/or having one, two, three or more substitutions, insertions or deletions, e.g., conserved substitutions).

In some embodiments, the anti-LAG-3 antibody molecule comprises the heavy chain framework regions 1-3 of BAP050-hum08 (e.g., SEQ ID NO: 187 (VHFW1), SEQ ID NO: 198 (VHFW2), and SEQ ID NO: 210 (VHFW3)), or the heavy chain framework regions 1-3 of BAP050-hum08-Ser (e.g., SEQ ID NO: 187 (VHFW1), SEQ ID NO: 198 (VHFW2), and SEQ ID NO: 212 (VHFW3)); and the light chain framework regions 1-3 of BAP050-hum08 (e.g., SEQ ID NO: 236 (VLFW1), SEQ ID NO: 244 (VLFW2), and SEQ ID NO: 265 (VLFW3)). In other embodiments, the antibody molecule comprises a heavy chain and a light chain framework region having a sequence, or encoded by a sequence, substantially identical (e.g., a sequence at least about 85%, 90%, 95%, 99% or more identical) to any of the aforesaid sequences, and/or having one, two, three or more substitutions, insertions or deletions, e.g., conserved substitutions).

In some embodiments, the anti-LAG-3 antibody molecule comprises the heavy chain framework regions 1-3 of BAP050-hum09 (e.g., SEQ ID NO: 190 (VHFW1), SEQ ID NO: 202 (VHFW2), and SEQ ID NO: 210 (VHFW3)), or BAP050-hum09-Ser or BAP050-Clone-H (e.g., SEQ ID NO: 190 (VHFW1), SEQ ID NO: 202 (VHFW2), and SEQ ID NO: 212 (VHFW3)); and the light chain framework regions 1-3 of BAP050-hum09, BAP050-hum09-Ser, or BAP050-Clone-H (e.g., SEQ ID NO: 226 (VLFW1), SEQ ID NO: 240 (VLFW2), and SEQ ID NO: 255 (VLFW3)). In other embodiments, the antibody molecule comprises a heavy chain and a light chain framework region having a sequence, or encoded by a sequence, substantially identical (e.g., a sequence at least about 85%, 90%, 95%, 99% or more identical) to any of the aforesaid sequences, and/or having one, two, three or more substitutions, insertions or deletions, e.g., conserved substitutions).

In some embodiments, the anti-LAG-3 antibody molecule comprises the heavy chain framework regions 1-3 of BAP050-hum10 (e.g., SEQ ID NO: 190 (VHFW1), SEQ ID NO: 202 (VHFW2), and SEQ ID NO: 210 (VHFW3)), or the heavy chain framework regions 1-3 of BAP050-hum10-Ser (e.g., SEQ ID NO: 190 (VHFW1), SEQ ID NO: 202 (VHFW2), and SEQ ID NO: 212 (VHFW3)); and the light chain framework regions 1-3 of BAP050-hum10 (e.g., SEQ ID NO: 230 (VLFW1), SEQ ID NO: 244 (VLFW2), and SEQ ID NO: 252 (VLFW3)). In other embodiments, the antibody molecule comprises a heavy chain and a light chain framework region having a sequence, or encoded by a sequence, substantially identical (e.g., a sequence at least about 85%, 90%, 95%, 99% or more identical) to any of the aforesaid sequences, and/or having one, two, three or more substitutions, insertions or deletions, e.g., conserved substitutions).

In some embodiments, the anti-LAG-3 antibody molecule comprises the heavy chain framework regions 1-3 of BAP050-hum11 (e.g., SEQ ID NO: 190 (VHFW1), SEQ ID NO: 202 (VHFW2), and SEQ ID NO: 210 (VHFW3)), or BAP050-hum11-Ser, or BAP050-Clone-I (e.g., SEQ ID NO: 190 (VHFW1), SEQ ID NO: 202 (VHFW2), and SEQ ID NO: 212 (VHFW3)); and the light chain framework regions 1-3 of BAP050-hum11, BAP050-hum11-Ser, or BAP050-Clone-I (e.g., SEQ ID NO: 226 (VLFW1), SEQ ID NO: 248 (VLFW2), and SEQ ID NO: 261 (VLFW3)). In other embodiments, the antibody molecule comprises a heavy chain and a light chain framework region having a sequence, or encoded by a sequence, substantially identical (e.g., a sequence at least about 85%, 90%, 95%, 99% or more identical) to any of the aforesaid sequences, and/or having one, two, three or more substitutions, insertions or deletions, e.g., conserved substitutions).

In some embodiments, the anti-LAG-3 antibody molecule comprises the heavy chain framework regions 1-3 of BAP050-hum12 (e.g., SEQ ID NO: 190 (VHFW1), SEQ ID NO: 202 (VHFW2), and SEQ ID NO: 210 (VHFW3)) or BAP050-hum12-Ser (e.g., SEQ ID NO: 190 (VHFW1), SEQ ID NO: 202 (VHFW2), and SEQ ID NO: 212 (VHFW3)); and the light chain framework regions 1-3 of BAP050-hum12 or BAP050-hum12-Ser (e.g., SEQ ID NO: 236 (VLFW1), SEQ ID NO: 244 (VLFW2), and SEQ ID NO: 265 (VLFW3)). In other embodiments, the antibody molecule comprises a heavy chain and a light chain framework region having a sequence, or encoded by a sequence, substantially identical (e.g., a sequence at least about 85%, 90%, 95%, 99% or more identical) to any of the aforesaid sequences, and/or having one, two, three or more substitutions, insertions or deletions, e.g., conserved substitutions).

In some embodiments, the anti-LAG-3 antibody molecule comprises the heavy chain framework regions 1-3 of BAP050-hum13 (e.g., SEQ ID NO: 190 (VHFW1), SEQ ID NO: 198 (VHFW2), and SEQ ID NO: 210 (VHFW3)), or the heavy chain framework regions 1-3 of BAP050-hum13-Ser or BAP050-Clone-J (e.g., SEQ ID NO: 190 (VHFW1), SEQ ID NO: 198 (VHFW2), and SEQ ID NO: 212 (VHFW3)); and the light chain framework regions 1-3 of BAP050-hum13, BAP050-hum13-Ser, or BAP050-Clone-J (e.g., SEQ ID NO: 226 (VLFW1), SEQ ID NO: 240 (VLFW2), and SEQ ID NO: 255 (VLFW3)). In other embodiments, the antibody molecule comprises a heavy chain and a light chain framework region having a sequence, or encoded by a sequence, substantially identical (e.g., a sequence at least about 85%, 90%, 95%, 99% or more identical) to any of the aforesaid sequences, and/or having one, two, three or more substitutions, insertions or deletions, e.g., conserved substitutions).

In some embodiments, the anti-LAG-3 antibody molecule comprises the heavy chain framework regions 1-3 of BAP050-hum14 (e.g., SEQ ID NO: 187 (VHFW1), SEQ ID NO: 206 (VHFW2), and SEQ ID NO: 210 (VHFW3)), or the heavy chain framework regions 1-3 of BAP050-hum14-Ser (e.g., SEQ ID NO: 187 (VHFW1), SEQ ID NO: 206 (VHFW2), and SEQ ID NO: 210 (VHFW3)); and the light chain framework regions 1-3 of BAP050-hum14 (e.g., SEQ ID NO: 230 (VLFW1), SEQ ID NO: 244 (VLFW2), and SEQ ID NO: 252 (VLFW3)). In other embodiments, the antibody molecule comprises a heavy chain and a light chain framework region having a sequence, or encoded by a sequence, substantially identical (e.g., a sequence at least about 85%, 90%, 95%, 99% or more identical) to any of the aforesaid sequences, and/or having one, two, three or more substitutions, insertions or deletions, e.g., conserved substitutions).

In some embodiments, the anti-LAG-3 antibody molecule comprises the heavy chain framework regions 1-3 of BAP050-hum15 (e.g., SEQ ID NO: 187 (VHFW1), SEQ ID NO: 206 (VHFW2), and SEQ ID NO: 210 (VHFW3)), or the heavy chain framework regions 1-3 of BAP050-hum15-Ser (e.g., SEQ ID NO: 187 (VHFW1), SEQ ID NO: 206 (VHFW2), and SEQ ID NO: 210 (VHFW3)); and the light chain framework regions 1-3 of BAP050-hum15 (e.g., SEQ ID NO: 236 (VLFW1), SEQ ID NO: 244 (VLFW2), and SEQ ID NO: 265 (VLFW3)). In other embodiments, the antibody molecule comprises a heavy chain and a light chain framework region having a sequence, or encoded by a sequence, substantially identical (e.g., a sequence at least about 85%, 90%, 95%, 99% or more identical) to any of the aforesaid sequences, and/or having one, two, three or more substitutions, insertions or deletions, e.g., conserved substitutions).

In some embodiments, the anti-LAG-3 antibody molecule comprises the heavy chain framework regions 1-3 of BAP050-hum16 (e.g., SEQ ID NO: 194 (VHFW1), SEQ ID NO: 208 (VHFW2), and SEQ ID NO: 217 (VHFW3)); and the light chain framework regions 1-3 of BAP050-hum16 (e.g., SEQ ID NO: 236 (VLFW1), SEQ ID NO: 244 (VLFW2), and SEQ ID NO: 265 (VLFW3)). In other embodiments, the antibody molecule comprises a heavy chain and a light chain framework region having a sequence, or encoded by a sequence, substantially identical (e.g., a sequence at least about 85%, 90%, 95%, 99% or more identical) to any of the aforesaid sequences, and/or having one, two, three or more substitutions, insertions or deletions, e.g., conserved substitutions).

In some embodiments, the anti-LAG-3 antibody molecule comprises the heavy chain framework regions 1-3 of BAP050-hum17 (e.g., SEQ ID NO: 196 (VHFW1), SEQ ID NO: 198 (VHFW2), and SEQ ID NO: 219 (VHFW3)); and the light chain framework regions 1-3 of BAP050-hum17 (e.g., SEQ ID NO: 226 (VLFW1), SEQ ID NO: 240 (VLFW2), and SEQ ID NO: 267 (VLFW3)). In other embodiments, the antibody molecule comprises a heavy chain and a light chain framework region having a sequence, or encoded by a sequence, substantially identical (e.g., a sequence at least about 85%, 90%, 95%, 99% or more identical) to any of the aforesaid sequences, and/or having one, two, three or more substitutions, insertions or deletions, e.g., conserved substitutions).

In some embodiments, the anti-LAG-3 antibody molecule comprises the heavy chain framework regions 1-3 of BAP050-hum18 (e.g., SEQ ID NO: 187 (VHFW1), SEQ ID NO: 198 (VHFW2), and SEQ ID NO: 210 (VHFW3)), or the heavy chain framework regions 1-3 of BAP050-hum18-Ser (e.g., SEQ ID NO: 187 (VHFW1), SEQ ID NO: 198 (VHFW2), and SEQ ID NO: 212 (VHFW3)); and the light chain framework regions 1-3 of BAP050-hum18 (e.g., SEQ ID NO: 238 (VLFW1), SEQ ID NO: 244 (VLFW2), and SEQ ID NO: 265 (VLFW3)). In other embodiments, the antibody molecule comprises a heavy chain and a light chain framework region having a sequence, or encoded by a sequence, substantially identical (e.g., a sequence at least about 85%, 90%, 95%, 99% or more identical) to any of the aforesaid sequences, and/or having one, two, three or more substitutions, insertions or deletions, e.g., conserved substitutions).

In some embodiments, the anti-LAG-3 antibody molecule comprises the heavy chain framework regions 1-3 of BAP050-hum19 (e.g., SEQ ID NO: 187 (VHFW1), SEQ ID NO: 198 (VHFW2), and SEQ ID NO: 210 (VHFW3)), or the heavy chain framework regions 1-3 of BAP050-hum18-Ser (e.g., SEQ ID NO: 187 (VHFW1), SEQ ID NO: 198 (VHFW2), and SEQ ID NO: 212 (VHFW3)); and the light chain framework regions 1-3 of BAP050-hum19 (e.g., SEQ ID NO: 236 (VLFW1), SEQ ID NO: 244 (VLFW2), and SEQ ID NO: 252 (VLFW3)). In other embodiments, the antibody molecule comprises a heavy chain and a light chain framework region having a sequence, or encoded by a sequence, substantially identical (e.g., a sequence at least about 85%, 90%, 95%, 99% or more identical) to any of the aforesaid sequences, and/or having one, two, three or more substitutions, insertions or deletions, e.g., conserved substitutions).

In some embodiments, the anti-LAG-3 antibody molecule comprises the heavy chain framework regions 1-3 of BAP050-hum20 (e.g., SEQ ID NO: 190 (VHFW1), SEQ ID NO: 202 (VHFW2), and SEQ ID NO: 210 (VHFW3)), or BAP050-hum20-Ser (e.g., SEQ ID NO: 190 (VHFW1), SEQ ID NO: 202 (VHFW2), and SEQ ID NO: 212 (VHFW3)); and the light chain framework regions 1-3 of BAP050-hum20 (e.g., SEQ ID NO: 234 (VLFW1), SEQ ID NO: 244 (VLFW2), and SEQ ID NO: 269 (VLFW3)). In other embodiments, the antibody molecule comprises a heavy chain and a light chain framework region having a sequence, or encoded by a sequence, substantially identical (e.g., a sequence at least about 85%, 90%, 95%, 99% or more identical) to any of the aforesaid sequences, and/or having one, two, three or more substitutions, insertions or deletions, e.g., conserved substitutions).

In some embodiments, the anti-LAG-3 antibody molecule comprises a heavy chain framework region having a combination of framework regions FW1, FW2 and FW3 as shown in Figures. 4 or 6. In other embodiment, antibody molecule comprises a light chain framework region having a combination of framework regions FW1, FW2 and FW3 as shown in Figures. 4 or 6. In yet other embodiments, the antibody molecule comprises a heavy chain framework region having a combination of framework regions FW1, FW2 and FW3 as shown in Figures. 4 or 6, and a light chain framework region having a combination of framework regions FW1, FW2 and FW3 as shown in Figures. 4 or 6.

In one embodiment, the heavy or light chain variable domain, or both, of the of the anti-LAG-3 antibody molecule includes an amino acid sequence, which is substantially identical to an amino acid disclosed herein, e.g., at least 70%, 75%, 80%, 85%, 90%, 92%, 95%, 97%, 98%, 99% or higher identical to a variable region of an antibody described herein, e.g., an antibody chosen from any of BAP050-hum01, BAP050-hum02, BAP050-hum03, BAP050-hum04, BAP050-hum05, BAP050-hum06, BAP050-hum07, BAP050-hum08, BAP050-hum09, BAP050-hum10, BAP050-hum11, BAP050-hum12, BAP050-hum13, BAP050-hum14, BAP050-hum15, BAP050-hum16, BAP050-hum17, BAP050-hum18, BAP050-hum19, BAP050-hum20, huBAP050 (Ser) (e.g., BAP050-hum01-Ser, BAP050-hum02-Ser, BAP050-hum05-Ser, BAP050-hum09-Ser, BAP050-hum11-Ser, BAP050-hum12-Ser, BAP050-hum13-Ser), BAP050-Clone-F, BAP050-Clone-G, BAP050-Clone-H, BAP050-Clone-I, or BAP050-Clone-J; or as described in Table 1, or encoded by the nucleotide sequence in Table 1; or which differs at least 1 or 5 residues, but less than 40, 30, 20, or 10 residues, from a variable region of an antibody described herein.

In one embodiment, the heavy or light chain variable region, or both, of the of the anti-LAG-3 antibody molecule includes an amino acid sequence encoded by a nucleic acid sequence described herein or a nucleic acid that hybridizes to a nucleic acid sequence described herein (e.g., a specific nucleic acid sequence or a nucleic acid sequence that encodes an amino acid sequence described herein, e.g., as shown in Tables 1 and 2) or its complement, e.g., under low stringency, medium stringency, or high stringency, or other hybridization condition described herein.

In another embodiment, the anti-LAG-3 antibody molecule comprises at least one, two, three, or four antigen-binding regions, e.g., variable regions, having an amino acid sequence as set forth in Table 1, or a sequence substantially identical thereto (e.g., a sequence at least about 85%, 90%, 95%, 99% or more identical thereto, or which differs by no more than 1, 2, 5, 10, or 15 amino acid residues from the sequences shown in Table 1). In another embodiment, the anti-LAG-3 antibody molecule includes a VH and/or VL domain encoded by a nucleic acid having a nucleotide sequence as set forth in Table 1, or a sequence substantially identical thereto (e.g., a sequence at least about 70%, 75%, 85%, 90%, 95%, 99% or more identical thereto, or which differs by no more than 3, 6, 15, 30, or 45 nucleotides from the sequences shown in Table 1).

In yet another embodiment, the anti-LAG-3 antibody molecule comprises at least one, two, or three CDRs from a heavy chain variable region having an amino acid sequence as set forth in Table 1, or a sequence substantially homologous thereto (e.g., a sequence at least about 85%, 90%, 95%, 99% or more identical thereto, and/or having one, two, three or more substitutions, insertions or deletions, e.g., conserved substitutions). In yet another embodiment, the anti-LAG-3 antibody molecule comprises at least one, two, or three CDRs from a light chain variable region having an amino acid sequence as set forth in Table 1, or a sequence substantially homologous thereto (e.g., a sequence at least about 85%, 90%, 95%, 99% or more identical thereto, and/or having one, two, three or more substitutions, insertions or deletions, e.g., conserved substitutions). In yet another embodiment, the anti-LAG-3 antibody molecule comprises at least one, two, three, four, five or six CDRs from heavy and light chain variable regions having an amino acid sequence as set forth in Table 1), or a sequence substantially homologous thereto (e.g., a sequence at least about 85%, 90%, 95%, 99% or more identical thereto, and/or having one, two, three or more substitutions, insertions or deletions, e.g., conserved substitutions). In one embodiment, at least one, two, three, four, five or six CDR is defined according to Kabat, e.g., as shown in Table 1. In another embodiment, at least one, two, three, four, five or six CDR is defined according to Chothia, e.g., as shown in Table 1.

In one embodiment, the anti-LAG-3 antibody molecule comprises at least one, two, or three CDRs and/or hypervariable loops from a heavy chain variable region having an amino acid sequence of an antibody described herein, e.g., an antibody chosen from any of BAP050-hum01. BAP050-hum02, BAP050-hum03, BAP050-hum04, BAP050-hum05, BAP050-hum06, BAP050-hum07, BAP050-hum08, BAP050-hum09, BAP050-hum10, BAP050-hum11, BAP050-hum12, BAP050-hum13, BAP050-hum14, BAP050-hum15, BAP050-hum16, BAP050-hum17, BAP050-hum18, BAP050-hum19, BAP050-hum20, huBAP050 (Ser) (e.g., BAP050-hum01-Ser, BAP050-hum02-Ser, BAP050-hum05-Ser, BAP050-hum09-Ser, BAP050-hum11-Ser, BAP050-hum12-Ser, BAP050-hum13-Ser), BAP050-Clone-F. BAP050-Clone-G, BAP050-Clone-H, BAP050-Clone-I, or BAP050-Clone-J, as summarized in Table 1, or a sequence substantially identical thereto (e.g., a sequence at least about 85%, 90%, 95%, 99% or more identical thereto, and/or having one, two, three or more substitutions, insertions or deletions, e.g., conserved substitutions). In another embodiment, the anti-LAG-3 antibody molecule comprises at least one, two, or three CDRs from a light chain variable region having an amino acid sequence of an antibody described herein, e.g., an antibody chosen from any of BAP050-hum01, BAP050-hum02, BAP050-hum03, BAP050-hum04, BAP050-hum05, BAP050-hum06, BAP050-hum07, BAP050-hum08, BAP050-hum09, BAP050-hum10, BAP050-hum11, BAP050-hum12, BAP050-hum13, BAP050-hum14, BAP050-hum15, BAP050-hum16, BAP050-hum17, BAP050-hum18, BAP050-hum19, BAP050-hum20, huBAP050 (Ser) (e.g., BAP050-hum01-Ser, BAP050-hum02-Ser, BAP050-hum05-Ser, BAP050-hum09-Ser, BAP050-hum11-Ser, BAP050-hum12-Ser, BAP050-hum13-Ser), BAP050-Clone-F. BAP050-Clone-G, BAP050-Clone-H, BAP050-Clone-I, or BAP050-Clone-J, as summarized in Table 1, or a sequence substantially identical thereto (e.g., a sequence at least about 85%, 90%, 95%, 99% or more identical thereto, and/or having one, two, three or more substitutions, insertions or deletions, e.g., conserved substitutions). In one embodiment, the anti-LAG-3 antibody molecule comprises all six CDRs and/or hypervariable loops described herein, e.g., described in Table 1.

In one embodiment, the anti-LAG-3 antibody molecule has a variable region that is identical in sequence, or which differs by 1, 2, 3, or 4 amino acids from a variable region described herein (e.g., an FR region disclosed herein).

In one embodiment, the anti-LAG-3 antibody molecule is a full antibody or fragment thereof (e.g., a Fab, F(ab')$_2$. Fv, or a single chain Fv fragment (scFv)). In certain embodiments, the anti-LAG-3 antibody molecule is a monoclonal antibody or an antibody with single specificity. The anti-LAG-3 antibody molecule can also be a humanized, chimeric, camelid, shark, or in vitro-generated antibody molecules. In one embodiment, the anti-LAG-3 antibody molecule thereof is a humanized antibody molecule. The heavy and light chains of the anti-LAG-3 antibody molecule can be full-length (e.g., an antibody can include at least one, and preferably two, complete heavy chains, and at least one, and preferably two, complete light chains) or can include an antigen-binding fragment (e.g., a Fab, F(ab')$_2$. Fv, a single chain Fv fragment, a single domain antibody, a diabody (dAb), a bivalent or bispecific antibody or fragment thereof, a single domain variant thereof, or a camelid antibody).

In certain embodiments, the anti-LAG-3 antibody molecule is in the form of a bispecific or a multispecific antibody molecule. In one embodiment, the bispecific antibody molecule has a first binding specificity for LAG-3 and a second binding specifity for PD-1, TIM-3, CEACAM (e.g., CEACAM-1 and/or CEACAM-5), PD-L1 or PD-L2. In one embodiment, the bispecific antibody molecule binds to LAG-3 and PD-1. In another embodiment, the bispecific antibody molecule binds to LAG-3 and TIM-3. In another embodiment, the bispecific antibody molecule binds to LAG-3 and CEACAM (e.g., CEACAM-1 and/or CEACAM-5). In another embodiment, the bispecific antibody molecule binds to LAG-3 and CEACAM-1. In yet another embodiment, the bispecific antibody molecule binds to LAG-3 and CEACAM-5. In another embodiment, the bispecific antibody molecule binds to LAG-3 and PD-L1. In yet another embodiment, the bispecific antibody molecule binds to LAG-3 and PD-L2. Any combination of the aforesaid molecules can be made in a multispecific antibody molecule, e.g., a trispecific antibody that includes a first binding specificity to LAG-3, and a second and third binding specificity to one or more of: PD-1, TIM-3, CEACAM (e.g., CEACAM-1 or CEACAM-5), PD-L1 or PD-L2.

In other embodiments, the anti-LAG-3 antibody molecule is used in combination with a bispecific molecule comprising one or more of: PD-1, TIM-3, CEACAM (e.g., CEACAM-1 or CEACAM-5), PD-L1 or PD-L2. In one embodiment, the bispecific antibody molecule used in combination binds to CEACAM (e.g., CEACAM-1 and/or CEACAM-5) and PD-1. In another embodiment, the bispecific antibody molecule used in combination binds to CEACAM (e.g., CEACAM-1 and/or CEACAM-5) and TIM-3. In another embodiment, the bispecific antibody molecule used in combination binds to PD-1 and TIM-3.

In yet other embodiments, the anti-LAG-3 antibody molecule has a heavy chain constant region (Fc) chosen from, e.g., the heavy chain constant regions of IgG1, IgG2, IgG3, IgG4, IgM, IgA1, IgA2, IgD, and IgE; particularly, chosen from, e.g., the heavy chain constant regions of IgG1, IgG2, IgG3, and IgG4, more particularly, the heavy chain constant region of IgG1, IgG2 or IgG4 (e.g., human IgG1, IgG2 or IgG4). In one embodiment, the heavy chain constant region is human IgG1 or human IgG4. In another embodiment, the anti-LAG-3 antibody molecule has a light chain constant region chosen from, e.g., the light chain constant regions of kappa or lambda, preferably kappa (e.g., human kappa). In one embodiment, the constant region is altered, e.g., mutated, to modify the properties of the anti-LAG-3 antibody molecule (e.g., to increase or decrease one or more of: Fc receptor binding, antibody glycosylation, the number of cysteine residues, effector cell function, or complement function). For example, the constant region is mutated at positions 296 (M to Y), 298 (S to T), 300 (T to E), 477 (H to K) and 478 (N to F) to alter Fc receptor binding (e.g., the mutated positions correspond to positions 132 (M to Y), 134 (S to T), 136 (T to E), 313 (H to K) and 314 (N to F) of SEQ ID NOs: 212 or 214; or positions 135 (M to Y), 137 (S to T), 139 (T to E), 316 (H to K) and 317 (N to F) of SEQ ID NOs: 215, 216, 217 or 218). In another embodiment, the heavy chain constant region of an IgG4, e.g., a human IgG4, is mutated at position 228 (e.g., S to P), e.g., as shown in Table 3. In certain embodiments, the anti-LAG-3 antibody molecules comprises a human IgG4 mutated at position 228 (e.g., S to P), e.g., as shown in Table 3; and a kappa light chain constant region, e.g., as shown in Table 3. In still another embodiment, the heavy chain constant region of an IgG1, e.g., a human IgG1, is mutated at one or more of position 297 (e.g., N to A), position 265 (e.g., D to A), position 329 (e.g., P to A), position 234 (e.g., L to A), or position 235 (e.g., L to A), e.g., as shown in Table 3. In certain embodiments, the anti-LAG-3 antibody molecules comprises a human IgG1 mutated at one or more of the aforesaid positions, e.g., as shown in Table 3; and a kappa light chain constant region, e.g., as shown in Table 3.

In one embodiment, the anti-LAG-3 antibody molecule is isolated or recombinant.

In one embodiment, the anti-LAG-3 antibody molecule is a humanized antibody molecule.

In one embodiment, the anti-LAG-3 antibody molecule has a risk score based on T cell epitope analysis of less than 1200, 1150, 1100, 1050, 1000, 950, 900, 850, or 800.

In one embodiment, the anti-LAG-3 antibody molecule is a humanized antibody molecule and has a risk score based on T cell epitope analysis of 800 to 1200, 850 to 1150, 900 to 1100, 950 to 1050, or a risk score as described herein.

The invention also features a nucleic acid molecule that comprises one or more nucleotide sequences that encode heavy and light chain variable regions, CDRs, hypervariable loops, and/or framework regions of the anti-LAG-3 antibody molecules, as described herein. In certain embodiments, the nucleotide sequence that encodes the anti-LAG-3 antibody molecule is codon optimized. For example, the invention features a first and second nucleic acid encoding heavy and light chain variable regions, respectively, of an anti-LAG-3 antibody molecule chosen from one or more of, e.g., any of BAP050-hum01, BAP050-hum02, BAP050-hum03, BAP050-hum04, BAP050-hum05, BAP050-hum06, BAP050-hum07, BAP050-hum08, BAP050-hum09, BAP050-hum10, BAP050-hum11, BAP050-hum12, BAP050-hum13, BAP050-hum14, BAP050-hum15, BAP050-hum16, BAP050-hum17, BAP050-hum18, BAP050-hum19, BAP050-hum20, huBAP050 (Ser) (e.g., BAP050-hum01-Ser, BAP050-hum02-Ser, BAP050-hum03-Ser, BAP050-hum04-Ser, BAP050-hum05-Ser, BAP050-hum06-Ser, BAP050-hum07-Ser, BAP050-hum08-Ser, BAP050-hum09-Ser, BAP050-hum10-Ser, BAP050-hum11-Ser, BAP050-hum12-Ser, BAP050-hum13-Ser, BAP050-hum14-Ser, BAP050-hum15-Ser, BAP050-hum18-Ser, BAP050-hum19-Ser, or BAP050-hum20-Ser), BAP050-Clone-F. BAP050-Clone-G, BAP050-Clone-H, BAP050-Clone-I, or BAP050-Clone-J, as summarized in Table 1, or a sequence substantially identical thereto. For example, the nucleic acid can comprise a nucleotide sequence as set forth in Tables 1 and 2, or a sequence substantially identical thereto (e.g., a sequence at least about 85%, 90%, 95%, 99% or more identical thereto, or which differs by no more than 3, 6, 15, 30, or 45 nucleotides from the sequences shown in Tables 1 and 2.

In other embodiments, the nucleic acid molecule comprises a nucleotide sequence that encodes a heavy chain variable domain and a heavy chain constant region comprising the amino acid sequence of BAP050-Clone-F. BAP050-Clone-G, BAP050-Clone-H, BAP050-Clone-I, or BAP050-Clone-J; or as described in Table 1, or encoded by the nucleotide sequence in Table 1; or a sequence substantially identical (e.g., at least 80%, 85%, 90%, 92%, 95%, 97%, 98%, 99% or higher identical) to any of the aforesaid sequences.

In other embodiments, the nucleic acid comprises a nucleotide sequence that encodes a light chain variable domain and/or a light chain constant region comprising the amino acid sequence of BAP050-Clone-F, BAP050-Clone-G, BAP050-Clone-H, BAP050-Clone-I, or BAP050-Clone-J; or as described in Table 1, or encoded by the nucleotide sequence in Table 1; or a sequence substantially identical (e.g., at least 80%, 85%, 90%, 92%, 95%, 97%, 98%, 99% or higher identical) to any of the aforesaid sequences.

The aforesaid nucleotide sequences encoding the anti-LAG-3 heavy and light chain variable domain and constant regions can be present in a separate nucleic acid molecule, or in the same nucleic acid molecule. In certain embodiments, the nucleic acid molecules comprise a nucleotide sequence encoding a leader sequence, e.g., a leader sequence as shown in Table 4, or a sequence substantially identical thereto.

In certain embodiments, the nucleic acid molecule comprise a nucleotide sequence encoding at least one, two, or three CDRs or hypervariable loops, from a heavy chain variable region having an amino acid sequence as set forth in Table 1, or a sequence substantially homologous thereto (e.g., a sequence at least about 85%, 90%, 95%, 99% or more identical thereto, and/or having one, two, three or more substitutions, insertions or deletions, e.g., conserved substitutions).

In another embodiment, the nucleic acid molecule comprise a nucleotide sequence encoding at least one, two, or three CDRs or hypervariable loops, from a light chain variable region having an amino acid sequence as set forth in Table 1, or a sequence substantially homologous thereto (e.g., a sequence at least about 85%, 90%, 95%, 99% or more identical thereto, and/or having one, two, three or more substitutions, insertions or deletions, e.g., conserved substitutions).

In yet another embodiment, the nucleic acid molecule can comprise a nucleotide sequence encoding at least one, two, three, four, five, or six CDRs or hypervariable loops, from heavy and light chain variable regions having an amino acid sequence as set forth in Table 1, or a sequence substantially homologous thereto (e.g., a sequence at least about 85%, 90%, 95%, 99% or more identical thereto, and/or having one, two, three or more substitutions, insertions or deletions, e.g., conserved substitutions).

In one embodiment, the nucleic acid molecule includes a nucleotide sequence encoding an anti-LAG-3 antibody molecule that includes a substitution (e.g., a Cys to Ser substitution at position 84) in the heavy chain framework region 3 (VHFW3) (e.g., as shown in Tables 1 and 2).

In another embodiment, the nucleic acid molecule includes one or more heavy chain framework region (e.g., any of VHFW1 (type a), VHFW1 (type b), VHFW1 (type c), VHFW1 (type d), VHFW2 (type a), VHFW2 (type b), VHFW2 (type c), VHFW2 (type d), VHFW3 (type a), VHFW3 (type a'), VHFW3 (type b), VHFW3 (type c), or VHFW4, or any combination thereof, e.g., a framework combination as described herein) for any of BAP050-hum01, BAP050-hum02, BAP050-hum03, BAP050-hum04, BAP050-hum05, BAP050-hum06, BAP050-hum07, BAP050-hum08, BAP050-hum09, BAP050-hum10, BAP050-hum11, BAP050-hum12, BAP050-hum13, BAP050-hum14, BAP050-hum15, BAP050-hum16, BAP050-hum17, BAP050-hum18, BAP050-hum19, BAP050-hum20, huBAP050 (Ser) (e.g., BAP050-hum01-Ser, BAP050-hum02-Ser, BAP050-hum03-Ser, BAP050-hum04-Ser, BAP050-hum05-Ser, BAP050-hum06-Ser, BAP050-hum07-Ser, BAP050-hum08-Ser, BAP050-hum09-Ser, BAP050-hum10-Ser, BAP050-hum11-Ser, BAP050-hum12-Ser, BAP050-hum13-Ser, BAP050-hum14-Ser, BAP050-hum15-Ser, BAP050-hum18-Ser, BAP050-hum19-Ser, or BAP050-hum20-Ser), BAP049-Clone-F, BAP049-Clone-G, BAP049-Clone-H, BAP049-Clone-I, or BAP049-Clone-J, as summarized in Table 1 and 2, or a sequence substantially identical thereto. For example, the nucleic acid molecule can comprise a nucleotide sequence as set forth in Tables 1 and 2, or a sequence substantially identical thereto (e.g., a sequence at least about 85%, 90%, 95%, 99% or more identical thereto, or which differs by no more than 3, 6, 15, 30, or 45 nucleotides from the sequences shown in Tables 1 and 2).

In another embodiment, the nucleic acid molecule includes one or more light chain framework region (e.g., any of VLFW1 (type a), VLFW1 (type b), VLFW1 (type c), VLFW1 (type d), VLFW1 (type e), VLFW1 (type f), VLFW2 (type a), VLFW2 (type b), VLFW2 (type c), VLFW2 (type d), VLFW3 (type a), VLFW3 (type b), VLFW3 (type c), VLFW3 (type d), VLFW3 (type e), VLFW3 (type f), VLFW3 (type g), or VLFW4, or any combination thereof, e.g., a framework combination as described herein) for any of BAP050-hum01, BAP050-hum02, BAP050-hum03, BAP050-hum04, BAP050-hum05, BAP050-hum06, BAP050-hum07, BAP050-hum08, BAP050-hum09, BAP050-hum10, BAP050-hum11, BAP050-hum12, BAP050-hum13, BAP050-hum14, BAP050-hum15, BAP050-hum16, BAP050-hum17, BAP050-hum18, BAP050-hum19, BAP050-hum20, huBAP050 (Ser) (e.g., BAP050-hum01-Ser, BAP050-hum02-Ser, BAP050-hum03-Ser, BAP050-hum04-Ser, BAP050-hum05-Ser, BAP050-hum06-Ser, BAP050-hum07-Ser, BAP050-hum08-Ser, BAP050-hum09-Ser, BAP050-hum10-Ser, BAP050-hum11-Ser, BAP050-hum12-Ser, BAP050-hum13-Ser, BAP050-hum14-Ser, BAP050-hum15-Ser, BAP050-hum18-Ser, BAP050-hum19-Ser, or BAP050-hum20-Ser), BAP049-Clone-F, BAP049-Clone-G, BAP049-Clone-H, BAP049-Clone-I, or BAP049-Clone-J, as summarized in Tables 1 and 2, or a sequence substantially identical thereto. For example, the nucleic acid molecule can comprise a nucleotide sequence as set forth in Tables 1 and 2, or a sequence substantially identical thereto (e.g., a sequence at least about 85%, 90%, 95%, 99% or more identical thereto, or which differs by no more than 3, 6, 15, 30, or 45 nucleotides from the sequences shown in Tables 1 and 2).

In another embodiment, the nucleic acid molecule includes one or more heavy chain framework region and one or more light chain framework region as described herein. The heavy and light chain framework regions may be present in the same vector or separate vectors.

In another aspect, the application features host cells and vectors containing the nucleic acids described herein. The nucleic acids may be present in a single vector or separate vectors present in the same host cell or separate host cell. The host cell can be a eukaryotic cell, e.g., a mammalian cell, an insect cell, a yeast cell, or a prokaryotic cell, e.g., E. coli. For example, the mammalian cell can be a cultured cell or a cell line. Exemplary mammalian cells include lymphocytic cell lines (e.g., NSO), Chinese hamster ovary cells (CHO), human Per C6 cell line (e.g., PER C6 cells from Crucell), COS cells, oocyte cells, and cells from a transgenic animal, e.g., mammary epithelial cell.

In one aspect, the invention features a method of providing an antibody molecule described herein. The method includes: providing a LAG-3 antigen (e.g., an antigen comprising at least a portion of a LAG-3 epitope); obtaining an antibody molecule that specifically binds to the LAG-3 polypeptide; and evaluating if the antibody molecule specifically binds to the LAG-3 polypeptide, or evaluating efficacy of the antibody molecule in modulating, e.g., inhibiting, the activity of the LAG-3. The method can further include administering the antibody molecule to a subject, e.g., a human or non-human animal.

In another aspect, the invention provides, compositions, e.g., pharmaceutical compositions, which include a pharmaceutically acceptable carrier, excipient or stabilizer, and at least one of anti-LAG3 antibody molecule described herein. In one embodiment, the composition, e.g., the pharmaceutical composition, includes a combination of the anti-LAG-3 antibody molecule and one or more agents, e.g., a therapeutic agent or other antibody molecule, as described herein. In one embodiment, the antibody molecule is conjugated to a label or a therapeutic agent.

The antibody molecules disclosed herein can inhibit, reduce or neutralize one or more activities of LAG-3. In one embodiment, the anti-LAG-3 antibody molecule results in one or more of: an increase in antigen-dependent stimulation of CD4+T lymphocytes or CD8+T lymphocytes, an increase in T cell proliferation; an increase in expression of an activation antigen, e.g., CD25; an increase in expression of a cytokine, e.g., interferon-gamma (IFN-γ), interleukin-2 (IL-2), interleukin-4 (IL-4), chemokine (C-C motif) ligand 3 (CCL3), chemokine (C-C motif) ligand 4 (CCL4), or chemokine (C-C motif) ligand 5 (CCL5); a decrease in the suppressor activity of $T_{reg}$ cells, an increase in T cell homeostasis, an increase in tumor infiltrating lymphocytes, or a decrease in immune evasion by the cancerous cells. Thus, such antibody molecules can be used, alone or in combination, to treat or prevent disorders where enhancing an immune response in a subject is desired.

Uses of the Anti-LAG-3 Antibody Molecules

Accordingly, in another aspect, a method of modulating an immune response in a subject is provided. The method comprises administering to the subject an antibody molecule disclosed herein (e.g., a therapeutically effective amount of an anti-LAG-3 antibody molecule), alone or in combination with one or more agents or procedures, such that the immune response in the subject is modulated. In one embodiment, the antibody molecule restores, enhances, stimulates or increases an immune response in the subject.

The subject can be a mammal, e.g., a primate, preferably a higher primate, e.g., a human (e.g., a patient having, or at risk of having, a disorder described herein). In one embodiment, the subject is in need of enhancing an immune response. In some embodiments, the anti-LAG-3 antibody molecule restores, enhances or stimulates an antigen-specific T cell response, e.g., interleukin-2 (IL-2) or interferon-gamma (IFN-γ) production in an antigen-specific T cell response, in the subject. In some embodiments, the immune response is an anti-tumor response. In one embodiment, the subject has, or is at risk of, having a disorder described herein, e.g., a cancer or an infectious disorder as described herein. In certain embodiments, the subject is, or is at risk of being, immunocompromised. For example, the subject is undergoing or has undergone a chemotherapeutic treatment and/or radiation therapy. Alternatively, or in combination, the subject is, or is at risk of being, immunocompromised as a result of an infection.

In one aspect, a method of treating (e.g., one or more of reducing, inhibiting, or delaying progression) a cancer or tumor in a subject is provided. The method comprises administering to the subject an anti-LAG-3 antibody molecule described herein, e.g., a therapeutically effective amount of an anti-LAG-3 antibody molecule, alone, e.g., as a monotherapy, or in combination, e.g., with one or more agents or procedures. In certain embodiments, the anti-LAG-3 antibody molecule is administered in combination with a modulator of a costimulatory molecule (e.g., an agonist of a costimulatory molecule) or a modulator of an inhibitory molecule (e.g., an inhibitor of an immune checkpoint inhibitor), e.g., as described herein. In one embodiment, the anti-LAG-3 antibody molecule is administered in combination with an inhibitor or activator of an immune checkpoint modulator (e.g., a PD-1 inhibitor (e.g., an anti-PD-1 antibody molecule), a PD-L1 inhibitor (e.g., an anti-PD-L1 antibody molecule), a TIM-3 modulator (e.g., a TIM-3 activator or inhibitor, e.g., an anti-TIM-3 antibody molecule), or a CTLA-4 inhibitor (e.g., an anti-CTLA4 antibody).

In certain embodiments, the cancer treated with the anti-LAG-3 antibody molecule, alone or in combination, includes but is not limited to, a solid tumor, a hematological cancer (e.g., leukemia, lymphoma, myeloma), and a metastatic lesion thereof. In one embodiment, the cancer is a solid tumor. Examples of solid tumors include malignancies, e.g., sarcomas and carcinomas (e.g., adenocarcinomas), of the various organ systems, such as those affecting lung, breast, lymphoid, gastrointestinal or colorectal, genitals and genitourinary tract (e.g., renal, urothelial, bladder cells), pharynx, CNS (e.g., brain, neural or glial cells), skin (e.g., melanoma), head and neck (e.g., head and neck squamous cell carcinoma (HNCC)), and pancreas. For example, melanoma, colon cancers, gastric cancer, rectal cancer, renal-cell carcinoma, breast cancer (e.g., a breast cancer that does not express one, two or all of estrogen receptor, progesterone receptor, or Her2/neu, e.g., a triple negative breast cancer), liver cancer, a lung cancer (e.g., a non-small cell lung cancer (NSCLC) (e.g., a NSCLC with squamous and/or non-squamous histology) or small cell lung cancer), prostate cancer, cancer of head or neck (e.g., HPV+ squamous cell carcinoma), cancer of the small intestine and cancer of the esophagus. Examples of hematological cancer include, but is not limited to, leukemia (e.g., a myeloid leukemia, lymphoid leukemia, or chronic lymphocytic leukemia (CLL)), lymphoma (e.g., Hogkin lymphoma (HL), non-Hogkin lymphoma (NHL), Diffuse large B-cell lymphoma (DLBCL), T-cell lymphoma, or mantle cell lymphoma (MCL)), and myeloma, e.g., multiple myeloma. The cancer may be at an early, intermediate, late stage or metastatic cancer.

In some embodiments, the cancer is chosen from a colorectal cancer (e.g., CRC), melanoma, e.g., advanced stage melanoma (e.g., stage II-IV melanoma) or HLA-A2 positive-melanoma; a pancreatic cancer, e.g., advanced pancreatic cancer; a breast cancer, e.g., metastatic breast carcinoma or triple negative breast cancer; a head and neck cancer (e.g., HNSCC); an esophageal cancer; a renal cell carcinoma (RCC), e.g., clear renal cell carcinoma (ccRCC) or metastatic renal cell carcinoma (MRCC); a lung cancer (e.g., NSCLC); a cervical cancer; bladder cancer; or a hematologic malignancy, e.g., a leukemia (e.g., a lymphocytic leukemia), or a lymphoma (e.g., a Hogdkin's lymphoma (HL), a non-Hogdkin's lymphoma (NHL), a diffuse large B-cell lymphoma (DLBCL), a mantle cell lymphoma (MCL), or a CLL, e.g., a relapsed or refractory chronic lymphocytic leukemia).

In one embodiment, the cancer is an advanced or unresectable melanoma that does not respond to other therapies. In other embodiments, the cancer is a melanoma with a BRAF mutation (e.g., a BRAF V600 mutation). In yet other embodiments, the anti-LAG-3 antibody molecule is alone (e.g., as a monotherapy), or in combination with one or more second agents (e.g., a BRAF inhibitor). In one embodiment, the anti-LAG-3 antibody molecule is administered in combination with (e.g., before or after treatment or simultaneously with) an inhibitor of an immune checkpoint modulator (e.g., a PD-1 inhibitor, a PD-L1 inhibitor, a TIM-3 inhibitor, a CEACAM (e.g., CEACAM1 and/or CEACAM5) inhibitor, or a CTLA4 inhibitor (e.g., an anti-CLA4 antibody, e.g., ipilimumab)) with or without a BRAF inhibitor (e.g., vemurafenib or dabrafenib) to treat a melanoma. In one embodiment, the anti-LAG-3 antibody molecule is administered in combination with a PD-1 or a PD-L1 inhibitor, e.g., an anti-PD-1 or an anti-PD-L1 antibody molecule, to treat a melanoma as described herein.

In one embodiment, the anti-LAG-3 antibody molecule is administered alone, e.g., as a monotherapy, or in combination with an inhibitor of an immune checkpoint modulator (e.g., a PD-1 inhibitor (e.g., an anti-PD-1 antibody molecule), a PD-L1 inhibitor (e.g., an anti-PD-L1 antibody molecule), a TIM-3 inhibitor (e.g., an anti-TIM-3 antibody molecule), a CEACAM (e.g., CEACAM1 and/or CEACAM5) inhibitor (e.g., an anti-CEACAM antibody molecule), or a CTLA-4 inhibitor (e.g., an anti-CTLA4 antibody) to treat a head and neck cancer (e.g., HNSCC). In one embodiment, the anti-LAG-3 antibody molecule is administered in combination with a PD-1 or a PD-L1 inhibitor, e.g., an anti-PD-1 or anti-PD-L1 antibody molecule, to treat a head and neck cancer as described herein.

In one embodiment, the anti-LAG-3 antibody molecule is administered alone, e.g., as a monotherapy, or in combination with an inhibitor or activator of an immune checkpoint modulator (e.g., a PD-1 inhibitor (e.g., an anti-PD-1 antibody molecule), a PD-L1 inhibitor (e.g., an anti-PD-L1 antibody molecule), a TIM-3 modulator (e.g., a TIM-3 activator or inhibitor, e.g., an anti-TIM-3 antibody molecule), a CEACAM (e.g., CEACAM1 and/or CEACAM5) inhibitor (e.g., an anti-CEACAM antibody molecule), or a CTLA-4 inhibitor (e.g., an anti-CTLA4 antibody) to treat a lung cancer (e.g., a NSCLC). In one embodiment, the anti-LAG-3 antibody molecule is administered in combination with a PD-1 or a PD-L1 inhibitor, e.g., an anti-PD-1 or anti-PD-L1 antibody molecule, to treat a lung cancer (e.g., a NSCLC) as described herein.

In one embodiment, the anti-LAG-3 antibody molecule is administered alone, e.g., as a monotherapy, or in combination with an inhibitor of an immune checkpoint modulator (e.g., a PD-1 inhibitor (e.g., an anti-PD-1 antibody molecule), a PD-L1 inhibitor (e.g., an anti-PD-L1 antibody molecule), a TIM-3 inhibitor (e.g., an anti-TIM-3 antibody molecule), a CEACAM (e.g., CEACAM1 and/or CEACAM5) inhibitor (e.g., an anti-CEACAM antibody molecule), or a CTLA-4 inhibitor (e.g., an anti-CTLA4 antibody) to treat a gastric cancer. In one embodiment, the anti-LAG-3 antibody molecule is administered in combination with a PD-1 or a PD-L1 inhibitor, e.g., an anti-PD-1 or anti-PD-L1 antibody molecule, to treat a gastric cancer as described herein.

In one embodiment, the anti-LAG-3 antibody molecule is administered alone, e.g., as a monotherapy, or in combination with an inhibitor of an immune checkpoint modulator (e.g., a PD-1 inhibitor (e.g., an anti-PD-1 antibody molecule), a PD-L1 inhibitor (e.g., an anti-PD-L1 antibody molecule), a TIM-3 inhibitor (e.g., an anti-TIM-3 antibody molecule), a CEACAM (e.g., CEACAM1 and/or CEACAM5) inhibitor (e.g., an anti-CEACAM antibody molecule), or a CTLA-4 inhibitor (e.g., an anti-CTLA4 antibody) to treat a lymphoma (e.g., Hogdkin's lymphoma (HL), non-Hogdkin's lymphoma (NHL), Diffuse large B-cell lymphoma (DLBCL), mantle cell lymphoma (MCL), or CLL, e.g., a relapsed or refractory chronic lymphocytic leukemia). In one embodiment, the anti-LAG-3 antibody molecule is administered in combination with a PD-1 or a PD-L1 inhibitor, e.g., an anti-PD-1 or anti-PD-L1 antibody molecule, to treat a lymphoma as described herein.

In one embodiment, the cancer microenvironment has an elevated level of PD-L1 expression. Alternatively, or in combination, the cancer microenvironment can have increased IFNγ and/or CD8 expression.

In some embodiments, the anti-LAG-3 antibody molecule is administered, alone or in combination with a PD-1 inhibitor (e.g., an anti-PD-1 antibody molecule) or a PD-L1 inhibitor (e.g., an anti-PD-L1 antibody molecule), to treat a subject who has or is identified as having a tumor that has one or more of high PD-L1 level or expression, or as being Tumor Infiltrating Lymphocyte (TIL)+ (e.g., as having an increased number of TILs), or both. In certain embodiments, the subject has, or is identified as having, a tumor that has high PD-L1 level or expression and that is TIL+. In some embodiments, the methods described herein further include identifying a subject based on having a tumor that has one or more of high PD-L1 level or expression or as being TIL+, or both. In certain embodiments, the methods described herein further include identifying a subject based on having a tumor that has high PD-L1 level or expression and as being TIL+. In some embodiments, tumors that are TIL+ are positive for CD8 and IFNγ. In some embodiments, the subject has, or is identified as having, a high percentage of cells that are positive for one, two or more of PD-L1, CD8, and/or IFNγ. In certain embodiments, the subject has or is identified as having a high percentage of cells that are positive for all of PD-L1, CD8, and IFNγ.

In some embodiments, the methods described herein further include identifying a subject based on having a high percentage of cells that are positive for one, two or more of PD-L1, CD8, and/or IFNγ. In certain embodiments, the methods described herein further include identifying a subject based on having a high percentage of cells that are positive for all of PD-L1, CD8, and IFNγ. In some embodiments, the subject has, or is identified as having, one, two or more of PD-L1, CD8, and/or IFNγ, and one or more of a lung cancer, e.g., squamous cell lung cancer or lung adenocarcinoma; a head and neck cancer; a squamous cell cervical cancer; a stomach cancer; an esophageal cancer; a thyroid cancer; a melanoma, and/or a nasopharyngeal cancer (NPC). In certain embodiments, the methods described herein further describe identifying a subject based on having one, two or more of PD-L1, CD8, and/or IFNγ, and one or more of a lung cancer, e.g., squamous cell lung cancer or lung adenocarcinoma; a head and neck cancer; a squamous cell cervical cancer; a stomach cancer; a thyroid cancer; a melanoma, and or a nasopharyngeal cancer.

Methods and compositions disclosed herein are useful for treating metastatic lesions associated with the aforementioned cancers.

In a further aspect, the invention provides a method of treating an infectious disease in a subject, comprising administering to a subject a therapeutically effective amount of an anti-LAG-3 antibody molecule described herein, alone or in combination with one or more agents or procedures.

The antibodies of the invention are preferred for use in the method although other anti-LAG-3 antibodies, or antigen-binding fragments thereof, can be used instead (or in combination with an anti-LAG-3 antibody molecule described herein).

In one embodiment, the infectious disease is hepatitis (e.g., hepatitis B infection). In certain embodiment, the anti-LAG-3 antibody molecule is administered in combination with a hepatitis B antigen or vaccine, and optionally in combination with an aluminum-containing adjuvant.

In another embodiment, the infectious disease is influenza. In certain embodiment, the anti-LAG-3 antibody molecule is administered in combination with an influenza antigen or vaccine.

Still further, the invention provides a method of enhancing an immune response to an antigen in a subject, comprising administering to the subject: (i) the antigen; and (ii) an anti-LAG-3 antibody molecule, such that an immune response to the antigen in the subject is enhanced. The antigen can be, for example, a tumor antigen, a viral antigen, a bacterial antigen or an antigen from a pathogen.

The anti-LAG-3 antibody molecule, alone or in combination, can be administered to the subject systemically (e.g., orally, parenterally, subcutaneously, intravenously, rectally, intramuscularly, intraperitoneally, intranasally, transdermally, or by inhalation or intracavitary installation), topically, or by application to mucous membranes, such as the nose, throat and bronchial tubes.

Dosages and therapeutic regimens of the anti-LAG-3 antibody molecule can be determined by a skilled artisan. In certain embodiments, the anti-LAG-3 antibody molecule is administered by injection (e.g., subcutaneously or intravenously) at a dose of about 1 to 30 mg/kg. e.g., about 5 to 25 mg/kg, about 10 to 20 mg/kg, about 1 to 10 mg/kg, or about 1 mg/kg, 3 mg/kg, or 10 mg/kg. The dosing schedule can vary from e.g., once a week to once every 2, 3, or 4 weeks. In one embodiment, the anti-LAG-3 antibody molecule is administered at a dose from about 10 to 20 mg/kg every other week. In one embodiment, the anti-LAG-3 antibody molecule is administered (e.g., intravenously) at a dose from about 3 to 800 mg, e.g., about 3, 20, 80, 240, or 800 mg. In certain embodiments, the anti-LAG-3 antibody molecule is administered alone at a dose from about 20 to 800 mg, e.g., about 3, 20, 80, 240, or 800 mg. In other embodiments, the anti-LAG-3 antibody molecule is administered at a dose from about 3 to 240 mg. e.g., about 3, 20, 80, or 240 mg, when it is combined with a second agent or therapeutic modality, e.g., a second agent or therapeutic modality described herein. In one embodiment, the anti-LAG-3 antibody molecule is administered every 2 weeks (e.g., during weeks 1, 3, 5, 7) during each 8 week cycle, e.g., up to 96 weeks.

The antibody molecules described herein are preferred for use in the methods described herein, although other anti-LAG-3 antibodies can be used instead, or in combination with an anti-LAG-3 antibody molecule of the invention.

Combination Therapies

The methods and compositions described herein can be used in combination with other agents or therapeutic modalities. In one embodiment, the methods described herein include administering to the subject an anti-LAG-3 antibody molecule as described herein, in combination with an agent or therapeutic procedure or modality, in an amount effective to treat or prevent a disorder. The anti-LAG-3 antibody molecule and the agent or therapeutic procedure or modality can be administered simultaneously or sequentially in any order. Any combination and sequence of the anti-LAG-3 antibody molecules and other therapeutic agents, procedures or modalities (e.g., as described herein) can be used. The antibody molecule and/or other therapeutic agents, procedures or modalities can be administered during periods of active disorder, or during a period of remission or less active disease. The antibody molecule can be administered before the other treatment, concurrently with the treatment, post-treatment, or during remission of the disorder.

In certain embodiments, the methods and compositions described herein are administered in combination with one or more of other antibody molecules, chemotherapy, other anti-cancer therapy (e.g., targeted anti-cancer therapies, gene therapy, viral therapy, RNA therapy bone marrow transplantation, nanotherapy, or oncolytic drugs), cytotoxic agents, immune-based therapies (e.g., cytokines or cell-based immune therapies), surgical procedures (e.g., lumpectomy or mastectomy) and/or radiation procedures, or a combination of any of the foregoing. The additional therapy may be in the form of adjuvant or neoadjuvant therapy. In some embodiments, the additional therapy is an enzymatic inhibitor (e.g., small molecule enzymatic inhibitor) or a metastatic inhibitor.

Exemplary cytotoxic agents that can be administered in combination with include antimicrotubule agents, topoisomerase inhibitors, anti-metabolites, mitotic inhibitors, alkylating agents, anthracyclines, *vinca* alkaloids, intercalating agents, agents capable of interfering with a signal transduction pathway, agents that promote apoptosis, proteosome inhibitors, and radiation (e.g., local or whole body irradiation (e.g., gamma irradiation). In other embodiments, the additional therapy is surgery or radiation, or a combination thereof. In other embodiments, the additional therapy is a therapy targeting one or more of PI3K/AKT/mTOR pathway, an HSP90 inhibitor, or a tubulin inhibitor. Exemplary other antibody molecules that can be administered in combination include, but are not limited to, checkpoint inhibitors (e.g., anti-PD-1, anti-PD-L1); antibodies that stimulate an immune cell (e.g., agonistic GITR or CD137 antibodies); anti-cancer antibodies (e.g., rituximab (Rituxan® or MabThera®), trastuzumab (Herceptin®), cetuximab (Erbitux®), among others.

Alternatively, or in combination with the aforesaid combinations, the methods and compositions described herein can be administered in combination with one or more of: an immunomodulator (e.g., an activator of a costimulatory molecule or an inhibitor of an immunoinhibitory molecule, e.g., an immune checkpoint molecule); a vaccine, e.g., a therapeutic cancer vaccine; or other forms of cellular immunotherapy.

Exemplary non-limiting combinations and uses of the anti-LAG-3 antibody molecules include the following.

In certain embodiments, the anti-LAG-3 antibody molecule is administered in combination with a modulator of a costimulatory molecule (e.g., an agonist of a costimulatory molecule) or a modulator of an inhibitory molecule (e.g., an inhibitor of an immune checkpoint inhibitor).

In one embodiment, the anti-LAG-3 antibody molecule is administered in combination with a modulator, e.g., an agonist, of a costimulatory molecule. In one embodiment, the agonist of the costimulatory molecule is chosen from an agonist (e.g., an agonistic antibody or soluble fusion) of OX40, CD2, CD27, CDS, ICAM-1, LFA-1 (CD11a/CD18), ICOS (CD278), 4-1BB (CD137), GITR, CD30, CD40, BAFFR, HVEM, CD7, LIGHT, NKG2C, SLAMF7, NKp80, CD160, B7-H3 or CD83 ligand.

In one embodiment, the anti-LAG-3 antibody molecule is administered in combination with an inhibitor of an inhibitory (or immune checkpoint) molecule chosen from PD-1, PD-L1, PD-L2, CTLA-4, TIM-3, VISTA, BTLA, TIGIT, LAIR1, CD160, 2B4, CEACAM (e.g., CEACAM-1 and/or CEACAM-5)., and/or TGFR beta. Inhibition of an inhibitory molecule can be performed by inhibition at the DNA, RNA or protein level. In embodiments, an inhibitory nucleic acid (e.g., a dsRNA, siRNA or shRNA), can be used to inhibit expression of an inhibitory molecule. In other embodiments, the inhibitor of an inhibitory signal is, a polypeptide e.g., a soluble ligand, or an antibody or antibody fragment, that binds to the inhibitory molecule. In one embodiment, the inhibitor is a soluble ligand (e.g., a CTLA-4-Ig), or an antibody or antibody fragment that binds to PD-1, PD-L1, PD-L2 or CTLA-4.

For example, the anti-LAG-3 antibody molecule can be administered in combination with an inhibitor of, e.g., an antibody or antibody fragment that binds to, PD-1, PD-L1, PD-L2 or CTLA-4, to treat a cancer (e.g., a cancer chosen from: a colorectal cancer (e.g., CRC); a melanoma, e.g., advanced stage melanoma (e.g., stage II-IV melanoma) or HLA-A2 positive-melanoma; a pancreatic cancer, e.g., advanced pancreatic cancer; a breast cancer, e.g., metastatic breast carcinoma or triple negative breast cancer; a head and neck cancer (e.g., HNSCC); an esophageal cancer; a renal cell carcinoma (RCC), e.g., clear renal cell carcinoma (ccRCC) or metastatic renal cell carcinoma (MRCC); a lung cancer (e.g., NSCLC); a cervical cancer; a bladder cancer; or a hematologic malignancy, e.g., a leukemia (e.g., a lymphocytic leukemia), or a lymphoma (e.g., a Hogdkin's lymphoma (HL), a non-Hogdkin's lymphoma (NHL), a diffuse large B-cell lymphoma (DLBCL), a mantle cell lymphoma (MCL), or a CLL, e.g., a relapsed or refractory chronic lymphocytic leukemia).

In one embodiment, the anti-LAG-3-1 antibody molecule is administered in combination with (e.g., before, with, or after) treatment with an anti-CTLA4 antibody (e.g., ipilimumab) with or without a BRAF inhibitor (e.g., vemurafenib or dabrafenib).

In another embodiment, the anti-LAG-3 antibody molecule is administered in combination with an anti-PD-1 antibody (e.g., Nivolumab or Pembrokizumab) or antigen-binding fragment thereof. In another embodiment, the anti-LAG-3 antibody molecule is administered in combination with an anti-TIM-3 antibody or antigen-binding fragment thereof. In still another embodiment, the anti-LAG-3 antibody molecule is administered in combination with an anti-PD-L1 antibody or antigen-binding fragment thereof. In yet other embodiments, the anti-LAG-3 antibody molecule is administered in combination with an anti-PD-1 antibody and an anti-TIM-3 antibody (or antigen-binding fragments thereof). In certain embodiments, the anti-LAG-3 antibody molecule is administered in combination with an anti-PD-1 antibody and an anti-PD-L1 antibody (or antigen-binding fragments thereof). In certain embodiments, the anti-LAG-3 antibody molecule is administered in combination with an anti-TIM-3 antibody and an anti-PD-L1 antibody (or antigen-binding fragments thereof).

In another embodiment, the anti-LAG-3 antibody molecule is administered in combination with a CEACAM inhibitor (e.g., CEACAM-1 and/or CEACAM-5 inhibitor), e.g., an anti-CEACAM antibody molecule. In another embodiment, the anti-LAG-3 antibody molecule is administered in combination with a CEACAM-1 inhibitor, e.g., an anti-CEACAM-1 antibody molecule. In another embodiment, the anti-LAG-3 antibody molecule is administered in combination with a CEACAM-5 inhibitor, e.g., an anti-CEACAM-5 antibody molecule.

In yet other embodiments, the anti-LAG-3 antibody molecule is administered in combination with an anti-CEACAM (e.g., anti-CEACAM-1 and/or anti-CEACAM-5) antibody molecule and an anti-PD-1 antibody molecule. In yet other embodiments, the anti-LAG-3 antibody molecule is administered in combination with an anti-CEACAM (e.g., anti-CEACAM-1 and/or anti-CEACAM-5) antibody molecule and an anti-TIM-3 antibody molecule. In yet other embodiments, the anti-LAG-3 antibody molecule is administered in combination with an anti-CEACAM (e.g., anti-CEACAM-1 and/or anti-CEACAM-5) antibody molecule and an anti-PD-L1 antibody molecule. The combination of antibodies recited herein can be administered separately, e.g., as separate antibodies or antigen-binding fragments thereof, or linked, e.g., as a bispecific or trispecific antibody molecule. In one embodiment, a bispecific antibody that includes an anti-LAG-3 antibody molecule and one of: an anti-TIM-3 antibody, anti-CEACAM (e.g., anti-CEACAM-1 and/or anti-CEACAM-5) antibody, anti-PD-L1 antibody, or anti-PD-1 antibody, or an antigen-binding fragment thereof, is administered. In certain embodiments, the combination of antibodies recited herein is used to treat a cancer, e.g., a cancer as described herein (e.g., a solid tumor or a hematolgocial malignancy). In one embodiment, the anti-LAG-3 antibody molecule is administered in combination with an anti-PD-1 or anti-PD-L1 antibody to treat a solid tumor.

In other embodiments, the anti-LAG-3 antibody molecule is administered in combination with a cytokine. The cytokine can be administered as a fusion molecule to the anti-LAG-3 antibody molecule, or as separate compositions. In one embodiment, the anti-LAG-3 antibody is administered in combination with one, two, three or more cytokines, e.g., as a fusion molecule or as separate compositions. In one embodiment, the cytokine is an interleukin (IL) chosen from one, two, three or more of IL-1, IL-2, IL-12, IL-12, IL-15 or IL-21. In one embodiment, a bispecific antibody molecule has a first binding specificity to a first target (e.g., to LAG-3), a second binding specificity to a second target (e.g., PD-1, TIM-3, or PD-L1), and is optionally linked to an interleukin (e.g., IL-12) domain e.g., full length IL-12 or a portion thereof. In certain embodiments, the combination of anti-LAG-3 antibody molecule and the cytokine described herein is used to treat a cancer, e.g., a cancer as described herein (e.g., a solid tumor).

In other embodiments, the anti-LAG-3 antibody molecule is administered in combination with a vaccine, e.g., a therapeutic cancer vaccine, or other forms of cellular immunotherapy. In one embodiment, the vaccine is peptide-based, DNA-based, RNA-based, or antigen-based, or a combination thereof. In embodiments, the vaccine comprises one or more peptides, nucleic acids (e.g., DNA or RNA), antigens, or a combination thereof. In certain embodiments, the cancer vaccine comprises an adjuvant (e.g., aluminium phosphate or aluminum hydroxide). In some embodiments, the methods described herein are administered in combination with one or more of surgical removal of a tissue, chemotherapy, or other anti-cancer therapy and the primary or sole target will be metastatic lesions, e.g., metastases in the bone marrow or lymph nodes.

In one embodiment, the cancer is a melanoma, e.g., an advanced stage melanoma (e.g., stage II-IV melanoma) or HLA-A2 positive melanoma. In certain embodiment, the anti-LAG-3 antibody molecule is administered in combination with a tumor antigenic peptide, e.g., one or more HLA-A2 peptides, and optionally in combination with an adjuvant, e.g., Montanide™. Exemplary tumor peptides that can be administered in combination with the anti-LAG-3 antibody molecule include one or more of Tyrosinase.A2, MAGE-C2.A2, NY-ESO-1b.A2, MAGE-4.A2, MAGE-3.A2, MAGE-1.A2, NA17.A2 (GnTV), and MAGE-10.A2.

In another embodiment, the cancer is a pancreatic cancer, e.g., advanced pancreatic cancer. In certain embodiment, the antibody molecule can be administered in combination with a chemotherapeutic agent, e.g., gemcitabine.

In another embodiment, the cancer is a breast cancer, e.g., metastatic breast carcinoma or triple negative breast cancer. In certain embodiment, the antibody molecule can be administered in combination with a chemotherapeutic agent, e.g., paclitaxel.

In another embodiment, the cancer is a renal cell carcinoma, e.g., clear cell carcinoma, advanced (e.g., stage IV) or metastatic renal cell carcinoma (MRCC).

In another embodiment, the cancer is a cancer of head or neck, e.g., HPV+ squamous cell carcinoma.

In another embodiment, the anti-LAG-3 antibody molecule is administered in combination with an antigen. For example, the anti-LAG-3 antibody molecule can be combined with a hepatitis B antigen (e.g., Engerix B). In other embodiments, the anti-LAG-3 antibody molecule is administered in combination with a flu antigen.

The anti-LAG-3 antibody molecule can be used alone in unconjugated form, or can be bound to a substance, e.g., a cytotoxic agent or moiety (e.g., a therapeutic drug; a compound emitting radiation; molecules of plant, fungal, or bacterial origin; or a biological protein (e.g., a protein toxin) or particle (e.g., a recombinant viral particle, e.g., via a viral coat protein). For example, the antibody can be coupled to a radioactive isotope such as an α-, β-, or γ-emitter, or a β- and γ-emitter.

Additional Combination Therapies

The methods and compositions described herein (e.g., LAG-3 antibodies and methods of using them) can be used in combination with other agents or therapeutic modalities, e.g., a second therapeutic agent chosen from one or more of the agents listed in Table 7. In one embodiment, the methods described herein include administering to the subject an anti-LAG-3 antibody molecule as described herein (optionally in combination with one or more inhibitors of PD-1, PD-L1, TIM-3, CEACAM (e.g., CEACAM-1 and/or CEACAM-5), or CTLA-4)), further include administration of a second therapeutic agent chosen from one or more of the agents listed in Table 7, in an amount effective to treat or prevent a disorder, e.g., a disorder as described herein, e.g., a cancer. When administered in combination, the anti-LAG-3 antibody molecule, the additional agent (e.g., second or third agent), or all, can be administered in an amount or dose that is higher, lower or the same than the amount or dosage of each agent used individually, e.g., as a monotherapy. In certain embodiments, the administered amount or dosage of the anti-LAG-3 antibody, the additional agent (e.g., second or third agent), or all, is lower (e.g., at least 20%, at least 30%, at least 40%, or at least 50%) than the amount or dosage of each agent used individually, e.g., as a monotherapy. In other embodiments, the amount or dosage of the anti-LAG-3 antibody, the additional agent (e.g., second or third agent), or all, that results in a desired effect (e.g., treatment of cancer) is lower (e.g., at least 20%, at least 30%, at least 40%, or at least 50% lower).

In other embodiments, the second therapeutic agent is chosen from one or more of the agents listed in Table 7. In one embodiment, the cancer is chosen from a lung cancer (e.g., a non-small cell lung cancer (NSCLC) (e.g., a NSCLC with squamous and/or non-squamous histology, or a NSCLC adenocarcinoma), or disclosed in a publication listed in Table 7. In some embodiments, the second therapeutic agent is chosen from one or more of: 1) a protein kinase C (PKC) inhibitor; 2) a heat shock protein 90 (HSP90) inhibitor; 3) an inhibitor of a phosphoinositide 3-kinase (PI3K) and/or target of rapamycin (mTOR); 4) an inhibitor of cytochrome P450 (e.g., a CYP17 inhibitor or a 17alpha-Hydroxylase/C17-20 Lyase inhibitor); 5) an iron chelating agent; 6) an aromatase inhibitor; 7) an inhibitor of p53, e.g., an inhibitor of a p53/Mdm2 interaction; 8) an apoptosis inducer; 9) an angiogenesis inhibitor; 10) an aldosterone synthase inhibitor; 11) a smoothened (SMO) receptor inhibitor; 12) a prolactin receptor (PRLR) inhibitor; 13) a Wnt signaling inhibitor; 14) a CDK4/6 inhibitor; 15) a fibroblast growth factor receptor 2 (FGFR2)/fibroblast growth factor receptor 4 (FGFR4) inhibitor; 16) an inhibitor of macrophage colony-stimulating factor (M-CSF); 17) an inhibitor of one or more of c-KIT, histamine release, Flt3 (e.g., FLK2/STK1) or PKC; 18) an inhibitor of one or more of VEGFR-2 (e.g., FLK-1/KDR), PDGFRbeta, c-KIT or Raf kinase C; 19) a somatostatin agonist and/or a growth hormone release inhibitor; 20) an anaplastic lymphoma kinase (ALK) inhibitor; 21) an insulin-like growth factor 1 receptor (IGF-1R) inhibitor; 22) a P-Glycoprotein 1 inhibitor; 23) a vascular endothelial growth factor receptor (VEGFR) inhibitor; 24) a BCR-ABL kinase inhibitor; 25) an FGFR inhibitor; 26) an inhibitor of CYP11B2; 27) a HDM2 inhibitor, e.g., an inhibitor of the HDM2-p53 interaction; 28) an inhibitor of a tyrosine kinase; 29) an inhibitor of c-MET; 30) an inhibitor of JAK; 31) an inhibitor of DAC; 32) an inhibitor of 11ß-hydroxylase; 33) an inhibitor of IAP; 34) an inhibitor of PIM kinase; 35) an inhibitor of Porcupine; 36) an inhibitor of BRAF, e.g., BRAF V600E or wild-type BRAF; 37) an inhibitor of HER3; 38) an inhibitor of MEK; or 39) an inhibitor of a lipid kinase, e.g., as described herein and in Table 7.

In one embodiment, the second therapeutic agent is chosen from one or more of: Compound A8, Compound A17, Compound A23, Compound A24, Compound A27, Compound A29, Compound A33, and Compound A13.

In other embodiments, the second therapeutic agent is chosen from one or more of: Compound A5, Compound A8, Compound A17, Compound A23, Compound A24, Compound A29, and Compound A40.

In other embodiments, the second therapeutic agent is chosen from one or more of: Compound A9, Compound A16, Compound A17, Compound A21, Compound A22, Compound A25, Compound A28, Compound A48, and Compound 49.

In embodiments, the second therapeutic agent is administered at a therapeutic or lower-than therapeutic dose. In certain embodiments, the concentration of the second therapeutic agent that is required to achieve inhibition, e.g., growth inhibition, is lower when the second therapeutic agent is administered in combination with the anti-LAG-3 antibody molecule than when the second therapeutic agent is administered individually. In certain embodiments, the concentration of the anti-LAG-3 antibody molecule that is required to achieve inhibition, e.g., growth inhibition, is lower when the anti-LAG-3 antibody molecule is administered in combination with the second therapeutic agent than when the anti-LAG-3 antibody molecule is administered individually. In certain embodiments, in a combination therapy, the concentration of the second therapeutic agent that is required to achieve inhibition, e.g., growth inhibition, is lower than the therapeutic dose of the second therapeutic agent as a monotherapy, e.g., 10-20%, 20-30%, 30-40%, 40-50%, 50-60%, 60-70%, 70-80%, or 80-90% lower. In certain embodiments, in a combination therapy, the concentration of the anti-LAG-3 antibody molecule that is required to achieve inhibition, e.g., growth inhibition, is lower than the therapeutic dose of the anti-PD-1 antibody molecule as a monotherapy, e.g., 10-20%, 20-30%, 30-40%, 40-50%, 50-60%, 60-70%, 70-80%, or 80-90% lower.

Detection

In another aspect, the invention features methods for detecting the presence of LAG-3 in a sample, e.g., in vitro or in vivo (e.g., a biological sample, e.g., serum, semen or urine, or a tissue biopsy, e.g., from a hyperproliferative or cancerous lesion). The subject method can be used to evaluate (e.g., monitor treatment or progression of, diagnose and/or stage a disorder described herein, e.g., a hyperproliferative or cancerous disorder, in a subject). The method includes: (i) contacting the sample with (and optionally, a reference, e.g., a control sample), or administering to the subject, an anti-LAG-3 antibody molecule as described herein, under conditions that allow interaction to occur, and (ii) detecting formation of a complex between the antibody molecule, and the sample (and optionally, the reference, e.g., control, sample). Formation of the complex is indicative of the presence of LAG-3, and can indicate the suitability or need for a treatment described herein. The method can involve an immunohistochemistry, immunocytochemistry, flow cytometry (e.g., FACS), antibody molecule complexed magnetic beads, ELISA assays, PCR-techniques (e.g., RT-PCR).

Typically, the anti-LAG-3 antibody molecule used in the in vivo and in vitro diagnostic methods is directly or indirectly labeled with a detectable substance to facilitate detection of the bound or unbound binding agent. Suitable detectable substances include various biologically active enzymes, prosthetic groups, fluorescent materials, luminescent materials, paramagnetic (e.g., nuclear magnetic resonance active) materials, and radioactive materials.

Additional embodiments provide a method of treating a cancer, comprising: identifying in a sample (e.g., a subject's sample comprising cancer cells and optionally immune cells such as TILs) the presence of one, two or all of PD-L1, CD8, or IFN-γ, thereby providing a value for one, two or all of PD-L1, CD8, and IFN-γ. The method can further include comparing the PD-L1, CD8, and/or IFN-γ values to a reference value, e.g., a control value. If the PD-L1, CD8, and/or IFN-γ values are greater than the reference value, e.g., the control values, administering a therapeutically effective amount of an anti-LAG-3 antibody (e.g., an anti-LAG-3 antibody described herein), alone or incombination with an anti-PD-1 antibody molecule, an anti-PD-L1 antibody molecule, or both, to the subject, optionally in combination with one or more other agents, thereby treating the cancer. The cancer may be, e.g., a cancer described herein, such as lung cancer (squamous), lung cancer (adenocarcinoma), head and neck cancer, cervical cancer (squamous), stomach cancer, thyroid cancer, melanoma, nasopharyngeal cancer, or breast cancer, e.g., TN breast cancer, e.g., IM-TN breast cancer. In some embodiments, the cancer is ER+ breast cancer or pancreatic cancer.

Also provided is a method of treating a cancer, comprising: testing a sample (e.g., a subject's sample comprising cancer cells) for the presence of PD-L1, thereby identifying a PD-L1 value, comparing the PD-L1 value to a control value, and if the PD-L1 value is greater than the control value, administering a therapeutically effective amount of an anti-LAG-3 antibody (e.g., an anti-LAG-3 antibody described herein), alone or incombination with an anti-PD-1 antibody molecule, an anti-PD-L1 antibody molecule, or both, to the subject, optionally in combination with one or more other agents, thereby treating the cancer. The cancer may be, e.g., a cancer as described herein, such as cancer is non-small cell lung (NSCLC) adenocarcinoma (ACA), NSCLC squamous cell carcinoma (SCC), or hepatocellular carcinoma (HCC).

In another aspect, the invention features diagnostic or therapeutic kits that include the anti-LAG-3 antibody molecules described herein and instructions for use.

All publications, patent applications, patents, and other references mentioned herein are incorporated by reference in their entirety.

Other features, objects, and advantages of the invention will be apparent from the description and drawings, and from the claims.

BRIEF DESCRIPTION OF THE DRAWINGS

FIG. 1 depicts the amino acid sequences of the light (SEQ ID NO: 16) and heavy (SEQ ID NO: 6) chain variable regions of murine anti-LAG-3 mAb BAP050. The light and heavy chain CDR sequences based on Kabat numbering are underlined. The light and heavy chain CDR sequences based on Chothia numbering are shown in bold italics.

FIG. 2 depicts the amino acid sequences of the light (SEQ ID NO: 16) and heavy (SEQ ID NO: 6) chain variable regions of murine anti-LAG-3 mAb BAP050 aligned with the germline sequences (SEQ ID NOs: 290-291, respectively, in order of appearance). The upper and lower sequences are the germline (GL) and BAP050 (Mu mAb) sequences, respectively. The light and heavy chain CDR sequences based on Kabat numbering are underlined. The light and heavy chain CDR sequences based on Chothia numbering are shown in bold italics. "-" means identical amino acid residue.

FIG. 4 depicts the structural analysis of the humanized BAP049 clones (a, b, c, d, e, f, g represent various types of framework region sequences). The concentrations of the mAbs in the samples are also shown.

FIG. 6 depicts the ranking of humanized BAP050 clones based on FACS data, competition binding and structural analysis. The concentrations of the mAbs in the samples are also shown.

FIGS. 9A-9B depict the alignment of heavy chain variable domain sequences for the twenty humanized BAP050 clones and BAP050 chimera (BAP050-chi). In FIG. 9A, all of the sequences are shown (SEQ ID NOs: 20, 28, 28, 28, 28, 28, 28, 28, 28, 28, 28, 64, 64, 64, 64, 64, 68, 72, 72, 76 and 80, respectively, in order of appearance). In FIG. 9B, only amino acid sequences that are different from mouse sequence are shown (SEQ ID NOs: 20, 28, 28, 28, 28, 28, 28, 28, 28, 28, 28, 64, 64, 64, 64, 64, 68, 72, 72, 76 and 80, respectively, in order of appearance).

FIGS. 10A-10B depict the alignment of light chain variable domain sequences for the twenty humanized BAP050 clones and BAP050 chimera (BAP050-chi). In FIG. 10A, all of the sequences are shown (SEQ ID NOs: 24, 32, 36, 36, 36, 292, 292, 292, 44, 48, 52, 56, 56, 60, 60, 60, 60, 84, 88, 92 and 96, respectively, in order of appearance). In FIG. 10B, only amino acid sequences that are different from mouse sequence are shown (SEQ ID NOs: 24, 32, 36, 36, 36, 292, 292, 292, 44, 48, 52, 56, 56, 60, 60, 60, 60, 84, 88, 92 and 96, respectively, in order of appearance).

BRIEF DESCRIPTION OF THE TABLES

Figure 3:
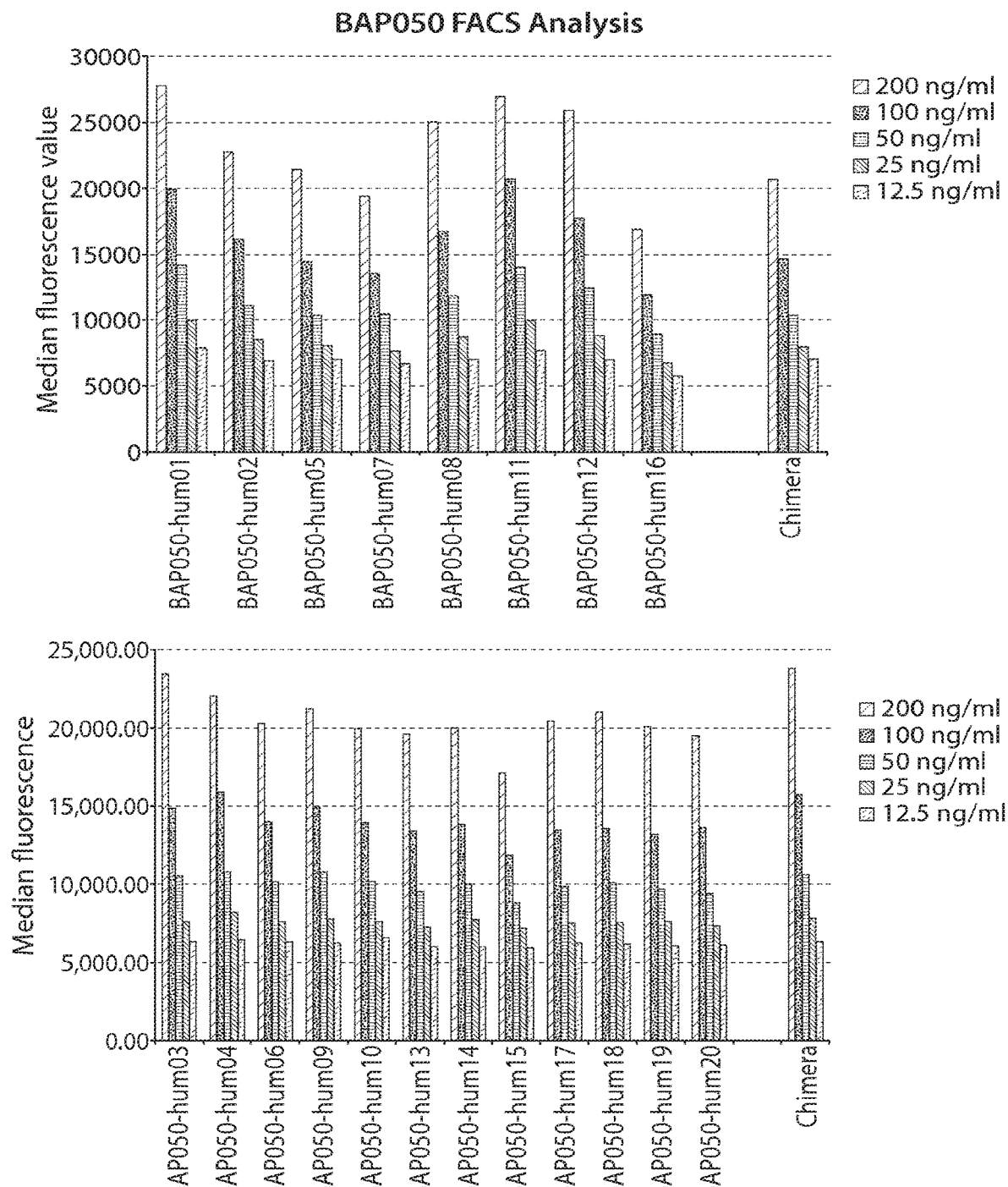
FIG. 3 depicts bar graphs showing the results of FACS binding analysis for the twenty humanized BAP050 clones (BAP050-hum01 to BAP050-hum20) and the chimeric mAb (BAP050-chi). The antibody concentrations are 200, 100, 50, 25 and 12.5 ng/ml from the leftmost bar to the rightmost bar for each tested mAb.

Table 1 is a summary of the amino acid and nucleotide sequences for the murine, chimeric and humanized anti-LAG-3 antibody molecules. The antibody molecules include murine mAb BAP050 and chimeric mAbs BAP050-chi, humanized mAbs BAP050-hum01 to BAP050-hum20, BAP050-hum01-Ser to BAP050-hum15-Ser, BAP050-hum18-Ser to BAP050-hum20-Ser, and BAP050-Clone-F to BAP050-Clone-J. The amino acid and nucleotide sequences of the heavy and light chain CDRs, the amino acid and nucleotide sequences of the heavy and light chain variable regions, and the amino acid and nucleotide sequences of the heavy and light chains are shown in this Table.

Table 2 depicts the amino acid and nucleotide sequences of the heavy and light chain framework regions for humanized mAbs BAP050-hum01 to BAP049-hum20, BAP050-hum01-Ser to BAP050-hum15-Ser, BAP050-hum18-Ser to BAP050-hum20-Ser, and BAP049-Clone-F to BAP049-Clone-J.

Table 3 depicts the constant region amino acid sequences of human IgG heavy chains and human kappa light chain.

Table 4 shows the amino acid sequences of the heavy and light chain leader sequences for humanized mAbs BAP050-Clone-F to BAP050-Clone-J.

Table 5 is a summary of yield, titre, monomer content and endotoxin levels for exemplary humanized BAP050 mAbs expressed in CHO cells.

Table 6 shows the charge isoforms as detected by NOVEX™ IEF analysis for exemplary humanized BAP050 mAbs expressed in CHO cells.

Table 7 is a summary of selected therapeutic agents that can be administered in combination with the anti-LAG-3 antibody molecules and other immunomodulators (e.g., one or more of: an activator of a costimulatory molecule and/or an inhibitor of an immune checkpoint molecule) described herein. Table 7 provides from left to right the following: the Compound Designation of the second therapeutic agent, the Compound structure, and Patent publication(s) disclosing the Compound.

DETAILED DESCRIPTION

The immune system has the capability of recognizing and eliminating tumor cells; however, tumors can use multiple strategies to evade immunity. Blockade of immune checkpoints is one of the approaches to activating or reactivating therapeutic antitumor immunity. Lymphocyte Activation Gene-3 (LAG-3) has been described as an inhibitory receptor in the immunological synapse (Chen and Flies (2013) *Nat Rev Immunol.* 13 (4): 227-42). Thus, blocking of LAG-3 can lead to enhancement of antitumor immunity.

Several cell types express LAG-3. For example, LAG-3 is expressed on activated CD4+ and CD8+ T cells, $T_{reg}$ cells, natural killer (NK) cells, and plasmacytoid dendritic cells (DCs). LAG-3 is expressed in tumor-infiltrating lymphocytes, e.g., infiltrating lymphocytes in head and neck squamous cell carcinoma (HNSCC). LAG-3 is expressed on highly suppressive induced and natural Tregs. For example, highly suppressive FoxP3+ nTregs and FoxP3-iTregs are LAG-3 positive in melanoma and colorectal cancer (Camisaschi et al. (2010) *J. Immunol.* 184 (11): 6545-6551; Scurr et al. (2014) *Mucosal. Immunol.* 7 (2): 428-439).

LAG-3 negatively regulates T cell signaling and functions. Ligands for LAG-3 includes, e.g., MHC Class II and L-SECtin. Anti-LSECtin has been shown to inhibit B16 melanoma cell growth (Xu et al. (2014) *Cancer Res.* 74 (13): 3418-3428). Blockade of LAG-3 can restore activities of effector cells, dimish suppressor activity of $T_{regs}$, and/or enhance anti-PD-1 antitumor activity.

LAG-3 is typically though not exclusively co-expressed on PD-1+ cells and single blockade can restore in vitro activities of the cells. The degree of CD8+ T cell exhaustion, e.g., as shown by the percentages of dual IFN-γ/TNF-α producers, correlates with the number of inhibitory receptors expressed (Blackburn et al. (2009) *Nat. Immunol.* 10 (1): 29-37). High PD-1/LAG-3 expression correlates with T cell infiltration in melanoma. Co-blockade of LAG-3 with anti-PD-1 or PD-L1 can result in tumor suppressive activities in preclinical models. For example, anti-LAG-3 and anti-PD-1 blockade show efficacy in Sa1N fibrosarcoma and MC38 colon carcinoma models (Woo et al. (2012) *Cancer Res.* 72 (4): 917-27). LAG-3 blockade is also efficacious in a lymphocytic choriomeningitis virus (LCMV) model. For example, PD-L1 plus LAG-3 blockade during chronic LCMV infection enhances antiviral CD8+ T cell responses (Blackburn et al. (2009) *Nat. Immunol.* 10 (1): 29-37).

Accordingly, the present invention provides, at least in part, antibody molecules (e.g., humanized antibody molecules) that bind to Lymphocyte Activation Gene-3 (LAG-3) with high affinity and specificity. In one embodiment, humanized antibodies against LAG-3 are disclosed, which show low immunogenicity. For example, humanized BAP050 antibodies were found to have a risk score of less than 1200, 1150, 1100, 1050, 1000, 950, 900, 850, or 800, according to the T cell epitope assays described herein. In other embodiments, selected combination of framework regions, e.g., as shown in FIGS. 4 and 6, were shown to have distinct production efficiencies and binding properties.

Additional aspects of the invention include nucleic acid molecules encoding the antibody molecules, expression vectors, host cells and methods for making the antibody molecules. Immunoconjugates, multi- or bispecific molecules and pharmaceutical compositions comprising the antibody molecules are also provided. The anti-LAG-3 antibody molecules disclosed herein can be used to treat, prevent and/or diagnose cancerous or malignant disorders (e.g., cancers such melanoma, e.g., advanced stage melanoma; pancreatic cancer, e.g., advanced pancreatic cancer; solid tumors; breast cancer, e.g., metastatic breast carcinoma; renal cell carcinoma, e.g., advanced or metastatic renal cell carcinoma (MRCC) or clear cell renal cell carcinoma), as well as infectious diseases (e.g., hepatitis, e.g., hepatitis B; influenza). Thus, methods for detecting LAG-3, as well as methods for treating various disorders, including cancer and infectious diseases using the anti-LAG-3 antibody molecules, alone or in combination, are disclosed herein.

The term "Lymphocyte Activation Gene-3" or "LAG-3" include all isoforms, mammalian, e.g., human LAG-3, species homologs of human LAG-3, and analogs comprising at least one common epitope with LAG-3. The amino acid and nucleotide sequences of LAG-3. e.g., human LAG-3, is known in the art, e.g., Triebel et al. (1990) *J. Exp. Med.* 171:1393-1405.

Additional terms are defined below and throughout the application.

As used herein, the articles "a" and "an" refer to one or to more than one (e.g., to at least one) of the grammatical object of the article.

The term "or" is used herein to mean, and is used interchangeably with, the term "and/or", unless context clearly indicates otherwise.

"About" and "approximately" shall generally mean an acceptable degree of error for the quantity measured given the nature or precision of the measurements. Exemplary degrees of error are within 20 percent (%), typically, within 10%, and more typically, within 5% of a given value or range of values.

The compositions and methods of the present invention encompass polypeptides and nucleic acids having the sequences specified, or sequences substantially identical or similar thereto, e.g., sequences at least 70%, 75%, 80%, 85%, 90%, 95% identical or higher to the sequence specified. In the context of an amino acid sequence, the term "substantially identical" is used herein to refer to a first amino acid that contains a sufficient or minimum number of amino acid residues that are i) identical to, or ii) conservative substitutions of aligned amino acid residues in a second amino acid sequence such that the first and second amino acid sequences can have a common structural domain and/or common functional activity. For example, amino acid sequences that contain a common structural domain having at least about 85%, 90%, 91%, 92%, 93%, 94%, 95%, 96%, 97%, 98% or 99% identity to a reference sequence, e.g., a sequence provided herein.

In the context of nucleotide sequence, the term "substantially identical" is used herein to refer to a first nucleic acid sequence that contains a sufficient or minimum number of nucleotides that are identical to aligned nucleotides in a second nucleic acid sequence such that the first and second nucleotide sequences encode a polypeptide having common functional activity, or encode a common structural polypeptide domain or a common functional polypeptide activity. For example, nucleotide sequences having at least about 85%, 90%, 91%, 92%, 93%, 94%, 95%, 96%, 97%, 98% or 99% identity to a reference sequence, e.g., a sequence provided herein.

The term "functional variant" refers to polypeptides that have a substantially identical amino acid sequence to the naturally-occurring sequence, or are encoded by a substantially identical nucleotide sequence, and are capable of having one or more activities of the naturally-occurring sequence.

Calculations of homology or sequence identity between sequences (the terms are used interchangeably herein) are performed as follows.

To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, the length of a reference sequence aligned for comparison purposes is at least 30%, preferably at least 40%, more preferably at least 50%, 60%, and even more preferably at least 70%, 80%, 90%, 100% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology").

The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In a preferred embodiment, the percent identity between two amino acid sequences is determined using the Needleman and Wunsch ((1970) *J. Mol. Biol.* 48:444-453) algorithm which has been incorporated into the GAP program in the GCG software package (available at gcg.com), using either a Blossum 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (available at gcg.com), using a NWSgapdna.CMP matrix and a gap weight of 40, 50, 60, 70, or 80 and a length weight of 1, 2, 3, 4, 5, or 6. A particularly preferred set of parameters (and the one that should be used unless otherwise specified) are a Blossum 62 scoring matrix with a gap penalty of 12, a gap extend penalty of 4, and a frameshift gap penalty of 5.

The percent identity between two amino acid or nucleotide sequences can be determined using the algorithm of E. Meyers and W. Miller ((1989) CABIOS, 4:11-17) which has been incorporated into the ALIGN program (version 2.0), using a PAM120 weight residue table, a gap length penalty of 12 and a gap penalty of 4.

The nucleic acid and protein sequences described herein can be used as a "query sequence" to perform a search against public databases to, for example, identify other family members or related sequences. Such searches can be performed using the NBLAST and XBLAST programs (version 2.0) of Altschul, et al. (1990) *J. Mol. Biol.* 215: 403-10. BLAST nucleotide searches can be performed with the NBLAST program, score=100, wordlength=12 to obtain nucleotide sequences homologous to a nucleic acid (SEQ ID NO: 1) molecules of the invention. BLAST protein searches can be performed with the XBLAST program, score=50, wordlength=3 to obtain amino acid sequences homologous to protein molecules of the invention. To obtain gapped alignments for comparison purposes, Gapped BLAST can be utilized as described in Altschul et al., (1997) *Nucleic Acids Res.* 25:3389-3402. When utilizing BLAST and Gapped BLAST programs, the default parameters of the respective programs (e.g., XBLAST and NBLAST) can be used. See ncbi.nlm.nih.gov.

As used herein, the term "hybridizes under low stringency, medium stringency, high stringency, or very high stringency conditions" describes conditions for hybridization and washing. Guidance for performing hybridization reactions can be found in *Current Protocols in Molecular Biology*, John Wiley & Sons, N.Y. (1989), 6.3.1-6.3.6, which is incorporated by reference. Aqueous and nonaqueous methods are described in that reference and either can be used. Specific hybridization conditions referred to herein are as follows: 1) low stringency hybridization conditions in 6× sodium chloride/sodium citrate (SSC) at about 45° C., followed by two washes in 0.2×SSC. 0.1% SDS at least at 50° C. (the temperature of the washes can be increased to 55° C. for low stringency conditions); 2) medium stringency hybridization conditions in 6×SSC at about 45° C., followed by one or more washes in 0.2×SSC, 0.1% SDS at 60° C.; 3) high stringency hybridization conditions in 6×SSC at about 45° C., followed by one or more washes in 0.2×SSC. 0.1% SDS at 65° C.; and preferably 4) very high stringency hybridization conditions are 0.5M sodium phosphate, 7% SDS at 65° C., followed by one or more washes at 0.2×SSC. 1% SDS at 65° C. Very high stringency conditions (4) are the preferred conditions and the ones that should be used unless otherwise specified.

It is understood that the molecules of the present invention may have additional conservative or non-essential amino acid substitutions, which do not have a substantial effect on their functions.

The term "amino acid" is intended to embrace all molecules, whether natural or synthetic, which include both an amino functionality and an acid functionality and capable of being included in a polymer of naturally-occurring amino acids. Exemplary amino acids include naturally-occurring amino acids; analogs, derivatives and congeners thereof; amino acid analogs having variant side chains; and all stereoisomers of any of any of the foregoing. As used herein the term "amino acid" includes both the D- or L-optical isomers and peptidomimetics.

A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

The terms "polypeptide", "peptide" and "protein" (if single chain) are used interchangeably herein to refer to polymers of amino acids of any length. The polymer may be linear or branched, it may comprise modified amino acids, and it may be interrupted by non-amino acids. The terms also encompass an amino acid polymer that has been modified; for example, disulfide bond formation, glycosylation, lipidation, acetylation, phosphorylation, or any other manipulation, such as conjugation with a labeling component. The polypeptide can be isolated from natural sources, can be a produced by recombinant techniques from a eukaryotic or prokaryotic host, or can be a product of synthetic procedures.

The terms "nucleic acid." "nucleic acid sequence," "nucleotide sequence," or "polynucleotide sequence," and "polynucleotide" are used interchangeably. They refer to a polymeric form of nucleotides of any length, either deoxyribonucleotides or ribonucleotides, or analogs thereof. The polynucleotide may be either single-stranded or double-stranded, and if single-stranded may be the coding strand or non-coding (antisense) strand. A polynucleotide may comprise modified nucleotides, such as methylated nucleotides and nucleotide analogs. The sequence of nucleotides may be interrupted by non-nucleotide components. A polynucleotide may be further modified after polymerization, such as by conjugation with a labeling component. The nucleic acid may be a recombinant polynucleotide, or a polynucleotide of genomic, cDNA, semisynthetic, or synthetic origin which either does not occur in nature or is linked to another polynucleotide in a nonnatural arrangement.

The term "isolated," as used herein, refers to material that is removed from its original or native environment (e.g., the natural environment if it is naturally occurring). For example, a naturally-occurring polynucleotide or polypeptide present in a living animal is not isolated, but the same polynucleotide or polypeptide, separated by human intervention from some or all of the co-existing materials in the natural system, is isolated. Such polynucleotides could be part of a vector and/or such polynucleotides or polypeptides could be part of a composition, and still be isolated in that such vector or composition is not part of the environment in which it is found in nature.

Various aspects of the invention are described in further detail below. Additional definitions are set out throughout the specification.

Antibody Molecules

In one embodiment, the antibody molecule binds to a mammalian, e.g., human, LAG-3. For example, the antibody molecule binds specifically to an epitope, e.g., linear or conformational epitope, (e.g., an epitope as described herein) on LAG-3. In some embodiments, the antibody molecule binds to one or more extracellular Ig-like domains of LAG-3, e.g., the first, second, third or fourth extracellular Ig-like domain of LAG-3.

As used herein, the term "antibody molecule" refers to a protein, e.g., an immunoglobin chain or fragment thereof, comprising at least one immunoglobulin variable domain sequence. The term "antibody molecule" includes, for example, a monoclonal antibody (including a full length antibody which has an immunoglobulin Fc region). In an embodiment, an antibody molecule comprises a full length antibody, or a full length immunoglobin chain. In an embodiment, an antibody molecule comprises an antigen binding or functional fragment of a full length antibody, or a full length immunoglobulin chain.

In an embodiment, an antibody molecule is a monospecific antibody molecule and binds a single epitope. E.g., a monospecific antibody molecule having a plurality of immunoglobulin variable domain sequences, each of which binds the same epitope.

In an embodiment an antibody molecule is a multispecific antibody molecule, e.g., it comprises a plurality of immunoglobulin variable domains sequences, wherein a first immunoglobulin variable domain sequence of the plurality has binding specificity for a first epitope and a second immunoglobulin variable domain sequence of the plurality has binding specificity for a second epitope. In an embodiment the first and second epitopes are on the same antigen, e.g., the same protein (or subunit of a multimeric protein). In an embodiment the first and second epitopes overlap. In an embodiment the first and second epitopes do not overlap. In an embodiment the first and second epitopes are on different antigens, e.g., the different proteins (or different subunits of a multimeric protein). In an embodiment a multispecific antibody molecule comprises a third, fourth or fifth immunoglobulin variable domain. In an embodiment, a multispecific antibody molecule is a bispecific antibody molecule, a trispecific antibody molecule, or tetraspecific antibody molecule, In an embodiment a multispecific antibody molecule is a bispecific antibody molecule. A bispecific antibody has specificity for no more than two antigens. A bispecific antibody molecule is characterized by a first immunoglobulin variable domain sequence which has binding specificity for a first epitope and a second immunoglobulin variable domain sequence that has binding specificity for a second epitope. In an embodiment the first and second epitopes are on the same antigen, e.g., the same protein (or subunit of a multimeric protein). In an embodiment the first and second epitopes overlap. In an embodiment the first and second epitopes do not overlap. In an embodiment the first and second epitopes are on different antigens, e.g., the different proteins (or different subunits of a multimeric protein). In an embodiment a bispecific antibody molecule comprises a heavy chain variable domain sequence and a light chain variable domain sequence which have binding specificity for a first epitope and a heavy chain variable domain sequence and a light chain variable domain sequence which have binding specificity for a second epitope. In an embodiment a bispecific antibody molecule comprises a half antibody having binding specificity for a first epitope and a half antibody having binding specificity for a second epitope. In an embodiment a bispecific antibody molecule comprises a half antibody, or fragment thereof, having binding specificity for a first epitope and a half antibody, or fragment thereof, having binding specificity for a second epitope. In an embodiment a bispecific antibody molecule comprises a scFv, or fragment thereof, have binding specificity for a first epitope and a scFv, or fragment thereof, have binding specificity for a second epitope. In an embodiment, the first epitope is located on LAG-3 and the second epitope is located on a PD-1, TIM-3, CEACAM (e.g., CEACAM-1 and/or CEACAM-5), PD-L1, or PD-L2.

In an embodiment, an antibody molecule comprises a diabody, and a single-chain molecule, as well as an antigen-binding fragment of an antibody (e.g., Fab, F(ab')$_2$, and Fv). For example, an antibody molecule can include a heavy (H) chain variable domain sequence (abbreviated herein as VH), and a light (L) chain variable domain sequence (abbreviated herein as VL). In an embodiment an antibody molecule comprises or consists of a heavy chain and a light chain (referred to herein as a half antibody. In another example, an antibody molecule includes two heavy (H) chain variable domain sequences and two light (L) chain variable domain sequence, thereby forming two antigen binding sites, such as Fab, Fab', F(ab')$_2$, Fc, Fd, Fd', Fv, single chain antibodies (scFv for example), single variable domain antibodies, diabodies (Dab) (bivalent and bispecific), and chimeric (e.g., humanized) antibodies, which may be produced by the modification of whole antibodies or those synthesized de novo using recombinant DNA technologies. These functional antibody fragments retain the ability to selectively bind with their respective antigen or receptor. Antibodies and antibody fragments can be from any class of antibodies including, but not limited to, IgG, IgA, IgM, IgD, and IgE, and from any subclass (e.g., IgG1, IgG2, IgG3, and IgG4) of antibodies. The a preparation of antibody molecules can be monoclonal or polyclonal. An antibody molecule can also be a human, humanized, CDR-grafted, or in vitro generated antibody. The antibody can have a heavy chain constant region chosen from, e.g., IgG1, IgG2, IgG3, or IgG4. The antibody can also have a light chain chosen from, e.g., kappa or lambda. The term "immunoglobulin" (Ig) is used interchangeably with the term "antibody" herein.

Examples of antigen-binding fragments of an antibody molecule include: (i) a Fab fragment, a monovalent fragment consisting of the VL, VH, CL and CH1 domains; (ii) a F(ab')$_2$ fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a diabody (dAb) fragment, which consists of a VH domain; (vi) a camelid or camelized variable domain; (vii) a single chain Fv (scFv), see e.g., Bird et al. (1988) *Science* 242:423-426; and Huston et al. (1988) *Proc. Natl. Acad. Sci. USA* 85:5879-5883); (viii) a single domain antibody. These antibody fragments are obtained using conventional techniques known to those with skill in the art, and the fragments are screened for utility in the same manner as are intact antibodies.

The term "antibody" includes intact molecules as well as functional fragments thereof. Constant regions of the antibodies can be altered, e.g., mutated, to modify the properties of the antibody (e.g., to increase or decrease one or more of: Fc receptor binding, antibody glycosylation, the number of cysteine residues, effector cell function, or complement function).

Antibodies of the present invention can also be single domain antibodies. Single domain antibodies can include antibodies whose complementary determining regions are part of a single domain polypeptide. Examples include, but are not limited to, heavy chain antibodies, antibodies naturally devoid of light chains, single domain antibodies derived from conventional 4-chain antibodies, engineered antibodies and single domain scaffolds other than those derived from antibodies. Single domain antibodies may be any of the art, or any future single domain antibodies. Single domain antibodies may be derived from any species including, but not limited to mouse, human, camel, llama, fish, shark, goat, rabbit, and bovine. According to another aspect of the invention, a single domain antibody is a naturally occurring single domain antibody known as heavy chain antibody devoid of light chains. Such single domain antibodies are disclosed in WO 94/04678, for example. For clarity reasons, this variable domain derived from a heavy chain antibody naturally devoid of light chain is known herein as a VHH or nanobody to distinguish it from the conventional VH of four chain immunoglobulins. Such a VHH molecule can be derived from antibodies raised in Camelidae species, for example in camel, llama, dromedary, alpaca and guanaco. Other species besides Camelidae may produce heavy chain antibodies naturally devoid of light chain; such VHHs are within the scope of the invention.

The VH and VL regions can be subdivided into regions of hypervariability, termed "complementarity determining regions" (CDR), interspersed with regions that are more conserved, termed "framework regions" (FR or FW). The extent of the framework region and CDRs has been precisely defined by a number of methods (see, Kabat, E. A., et al. (1991) Sequences of Proteins of Immunological Interest, Fifth Edition, U.S. Department of Health and Human Services, NIH Publication No. 91-3242; Chothia, C. et al. (1987) *J. Mol. Biol.* 196:901-917; and the AbM definition used by Oxford Molecular's AbM antibody modeling software. See, generally, e.g., *Protein Sequence and Structure Analysis of Antibody Variable Domains.* In: Antibody Engineering Lab Manual (Ed.: Duebel, S. and Kontermann, R., Springer-Verlag, Heidelberg).

The terms "complementarity determining region." and "CDR." as used herein refer to the sequences of amino acids within antibody variable regions which confer antigen specificity and binding affinity. In general, there are three CDRs in each heavy chain variable region (HCDR1, HCDR2, HCDR3) and three CDRs in each light chain variable region (LCDR1, LCDR2, LCDR3).

The precise amino acid sequence boundaries of a given CDR can be determined using any of a number of well-known schemes, including those described by Kabat et al. (1991), "Sequences of Proteins of Immunological Interest," 5th Ed. Public Health Service, National Institutes of Health, Bethesda, MD ("Kabat" numbering scheme), Al-Lazikani et al., (1997) JMB 273,927-948 ("Chothia" numbering scheme). As used herein, the CDRs defined according the "Chothia" number scheme are also sometimes referred to as "hypervariable loops."

For example, under Kabat, the CDR amino acid residues in the heavy chain variable domain (VH) are numbered 31-35 (HCDR1), 50-65 (HCDR2), and 95-102 (HCDR3); and the CDR amino acid residues in the light chain variable domain (VL) are numbered 24-34 (LCDR1), 50-56 (LCDR2), and 89-97 (LCDR3). Under Chothia the CDR amino acids in the VH are numbered 26-32 (HCDR1), 52-56 (HCDR2), and 95-102 (HCDR3); and the amino acid residues in VL are numbered 26-32 (LCDR1), 50-52 (LCDR2), and 91-96 (LCDR3). By combining the CDR definitions of both Kabat and Chothia, the CDRs consist of amino acid residues 26-35 (HCDR1), 50-65 (HCDR2), and 95-102 (HCDR3) in human VH and amino acid residues 24-34 (LCDR1), 50-56 (LCDR2), and 89-97 (LCDR3) in human VL.

Generally, unless specifically indicated, the anti-LAG-3 antibody molecules can include any combination of one or more Kabat CDRs and/or Chothia hypervariable loops, e.g., described in Table 1. In one embodiment, the following definitions are used for the anti-LAG-3 antibody molecules described in Table 1: HCDR1 according to the combined CDR definitions of both Kabat and Chothia, and HCCDRs 2-3 and LCCDRs 1-3 according the CDR definition of Kabat. Under all definitions, each VH and VL typically includes three CDRs and four FRs, arranged from amino-terminus to carboxy-terminus in the following order: FR1, CDR1, FR2, CDR2, FR3, CDR3, FR4.

As used herein, an "immunoglobulin variable domain sequence" refers to an amino acid sequence which can form the structure of an immunoglobulin variable domain. For example, the sequence may include all or part of the amino acid sequence of a naturally-occurring variable domain. For example, the sequence may or may not include one, two, or more N- or C-terminal amino acids, or may include other alterations that are compatible with formation of the protein structure.

The term "antigen-binding site" refers to the part of an antibody molecule that comprises determinants that form an interface that binds to the LAG-3 polypeptide, or an epitope thereof. With respect to proteins (or protein mimetics), the antigen-binding site typically includes one or more loops (of at least four amino acids or amino acid mimics) that form an interface that binds to the LAG-3 polypeptide. Typically, the antigen-binding site of an antibody molecule includes at least one or two CDRs and/or hypervariable loops, or more typically at least three, four, five or six CDRs and/or hypervariable loops.

The terms "compete" or "cross-compete" are used interchangeably herein to refer to the ability of an antibody molecule to interfere with binding of an anti-LAG-3 antibody molecule, e.g., an anti-LAG-3 antibody molecule provided herein, to a target, e.g., human LAG-3. The interference with binding can be direct or indirect (e.g., through an allosteric modulation of the antibody molecule or the target). The extent to which an antibody molecule is able to interfere with the binding of another antibody molecule to the target, and therefore whether it can be said to compete, can be determined using a competition binding assay, for example, a FACS assay, an ELISA or BIACORE™ assay. In some embodiments, a competition binding assay is a quantitative competition assay. In some embodiments, a first anti-LAG-3 antibody molecule is said to compete for binding to the target with a second anti-LAG-3 antibody molecule when the binding of the first antibody molecule to the target is reduced by 10% or more, e.g., 20% or more, 30% or more, 40% or more, 50% or more, 55% or more, 60% or more, 65% or more, 70% or more, 75% or more, 80% or more, 85% or more, 90% or more, 95% or more, 98% or more, 99% or more in a competition binding assay (e.g., a competition assay described herein).

As used herein, the term "epitope" refers to the moieties of an antigen (e.g., human LAG-3) that specifically interact with an antibody molecule. Such moieties, referred to herein as epitopic determinants, typically comprise, or are part of, elements such as amino acid side chains or sugar side chains. An epitopic determinate can be defined by methods known in the art or disclosed herein, e.g., by crystallography or by hydrogen-deuterium exchange. At least one or some of the moieties on the antibody molecule, that specifically interact with an epitopic determinant, are typically located in a CDR(s). Typically an epitope has a specific three dimensional structural characteristics. Typically an epitope has specific charge characteristics. Some epitopes are linear epitopes while others are conformational epitopes.

The terms "monoclonal antibody" or "monoclonal antibody composition" as used herein refer to a preparation of antibody molecules of single molecular composition. A monoclonal antibody composition displays a single binding specificity and affinity for a particular epitopic. A monoclonal antibody can be made by hybridoma technology or by methods that do not use hybridoma technology (e.g., recombinant methods).

An "effectively human" protein is a protein that does not evoke a neutralizing antibody response, e.g., the human anti-murine antibody (HAMA) response. HAMA can be problematic in a number of circumstances, e.g., if the antibody molecule is administered repeatedly, e.g., in treatment of a chronic or recurrent disease condition. A HAMA response can make repeated antibody administration potentially ineffective because of an increased antibody clearance from the serum (see, e.g., Salch et al., *Cancer Immunol. Immunother.*, 32:180-190 (1990)) and also because of potential allergic reactions (see, e.g., LoBuglio et al., *Hybridoma*, 5:5117-5123 (1986)).

The antibody molecule can be a polyclonal or a monoclonal antibody. In other embodiments, the antibody can be recombinantly produced, e.g., produced by phage display or by combinatorial methods.

Phage display and combinatorial methods for generating antibodies are known in the art (as described in, e.g., Ladner et al. U.S. Pat. No. 5,223,409; Kang et al. International Publication No. WO 92/18619; Dower et al. International Publication No. WO 91/17271; Winter et al. International Publication WO 92/20791; Markland et al. International Publication No. WO 92/15679; Breitling et al. International Publication WO 93/01288; McCafferty et al. International Publication No. WO 92/01047; Garrard et al. International Publication No. WO 92/09690; Ladner et al. International Publication No. WO 90/02809; Fuchs et al. (1991) *Bio/Technology* 9:1370-1372; Hay et al. (1992) *Hum Antibod Hybridomas* 3:81-85; Huse et al. (1989) *Science* 246:1275-1281; Griffths et al. (1993) *EMBO J* 12:725-734; Hawkins et al. (1992) *J Mol Biol* 226:889-896; Clackson et al. (1991) *Nature* 352:624-628; Gram et al. (1992) *PNAS* 89:3576-3580; Garrad et al. (1991) *Bio/Technology* 9:1373-1377; Hoogenboom et al. (1991) *Nuc Acid Res* 19:4133-4137; and Barbas et al. (1991) *PNAS* 88:7978-7982, the contents of all of which are incorporated by reference herein).

In one embodiment, the antibody is a fully human antibody (e.g., an antibody made in a mouse which has been genetically engineered to produce an antibody from a human immunoglobulin sequence), or a non-human antibody, e.g., a rodent (mouse or rat), goat, primate (e.g., monkey), camel antibody. Preferably, the non-human antibody is a rodent (mouse or rat antibody). Methods of producing rodent antibodies are known in the art.

Human monoclonal antibodies can be generated using transgenic mice carrying the human immunoglobulin genes rather than the mouse system. Splenocytes from these transgenic mice immunized with the antigen of interest are used to produce hybridomas that secrete human mAbs with specific affinities for epitopes from a human protein (see, e.g., Wood et al. International Application WO 91/00906, Kucherlapati et al. PCT publication WO 91/10741; Lonberg et al. International Application WO 92/03918; Kay et al. International Application 92/03917; Lonberg, N. et al. 1994 *Nature* 368:856-859; Green, L. L. et al. 1994 *Nature Genet.* 7:13-21; Morrison, S. L. et al. 1994 *Proc. Natl. Acad. Sci. USA* 81:6851-6855; Bruggeman et al. 1993 Year *Immunol* 7:33-40; Tuaillon et al. 1993 *PNAS* 90:3720-3724; Bruggeman et al. 1991 *Eur J Immunol* 21:1323-1326).

An antibody can be one in which the variable region, or a portion thereof, e.g., the CDRs, are generated in a non-human organism, e.g., a rat or mouse. Chimeric, CDR-grafted, and humanized antibodies are within the invention. Antibodies generated in a non-human organism, e.g., a rat or mouse, and then modified, e.g., in the variable framework or constant region, to decrease antigenicity in a human are within the invention.

Chimeric antibodies can be produced by recombinant DNA techniques known in the art (see Robinson et al., International Patent Publication PCT/US86/02269; Akira, et al., European Patent Application 184,187; Taniguchi, M., European Patent Application 171,496; Morrison et al., European Patent Application 173,494; Neuberger et al., International Application WO 86/01533; Cabilly et al. U.S. Pat. No. 4,816,567; Cabilly et al., European Patent Application 125,023; Better et al. (1988 *Science* 240:1041-1043); Liu et al. (1987) *PNAS* 84:3439-3443; Liu et al., 1987, *J. Immunol.* 139:3521-3526; Sun et al. (1987) *PNAS* 84:214-218; Nishimura et al., 1987, *Canc. Res.* 47:999-1005; Wood et al. (1985) *Nature* 314:446-449; and Shaw et al., 1988, *J. Natl Cancer Inst.* 80:1553-1559).

A humanized or CDR-grafted antibody will have at least one or two but generally all three recipient CDRs (of heavy and or light immuoglobulin chains) replaced with a donor CDR. The antibody may be replaced with at least a portion of a non-human CDR or only some of the CDRs may be replaced with non-human CDRs. It is only necessary to replace the number of CDRs required for binding of the humanized antibody to LAG-3. Preferably, the donor will be a rodent antibody, e.g., a rat or mouse antibody, and the recipient will be a human framework or a human consensus framework. Typically, the immunoglobulin providing the CDRs is called the "donor" and the immunoglobulin providing the framework is called the "acceptor." In one embodiment, the donor immunoglobulin is a non-human (e.g., rodent). The acceptor framework is a naturally-occurring (e.g., a human) framework or a consensus framework, or a sequence about 85% or higher, preferably 90%, 95%, 99% or higher identical thereto.

As used herein, the term "consensus sequence" refers to the sequence formed from the most frequently occurring amino acids (or nucleotides) in a family of related sequences (See e.g., Winnaker, From Genes to Clones (Verlagsgesellschaft, Weinheim, Germany 1987). In a family of proteins, each position in the consensus sequence is occupied by the amino acid occurring most frequently at that position in the family. If two amino acids occur equally frequently, either can be included in the consensus sequence. A "consensus framework" refers to the framework region in the consensus immunoglobulin sequence.

An antibody can be humanized by methods known in the art (see e.g., Morrison, S. L., 1985, *Science* 229:1202-1207, by Oi et al., 1986, *BioTechniques* 4:214, and by Queen et al. U.S. Pat. Nos. 5,585,089, 5,693,761 and 5,693,762, the contents of all of which are hereby incorporated by reference).

Humanized or CDR-grafted antibodies can be produced by CDR-grafting or CDR substitution, wherein one, two, or all CDRs of an immunoglobulin chain can be replaced. See e.g., U.S. Pat. No. 5,225,539; Jones et al. 1986 *Nature* 321:552-525; Verhocyan et al. 1988 *Science* 239:1534; Beidler et al. 1988 *J. Immunol.* 141:4053-4060; Winter U.S. Pat. No. 5,225,539, the contents of all of which are hereby expressly incorporated by reference. Winter describes a CDR-grafting method which may be used to prepare the humanized antibodies of the present invention (UK Patent Application GB 2188638A, filed on Mar. 26, 1987; Winter U.S. Pat. No. 5,225,539), the contents of which is expressly incorporated by reference.

Also within the scope of the invention are humanized antibodies in which specific amino acids have been substituted, deleted or added. Criteria for selecting amino acids from the donor are described in U.S. Pat. No. 5,585,089, e.g., columns 12-16 of U.S. Pat. No. 5,585,089, the e.g., columns 12-16 of U.S. Pat. No. 5,585,089, the contents of which are hereby incorporated by reference. Other techniques for humanizing antibodies are described in Padlan et al. EP 519596 A1, published on Dec. 23, 1992.

The antibody molecule can be a single chain antibody. A single-chain antibody (scFV) may be engineered (see, for example, Colcher, D. et al. (1999) *Ann N Y Acad Sci* 880:263-80; and Reiter, Y. (1996) *Clin Cancer Res* 2:245-

52). The single chain antibody can be dimerized or multimerized to generate multivalent antibodies having specificities for different epitopes of the same target protein.

In yet other embodiments, the antibody molecule has a heavy chain constant region chosen from, e.g., the heavy chain constant regions of IgG1, IgG2, IgG3, IgG4, IgM, IgA1, IgA2, IgD, and IgE; particularly, chosen from, e.g., the (e.g., human) heavy chain constant regions of IgG1, IgG2, IgG3, and IgG4. In another embodiment, the antibody molecule has a light chain constant region chosen from, e.g., the (e.g., human) light chain constant regions of kappa or lambda. The constant region can be altered, e.g., mutated, to modify the properties of the antibody (e.g., to increase or decrease one or more of: Fc receptor binding, antibody glycosylation, the number of cysteine residues, effector cell function, and/or complement function). In one embodiment the antibody has: effector function; and can fix complement. In other embodiments the antibody does not; recruit effector cells; or fix complement. In another embodiment, the antibody has reduced or no ability to bind an Fc receptor. For example, it is an isotype or subtype, fragment or other mutant, which does not support binding to an Fc receptor, e.g., it has a mutagenized or deleted Fc receptor binding region.

Methods for altering an antibody constant region are known in the art. Antibodies with altered function, e.g., altered affinity for an effector ligand, such as FcR on a cell, or the C1 component of complement can be produced by replacing at least one amino acid residue in the constant portion of the antibody with a different residue (see e.g., EP 388,151 A1, U.S. Pat. Nos. 5,624,821 and 5,648,260, the contents of all of which are hereby incorporated by reference). Similar type of alterations could be described which if applied to the murine, or other species immunoglobulin would reduce or eliminate these functions.

An antibody molecule can be derivatized or linked to another functional molecule (e.g., another peptide or protein). As used herein, a "derivatized" antibody molecule is one that has been modified. Methods of derivatization include but are not limited to the addition of a fluorescent moiety, a radionucleotide, a toxin, an enzyme or an affinity ligand such as biotin. Accordingly, the antibody molecules of the invention are intended to include derivatized and otherwise modified forms of the antibodies described herein, including immunoadhesion molecules. For example, an antibody molecule can be functionally linked (by chemical coupling, genetic fusion, noncovalent association or otherwise) to one or more other molecular entities, such as another antibody (e.g., a bispecific antibody or a diabody), a detectable agent, a cytotoxic agent, a pharmaceutical agent, and/or a protein or peptide that can mediate association of the antibody or antibody portion with another molecule (such as a streptavidin core region or a polyhistidine tag).

One type of derivatized antibody molecule is produced by crosslinking two or more antibodies (of the same type or of different types, e.g., to create bispecific antibodies). Suitable crosslinkers include those that are heterobifunctional, having two distinctly reactive groups separated by an appropriate spacer (e.g., m-maleimidobenzoyl-N-hydroxysuccinimide ester) or homobifunctional (e.g., disuccinimidyl suberate). Such linkers are available from Pierce Chemical Company, Rockford, Ill.

Useful detectable agents with which an antibody molecule of the invention may be derivatized (or labeled) to include fluorescent compounds, various enzymes, prosthetic groups, luminescent materials, bioluminescent materials, fluorescent emitting metal atoms, e.g., europium (Eu), and other anthanides, and radioactive materials (described below). Exemplary fluorescent detectable agents include fluorescein, fluorescein isothiocyanate, rhodamine, 5dimethylamine-1-napthalenesulfonyl chloride, phycoerythrin and the like. An antibody may also be derivatized with detectable enzymes, such as alkaline phosphatase, horseradish peroxidase, β-galactosidase, acetylcholinesterase, glucose oxidase and the like. When an antibody is derivatized with a detectable enzyme, it is detected by adding additional reagents that the enzyme uses to produce a detectable reaction product. For example, when the detectable agent horseradish peroxidase is present, the addition of hydrogen peroxide and diaminobenzidine leads to a colored reaction product, which is detectable. An antibody molecule may also be derivatized with a prosthetic group (e.g., streptavidin/biotin and avidin/biotin). For example, an antibody may be derivatized with biotin, and detected through indirect measurement of avidin or streptavidin binding. Examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; and examples of bioluminescent materials include luciferase, luciferin, and acquorin.

Labeled antibody molecule can be used, for example, diagnostically and/or experimentally in a number of contexts, including (i) to isolate a predetermined antigen by standard techniques, such as affinity chromatography or immunoprecipitation; (ii) to detect a predetermined antigen (e.g., in a cellular lysate or cell supernatant) in order to evaluate the abundance and pattern of expression of the protein; (iii) to monitor protein levels in tissue as part of a clinical testing procedure, e.g., to determine the efficacy of a given treatment regimen.

An antibody molecules may be conjugated to another molecular entity, typically a label or a therapeutic (e.g., a cytotoxic or cytostatic) agent or moiety. Radioactive isotopes can be used in diagnostic or therapeutic applications. Radioactive isotopes that can be coupled to the anti-PSMA antibodies include, but are not limited to α-, β-, or γ-emitters, or β- and γ-emitters. Such radioactive isotopes include, but are not limited to iodine ($^{131}$I or $^{125}$I), yttrium ($^{90}$Y), lutetium ($^{177}$Lu), actinium ($^{225}$Ac), prascodymium, astatine ($^{211}$At), rhenium ($^{186}$Re), bismuth ($^{212}$Bi or $^{213}$Bi), indium ($^{111}$In), technetium ($^{99}$mTc), phosphorus ($^{32}$P), rhodium ($^{188}$Rh), sulfur ($^{35}$S), carbon ($^{14}$C), tritium ($^{3}$H), chromium ($^{51}$Cr), chlorine ($^{36}$Cl), cobalt ($^{57}$Co or $^{58}$Co), iron ($^{59}$Fe), selenium ($^{15}$Sc), or gallium ($^{67}$Ga). Radioisotopes useful as therapeutic agents include yttrium ($^{90}$Y), lutetium ($^{177}$Lu), actinium ($^{225}$Ac), prascodymium, astatine ($^{211}$At), rhenium ($^{186}$Re), bismuth ($^{212}$Bi or $^{213}$Bi), and rhodium ($^{188}$Rh). Radioisotopes useful as labels, e.g., for use in diagnostics, include iodine ($^{131}$I or $^{125}$I), indium ($^{111}$In), technetium ($^{99}$mTc), phosphorus ($^{32}$P), carbon ($^{14}$C), and tritium ($^{3}$H), or one or more of the therapeutic isotopes listed above.

The invention provides radiolabeled antibody molecules and methods of labeling the same. In one embodiment, a method of labeling an antibody molecule is disclosed. The method includes contacting an antibody molecule, with a chelating agent, to thereby produce a conjugated antibody. The conjugated antibody is radiolabeled with a radioisotope, e.g., $^{111}$Indium, $^{90}$Yttrium and $^{177}$Lutetium, to thereby produce a labeled antibody molecule.

As is discussed above, the antibody molecule can be conjugated to a therapeutic agent. Therapeutically active radioisotopes have already been mentioned. Examples of other therapeutic agents include taxol, cytochalasin B, gramicidin D, ethidium bromide, emetine, mitomycin, etoposide, tenoposide, vincristine, vinblastine, colchicine, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, puromycin, maytansinoids, e.g., maytansinol (see U.S. Pat. No. 5,208,020), CC-1065 (see U.S. Pat. Nos. 5,475,092, 5,585,499, 5,846, 545) and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, CC-1065, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclinics (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine, vinblastine, taxol and maytansinoids).

In one aspect, the invention features a method of providing a target binding molecule that specifically binds to a LAG-3 receptor. For example, the target binding molecule is an antibody molecule. The method includes: providing a target protein that comprises at least a portion of non-human protein, the portion being homologous to (at least 70, 75, 80, 85, 87, 90, 92, 94, 95, 96, 97, 98% identical to) a corresponding portion of a human target protein, but differing by at least one amino acid (e.g., at least one, two, three, four, five, six, seven, eight, or nine amino acids); obtaining an antibody molecule that specifically binds to the antigen; and evaluating efficacy of the binding agent in modulating activity of the target protein. The method can further include administering the binding agent (e.g., antibody molecule) or a derivative (e.g., a humanized antibody molecule) to a human subject.

This invention provides an isolated nucleic acid molecule encoding the above antibody molecule, vectors and host cells thereof. The nucleic acid molecule includes but is not limited to RNA, genomic DNA and cDNA.

In certain embodiments, the antibody molecule is a multispecific (e.g., a bispecific or a trispecific) antibody molecule. Protocols for generating bispecific or heterodimeric antibody molecules are known in the art; including but not limited to, for example, the "knob in a hole" approach described in, e.g., U.S. Pat. No. 5,731,168; the electrostatic steering Fc pairing as described in, e.g., WO 09/089004, WO 06/106905 and WO 2010/129304; Strand Exchange Engineered Domains (SEED) heterodimer formation as described in, e.g., WO 07/110205; Fab arm exchange as described in, e.g., WO 08/119353, WO 2011/131746, and WO 2013/060867; double antibody conjugate, e.g., by antibody cross-linking to generate a bi-specific structure using a heterobifunctional reagent having an amine-reactive group and a sulfhydryl reactive group as described in, e.g., U.S. Pat. No. 4,433,059; bispecific antibody determinants generated by recombining half antibodies (heavy-light chain pairs or Fabs) from different antibodies through cycle of reduction and oxidation of disulfide bonds between the two heavy chains, as described in, e.g., U.S. Pat. No. 4,444,878; trifunctional antibodies, e.g., three Fab' fragments cross-linked through sulfhydryl reactive groups, as described in, e.g., U.S. Pat. No. 5,273,743; biosynthetic binding proteins, e.g., pair of scFvs cross-linked through C-terminal tails preferably through disulfide or amine-reactive chemical cross-linking, as described in, e.g., U.S. Pat. No. 5,534,254; bifunctional antibodies, e.g., Fab fragments with different binding specificities dimerized through leucine zippers (e.g., c-fos and c-jun) that have replaced the constant domain, as described in, e.g., U.S. Pat. No. 5,582,996; bispecific and oligospecific mono- and oligovalent receptors, e.g., VH-CH1 regions of two antibodies (two Fab fragments) linked through a polypeptide spacer between the CH1 region of one antibody and the VH region of the other antibody typically with associated light chains, as described in, e.g., U.S. Pat. No. 5,591,828; bispecific DNA-antibody conjugates, e.g., crosslinking of antibodies or Fab fragments through a double stranded piece of DNA, as described in, e.g., U.S. Pat. No. 5,635,602; bispecific fusion proteins, e.g., an expression construct containing two scFvs with a hydrophilic helical peptide linker between them and a full constant region, as described in, e.g., U.S. Pat. No. 5,637,481; multivalent and multispecific binding proteins, e.g., dimer of polypeptides having first domain with binding region of Ig heavy chain variable region, and second domain with binding region of Ig light chain variable region, generally termed diabodies (higher order structures are also encompassed creating for bispecific, trispecific, or tetraspecific molecules, as described in, e.g., U.S. Pat. No. 5,837,242; minibody constructs with linked VL and VH chains further connected with peptide spacers to an antibody hinge region and CH3 region, which can be dimerized to form bispecific/multivalent molecules, as described in, e.g., U.S. Pat. No. 5,837,821; VH and VL domains linked with a short peptide linker (e.g., 5 or 10 amino acids) or no linker at all in either orientation, which can form dimers to form bispecific diabodies; trimers and tetramers, as described in, e.g., U.S. Pat. No. 5,844,094; String of VH domains (or VL domains in family members) connected by peptide linkages with crosslinkable groups at the C-terminus further associated with VL domains to form a series of FVs (or scFvs), as described in, e.g., U.S. Pat. No. 5,864,019; and single chain binding polypeptides with both a VH and a VL domain linked through a peptide linker are combined into multivalent structures through non-covalent or chemical crosslinking to form, e.g., homobivalent, heterobivalent, trivalent, and tetravalent structures using both scFV or diabody type format, as described in, e.g., U.S. Pat. No. 5,869,620. Additional exemplary multispecific and bispecific molecules and methods of making the same are found, for example, in U.S. Pat. Nos. 5,910,573, 5,932,448, U.S. Pat. Nos. 5,959,083, 5,989, 830, 6,005,079, 6,239,259, 6,294,353, 6,333,396, 6,476,198, 6,511,663, 6,670,453, 6,743,896, 6,809,185, 6,833,441, 7,129,330, 7,183,076, 7,521,056, 7,527,787, 7,534,866, 7,612,181, US2002004587A1, US2002076406A1, US2002103345A1, US2003207346A1, US2003211078A1, US2004219643A1, US2004220388A1, US2004242847A1, US2005003403A1, US2005004352A1, US2005069552A1, US2005079170A1, US2005100543A1, US2005136049A1, US2005136051A1, US2005163782A1, US2005266425A1, US2006083747A1, US2006120960A1, US2006204493A1, US2006263367A1, US2007004909A1, US2007087381A1, US2007128150A1, US2007141049A1, US2007154901A1, US2007274985A1, US2008050370A1, US2008069820A1, US2008152645A1, US2008171855A1, US2008241884A1, US2008254512A1, US2008260738A1, US2009130106A1, US2009148905A1, US2009155275A1, US2009162359A1, US2009162360A1, US2009175851A1, US2009175867A1, US2009232811A1, US2009234105A1, US2009263392A1, US2009274649A1, EP346087A2, WO0006605A2, WO02072635A2, WO04081051A1, WO06020258A2, WO2007044887A2, WO2007095338A2, WO2007137760A2, WO2008119353A1, WO2009021754A2, WO2009068630A1, WO9103493A1, WO9323537A1, WO9409131A1, WO9412625A2, WO9509917A1. WO9637621A2, WO9964460A1. The contents of the above-referenced applications are incorporated herein by reference in their entireties.

In other embodiments, the anti-LAG-3 antibody molecule (e.g., a monospecific, bispecific, or multispecific antibody molecule) is covalently linked, e.g., fused, to another partner e.g., a protein e.g., one, two or more cytokines, e.g., as a fusion molecule for example a fusion protein. In other embodiments, the fusion molecule comprises one or more proteins, e.g., one, two or more cytokines. In one embodiment, the cytokine is an interleukin (IL) chosen from one, two, three or more of IL-1, IL-2, IL-12, IL-15 or IL-21. In one embodiment, a bispecific antibody molecule has a first binding specificity to a first target (e.g., to LAG-3), a second binding specificity to a second target (e.g., PD-1, TIM-3, or PD-L1), and is optionally linked to an interleukin (e.g., IL-12) domain e.g., full length IL-12 or a portion thereof.

A "fusion protein" and a "fusion polypeptide" refer to a polypeptide having at least two portions covalently linked together, where each of the portions is a polypeptide having a different property. The property may be a biological property, such as activity in vitro or in vivo. The property can also be simple chemical or physical property, such as binding to a target molecule, catalysis of a reaction, etc. The two portions can be linked directly by a single peptide bond or through a peptide linker, but are in reading frame with each other.

This invention provides an isolated nucleic acid molecule encoding the above antibody molecules, vectors and host cells thereof. The nucleic acid molecule includes but is not limited to RNA, genomic DNA and cDNA.

Exemplary Anti-LAG-3 Antibody Molecules

In certain embodiments, the anti-LAG-3 antibody molecule comprises:
  (i) a heavy chain variable region (VH) comprising a VHCDR1 amino acid sequence chosen from SEQ ID NO: 1, SEQ ID NO: 4 or SEQ ID NO: 286; a VHCDR2 amino acid sequence of SEQ ID NO: 2; and a VHCDR3 amino acid sequence of SEQ ID NO: 3; and
  (ii) a light chain variable region (VL) comprising a VLCDR1 amino acid sequence of SEQ ID NO: 10, a VLCDR2 amino acid sequence of SEQ ID NO: 11, and a VLCDR3 amino acid sequence of SEQ ID NO: 12.

In other embodiments, the anti-LAG-3 antibody molecule comprises:
  (i) a heavy chain variable region (VH) comprising a VHCDR1 amino acid sequence chosen from SEQ ID NO: 1, SEQ ID NO: 4 or SEQ ID NO: 286; a VHCDR2 amino acid sequence of SEQ ID NO: 5, and a VHCDR3 amino acid sequence of SEQ ID NO: 3; and
  (ii) a light chain variable region (VL) comprising a VLCDR1 amino acid sequence of SEQ ID NO: 13, a VLCDR2 amino acid sequence of SEQ ID NO: 14, and a VLCDR3 amino acid sequence of SEQ ID NO: 15.

In embodiments of the aforesaid antibody molecules, the VHCDR1 comprises the amino acid sequence of SEQ ID NO: 1. In other embodiments, the VHCDR1 comprises the amino acid sequence of SEQ ID NO: 4. In yet other embodiments, the VHCDR1 amino acid sequence of SEQ ID NO: 286.

In embodiments, the aforesaid antibody molecules have a heavy chain variable region comprising at least one framework (FW) region comprising the amino acid sequence of any of SEQ ID NOs: 187, 190, 194, 196, 198, 202, 206, 208, 210, 212, 217, 219, or 221, or an amino acid sequence at least 90% identical thereto, or having no more than two amino acid substitutions, insertions or deletions compared to the amino acid sequence of any of SEQ ID NOs: 187, 190, 194, 196, 198, 202, 206, 208, 210, 212, 217, 219, or 221.

In other embodiments, the aforesaid antibody molecules have a heavy chain variable region comprising at least one framework region comprising the amino acid sequence of any of SEQ ID NOs: 187, 190, 194, 196, 198, 202, 206, 208, 210, 212, 217, 219, or 221.

In yet other embodiments, the aforesaid antibody molecules have a heavy chain variable region comprising at least two, three, or four framework regions comprising the amino acid sequences of any of SEQ ID NOs: 187, 190, 194, 196, 198, 202, 206, 208, 210, 212, 217, 219, or 221.

In other embodiments, the aforesaid antibody molecules comprise a VHFW1 amino acid sequence of SEQ ID NO: 187, 190, 194, or 196, a VHFW2 amino acid sequence of SEQ ID NO: 198, 202, 206, or 208, and a VHFW3 amino acid sequence of SEQ ID NO: 210, 212, 217, or 219, and, optionally, further comprising a VHFW4 amino acid sequence of SEQ ID NO: 221.

In other embodiments, the aforesaid antibody molecules have a light chain variable region comprising at least one framework region comprising the amino acid sequence of any of SEQ ID NOs: 226, 230, 232, 234, 236, 238, 240, 244, 246, 248, 252, 255, 259, 261, 265, 267, 269, or 271, or an amino acid sequence at least 90% identical thereto, or having no more than two amino acid substitutions, insertions or deletions compared to the amino acid sequence of any of 226, 230, 232, 234, 236, 238, 240, 244, 246, 248, 252, 255, 259, 261, 265, 267, 269, or 271.

In other embodiments, the aforesaid antibody molecules have a light chain variable region comprising at least one framework region comprising the amino acid sequence of any of SEQ ID NOs: 226, 230, 232, 234, 236, 238, 240, 244, 246, 248, 252, 255, 259, 261, 265, 267, 269, or 271.

In other embodiments, the aforesaid antibody molecules have a light chain variable region comprising at least two, three, or four framework regions comprising the amino acid sequences of any of SEQ ID NOs: 226, 230, 232, 234, 236, 238, 240, 244, 246, 248, 252, 255, 259, 261, 265, 267, 269, or 271.

In other embodiments, the aforesaid antibody molecules comprise a VLFW1 amino acid sequence of SEQ ID NO: 226, 230, 232, 234, 236, or 2385, a VLFW2 amino acid sequence of SEQ ID NO: 240, 244, 246, or 248, and a VLFW3 amino acid sequence of SEQ ID NO: 252, 255, 259, 261, 265, 267, or 269, and, optionally, further comprising a VLFW4 amino acid sequence of SEQ ID NO: 271.

In other embodiments, the aforesaid antibody molecules comprise a heavy chain variable domain comprising an amino acid sequence at least 85% identical to any of SEQ ID NOs: 8, 28, 64, 68, 72, 76, 80, 100, 104, or 108.

In other embodiments, the aforesaid antibody molecules comprise a heavy chain variable domain comprising the amino acid sequence of SEQ ID NO: 8, 28, 64, 68, 72, 76, 80, 100, 104, or 108.

In other embodiments, the aforesaid antibody molecules comprise a light chain variable domain comprising an amino acid sequence at least 85% identical to any of SEQ ID NOs: 32, 36, 40, 44, 48, 52, 56, 60, 84, 88, 92, or 96.

In other embodiments, the aforesaid antibody molecules comprise a light chain variable domain comprising the amino acid sequence of SEQ ID NO: 32, 36, 40, 44, 48, 52, 56, 60, 84, 88, 92, or 96.

In other embodiments, the aforesaid antibody molecules comprise a heavy chain variable domain comprising the amino acid sequence of SEQ ID NO: 8.

In other embodiments, the aforesaid antibody molecules comprise a heavy chain comprising the amino acid sequence of SEQ ID NO: 18.

In other embodiments, the aforesaid antibody molecules comprise a heavy chain variable domain comprising the amino acid sequence of SEQ ID NO: 28.

In other embodiments, the aforesaid antibody molecules comprise a heavy chain comprising the amino acid sequence of SEQ ID NO: 30.

In other embodiments, the aforesaid antibody molecules comprise a heavy chain variable domain comprising the amino acid sequence of SEQ ID NO: 64.

In other embodiments, the aforesaid antibody molecules comprise a heavy chain comprising the amino acid sequence of SEQ ID NO: 66.

In other embodiments, the aforesaid antibody molecules comprise a heavy chain variable domain comprising the amino acid sequence of SEQ ID NO: 68.

In other embodiments, the aforesaid antibody molecules comprise a heavy chain comprising the amino acid sequence of SEQ ID NO: 70.

In other embodiments, the aforesaid antibody molecules comprise a heavy chain variable domain comprising the amino acid sequence of SEQ ID NO: 72.

In other embodiments, the aforesaid antibody molecules comprise a heavy chain comprising the amino acid sequence of SEQ ID NO: 74.

In other embodiments, the aforesaid antibody molecules comprise a heavy chain variable domain comprising the amino acid sequence of SEQ ID NO: 76.

In other embodiments, the aforesaid antibody molecules comprise a heavy chain comprising the amino acid sequence of SEQ ID NO: 78.

In other embodiments, the aforesaid antibody molecules comprise a heavy chain variable domain comprising the amino acid sequence of SEQ ID NO: 80.

In other embodiments, the aforesaid antibody molecules comprise a heavy chain comprising the amino acid sequence of SEQ ID NO: 82.

In other embodiments, the aforesaid antibody molecules comprise a heavy chain variable domain comprising the amino acid sequence of SEQ ID NO: 100.

In other embodiments, the aforesaid antibody molecules comprise a heavy chain comprising the amino acid sequence of SEQ ID NO: 102 or SEQ ID NO: 113.

In other embodiments, the aforesaid antibody molecules comprise a heavy chain variable domain comprising the amino acid sequence of SEQ ID NO: 104.

In other embodiments, the aforesaid antibody molecules comprise a heavy chain comprising the amino acid sequence of SEQ ID NO: 106.

In other embodiments, the aforesaid antibody molecules comprise a heavy chain comprising the amino acid sequence of SEQ ID NO: 122.

In other embodiments, the aforesaid antibody molecules comprise a heavy chain variable domain comprising the amino acid sequence of SEQ ID NO: 108.

In other embodiments, the aforesaid antibody molecules comprise a heavy chain comprising the amino acid sequence of SEQ ID NO: 110.

In other embodiments, the aforesaid antibody molecules comprise a heavy chain comprising the amino acid sequence of SEQ ID NO: 134.

In other embodiments, the aforesaid antibody molecules comprise a light chain variable domain comprising the amino acid sequence of SEQ ID NO: 32.

In other embodiments, the aforesaid antibody molecules comprise a light chain comprising the amino acid sequence of SEQ ID NO: 34.

In other embodiments, the aforesaid antibody molecules comprise a light chain variable domain comprising the amino acid sequence of SEQ ID NO: 36.

In other embodiments, the aforesaid antibody molecules comprise a light chain comprising the amino acid sequence of SEQ ID NO: 38.

In other embodiments, the aforesaid antibody molecules comprise a light chain variable domain comprising the amino acid sequence of SEQ ID NO: 40.

In other embodiments, the aforesaid antibody molecules comprise a light chain comprising the amino acid sequence of SEQ ID NO: 42.

In other embodiments, the aforesaid antibody molecules comprise a light chain variable domain comprising the amino acid sequence of SEQ ID NO: 44.

In other embodiments, the aforesaid antibody molecules comprise a light chain comprising the amino acid sequence of SEQ ID NO: 46.

In other embodiments, the aforesaid antibody molecules comprise a light chain variable domain comprising the amino acid sequence of SEQ ID NO: 48.

In other embodiments, the aforesaid antibody molecules comprise a light chain comprising the amino acid sequence of SEQ ID NO: 50.

In other embodiments, the aforesaid antibody molecules comprise a light chain variable domain comprising the amino acid sequence of SEQ ID NO: 52.

In other embodiments, the aforesaid antibody molecules comprise a light chain comprising the amino acid sequence of SEQ ID NO: 54.

In other embodiments, the aforesaid antibody molecules comprise a light chain variable domain comprising the amino acid sequence of SEQ ID NO: 56.

In other embodiments, the aforesaid antibody molecules comprise a light chain comprising the amino acid sequence of SEQ ID NO: 58.

In other embodiments, the aforesaid antibody molecules comprise a light chain variable domain comprising the amino acid sequence of SEQ ID NO: 60.

In other embodiments, the aforesaid antibody molecules comprise a light chain comprising the amino acid sequence of SEQ ID NO: 62.

In other embodiments, the aforesaid antibody molecules comprise a light chain variable domain comprising the amino acid sequence of SEQ ID NO: 84.

In other embodiments, the aforesaid antibody molecules comprise a light chain comprising the amino acid sequence of SEQ ID NO: 86.

In other embodiments, the aforesaid antibody molecules comprise a light chain variable domain comprising the amino acid sequence of SEQ ID NO: 88.

In other embodiments, the aforesaid antibody molecules comprise a light chain comprising the amino acid sequence of SEQ ID NO: 90.

In other embodiments, the aforesaid antibody molecules comprise a light chain variable domain comprising the amino acid sequence of SEQ ID NO: 92.

In other embodiments, the aforesaid antibody molecules comprise a light chain comprising the amino acid sequence of SEQ ID NO: 94.

In other embodiments, the aforesaid antibody molecules comprise a light chain variable domain comprising the amino acid sequence of SEQ ID NO: 96.

In other embodiments, the aforesaid antibody molecules comprise a light chain comprising the amino acid sequence of SEQ ID NO: 98.

In other embodiments, the aforesaid antibody molecules comprise a heavy chain variable domain comprising the amino acid sequence of SEQ ID NO: 28 or SEQ ID NO: 100; and a light chain variable domain comprising the amino acid sequence of SEQ ID NO: 32.

In other embodiments, the aforesaid antibody molecules comprise a heavy chain variable domain comprising the amino acid sequence of SEQ ID NO: 28 or SEQ ID NO: 100; and a light chain variable domain comprising the amino acid sequence of SEQ ID NO: 36.

In other embodiments, the aforesaid antibody molecules comprise a heavy chain variable domain comprising the amino acid sequence of SEQ ID NO: 28 or SEQ ID NO: 100; and a light chain variable domain comprising the amino acid sequence of SEQ ID NO: 40.

In other embodiments, the aforesaid antibody molecules comprise a heavy chain variable domain comprising the amino acid sequence of SEQ ID NO: 28 or SEQ ID NO: 100; and a light chain variable domain comprising the amino acid sequence of SEQ ID NO: 44.

In other embodiments, the aforesaid antibody molecules comprise a heavy chain variable domain comprising the amino acid sequence of SEQ ID NO: 28 or SEQ ID NO: 100; and a light chain variable domain comprising the amino acid sequence of SEQ ID NO: 48.

In other embodiments, the aforesaid antibody molecules comprise a heavy chain variable domain comprising the amino acid sequence of SEQ ID NO: 28 or SEQ ID NO: 100; and a light chain variable domain comprising the amino acid sequence of SEQ ID NO: 52.

In other embodiments, the aforesaid antibody molecules comprise a heavy chain variable domain comprising the amino acid sequence of SEQ ID NO: 28 or SEQ ID NO: 100; and a light chain variable domain comprising the amino acid sequence of SEQ ID NO: 56.

In other embodiments, the aforesaid antibody molecules comprise a heavy chain variable domain comprising the amino acid sequence of SEQ ID NO: 28 or SEQ ID NO: 100; and a light chain variable domain comprising the amino acid sequence of SEQ ID NO: 60.

In other embodiments, the aforesaid antibody molecules comprise a heavy chain variable domain comprising the amino acid sequence of SEQ ID NO: 64 or SEQ ID NO: 104; and a light chain variable domain comprising the amino acid sequence of SEQ ID NO: 36.

In other embodiments, the aforesaid antibody molecules comprise a heavy chain variable domain comprising the amino acid sequence of SEQ ID NO: 64 or SEQ ID NO: 104; and a light chain variable domain comprising the amino acid sequence of SEQ ID NO: 40.

In other embodiments, the aforesaid antibody molecules comprise a heavy chain variable domain comprising the amino acid sequence of SEQ ID NO: 64 or SEQ ID NO: 104; and a light chain variable domain comprising the amino acid sequence of SEQ ID NO: 56.

In other embodiments, the aforesaid antibody molecules comprise a heavy chain variable domain comprising the amino acid sequence of SEQ ID NO: 64 or SEQ ID NO: 104; and a light chain variable domain comprising the amino acid sequence of SEQ ID NO: 60.

In other embodiments, the aforesaid antibody molecules comprise a heavy chain variable domain comprising the amino acid sequence of SEQ ID NO: 68 or SEQ ID NO: 108; and a light chain variable domain comprising the amino acid sequence of SEQ ID NO: 36.

In other embodiments, the aforesaid antibody molecules comprise a heavy chain variable domain comprising the amino acid sequence of SEQ ID NO: 72 or SEQ ID NO: 8; and a light chain variable domain comprising the amino acid sequence of SEQ ID NO: 40.

In other embodiments, the aforesaid antibody molecules comprise a heavy chain variable domain comprising the amino acid sequence of SEQ ID NO: 72 or SEQ ID NO: 8; and a light chain variable domain comprising the amino acid sequence of SEQ ID NO: 60.

In other embodiments, the aforesaid antibody molecules comprise a heavy chain variable domain comprising the amino acid sequence of SEQ ID NO: 76 and a light chain variable domain comprising the amino acid sequence of SEQ ID NO: 60.

In other embodiments, the aforesaid antibody molecules comprise a heavy chain variable domain comprising the amino acid sequence of SEQ ID NO: 80 and a light chain variable domain comprising the amino acid sequence of SEQ ID NO: 84.

In other embodiments, the aforesaid antibody molecules comprise a heavy chain variable domain comprising the amino acid sequence of SEQ ID NO: 28 or SEQ ID NO: 100; and a light chain variable domain comprising the amino acid sequence of SEQ ID NO: 88.

In other embodiments, the aforesaid antibody molecules comprise a heavy chain variable domain comprising the amino acid sequence of SEQ ID NO: 28 or SEQ ID NO: 100; and a light chain variable domain comprising the amino acid sequence of SEQ ID NO: 92.

In other embodiments, the aforesaid antibody molecules comprise a heavy chain variable domain comprising the amino acid sequence of SEQ ID NO: 64 or SEQ ID NO: 104; and a light chain variable domain comprising the amino acid sequence of SEQ ID NO: 96.

In other embodiments, the aforesaid antibody molecules comprise a heavy chain comprising the amino acid sequence of SEQ ID NO: 30 or SEQ ID NO: 102; and a light chain comprising the amino acid sequence of SEQ ID NO: 34.

In other embodiments, the aforesaid antibody molecules comprise a heavy chain comprising the amino acid sequence of SEQ ID NO: 30 or SEQ ID NO: 102; and a light chain comprising the amino acid sequence of SEQ ID NO: 38.

In other embodiments, the aforesaid antibody molecules comprise a heavy chain comprising the amino acid sequence of SEQ ID NO: 30 or SEQ ID NO: 102; and a light chain comprising the amino acid sequence of SEQ ID NO: 42.

In other embodiments, the aforesaid antibody molecules comprise a heavy chain comprising the amino acid sequence of SEQ ID NO: 30 or SEQ ID NO: 102; and a light chain comprising the amino acid sequence of SEQ ID NO: 46.

In other embodiments, the aforesaid antibody molecules comprise a heavy chain comprising the amino acid sequence of SEQ ID NO: 30 or SEQ ID NO: 102; and a light chain comprising the amino acid sequence of SEQ ID NO: 50.

In other embodiments, the aforesaid antibody molecules comprise a heavy chain comprising the amino acid sequence of SEQ ID NO: 30 or SEQ ID NO: 102; and a light chain comprising the amino acid sequence of SEQ ID NO: 54.

In other embodiments, the aforesaid antibody molecules comprise a heavy chain comprising the amino acid sequence of SEQ ID NO: 30 or SEQ ID NO: 102; and a light chain comprising the amino acid sequence of SEQ ID NO: 58.

In other embodiments, the aforesaid antibody molecules comprise a heavy chain comprising the amino acid sequence of SEQ ID NO: 30 or SEQ ID NO: 102; and a light chain comprising the amino acid sequence of SEQ ID NO: 62.

In other embodiments, the aforesaid antibody molecules comprise a heavy chain comprising the amino acid sequence of SEQ ID NO: 66 or SEQ ID NO: 106; and a light chain comprising the amino acid sequence of SEQ ID NO: 38.

In other embodiments, the aforesaid antibody molecules comprise a heavy chain comprising the amino acid sequence of SEQ ID NO: 66 or SEQ ID NO: 106; and a light chain comprising the amino acid sequence of SEQ ID NO: 42.

In other embodiments, the aforesaid antibody molecules comprise a heavy chain comprising the amino acid sequence of SEQ ID NO: 66 or SEQ ID NO: 106; and a light chain comprising the amino acid sequence of SEQ ID NO: 58.

In other embodiments, the aforesaid antibody molecules comprise a heavy chain comprising the amino acid sequence of SEQ ID NO: 66 or SEQ ID NO: 106; and a light chain comprising the amino acid sequence of SEQ ID NO: 62.

In other embodiments, the aforesaid antibody molecules comprise a heavy chain comprising the amino acid sequence of SEQ ID NO: 70 or SEQ ID NO: 110; and a light chain comprising the amino acid sequence of SEQ ID NO: 38.

In other embodiments, the aforesaid antibody molecules comprise a heavy chain comprising the amino acid sequence of SEQ ID NO: 74 or SEQ ID NO: 18; and a light chain comprising the amino acid sequence of SEQ ID NO: 42.

In other embodiments, the aforesaid antibody molecules comprise a heavy chain comprising the amino acid sequence of SEQ ID NO: 74 or SEQ ID NO: 18; and a light chain comprising the amino acid sequence of SEQ ID NO: 62.

In other embodiments, the aforesaid antibody molecules comprise a heavy chain comprising the amino acid sequence of SEQ ID NO: 78 and a light chain comprising the amino acid sequence of SEQ ID NO: 62.

In other embodiments, the aforesaid antibody molecules comprise a heavy chain comprising the amino acid sequence of SEQ ID NO: 82 and a light chain comprising the amino acid sequence of SEQ ID NO: 86.

In other embodiments, the aforesaid antibody molecules comprise a heavy chain comprising the amino acid sequence of SEQ ID NO: 30 or SEQ ID NO: 102; and a light chain comprising the amino acid sequence of SEQ ID NO: 94.

In other embodiments, the aforesaid antibody molecules comprise a heavy chain comprising the amino acid sequence of SEQ ID NO: 66 or SEQ ID NO: 106; and a light chain comprising the amino acid sequence of SEQ ID NO: 98.

In other embodiments, the aforesaid antibody molecules comprise a heavy chain comprising the amino acid sequence of SEQ ID NO: 113 and a light chain comprising the amino acid sequence of SEQ ID NO: 34.

In other embodiments, the aforesaid antibody molecules comprise a heavy chain comprising the amino acid sequence of SEQ ID NO: 113 and a light chain comprising the amino acid sequence of SEQ ID NO: 38.

In other embodiments, the aforesaid antibody molecules comprise a heavy chain comprising the amino acid sequence of SEQ ID NO: 122 and a light chain comprising the amino acid sequence of SEQ ID NO: 38.

In other embodiments, the aforesaid antibody molecules comprise a heavy chain comprising the amino acid sequence of SEQ ID NO: 122 and a light chain comprising the amino acid sequence of SEQ ID NO: 58.

In other embodiments, the aforesaid antibody molecules comprise a heavy chain comprising the amino acid sequence of SEQ ID NO: 134 and a light chain comprising the amino acid sequence of SEQ ID NO: 38.

In other embodiments, the aforesaid antibody molecules are chosen from a Fab, F(ab')$_2$, Fv, or a single chain Fv fragment (scFv).

In other embodiments, the aforesaid antibody molecules comprise a heavy chain constant region selected from IgG1, IgG2, IgG3, and IgG4.

In other embodiments, the aforesaid antibody molecules comprise a light chain constant region chosen from the light chain constant regions of kappa or lambda.

In other embodiments, the aforesaid antibody molecules comprise a human IgG4 heavy chain constant region with a mutation at position 228 according to EU numbering or position 108 of SEQ ID NO: 275 or 277 and a kappa light chain constant region.

In other embodiments, the aforesaid antibody molecules comprise a human IgG4 heavy chain constant region with a Serine to Proline mutation at position 228 according to EU numbering or position 108 of SEQ ID NO: 275 or 277 and a kappa light chain constant region.

In other embodiments, the aforesaid antibody molecules comprise a human IgG1 heavy chain constant region with an Asparagine to Alanine mutation at position 297 according to EU numbering or position 180 of SEQ ID NO: 279 and a kappa light chain constant region.

In other embodiments, the aforesaid antibody molecules comprise a human IgG1 heavy chain constant region with an Aspartate to Alanine mutation at position 265 according to EU numbering or position 148, and Proline to Alanine mutation at position 329 according to EU numbering or position 212 of SEQ ID NO: 280 and a kappa light chain constant region.

In other embodiments, the aforesaid antibody molecules comprise a human IgG1 heavy chain constant region with a Leucine to Alanine mutation at position 234 according to EU numbering or position 117 and Leucine to Alanine mutation at position 235 according to EU numbering or position 118 of SEQ ID NO: 281 and a kappa light chain constant region.

In other embodiments, the aforesaid antibody molecules are capable of binding to human LAG-3 with a dissociation constant ($K_D$) of less than about 0.2 nM.

In some embodiments, the aforesaid antibody molecules bind to human LAG-3 with a $K_D$ of less than about 0.2 nM, 0.15 nM, 0.1 nM, 0.05 nM, or 0.02 nM, e.g., about 0.05 nM to 0.15 nM, e.g., about 0.11 nM, e.g., as measured by a BIACORE™ method.

In other embodiments, the aforesaid antibody molecules bind to cynomolgus LAG-3 with a $K_D$ of less than about 0.2 nM, 0.15 nM, 0.1 nM, 0.05 nM, or 0.02 nM, e.g., about 0.05 nM to 0.15 nM, e.g., as measured by a BIACORE™ method.

In certain embodiments, the aforesaid antibody molecules bind to both human LAG-3 and cynomolgus LAG-3 with similar $K_D$, e.g., in the nM range, e.g., as measured by a BIACORE™ method. In some embodiments, the aforesaid antibody molecules bind to a human LAG-3-Ig fusion protein with a $K_D$ of less than about 0.5 nM, 0.2 nM, 0.1 nM, 0.05 nM, 0.025 nM, or 0.01 nM, e.g., as measured by ELISA.

In some embodiments, the aforesaid antibody molecules bind to CHO cells that express human LAG-3 (e.g., human LAG-3-transfected CHO cells) with a $K_D$ of less than about 4 nM. 2.5 nM. 2 nM, 1.5 nM, 1 nM, 0.75 nM, 0.5 nM, 0.4 nM, 0.3 nM, 0.2 nM, 0.1 nM, or 0.05 nM, e.g., about 2.3, 1.92 nM or about 0.2 nM, e.g., as measured by FACS analysis.

In some embodiments, the aforesaid antibody molecules bind to human T cells with a $K_D$ of less than about 0.5 nM, 0.4 nM, 0.3 nM, 0.2 nM, 0.1 nM, or 0.05 nM, e.g., about 0.26 nM, e.g., as measured by FACS analysis.

In some embodiments, the aforesaid antibody molecules bind to cells that express LAG-3 (e.g., human LAG-3-expressing 300.19 cells) with a $K_D$ of less than about 20 nM, 15 nM, 10 nM. 5 nM, 2 nM, or 1 nM, e.g., about 13.6 nM, e.g., as measured by FACS analysis.

In some embodiments, the aforesaid antibody molecules bind to cells that express rhesus LAG-3 (e.g., cells transfected with rhesus LAG-3) with a $K_D$ of less than about 15 nM, 10 nM, 9 nM, 8 nM, 6 nM, 5 nM, 2 nM, or 1 nM, e.g., about 8.03 nM, e.g., as measured by FACS analysis.

In certain embodiments, the aforesaid antibody molecules are not cross-reactive with mouse LAG-3. In some embodiments, the aforesaid antibodies are not cross-reactive with rat LAG-3. In other embodiments, the aforesaid antibodies are cross-reactive with rhesus LAG-3. In some embodiments, the aforesaid antibodies are cross-reactive with rat LAG-3. For example, the cross-reactivity can be measured by a BIACORE™ method or a binding assay using cells that expresses LAG-3 (e.g., human LAG-3-expressing 300.19 cells).

In other embodiments, the aforesaid antibody molecules bind an extracellular Ig-like domain of LAG-3 (e.g., human LAG-3), e.g., any of Domain 1 (D1), Domain 2 (D2), Domain 3 (D3), or Domain 4 (D4). In some embodiments, the aforesaid antibody molecules bind one or more amino acid residues in D1. In some embodiments, the aforesaid antibody molecules do not bind the extra loop of D1 or a fragment thereof (e.g., as measured by a BIACORE™ method or a FACS method). In some embodiments, the aforesaid antibodies do not bind D2. In some embodiments, the aforesaid antibody molecules bind both D1 and D2. In some embodiments, the aforesaid antibody molecules bind one or more amino acid residues in D1 and/or D2 that bind an MHC class II molecule. In other embodiments, the aforesaid antibody molecules are capable of reducing binding of LAG-3 to a major histocompatibility (MHC) class II molecule, or a cell that expresses an MHC class II molecule. In some embodiments, the aforesaid antibody molecules reduce (e.g., block) LAG-3-Ig binding to a MHC class II molecule, e.g., on Raji cells or Daudi cells, with an $IC_{50}$ of less than about 10 nM, 8 nM, 5 nM, 4 nM, 3 nM. 2 nM, 1 nM, or 0.5 nM, e.g., between about 8 nM and about 10 nM or between about 2 nM and about 3 nM, e.g., about 5.5 nM or about 2.3 nM.

In other embodiments, the aforesaid antibody molecules are capable of enhancing an antigen-specific T cell response.

In embodiments, the antibody molecule is a monospecific antibody molecule or a bispecific antibody molecule. In embodiments, the antibody molecule has a first binding specificity for LAG-3 and a second binding specificity for PD-1, TIM-3, CEACAM (e.g., CEACAM-1 and/or CEACAM-5), PD-L1 or PD-L2. In embodiments, the antibody molecule comprises an antigen binding fragment of an antibody, e.g., a half antibody or antigen binding fragment of a half antibody.

In some embodiments, the aforesaid antibody molecules increase the expression of IL-2 from cells activated by Staphylococcal enterotoxin B (SEB) (e.g., at 25 μg/mL) by at least about 2, 3, 4, 5-fold, e.g., about 2 to 3-fold, compared to the expression of IL-2 when an isotype control (e.g., IgG4) is used, e.g., as measured in a SEB T cell activation assay or a human whole blood ex vivo assay.

In some embodiments, the aforesaid antibody molecules increase the expression of IFN-γ from T cells stimulated by anti-CD3 (e.g., at 0.1 μg/mL) by at least about 0.5, 1, 2, 3, 4, 5, 6, 7, or 8-fold, e.g., about 0.9 to 5.1-fold, e.g., about 3-fold, compared to the expression of IFN-γ when an isotype control (e.g., IgG4) is used, e.g., as measured in an IFN-γ activity assay.

In some embodiments, the aforesaid antibody molecules increase the expression of IFN-γ from T cells activated by SEB (e.g., at 3 μg/mL) by at least about 2, 3, 4, 5-fold, e.g., about 1.2 to 2-fold, e.g., about 1.6-fold, compared to the expression of IFN-γ when an isotype control (e.g., IgG4) is used, e.g., as measured in an IFN-γ activity assay.

In some embodiments, the aforesaid antibody molecules do not increase the expression of IL-2 or IFN-γ without T cell receptor activation (e.g. in the absence of SEB).

In some embodiments, the aforesaid antibody molecules increase the expression of IFN-γ from T cells activated with an CMV peptide by at least about 2, 3, 4, 5-fold, e.g., about 1.1 to 1.7-fold, e.g., about 1.4-fold, compared to the expression of IFN-γ when an isotype control (e.g., IgG4) is used, e.g., as measured in an IFN-γ activity assay. In some embodiments, the aforesaid antibody molecules increase the proliferation of CD8+ T cells activated with an CMV peptide by at least about 1, 2, 3, 4, 5-fold, e.g., about 1.5-fold, compared to the proliferation of CD8+ T cells when an isotype control (e.g., IgG4) is used, e.g., as measured by the percentage of CD8+ T cells that passed through at least n (e.g., n=2 or 4) cell divisions.

In certain embodiments, the aforesaid antibody molecules has a Cmax between about 50 μg/mL and about 400 μg/mL, between about 100 μg/mL and about 350 μg/mL, between about 150 μg/mL and about 300 μg/mL, or between about 200 μg/mL and about 250 μg/mL, e.g., about 166 μg/mL, e.g., as measured in an animal.

In certain embodiments, the aforesaid antibody molecules has a Tin between about 50 hours and about 400 hours, between about 100 hours and about 350 hours, between about 150 hours and about 300 hours, or between about 200 hours and about 250 hours, e.g., about 231.9 hours, e.g., as measured in an animal.

In some embodiments, the aforesaid antibody molecules bind to LAG-3 with a $K_D$ slower than $5\times10^{-4}$, $1\times10^{-4}$, $5\times10^{-5}$, or $1\times10^{-5}$ s$^{-1}$, e.g., about $7\times10^{-5}$ s$^{-1}$, e.g., as measured by a BIACORE™ method. In some embodiments, the aforesaid antibodies bind to LAG-3 with a Ka faster than $1\times10^4$, $5\times10^4$, $1\times10^5$, $5\times10^5$, or $1\times10^6$ M$^{-1}$ s$^{-1}$, e.g., about $6.41\times10^5$ M$^{-1}$s$^{-1}$, e.g., as measured by a BIACORE™ method.

In another aspect, the invention provides an isolated nucleic acid molecule encoding any of the aforesaid antibody molecules, vectors and host cells thereof.

In one embodiment, the isolated nucleic acid encodes the antibody heavy chain variable region or light chain variable region, or both, of any the aforesaid antibody molecules.

In one embodiment, the isolated nucleic acid encodes heavy chain CDRs 1-3, wherein said nucleic acid comprises a nucleotide sequence of SEQ ID NO: 140-144, 151-155, 162-166, 173-177, 184-186, or 287.

In another embodiment, the isolated nucleic acid encodes light chain CDRs 1-3, wherein said nucleic acid comprises a nucleotide sequence of SEQ ID NO: 145-150, 156-161, 167-172, or 178-183.

In other embodiments, the aforesaid nucleic acid further comprises a nucleotide sequence encoding a heavy chain variable domain, wherein said nucleotide sequence is at least 85% identical to any of SEQ ID NO: 9, 29, 65, 69, 73, 77, 81, 101, 105, 109, 112, 121, 124, 125, 132, or 133.

In other embodiments, the aforesaid nucleic acid further comprises a nucleotide sequence encoding a heavy chain variable domain, wherein said nucleotide sequence comprises any of SEQ ID NO: 9, 29, 65, 69, 73, 77, 81, 101, 105, 109, 112, 121, 124, 125, 132, or 133.

In other embodiments, the aforesaid nucleic acid further comprises a nucleotide sequence encoding a heavy chain, wherein said nucleotide sequence is at least 85% identical to any of SEQ ID NO: 19, 31, 67, 71, 75, 79, 83, 103, 107, 111, 114, 123, 126, 127, 135, or 136.

In other embodiments, the aforesaid nucleic acid further comprises a nucleotide sequence encoding a heavy chain, wherein said nucleotide sequence comprises any of SEQ ID NO: 19, 31, 67, 71, 75, 79, 83, 103, 107, 111, 114, 123, 126, 127, 135, or 136.

In other embodiments, the aforesaid nucleic acid further comprises a nucleotide sequence encoding a light chain variable domain, wherein said nucleotide sequence is at least 85% identical to any of SEQ ID NO: 33, 37, 41, 45, 49, 53, 57, 61, 85, 89, 93, 97, 115, 118, 128, 129, or 137.

In other embodiments, the aforesaid nucleic acid further comprises a nucleotide sequence encoding a light chain variable domain, wherein said nucleotide sequence comprises any of SEQ ID NO: 33, 37, 41, 45, 49, 53, 57, 61, 85, 89, 93, 97, 115, 118, 128, 129, or 137.

In other embodiments, the aforesaid nucleic acid further comprises a nucleotide sequence encoding a light chain, wherein said nucleotide sequence is at least 85% identical to any of SEQ ID NO: 35, 39, 43, 47, 51, 55, 59, 63, 87, 91, 95, 99, 117, 120, 130, 131, 138, or 139.

In other embodiments, the aforesaid nucleic acid further comprises a nucleotide sequence encoding a light chain, wherein said nucleotide sequence comprises any of SEQ ID NO: 35, 39, 43, 47, 51, 55, 59, 63, 87, 91, 95, 99, 117, 120, 130, 131, 138, or 139.

In certain embodiments, one or more expression vectors and host cells comprising the aforesaid nucleic acids are provided.

A method of producing an antibody molecule or fragment thereof, comprising culturing the host cell as described herein under conditions suitable for gene expression is also provided.

Pharmaceutical Compositions and Kits

In another aspect, the present invention provides compositions, e.g., pharmaceutically acceptable compositions, which include an antibody molecule described herein, formulated together with a pharmaceutically acceptable carrier. As used herein, "pharmaceutically acceptable carrier" includes any and all solvents, dispersion media, isotonic and absorption delaying agents, and the like that are physiologically compatible. The carrier can be suitable for intravenous, intramuscular, subcutaneous, parenteral, rectal, spinal or epidermal administration (e.g., by injection or infusion).

The compositions of this invention may be in a variety of forms. These include, for example, liquid, semi-solid and solid dosage forms, such as liquid solutions (e.g., injectable and infusible solutions), dispersions or suspensions, liposomes and suppositories. The preferred form depends on the intended mode of administration and therapeutic application. Typical preferred compositions are in the form of injectable or infusible solutions. The preferred mode of administration is parenteral (e.g., intravenous, subcutaneous, intraperitoneal, intramuscular). In a preferred embodiment, the antibody is administered by intravenous infusion or injection. In another preferred embodiment, the antibody is administered by intramuscular or subcutaneous injection.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion.

Therapeutic compositions typically should be sterile and stable under the conditions of manufacture and storage. The composition can be formulated as a solution, microemulsion, dispersion, liposome, or other ordered structure suitable to high antibody concentration. Sterile injectable solutions can be prepared by incorporating the active compound (i.e., antibody or antibody portion) in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying that yields a powder of the active ingredient plus any additional desired ingredient from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition an agent that delays absorption, for example, monostearate salts and gelatin.

The antibody molecules can be administered by a variety of methods known in the art, although for many therapeutic applications, the preferred route/mode of administration is intravenous injection or infusion. In one embodiment, the antibody molecule is administered by intravenous infusion at a rate of more than 20 mg/min, e.g., 20-40 mg/min, and preferably greater than or equal to 40 mg/min to reach a dose of about 35 to 440 mg/m$^2$, preferably about 70 to 310 mg/m$^2$, and more preferably, about 110 to 130 mg/m$^2$. In another embodiment, the antibody molecule is administered by intravenous infusion at a rate of less than 10 mg/min; preferably less than or equal to 5 mg/min to reach a dose of about 1 to 100 mg/m 2, preferably about 5 to 50 mg/m$^2$, about 7 to 25 mg/m$^2$ and more preferably, about 10 mg/m$^2$. As will be appreciated by the skilled artisan, the route and/or mode of administration will vary depending upon the desired results. In certain embodiments, the active compound may be prepared with a carrier that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., *Sustained and Controlled Release Drug Delivery Systems*, J. R. Robinson, ed., Marcel Dekker, Inc., New York, 1978.

In certain embodiments, an antibody molecule can be orally administered, for example, with an inert diluent or an assimilable edible carrier. The compound (and other ingredients, if desired) may also be enclosed in a hard or soft shell gelatin capsule, compressed into tablets, or incorporated directly into the subject's diet. For oral therapeutic administration, the compounds may be incorporated with excipients and used in the form of ingestible tablets, buccal tablets, troches, capsules, elixirs, suspensions, syrups, wafers, and the like. To administer a compound of the invention by other than parenteral administration, it may be necessary to coat the compound with, or co-administer the compound with, a material to prevent its inactivation. Therapeutic compositions can also be administered with medical devices known in the art.

Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for case of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic effect to be achieved, and (b) the limitations inherent in the art of compounding such an active compound for the treatment of sensitivity in individuals.

An exemplary, non-limiting range for a therapeutically or prophylactically effective amount of an antibody molecule is 0.1-30 mg/kg, more preferably 1-25 mg/kg. Dosages and therapeutic regimens of the anti-LAG-3 antibody molecule can be determined by a skilled artisan. In certain embodiments, the anti-LAG-3 antibody molecule is administered by injection (e.g., subcutaneously or intravenously) at a dose of about 1 to 40 mg/kg, e.g., 1 to 30 mg/kg, e.g., about 5 to 25 mg/kg, about 10 to 20 mg/kg, about 1 to 5 mg/kg, 1 to 10 mg/kg, 5 to 15 mg/kg, 10 to 20 mg/kg, 15 to 25 mg/kg, or about 3 mg/kg. The dosing schedule can vary from e.g., once a week to once every 2, 3, or 4 weeks. In one embodiment, the anti-LAG-3 antibody molecule is administered at a dose from about 10 to 20 mg/kg every other week. The antibody molecule can be administered by intravenous infusion at a rate of more than 20 mg/min, e.g., 20-40 mg/min, and preferably greater than or equal to 40 mg/min to reach a dose of about 35 to 440 mg/m$^2$, preferably about 70 to 310 mg/m$^2$, and more preferably, about 110 to 130 mg/m$^2$. In embodiments, the infusion rate of about 110 to 130 mg/m$^2$ achieves a level of about 3 mg/kg. In one embodiment, the anti-LAG-3 antibody molecule is administered (e.g., intravenously) at a dose from about 3 to 800 mg, e.g., about 3, 20, 80, 240, or 800 mg. In certain embodiments, the anti-LAG-3 antibody molecule is administered alone at a dose from about 20 to 800 mg, e.g., about 3, 20, 80, 240, or 800 mg. In other embodiments, the anti-LAG-3 antibody molecule is administered at a dose from about 3 to 240 mg, e.g., about 3, 20, 80, or 240 mg, in combination with a second agent or therapeutic modality, e.g., a second agent or therapeutic modality described herein. In one embodiment, the anti-LAG-3 antibody molecule is administered every 2 weeks (e.g., during weeks 1, 3, 5, 7) during each 8 week cycle, e.g., up to 96 weeks.

The antibody molecule can be administered by intravenous infusion at a rate of more than 20 mg/min, e.g., 20-40 mg/min, and preferably greater than or equal to 40 mg/min to reach a dose of about 35 to 440 mg/m$^2$, preferably about 70 to 310 mg/m$^2$, and more preferably, about 110 to 130 mg/m$^2$. In embodiments, the infusion rate of about 110 to 130 mg/m$^2$ achieves a level of about 3 mg/kg. In other embodiments, the antibody molecule is administered by intravenous infusion at a rate of less than 10 mg/min, e.g., less than or equal to 5 mg/min to reach a dose of about 1 to 100 mg/m$^2$, e.g., about 5 to 50 mg/m$^2$, about 7 to 25 mg/m$^2$, and more preferably, about 10 mg/m$^2$. In some embodiments, the antibody is infused over a period of about 30 min.

It is to be noted that dosage values may vary with the type and severity of the condition to be alleviated. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition.

The pharmaceutical compositions of the invention may include a "therapeutically effective amount" or a "prophylactically effective amount" of an antibody or antibody portion of the invention. A "therapeutically effective amount" refers to an amount effective, at dosages and for periods of time necessary, to achieve the desired therapeutic result. A therapeutically effective amount of the modified antibody or antibody fragment may vary according to factors such as the disease state, age, sex, and weight of the individual, and the ability of the antibody or antibody portion to elicit a desired response in the individual. A therapeutically effective amount is also one in which any toxic or detrimental effects of the modified antibody or antibody fragment is outweighed by the therapeutically beneficial effects. A "therapeutically effective dosage" preferably inhibits a measurable parameter, e.g., tumor growth rate by at least about 20%, more preferably by at least about 40%, even more preferably by at least about 60%, and still more preferably by at least about 80% relative to untreated subjects. The ability of a compound to inhibit a measurable parameter, e.g., cancer, can be evaluated in an animal model system predictive of efficacy in human tumors. Alternatively, this property of a composition can be evaluated by examining the ability of the compound to inhibit, such inhibition in vitro by assays known to the skilled practitioner A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

Also within the scope of the invention is a kit comprising an antibody molecule described herein. The kit can include one or more other elements including: instructions for use; other reagents, e.g., a label, a therapeutic agent, or an agent useful for chelating, or otherwise coupling, an antibody to a label or therapeutic agent, or a radioprotective composition; devices or other materials for preparing the antibody for administration; pharmaceutically acceptable carriers; and devices or other materials for administration to a subject.

Uses of Anti-LAG-3 Antibody Molecules

The anti-LAG-3 antibody molecules disclosed herein have in vitro and in vivo diagnostic, as well as therapeutic and prophylactic utilities. For example, these molecules can be administered to cells in culture, in vitro or ex vivo, or to a subject, e.g., a human subject, e.g., in vivo, to enhance immunity. In one embodiment, the anti-LAG-3 antibody molecules enhance an immune response in a subject, e.g., by blockade of LAG-3 (e.g., by blockade of LAG-3 binding to an MHC molecule or other ligands).

Accordingly, in one aspect, the invention provides a method of modifying an immune response in a subject comprising administering to the subject the antibody, molecule described herein, such that the immune response in the subject is modified. In one embodiment, the immune response is enhanced, stimulated or up-regulated. In some embodiments, the anti-LAG-3 antibody molecule restores, enhances or stimulates an antigen-specific T cell response, e.g., interleukin-2 (IL-2) or interferon-gamma (IFN-γ), production in an antigen-specific T cell response, in the subject. In some embodiments, the immune response is an anti-tumor response. The methods and compositions described herein are suitable for treating human patients having a disorder that can be treated by augmenting the T-cell mediated immune response. For example, the anti-LAG-3 antibody molecules, alone or in combination, can be administered to a subject to treat, prevent, and/or diagnose a variety of disorders, such as cancers (melanoma or hepatic cancers), or an infectious disorder.

As used herein, the term "subject" is intended to include human and non-human animals. In one embodiment, the subject is a human subject, e.g., a human patient having a disorder or condition characterized by abnormal LAG-3 functioning. The term "non-human animals" of the invention includes mammals and non-mammals, such as non-human primates. In one embodiment, the subject is a human. In one embodiment, the subject is a human patient in need of enhancement of an immune response. In one embodiment, the subject has, or is at risk of, having a disorder described herein, e.g., a cancer or an infectious disorder as described herein. In certain embodiments, the subject is, or is at risk of being, immunocompromised. For example, the subject is undergoing or has undergone a chemotherapeutic treatment and/or radiation therapy. Alternatively, or in combination, the subject is, or is at risk of being, immunocompromised as a result of an infection. For example, the methods and compositions described herein can enhance a number of immune activities. In one embodiment, the subject has increased number or activity of tumour-infiltrating T lymphocytes (TILs). In another embodiment, the subject has increased expression or activity of interferon-gamma (IFN-γ). In yet another embodiment, the subject has decreased PD-L1 expression or activity. Accordingly, in certain embodiments, any (e.g., one, two, three, or all) of TILs, IFN-γ, CD8, or PD-L1, can be used as biomarkers for the anti-LAG-3 immunotherapies described herein.

Therapeutic Uses
Cancer

Blockade of LAG-3 by antibodies can enhance an immune response to cancerous cells in a subject. Similar to CD4, LAG-3 interacts with MHC class II molecules but, unlike CD4, LAG-3 does not interact with the human immunodeficiency virus gp120 protein (Baixeras et al. (1992) *J. Exp. Med.* 176:327-337). Studies have demonstrated direct and specific binding of LAG-3 to MHC class II on the cell surface (Huard et al. (1996) *Eur. J. Immunol.* 26:1180-1186). The LAG-3/MHC class II interaction plays a role in down-regulating antigen-dependent stimulation of $CD4^+$ and $CD8^+$ T lymphocytes. The addition of anti-LAG-3 antibodies can result in increased T cell proliferation, higher expression of activation antigens such as CD25, and higher concentrations of cytokines such as interferon-gamma and interleukin-4 (Huard et al. (1994) *Eur. J. Immunol.* 24:3216-3221). The intra-cytoplasmic region of LAG-3 can also interact with LAP, a signal transduction molecule involved in the downregulation of the CD3/TCR activation pathway (Iouzalen et al. (2001) *Eur. J. Immunol.* 31:2885-2891). Further, LAG-3 contributes to the suppressor activity of $CD4^+CD25^+$ regulatory T cells ($T_{reg}$). $T_{reg}$ cells express LAG-3 upon activation and antibodies to LAG-3 inhibit suppression by induced $T_{reg}$ cells (Huang, C. et al. (2004) *Immunity* 21:503-513). LAG-3 can also negatively regulate T cell homeostasis by regulatory T cells in both T cell-dependent and independent mechanisms (Workman, C. J. and Vignali, D. A. (2005) *J. Immunol.* 174:688-695). Thus, inhibition of LAG-3 can result in augmenting an immune response.

Accordingly, in one aspect, a method of treating (e.g., reducing or inhibiting) a cancer or tumor in a subject is provided. The method comprises administering to the subject an anti-LAG-3 antibody molecule described herein, e.g., a therapeutically effective amount of an anti-LAG-3 antibody molecule, alone or in combination, e.g., with one or more agents or procedures. In one embodiment, an anti-LAG-3 antibody molecule may be used alone to inhibit the growth of cancerous tumors. Alternatively, an anti-LAG-3 antibody may be used in combination with one or more of: a standard of care treatment (e.g., for cancers or infectious disorders), another antibody, an immunomodulator (e.g., an activator of a costimulatory molecule or an inhibitor of an inhibitory molecule); a vaccine, e.g., a therapeutic cancer vaccine; or other forms of cellular immunotherapy, as described below. In certain embodiments, the anti-LAG-3 antibody molecule is administered in combination with a modulator of a costimulatory molecule (e.g., an agonist of a costimulatory molecule) or a modulator of an inhibitory molecule (e.g., an inhibitor of an immune checkpoint inhibitor), e.g., as described herein.

In one embodiment, the methods are suitable for the treatment of cancer in vivo. To achieve antigen-specific enhancement of immunity, the anti-LAG-3 antibody molecule can be administered together with an antigen of interest. When antibodies to LAG-3 are administered in combination with one or more agents, the combination can be administered in either order or simultaneously.

Types of Cancer; Theranostic Methods

In certain embodiments, a method of treating a subject, e.g., reducing or ameliorating, a hyperproliferative condition or disorder (e.g., a cancer), e.g., solid tumor, a hematological cancer, soft tissue tumor, or a metastatic lesion, in a subject is provided. The method includes administering to the subject one or more anti-LAG-3 antibody molecules described herein, alone or in combination with other agents or therapeutic modalities.

As used herein, the term "cancer" is meant to include all types of cancerous growths or oncogenic processes, metastatic tissues or malignantly transformed cells, tissues, or organs, irrespective of histopathologic type or stage of invasiveness. Examples of cancerous disorders include, but are not limited to, solid tumors, hematological cancers, soft tissue tumors, and metastatic lesions. Examples of solid tumors include malignancies, e.g., sarcomas, and carcinomas (including adenocarcinomas and squamous cell carcinomas), of the various organ systems, such as those affecting liver, lung, breast, lymphoid, gastrointestinal (e.g., colon), genitourinary tract (e.g., renal, urothelial cells), prostate and pharynx. Adenocarcinomas include malignancies such as most colon cancers, rectal cancer, renal-cell carcinoma, liver cancer, non-small cell carcinoma of the lung, cancer of the small intestine and cancer of the esophagus. Squamous cell carcinomas include malignancies such as those affecting the lung, esophagus, skin, head and neck region, oral cavity, anus, and cervix. Metastatic lesions of the aforementioned cancers can also be treated or prevented using the methods and compositions of the invention.

Exemplary cancers whose growth can be inhibited using the antibodies molecules disclosed herein include cancers typically responsive to immunotherapy. Non-limiting examples of preferred cancers for treatment include melanoma (e.g., an advanced stage (e.g., stage II-IV) melanoma or an HLA-A2 positive melanoma), pancreatic cancer (e.g., advanced pancreatic cancer), solid tumors, breast cancer (e.g., metastatic breast carcinoma, a breast cancer that does not express one, two or all of estrogen receptor, progesterone receptor, or Her2/neu, e.g., a triple negative breast cancer), and renal cell carcinoma (e.g., advanced (e.g., stage IV) or metastatic renal cell carcinoma (MRCC)). Additionally, refractory or recurrent malignancies can be treated using the antibody molecules described herein.

Examples of other cancers that can be treated include, e.g., a solid tumor, e.g., prostate cancer (e.g., hormone refractory prostate adenocarcinoma), colon cancer, lung cancer (e.g., non-small cell lung cancer), bone cancer, skin cancer, cancer of the head or neck (e.g., HPV+ squamous cell carcinoma), cutaneous or intraocular malignant melanoma, uterine cancer, ovarian cancer, rectal cancer, cancer of the anal region, stomach cancer, testicular cancer, uterine cancer, carcinoma of the fallopian tubes, carcinoma of the endometrium, carcinoma of the cervix, carcinoma of the vagina, carcinoma of the vulva, Merkel cell cancer, solid tumors of childhood, cancer of the bladder, cancer of the kidney or ureter, carcinoma of the renal pelvis, neoplasm of the central nervous system (CNS), tumor angiogenesis, spinal axis tumor, brain stem glioma, pituitary adenoma, Kaposi's sarcoma, epidermoid cancer, or squamous cell cancer or a hematological malignancy, e.g., Hodgkin lymphoma, non-Hodgkin lymphoma, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, chronic or acute leukemias including acute myeloid leukemia, chronic myeloid leukemia, acute lymphoblastic leukemia, chronic lymphocytic leukemia (e.g., relapsed or refractory chronic lymphocytic leukemia), solid tumors of childhood, lymphocytic lymphoma, multiple myeloma, myelodisplastic syndromes, cancer of the bladder, cancer of the kidney or ureter, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, squamous cell cancer, T-cell lymphoma, environmentally induced cancers including those induced by asbestos (e.g., mesothelioma), and combinations of said cancers. Treatment of metastatic cancers, e.g., metastatic cancers that express MHC class II molecules or LAG-3, can be effected using the antibody molecules described herein.

While not wishing to be bound by theory, in some embodiments, a patient is more likely to respond to treatment with anti-LAG-3, alone or in combination with anti-PD-1 or PD-L1 antibody molecules (optionally in combination with one or more agents as described herein) if the patient has a cancer that highly expresses PD-L1, and/or the cancer is infiltrated by anti-tumor immune cells, e.g., TILs. The anti-tumor immune cells may be positive for CD8, PD-L1, and/or IFN-γ; thus levels of CD8, PD-L1, and/or IFN-γ can serve as a readout for levels of TILs in the microenvironment. In certain embodiments, the cancer microenvironment is referred to as triple-positive for PD-L1/CD8/IFN-γ.

Accordingly, in certain aspects, this application provides methods of determining whether a tumor sample is positive for one or more of PD-L1, CD8, and IFN-γ, and if the tumor sample is positive for one or more, e.g., two, or all three, of the markers, then administering to the patient a therapeutically effective amount of an anti-PD-1 antibody molecule, optionally in combination with one or more other immunomodulators or anti-cancer agents.

In the following indications, a large fraction of patients are triple-positive for PD-L1/CD8/IFN-γ: lung cancer (squamous); lung cancer (adenocarcinoma); head and neck cancer; stomach cancer; NSCLC; HNSCC; gastric cancers (e.g., MSIhi and/or EBV+); CRC (e.g., MSIhi); nasopharyngeal cancer (NPC); cervical cancer (e.g., squamous); thyroid cancer e.g., papillary thyroid; melanoma; TN breast cancer; and DLBCL (Diffuse Large B-Cell Lymphoma). In breast cancer generally and in colon cancer generally, a moderate fraction of patients is triple-positive for PD-L1/CD8/IFN-γ. In the following indications, a small fraction of patients are triple-positive for PD-L1/CD8/IFN-γ: ER+ breast cancer, and pancreatic cancer. These findings are discussed further in Example 4. Regardless of whether a large or small fraction of patients is triple-positive for these markers, screening the patients for these markers allows one to identify a fraction of patients that has an especially high likelihood of responding favorably to therapy with a LAG-3 antibody, alone or in combination with a PD-1 antibody (e.g., a blocking PD-1 antibody), optionally in combination with one or more other immunomodulators (e.g., an anti-TIM-3 antibody molecule or an anti-PD-L1 antibody molecule) and/or anti-cancer agents, e.g., those listed in Table 7 and disclosed in the publications listed in Table 7.

In some embodiments, the cancer sample is classified as triple-positive for PDL1/CD8/IFN-γ. This measurement can roughly be broken down into two thresholds: whether an individual cell is classified as positive, and whether the sample as a whole is classified as positive. First, one can measure, within an individual cell, the level of PD-L1, CD8, and/or IFN-γ. In some embodiments, a cell that is positive for one or more of these markers is a cell that has a higher level of the marker compared to a control cell or a reference value. For example, in some embodiments, a high level of PD-L1 in a given cell is a level higher than the level of PD-L1 in a corresponding non-cancerous tissue in the patient. As another example, in some embodiments, a high level of CD8 or IFN-γ in a given cell is a level of that protein typically seen in a TIL. Second, one can also measure the percentage of cells in the sample that are positive for PD-L1, CD8, and/or IFN-γ. (It is not necessary for a single cell to express all three markers.) In some embodiments, a triple positive sample is one that has a high percentage of cells, e.g., higher than a reference value or higher than a control sample, that are positive for these markers.

In other embodiments, one can measure the levels of PD-L1, CD8, and/or IFN-γ overall in the sample. In this case, a high level of CD8 or IFN-γ in the sample can be the level of that protein typically seen in a tumor infiltrated with TIL. Similarly, a high level of PD-L1 can be the level of that protein typically seen in a tumor sample, e.g., a tumor microenvironment.

The identification of subsets of patients that are triple-positive for PD-L1/CD8/IFN-γ, as shown in Example 4 herein, reveals certain sub-populations of patients that are likely to be especially responsive to PD-1 antibody therapy.

For instance, many IM-TN (immunomodulatory, triple negative) breast cancer patients are triple-positive for PDL1/CD8/IFN-γ. IM-TN breast cancer is described in, e.g., Brian D. Lehmann et al., "Identification of human triple-negative breast cancer subtypes and preclinical models for selection of targeted therapies", *J Clin Invest*. Jul. 1, 2011; 121 (7): 2750-2767. Triple-negative breast cancers are those that do not express estrogen receptor (ER), progesterone receptor (PR) and Her2/neu. These cancers are difficult to treat because they are typically not responsive to agents that target ER, PR, and Her2/neu. Triple-negative breast cancers can be further subdivided into different classes, one of which is immunomodulatory. As described in Lehmann et al., IM-TN breast cancer is enriched for factors involved in immune cell processes, for example, one or more of immune cell signaling (e.g., TH1/TH2 pathway, NK cell pathway, B cell receptor signaling pathway, DC pathway, and T cell receptor signaling), cytokine signaling (e.g., cytokine pathway, IL-12 pathway, and IL-7 pathway), antigen processing and presentation, signaling through core immune signal transduction pathways (e.g., NFKB, TNF, and JAK/STAT signaling), genes involved in T-cell function, immune transcription, interferon (IFN) response and antigen processing. Accordingly, in some embodiments, the cancer treated is a cancer that is, or is determined to be, positive for one or more marker of IM-TN breast cancer, e.g., a factor that promotes one or more of immune cell signaling (e.g., TH1/TH2 pathway, NK cell pathway, B cell receptor signaling pathway, DC pathway, and T cell receptor signaling), cytokine signaling (e.g., cytokine pathway, IL-12 pathway, and IL-7 pathway), antigen processing and presentation, signaling through core immune signal transduction pathways (e.g., NFKB, TNF, and JAK/STAT signaling), genes involved in T-cell function, immune transcription, interferon (IFN) response and antigen processing.

As another example, it is shown herein that a subset of colon cancer patients having high MSI (microsatellite instability) is also triple-positive for PD-L1/CD8/IFN-γ. Accordingly, in some embodiments, a LAG-3 antibody, e.g., a LAG-3 antibody as described herein, alone or in combination with a PD-1 antibody, (optionally in combination with one or more immunomodulators such as a TIM-3 antibody or a PD-L1 antibody, and one or more anti-cancer agents, e.g., an anti-cancer agent described in Table 7 or in a publication in Table 7) is administered to a patient who has, or who is identified as having, colon cancer with high MSI, thereby treating the cancer. In some embodiments, a cell with high MSI is a cell having MSI at a level higher than a reference value or a control cell, e.g., a non-cancerous cell of the same tissue type as the cancer.

As another example, it is shown herein that a subset of gastric cancer patients having high MSI, and/or which is EBV+, is also triple-positive for PD-L1/CD8/IFN-γ. Accordingly, in some embodiments, a LAG-3 antibody, e.g., a LAG-3 antibody as described herein, alone or in combination with a PD-1 antibody, (optionally in combination with one or more immunomodulators such as a TIM-3 antibody or a PD-L1 antibody, and one or more anti-cancer agents, e.g., an anti-cancer agent described in Table 7 or in a publication in Table 7) is administered to a patient who has, or who is identified as having, gastric cancer with high MSI and/or EBV+, thereby treating the cancer. In some embodiments, a cell with high MSI is a cell having MSI at a level higher than a reference value or a control cell, e.g., a non-cancerous cell of the same tissue type as the cancer.

Additionally disclosed herein are methods of assaying a cancer for PD-L1, and then treating the cancer with a LAG-3 antibody, alone or in combination with a PD-1 antibody. As described in Example 5 herein, a cancer sample can be assayed for PD-L1 protein levels or mRNA levels. A sample having levels of PD-L1 (protein or mRNA) higher than a reference value or a control cell (e.g., a non-cancerous cell) can be classified as PD-L1 positive. Accordingly, in some embodiments, a LAG-3 antibody, e.g., a LAG-3 antibody as described herein, alone or in combination with a PD-1 antibody, (optionally in combination with one or more anti-cancer agents) is administered to a patient who has, or who is identified as having, a cancer that is PD-L1 positive. The cancer may be, e.g., non-small cell lung (NSCLC) adenocarcinoma (ACA), NSCLC squamous cell carcinoma (SCC), or hepatocellular carcinoma (HCC).

In some embodiments, the methods herein involve using a LAG-3 antibody, e.g., a LAG-3 antibody as described herein, e.g., in combination with a PD-1 antibody, for treating a cancer that is (or is identified as being) positive for PD-L1. In some embodiments, the cancer is colorectal cancer (e.g., MSI-high), gastric cancer (e.g., MSI-high and/or EBV+), NPC, cervical cancer, breast cancer (e.g., TN breast cancer), and ovarian cancer. In some embodiments, the cancer is NSCLC, melanoma, or HNSCC. In some embodiments, the LAG-3 antibody is administered at a dose of, e.g., 1, 3, 10, or 20 mg/kg.

Based on, e.g. Example 4 herein, it was found that certain gastric cancers that are triple-positive for PDL1/CD8/IFN-γ are also positive for PIK3CA. Accordingly, in some embodiments, a cancer can be treated with a LAG-3 antibody, alone or in combination with an anti-PD1 antibody molecule (optionally in combination with one or more immunomodulators, e.g., an anti-TIM-3 antibody molecule or an anti-PD-L1 antibody molecule) and an agent that inhibits PIK3CA. Exemplary agents in this category are described in Stein RC (September 2001). "Prospects for phosphoinositide 3-kinase inhibition as a cancer treatment". Endocrine-related Cancer 8 (3): 237-48 and Marone R, Cmiljanovic V, Giese B, Wymann M P (January 2008). "Targeting phosphoinositide 3-kinase: moving towards therapy". Biochimica et Biophysica Acta 1784 (1): 159-85.

Based on, e.g. Example 4 herein, CRC, e.g., a patient that has (or is identified as having) MSI-high CRC may be treated with a LAG-3 antibody, alone or in combination with a PD-1 antibody, optionally in combination with a therapeutic that targets one or both of RNF43 and BRAF. For instance, these cancers may be treated with a LAG-3 antibody and a PD-1 antibody, optionally in combination with one or more therapeutics that target one or more of RNF43 and BRAF. In embodiments, the one or more therapeutics include an anti-cancer agent described in Table 7 or a publication listed in Table 7. PD-1 inhibitors, e.g., antibodies, are described herein. RNF43 can be inhibited, e.g., with an antibody, small molecule (e.g., 2-(2',3-dimethyl-[2,4'-bipyridin]-5-yl)-N-(5-(pyrazin-2-yl)pyridin-2-yl) acetamide (Compound A28)), siRNA, or a Rspo ligand or derivative thereof. BRAF inhibitors (e.g., vemurafenib or dabrafenib) are described herein.

Based on, e.g. Example 4 herein, a patient that has (or is identified as having) a squamous cell lung cancer may be treated with a LAG-3 antibody molecule in combination with a therapeutic that targets PD-1, e.g., a PD-1 antibody molecule, and optionally with one or more anti-cancer agents, e.g., an anti-cancer agent described in Table 7 or in a publication in Table 7, or a therapeutic that targets TIM-3, e.g., a TIM-3 antibody.

Based on, e.g. Example 4 herein, a patient that has (or is identified as having) a thyroid cancer may be treated with a LAG-3 antibody molecule, alone or in combination with a PD-1 antibody molecule, optionally in combination with a therapeutic that targets BRAF, and optionally in combination with one or more immunomodulators, e.g., an anti-TIM-3 antibody molecule, and an anti-PD-L1 antibody molecule. BRAF inhibitors (e.g., vemurafenib or dabrafenib) are described herein, e.g., in Table 7 and the publications listed in Table 7.

In some embodiments, the therapies here can be used to treat a patient that has (or is identified as having) a cancer associated with an infection, e.g., a viral or bacterial infection. Exemplary cancers include cervical cancer, anal cancer, HPV-associated head and neck squamous cell cancer, HPV-associated esophageal papillomas, HHV6-associated lymphomas, EBV-associated lymphomas (including Burkitt lymphoma), Gastric MALT lymphoma, other infection-associated MALT lymphomas, HCC, Kaposi's sarcoma. In other embodiments, the cancer is a hematological cancer including but is not limited to a leukemia or a lymphoma. For example, the anti-LAG-3 antibody molecule can be used to treat cancers and malignancies including, but not limited to, e.g., acute leukemias including but not limited to, e.g., B-cell acute lymphoid leukemia ("BALL"), T-cell acute lymphoid leukemia ("TALL"), acute lymphoid leukemia (ALL); one or more chronic leukemias including but not limited to, e.g., chronic myelogenous leukemia (CML), chronic lymphocytic leukemia (CLL); additional hematologic cancers or hematologic conditions including, but not limited to, e.g., B cell prolymphocytic leukemia, blastic plasmacytoid dendritic cell neoplasm, Burkitt's lymphoma, diffuse large B cell lymphoma. Follicular lymphoma, Hairy cell leukemia, small cell- or a large cell-follicular lymphoma, malignant lymphoproliferative conditions, MALT lymphoma, mantle cell lymphoma, Marginal zone lymphoma, multiple myeloma, myelodysplasia and myelodysplastic syndrome, non-Hodgkin's lymphoma, plasmablastic lymphoma, plasmacytoid dendritic cell neoplasm. Waldenstrom macroglobulinemia, and "preleukemia" which are a diverse collection of hematological conditions united by ineffective production (or dysplasia) of myeloid blood cells, and the like.

In one embodiment, the cancer is a melanoma, e.g., an advanced melanoma. In one embodiment, the cancer is an advanced or unresectable melanoma that does not respond to other therapies. In other embodiments, the cancer is a melanoma with a BRAF mutation (e.g., a BRAF V600 mutation). In yet other embodiments, the anti-LAG-3 antibody molecule is administered after treatment with an anti-CTLA4 antibody (e.g., ipilimumab) with or without a BRAF inhibitor (e.g., vemurafenib or dabrafenib).

Methods and compositions disclosed herein are useful for treating metastatic lesions associated with the aforementioned cancers.

Combination of Anti-LAG-3 Antibodies with Cancer Vaccines

Antibody molecules to LAG-3 can be combined with an immunogenic agent, such as cancerous cells, purified tumor antigens (including recombinant proteins, peptides (e.g., HLA-A2 peptides), and carbohydrate molecules), cells, and cells transfected with genes encoding immune stimulating cytokines (He et al. (2004) J. Immunol. 173:4919-28). Non-limiting examples of tumor vaccines that can be used include, e.g., peptides of melanoma antigens, such as peptides of gp100, MAGE antigens, Trp-2, MARTI and/or tyrosinase, or tumor cells transfected to express the cytokine GM-CSF, DNA-based vaccines, RNA-based vaccines, and virally transduced-based vaccines. The cancer vaccine may be prophylactic or therapeutic.

LAG-3 blockade can be combined with a vaccination protocol. Many experimental strategies for vaccination against tumors have been devised (see Rosenberg, S., 2000, Development of Cancer Vaccines, ASCO Educational Book Spring: 60-62; Logothetis, C., 2000, ASCO Educational Book Spring: 300-302; Khayat, D. 2000, ASCO Educational Book Spring: 414-428; Foon, K. 2000, ASCO Educational Book Spring: 730-738; see also Restifo, N. and Sznol, M., Cancer Vaccines, Ch. 61, pp. 3023-3043 in DeVita, V. et al. (eds.), 1997, Cancer: Principles and Practice of Oncology. Fifth Edition). In one of these strategies, a vaccine is prepared using autologous or allogeneic tumor cells. These cellular vaccines have been shown to be most effective when the tumor cells are transduced to express GM-CSF. GM-CSF has been shown to be a potent activator of antigen presentation for tumor vaccination (Dranoff et al. (1993) Proc. Natl. Acad. Sci. U.S.A. 90:3539-43).

LAG-3 blockade can be used in conjunction with a collection of recombinant proteins and/or peptides expressed in a tumor in order to generate an immune response to these proteins. These proteins are normally viewed by the immune system as self antigens and are therefore tolerant to them. The tumor antigen may also include the protein telomerase, which is required for the synthesis of telomeres of chromosomes and which is expressed in more than 85% of human cancers and in only a limited number of somatic tissues (Kim, N. et al. (1994) Science 266:2011-2013). (These somatic tissues may be protected from immune attack by various means). Tumor antigen may also be "neo-antigens" expressed in cancer cells because of somatic mutations that alter protein sequence or create fusion proteins between two unrelated sequences (e.g., bcr-abl in the Philadelphia chromosome), or idiotype from B cell tumors.

Other tumor vaccines may include the proteins from viruses implicated in human cancers such a Human Papilloma Viruses (HPV), Hepatitis Viruses (HBV and HCV), Epstein-Barr virus (EBV), and Kaposi's Herpes Sarcoma Virus (KHSV). Another form of tumor specific antigen which may be used in conjunction with LAG-3 blockade is purified heat shock proteins (HSP) isolated from the tumor tissue itself. These heat shock proteins contain fragments of proteins from the tumor cells and these HSPs are highly efficient at delivery to antigen presenting cells for eliciting tumor immunity (Suot, R & Srivastava, P (1995) Science 269:1585-1588; Tamura, Y. et al. (1997) Science 278:117-120).

Dendritic cells (DC) are potent antigen presenting cells that can be used to prime antigen-specific responses. DC's can be produced ex vivo and loaded with various protein and peptide antigens as well as tumor cell extracts (Nestle, F. et al. (1998) Nature Medicine 4:328-332). DCs may also be transduced by genetic means to express these tumor antigens as well. DCs have also been fused directly to tumor cells for the purposes of immunization (Kugler, A. et al. (2000) Nature Medicine 6:332-336). As a method of vaccination, DC immunization may be effectively combined with LAG-3 blockade to activate more potent anti-tumor responses.

In some embodiments, the combination further includes an inhibitor or activator of an immune checkpoint modulator (e.g., a PD-1 inhibitor (e.g., an anti-PD-1 antibody molecule), a PD-L1 inhibitor (e.g., an anti-PD-L1 antibody molecule), a TIM-3 modulator (e.g., a TIM-3 activator or inhibitor, e.g., an anti-TIM-3 antibody molecule), or a CTLA-4 inhibitor (e.g., an anti-CTLA4 antibody), or any combination thereof.

LAG-3 blockade may also be combined with a standard cancer treatment. LAG-3 blockade may be effectively combined with chemotherapeutic regimes. In these instances, it may be possible to reduce the dose of chemotherapeutic reagent administered (Mokyr, M. et al. (1998) *Cancer Research* 58:5301-5304). In certain embodiments, the methods and compositions described herein are administered in combination with one or more of other antibody molecules, chemotherapy, other anti-cancer therapy (e.g., targeted anti-cancer therapies, or oncolytic drugs), cytotoxic agents, immune-based therapies (e.g., cytokines), surgical and/or radiation procedures. Exemplary cytotoxic agents that can be administered in combination with include antimicrotubule agents, topoisomerase inhibitors, anti-metabolites, mitotic inhibitors, alkylating agents, anthracyclines, *vinca* alkaloids, intercalating agents, agents capable of interfering with a signal transduction pathway, agents that promote apoptosis, proteosome inhibitors, and radiation (e.g., local or whole body irradiation).

Alternatively, or in combination with the aforesaid combinations, the methods and compositions described herein can be administered in combination with one or more of: an immunomodulator (e.g., an activator of a costimulatory molecule or an inhibitor of an inhibitory molecule); a vaccine, e.g., a therapeutic cancer vaccine; or other forms of cellular immunotherapy.

Exemplary non-limiting combinations and uses of the anti-LAG-3 antibody molecules include the following.

In certain embodiments, the anti-LAG-3 antibody molecule is administered in combination with a modulator of a costimulatory molecule or an inhibitory molecule, e.g., a co-inhibitory ligand or receptor.

In one embodiment, the anti-LAG-3 antibody molecule is administered in combination with a modulator, e.g., agonist, of a costimulatory molecule. In one embodiment, the agonist of the costimulatory molecule is chosen from an agonist (e.g., an agonistic antibody or soluble fusion) of OX40, CD2, CD27, CDS, ICAM-1, LFA-1 (CD11a/CD18), ICOS (CD278), 4-1BB (CD137), GITR, CD30, CD40, BAFFR, HVEM, CD7, LIGHT, NKG2C, SLAMF7, NKp80, CD160, B7-H3, or CD83 ligand.

In another embodiment, the anti-LAG-3 antibody molecule is used in combination with a costimulatory molecule, e.g., an agonist associated with a positive signal that includes a costimulatory domain of CD28, CD27, ICOS and GITR.

Exemplary GITR agonists include, e.g., GITR fusion proteins and anti-GITR antibodies (e.g., bivalent anti-GITR antibodies) such as, e.g., a GITR fusion protein described in U.S. Pat. No. 6,111,090, European Patent No.: 090505B1, U.S. Pat. No. 8,586,023, PCT Publication Nos.: WO 2010/003118 and 2011/090754, or an anti-GITR antibody described, e.g., in U.S. Pat. No. 7,025,962, European Patent No.: 1947183B1, U.S. Pat. Nos. 7,812,135, 8,388,967, 8,591,886, European Patent No.: EP 1866339, PCT Publication No.: WO 2011/028683, PCT Publication No.: WO 2013/039954, PCT Publication No.: WO2005/007190, PCT Publication No.: WO 2007/133822, PCT Publication No.: WO2005/055808, PCT Publication No.: WO 99/40196, PCT Publication No.: WO 2001/03720, PCT Publication No.: WO99/20758, PCT Publication No.: WO2006/083289, PCT Publication No.: WO 2005/115451, U.S. Pat. No. 7,618,632, and PCT Publication No.: WO 2011/051726. One exemplary anti-GITR antibody is TRX518.

In one embodiment, the anti-LAG-3 antibody molecule is administered in combination with an inhibitor of an inhibitory molecule (e.g., an inhibitor of an immune checkpoint molecule). It will be understood by those of ordinary skill in the art, that the term "immune checkpoints" means a group of molecules on the cell surface of CD4 and CD8 T cells. These molecules can effectively serve as "brakes" to down-modulate or inhibit an anti-tumor immune response. Immune checkpoint molecules include, but are not limited to, Programmed Death 1 (PD-1), Cytotoxic T-Lymphocyte Antigen 4 (CTLA-4), B7H1, B7H4, OX-40, CD137, CD40, and TIM-3, which directly inhibit immune cells, immunotherapeutic agents which can act as immune checkpoint inhibitors useful in the methods of the present invention, include, but are not limited to, inhibitors of PD-1, PD-L1, PD-L2, CTLA-4, TIM-3, VISTA, BTLA, TIGIT, LAIR1, CD160, 2B4, CEACAM (e.g., CEACAM-1 and/or CEACAM-5), and/or TGFR beta. Inhibition of an inhibitory molecule can be performed by inhibition at the DNA, RNA or protein level. In embodiments, an inhibitory nucleic acid (e.g., a dsRNA, siRNA or shRNA), can be used to inhibit expression of an inhibitory molecule. In other embodiments, the inhibitor of an inhibitory signal is, a polypeptide e.g., a soluble ligand, or an antibody or antibody fragment, that binds to the inhibitory molecule. Exemplary TIM-3 antibody molecules include, but are not limited to, MBG220, MBG227, and MBG219.Exemplary TIGIT inhibitors include, but are not limited to, 10A7 and 1F4 (Roche).

Further examples of modulators include but are not limited to B7-H5, ENTPD1, ENTPD2, SIGGIR, B7-1, B7-2, VSIG4, TIM-1, CD200, RANKL, and P2X7.

In one embodiment, the inhibitor is a soluble ligand (e.g., a CTLA-4-Ig or a TIM-3-Ig), or an antibody or antibody fragment that binds to PD-L1, PD-L2 or CTLA4. For example, the anti-LAG-3 antibody molecule can be administered in combination with an anti-CTLA-4 antibody, e.g., ipilimumab. Exemplary anti-CTLA4 antibodies include Tremelimumab (IgG2 monoclonal antibody available from Pfizer, formerly known as ticilimumab, CP-675,206); and Ipilimumab (CTLA-4 antibody, also known as MDX-010, CAS No. 477202-00-9). In one embodiment, the anti-LAG-3 antibody molecule is administered after treatment, e.g., after treatment of a melanoma, with an anti-CTLA4 antibody (e.g., ipilimumab) with or without a BRAF inhibitor (e.g., vemurafenib or dabrafenib). In one embodiment, the anti-CTLA-4 antibody, e.g., ipilimumab, is administered at a dose of about 3 mg/kg. The anti-LAG-3 antibody molecule can be administered in combination at a dose from about 20 to 800 mg, e.g., about 20, 80, 240, or 800 mg. In one embodiment, the anti-LAG-3 antibody molecule is administered every 2 weeks (e.g., during weeks 1, 3, 5, 7) during each 8 week cycle, e.g., up to 96 weeks.

In another embodiment, the anti-LAG-3 antibody molecule is administered in combination with an anti-PD-1 antibody molecule. Exemplary doses that can be use include a dose of anti-PD-1 antibody molecule of about 1 to 10 mg/kg, e.g., 3 mg/kg. The anti-LAG-3 antibody molecule can be administered in combination at a dose from about 20 to 800 mg, e.g., about 20, 80, 240, or 800 mg. In one embodiment, the anti-LAG-3 antibody molecule is administered every 2 weeks (e.g., during weeks 1, 3, 5, 7) during each 8 week cycle, e.g., up to 96 weeks.

Immune inhibitory molecules, e.g., PD-1 and LAG-3, can regulate, e.g., synergistically, T-cell function to promote tumoral immune escape. In another embodiment, the anti-LAG-3 antibody molecule is administered in combination with an anti-TIM-3 antibody molecule. In still another embodiment, the anti-LAG-3 antibody molecule is administered in combination with an anti-PD-L1 antibody molecule. In yet other embodiments, the anti-LAG-3 antibody molecule is administered in combination with an anti-PD-1 antibody and an anti-TIM-3 antibody. In certain embodiments, the anti-LAG-3 antibody molecule is administered in combination with an anti-PD-1 antibody and an anti-PD-L1 antibody. In certain embodiments, the anti-LAG-3 antibody molecule is administered in combination with an anti-TIM-3 antibody and an anti-PD-L1 antibody. The combination of antibodies recited herein can be administered separately, e.g., as separate antibodies, or linked, e.g., as a bispecific or trispecific antibody molecule. In another embodiment, the anti-LAG-3 antibody molecule is administered in combination with a CEACAM inhibitor (e.g., CEACAM-1 and/or CEACAM-5 inhibitor), e.g., an anti-CEACAM antibody molecule. In another embodiment, the anti-LAG-3 antibody molecule, is administered in combination with a CEACAM-1 inhibitor, e.g., an anti-CEACAM-1 antibody molecule. In another embodiment, the anti-LAG-3 antibody molecule is administered in combination with a CEACAM-5 inhibitor, e.g., an anti-CEACAM-5 antibody molecule. In one embodiment, a bispecific antibody that includes an anti-LAG-3 antibody molecule and an anti-PD-1 or anti-LAG-3 antibody is administered. In certain embodiments, the combination of antibodies recited herein is used to treat a cancer, e.g., a cancer as described herein (e.g., a solid tumor). The efficacy of the aforesaid combinations can be tested in animal models known in the art. For example, the animal models to test the synergistic effect of anti-LAG-3 and anti-PD-1 are described, e.g., in Woo et al. (2012) *Cancer Res.* 72 (4): 917-27). In one embodiment, the inhibitor of CEACAM (e.g., CEACAM-1 and/or CEACAM-5) is an anti-CEACAM antibody molecule. Without wishing to be bound by theory, CEACAM-1 has been described as a ligand and partner of TIM-3 (see e.g., WO 2014/022332). Synergistic in vivo effect of the combination of anti-TIM-3 and anti-CEACAM-1 antibodies have been detected in xenograft cancer models (see e.g., WO 2014/022332). Tumors are believed to use CEACAM-1 or CEACAM-5 to inhibit the immune system, as described in, e.g., Markel et al. *J Immunol.* 2002-3-15;168 (6): 2803-10; Markel et al. *J Immunol.* 2006-11-1; 177 (9): 6062-71; Markel et al. *Immunology.* 2009 February; 126 (2): 186-200; Markel et al. *Cancer Immunol Immunother.* 2010 February; 59 (2): 215-30; Ortenberg et al. *Mol Cancer Ther.* 2012 June; 11 (6): 1300-10; Stern et al. *J Immunol.* 2005 Jun. 1; 174 (11): 6692-701; Zheng et al. *PLOS One.* 2010-9-2; 5 (9). pii: e12529. Thus, CEACAM inhibitors can be used with the other immunomodulators described herein (e.g., anti-LAG-3, anti-PD-1, or anti-TIM-3 inhibitors) to enhance an immune response against a cancer, e.g., melanoma, lung cancer (e.g., NSCLC), bladder, colon or ovarian cancer, or other cancers as described herein. In one embodiment, the inhibitor of CEACAM is an anti-CEACAM-1 antibody as described in WO 2010/125571, WO 2013/82366 and WO 2014/022332, e.g., a monoclonal antibody 34B1, 26H7, and 5F4 or a recombinant form thereof, as described in, e.g., US 2004/0047858, U.S. Pat. No. 7,132,255 and WO 99/52552. In other embodiments, the anti-CEACAM antibody is an anti-CEACAM-1 and/or anti-CEACAM-5 antibody molecule as described in, e.g., WO 2010/125571, WO 2013/054331 and US 2014/0271618.

In some embodiments, the LAG-3 and PD-1 immune inhibitory molecules (e.g., antibody molecules) are administered in combination with each other, e.g., to treat cancer. In some embodiments, the patient is a patient who progressed (e.g., experienced tumor growth) during therapy with a PD-1 inhibitor (e.g., an antibody molecule as described herein) and/or a PD-L1 inhibitor (e.g., antibody molecule). In some embodiments, therapy with the PD-1 antibody molecule and/or PDL1 antibody molecule is continued, and a LAG-3 immune inhibitory molecule (e.g., antibody) is added to the therapy. In other embodiments, the anti-LAG-3 antibody molecule is administered in combination with a cytokine, e.g., interleukin-21, interleukin-2, or interleukin 15. In certain embodiments, the combination of anti-LAG-3 antibody molecule and cytokine described herein is used to treat a cancer, e.g., a cancer as described herein (e.g., a solid tumor or melanoma).

Exemplary immunomodulators that can be used in combination with the anti-LAG-3 antibody molecules include, but are not limited to, e.g., afutuzumab (available from Roche®); pegfilgrastim (Neulasta®); lenalidomide (CC-5013, Revlimid®); thalidomide (Thalomid®), actimid (CC4047); and cytokines, e.g., IL-21 or IRX-2 (mixture of human cytokines including interleukin 1, interleukin 2, and interferon γ, CAS 951209-71-5, available from IRX Therapeutics).

Another example of such a combination is an anti-LAG-3 antibody in combination with decarbazine for the treatment of melanoma. Another example of such a combination is an anti-LAG-3 antibody molecule in combination with interleukin-2 (IL-2) for the treatment of melanoma. In one embodiment the anti-LAG-3 antibody molecule can be combined with IL-21. Without being bound by theory, the combined use of LAG-3 blockade and chemotherapy is that cell death, is believed to be facilitated by cell death, that is a consequence of the cytotoxic action of most chemotherapeutic compounds, which can result in increased levels of tumor antigen in the antigen presentation pathway. Other combination therapies that may result in synergy with LAG-3 blockade through cell death are radiation, surgery, and hormone deprivation. Each of these protocols creates a source of tumor antigen in the host. Angiogenesis inhibitors may also be combined with LAG-3 blockade. Inhibition of angiogenesis leads to tumor cell death which may feed tumor antigen into host antigen presentation pathways.

LAG-3 blocking antibodies can also be used in combination with bispecific antibodies. Bispecific antibodies can be used to target two separate antigens. For example anti-Fc receptor/anti tumor antigen (e.g., Her-2/neu) bispecific antibodies have been used to target macrophages to sites of tumor. This targeting may more effectively activate tumor specific responses. The T cell arm of these responses would by augmented by the use of LAG-3 blockade. Alternatively, antigen may be delivered directly to DCs by the use of bispecific antibodies which bind to tumor antigen and a dendritic cell specific cell surface marker.

Tumors evade host immune surveillance by a large variety of mechanisms. Many of these mechanisms may be overcome by the inactivation of proteins which are expressed by the tumors and which are immunosuppressive. These include among others TGF-beta (Kehrl, J. et al. (1986) *J. Exp. Med.* 163:1037-1050), IL-10 (Howard, M. & O'Garra, A. (1992) *Immunology Today* 13:198-200), and Fas ligand (Hahne, M. et al. (1996) *Science* 274:1363-1365). Antibodies to each of these entities may be used in combination with anti-LAG-3 to counteract the effects of the immunosuppressive agent and favor tumor immune responses by the host.

Other antibodies which may be used to activate host immune responsiveness can be used in combination with anti-LAG-3. These include molecules on the surface of dendritic cells which activate DC function and antigen presentation. Anti-CD40 antibodies are able to substitute effectively for T cell helper activity (Ridge, J. et al. (1998) *Nature* 393:474-478) and can be used in conjunction with LAG-3 antibodies (Ito, N. et al. (2000) *Immunobiology* 201 (5) 527-40). Activating antibodies to T cell costimulatory molecules such as CTLA-4 (e.g., U.S. Pat. No. 5,811,097), OX-40 (Weinberg, A. et al. (2000) *Immunol* 164:2160-2169), 4-1BB (Melero, I. et al. (1997) *Nature Medicine* 3:682-685 (1997), and ICOS (Hutloff, A. et al. (1999) *Nature* 397:262-266) may also provide for increased levels of T cell activation.

Additional exemplary treatments that can be used in combination with the anti-LAG-3 antibody molecules are described in the section entitled "Combination Therapies" below.

In all of the above methods, LAG-3 blockade can be combined with other forms of immunotherapy such as cytokine treatment (e.g., interferons, GM-CSF, G-CSF, IL-2, IL-21), or bispecific antibody therapy, which provides for enhanced presentation of tumor antigens (see, e.g., Holliger (1993) *Proc. Natl. Acad. Sci. USA* 90:6444-6448; Poljak (1994) *Structure* 2:1121-1123).

Methods of administering the anti-LAG-3 antibody molecules are known in the art and are described below. Suitable dosages of the molecules used will depend on the age and weight of the subject and the particular drug used. Dosages and therapeutic regimens of the anti-LAG-3 antibody molecule can be determined by a skilled artisan. In certain embodiments, the anti-LAG-3 antibody molecule is administered by injection (e.g., subcutaneously or intravenously) at a dose of about 1 to 30 mg/kg, e.g., about 5 to 25 mg/kg, about 10 to 20 mg/kg, about 1 to 5 mg/kg, or about 3 mg/kg, or about 10 mg/kg, about 20 mg/kg, about 30 mg/kg, or about 40 mg/kg. In some embodiments, the anti-LAG-3 antibody molecule is administered at a dose of about 1-3 mg/kg, or about 3-10 mg/kg. In some embodiments, the anti-LAG-3 antibody molecule is administered at a dose of about 0.5-2, 2-4, 2-5, 5-15, or 5-20 mg/kg. The dosing schedule can vary from e.g., once a week to once every 2, 3, or 4 weeks. In one embodiment, the anti-LAG-3 antibody molecule is administered at a dose from about 10 to 20 mg/kg every other week.

The antibody molecule can be used in unconjugated forms or conjugated to a second agent, e.g., a cytotoxic drug, radioisotope, or a protein, e.g., a protein toxin or a viral protein. This method includes: administering the antibody molecule, alone or conjugated to a cytotoxic drug, to a subject requiring such treatment. The antibody molecule can be used to deliver a variety of therapeutic agents, e.g., a cytotoxic moiety, e.g., a therapeutic drug, a radioisotope, molecules of plant, fungal, or bacterial origin, or biological proteins (e.g., protein toxins) or particles (e.g., a recombinant viral particles, e.g.; via a viral coat protein), or mixtures thereof.

Additional Combination Therapy

The anti-LAG-3 antibody molecule can be used in combination with other therapies. For example, the combination therapy can include a composition of the present invention co-formulated with, and/or co-administered with, one or more additional therapeutic agents, e.g., one or more anti-cancer agents, cytotoxic or cytostatic agents, hormone treatment, vaccines, and/or other immunotherapies. In other embodiments, the antibody molecules are administered in combination with other therapeutic treatment modalities, including surgery, radiation, cryosurgery, and/or thermo-therapy. Such combination therapies may advantageously utilize lower dosages of the administered therapeutic agents, thus avoiding possible toxicities or complications associated with the various monotherapies. In one embodiment, the anti-LAG-3 antibody is administered in combination with the therapies disclosed herein at a dose from about 20 to 800 mg, e.g., about 20, 80, 240, or 800 mg. In one embodiment, the anti-LAG-3 antibody molecule is administered weekly, every 2 weeks (e.g., during weeks 1, 3, 5, 7) during each 8 week cycle, e.g., up to 96 weeks.

In one embodiment, the compositions described herein are administered in combination with other antibody molecules, e.g., one or more of: an antibody described herein, a chemotherapeutic agent, a cytotoxic agent, surgical and/or radiation procedures. Exemplary chemotherapeutic and/or cytotoxic agents that can be administered in combination with include antimicrotubule agents, topoisomerase inhibitors, antimetabolites, mitotic inhibitors, alkylating agents, intercalating agents, agents capable of interfering with a signal transduction pathway, agents that promote apoptosis and radiation. Exemplary other antibody molecules that can be administered in combination include, but are not limited to, checkpoint inhibitors (e.g., PD-1, PD-L1); antibodies that stimulate an immune cell (e.g., agonistic GITR or CD137 antibodies); anti-cancer antibodies (e.g., rituximab (Rituxan® or MabThera®), trastuzumab (Herceptin®), cetuximab (Erbitux®), among others.

By "in combination with," it is not intended to imply that the therapy or the therapeutic agents must be administered at the same time and/or formulated for delivery together, although these methods of delivery are within the scope described herein. The anti-LAG-3 antibody molecules can be administered concurrently with, prior to, or subsequent to, one or more other additional therapies or therapeutic agents. The anti-LAG-3 antibody molecule and the other agent or therapeutic protocol can be administered in any order. In general, each agent will be administered at a dose and/or on a time schedule determined for that agent. In will further be appreciated that the additional therapeutic agent utilized in this combination may be administered together in a single composition or administered separately in different compositions. In general, it is expected that additional therapeutic agents utilized in combination be utilized at levels that do not exceed the levels at which they are utilized individually. In some embodiments, the levels utilized in combination will be lower than those utilized individually. The effect of the two treatments can be partially additive, wholly additive, or greater than additive. The delivery can be such that an effect of the first treatment delivered is still detectable when the second is delivered.

Antibody molecules can be administered in combination with one or more of the existing modalities for treating cancers, including, but not limited to: surgery; radiation therapy (e.g., external-beam therapy which involves three dimensional, conformal radiation therapy where the field of radiation is designed.

In certain embodiments, the anti-LAG-3 molecules described herein are administered in combination with one or more inhibitors of PD-1, PD-L1 and/or PD-L2 known in the art. The antagonist may be an antibody, an antigen binding fragment thereof, an immunoadhesin, a fusion protein, or oligopeptide.

In some embodiments, the other anti-PD-1 antibody is chosen from MDX-1106, Merck 3475 or CT-011.

In some embodiments, the PD-1 inhibitor is an immunoadhesin (e.g., an immunoadhesin comprising an extracellular or PD-1 binding portion of PD-L1 or PD-L2 fused to a constant region (e.g., an Fc region of an immunoglobulin sequence).

In some embodiments, the PD-L1 inhibitor is anti-PD-L1 antibody. In some embodiments, the anti-PD-L1 binding antagonist is chosen from YW243.55.S70, MPDL3280A, MEDI-4736, MSB-0010718C, or MDX-1105. MDX-1105, also known as BMS-936559, is an anti-PD-L1 antibody described in WO2007/005874. Antibody YW243.55.S70 (heavy and light chain variable region sequences shown in SEQ ID Nos. 20 and 21, respectively) is an anti-PD-L1 described in WO 2010/077634.

In some embodiments, the anti-PD-1 antibody is Nivolumab. Alternative names for Nivolumab include MDX-1106, MDX-1106-04. ONO-4538, or BMS-936558. In some embodiments, the anti-PD-1 antibody is Nivolumab (CAS Registry Number: 946414-94-4). Nivolumab (also referred to as BMS-936558 or MDX1106; Bristol-Myers Squibb) is a fully human IgG4 monoclonal antibody which specifically blocks PD-1. Nivolumab (clone 5C4) and other human monoclonal antibodies that specifically bind to PD-1 are disclosed in U.S. Pat. No. 8,008,449, EP2161336 and WO2006/121168.

Pidilizumab (CT-011; Cure Tech) is a humanized IgG1k monoclonal antibody that binds to PD-1. Pidilizumab and other humanized anti-PD-1 monoclonal antibodies are disclosed in WO2009/101611.

In other embodiments, the anti-PD-1 antibody is pembrolizumab. Pembrolizumab (Trade name Keytruda formerly lambrolizumab—also known as MK-3475) disclosed, e.g., in Hamid, O. et al. (2013) *New England Journal of Medicine* 369 (2): 134-44.

Other anti-PD-1 antibodies include AMP 514 (Amplimmune), LZV178, and LZV181, among others, e.g., anti-PD1 antibodies disclosed in U.S. Pat. No. 8,609,089, US2010028330, and/or US 20120114649.

In some embodiments, the anti-PD-L1 antibody is MSB0010718C. MSB0010718C (also referred to as A09-246-2; Merck Serono) is a monoclonal antibody that binds to PD-L1. Pembrolizumab and other humanized anti-PD-L1 antibodies are disclosed in WO2013/079174.

MDPL3280A (Genentech/Roche) is a human Fc optimized IgG1 monoclonal antibody that binds to PD-L1. MDPL3280A and other human monoclonal antibodies to PD-L1 are disclosed in U.S. Pat. No. 7,943,743 and U.S Publication No.: 20120039906. Other anti-PD-L1 binding agents include YW243.55.S70 (heavy and light chain variable regions are shown in SEQ ID NOs 20 and 21 in WO2010/077634) and MDX-1105 (also referred to as BMS-936559, and, e.g., anti-PD-L1 binding agents disclosed in WO2007/005874).

In some embodiments, the PD-1 inhibitor is AMP-224. AMP-224 (B7-DCIg; Amplimmune; e.g., disclosed in WO2010/027827 and WO2011/066342), is a PD-L2 Fc fusion soluble receptor that blocks the interaction between PD1 and B7-H1.

In some embodiments, the PD-1 inhibitor is MEDI4736.

Cancer Therapies

Exemplary combinations of anti-LAG-3 antibody molecules (alone or in combination with other stimulatory agents) and standard of care for cancer, include at least the following. In certain embodiments, the anti-LAG-3 antibody molecule, e.g., the anti-LAG-3 antibody molecule described herein, is used in combination with a standard of cancer care chemotherapeutic agent including, but not limited to, anastrozole (Arimidex®), bicalutamide (Casodex®)), bleomycin sulfate (Blenoxane®), busulfan (Myleran®), busulfan injection (Busulfex®), capecitabine (Xeloda®), N4-pentoxycarbonyl-5-deoxy-5-fluorocytidine, carboplatin (Paraplatin®), carmustine (BICNU®), chlorambucil (Leukeran®), cisplatin (Platinol®), cladribine (Leustatin®), cyclophosphamide (Cytoxan® or Neosar®), cytarabine, cytosine arabinoside (Cytosar-U®), cytarabine liposome injection (DepoCyt®), dacarbazine (DTIC-Dome®), dactinomycin (Actinomycin D, Cosmegan), daunorubicin hydrochloride (Cerubidine®), daunorubicin citrate liposome injection (DaunoXome®), dexamethasone, docetaxel (Taxotere®), doxorubicin hydrochloride (Adriamycin®, Rubex®), etoposide (Vepesid®), fludarabine phosphate (Fludara®), 5-fluorouracil (Adrucil®, Efudex®), flutamide (Eulexin®), tezacitibine, Gemcitabine (difluorodeoxycitidine), hydroxyurca (Hydrea®), Idarubicin (Idamycin®), ifosfamide (IFEX®), irinotecan (Camptosar®), L-asparaginase (ELSPAR®), leucovorin calcium, melphalan (Alkeran®), 6-mercaptopurine (Purinethol®)), methotrexate (Folex®), mitoxantrone (Novantrone®), mylotarg, paclitaxel (Taxol®), phoenix (Yttrium90/MX-DTPA), pentostatin, polifeprosan 20 with carmustine implant (Gliadel®), tamoxifen citrate (Nolvadex®), teniposide (Vumon®), 6-thioguanine, thiotepa, tirapazamine (Tirazone®), topotecan hydrochloride for injection (Hycamptin®), vinblastine (Velban® vincristine (Oncovin®), vinorelbine (Navelbine®), ibrutinib, idelalisib, and brentuximab vedotin.

Exemplary alkylating agents include, without limitation, nitrogen mustards, ethylenimine derivatives, alkyl sulfonates, nitrosoureas and triazenes): uracil mustard (Aminouracil Mustard®, Chlorethaminacil®, Demethyldopan®, Desmethyldopan®, Hacmanthamine®, Nordopan®, Uracil nitrogen mustard®, Uracillost®, Uracilmostaza®, Uramustin®, Uramustine®), chlormethine (Mustargen®), cyclophosphamide (Cytoxan®, Neosar®, Clafen®, Endoxan®, Procytox®, Revimmune™), ifosfamide (Mitoxana®), melphalan (Alkcran®), Chlorambucil (Leukeran®), pipobroman (Amedel®, Vercyte®), tricthylenemelamine (Hemel®, Hexalen®, Hexastat®), triethylenethiophosphoramine, Temozolomide (Temodar®), thiotepa (Thioplex®), busulfan (Busilvex®, Myleran®), carmustine (BiCNU®), lomustine (CeeNU®), streptozocin (Zanosar®), and Dacarbazine (DTIC-Dome®). Additional exemplary alkylating agents include, without limitation, Oxaliplatin (Eloxatin®); Temozolomide (Temodar® and Temodal®); Dactinomycin (also known as actinomycin-D, Cosmegen®); Melphalan (also known as L-PAM, L-sarcolysin, and phenylalanine mustard, Alkeran®); Altretamine (also known as hexamethylmelamine (HMM), Hexalen®); Carmustine (BICNUR); Bendamustine (Treanda®); Busulfan (Busulfcx® and Myleran®); Carboplatin (Paraplatin®); Lomustine (also known as CCNU, CecNU®); Cisplatin (also known as CDDP, Platinol® and Platinol®-AQ); Chlorambucil (Leukeran®); Cyclophosphamide (Cytoxan® and Neosar®); Dacarbazine (also known as DTIC, DIC and imidazole carboxamide, DTIC-Dome®); Altretamine (also known as hexamethylmelamine (HMM), Hexalen®); Ifosfamide (Ifex®); Prednumustine; Procarbazine (Matulane®); Mechlorethamine (also known as nitrogen mustard, mustine and mechloroethamine hydrochloride, Mustargen®); Streptozocin (Zanosar®); Thiotepa (also known as thiophosphoamide, TESPA and TSPA, Thioplex®); Cyclophosphamide (Endoxan®, Cytoxan®, Neosar®, Procytox®, Revimmune®); and Bendamustine HCl (Treanda®).

Exemplary anthracyclines include, e.g., doxorubicin (Adriamycin® and Rubex®); bleomycin (Ienoxane®); daunorubicin (dauorubicin hydrochloride, daunomycin, and rubidomycin hydrochloride, Cerubidine®); daunorubicin liposomal (daunorubicin citrate liposome, DaunoXome®); mitoxantrone (DHAD, Novantrone®); epirubicin (Ellence™); idarubicin (Idamycin®, Idamycin PFS®); mitomycin C (Mutamycin®); geldanamycin; herbimycin; ravidomycin; and desacetylravidomycin.

Exemplary vinca alkaloids that can be used in combination with the anti-LAG-3 antibody molecules, alone or in combination with another immunomodulator (e.g., an anti-PD-1, anti-PD-L1 or anti-TIM-3 antibody molecule) include, but ate not limited to, vinorelbine tartrate (Navelbine®), Vincristine (Oncovin®), and Vindesine (Eldisine®)); vinblastine (also known as vinblastine sulfate, vincaleukoblastine and VLB, Alkaban-AQ® and Velban®); and vinorelbine (Navelbine®).

Exemplary proteosome inhibitors that can be used in combination with the anti-LAG-3 antibody molecules, alone or in combination with another immunomodulator (e.g., an anti-PD-1, anti-PD-L1 or anti-TIM-3 antibody molecule), include, but are not limited to, bortezomib (Velcade®); carfilzomib (PX-171-007, (S)-4-Methyl-N—((S)-1-(((S)-4-methyl-1-((R)-2-methyloxiran-2-yl)-1-oxopentan-2-yl) amino)-1-oxo-3-phenylpropan-2-yl)-2-((S)-2-(2-morpholinoacetamido)-4-phenylbutanamido)-pentanamide); marizomib (NPI-0052); ixazomib citrate (MLN-9708); delanzomib (CEP-18770); and O-Methyl-N-[(2-methyl-5-thiazolyl) carbonyl]-L-scryl-O-methyl-N-[(1S)-2-[(2R)-2-methyl-2-oxiranyl]-2-oxo-1-(phenylmethyl)ethyl]-L-serinamide (ONX-0912).

In some embodiments, the anti-LAG-3 antibody molecule, e.g., the anti-LAG-3 antibody molecule described herein, alone or in combination with another immunomodulator (e.g., an anti-PD-1, anti-PD-L1 or anti-TIM-3 antibody molecule), is used in combination with a tyrosine kinase inhibitor (e.g., a receptor tyrosine kinase (RTK) inhibitor). Exemplary tyrosine kinase inhibitor include, but are not limited to, an epidermal growth factor (EGF) pathway inhibitor (e.g., an epidermal growth factor receptor (EGFR) inhibitor), a vascular endothelial growth factor (VEGF) pathway inhibitor (e.g., a vascular endothelial growth factor receptor (VEGFR) inhibitor (e.g., a VEGFR-1 inhibitor, a VEGFR-2 inhibitor, a VEGFR-3 inhibitor)), a platelet derived growth factor (PDGF) pathway inhibitor (e.g., a platelet derived growth factor receptor (PDGFR) inhibitor (e.g., a PDGFR-β inhibitor)), a RAF-1 inhibitor, a KIT inhibitor, and a RET inhibitor. In some embodiments, the anti-cancer agent used in combination with the hedgehog inhibitor is selected from the group consisting of: axitinib (AG013736), bosutinib (SKI-606), cediranib (RECENTIN™, AZD2171), dasatinib (SPRYCEL®, BMS-354825), erlotinib (TARCEVA®), gefitinib (IRESSA®), imatinib (GLEEVEC®, CGP57148B, STI-571), lapatinib (TYKERB®, TYVERB®), lestaurtinib (CEP-701), neratinib (HKI-272), nilotinib (TASIGNA®), semaxanib (scmaxinib, SU5416), sunitinib (SUTENT®, SU11248), toceranib (PALLADIA®), vandctanib (ZACTIMA®, ZD6474), vatalanib (PTK787, PTK/ZK), trastuzumab (HERCEPTIN®), bevacizumab (AVASTIN®), rituximab (RITUXAN®), cetuximab (ERBITUX®), panitumumab (VECTIBIX®), ranibizumab (Lucentis®), nilotinib (TASIGNA®), sorafenib (NEXAVAR®), alemtuzumab (CAMPATH®), gemtuzumab ozogamicin (MYLOTARG®), ENMD-2076, PCI-32765, AC220, dovitinib lactate (TKI258, CHIR-258), BIBW 2992 (TOVOK™), SGX523, PF-04217903, PF-02341066, PF-299804, BMS-777607, ABT-869, MP470, BIBF 1120 (VARGATEF®), AP24534, JNJ-26483327, MGCD265, DCC-2036, BMS-690154, CEP-11981, tivozanib (AV-951), OSI-930, MM-121, XL-184, XL-647, XL228, AEE788, AG-490, AST-6, BMS-599626, CUDC-101, PD153035, pelitinib (EKB-569), vandetanib (zactima), WZ3146, WZ4002, WZ8040, ABT-869 (linifanib), AEE788, AP24534 (ponatinib), AV-951 (tivozanib), axitinib, BAY 73-4506 (regorafenib), brivanib alaninate (BMS-582664), brivanib (BMS-540215), cediranib (AZD2171), CHIR-258 (dovitinib), CP 673451, CYC116, E7080, Ki8751, masitinib (AB1010), MGCD-265, motesanib diphosphate (AMG-706), MP-470, OSI-930, Pazopanib Hydrochloride, PD173074, Sorafenib Tosylate (Bay 43-9006), SU 5402, TSU-68 (SU6668), vatalanib, XL880 (GSK1363089, EXEL-2880). Selected tyrosine kinase inhibitors are chosen from sunitinib, erlotinib, gefitinib, or sorafenib.

In certain embodiments, the anti-LAG-3 antibody molecule, e.g., the anti-LAG-3 antibody molecule described herein, alone or in combination with another immunomodulator (e.g., an anti-PD-1, anti-PD-L1 or anti-TIM-3 antibody molecule), is used in combination with a Vascular Endothelial Growth Factor (VEGF) receptor inhibitors, including but not limited to, Bevacizumab (Avastin®), axitinib (Inlyta®); Brivanib alaninate (BMS-582664, (S)—(R)-1-(4-(4-Fluoro-2-methyl-1H-indol-5-yloxy)-5-methylpyrrolo[2,1-f][1,2,4]triazin-6-yloxy) propan-2-yl) 2-aminopropanoate); Sorafenib (Nexavar®); Pazopanib (Votrient®); Sunitinib malate (Sutent®); Cediranib (AZD2171, CAS 288383-20-1); Vargatef (BIBF1120, CAS 928326-83-4); Forctinib (GSK1363089); Telatinib (BAY57-9352, CAS 332012-40-5); Apatinib (YN968D1, CAS 811803-5-1); Imatinib (GLEEVEC®); Ponatinib (AP24534, CAS 943319-70-8); Tivozanib (AV951, CAS 475108-18-0); Regorafenib (BAY73-4506, CAS 755037-3-7); Vatalanib dihydrochloride (PTK787, CAS 212141-51-0); Brivanib (BMS-540215, CAS 649735-46-6); Vandetanib (Caprelsa® or AZD6474); Motesanib diphosphate (AMG706, CAS 857876-30-3, N-(2,3-dihydro-3,3-dimethyl-1H-indol-6-yl)-2-[(4-pyridinylmethyl)amino]-3-pyridinecarboxamide, described in PCT Publication No. WO 02/066470); Dovitinib dilactic acid (TKI258, CAS 852433-84-2); Linfanib (ABT869, CAS 796967-16-3); Cabozantinib (XL184, CAS 849217-68-1); Lestaurtinib (CAS 111358-88-4); N-[5-[[[5-(1,1-Dimethylethyl)-2-oxazolyl]methyl]thio]-2-thiazolyl]-4-piperidinecarboxamide (BMS38703, CAS 345627-80-7); (3R,4R)-4-Amino-1-((4-((3-methoxyphenyl)amino) pyrrolo[2,1-f][1,2,4]triazin-5-yl)methyl) piperidin-3-ol (BMS690514); N-(3,4-Dichloro-2-fluorophenyl)-6-methoxy-7-[[(3aα,5B,6aα)-octahydro-2-methylcyclopenta[c]pyrrol-5-yl]methoxy]-4-quinazolinamine (XL647, CAS 781613-23-8); 4-Methyl-3-[[1-methyl-6-(3-pyridinyl)-1H-pyrazolo[3,4-d]pyrimidin-4-yl]amino]-N-[3-(trifluoromethyl)phenyl]-benzamide (BHG712, CAS 940310-85-0); and Aflibercept (Eylea®).

Exemplary anti-VEGF antibodies include, but are not limited to, a monoclonal antibody that binds to the same epitope as the monoclonal anti-VEGF antibody A4.6.1 produced by hybridoma ATCC™ HB 10709; a recombinant humanized anti-VEGF monoclonal antibody generated according to Presta et al. (1997) Cancer Res. 57:4593-4599. In one embodiment, the anti-VEGF antibody is Bevacizumab (BV), also known as rhuMAb VEGF or AVASTIN®. It comprises mutated human IgG1 framework regions and antigen-binding complementarity-determining regions from the murine anti-hVEGF monoclonal antibody A.4.6.1 that blocks binding of human VEGF to its receptors. Bevacizumab and other humanized anti-VEGF antibodies are further described in U.S. Pat. No. 6,884,879 issued Feb. 26, 2005. Additional antibodies include the G6 or B20 series antibodies (e.g., G6-31, B20-4.1), as described in PCT Publication No. WO2005/012359, PCT Publication No. WO2005/044853, the contents of these patent applications are expressly incorporated herein by reference. For additional antibodies see U.S. Pat. Nos. 7,060,269, 6,582,959, 6,703,020, 6,054,297; WO98/45332; WO 96/30046; WO94/10202; EP 0666868B1; U.S. Patent Application Publication Nos. 2006009360, 20050186208, 20030206899, 20030190317, 20030203409, and 20050112126; and Popkov et al. Journal of Immunological Methods 288:149-164 (2004). Other antibodies include those that bind to a functional epitope on human VEGF comprising of residues F17, M1 8, D19, Y21, Y25, Q89, 191, K1 01, E1 03, and C104 or, alternatively, comprising residues F17, Y21, Q22, Y25, D63, 183 and Q89.

In some embodiments, the anti-LAG-3 antibody molecule, e.g., the anti-LAG-3 antibody molecule described herein, alone or in combination with another immunomodulator (e.g., an anti-PD-1, anti-PD-L1 or anti-TIM-3 antibody molecule), is used in combination with a PI3K inhibitor. In one embodiment, the PI3K inhibitor is an inhibitor of delta and gamma isoforms of PI3K. Exemplary PI3K inhibitors that can be used in combination are described in, e.g., WO 2010/036380; WO 2010/006086, WO 09/114870, WO 05/113556. Exemplary PI3K inhibitors that can be used in combination include, e.g., GSK 2126458, GDC-0980, GDC-0941, Sanofi XL147, XL756, XL147, PF-46915032, BKM 120, CAL-101, CAL 263, SF1126, PX-886, and a dual PI3K inhibitor (e.g., Novartis BEZ235).

In some embodiments, the anti-LAG-3 antibody molecule described herein, alone or in combination with another immunomodulator (e.g., an anti-PD-1, anti-PD-L1 or anti-TIM-3 antibody molecule), is used in combination with a mTOR inhibitor, e.g., one or more mTOR inhibitors chosen from one or more of rapamycin, temsirolimus (TORISEL®), AZD8055, BEZ235, BGT226, XL765, PF-4691502, GDC0980, SF1126, OSI-027, GSK1059615, KU-0063794, WYE-354, Palomid 529 (P529), PF-04691502, or PKI-587, ridaforolimus (formally known as deferolimus, (1R,2R,4S)-4-[(2R)-2 [(1R,9S,12S, 15R, 16E, 18R, 19R,21R, 23S,24E, 26E,28Z,30S,32S,35R)-1,18-dihydroxy-19,30-dimethoxy-15,17,21,23, 29,35-hexamethyl-2,3,10,14,20-pentaoxo-11, 36-dioxa-4-azatricyclo[30.3.1.0$^{4,9}$] hexatriaconta-16,24,26, 28-tetraen-12-yl]propyl]-2-methoxycyclohexyl dimethylphosphinate, also known as AP23573 and MK8669, and described in PCT Publication No. WO 03/064383); everolimus (AFINITOR® or RAD001); rapamycin (AY22989, Sirolimus®); simapimod (CAS 164301-51-3); emsirolimus, (5-{2,4-Bis[(3S)-3-methylmorpholin-4-yl]pyrido[2,3-d]pyrimidin-7-yl}-2-methoxyphenyl) methanol (AZD8055); 2-Amino-8-[trans-4-(2-hydroxyethoxy)cyclohexyl]-6-(6-methoxy-3-pyridinyl)-4-methylpyrido[2,3-d]pyrimidin-7 (8H)-one (PF04691502, CAS 1013101-36-4); and N$^2$-[1,4-dioxo-4-[[4-(4-oxo-8-phenyl-4H-1-benzopyran-2-yl) morpholinium-4-yl]methoxy] butyl]-L-arginylglycyl-L-α-aspartyIL-serine-, inner salt (SF1126, CAS 936487-67-1), and XL765.

In some embodiments, the anti-LAG-3 antibody molecule, e.g., the anti-LAG-3 antibody molecule described herein, alone or in combination with another immunomodulator (e.g., an anti-PD-1, anti-PD-L1 or anti-TIM-3 antibody molecule), is used in combination with a BRAF inhibitor, e.g., GSK2118436, RG7204, PLX4032, GDC-0879, PLX4720, and sorafenib tosylate (Bay 43-9006).

In some embodiments, the anti-LAG-3 antibody molecule, e.g., the anti-LAG-3 antibody molecule described herein, alone or in combination with another immunomodulator (e.g., an anti-PD-1, anti-PD-L1 or anti-TIM-3 antibody molecule), is used in combination with a MEK inhibitor. In some embodiments, the combination of the anti-LAG-3 antibody and the MEK inhibitor is used to treat a cancer (e.g., a cancer described herein). In some embodiments, the cancer treated with the combination is chosen from a melanoma, a colorectal cancer, a non-small cell lung cancer, an ovarian cancer, a breast cancer, a prostate cancer, a pancreatic cancer, a hematological malignancy or a renal cell carcinoma. In certain embodiments, the cancer includes a BRAF mutation (e.g., a BRAF V600E mutation), a BRAF wildtype, a KRAS wildtype or an activating KRAS mutation. The cancer may be at an early, intermediate or late stage. Any MEK inhibitor can be used in combination including, but not limited to, ARRY-142886, G02442104 (also known as GSK1120212), RDEA436, RDEA119/BAY 869766, AS703026, G00039805 (also known as AZD6244 orselumetinib), BIX 02188, BIX 02189, CI-1040 (PD-184352), PD0325901, PD98059, U0126, GDC-0973 (Methanone, [3,4-difluoro-2-[(2-fluoro-4-iodophenyl) amino]phenyl][3-hydroxy-3-(25)-2-piperidinyl-1-azetidinyl]-), G-38963, G02443714 (also known as AS703206), or a pharmaceutically acceptable salt or solvate thereof. Additional examples of MEK inhibitors are disclosed in WO 2013/019906, WO 03/077914, WO 2005/121142, WO 2007/04415, WO 2008/024725 and WO 2009/085983, the contents of which are incorporated herein by reference.

In another embodiment, the anti-LAG-3 antibody molecule, alone or in combination with another immunomodulator (e.g., an anti-PD-1, anti-PD-L1 or anti-TIM-3 antibody molecule), is used in combination with one, two or all of oxaliplatin, leucovorin or 5-FU (e.g., a FOLFOX co-treatment). Alternatively or in combination, the combination further includes a VEGF inhibitor (e.g., a VEGF inhibitor as disclosed herein). In some embodiments, the combination of the anti-LAG-3 antibody, the FOLFOX co-treatment, and the VEGF inhibitor is used to treat a cancer (e.g., a cancer described herein). In some embodiments, the cancer treated with the combination is chosen from a melanoma, a colorectal cancer, a non-small cell lung cancer, an ovarian cancer, a breast cancer, a prostate cancer, a pancreatic cancer, a hematological malignancy or a renal cell carcinoma. The cancer may be at an early, intermediate or late stage.

In some embodiments, the anti-LAG-3 antibody molecule, e.g., the anti-LAG-3 antibody molecule described herein, alone or in combination with another immunomodulator (e.g., an anti-PD-1, anti-PD-L1 or anti-TIM-3 antibody molecule), is used in combination with a JAK2 inhibitor, e.g., CEP-701, INCB18424, CP-690550 (tasocitinib).

In some embodiments, the pharmaceutical composition described herein, alone or in combination with another immunomodulator (e.g., an anti-PD-1, anti-PD-L1 or anti-TIM-3 antibody molecule), is used in combination with paclitaxel or a paclitaxel agent, e.g., TAXOL®, protein-bound paclitaxel (e.g., ABRAXANE®). Exemplary paclitaxel agents include, but are not limited to, nanoparticle albumin-bound paclitaxel (ABRAXANE, marketed by Abraxis Bioscience), docosahexaenoic acid bound-paclitaxel (DHA-paclitaxel, Taxoprexin, marketed by Protarga), polyglutamate bound-paclitaxel (PG-paclitaxel, paclitaxel poliglumex, CT-2103, XYOTAX, marketed by Cell Therapeutic), the tumor-activated prodrug (TAP), ANG105 (Angiopep-2 bound to three molecules of paclitaxel, marketed by ImmunoGen), paclitaxel-EC-1 (paclitaxel bound to the erbB2-recognizing peptide EC-1; see Li et al., *Biopolymers* (2007) 87:225-230), and glucose-conjugated paclitaxel (e.g., 2'-paclitaxel methyl 2-glucopyranosyl succinate, see Liu et al., *Bioorganic & Medicinal Chemistry Letters* (2007) 17:617-620).

Radiation therapy can be administered through one of several methods, or a combination of methods, including without limitation external-beam therapy, internal radiation therapy, implant radiation, stereotactic radiosurgery, systemic radiation therapy, radiotherapy and permanent or temporary interstitial brachytherapy. The term "brachytherapy," refers to radiation therapy delivered by a spatially confined radioactive material inserted into the body at or near a tumor or other proliferative tissue disease site. The term is intended without limitation to include exposure to radioactive isotopes (e.g. At-211, I-131, I-125, Y-90, Re-186, Re-188, Sm-153, Bi-212. P-32, and radioactive isotopes of Lu). Suitable radiation sources for use as a cell conditioner of the present invention include both solids and liquids. By way of non-limiting example, the radiation source can be a radionuclide, such as I-125, I-131, Yb-169, Ir-192 as a solid source, I-125 as a solid source, or other radionuclides that emit photons, beta particles, gamma radiation, or other therapeutic rays. The radioactive material can also be a fluid made from any solution of radionuclide (s), e.g., a solution of I-125 or I-131, or a radioactive fluid can be produced using a slurry of a suitable fluid containing small particles of solid radionuclides, such as Au-198, Y-90. Moreover, the radionuclide(s) can be embodied in a gel or radioactive micro spheres.

Anti-LAG-3 antibody molecules, alone or in combination with another immunomodulator (e.g., an anti-PD-1, anti-PD-L1 or anti-TIM-3 antibody molecule), can be administered in combination with one or more of the existing modalities for treating cancers, including, but not limited to: surgery; radiation therapy (e.g., external-beam therapy which involves three dimensional, conformal radiation therapy where the field of radiation is designed, local radiation (e.g., radition directed to a preselected target or organ), or focused radiation). Focused radiation can be selected from the group consisting of stereotactic radiosurgery, fractionated stereotactic radiosurgery, and intensity-modulated radiation therapy. The focused radiation can have a radiation source selected from the group consisting of a particle beam (proton), cobalt-60 (photon), and a linear accelerator (x-ray), e.g., as described in WO 2012/177624.

In certain embodiments, the anti-LAG-3 antibody molecule, alone or in combination with another immunomodulator (e.g., an anti-PD-1, anti-PD-L1 or anti-TIM-3 antibody molecule), is used with an antibody against a Killer-cell Immunoglobulin-like Receptor (also referred to herein as an "anti-KIR antibody"), a pan-KIR antibody, an anti-NKG2D antibody, and an anti-MICA antibody. In certain embodiments, the combination of anti-LAG-3 antibody molecule, anti-PD-1 antibody molecule and anti-KIR antibody, pan-KIR antibody, anti-MICA antibody, or anti-NKG2D antibody described herein is used to treat a cancer, e.g., a cancer as described herein (e.g., a solid tumor, e.g., an advanced solid tumor).

In one embodiment, the anti-LAG-3 antibody molecule, alone or in combination with another immunomodulator (e.g., an anti-PD-1, anti-PD-L1 or anti-TIM-3 antibody molecule), is used with a cellular immunotherapy (e.g., Provenge (e.g., Sipuleucel)), and optionally in combination with cyclophosphamide. In certain embodiments, the combination of anti-LAG-3 antibody molecule, anti-PD-1 antibody molecule, Provenge and/or cyclophosphamide is used to treat a cancer, e.g., a cancer as described herein (e.g., a prostate cancer, e.g., an advanced prostate cancer).

In another embodiment, anti-LAG-3 antibody molecule, alone or in combination with another immunomodulator (e.g., an anti-PD-1, anti-PD-L1 or anti-TIM-3 antibody molecule), is used with a vaccine, e.g., a dendritic cell renal carcinoma (DC-RCC) vaccine. In certain embodiments, the combination of anti-LAG-3 antibody molecule, anti-PD-1 antibody molecule and/or the DC-RCC vaccine is used to treat a cancer, e.g., a cancer as described herein (e.g., a renal carcinoma, e.g., metastatic renal cell carcinoma (RCC)).

In one embodiment, the anti-LAG-3 antibody molecule, alone or in combination with another immunomodulator (e.g., an anti-PD-1, anti-PD-L1 or anti-TIM-3 antibody molecule), is used in combination with chemotherapy to treat a lung cancer, e.g., non-small cell lung cancer. In one embodiment, the anti-LAG-3 antibody molecule is used with platinum doublet therapy to treat lung cancer.

In yet another embodiment, the anti-LAG-3 antibody molecule, alone or in combination with another immunomodulator (e.g., an anti-PD-1, anti-PD-L1 or anti-TIM-3 antibody molecule), is used to treat a renal cancer, e.g., renal cell carcinoma (RCC) or metastatic RCC. The anti-LAG-3 antibody molecule can be administered in combination with one or more of: an immune-based strategy (e.g., interleukin-2 or interferon-«), a targeted agent (e.g., a VEGF inhibitor such as a monoclonal antibody to VEGF); a VEGF tyrosine kinase inhibitor such as sunitinib, sorafenib, axitinib and pazopanib; an RNAi inhibitor), or an inhibitor of a downstream mediator of VEGF signaling. e.g., an inhibitor of the mammalian target of rapamycin (mTOR), e.g., everolimus and temsirolimus.

An example of suitable therapeutics for use in combination with the anti-LAG-3 antibody molecule, alone or in combination with another immunomodulator (e.g., an anti-PD-1, anti-PD-L1 or anti-TIM-3 antibody molecule), described herein for treatment of pancreatic cancer includes, but is not limited to, a chemotherapeutic agent, e.g., paclitaxel or a paclitaxel agent (e.g., a paclitaxel formulation such as TAXOL, an albumin-stabilized nanoparticle paclitaxel formulation (e.g., ABRAXANE) or a liposomal paclitaxel formulation); gemcitabine (e.g., gemcitabine alone or in combination with AXP107-11); other chemotherapeutic agents such as oxaliplatin, 5-fluorouracil, capecitabine, rubitecan, epirubicin hydrochloride, NC-6004, cisplatin, docetaxel (e.g., TAXOTERE), mitomycin C, ifosfamide; interferon; tyrosine kinase inhibitor (e.g., EGFR inhibitor (e.g., erlotinib, panitumumab, cetuximab, nimotuzumab); HER2/neu receptor inhibitor (e.g., trastuzumab); dual kinase inhibitor (e.g., bosutinib, saracatinib, lapatinib, vandetanib); multikinase inhibitor (e.g., sorafenib, sunitinib, XL184, pazopanib); VEGF inhibitor (e.g., bevacizumab, AV-951, brivanib); radioimmunotherapy (e.g., XR303); cancer vaccine (e.g., GVAX, survivin peptide); COX-2 inhibitor (e.g., celecoxib); IGF-1 receptor inhibitor (e.g., AMG 479, MK-0646); mTOR inhibitor (e.g., everolimus, temsirolimus); IL-6 inhibitor (e.g., CNTO 328); cyclin-dependent kinase inhibitor (e.g., P276-00, UCN-01); Altered Energy Metabolism-Directed (AEMD) compound (e.g., CPI-613); HDAC inhibitor (e.g., vorinostat); TRAIL receptor 2 (TR-2) agonist (e.g., conatumumab); MEK inhibitor (e.g., AS703026, selumctinib, GSK1120212); Raf/MEK dual kinase inhibitor (e.g., RO5126766); Notch signaling inhibitor (e.g., MK0752); monoclonal antibody-antibody fusion protein (e.g., L19IL2); curcumin; HSP90 inhibitor (e.g., tanespimycin, STA-9090); rIL-2; denileukin diftitox; topoisomerase 1 inhibitor (e.g., irinotecan, PEP02); statin (e.g., simvastatin); Factor VIIa inhibitor (e.g., PCI-27483); AKT inhibitor (e.g., RX-0201); hypoxia-activated prodrug (e.g., TH-302); metformin hydrochloride, gamma-secretase inhibitor (e.g., RO4929097); ribonucleotide reductase inhibitor (e.g., 3-AP); immunotoxin (e.g., HuC242-DM4);

PARP inhibitor (e.g., KU-0059436, veliparib); CTLA-4 inhibitor (e.g., CP-675,206, ipilimumab); AdV-tk therapy; proteasome inhibitor (e.g., bortezomib (Velcade), NPI-0052); thiazolidinedione (e.g., pioglitazone); NPC-1C; Aurora kinase inhibitor (e.g., R763/AS703569), CTGF inhibitor (e.g., FG-3019); siG12D LODER; and radiation therapy (e.g., tomotherapy, stereotactic radiation, proton therapy), surgery, and a combination thereof. In certain embodiments, a combination of paclitaxel or a paclitaxel agent, and gemcitabine can be used with the anti-PD-1 antibody molecules described herein.

An example of suitable therapeutics for use in combination with the anti-LAG-3 antibody molecule, alone or in combination with another immunomodulator (e.g., an anti-PD-1, anti-PD-L1 or anti-TIM-3 antibody molecule), for treatment of small cell lung cancer includes, but is not limited to, a chemotherapeutic agent, e.g., etoposide, carboplatin, cisplatin, oxaliplatin, irinotecan, topotecan, gemcitabine, liposomal SN-38, bendamustine, temozolomide, belotecan, NK012, FR901228, flavopiridol); tyrosine kinase inhibitor (e.g., EGFR inhibitor (e.g., erlotinib, gefitinib, cetuximab, panitumumab); multikinase inhibitor (e.g., sorafenib, sunitinib); VEGF inhibitor (e.g., bevacizumab, vandetanib); cancer vaccine (e.g., GVAX); Bcl-2 inhibitor (e.g., oblimersen sodium, ABT-263); proteasome inhibitor (e.g., bortezomib (Velcade), NPI-0052), paclitaxel or a paclitaxel agent; docetaxel; IGF-1 receptor inhibitor (e.g., AMG 479); HGF/SF inhibitor (e.g., AMG 102, MK-0646); chloroquine; Aurora kinase inhibitor (e.g., MLN8237); radioimmunotherapy (e.g., TF2); HSP90 inhibitor (e.g., tanespimycin, STA-9090); mTOR inhibitor (e.g., everolimus); Ep-CAM-/CD3-bispecific antibody (e.g., MT110); CK-2 inhibitor (e.g., CX-4945); HDAC inhibitor (e.g., belinostat); SMO antagonist (e.g., BMS 833923); peptide cancer vaccine, and radiation therapy (e.g., intensity-modulated radiation therapy (IMRT), hypofractionated radiotherapy, hypoxia-guided radiotherapy), surgery, and combinations thereof.

An example of suitable therapeutics for use in combination with the anti-LAG-3 antibody molecule, alone or in combination with another immunomodulator (e.g., an anti-PD-1, anti-PD-L1 or anti-TIM-3 antibody molecule), for treatment of non-small cell lung cancer includes, but is not limited to, a chemotherapeutic agent, e.g., vinorelbine, cisplatin, docetaxel, pemetrexed disodium, etoposide, gemcitabine, carboplatin, liposomal SN-38, TLK286, temozolomide, topotecan, pemetrexed disodium, azacitidine, irinotecan, tegafur-gimeracil-oteracil potassium, sapacitabine); tyrosine kinase inhibitor (e.g., EGFR inhibitor (e.g., erlotinib, gefitinib, cetuximab, panitumumab, necitumumab, PF-00299804, nimotuzumab, RO5083945), MET inhibitor (e.g., PF-02341066, ARQ 197), PI3K kinase inhibitor (e.g., XL147, GDC-0941), Raf/MEK dual kinase inhibitor (e.g., RO5126766), PI3K/mTOR dual kinase inhibitor (e.g., XL765), SRC inhibitor (e.g., dasatinib), dual inhibitor (e.g., BIBW 2992, GSK1363089, ZD6474, AZD0530, AG-013736, lapatinib, MEHD7945A, linifanib), multikinase inhibitor (e.g., sorafenib, sunitinib, pazopanib, AMG 706, XL184, MGCD265, BMS-690514, R935788), VEGF inhibitor (e.g., endostar, endostatin, bevacizumab, cediranib, BIBF 1120, axitinib, tivozanib, AZD2171), cancer vaccine (e.g., BLP25 liposome vaccine, GVAX, recombinant DNA and adenovirus expressing L523S protein), Bcl-2 inhibitor (e.g., oblimersen sodium), proteasome inhibitor (e.g., bortezomib, carfilzomib, NPI-0052, MLN9708), paclitaxel or a paclitaxel agent, docetaxel, IGF-1 receptor inhibitor (e.g., cixutumumab, MK-0646, OSI 906, CP-751,871, BIIB022), hydroxychloroquine, HSP90 inhibitor (e.g., tanespimycin, STA-9090, AUY922, XL888), mTOR inhibitor (e.g., everolimus, temsirolimus, ridaforolimus), Ep-CAM-/CD3-bispecific antibody (e.g., MT110), CK-2 inhibitor (e.g., CX-4945), HDAC inhibitor (e.g., MS 275, LBH589, vorinostat, valproic acid, FR901228), DHFR inhibitor (e.g., pralatrexate), retinoid (e.g., bexarotene, tretinoin), antibody-drug conjugate (e.g., SGN-15), bisphosphonate (e.g., zoledronic acid), cancer vaccine (e.g., belagenpumatucel-L), low molecular weight heparin (LMWH) (e.g., tinzaparin, enoxaparin), GSK1572932A, melatonin, talactoferrin, dimesna, topoisomerase inhibitor (e.g., amrubicin, etoposide, karenitecin), nelfinavir, cilengitide, ErbB3 inhibitor (e.g., MM-121, U3-1287), survivin inhibitor (e.g., YM155, LY2181308), eribulin mesylate, COX-2 inhibitor (e.g., celecoxib), pegfilgrastim, Polo-like kinase 1 inhibitor (e.g., BI 6727), TRAIL receptor 2 (TR-2) agonist (e.g., CS-1008), CNGRC peptide (SEQ ID NO: 293)-TNF alpha conjugate, dichloroacetate (DCA), HGF inhibitor (e.g., SCH 900105), SAR240550, PPAR-gamma agonist (e.g., CS-7017), gamma-secretase inhibitor (e.g., RO4929097), epigenetic therapy (e.g., 5-azacitidine), nitroglycerin, MEK inhibitor (e.g., AZD6244), cyclin-dependent kinase inhibitor (e.g., UCN-01), cholesterol-Fus1, antitubulin agent (e.g., E7389), farnesyl-OH-transferase inhibitor (e.g., lonafarnib), immunotoxin (e.g., BB-10901, SS1 (dsFv) PE38), fondaparinux, vascular-disrupting agent (e.g., AVE8062), PD-L1 inhibitor (e.g., MDX-1105, MDX-1106), beta-glucan, NGR-hTNF, EMD 521873, MEK inhibitor (e.g., GSK1120212), epothilone analog (e.g., ixabepilone), kinesin-spindle inhibitor (e.g., 4SC-205), telomere targeting agent (e.g., KML-001), P70 pathway inhibitor (e.g., LY2584702), AKT inhibitor (e.g., MK-2206), angiogenesis inhibitor (e.g., lenalidomide), Notch signaling inhibitor (e.g., OMP-21M18), radiation therapy, surgery, and combinations thereof.

An example of suitable therapeutics for use in combination with the anti-LAG-3 antibody molecule, alone or in combination with another immunomodulator (e.g., an anti-PD-1, anti-PD-L1 or anti-TIM-3 antibody molecule), for treatment of ovarian cancer includes, but is not limited to, a chemotherapeutic agent (e.g., paclitaxel or a paclitaxel agent; docetaxel; carboplatin; gemcitabine; doxorubicin; topotecan; cisplatin; irinotecan, TLK286, ifosfamide, olaparib, oxaliplatin, melphalan, pemetrexed disodium, SJG-136, cyclophosphamide, etoposide, decitabine); ghrelin antagonist (e.g., AEZS-130), immunotherapy (e.g., APC8024, oregovomab, OPT-821), tyrosine kinase inhibitor (e.g., EGFR inhibitor (e.g., erlotinib), dual inhibitor (e.g., E7080), multikinase inhibitor (e.g., AZD0530, JI-101, sorafenib, sunitinib, pazopanib), ON 01910.Na), VEGF inhibitor (e.g., bevacizumab, BIBF 1120, cediranib, AZD2171), PDGFR inhibitor (e.g., IMC-3G3), paclitaxel, topoisomerase inhibitor (e.g., karenitecin, Irinotecan), HDAC inhibitor (e.g., valproate, vorinostat), folate receptor inhibitor (e.g., farletuzumab), angiopoietin inhibitor (e.g., AMG 386), epothilone analog (e.g., ixabepilone), proteasome inhibitor (e.g., carfilzomib), IGF-1 receptor inhibitor (e.g., OSI 906, AMG 479), PARP inhibitor (e.g., veliparib, AG014699, iniparib, MK-4827), Aurora kinase inhibitor (e.g., MLN8237, ENMD-2076), angiogenesis inhibitor (e.g., lenalidomide), DHFR inhibitor (e.g., pralatrexate), radioimmunotherapeutic agnet (e.g., Hu3S193), statin (e.g., lovastatin), topoisomerase 1 inhibitor (e.g., NKTR-102), cancer vaccine (e.g., p53 synthetic long peptides vaccine, autologous OC-DC vaccine), mTOR inhibitor (e.g., temsirolimus, everolimus), BCR/ABL inhibitor (e.g., imatinib), ET-A receptor antagonist (e.g., ZD4054), TRAIL receptor 2 (TR-2) agonist (e.g., CS-1008), HGF/SF inhibitor (e.g., AMG 102), EGEN-001, Polo-like kinase 1 inhibitor (e.g., BI 6727), gamma-secretase inhibitor (e.g., RO4929097), Wee-1 inhibitor (e.g., MK-1775), antitubulin agent (e.g., vinorelbine, E7389), immunotoxin (e.g., denileukin diftitox), SB-485232, vascular-disrupting agent (e.g., AVE8062), integrin inhibitor (e.g., EMD 525797), kinesin-spindle inhibitor (e.g., 4SC-205), revlimid, HER2 inhibitor (e.g., MGAH22), ErrB3 inhibitor (e.g., MM-121), radiation therapy; and combinations thereof.

In one exemplary embodiment, the anti-LAG-3 antibody molecule, alone or in combination with another immunomodulator (e.g., an anti-PD-1, anti-PD-L1 or anti-TIM-3 antibody molecule), is used to treat a myeloma, alone or in combination with one or more of: chemotherapy or other anti-cancer agents (e.g., thalidomide analogs, e.g., lenalidomide), HSCT (Cook, R. (2008) *J Manag Care Pharm.* 14 (7 Suppl): 19-25), an anti-TIM3 antibody (Hallett, W H D et al. (2011) *J of American Society for Blood and Marrow Transplantation* 17 (8): 1133-145), tumor antigen-pulsed dendritic cells, fusions (e.g., electrofusions) of tumor cells and dendritic cells, or vaccination with immunoglobulin idiotype produced by malignant plasma cells (reviewed in Yi, Q. (2009) *Cancer J.* 15 (6): 502-10).

In yet another embodiment, the anti-LAG-3 antibody molecule, alone or in combination with another immunomodulator (e.g., an anti-PD-1, anti-PD-L1 or anti-TIM-3 antibody molecule), is used to treat a renal cancer, e.g., renal cell carcinoma (RCC) or metastatic RCC. The anti-PD-1 antibody molecule can be administered in combination with one or more of: an immune-based strategy (e.g., interleukin-2 or interferon-«), a targeted agent (e.g., a VEGF inhibitor such as a monoclonal antibody to VEGF, e.g., bevacizumab (Rini, B. I. et al. (2010) *J. Clin. Oncol.* 28 (13): 2137-2143)); a VEGF tyrosine kinase inhibitor such as sunitinib, sorafenib, axitinib and pazopanib (reviewed in Pal. S. K. et al. (2014) *Clin. Advances in Hematology & Oncology* 12 (2): 90-99)); an RNAi inhibitor), or an inhibitor of a downstream mediator of VEGF signaling, e.g., an inhibitor of the mammalian target of rapamycin (mTOR), e.g., everolimus and temsirolimus (Hudes, G. et al. (2007) *N. Engl. J. Med.* 356 (22): 2271-2281, Motzer, R. J. et al. (2008) *Lancet* 372:449-456).

An example of suitable therapeutics for use in combination with the anti-LAG-3 antibody molecule, alone or in combination with another immunomodulator (e.g., an anti-PD-1, anti-PD-L1 or anti-TIM-3 antibody molecule), for treatment of chronic myelogenous leukemia (AML) according to the invention includes, but is not limited to, a chemotherapeutic (e.g., cytarabine, hydroxyurea, clofarabine, melphalan, thiotepa, fludarabine, busulfan, etoposide, cordycepin, pentostatin, capecitabine, azacitidine, cyclophosphamide, cladribine, topotecan), tyrosine kinase inhibitor (e.g., BCR/ABL inhibitor (e.g., imatinib, nilotinib), ON 01910.Na, dual inhibitor (e.g., dasatinib, bosutinib), multi-kinase inhibitor (e.g., DCC-2036, ponatinib, sorafenib, sunitinib, RGB-286638)), interferon alfa, steroids, apoptotic agent (e.g., omacetaxine mepesuccinat), immunotherapy (e.g., allogeneic CD4+ memory Th1-like T cells/microparticle-bound anti-CD3/anti-CD28, autologous cytokine induced killer cells (CIK), AHN-12), CD52 targeting agent (e.g., alemtuzumab), HSP90 inhibitor (e.g., tanespimycin, STA-9090, AUY922, XL888), mTOR inhibitor (e.g., everolimus), SMO antagonist (e.g., BMS 833923), ribonucleotide reductase inhibitor (e.g., 3-AP), JAK-2 inhibitor (e.g., INCB018424), Hydroxychloroquine, retinoid (e.g., fenretinide), cyclin-dependent kinase inhibitor (e.g., UCN-01), HDAC inhibitor (e.g., belinostat, vorinostat, JNJ-26481585), PARP inhibitor (e.g., veliparib), MDM2 antagonist (e.g., RO5045337), Aurora B kinase inhibitor (e.g., TAK-901), radioimmunotherapy (e.g., actinium-225-labeled anti-CD33 antibody HuM195), Hedgehog inhibitor (e.g., PF-04449913), STAT3 inhibitor (e.g., OPB-31121), KB004, cancer vaccine (e.g., AG858), bone marrow transplantation, stem cell transplantation, radiation therapy, and combinations thereof.

An example of suitable therapeutics for use in combination with the anti-LAG-3 antibody molecule, alone or in combination with another immunomodulator (e.g., an anti-PD-1, anti-PD-L1 or anti-TIM-3 antibody molecule), for treatment of chronic lymphocytic leukemia (CLL) includes, but is not limited to, a chemotherapeutic agent (e.g., fludarabine, cyclophosphamide, doxorubicin, vincristine, chlorambucil, bendamustine, chlorambucil, busulfan, gemcitabine, melphalan, pentostatin, mitoxantrone, 5-azacytidine, pemetrexed disodium), tyrosine kinase inhibitor (e.g., EGFR inhibitor (e.g., erlotinib), BTK inhibitor (e.g., PCI-32765), multikinase inhibitor (e.g., MGCD265, RGB-286638), CD-20 targeting agent (e.g., rituximab, ofatumumab, RO5072759, LFB-R603), CD52 targeting agent (e.g., alemtuzumab), prednisolone, darbepoetin alfa, lenalidomide, Bcl-2 inhibitor (e.g., ABT-263), immunotherapy (e.g., allogeneic CD4+ memory Th1-like T cells/microparticle-bound anti-CD3/anti-CD28, autologous cytokine induced killer cells (CIK)), HDAC inhibitor (e.g., vorinostat, valproic acid, LBH589, JNJ-26481585, AR-42), XIAP inhibitor (e.g., AEG35156), CD-74 targeting agent (e.g., milatuzumab), mTOR inhibitor (e.g., everolimus), AT-101, immunotoxin (e.g., CAT-8015, anti-Tac (Fv)-PE38 (LMB-2)), CD37 targeting agent (e.g., TRU-016), radioimmunotherapy (e.g., 131-tositumomab), hydroxychloroquine, perifosine, SRC inhibitor (e.g., dasatinib), thalidomide, PI3K delta inhibitor (e.g., CAL-101), retinoid (e.g., fenretinide), MDM2 antagonist (e.g., RO5045337), plerixafor, Aurora kinase inhibitor (e.g., MLN8237, TAK-901), proteasome inhibitor (e.g., bortezomib), CD-19 targeting agent (e.g., MEDI-551, MOR208), MEK inhibitor (e.g., ABT-348), JAK-2 inhibitor (e.g., INCB018424), hypoxia-activated prodrug (e.g., TH-302), paclitaxel or a paclitaxel agent, HSP90 inhibitor, AKT inhibitor (e.g., MK2206), HMG-COA inhibitor (e.g., simvastatin), GNKG186, radiation therapy, bone marrow transplantation, stem cell transplantation, and a combination thereof.

An example of suitable therapeutics for use in combination with the anti-LAG-3 antibody molecule, alone or in combination with another immunomodulator (e.g., an anti-PD-1, anti-PD-L1 or anti-TIM-3 antibody molecule), for treatment of acute lymphocytic leukemia (ALL) includes, but is not limited to, a chemotherapeutic agent (e.g., prednisolone, dexamethasone, vincristine, asparaginase, daunorubicin, cyclophosphamide, cytarabine, etoposide, thioguanine, mercaptopurine, clofarabine, liposomal annamycin, busulfan, etoposide, capecitabine, decitabine, azacitidine, topotecan, temozolomide), tyrosine kinase inhibitor (e.g., BCR/ABL inhibitor (e.g., imatinib, nilotinib), ON 01910.Na, multikinase inhibitor (e.g., sorafenib)), CD-20 targeting agent (e.g., rituximab), CD52 targeting agent (e.g., alemtuzumab), HSP90 inhibitor (e.g., STA-9090), mTOR inhibitor (e.g., everolimus, rapamycin), JAK-2 inhibitor (e.g., INCB018424), HER2/neu receptor inhibitor (e.g., trastuzumab), proteasome inhibitor (e.g., bortezomib), methotrexate, asparaginase, CD-22 targeting agent (e.g., epratuzumab, inotuzumab), immunotherapy (e.g., autologous cytokine induced killer cells (CIK), AHN-12), blinatumomab, cyclin-dependent kinase inhibitor (e.g., UCN-01), CD45 targeting agent (e.g., BC8), MDM2 antagonist (e.g., RO5045337), immunotoxin (e.g., CAT-8015, DT2219ARL), HDAC inhibitor (e.g., JNJ-26481585), JVRS-100, paclitaxel or a paclitaxel agent, STAT3 inhibitor (e.g., OPB-31121), PARP inhibitor (e.g., veliparib), EZN-2285, radiation therapy, steroid, bone marrow transplantation, stem cell transplantation, or a combination thereof.

An example of suitable therapeutics for use in combination with the anti-LAG-3 antibody molecule, alone or in combination with another immunomodulator (e.g., an anti-PD-1, anti-PD-L1 or anti-TIM-3 antibody molecule), for treatment of acute myeloid leukemia (AML) includes, but is not limited to, a chemotherapeutic agent (e.g., cytarabine, daunorubicin, idarubicin, clofarabine, decitabine, vosaroxin, azacitidine, clofarabine, ribavirin, CPX-351, treosulfan, elacytarabine, azacitidine), tyrosine kinase inhibitor (e.g., BCR/ABL inhibitor (e.g., imatinib, nilotinib), ON 01910.Na, multikinase inhibitor (e.g., midostaurin, SU 11248, quizartinib, sorafinib)), immunotoxin (e.g., gemtuzumab ozogamicin), DT388IL3 fusion protein, HDAC inhibitor (e.g., vorinostat, LBH589), plerixafor, mTOR inhibitor (e.g., everolimus), SRC inhibitor (e.g., dasatinib), HSP90 inhibitor (e.g., STA-9090), retinoid (e.g., bexarotene, Aurora kinase inhibitor (e.g., BI 811283), JAK-2 inhibitor (e.g., INCB018424), Polo-like kinase inhibitor (e.g., BI 6727), cenersen, CD45 targeting agent (e.g., BC8), cyclin-dependent kinase inhibitor (e.g., UCN-01), MDM2 antagonist (e.g., RO5045337), mTOR inhibitor (e.g., everolimus), LY573636-sodium, ZRx-101, MLN4924, lenalidomide, immunotherapy (e.g., AHN-12), histamine dihydrochloride, radiation therapy, bone marrow transplantation, stem cell transplantation, and a combination thereof.

An example of suitable therapeutics for use in combination with the anti-LAG-3 antibody molecule, alone or in combination with another immunomodulator (e.g., an anti-PD-1, anti-PD-L1 or anti-TIM-3 antibody molecule), for treatment of multiple myeloma (MM) includes, but is not limited to, a chemotherapeutic agent (e.g., melphalan, amifostine, cyclophosphamide, doxorubicin, clofarabine, bendamustine, fludarabine, adriamycin, SyB L-0501), thalidomide, lenalidomide, dexamethasone, prednisone, pomalidomide, proteasome inhibitor (e.g., bortezomib, carfilzomib, MLN9708), cancer vaccine (e.g., GVAX), CD-40 targeting agent (e.g., SGN-40, CHIR-12.12), perifosine, zoledronic acid, Immunotherapy (e.g., MAGE-A3, NY-ESO-1, HuMax-CD38), HDAC inhibitor (e.g., vorinostat, LBH589, AR-42), aplidin, cycline-dependent kinase inhibitor (e.g., PD-0332991, dinaciclib), arsenic trioxide, CB3304, HSP90 inhibitor (e.g., KW-2478), tyrosine kinase inhibitor (e.g., EGFR inhibitor (e.g., cetuximab), multikinase inhibitor (e.g., AT9283)), VEGF inhibitor (e.g., bevacizumab), plerixafor, MEK inhibitor (e.g., AZD6244), IPH2101, atorvastatin, immunotoxin (e.g., BB-10901), NPI-0052, radioimmunotherapeutic (e.g., yttrium Y 90 ibritumomab tiuxetan), STAT3 inhibitor (e.g., OPB-31121), MLN4924, Aurora kinase inhibitor (e.g., ENMD-2076), IMGN901, ACE-041, CK-2 inhibitor (e.g., CX-4945), radiation therapy, bone marrow transplantation, stem cell transplantation, and a combination thereof.

An example of suitable therapeutics for use in combination with the anti-LAG-3 antibody molecule, alone or in combination with another immunomodulator (e.g., an anti-PD-1, anti-PD-L1 or anti-TIM-3 antibody molecule), for treatment of prostate cancer includes, but is not limited to, a chemotherapeutic agent (e.g., docetaxel, carboplatin, fludarabine), abiraterone, hormonal therapy (e.g., flutamide, bicalutamide, nilutamide, cyproterone acetate, ketoconazole, aminoglutethimide, abarelix, degarelix, leuprolide, goserelin, triptorelin, buserelin), tyrosine kinase inhibitor (e.g., dual kinase inhibitor (e.g., lapatanib), multikinase inhibitor (e.g., sorafenib, sunitinib)), VEGF inhibitor (e.g., bevacizumab), TAK-700, cancer vaccine (e.g., BPX-101, PEP223), lenalidomide, TOK-001, IGF-1 receptor inhibitor (e.g., cixutumumab), TRC105, Aurora A kinase inhibitor (e.g., MLN8237), proteasome inhibitor (e.g., bortezomib), OGX-011, radioimmunotherapy (e.g., HuJ591-GS), HDAC inhibitor (e.g., valproic acid, SB939, LBH589), hydroxychloroquine, mTOR inhibitor (e.g., everolimus), dovitinib lactate, diindolylmethane, efavirenz, OGX-427, genistein, IMC-3G3, bafetinib, CP-675,206, radiation therapy, surgery, or a combination thereof.

An example of suitable therapeutics for use in combination with the anti-LAG-3 antibody molecules, alone or in combination with another immunomodulator (e.g., an anti-PD-1, anti-PD-L1 or anti-TIM-3 antibody molecule), for treatment of HNSCC includes, but is not limited to, one or both of Compound A8 as described herein (or a compound described in PCT Publication No. WO2010/029082) and cetuximab (e.g., Erbitux, marketed by BMS). In some embodiments, the therapeutic (e.g., the Compound A8 or compound related to A8) is a PI3K modulator, e.g., a PI3K inhibitor. In some embodiments, the therapeutic (e.g., cetuximab) modulates, e.g., inhibits, EGFR. In some embodiments, the cancer has, or is identified as having, elevated levels or activity of PI3K or EGFR compared to a control cell or reference value.

An example of suitable therapeutics for use in combination with the anti-LAG-3 antibody molecules, alone or in combination with another immunomodulator (e.g., an anti-PD-1, anti-PD-L1 or anti-TIM-3 antibody molecule), for treatment of gastric cancer, e.g., MSI-high and/or EBV+ gastric cancer, includes, but is not limited to, Compound A8 as described herein (or a compound described in PCT Publication No. WO2010/029082). In some embodiments, the therapeutic (e.g., the Compound A8 or compound related to A8) is a PI3K modulator, e.g., a PI3K inhibitor. In some embodiments, the cancer has, or is identified as having, elevated levels or activity of PI3K compared to a control cell or reference value.

An example of suitable therapeutics for use in combination with the anti-LAG-3 antibody molecules, alone or in combination with another immunomodulator (e.g., an anti-PD-1, anti-PD-L1 or anti-TIM-3 antibody molecule), for treatment of gastric cancer, e.g., MSI-high and/or RNF43-inactivated gastric cancer, includes, but is not limited to, Compound A28 as described herein (or a compound described in PCT Publication No. WO2010/101849). In some embodiments, the therapeutic (e.g., the Compound A28 or compound related to A28) is a modulator, e.g., inhibitor, of porcupine. In some embodiments, the cancer has, or is identified as having, elevated levels or activity of porcupine compared to a control cell or reference value.

An example of suitable therapeutics for use in combination with the anti-LAG-3 antibody molecules, alone or in combination with another immunomodulator (e.g., an anti-PD-1, anti-PD-L1 or anti-TIM-3 antibody molecule), for treatment of GI stromal tumor (GIST), includes, but is not limited to, Compound A16 as described herein (or a compound described in PCT Publication No. WO1999/003854). In some embodiments, the therapeutic (e.g., the Compound A16 or compound related to A16) is a modulator, e.g., inhibitor, of a tyrosine kinase. In some embodiments, the cancer has, or is determined to have, elevated levels or activity of a tyrosine kinase compared to a control cell or reference value.

An example of suitable therapeutics for use in combination with the anti-LAG-3antibody molecules, alone or in combination with another immunomodulator (e.g., an anti-PD-1, anti-PD-L1 or anti-TIM-3 antibody molecule), for treatment of NSCLC, e.g., squamous or adenocarcinoma, includes, but is not limited to, one or both of Compound A17 as described herein (or a compound described in U.S. Pat. Nos. 7,767,675 and 8,420,645) and Compound A23 as described herein (or a compound described in PCT Publication No. WO2003/077914). In some embodiments, the compound (e.g., the Compound A17 or compound related to A17) modulates, e.g., inhibits, c-MET. In some embodiments, the compound (e.g., the Compound A23 or compound related to A23) modulates, e.g., inhibits, Alk. In some embodiments, the cancer has, or is determined to have, elevated levels or activity of one or both of c-MET or Alk compared to a control cell or reference value. In some embodiments, the cancer has, or is identified as having, a mutation in EGFR.

An example of suitable therapeutics for use in combination with the anti-LAG-3 antibody molecules, alone or in combination with another immunomodulator (e.g., an anti-PD-1, anti-PD-L1 or anti-TIM-3 antibody molecule), for treatment of melanoma (e.g., NRAS melanoma) includes, but is not limited to, one or both of Compound A24 as described herein (or a compound described in U.S. Pat. Nos. 8,415,355 and 8,685,980) and Compound A34 as described herein (or a compound described in PCT Publication No. WO2003/077914). In some embodiments, the compound (e.g., the Compound A24 or compound related to A24) modulates, e.g., inhibits, one or more of JAK and CDK4/6. In some embodiments, the compound (e.g., the Compound A34 or compound related to A34) modulates, e.g., inhibits, MEK. In some embodiments, the cancer has, or is identified as having, elevated levels or activity of one or more of JAK, CDK4/6, and MEK compared to a control cell or reference value.

An example of suitable therapeutics for use in combination with the anti-LAG-3 antibody molecules, alone or in combination with another immunomodulator (e.g., an anti-PD-1, anti-PD-L1 or anti-TIM-3 antibody molecule), for treatment of melanoma (e.g., NRAS melanoma) includes, but is not limited to, one or both of Compound A29 as described herein (or a compound described in PCT Publication No. WO2011/025927) and Compound A34 as described herein (or a compound described in PCT Publication No. WO2003/077914). In some embodiments, the compound (e.g., the Compound A29 or compound related to A29) modulates, e.g., inhibits, BRAF. In some embodiments, the compound (e.g., the Compound A34 or compound related to A34) modulates, e.g., inhibits, MEK. In some embodiments, the cancer has, or is identified as having elevated levels or activity of one or both of BRAF and MEK compared to a control cell or reference value.

An example of suitable therapeutics for use in combination with the anti-LAG-3 antibody molecules, alone or in combination with another immunomodulator (e.g., an anti-PD-1, anti-PD-L1 or anti-TIM-3 antibody molecule), for treatment of squamous NSCLC includes, but is not limited to, Compound A5 as described herein (or a compound described in U.S. Pat. No. 8,552,002). In some embodiments, the compound (e.g., the Compound A5 or compound related to A5) modulates, e.g., inhibits, FGFR. In some embodiments, the cancer has, or is identified as having, elevated levels or activity of FGFR compared to a control cell or reference value.

An example of suitable therapeutics for use in combination with the anti-LAG-3antibody molecules, alone or in combination with another immunomodulator (e.g., an anti-PD-1, anti-PD-L1 or anti-TIM-3 antibody molecule), for treatment of colorectal cancer includes, but is not limited to, one or both of Compound A29 as described herein (or a compound PCT Publication No. WO2011/025927) and cetuximab (e.g., Erbitux, marketed by BMS). In some embodiments, the therapeutic (e.g., the Compound A29 or compound related to A29) modulates, e.g., inhibits, BRAF. In some embodiments, the therapeutic (e.g., cetuximab) modulates, e.g., inhibits EGFR. In some embodiments, the cancer has, or is identified as having, elevated levels or activity of BRAF or EGFR compared to a control cell or reference value.

This disclosure also provides a method of treating cancer with Compound A8, cetuximab, and a LAG-3 antibody molecule (optionally in combination with a PD-1 antibody molecule or TIM-3 antibody molecule). In some embodiments, the patient is first treated with Compound A8 and cetuximab. This treatment continues for an amount of time, e.g., a predetermined amount of time, e.g., about 1, 2, 4, 6, 8, 10, or 12 months. Next, the LAG-3 antibody molecule (optionally in combination with a PD-1 antibody molecule or TIM-3 antibody molecule) is administered. The LAG-3 antibody can optionally be administered in combination with cetuximab.

In some embodiments, the patient is first treated with all three of Compound A8, cetuximab, and a LAG-3 antibody molecule (optionally in combination with a PD-1 antibody molecule or TIM-3 antibody molecule). This treatment continues for an amount of time, e.g., a predetermined amount of time, e.g., about 6, 8, 10, or 12 months. Next, the Compound A8 and/or cetuximab can be tapered off, so that the maintenance phase involves treatment with the LAG-3 antibody molecule (e.g., as a monotherapy, or in combination with a PD-1 antibody molecule or TIM-3 antibody molecule) but not Compound A8 or cetuximab.

In other embodiments, the three compounds (Compound A8, cetuximab, and a LAG-3 antibody molecule, optionally in combination with a PD-1 antibody molecule or TIM-3 antibody molecule) are given sequentially at the outset of the treatment. For instance, Compound A8 and cetuximab can be given first, as described above. Next, the LAG-3 antibody molecule (optionally in combination with a PD-1 antibody molecule or TIM-3 antibody molecule) is added to the regimen. Next, the Compound A8 and/or cetuximab can be tapered off as described above.

Exemplary doses for the three (or more) agent regimens are as follows. The LAG-3 antibody molecule can be administered, e.g., at a dose of about 1 to 40 mg/kg, e.g., 1 to 30 mg/kg, e.g., about 5 to 25 mg/kg, about 10 to 20 mg/kg, about 1 to 5 mg/kg, or about 3 mg/kg. In some embodiments, the Compound A8 is administered at a dose of approximately 200-300, 300-400, or 200-400 mg. In some embodiments, the cetuximab is administered at a 400 mg/m$^2$ initial dose as a 120-minute intravenous infusion followed by 250 mg/m$^2$ weekly infused over 60 minutes. In embodiments, one or more of the Compound A8, cetuximab, and LAG-3 antibody molecule is administered at a dose that is lower than the dose at which that agent is typically administered as a monotherapy, e.g., about 0-10%, 10-20%, 20-30%, 30-40%, 40-50%, 50-60%, 60-70%, 70-80%, or 80-90% lower than the dose at which that agent is typically administered as a monotherapy. In embodiments, the one or more of the Compound A8, cetuximab, and LAG-3 antibody molecule is administered at a dose that is lower than the dose of that agent recited in this paragraph, e.g., about 0-10%, 10-20%, 20-30%, 30-40%, 40-50%, 50-60%, 60-70%, 70-80%, or 80-90% lower than the dose of that agent recited in this paragraph. In certain embodiments, the concentration of the Compound A8 that is required to achieve inhibition, e.g., growth inhibition, is lower when the Compound A8 is administered in combination with one or both of the cetuximab and LAG-3 antibody molecule than when the Compound A8 is administered individually. In certain embodiments, the concentration of the cetuximab that is required to achieve inhibition, e.g., growth inhibition, is lower when the cetuximab is administered in combination with one or both of the Compound A8 and LAG-3 antibody molecule than when the cetuximab is administered individually. In certain embodiments, the concentration of the LAG-3 antibody molecule that is required to achieve inhibition, e.g., growth inhibition, is lower when the LAG-3 antibody molecule is administered in combination with one or both of the cetuximab and Compound A8 than when the LAG-3 antibody molecule is administered individually.

Additionally disclosed herein is a method of treating cancer with the anti-LAG-3 antibody molecules, alone or in combination with another immunomodulator (e.g., an anti-PD-1, anti-PD-L1 or anti-TIM-3 antibody molecule), and a targeted anti-cancer agent, e.g., an agent that targets one or more proteins. In some embodiments, the anti-LAG-3 antibody molecule (and optionally other immunomodulator(s)) are administered first, and the targeted anti-cancer agent is administered second. The length of time between administration of the anti-LAG-3 antibody molecule and the targeted anti-cancer agent can be, e.g., 10, 20, or 30 minutes, 1, 2, 4, 6, or 12 hours, or 1, 2, 3, 4, 5, 6, or 7 days, or any span of time within this range. In certain embodiments, the anti-LAG-3 antibody molecule is administered repeatedly over a period of time (e.g., 1, 2, 3, 4, 5, or 6 days, or 1, 2, 4, 8, 12, 16, or 20 weeks, or any span of time within this range) before the targeted anti-cancer agent is administered. In other embodiments, the anti-LAG-3 antibody molecule and the targeted anti-cancer agent are administered at substantially the same time.

Infectious Diseases

Other methods of the invention are used to treat patients that have been exposed to particular toxins or pathogens. Accordingly, another aspect of the invention provides a method of treating an infectious disease in a subject comprising administering to the subject an anti-LAG-3 antibody molecule, such that the subject is treated for the infectious disease.

In the treatment of infection (e.g., acute and/or chronic), administration of the anti-LAG-3 antibody molecules (alone or in combination with an anti-PD-1, anti-PD-L1 or anti-TIM-3 antibody molecule) can be combined with conventional treatments in addition to or in lieu of stimulating natural host immune defenses to infection. Natural host immune defenses to infection include, but are not limited to inflammation, fever, antibody-mediated host defense, T-lymphocyte-mediated host defenses, including lymphokine secretion and cytotoxic T-cells (especially during viral infection), complement mediated lysis and opsonization (facilitated phagocytosis), and phagocytosis. The ability of the anti-LAG-3 antibody molecules to reactivate dysfunctional T-cells would be useful to treat chronic infections, in particular those in which cell-mediated immunity is important for complete recovery.

Similar to its application to tumors as discussed above, antibody mediated LAG-3 blockade can be used alone, or as an adjuvant, in combination with vaccines, to stimulate the immune response to pathogens, toxins, and self-antigens. Examples of pathogens for which this therapeutic approach may be particularly useful, include pathogens for which there is currently no effective vaccine, or pathogens for which conventional vaccines are less than completely effective. These include, but are not limited to Hepatitis (A, B, and C), Influenza, HIV, Herpes, Giardia, Malaria, *Leishmania, Staphylococcus aureus, Pseudomonas Aeruginosa*. LAG-3 blockade is particularly useful against established infections by agents such as HIV that present altered antigens over the course of the infections. These novel epitopes are recognized as foreign at the time of anti-human LAG-3 administration, thus provoking a strong T cell response that is not dampened by negative signals through LAG-3.

Viruses

For infections resulting from viral causes, the anti-LAG-3 antibody molecules (alone or in combination with an anti-PD-1, anti-PD-L1 or anti-TIM-3 antibody molecule) can be combined by application simultaneous with, prior to or subsequent to application of standard therapies for treating viral infections. Such standard therapies vary depending upon type of virus, although in almost all cases, administration of human serum containing antibodies (e.g., IgA, IgG) specific to the virus can be effective.

Some examples of pathogenic viruses causing infections treatable by methods include hepatitis (A, B, or C), influenza virus (A, B, or C), HIV, herpes virus (e.g., VZV, HSV-1, HAV-6, HSV-II, CMV. Epstein Barr virus), adenovirus, flaviviruses, echovirus, rhinovirus, coxsackie virus, cornovirus, respiratory syncytial virus, mumps virus, rotavirus, measles virus, rubella virus, parvovirus, vaccinia virus, HTLV virus, dengue virus, papillomavirus, molluscum virus, poliovirus, rabies virus, JC virus and arboviral encephalitis virus.

In one embodiment, the infection is an influenza infection. Influenza infection can result in fever, cough, myalgia, headache and malaise, which often occur in seasonal epidemics. Influenza is also associated with a number of postinfectious disorders, such as encephalitis, myopericarditis, Goodpasture's syndrome, and Reye's syndrome. Influenza infection also suppresses normal pulmonary antibacterial defenses, such that patient's recovering from influenza have an increased risk of developing bacterial pneumonia. Influenza viral surface proteins show marked antigenic variation, resulting from mutation and recombination. Thus, cytolytic T lymphocytes are the host's primary vehicle for the elimination of virus after infection. Influenza is classified into three primary types: A, B and C. Influenza A is unique in that it infects both humans and many other animals (e.g., pigs, horses, birds and seals) and is the principal cause of pandemic influenza. Also, when a cell is infected by two different influenza A strains, the segmented RNA genomes of two parental virus types mix during replication to create a hybrid replicant, resulting in new epidemic strains. Influenza B does not replicate in animals and thus has less genetic variation and influenza C has only a single serotype.

Most conventional therapies are palliatives of the symptoms resulting from infection, while the host's immune response actually clears the disease. However, certain strains (e.g., influenza A) can cause more serious illness and death. Influenza A may be treated both clinically and prophylactically by the administration of the cyclic amines inhibitors amantadine and rimantadine, which inhibit viral replication. However, the clinical utility of these drugs is limited due to the relatively high incidence of adverse reactions, their narrow anti-viral spectrum (influenza A only), and the propensity of the virus to become resistant. The administration of serum IgG antibody to the major influenza surface proteins, hemagglutinin and neuraminidase can prevent pulmonary infection, whereas mucosal IgA is required to prevent infection of the upper respiratory tract and trachea. The most effective current treatment for influenza is vaccination with the administration of virus inactivated with formalin or β-propiolactone. In one embodiment, the anti-LAG-3 antibody molecule is administered in combination with an influenza antigen or vaccine.

In another embodiment, the infection is a hepatitis infection, e.g., a Hepatitis B or C infection.

Hepatitis B virus (HB-V) is the most infectious known bloodborne pathogen. It is a major cause of acute and chronic heptatis and hepatic carcinoma, as well as life-long, chronic infection. Following infection, the virus replicates in hepatocytes, which also then shed the surface antigen HBsAg. The detection of excessive levels of HBsAg in serum is used a standard method for diagnosing a hepatitis B infection. An acute infection may resolve or it can develop into a chronic persistent infection. Current treatments for chronic HBV include α-interferon, which increases the expression of class I human leukocyte antigen (HLA) on the surface of hepatocytes, thereby facilitating their recognition by cytotoxic T lymphocytes. Additionally, the nucleoside analogs ganciclovir, famciclovir and lamivudine have also shown some efficacy in the treatment of HBV infection in clinical trials. Additional treatments for HBV include pegylated a-interferon, adenofovir, entecavir and telbivudine. While passive immunity can be conferred through parental administration of anti-HBsAg serum antibodies, vaccination with inactivated or recombinant HBsAg also confers resistance to infection. The anti-LAG-3 antibody molecule (alone or in combination with an anti-PD-1, anti-PD-L1 or anti-TIM-3 antibody molecule) may be combined with conventional treatments for hepatitis B infections for therapeutic advantage. In one embodiment, the anti-LAG-3 antibody molecule is administered in combination with a hepatitis B antigen or vaccine, and optionally in combination with an aluminum-containing adjuvant.

Hepatitis C virus (HC-V) infection may lead to a chronic form of hepatitis, resulting in cirrosis. While symptoms are similar to infections resulting from Hepatitis B, in distinct contrast to HB-V, infected hosts can be asymptomatic for 10-20 years. The anti-LAG-3 antibody molecule can be administered as a monotherapy (or in combination with an anti-PD-1, anti-PD-L1 or anti-TIM-3 antibody molecule), or all of the foregoing can be combined with the standard of care for hepatitis C infection. For example, the anti-LAG-3 antibody molecule can be administered with one or more of SOVALDI™ (sofosbuvir) OLYSIO™ (simeprevir), plus ribavirin or pegylated interferon. Although regimens that include INCIVEK™ (telaprevir) or VICTRELIS™ (boceprevir) plus ribavirin and pegylated interferon are also approved, they are associated with increased side effects and longer duration of treatment and are therefore not considered preferred regimens.

Conventional treatment for HC-V infection includes the administration of a combination of α-interferon and ribavirin. A promising potential therapy for HC-V infection is the protease inhibitor telaprevir (VX-960). Additional treatments include: anti-PD-1 antibody (e.g., MDX-1106, Medarex™), bavituximab (an antibody that binds anionic phospholipid phosphatidylserine in a B2-glycoprotein I dependent manner, Peregrine Pharmaceuticals), anti-HPV viral coat protein E2 antibod(y)(ies) (e.g., ATL 6865-Ab68+ Ab65, XTL Pharmaceuticals) and Civacir® (polyclonal anti-HCV human immune globulin). The anti-LAG-3 antibody molecules may be combined with one or more of these treatments for hepatitis C infections for therapeutic advantage. Protease, polymerase and NS5A inhibitors which may be used in combination with the anti-LAG-3 antibody molecules to specifically treat Hepatitis C infection include those described in US 2013/0045202, incorporated herein by reference.

In another embodiment, the infection is a measles virus. After an incubation of 9-11 days, hosts infected with the measles virus develop fever, cough, coryza and conjunctivitis. Within 1-2 days, an erythematous, maculopapular rash develop, which quickly spreads over the entire body. Because infection also suppresses cellular immunity, the host is at greater risk for developing bacterial superinfections, including otitis media, pneumonia and postinfectious encephalomyelitis. Acute infection is associated with significant morbidity and mortality, especially in malnourished adolescents.

Treatment for measles includes the passive administration of pooled human IgG, which can prevent infection in non-immune subjects, even if given up to one week after exposure. However, prior immunization with live, attenuated virus is the most effective treatment and prevents disease in more than 95% of those immunized. As there is one serotype of this virus, a single immunization or infection typically results in protection for life from subsequent infection.

In a small proportion of infected hosts, measles can develop into SSPE, which is a chronic progressive neurologic disorder resulting from a persistent infection of the central nervous system. SSPE is caused by clonal variants of measles virus with defects that interfere with virion assembly and budding. For these patients, reactivation of T-cells with the anti-LAG-3 antibody molecule so as to facilitate viral clearance would be desirable.

In another embodiment, the infection is HIV. HIV attacks CD4+ cells, including T-lymphocytes, monocyte-macrophages, follicular dendritic cells and Langerhan's cells, and CD4+ helper/inducer cells are depleted. As a result, the host acquires a severe defect in cell-mediated immunity. Infection with HIV results in AIDS in at least 50% of individuals, and is transmitted via sexual contact, administration of infected blood or blood products, artificial insemination with infected semen, exposure to blood-containing needles or syringes and transmission from an infected mother to infant during childbirth.

A host infected with HIV may be asymptomatic, or may develop an acute illness that resembling mononucleosis— fever, headache, sore throat, malaise and rash. Symptoms can progress to progressive immune dysfunction, including persistent fever, night sweats, weight loss, unexplained diarrhea, eczema, psoriasis, seborrheic dermatitis, herpes zoster, oral candidiasis and oral hairy leukoplakia. Opportunistic infections by a host of parasites are common in patients whose infections develop into AIDS.

Treatments for HIV include antiviral therapies including nucleoside analogs, zidovudine (AST) either alone or in combination with didanosine or zalcitabine, dideoxyinosine, dideoxycytidine, lamidvudine, stavudine; reverse transcriptive inhibitors such as delavirdine, nevirapine, loviride, and proteinase inhibitors such as saquinavir, ritonavir, indinavir and nelfinavir. The anti-LAG-3 antibody molecule (alone or in combination with an anti-PD-1, anti-PD-L1 or anti-TIM-3 antibody molecule) may be combined with conventional treatments for HIV infections for therapeutic advantage.

In another embodiment, the infection is a Cytomegalovirus (CMV). CMV infection is often associated with persistent, latent and recurrent infection. CMV infects and remains latent in monocytes and granulocyte-monocyte progenitor cells. The clinical symptoms of CMV include mononucleosis-like symptoms (i.e., fever, swollen glands, malaise), and a tendency to develop allergic skin rashes to antibiotics. The virus is spread by direct contact. The virus is shed in the urine, saliva, semen and to a lesser extent in other body fluids. Transmission can also occur from an infected mother to her fetus or newborn and by blood transfusion and organ transplants. CMV infection results in general impairment of cellular immunity, characterized by impaired blastogenic responses to nonspecific mitogens and specific CMV antigens, diminished cytotoxic ability and elevation of CD8 lymphocyte number of CD4+ lymphocytes.

Treatments of CMV infection include the anti-virals ganciclovir, foscarnet and cidovir, but these drugs are typically only prescribed in immunocompromised patients. The anti-LAG-3 antibody molecule (alone or in combination with an anti-PD-1, anti-PD-L1 or anti-TIM-3 antibody molecule) may be combined with conventional treatments for cytomegalovirus infections for therapeutic advantage.

In another embodiment, the infection is Epstein-Barr virus (EBV). EBV can establish persistent and latent infections and primarily attacks B cells. Infection with EBV results in the clinical condition of infectious mononucleosis, which includes fever, sore throat, often with exudate, generalized lymphadenopathy and splenomegaly. Hepatitis is also present, which can develop into jaundice.

While typical treatments for EBV infections are palliative of symptoms, EBV is associated with the development of certain cancers such as Burkitt's lymphoma and nasopharyngeal cancer. Thus, clearance of viral infection before these complications result would be of great benefit. The anti-LAG-3 antibody molecule (alone or in combination with an anti-PD-1, anti-PD-L1 or anti-TIM-3 antibody molecule) may be combined with conventional treatments for Epstein-Barr virus infections for therapeutic advantage.

In another embodiment, the infection is Herpes simplex virus (HSV). HSV is transmitted by direct contact with an infected host. A direct infection may be asymptomatic, but typically result in blisters containing infectious particles. The disease manifests as cycles of active periods of disease, in which lesions appear and disappear as the viral latently infect the nerve ganglion for subsequent outbreaks. Lesions may be on the face, genitals, eyes and/or hands. In some case, an infection can also cause encephalitis.

Treatments for herpes infections are directed primarily to resolving the symptomatic outbreaks, and include systemic antiviral medicines such as: acyclovir (e.g., Zovirax®), valaciclovir, famciclovir, penciclovir, and topical medications such as docosanol (Abreva®), tromantadine and zilactin. The clearance of latent infections of herpes would be of great clinical benefit. The anti-LAG-3 antibody molecule (alone or in combination with an anti-PD-1, anti-PD-L1 or anti-TIM-3 antibody molecule) may be combined with conventional treatments for herpes virus infections for therapeutic advantage.

In another embodiment, the infection is Human T-lymphotrophic virus (HTLV-1, HTLV-2). HTLV is transmitted via sexual contact, breast feeding or exposure to contaminated blood. The virus activates a subset of TH cells called Th1 cells, resulting in their overproliferation and overproduction of Th1 related cytokines (e.g., IFN-γ and TNF-α). This in turn results in a suppression of Th2 lymphocytes and reduction of Th2 cytokine production (e.g., IL-4, IL-5, IL-10 and IL-13), causing a reduction in the ability of an infected host to mount an adequate immune response to invading organisms requiring a Th2-dependent response for clearance (e.g., parasitic infections, production of mucosal and humoral antibodies).

HTLV infections cause lead to opportunistic infections resulting in bronchiectasis, dermatitis and superinfections with *Staphylococcus* spp. and *Strongyloides* spp. resulting in death from polymicrobial sepsis. HTLV infection can also lead directly to adult T-cell leukemia/lymphoma and progressive demyelinating upper motor neuron disease known as HAM/TSP. The clearance of HTLV latent infections would be of great clinical benefit. The anti-LAG-3 antibody molecules (alone or in combination with an anti-PD-1, anti-PD-L1 or anti-TIM-3 antibody molecule) may be combined with conventional treatments for HTLV infections for therapeutic advantage.

In another embodiment, the infection is Human papilloma virus (HPV). HPV primarily affects keratinocytes and occurs in two forms: cutaneous and genital. Transmission it believed to occur through direct contact and/or sexual activity. Both cutaneous and genital HPV infection, can result in warts and latent infections and sometimes recurring infections, which are controlled by host immunity which controls the symptoms and blocks the appearance of warts, but leaves the host capable of transmitting the infection to others.

Infection with HPV can also lead to certain cancers, such as cervical, anal, vulvar, penile and oropharynial cancer. There are no known cures for HPV infection, but current treatment is topical application of Imiquimod, which stimulates the immune system to attack the affected area. The clearance of HPV latent infections would be of great clinical benefit. The anti-LAG-3 antibody molecule (alone or in combination with an anti-PD-1, anti-PD-L1 or anti-TIM-3 antibody molecule) may be combined with conventional treatments for HPV infections for therapeutic advantage.

Bacterial Infections

Some examples of pathogenic bacteria causing infections treatable by methods of the invention include syphilis, *chlamydia*, rickettsial bacteria, mycobacteria, staphylococci, streptococci, pneumonococci, meningococci and conococci, *klebsiella, proteus, serratia, pseudomonas, legionella*, diphtheria, *salmonella*, bacilli, cholera, tetanus, botulism, anthrax, plague, leptospirosis, and Lymes disease bacteria. The anti-LAG-3 antibody molecule (alone or in combination with an anti-PD-1, anti-PD-L1 or anti-TIM-3 antibody molecule) can be used in combination with existing treatment modalities for the aforesaid infections. For example, Treatments for syphilis include penicillin (e.g., penicillin G.), tetracycline, doxycycline, ceftriaxone and azithromycin.

Lyme disease, caused by *Borrelia burgdorferi* is transmitted into humans through tick bites. The disease manifests initially as a localized rash, followed by flu-like symptoms including malaise, fever, headache, stiff neck and arthralgias. Later manifestations can include migratory and polyarticular arthritis, neurologic and cardiac involvement with cranial nerve palsies and radiculopathy, myocarditis and arrhythmias. Some cases of Lyme disease become persistent, resulting in irreversible damage analogous to tertiary syphilis. Current therapy for Lyme disease includes primarily the administration of antibiotics. Antibiotic-resistant strains may be treated with hydroxychloroquine or methotrexate. Antibiotic refractory patients with neuropathic pain can be treated with gabapentin. Minocycline may be helpful in late/chronic Lyme disease with neurological or other inflammatory manifestations.

Other forms of borreliois, such as those resulting from B. recurentis, *B. hermsii*, *B. turicatae*, B. parikeri., *B. hispanica, B. duttonii* and *B. persica*, as well leptospirosis (E.g., *L. interrogans*), typically resolve spontaneously unless blood titers reach concentrations to cause intrahepatic obstruction.

Fungi and Parasites

Some examples of pathogenic fungi causing infections treatable by methods of the invention include *Candida* (*albicans, krusei, glabrata, tropicalis*, etc.), *Cryptococcus neoformans, Aspergillus* (*fumigatus, niger*, etc.), Genus Mucorales (*mucor, absidia*, rhizophus), *Sporothrix schenkii, Blastomyces dermatitidis, Paracoccidioides brasiliensis, Coccidioides immitis* and *Histoplasma capsulatum*.

Some examples of pathogenic parasites causing infections treatable by methods of the invention include *Entamoeba histolytica, Balantidium coli*, Naegleriafowleri, *Acanthamoeba* sp., *Giardia lambia, Cryptosporidium* sp., *Pneumocystis carinii, Plasmodium vivax, Babesia microti, Trypanosoma brucei, Trypanosoma cruzi, Leishmania donovani, Toxoplasma* gondi, and *Nippostrongylus brasiliensis*.

Additional Combination Therapies

Combinations of anti-LAG-3 antibody molecules with one or more second therapeutics are provided herein. Many of the combinations in this section are useful in treating cancer, but other indications are also described. This section focuses on combinations of anti-LAG-3 antibody molecules, optionally in combination with one or more immunomodulators (e.g., an anti-PD-1 antibody molecule, an anti-TIM-3 antibody molecule, or an anti-PD-L1 antibody molecule), with one or more of the agents described in Table 7. In the combinations herein below, in one embodiment, the anti-LAG-3 antibody molecule comprises (i) a heavy chain variable region (VH) comprising a VHCDR1 amino acid sequence chosen from SEQ ID NO: 1, SEQ ID NO: 4 or SEQ ID NO: 286; a VHCDR2 amino acid sequence of SEQ ID NO: 2; and a VHCDR3 amino acid sequence of SEQ ID NO: 3; and (ii) a light chain variable region (VL) comprising a VLCDR amino acid sequence of SEQ ID NO: 10, a VLCDR2 amino acid sequence of SEQ ID NO: 11, and a VLCDR3 amino acid sequence of SEQ ID NO: 12.

In one embodiment, the anti-LAG-3 antibody molecule, e.g., an anti-LAG-3 antibody molecule as described herein, alone or in combination with one or more other immunomodulators, is used in combination with a PKC inhibitor, Sotrastaurin (Compound A1), or a compound disclosed in PCT Publication No. WO 2005/039549, to treat a disorder, e.g., a disorder described herein. In one embodiment, the PKC inhibitor is Sotrastaurin (Compound A1) or a compound disclosed in PCT Publication No. WO 2005/039549. In one embodiment, an anti-LAG-3 antibody molecule is used in combination with Sotrastaurin (Compound A1), or a compound as described in PCT Publication No. WO 2005/039549, to treat a disorder such as a cancer, a melanoma, a non-Hodgkin lymphoma, an inflammatory bowel disease, transplant rejection, an ophthalmic disorder, or psoriasis.

In certain embodiments, Sotrastaurin (Compound A1) is administered at a dose of about 20 to 600 mg, e.g., about 200 to about 600 mg, about 50 mg to about 450 mg, about 100 mg to 400 mg, about 150 mg to 350 mg, or about 200 mg to 300 mg, e.g., about 50 mg, 100 mg, 150 mg. 200 mg, 300 mg, 400 mg, 500 mg, or 600 mg. The dosing schedule can vary from e.g., every other day to daily, twice or three times a day.

In one embodiment, the anti-LAG-3 antibody molecule, e.g., an anti-LAG-3 antibody molecule as described herein, alone or in combination with one or more other immunomodulators, is used in combination with a BCR-ABL inhibitor, TASIGNA® (Compound A2, or a compound disclosed in PCT Publication No. WO 2004/005281, to treat a disorder, e.g., a disorder described herein. In one embodiment, the BCR-ABL inhibitor is TASIGNA®, or a compound disclosed in PCT Publication No. WO 2004/005281. In one embodiment, an anti-LAG-3 antibody molecule is used in combination with TASIGNA® (Compound A2), or a compound as described in PCT Publication No. WO 2004/005281, to treat a disorder such as a lymphocytic leukemia, Parkinson's Disease, a neurologic cancer, a melanoma, a digestive/gastrointestinal cancer, a colorectal cancer, a myeloid leukemia, a head and neck cancer, or pulmonary hypertension.

In one embodiment, the BCR-ABL inhibitor or TASIGNA® is administered at a dose of about 300 mg (e.g., twice daily, e.g., for newly diagnosed Ph+ CML-CP), or about 400 mg, e.g., twice daily, e.g., for resistant or intolerant Ph+ CML-CP and CML-AP). BCR-ABL inhibitor or a Compound A2 is administered at a dose of about 300-400 mg.

In another embodiment, the anti-LAG-3 antibody molecule, e.g., an anti-LAG-3 antibody molecule as described herein, alone or in combination with one or more other immunomodulators, is used in combination with an HSP90 inhibitor, such as 5-(2,4-dihydroxy-5-isopropylphenyl)-N-ethyl-4-(4-(morpholinomethyl)phenyl) isoxazole-3-carboxamide (Compound A3), or a compound disclosed in PCT Publication No. WO 2010/060937 or WO 2004/072051, to treat a disorder, e.g., a disorder described herein. In one embodiment, the HSP90 inhibitor is 5-(2,4-dihydroxy-5-isopropylphenyl)-N-ethyl-4-(4-(morpholinomethyl)phenyl) isoxazole-3-carboxamide (Compound A3), or a compound disclosed in PCT Publication No. WO 2010/060937 or WO 2004/072051. In one embodiment, an anti-LAG-3 antibody molecule is used in combination with 5-(2,4-dihydroxy-5-isopropylphenyl)-N-ethyl-4-(4-(morpholinomethyl)phenyl) isoxazole-3-carboxamide (Compound A3), or a compound as described in PCT Publication No. WO 2010/060937 or WO 2004/072051, to treat a disorder such as a cancer, a multiple myeloma, a non-small cell lung cancer, a lymphoma, a gastric cancer, a breast cancer, a digestive/gastrointestinal cancer, a pancreatic cancer, a colorectal cancer, a solid tumor, or a hematopoiesis disorder.

In another embodiment, the anti-LAG-3 antibody molecule, e.g., an anti-LAG-3 antibody molecule as described herein, alone or in combination with one or more other immunomodulators, is used in combination with an inhibitor of PI3K and/or mTOR, Dactolisib (Compound A4) or 8-(6-Methoxy-pyridin-3-yl)-3-methyl-1-(4-piperazin-1-yl-3-trifluoromethyl-phenyl)-1,3-dihydro-imidazo[4,5-c]quinolin-2-one (Compound A41), or a compound disclosed in PCT Publication No. WO 2006/122806, to treat a disorder, e.g., a disorder described herein. In one embodiment, the PI3K and/or mTOR inhibitor is Dactolisib (Compound A4), 8-(6-Methoxy-pyridin-3-yl)-3-methyl-1-(4-piperazin-1-yl-3-trifluoromethyl-phenyl)-1,3-dihydro-imidazo[4,5-c]quinolin-2-one (Compound A41), or a compound disclosed in PCT Publication No. WO 2006/122806. In one embodiment, an anti-LAG-3 antibody molecule is used in combination with Dactolisib (Compound A4), 8-(6-Methoxy-pyridin-3-yl)-3- methyl-1-(4-piperazin-1-yl-3-trifluoromethyl-phenyl)-1,3-dihydro-imidazo[4,5-c]quinolin-2-one (Compound A41), or a compound described in PCT Publication No. WO 2006/122806, to treat a disorder such as a cancer, a prostate cancer, a leukemia (e.g., lymphocytic leukemia), a breast cancer, a brain cancer, a bladder cancer, a pancreatic cancer, a renal cancer, a solid tumor, or a liver cancer.

In another embodiment, the anti-LAG-3 antibody molecule, e.g., an anti-LAG-3 antibody molecule as described herein, alone or in combination with one or more other immunomodulators, is used in combination with an FGFR inhibitor, 3-(2,6-dichloro-3,5-dimethoxyphenyl)-1-(6-((4-(4-ethylpiperazin-1-yl)phenyl)amino)pyrimidin-4-yl)-1-methylurea (Compound A5) or a compound disclosed in U.S. Pat. No. 8,552,002, to treat a disorder, e.g., a disorder described herein. In one embodiment, the FGFR inhibitor is 3-(2,6-dichloro-3,5-dimethoxyphenyl)-1-(6-((4-(4-ethylpiperazin-1-yl)phenyl)amino)pyrimidin-4-yl)-1-methylurca (Compound A5) or a compound disclosed in U.S. Pat. No. 8,552,002. In one embodiment, an anti-LAG-3 antibody molecule is used in combination with Compound A5, or a compound as described in U.S. Pat. No. 8,552,002, to treat a disorder such as a digestive/gastrointestinal cancer, a hematological cancer, or a solid tumor.

In one embodiment, the FGFR inhibitor or 3-(2,6-dichloro-3,5-dimethoxyphenyl)-1-(6-((4-(4-ethylpiperazin-1-yl)phenyl)amino)pyrimidin-4-yl)-1-methylurca (Compound A5) is administered at a dose of about 100-125 mg (e.g., per day), e.g., about 100 mg or about 125 mg.

In another embodiment, the anti-LAG-3 antibody molecule, e.g., an anti-LAG-3 antibody molecule as described herein, alone or in combination with one or more other immunomodulators, is used in combination with a PI3K inhibitor, Buparlisib (Compound A6), or a compound disclosed in PCT Publication No. WO 2007/084786, to treat a disorder, e.g., a disorder described herein. In one embodiment, the PI3K inhibitor is Buparlisib (Compound A6) or a compound disclosed in PCT Publication No. WO 2007/084786. In one embodiment, an anti-LAG-3 antibody molecule is used in combination with Buparlisib (Compound A6), or a compound disclosed in PCT Publication No. WO 2007/084786, to treat a disorder such as, a prostate cancer, a non-small cell lung cancer, an endocrine cancer, a leukemia, an ovarian cancer, a melanoma, a bladder cancer, a breast cancer, a female reproductive system cancer, a digestive/gastrointestinal cancer, a colorectal cancer, a glioblastoma multiforme, a solid tumor, a non-Hodgkin lymphoma, a hematopoiesis disorder, or a head and neck cancer.

In one embodiment, the PI3K inhibitor or Buparlisib (Compound A6) is administered at a dose of about 100 mg (e.g., per day).

In another embodiment, the anti-LAG-3 antibody molecule, e.g., an anti-LAG-3 antibody molecule as described herein, alone or in combination with one or more other immunomodulators, is used in combination with an FGFR inhibitor, 8-(2,6-difluoro-3,5-dimethoxyphenyl)-N-(4-((dimethylamino)methyl)-1H-imidazol-2-yl) quinoxaline-5-carboxamide (Compound A7) or a compound disclosed in PCT Publication No. WO 2009/141386 to treat a disorder, e.g., a disorder described herein. In one embodiment, the FGFR inhibitor is 8-(2,6-difluoro-3,5-dimethoxyphenyl)-N-(4-((dimethylamino)methyl)-1H-imidazol-2-yl) quinoxaline-5-carboxamide (Compound A7) or a compound disclosed in a PCT Publication No. WO 2009/141386. In one embodiment, the FGFR inhibitor is 8-(2,6-difluoro-3,5-dimethoxyphenyl)-N-(4-((dimethylamino)methyl)-1H-imidazol-2-yl) quinoxaline-5-carboxamide (Compound A7). In one embodiment, an anti-LAG-3 antibody molecule is used in combination with 8-(2,6-difluoro-3,5-dimethoxyphenyl)-N-(4-((dimethylamino)methyl)-1H-imidazol-2-yl) quinoxaline-5-carboxamide (Compound A7), or a compound disclosed in PCT Publication No. WO 2009/141386, to treat a disorder such as a cancer characterized by angiogenesis.

In one embodiment, the FGFR inhibitor or 8-(2,6-difluoro-3,5-dimethoxyphenyl)-N-(4-((dimethylamino)methyl)-1H-imidazol-2-yl) quinoxaline-5-carboxamide (Compound A7) is administered at a dose of e.g., from approximately 3 mg to approximately 5 g, more preferably from approximately 10 mg to approximately 1.5 g per person per day, optionally divided into 1 to 3 single doses which may, for example, be of the same size.

In another embodiment, the anti-LAG-3 antibody molecule, e.g., an anti-LAG-3 antibody molecule as described herein, alone or in combination with one or more other immunomodulators, is used in combination with a PI3K inhibitor, (S)—N1-(4-methyl-5-(2-(1,1,1-trifluoro-2-methylpropan-2-yl)pyridin-4-yl) thiazol-2-yl)pyrrolidine-1,2-dicarboxamide (Compound A8) or a compound disclosed PCT Publication No. WO 2010/029082 to treat a disorder, e.g., a disorder described herein. In one embodiment, the PI3K inhibitor is(S)—N1-(4-methyl-5-(2-(1,1,1-trifluoro-2-methylpropan-2-yl)pyridin-4-yl) thiazol-2-yl)pyrrolidine-1,2-dicarboxamide (Compound A8) or a compound disclosed PCT Publication No. WO 2010/029082. In one embodiment, an anti-LAG-3 antibody molecule is used in combination with (S)—N1-(4-methyl-5-(2-(1,1,1-trifluoro-2-methylpropan-2-yl)pyridin-4-yl) thiazol-2-yl)pyrrolidine-1,2-dicarboxamide (Compound A8), or a compound disclosed PCT Publication No. WO 2010/029082, to treat a disorder such as a gastric cancer, a breast cancer, a pancreatic cancer, a digestive/gastrointestinal cancer, a solid tumor, and a head and neck cancer.

In one embodiment, the PI3K inhibitor or(S)—N1-(4-methyl-5-(2-(1,1,1-trifluoro-2-methylpropan-2-yl)pyridin-4-yl) thiazol-2-yl)pyrrolidine-1,2-dicarboxamide (Compound A8) is administered at a dose of about 150-300, 200-300, 200-400, or 300-400 mg (e.g., per day), e.g., about 200, 300, or 400 mg.

In another embodiment, the anti-LAG-3 antibody molecule, e.g., an anti-LAG-3 antibody molecule as described herein, alone or in combination with one or more other immunomodulators, is used in combination with an inhibitor of cytochrome P450 (e.g., a CYP17 inhibitor) or a compound disclosed in PCT Publication No. WO 2010/149755, to treat a disorder, e.g., a disorder described herein. In one embodiment, the cytochrome P450 inhibitor (e.g., the CYP17 inhibitor) is a compound disclosed in PCT Publication No. WO 2010/149755. In one embodiment, an anti-LAG-3 antibody molecule is used in combination with a compound disclosed in PCT Publication No. WO 2010/149755, to treat prostate cancer.

In another embodiment, the anti-LAG-3 antibody molecule, e.g., an anti-LAG-3 antibody molecule as described herein, alone or in combination with one or more other immunomodulators, is used in combination with an HDM2 inhibitor, (S)-1-(4-chlorophenyl)-7-isopropoxy-6-methoxy-2-(4-(methyl(((1r,4S)-4-(4-methyl-3-oxopiperazin-1-yl)cyclohexyl)methyl)amino)phenyl)-1,2-dihydroisoquinolin-3(4H)-one (Compound A10) or a compound disclosed in PCT Publication No. WO 2011/076786 to treat a disorder, e.g., a disorder described herein). In one embodiment, the HDM2 inhibitor is(S)-1-(4-chlorophenyl)-7-isopropoxy-6-methoxy-2-(4-(methyl(((1r,4S)-4-(4-methyl-3-oxopiperazin-1-yl)cyclohexyl)methyl)amino)phenyl)-1,2-dihydroisoquinolin-3 (4H)-one (Compound A10) or a compound disclosed in PCT Publication No. WO 2011/076786. In one embodiment, an anti-LAG-3 antibody molecule is used in combination with(S)-1-(4-chlorophenyl)-7-isopropoxy-6-methoxy-2-(4-(methyl(((1r,4S)-4-(4-methyl-3-oxopiperazin-1-yl)cyclohexyl)methyl)amino)phenyl)-1,2-dihydroisoquinolin-3 (4H)-one (Compound A10), or a compound disclosed in PCT Publication No. WO 2011/076786, to treat a disorder such as a solid tumor.

In one embodiment, the HDM2 inhibitor or(S)-1-(4-chlorophenyl)-7-isopropoxy-6-methoxy-2-(4-(methyl(((1r, 4S)-4-(4-methyl-3-oxopiperazin-1-yl)cyclohexyl)methyl) amino)phenyl)-1,2-dihydroisoquinolin-3 (4H)-one (Compound A10) is administered at a dose of about 400 to 700 mg. e.g., administered three times weekly, 2 weeks on and one week off. In some embodiments, the dose is about 400, 500, 600, or 700 mg; about 400-500, 500-600, or 600-700 mg, e.g., administered three times weekly.

In another embodiment, the anti-LAG-3 antibody molecule, e.g., an anti-LAG-3 antibody molecule as described herein, alone or in combination with one or more other immunomodulators, is used in combination with an iron chelating agent, Deferasirox (also known as EXJADE®; Compound A11), or a compound disclosed in PCT Publication No. WO 1997/049395 to treat a disorder, e.g., a disorder described herein. In one embodiment, the iron chelating agent is Deferasirox or a compound disclosed in PCT Publication No. WO 1997/049395. In one embodiment, the iron chelating agent is Deferasirox (Compound A11). In one embodiment, an anti-LAG-3 antibody molecule is used in combination with Deferasirox (Compound A11), or a compound disclosed in PCT Publication No. WO 1997/049395, to treat iron overload, hemochromatosis, or myelodysplasia.

In another embodiment, the anti-LAG-3 antibody molecule, e.g., an anti-LAG-3 antibody molecule as described herein, alone or in combination with one or more other immunomodulators, is used in combination with an aromatase inhibitor, Letrozole (also known as FEMARA®; Compound A12), or a compound disclosed in U.S. Pat. No. 4,978,672 to treat a disorder, e.g., a disorder described herein. In one embodiment, the aromatase inhibitor is Letrozole (Compound A12) or a compound disclosed in U.S. Pat. No. 4,978,672. In one embodiment, an LAG-3 antibody molecule is used in combination with Letrozole (Compound A12), or a compound disclosed in U.S. Pat. No. 4,978,672, to treat a disorder such as a cancer, a leiomyosarcoma, an endometrium cancer, a breast cancer, a female reproductive system cancer, or a hormone deficiency.

In another embodiment, the anti-LAG-3 antibody molecule, e.g., an anti-LAG-3 antibody molecule as described herein, alone or in combination with one or more other immunomodulators, is used in combination with a PI3K inhibitor, e.g., a pan-PI3K inhibitor, (4S,5R)-3-(2'-amino-2-morpholino-4'-(trifluoromethyl)-[4,5'-bipyrimidin]-6-yl)-4-(hydroxymethyl)-5-methyloxazolidin-2-one (Compound A13) or a compound disclosed in PCT Publication No. WO2013/124826 to treat a disorder, e.g., a disorder described herein. In one embodiment, the PI3K inhibitor is (4S,5R)-3-(2'-amino-2-morpholino-4'-(trifluoromethyl)-[4, 5'-bipyrimidin]-6-yl)-4-(hydroxymethyl)-5-methyloxazolidin-2-one (Compound A13) or a compound disclosed in PCT Publication No. WO2013/124826. In one embodiment, an anti-LAG-3 antibody molecule is used in combination with (4S,5R)-3-(2'-amino-2-morpholino-4'-(trifluoromethyl)-[4,5'-bipyrimidin]-6-yl)-4-(hydroxymethyl)-5-methyloxazolidin-2-one (Compound A13), or a compound disclosed in PCT Publication No. WO2013/124826, to treat a disorder such as a cancer or an advanced solid tumor.

In another embodiment, the anti-LAG-3 antibody molecule, e.g., an anti-LAG-3 antibody molecule as described herein, alone or in combination with one or more other immunomodulators, is used in combination with an inhibitor of p53 and/or a p53/Mdm2 interaction, (S)-5-(5-chloro-1-methyl-2-oxo-1,2-dihydropyridin-3-yl)-6-(4-chlorophenyl)-2-(2,4-dimethoxypyrimidin-5-yl)-1-isopropyl-5,6-dihydropyrrolo[3,4-d]imidazol-4 (1H)-one (Compound A14), or a compound disclosed in PCT Publication No. WO2013/111105 to treat a disorder, e.g., a disorder described herein. In one embodiment, the p53 and/or a p53/Mdm2 interaction inhibitor is(S)-5-(5-chloro-1-methyl-2-oxo-1,2-dihydropyridin-3-yl)-6-(4-chlorophenyl)-2-(2,4-dimethoxypyrimidin-5-yl)-1-isopropyl-5,6-dihydropyrrolo[3,4-d]imidazol-4 (1H)-one (Compound A14) or a compound disclosed in PCT Publication No. WO2013/111105. In one embodiment, an anti-LAG-3 antibody molecule is used in combination with(S)-5-(5-chloro-1-methyl-2-oxo-1,2-dihydropyridin-3-yl)-6-(4-chlorophenyl)-2-(2,4-dimethoxypyrimidin-5-yl)-1-isopropyl-5, 6-dihydropyrrolo[3,4-d]imidazol-4 (1H)-one (Compound A14), or a compound disclosed in PCT Publication No. WO2013/111105, to treat a disorder such as a cancer or a soft tissue sarcoma.

In another embodiment, the anti-LAG-3 antibody molecule, e.g., an anti-LAG-3 antibody molecule as described herein, alone or in combination with one or more other immunomodulators, is used in combination with a CSF-1R tyrosine kinase inhibitor, 4-((2-(((1R,2R)-2-hydroxycyclohexyl)amino)benzo[d]thiazol-6-yl)oxy)-N-methylpicolinamide (Compound A15), or a compound disclosed in PCT Publication No. WO 2005/073224 to treat a disorder, e.g., a disorder described herein. In one embodiment, the CSF-1R tyrosine kinase inhibitor is 4-((2-(((1R,2R)-2-hydroxycyclohexyl)amino)benzo[d]thiazol-6-yl)oxy)-N-methylpicolinamide (Compound A15) or a compound disclosed in PCT Publication No. WO 2005/073224. In one embodiment, a LAG-3 antibody molecule is used in combination with 4-((2-(((1R,2R)-2-hydroxycyclohexyl)amino)benzo[d]thiazol-6-yl)oxy)-N-methylpicolinamide (Compound A15) or a compound disclosed in PCT Publication No. WO 2005/073224, to treat a disorder such as cancer.

In another embodiment, the anti-LAG-3 antibody molecule, e.g., an anti-LAG-3 antibody molecule as described herein, alone or in combination with one or more other immunomodulators, is used in combination with an apoptosis inducer and/or an angiogenesis inhibitor, such as Imatinib mesylate (also known as GLEEVEC®; Compound A16) or a compound disclosed in PCT Publication No. WO1999/003854 to treat a disorder, e.g., a disorder described. In one embodiment, the apoptosis inducer and/or an angiogenesis inhibitor is Imatinib mesylate (Compound A16) or a compound disclosed in PCT Publication No. WO1999/003854. In one embodiment, an anti-LAG-3 antibody molecule is used in combination with Imatinib mesylate (Compound A16), or a compound disclosed in PCT Publication No. WO1999/003854, to treat a disorder such as a cancer, a multiple myeloma, a prostate cancer, a non-small cell lung cancer, a lymphoma, a gastric cancer, a melanoma, a breast cancer, a pancreatic cancer, a digestive/gastrointestinal cancer, a colorectal cancer, a glioblastoma multiforme, a liver cancer, a head and neck cancer, asthma, multiple sclerosis, allergy, Alzheimer's dementia, amyotrophic lateral sclerosis, or rheumatoid arthritis.

In certain embodiments, Imatinib mesylate (Compound A16) is administered at a dose of about 100 to 1000 mg, e.g., about 200 mg to 800 mg, about 300 mg to 700 mg, or about 400 mg to 600 mg, e.g., about 200 mg. 300 mg, 400 mg, 500 mg, 600 mg, or 700 mg. The dosing schedule can vary from e.g., every other day to daily, twice or three times a day. In one embodiment, Imatinib mesylate is administered at an oral dose from about 100 mg to 600 mg daily, e.g., about 100 mg, 200 mg. 260 mg. 300 mg, 400 mg, or 600 mg daily.

In another embodiment, the anti-LAG-3 antibody molecule, e.g., an anti-LAG-3 antibody molecule as described herein, alone or in combination with one or more other immunomodulators, is used in combination with a JAK inhibitor, 2-fluoro-N-methyl-4-(7-(quinolin-6-ylmethyl) imidazo[1,2-b][1,2,4]triazin-2-yl)benzamide (Compound A17), or a dihydrochloric salt thereof, or a compound disclosed in PCT Publication No. WO 2007/070514, to treat a disorder, e.g., a disorder described herein. In one embodiment, the JAK inhibitor is 2-fluoro-N-methyl-4-(7-(quinolin-6-ylmethyl) imidazo[1,2-b][1,2,4]triazin-2-yl)benzamide (Compound A17), or a dihydrochloric salt thereof, or a compound disclosed in PCT Publication No. WO 2007/070514. In one embodiment, an LAG-3 antibody molecule is used in combination with 2-fluoro-N-methyl-4-(7-(quinolin-6-ylmethyl) imidazo[1,2-b][1,2,4]triazin-2-yl)benzamide (Compound A17), or a dihydrochloric salt thereof, or a compound disclosed in PCT Publication No. WO 2007/070514, to treat a disorder such as colorectal cancer, myeloid leukemia, hematological cancer, autoimmune disease, non-Hodgkin lymphoma, or thrombocythemia.

In one embodiment, the JAK inhibitor or a 2-fluoro-N-methyl-4-(7-(quinolin-6-ylmethyl) imidazo[1,2-b][1,2,4]triazin-2-yl)benzamide (Compound A17), or a dihydrochloric salt thereof is administered at a dose of about 400-600 mg (e.g., per day), e.g., about 400, 500, or 600 mg, or about 400-500 or 500-600 mg.

In another embodiment, the anti-LAG-3 antibody molecule, e.g., an anti-LAG-3 antibody molecule as described herein, alone or in combination with one or more other immunomodulators, is used in combination with a JAK inhibitor, Ruxolitinib Phosphate (also known as JAKAFI®; Compound A18) or a compound disclosed in PCT Publication No. WO 2007/070514 to treat a disorder, e.g., a disorder described herein. In one embodiment, the JAK inhibitor is Ruxolitinib Phosphate (Compound A18) or a compound disclosed in PCT Publication No. WO 2007/070514. In one embodiment, an anti-LAG-3 antibody molecule is used in combination with Ruxolitinib Phosphate (Compound A18), or a compound disclosed in PCT Publication No. WO 2007/070514, to treat a disorder such as a prostate cancer, a lymphocytic leukemia, a multiple myeloma, a lymphoma, a lung cancer, a leukemia, cachexia, a breast cancer, a pancreatic cancer, rheumatoid arthritis, psoriasis, a colorectal cancer, a myeloid leukemia, a hematological cancer, an autoimmune disease, a non-Hodgkin lymphoma, or thrombocythemia.

In one embodiment, the JAK inhibitor or Ruxolitinib Phosphate (Compound A18) is administered at a dose of about 15-25 mg. e.g., twice daily. In some embodiments, the dose is about 15, 20, or 25 mg, or about 15-20 or 20-25 mg.

In another embodiment, the anti-LAG-3 antibody molecule, e.g., an anti-LAG-3 antibody molecule as described herein, alone or in combination with one or more other immunomodulators, is used in combination with a deacetylase (DAC) inhibitor, Panobinostat (Compound A19), or a compound disclosed in PCT Publication No. WO 2014/072493 to treat a disorder, e.g., a disorder described herein.

In one embodiment, the DAC inhibitor is Panobinostat (Compound A19) or a compound disclosed in PCT Publication No. WO 2014/072493. In one embodiment, an anti-LAG-3 antibody molecule is used in combination with Panobinostat (Compound A19), a compound disclosed in PCT Publication No. WO 2014/072493, to treat a disorder such as a small cell lung cancer, a respiratory/thoracic cancer, a prostate cancer, a multiple myeloma, myelodysplastic syndrome, a bone cancer, a non-small cell lung cancer, an endocrine cancer, a lymphoma, a neurologic cancer, a leukemia, HIV/AIDS, an immune disorder, transplant rejection, a gastric cancer, a melanoma, a breast cancer, a pancreatic cancer, a colorectal cancer, a glioblastoma multiforme, a myeloid leukemia, a hematological cancer, a renal cancer, a non-Hodgkin lymphoma, a head and neck cancer, a hematopoiesis disorders, or a liver cancer.

In one embodiment, the DAC inhibitor or Panobinostat (Compound A19) is administered at a dose of about 20 mg (e.g., per day).

In another embodiment, the anti-LAG-3 antibody molecule, e.g., an anti-LAG-3 antibody molecule as described herein, alone or in combination with one or more other immunomodulators, is used in combination with an inhibitor of one or more of cytochrome P450 (e.g., 11B2), aldosterone or angiogenesis, Osilodrostat (Compound A20), or a compound disclosed in PCT Publication No. WO2007/024945 to treat a disorder, e.g., a disorder described herein. In one embodiment, the inhibitor of one or more of cytochrome P450 (e.g., 11B2), aldosterone or angiogenesis is Osilodrostat (Compound A20) or a compound disclosed in PCT Publication No. WO2007/024945. In one embodiment, an anti-LAG-3 antibody molecule is used in combination with Osilodrostat (Compound A20), or a compound disclosed in PCT Publication No. WO2007/024945, to treat a disorder such as Cushing's syndrome, hypertension, or heart failure therapy.

In another embodiment, the anti-LAG-3 antibody molecule, e.g., an anti-LAG-3 antibody molecule as described herein, alone or in combination with one or more other immunomodulators, is used in combination with a IAP inhibitor, (S)—N—((S)-1-cyclohexyl-2-((S)-2-(4-(4-fluorobenzoyl) thiazol-2-yl)pyrrolidin-1-yl)-2-oxoethyl)-2-(methylamino) propanamide (Compound A21) or a compound disclosed in U.S. Pat. No. 8,552,003 to treat a disorder, e.g., a disorder described herein. In one embodiment, the IAP inhibitor is(S)—N—((S)-1-cyclohexyl-2-((S)-2-(4-(4-fluorobenzoyl) thiazol-2-yl)pyrrolidin-1-yl)-2-oxoethyl)-2-(methylamino) propanamide (Compound A21) or a compound disclosed in U.S. Pat. No. 8,552,003. In one embodiment, an anti-LAG-3 antibody molecule is used in combination with(S)—N—((S)-1-cyclohexyl-2-((S)-2-(4-(4-fluorobenzoyl) thiazol-2-yl)pyrrolidin-1-yl)-2-oxoethyl)-2-(methylamino) propanamide (Compound A21), or a compound disclosed in U.S. Pat. No. 8,552,003, to treat a disorder such as a multiple myeloma, a breast cancer, an ovarian cancer, a pancreatic cancer, or a hematopoiesis disorder.

In one embodiment, the IAP inhibitor or(S)—N—((S)-1-cyclohexyl-2-((S)-2-(4-(4-fluorobenzoyl) thiazol-2-yl)pyrrolidin-1-yl)-2-oxoethyl)-2-(methylamino) propanamide (Compound A21) or a compound disclosed in U.S. Pat. No. 8,552,003 is administered at a dose of approximately 1800 mg, e.g., once weekly.

In another embodiment, the anti-LAG-3 antibody molecule, e.g., an anti-LAG-3 antibody molecule as described herein, alone or in combination with one or more other immunomodulators, is used in combination a Smoothened (SMO) inhibitor, Sonidegib phosphate (Compound A22), (R)-2-(5-(4-(6-benzyl-4,5-dimethylpyridazin-3-yl)-2-methylpiperazin-1-yl)pyrazin-2-yl) propan-2-ol (Compound A25), or a compound disclosed in PCT Publication No. WO 2007/131201 or WO 2010/007120 to treat a disorder, e.g., a disorder described herein. In one embodiment, the SMO inhibitor is Sonidegib phosphate (Compound A22), (R)-2-(5-(4-(6-benzyl-4,5-dimethylpyridazin-3-yl)-2-methylpiperazin-1-yl)pyrazin-2-yl) propan-2-ol (Compound A25), or a compound disclosed in PCT Publication No. WO 2007/131201 or WO 2010/007120. In one embodiment, an anti-LAG-3 antibody molecule is used in combination with Sonidegib phosphate (Compound A22), (R)-2-(5-(4-(6-benzyl-4,5-dimethylpyridazin-3-yl)-2-methylpiperazin-1-yl) pyrazin-2-yl) propan-2-ol (Compound A25), or a compound disclosed in PCT Publication No. WO 2007/131201 or WO 2010/007120 to treat a disorder such as a cancer, a medulloblastoma, a small cell lung cancer, a prostate cancer, a basal cell carcinoma, a pancreatic cancer, or an inflammation.

In certain embodiments, Sonidegib phosphate (Compound A22) is administered at a dose of about 20 to 500 mg, e.g., about 40 mg to 400 mg, about 50 mg to 300 mg, or about 100 mg to 200 mg, e.g., about 50 mg, 100 mg, 150 mg, 200 mg, 250 mg, or 300 mg. The dosing schedule can vary from e.g., every other day to daily, twice or three times a day.

In another embodiment, the anti-LAG-3 antibody molecule, e.g., an anti-LAG-3 antibody molecule as described herein, alone or in combination with one or more other immunomodulators, is used in combination with an Alk inhibitor, ceritinib (also known as ZYKADIA™; Compound A23) or a compound disclosed in PCT Publication No. WO 2007/131201 to treat a disorder, e.g., a disorder described herein. In one embodiment, the Alk inhibitor is ceritinib (Compound A23) or a compound disclosed in PCT Publication No. WO 2007/131201. In one embodiment, an anti-LAG-3 antibody molecule is used in combination with ceritinib (Compound A23), or a compound disclosed in PCT Publication No. WO 2007/131201, to treat a disorder such as non-small cell lung cancer or solid tumors.

In one embodiment, the Alk inhibitor or ceritinib (Compound A23) is administered at a dose of approximately 750 mg, e.g., once daily.

In another embodiment, the anti-LAG-3 antibody molecule, e.g., an anti-LAG-3 antibody molecule as described herein, alone or in combination with one or more other immunomodulators, is used in combination with a JAK and/or CDK4/6 inhibitor, 7-cyclopentyl-N,N-dimethyl-2-((5-(piperazin-1-yl)pyridin-2-yl)amino)-7H-pyrrolo[2,3-d]pyrimidine-6-carboxamide (Compound A24), or a compound disclosed in U.S. Pat. No. 8,415,355 or U.S. Pat. No. 8,685,980 to treat a disorder, e.g., a disorder described herein. In one embodiment, the JAK and/or CDK4/6 inhibitor is 7-cyclopentyl-N,N-dimethyl-2-((5-(piperazin-1-yl)pyridin-2-yl)amino)-7H-pyrrolo[2,3-d]pyrimidine-6-carboxamide (Compound A24) or a compound disclosed in U.S. Pat. No. 8,415,355 or U.S. Pat. No. 8,685,980. In one embodiment, an anti-LAG-3 antibody molecule is used in combination with 7-cyclopentyl-N,N-dimethyl-2-((5-(piperazin-1-yl)pyridin-2-yl)amino)-7H-pyrrolo[2,3-d]pyrimidine-6-carboxamide (Compound A24), or a compound disclosed in U.S. Pat. No. 8,415,355 or U.S. Pat. No. 8,685,980, to treat a disorder such as a lymphoma, a neurologic cancer, a melanoma, a breast cancer, or a solid tumor.

In one embodiment, the JAK and/or CDK4/6 inhibitor or 7-cyclopentyl-N,N-dimethyl-2-((5-(piperazin-1-yl)pyridin-2-yl)amino)-7H-pyrrolo[2,3-d]pyrimidine-6-carboxamide (Compound A24) is administered at a dose of approximately 200-600 mg, e.g., per day. In one embodiment, the compound is administered at a dose of about 200, 300, 400, 500, or 600 mg, or about 200-300, 300-400, 400-500, or 500-600 mg.

In another embodiment, the anti-LAG-3 antibody molecule, e.g., an anti-LAG-3 antibody molecule as described herein, alone or in combination with one or more other immunomodulators, is used in combination a prolactin receptor (PRLR) inhibitor, a human monoclonal antibody molecule (Compound A26) as disclosed in U.S. Pat. No. 7,867,493), to treat a disorder, e.g., a disorder described herein. In one embodiment, the PRLR inhibitor is a human monoclonal antibody (Compound A26) disclosed in U.S. Pat. No. 7,867,493. In one embodiment, an anti-LAG-3 antibody molecule is used in combination with human monoclonal antibody molecule (Compound A26) described in U.S. Pat. No. 7,867,493 to treat a disorder such as, a cancer, a prostate cancer, or a breast cancer.

In another embodiment, the anti-LAG-3 antibody molecule, e.g., an anti-LAG-3 antibody molecule as described herein, alone or in combination with one or more other immunomodulators, is used in combination with a PIM Kinase inhibitor, N-(4-((1R,3S,5S)-3-amino-5-methylcyclohexyl)pyridin-3-yl)-6-(2,6-difluorophenyl)-5-fluoropicolinamide (Compound A27) or a compound disclosed in PCT Publication No. WO 2010/026124 to treat a disorder, e.g., a disorder described herein. In one embodiment, the PIM Kinase inhibitor is N-(4-((1R,3S,5S)-3-amino-5-methylcyclohexyl)pyridin-3-yl)-6-(2,6-difluorophenyl)-5-fluoropicolinamide (Compound A27) or a compound disclosed in PCT Publication No. WO 2010/026124. In one embodiment, an anti-LAG-3 antibody molecule is used in combination with N-(4-((1R,3S,5S)-3-amino-5-methylcyclohexyl)pyridin-3-yl)-6-(2,6-difluorophenyl)-5-fluoropicolinamide (Compound A27), or a compound disclosed in PCT Publication No. WO 2010/026124, to treat a disorder such as a multiple myeloma, myelodysplastic syndrome, a myeloid leukemia, or a non-Hodgkin lymphoma.

In another embodiment, the anti-LAG-3 antibody molecule, e.g., an anti-LAG-3 antibody molecule as described herein, alone or in combination with one or more other immunomodulators, is used in combination a Wnt signaling inhibitor, 2-(2',3-dimethyl-[2,4'-bipyridin]-5-yl)-N-(5-(pyrazin-2-yl)pyridin-2-yl) acetamide (Compound A28) or a compound disclosed in PCT publication No. WO 2010/101849 to treat a disorder, e.g., a disorder described herein. In one embodiment, the Wnt signaling inhibitor is 2-(2',3-dimethyl-[2,4'-bipyridin]-5-yl)-N-(5-(pyrazin-2-yl)pyridin-2-yl) acetamide (Compound A28) or a compound disclosed in PCT publication No. WO 2010/101849. In one embodiment, the Wnt signaling inhibitor is 2-(2',3-dimethyl-[2,4'-bipyridin]-5-yl)-N-(5-(pyrazin-2-yl)pyridin-2-yl) acetamide (Compound A28). In one embodiment, an anti-LAG-3 antibody molecule is used in combination with 2-(2',3-dimethyl-[2,4'-bipyridin]-5-yl)-N-(5-(pyrazin-2-yl)pyridin-2-yl) acetamide (Compound A28), or a compound disclosed in PCT publication No. WO 2010/101849, to treat a disorder such as a solid tumor (e.g., a head and neck cancer, a squamous cell carcinoma, a breast cancer, a pancreatic cancer, or a colon cancer).

In certain embodiments, 2-(2',3-dimethyl-[2,4'-bipyridin]-5-yl)-N-(5-(pyrazin-2-yl)pyridin-2-yl) acetamide (Compound A28) is administered at a dose of about 1 to 50 mg, e.g., about 2 mg to 45 mg, about 3 mg to 40 mg, about 5 mg to 35 mg, 5 mg to 10 mg, or about 10 mg to 30 mg, e.g., about 2 mg. 5 mg, 10 mg, 20 mg. 30 mg, or 40 mg. The dosing schedule can vary from e.g., every other day to daily, twice or three times a day.

In another embodiment, the anti-LAG-3 antibody molecule, e.g., an anti-LAG-3 antibody molecule as described herein, alone or in combination with one or more other immunomodulators, is used in combination with a BRAF inhibitor, Encorafenib (Compound A29), or a compound disclosed in PCT Publication No. WO 2011/025927 to treat a disorder, e.g., a disorder described herein. In one embodiment, the BRAF inhibitor is Encorafenib (Compound A29) or a compound disclosed in PCT Publication No. WO 2011/025927. In one embodiment, an anti-LAG-3 antibody molecule is used in combination with Encorafenib (Compound A29), or a compound disclosed in PCT Publication No. WO 2011/025927, to treat a disorder such as a non-small cell lung cancer, a melanoma, or a colorectal cancer.

In one embodiment, the BRAF inhibitor or Encorafenib (Compound A29) is administered at a dose of about 200-300, 200-400, or 300-400 mg, e.g., per day. In one embodiment, the compound is administered at a dose of about 200, about 300 or about 400 mg.

In another embodiment, the anti-LAG-3 antibody molecule, e.g., an anti-LAG-3 antibody molecule as described herein, alone or in combination with one or more other immunomodulators, is used in combination a CDK4/6 inhibitor, 7-cyclopentyl-N,N-dimethyl-2-((5-((1R,6S)-9-methyl-4-oxo-3,9-diazabicyclo[4.2.1]nonan-3-yl)pyridin-2-yl)amino)-7H-pyrrolo[2,3-d]pyrimidine-6-carboxamide (Compound A30), or a compound disclosed in PCT publication No. WO 2011/101409 to treat a disorder, e.g., a disorder described herein. In one embodiment, the CDK4/6 inhibitor is 7-cyclopentyl-N,N-dimethyl-2-((5-((1R,6S)-9-methyl-4-oxo-3,9-diazabicyclo[4.2.1]nonan-3-yl)pyridin-2-yl)amino)-7H-pyrrolo[2,3-d]pyrimidine-6-carboxamide (Compound A30) or a compound disclosed in PCT publication No. WO 2011/101409. In one embodiment, an anti-LAG-3 antibody molecule is used in combination with 7-cyclopentyl-N,N-dimethyl-2-((5-((1R,6S)-9-methyl-4-oxo-3,9-diazabicyclo[4.2.1]nonan-3-yl)pyridin-2-yl) amino)-7H-pyrrolo[2,3-d]pyrimidine-6-carboxamide (Compound A30), or a compound disclosed in PCT publication No. WO 2011/101409, to treat a disorder such as a cancer, a mantle cell lymphoma, a liposarcoma, a non-small cell lung cancer, a melanoma, a squamous cell esophageal cancer, or a breast cancer.

In another embodiment, the anti-LAG-3 antibody molecule, e.g., an anti-LAG-3 antibody molecule as described herein, alone or in combination with one or more other immunomodulators, is used in combination with a HER3 inhibitor, Compound A31, or a compound disclosed in PCT Publication No. WO 2012/022814, to treat a disorder, e.g., a disorder described herein. In one embodiment, the HER3 inhibitor is Compound A31 or a compound disclosed in PCT Publication WO 2012/022814. In one embodiment, an anti-LAG-3 antibody molecule is used in combination with Compound A31, or a compound disclosed in PCT Publication WO 2012/022814, to treat a disorder such as a gastric cancer, an esophageal cancer, a head and neck cancer, a squamous cell carcinoma, a stomach cancer, a breast cancer (e.g., metastatic breast cancer), or a digestive/gastrointestinal cancer.

In some embodiments, Compound A31 is a human monoclonal antibody molecule.

In one embodiment, the HER3 inhibitor or Compound A31 is administered at a dose of about 3, 10, 20, or 40 mg/kg, e.g., once weekly (QW). In one embodiment, the compound is administered at a dose of about 3-10, 10-20, or 20-40 mg/kg.

In another embodiment, the anti-LAG-3 antibody molecule, e.g., an anti-LAG-3 antibody molecule as described herein, alone or in combination with one or more other immunomodulators, is used in combination an FGFR2 and/or FGFR4 inhibitor, Compound A32, or a compound disclosed in a publication PCT Publication No. WO 2014/160160 (e.g., an antibody molecule drug conjugate against an FGFR2 and/or FGFR4, e.g., mAb 12425), to treat a disorder, e.g., a disorder described herein. In one embodiment, the FGFR2 and/or FGFR4 inhibitor is Compound A32 or a compound disclosed in a publication PCT Publication No. WO 2014/160160. In one embodiment, an anti-LAG-3 antibody molecule is used in combination with Compound A32, or a compound as described in Table 7, to treat a disorder such as a cancer, a gastric cancer, a breast cancer, a rhabdomyosarcoma, a liver cancer, an adrenal cancer, a lung cancer, an esophageal cancer, a colon cancer, or an endometrial cancer.

In some embodiments, Compound A32 is an antibody molecule drug conjugate against an FGFR2 and/or FGFR4, e.g., mAb 12425.

In another embodiment, the anti-LAG-3 antibody molecule, e.g., an anti-LAG-3 antibody molecule as described herein, alone or in combination with one or more other immunomodulators, is used in combination an M-CSF inhibitor, Compound A33, or a compound disclosed in PCT Publication No. WO 2004/045532 (e.g., an antibody molecule or Fab fragment against M-CSF), to treat a disorder, e.g., a disorder described herein. In one embodiment, the M-CSF inhibitor is Compound A33 or a compound disclosed in PCT Publication No. WO 2004/045532. In one embodiment, an anti-LAG-3 antibody molecule is used in combination with Compound A33, or a compound as described in PCT Publication No. WO 2004/045532, to treat a disorder such as a cancer, a prostate cancer, a breast cancer, or pigmented villonodular synovitis (PVNS).

In embodiments, Compound A33 is a monoclonal antibody molecule against M-CSF or a fragment (e.g., Fab fragment) thereof. In embodiments, the M-CSF inhibitor or Compound A33 is administered at an average dose of about 10 mg/kg.

In another embodiment, the anti-LAG-3 antibody molecule, e.g., an anti-LAG-3 antibody molecule as described herein, alone or in combination with one or more other immunomodulators, is used in combination with a MEK inhibitor, Binimetinib (Compound A34), or a compound disclosed in PCT Publication No. WO 2003/077914 to treat a disorder, e.g., a disorder described herein. In one embodiment, the MEK inhibitor is Binimetinib (Compound A34), or a compound disclosed in PCT Publication No. WO 2003/077914. In one embodiment, an anti-LAG-3 antibody molecule is used in combination with Binimetinib (Compound A34), or a compound disclosed in PCT Publication No. WO 2003/077914, to treat a disorder such as a non-small cell lung cancer, a multisystem genetic disorder, a melanoma, an ovarian cancer, a digestive/gastrointestinal cancer, a rheumatoid arthritis, or a colorectal cancer.

In one embodiment, the MEK inhibitor or Binimetinib (Compound A34) is administered at a dose of about 45 mg, e.g., twice daily.

In another embodiment, the anti-LAG-3 antibody molecule, e.g., an anti-LAG-3 antibody molecule as described herein, alone or in combination with one or more other immunomodulators, is used in combination an inhibitor of one or more of c-KIT, histamine release, Flt3 (e.g., FLK2/STK1) or PKC, Midostaurin (Compound A35) or a compound disclosed in PCT Publication No. WO 2003/037347 to treat a disorder, e.g., a disorder described herein. In one embodiment, the inhibitor is Midostaurin (Compound A35) or compound disclosed in PCT Publication No. WO 2003/037347. In one embodiment, the inhibitor of one or more of c-KIT, histamine release, Flt3 (e.g., FLK2/STK1) or PKC is Midostaurin. In one embodiment, an anti-LAG-3 antibody molecule is used in combination with Midostaurin (Compound A35), or compound disclosed in PCT Publication No. WO 2003/037347, to treat a disorder such as a cancer, a colorectal cancer, a myeloid leukemia, myelodysplastic syndrome, an age-related muscular degeneration, a diabetic complication, or a dermatologic disorder.

In another embodiment, the anti-LAG-3 antibody molecule, e.g., an anti-LAG-3 antibody molecule as described herein, alone or in combination with one or more other immunomodulators, is used in combination with a TOR inhibitor (e.g., mTOR inhibitor), Everolimus (also known as AFINITOR®; Compound A36) or a Compound disclosed in PCT Publication No. WO 2014/085318 to treat a disorder, e.g., a disorder described herein). In one embodiment, the TOR inhibitor is Everolimus (Compound A36) or a Compound disclosed in PCT Publication No. WO 2014/085318. In one embodiment, an anti-LAG-3 antibody molecule is used in combination with Everolimus (Compound A36) to treat a disorder such as an interstitial lung disease, a small cell lung cancer, a respiratory/thoracic cancer, a prostate cancer, a multiple myeloma, a sarcoma, an age-related macular degeneration, a bone cancer, tuberous sclerosis, a non-small cell lung cancer, an endocrine cancer, a lymphoma, a neurologic disorders, an astrocytoma, a cervical cancer, a neurologic cancer, a leukemia, an immune disorders, transplant rejection, a gastric cancer, a melanoma, epilepsy, a breast cancer, or a bladder cancer.

In one embodiment, the TOR inhibitor or Everolimusis (Compound A36) administered at a dose of about 2.5-20 mg/day. In one embodiment, the compound is administered at a dose of about 2.5, 5, 10, or 20 mg/day, e.g., about 2.5-5, 5-10, or 10-20 mg/day.

In another embodiment, the anti-LAG-3 antibody molecule, e.g., an anti-LAG-3 antibody molecule as described herein, alone or in combination with one or more other immunomodulators, is used in combination an inhibitor of one or more of VEGFR-2, PDGFRbeta, KIT or Raf kinase C. 1-methyl-5-((2-(5-(trifluoromethyl)-1H-imidazol-2-yl)pyridin-4-yl)oxy)-N-(4-(trifluoromethyl)phenyl)-1H-benzo[d]imidazol-2-amine (Compound A37) or a compound disclosed in PCT Publication No. WO 2007/030377 to treat a disorder, e.g., a disorder described herein. In one embodiment, the inhibitor of one or more of VEGFR-2, PDGFRbeta, KIT or Raf kinase C is 1-methyl-5-((2-(5-(trifluoromethyl)-1H-imidazol-2-yl)pyridin-4-yl)oxy)-N-(4-(trifluoromethyl)phenyl)-1H-benzo[d]imidazol-2-amine (Compound A37) or a compound disclosed in PCT Publication No. WO 2007/030377. In one embodiment, an anti-LAG-3 antibody molecule is used in combination with 1-methyl-5-((2-(5-(trifluoromethyl)-1H-imidazol-2-yl)pyridin-4-yl)oxy)-N-(4-(trifluoromethyl)phenyl)-1H-benzo[d]imidazol-2-amine (Compound A37), or a compound disclosed in PCT Publication No. WO 2007/030377, to treat a disorder such as a cancer, a melanoma, or a solid tumor.

In another embodiment, the anti-LAG-3 antibody molecule, e.g., an anti-LAG-3 antibody molecule as described herein, alone or in combination with one or more other immunomodulators, is used in combination a somatostatin agonist and/or growth hormone release inhibitor, Pasireotide diaspartate (also known as SIGNIFOR®; Compound A38) or a compound disclosed in PCT Publication No. WO2002/010192 or U.S. Pat. No. 7,473,761 to treat a disorder, e.g., a disorder described herein. In one embodiment, the somatostatin agonist and/or growth hormone release inhibitor is Pasireotide diaspartate (Compound A38) or a compound disclosed in PCT Publication No. WO2002/010192 or U.S. Pat. No. 7,473,761. In one embodiment, an anti-LAG-3 antibody molecule is used in combination with Pasireotide diaspartate (Compound A38), or a compound disclosed in PCT Publication No. WO2002/010192 or U.S. Pat. No. 7,473,761, to treat a disorder such as a prostate cancer, an endocrine cancer, a nurologic cancer, a skin cancer (e.g., a melanoma), a pancreatic cancer, a liver cancer, Cushing's syndrome, a gastrointestinal disorder, acromegaly, a liver and biliary tract disorder, or liver cirrhosis.

In another embodiment, the anti-LAG-3 antibody molecule, e.g., an anti-LAG-3 antibody molecule as described herein, alone or in combination with one or more other immunomodulators, is used in combination a signal transduction modulator and/or angiogenesis inhibitor, Dovitinib (Compound A39) or a compound disclosed in PCT Publication No. WO 2009/115562 to treat a disorder, e.g., a disorder described herein. In one embodiment, the signal transduction modulator and/or angiogenesis inhibitor is Dovitinib (Compound A39) or a compound disclosed in PCT Publication No. WO 2009/115562. In one embodiment, an anti-LAG-3 antibody molecule is used in combination with Dovitinib (Compound A39), or a compound disclosed in PCT Publication No. WO 2009/115562, to treat a disorder such as a cancer, a respiratory/thoracic cancer, a multiple myeloma, a prostate cancer, a non-small cell lung cancer, an endocrine cancer, or a neurological genetic disorder.

In another embodiment, the anti-LAG-3 antibody molecule, e.g., an anti-LAG-3 antibody molecule as described herein, alone or in combination with one or more other immunomodulators, is used in combination with an EGFR inhibitor, (R,E)-N-(7-chloro-1-(1-(4-(dimethylamino)but-2-enoyl)azepan-3-yl)-1H-benzo[d]imidazol-2-yl)-2-methylisonicotinamide (Compound A40) or a compound disclosed in PCT Publication No. WO 2013/184757 to treat a disorder, e.g., a disorder described herein. In one embodiment, the EGFR inhibitor is (R,E)—N-(7-chloro-1-(1-(4-(dimethylamino) but-2-enoyl) azepan-3-yl)-1H-benzo[d]imidazol-2-yl)-2-methylisonicotinamide (Compound A40) or a compound disclosed in PCT Publication No. WO 2013/184757. In one embodiment, an anti-LAG-3 antibody molecule is used in combination with (R,E)—N-(7-chloro-1-(1-(4-(dimethylamino) but-2-enoyl) azepan-3-yl)-1H-benzo[d]imidazol-2-yl)-2-methylisonicotinamide (Compound A40), or a compound disclosed in PCT Publication No. WO 2013/184757, to treat a disorder such as a cancer, e.g., a solid tumor.

In one embodiment, the EGFR inhibitor or (R,E)—N-(7-chloro-1-(1-(4-(dimethylamino) but-2-enoyl) azepan-3-yl)-1H-benzo[d]imidazol-2-yl)-2-methylisonicotinamide (Compound A40) is administered at a dose of 150-250 mg, e.g., per day. In one embodiment, the compound is administered at a dose of about 150, 200, or 250 mg, or about 150-200 or 200-250 mg.

In another embodiment, the anti-LAG-3 antibody molecule, e.g., an anti-LAG-3 antibody molecule as described herein, alone or in combination with one or more other immunomodulators, is used in combination an ALK inhibitor, $N^6$-(2-isopropoxy-5-methyl-4-(1-methylpiperidin-4-yl)phenyl)-$N^4$-(2-(isopropylsulfonyl)phenyl)-1H-pyrazolo[3, 4-d]pyrimidine-4,6-diamine (Compound A42) or a compound disclosed in PCT Publication No. WO 2008/073687 to treat a disorder, e.g., a disorder described herein. In one embodiment, the ALK inhibitor is $N^6$-(2-isopropoxy-5-methyl-4-(1-methylpiperidin-4-yl)phenyl)-$N^4$-(2-(isopropylsulfonyl)phenyl)-1H-pyrazolo[3,4-d]pyrimidine-4,6-diamine (Compound A42) or a compound disclosed in PCT Publication No. WO 2008/073687. In one embodiment, an anti-LAG-3 antibody molecule is used in combination with $N^6$-(2-isopropoxy-5-methyl-4-(1-methylpiperidin-4-yl)phenyl)-$N^4$-(2-(isopropylsulfonyl)phenyl)-1H-pyrazolo[3,4-d]pyrimidine-4,6-diamine (Compound A42), or a compound disclosed in PCT Publication No. WO 2008/073687, to treat a disorder such as a cancer, an anaplastic large-cell lymphoma (ALCL), a non-small cell lung carcinoma (NSCLC), or a neuroblastoma.

In another embodiment, the anti-LAG-3 antibody molecule, e.g., an anti-LAG-3 antibody molecule as described herein, alone or in combination with one or more other immunomodulators, is used in combination an IGF-1R inhibitor, 3-(4-(4-((5-chloro-4-((5-methyl-1H-pyrazol-3-yl)amino)pyrimidin-2-yl)amino)-5-fluoro-2-methylphenyl)piperidin-1-yl) thietane 1,1-dioxide (Compound A43), 5-chloro-$N^2$-(2-fluoro-5-methyl-4-(1-(tetrahydro-2H-pyran-4-yl) piperidin-4-yl)phenyl)-$N^4$-(5-methyl-1H-pyrazol-3-yl)pyrimidine-2,4-diamine (Compound A44), or 5-chloro-N2-(4-(1-ethylpiperidin-4-yl)-2-fluoro-5-methylphenyl)-$N^4$-(5-methyl-1H-pyrazol-3-yl)pyrimidine-2,4-diamine (Compound A45) or a compound disclosed in PCT Publication No. WO 2010/002655 to treat a disorder, e.g., a disorder described. In one embodiment, the IGF-1R inhibitor is 3-(4-(4-((5-chloro-4-((5-methyl-1H-pyrazol-3-yl)amino)pyrimidin-2-yl)amino)-5-fluoro-2-methylphenyl)piperidin-1-yl) thietane 1,1-dioxide (Compound A43), 5-chloro-$N^2$-(2-fluoro-5-methyl-4-(1-(tetrahydro-2H-pyran-4-yl) piperidin-4-yl)phenyl)-$N^4$-(5-methyl-1H-pyrazol-3-yl)pyrimidine-2,4-diamine (Compound A44), 5-chloro-N2-(4-(1-ethylpiperidin-4-yl)-2-fluoro-5-methylphenyl)-$N^4$-(5-methyl-1H-pyrazol-3-yl)pyrimidine-2,4-diamine (Compound A45), or a compound disclosed in PCT Publication No. WO 2010/002655. In one embodiment, an anti-LAG-3 antibody molecule is used in combination with 3-(4-(4-((5-chloro-4-((5-methyl-1H-pyrazol-3-yl)amino)pyrimidin-2-yl)amino)-5-fluoro-2-methylphenyl) piperidin-1-yl) thietane 1,1-dioxide (Compound A43), 5-chloro-$N^2$-(2-fluoro-5-methyl-4-(1-(tetrahydro-2H-pyran-4-yl) piperidin-4-yl)phenyl)-$N^4$-(5-methyl-1H-pyrazol-3-yl)pyrimidine-2,4-diamine (Compound A44), 5-chloro-N2-(4-(1-ethylpiperidin-4-yl)-2-fluoro-5-methylphenyl)-$N^4$-(5-methyl-1H-pyrazol-3-yl)pyrimidine-2,4-diamine (Compound A45), or a compound disclosed in PCT Publication No. WO 2010/002655, to treat a disorder such as a cancer or a sarcoma.

In another embodiment, the anti-LAG-3 antibody molecule, e.g., an anti-LAG-3 antibody molecule as described herein, alone or in combination with one or more other immunomodulators, is used in combination a P-Glycoprotein 1 inhibitor, Valspodar (also known as AMDRAY™; Compound A46) or a compound disclosed in EP 296122 to treat a disorder, e.g., a disorder described herein. In one embodiment, the P-Glycoprotein 1 inhibitor is Valspodar (Compound A46) or a compound disclosed in EP 296122. In one embodiment, an anti-LAG-3 antibody molecule is used in combination with Valspodar (Compound A46), or a compound disclosed in EP 296122, to treat a disorder such as a cancer or a drug-resistant tumor.

In another embodiment, the anti-LAG-3 antibody molecule, e.g., an anti-LAG-3 antibody molecule as described herein, alone or in combination with one or more other immunomodulators, is used in combination one or more of a VEGFR inhibitor, Vatalanib succinate (Compound A47) or a compound disclosed in EP 296122 to treat a disorder, e.g., a disorder described herein. In one embodiment, the VEGFR inhibitor is Vatalanib succinate (Compound A47) or a compound disclosed in EP 296122. In one embodiment, an anti-LAG-3 antibody molecule is used in combination with Vatalanib succinate (Compound A47), or a compound disclosed in EP 296122, to treat cancer.

In another embodiment, the anti-LAG-3 antibody molecule, e.g., an anti-LAG-3 antibody molecule as described herein, alone or in combination with one or more other immunomodulators, is used in combination with an IDH inhibitor or a compound disclosed in WO2014/141104 to treat a disorder, e.g., a disorder described herein. In one embodiment, the IDH inhibitor is a compound disclosed in PCT Publication No. WO2014/141104. In one embodiment, an anti-LAG-3 antibody molecule is used in combination with a compound disclosed in WO2014/141104 to treat a disorder such as a cancer.

In another embodiment, the anti-LAG-3 antibody molecule, e.g., an anti-LAG-3 antibody molecule as described herein, alone or in combination with one or more other immunomodulators, is used in combination with a BCL-ABL inhibitor or a compound disclosed in PCT Publication No. WO2013/171639, WO2013/171640, WO2013/171641, or WO2013/171642 to treat a disorder, e.g., a disorder described herein. In one embodiment, the BCL-ABL inhibitor is a compound disclosed in PCT Publication No. WO2013/171639, WO2013/171640, WO2013/171641, or WO2013/171642. In one embodiment, an anti-LAG-3 antibody molecule is used in combination with a compound disclosed in PCT Publication No. WO2013/171639, WO2013/171640, WO2013/171641, or WO2013/171642 to treat a disorder such as a cancer.

In another embodiment, the anti-LAG-3 antibody molecule, e.g., an anti-LAG-3 antibody molecule as described herein, alone or in combination with one or more other immunomodulators, is used in combination with a c-RAF inhibitor or a compound disclosed in PCT Publication No. WO2014/151616 to treat a disorder, e.g., a disorder described herein. In one embodiment, the c-RAF inhibitor is Compound A50 or a compound disclosed in PCT Publication No. WO2014/151616. In one embodiment, an anti-LAG-3 antibody molecule is used in combination with a compound disclosed in PCT Publication No. WO2014/151616 to treat a disorder such as a cancer.

In another embodiment, the anti-LAG-3 antibody molecule, e.g., an anti-LAG-3 antibody molecule as described herein, alone or in combination with one or more other immunomodulators, is used in combination with an ERK1/2 ATP competitive inhibitor or a compound disclosed in International Patent Application No. PCT/US2014/062913 to treat a disorder, e.g., a disorder described herein. In one embodiment, the ERK1/2 ATP competitive inhibitor is a compound disclosed in International Patent Application No. PCT/US2014/062913. In one embodiment, an anti-LAG-3 antibody molecule is used in combination with Compound A51 or a compound disclosed in International Patent Application No. PCT/US2014/062913 to treat a disorder such as a cancer.

In another embodiment, the anti-LAG-3 antibody molecule, e.g., an anti-LAG-3 antibody molecule as described herein, alone or in combination with one or more other immunomodulators, is used in combination with a tyrosine kinase inhibitor, (Compound A52) or a compound disclosed in PCT Publication No. WO2005/073224 to treat a disorder, e.g., a disorder described herein. In one embodiment, the tyrosine kinase inhibitor is 4-((2-(((1R,2R)-2-hydroxycyclohexyl)amino)benzo[d]thiazol-6-yl)oxy)-N-methylpicolinamide (Compound A52) or a compound disclosed in PCT Publication No. WO2005/073224. In one embodiment, an anti-LAG-3 antibody molecule is used in combination with 4-((2-(((1R,2R)-2-hydroxycyclohexyl)amino)benzo[d]thiazol-6-yl)oxy)-N-methylpicolinamide (Compound A52), or a compound disclosed in PCT Publication No. WO2005/073224, to treat a disorder such as a cancer.

In some embodiments, the anti-LAG-3 antibody molecule is administered in combination with one or more agents selected from, Compound A8, Compound A17, Compound A23, Compound A24, Compound A27, Compound A29, and Compound A33.

In some embodiments, an anti-LAG-3 antibody molecule is administered in combination with an anti-cancer agent having a known activity in an immune cell assay, e.g., in one or more of a huMLR assay, a T cell proliferation assay, and a B-cell proliferation assay. Exemplary assays are described below. Based on the assay, an IC50 for can be calculated for each test agent. In embodiments, the anti-cancer agent has an IC50 of, e.g., 0-1 µM, 1-4 µM, or greater than 4 µM. e.g., 4-10 µM or 4-20 µM. In embodiments, the second therapeutic agent is chosen from one or more of: Compound A9, Compound A16, Compound A17, Compound A21, Compound A22, Compound A25, Compound A28, Compound A48, and Compound 49.

In some embodiments, the Compound A28 (or a compound related to Compound A28) is administered at a dose of approximately 5-10 or 10-30 mg. In some embodiments, the Compound A22 (or compound related to Compound A22) is administered at a dose of about 200 mg. In some embodiments, the Compound A17 (or compound related to Compound A17) is administered at a dose of approximately 400-600 mg. In some embodiments, the Compound A16 (or compound related to Compound A16) is administered at a dose of approximately 400-600 mg PO qDay. In some embodiments, the Compound A29 (or compound related to Compound A29) is administered at a dose of approximately 200-400 or 300-400 mg. In some embodiments, the Compound A24 (or compound related to Compound A24) is administered at a dose of approximately 200-600 mg. In some embodiments, the Compound A23 (ceritinib) (or compound related to ceritinib) is administered at a dose of approximately 750 mg once daily. In some embodiments, the Compound A8 (or compound related to Compound A8) is administered at a dose of approximately 200-400 or 300-400 mg. In some embodiments, the Compound A5 (or compound related to Compound A5) is administered at a dose of approximately 100-125 mg. In some embodiments, the Compound A6 (or compound related to Compound A6) is administered at a dose of about 100 mg. In some embodiments, the Compound A1 (or compound related to Compound A1) is administered at a dose of approximately 200-300 or 200-600 mg. In some embodiments, the Compound A40 (or compound related to Compound A40) is administered at a dose of approximately 150-250 mg. In some embodiments, the Compound A10 (or compound related to Compound A10) is administered at a dose of approximately 400 to 700 mg, e.g., administered three times weekly, 2 weeks on and one week off. In some embodiments, the BCR-ABL inhibitor is administered at a dose of approximately 20 mg bid-80 mg bid.

Exemplary huMLR assay and B or T cell proliferation assays are provided below.

Human Mixed Lymphocyte Reaction

The Mixed Lymphocyte Reaction (MLR) is a functional assay which measures the proliferative response of lymphocytes from one individual (the responder) to lymphocytes from another individual (the stimulator). To perform an allogeneic MLR, peripheral blood mononuclear cells (PBMC) from three donors were isolated from buffy-coats of unknown HLA type (Kantonspital Blutspendezentrum from Bern and Aarau, Switzerland). The cells were prepared at $2 \times 10^5$ in 0.2 mL of culture medium containing RPMI 1640 GlutaMAX™ with 10% fetal calf serum (FCS), 100 U penicillin/100 µg streptomycin, 50 µM 2-Mercaptoethanol. Individual 2-way reactions were set up by mixing PBMC from two different donors at a 1:1 ratio and co-cultures were done in triplicates in flat-bottomed 96-well tissue culture plates for 6 days at 37° C., 5% CO2, in presence or not of an 8-point concentration range of test compounds. Cells were pulsed with 3H-TdR (1 µCi/0.2 mL) for the last 16 h of culture and incorporated radioactivity was used as a measure of cell proliferation. The concentration that inhibited 50% of the maximal huMLR response (IC50) was calculated for each compound. Cyclosporine was used as a positive control of huMLR inhibition.

Human B Cell Proliferation Assay

PBMC were freshly isolated by Ficoll-Paque density gradient from human blood and subjected to negative B-cell isolation. B cells were resuspended in culture medium (RPMI 1640, HEPES, 10% FCS, 50 µg/mL gentamicine, 50 µM 2-Mercaptoethanol, 1× ITS (Insulin, Transferrin and Sodium Selenite), 1× Non-Essential Amino-Acids) at a concentration of 9.104 per well in a flat-bottom 96-well culture plate. B cell stimulation was performed by human anti-IgM antibody molecule (30 ug/mL) and IL-4 (75 ng/mL) or by CD40 ligand (3 ug/mL) and IL-4 (75 ng/mL) in presence or not of a 7-point concentration range of test compounds. After 72 h of culture at 37° C., 10% CO2, cells were pulsed with 3H-TdR (1 µCi/well) for the last 6 h of culture. B cells were then harvested and the incorporation of thymidine was measured using a scintillation counter. Of each duplicate treatment, the mean was calculated and these data were plotted in XLfit 4 to determine the respective IC50 values.

Human T Cell Proliferation Assay

PBMC were freshly isolated by Ficoll-Paque density gradient from human blood and subjected to negative isolation of T cells. T cells were prepared in culture medium (RPMI 1640, HEPES, 10% FCS, 50 µg/mL gentamicine, 50 µM 2-Mercaptoethanol, 1× ITS (Insulin, Transferrin and Sodium Selenite), 1× Non-Essential Amino-Acids) at a concentration of 8.104 per well in a flat-bottom 96-well culture plate. T cell stimulation was performed by human anti-CD3 antibody molecule (10 ug/mL) or by human anti-CD3 antibody molecule (5 µg/mL) and anti-CD28 antibody molecule (1 µg/mL) in presence or not of a 7-point concentration range of test compounds. After 72 h of culture at 37° C., 10% $CO_2$, cells were pulsed with 3H-TdR (1 µCi/well) for the last 6 h of culture. Cell proliferation was measured by the incorporation of thymidine allowing IC50 determination for each tested compound.

Decreasing an Immune Response

Anti-LAG-3 antibodies can be used to modulate, e.g., provoke and amplify, an immune response, e.g., an autoimmune response. For example, anti-LAG-3 blockade in conjunction with various self proteins can be used to devise vaccination protocols to efficiently generate immune responses against these self proteins for disease treatment. Indeed, many anti-tumor responses involve anti-self reactivities (van Elsas et al. (2001) *J. Exp. Med.* 194:481-489; Overwijk, et al. (1999) *Proc. Natl. Acad. Sci. U.S.A.* 96:2982-2987; Rosenberg & White (1996) *J. Immunother Emphasis Tumor Immunol* 19 (1): 81-4). Further, Alzheimer's disease involves inappropriate accumulation of AB peptide in amyloid deposits in the brain; antibody responses against amyloid are able to clear these amyloid deposits (Schenk et al., (1999) *Nature* 400:173-177).

Other self proteins can also be used as targets such as IgE for the treatment of allergy and asthma, and TNFc for rheumatoid arthritis. Antibody responses to various hormones can be induced by the use of anti-LAG-3 antibody. Neutralizing antibody responses to reproductive hormones can be used for contraception. Neutralizing antibody response to hormones and other soluble factors that are required for the growth of particular tumors can also be considered as candidate vaccination targets.

Analogous methods as described above for the use of anti-LAG-3 antibody can be used for induction of therapeutic autoimmune responses to treat patients having an inappropriate accumulation of other self-antigens, such as amyloid deposits, including Aβ in Alzheimer's disease, cytokines such as TNFa, and IgE.

In other embodiments, the anti-LAG-3 antibody molecules are administered to a subject in conjunction with (e.g., before, simultaneously or following) one or more of: bone marrow transplantation. T cell ablative therapy using chemotherapy agents such as, fludarabine, external-beam radiation therapy (XRT), cyclophosphamide, and/or antibodies such as OKT3 or CAMPATH®. In one embodiment, the anti-LAG-3 antibody molecules are administered following B-cell ablative therapy such as agents that react with CD20, e.g., Rituxan. For example, in one embodiment, subjects may undergo standard treatment with high dose chemotherapy followed by peripheral blood stem cell transplantation. In certain embodiments, following the transplant, subjects receive the anti-LAG-3 antibody molecules. In an additional embodiment, the anti-LAG-3 antibody molecules are administered before or following surgery.

Diagnostic Uses

In one aspect, the present invention provides a diagnostic method for detecting the presence of a LAG-3 protein in vitro (e.g., in a biological sample, such as a tissue biopsy, e.g., from a cancerous tissue) or in vivo (e.g., in vivo imaging in a subject). The method includes: (i) contacting the sample with an antibody molecule described herein, or administering to the subject, the antibody molecule; (optionally) (ii) contacting a reference sample, e.g., a control sample (e.g., a control biological sample, such as plasma, tissue, biopsy) or a control subject)); and (iii) detecting formation of a complex between the antibody molecule, and the sample or subject, or the control sample or subject, wherein a change, e.g., a statistically significant change, in the formation of the complex in the sample or subject relative to the control sample or subject is indicative of the presence of LAG-3 in the sample. The antibody molecule can be directly or indirectly labeled with a detectable substance to facilitate detection of the bound or unbound antibody. Suitable detectable substances include various enzymes, prosthetic groups, fluorescent materials, luminescent materials and radioactive materials, as described above and described in more detail below.

The term "sample," as it refers to samples used for detecting polypeptides includes, but is not limited to, cells, cell lysates, proteins or membrane extracts of cells, body fluids, or tissue samples.

Complex formation between the antibody molecule and LAG-3 can be detected by measuring or visualizing either the binding molecule bound to the LAG-3 antigen or unbound binding molecule. Conventional detection assays can be used, e.g., an enzyme-linked immunosorbent assays (ELISA), a radioimmunoassay (RIA) or tissue immunohistochemistry. Alternative to labeling the antibody molecule, the presence of LAG-3 can be assayed in a sample by a competition immunoassay utilizing standards labeled with a detectable substance and an unlabeled antibody molecule. In this assay, the biological sample, the labeled standards and the antibody molecule are combined and the amount of labeled standard bound to the unlabeled binding molecule is determined. The amount of LAG-3 in the sample is inversely proportional to the amount of labeled standard bound to the antibody molecule.

Nucleic Acids

The invention also features nucleic acids comprising nucleotide sequences that encode heavy and light chain variable regions and CDRs of the anti-LAG-3 antibody molecules, as described herein. For example, the invention features a first and second nucleic acid encoding heavy and light chain variable regions, respectively, of an anti-LAG-3 antibody molecule chosen from one or more of the antibody molecules disclosed herein. The nucleic acid can comprise a nucleotide sequence as set forth in the tables herein, or a sequence substantially identical thereto (e.g., a sequence at least about 85%, 90%, 95%, 99% or more identical thereto, or which differs by no more than 3, 6, 15, 30, or 45 nucleotides from the sequences shown in the tables herein.

In certain embodiments, the nucleic acid can comprise a nucleotide sequence encoding at least one, two, or three CDRs from a heavy chain variable region having an amino acid sequence as set forth in the tables herein, or a sequence substantially homologous thereto (e.g., a sequence at least about 85%, 90%, 95%, 99% or more identical thereto, and/or having one or more substitutions, e.g., conserved substitutions). In other embodiments, the nucleic acid can comprise a nucleotide sequence encoding at least one, two, or three CDRs from a light chain variable region having an amino acid sequence as set forth in the tables herein, or a sequence substantially homologous thereto (e.g., a sequence at least about 85%, 90%, 95%, 99% or more identical thereto, and/or having one or more substitutions, e.g., conserved substitutions). In yet another embodiment, the nucleic acid can comprise a nucleotide sequence encoding at least one, two, three, four, five, or six CDRs from heavy and light chain variable regions having an amino acid sequence as set forth in the tables herein, or a sequence substantially homologous thereto (e.g., a sequence at least about 85%, 90%, 95%, 99% or more identical thereto, and/or having one or more substitutions, e.g., conserved substitutions).

In certain embodiments, the nucleic acid can comprise a nucleotide sequence encoding at least one, two, or three CDRs from a heavy chain variable region having the nucleotide sequence as set forth in the tables herein, a sequence substantially homologous thereto (e.g., a sequence at least about 85%, 90%, 95%, 99% or more identical thereto, and/or capable of hybridizing under the stringency conditions described herein). In another embodiment, the nucleic acid can comprise a nucleotide sequence encoding at least one, two, or three CDRs from a light chain variable region having the nucleotide sequence as set forth in the tables herein, or a sequence substantially homologous thereto (e.g., a sequence at least about 85%, 90%, 95%, 99% or more identical thereto, and/or capable of hybridizing under the stringency conditions described herein). In yet another embodiment, the nucleic acid can comprise a nucleotide sequence encoding at least one, two, three, four, five, or six CDRs from heavy and light chain variable regions having the nucleotide sequence as set forth in the tables herein, or a sequence substantially homologous thereto (e.g., a sequence at least about 85%, 90%, 95%, 99% or more identical thereto, and/or capable of hybridizing under the stringency conditions described herein).

In another aspect, the application features host cells and vectors containing the nucleic acids described herein. The nucleic acids may be present in a single vector or separate vectors present in the same host cell or separate host cell, as described in more detail hereinbelow.

Vectors

Further provided herein are vectors comprising nucleotide sequences encoding an antibody molecule described herein. In one embodiment, the vectors comprise nucleotides encoding an antibody molecule described herein. In one embodiment, the vectors comprise the nucleotide sequences described herein. The vectors include, but are not limited to, a virus, plasmid, cosmid, lambda phage or a yeast artificial chromosome (YAC).

Numerous vector systems can be employed. For example, one class of vectors utilizes DNA elements which are derived from animal viruses such as, for example, bovine papilloma virus, polyoma virus, adenovirus, vaccinia virus, baculovirus, retroviruses (Rous Sarcoma Virus, MMTV or MOMLV) or SV40 virus. Another class of vectors utilizes RNA elements derived from RNA viruses such as Semliki Forest virus, Eastern Equine Encephalitis virus and Flaviviruses.

Additionally, cells which have stably integrated the DNA into their chromosomes may be selected by introducing one or more markers which allow for the selection of transfected host cells. The marker may provide, for example, prototropy to an auxotrophic host, biocide resistance, (e.g., antibiotics), or resistance to heavy metals such as copper, or the like. The selectable marker gene can be either directly linked to the DNA sequences to be expressed, or introduced into the same cell by cotransformation. Additional elements may also be needed for optimal synthesis of mRNA. These elements may include splice signals, as well as transcriptional promoters, enhancers, and termination signals.

Once the expression vector or DNA sequence containing the constructs has been prepared for expression, the expression vectors may be transfected or introduced into an appropriate host cell. Various techniques may be employed to achieve this, such as, for example, protoplast fusion, calcium phosphate precipitation, electroporation, retroviral transduction, viral transfection, gene gun, lipid based transfection or other conventional techniques. In the case of protoplast fusion, the cells are grown in media and screened for the appropriate activity.

Methods and conditions for culturing the resulting transfected cells and for recovering the antibody molecule produced are known to those skilled in the art, and may be varied or optimized depending upon the specific expression vector and mammalian host cell employed, based upon the present description.

Cells

The invention also provides host cells comprising a nucleic acid encoding an antibody molecule as described herein.

In one embodiment, the host cells are genetically engineered to comprise nucleic acids encoding the antibody molecule.

In one embodiment, the host cells are genetically engineered by using an expression cassette. The phrase "expression cassette," refers to nucleotide sequences, which are capable of affecting expression of a gene in hosts compatible with such sequences. Such cassettes may include a promoter, an open reading frame with or without introns, and a termination signal. Additional factors necessary or helpful in effecting expression may also be used, such as, for example, an inducible promoter.

The invention also provides host cells comprising the vectors described herein.

The cell can be, but is not limited to, a eukaryotic cell, a bacterial cell, an insect cell, or a human cell. Suitable eukaryotic cells include, but are not limited to, Vero cells, HeLa cells, COS cells, CHO cells, HEK293 cells, BHK cells, MDCKII cells and Per C6 cell line (e.g., PER C6 cells from Crucell). Suitable insect cells include, but are not limited to, Sf9 cells.

TABLE 1

Amino acid and nucleotide sequences for murine, chimeric and humanized antibody molecules. The antibody molecules include murine mAb BAP050, chimeric mAbs BAP050-chi, humanized mAbs BAP050-hum01 to BAP050-hum20, humanized mAbs BAP050-hum01-Ser to BAP050-hum15-Ser, BAP050-hum18-Ser to BAP050-hum20-Ser, and humanized mAbs BAP050-Clone-F to BAP050-Clone-J. The amino acid and nucleotide sequences of the heavy and light chain CDRs, the heavy and light chain variable regions, and the heavy and light chains are shown.

| BAP050 HC | | |
|---|---|---|
| SEQ ID NO: 1 (Kabat) | | HCDR1 NYGMN |
| SEQ ID NO: 2 (Kabat) | | HCDR2 WINTDTGEPTYADDFKG |
| SEQ ID NO: 3 (Kabat) | | HCDR3 NPPYYYGTNNAEAMDY |
| SEQ ID NO: 4 (Chothia) | | HCDR1 GFTLTNY |
| SEQ ID NO: 5 (Chothia) | | HCDR2 NTDTGE |
| SEQ ID NO: 3 (Chothia) | | HCDR3 NPPYYYGTNNAEAMDY |
| SEQ ID NO: 6 | VH | QIQLVQSGPELKKPGETVKISCKASGFTLTNYGMN WVRQTPGKGLKWMGWINTDTGEPTYADDFKGRFAF SLETSASTASLQINNLKNADTATYFCARNPPYYYG TNNAEAMDYWGQGTAVTVSS |
| SEQ ID NO: 7 | DNA VH | CAGATCCAGTTGGTGCAGTCTGGACCTGAGCTGAA GAAGCCTGGAGAGACAGTCAAGATCTCCTGCAAGG CTTCTGGATTTACCCTCACAAACTATGGAATGAAC TGGGTGAGGCAGACTCCAGGAAAGGGTTTAAAGTG GATGGGCTGGATAAACACCGACACTGGAGAGCCAA CATATGCTGATGACTTCAAGGGACGGTTTGCCTTC TCTTTGGAGACCTCTGCCAGCACTGCCTCTTTGCA GATCAACAACCTCAAAAATGCGGACACGGCTACAT |

TABLE 1-continued

Amino acid and nucleotide sequences for murine, chimeric and humanized antibody molecules. The antibody molecules include murine mAb BAP050, chimeric mAbs BAP050-chi, humanized mAbs BAP050-hum01 to BAP050-hum20, humanized mAbs BAP050-hum01-Ser to BAP050-hum15-Ser, BAP050-hum18-Ser to BAP050-hum20-Ser, and humanized mAbs BAP050-Clone-F to BAP050-Clone-J. The amino acid and nucleotide sequences of the heavy and light chain CDRs, the heavy and light chain variable regions, and the heavy and light chains are shown.

| | | |
|---|---|---|
| | | ATTTCTGTGCAAGAAACCCCCCTTATTACTACGGTACTAATAACGCGGAGGCTATGGACTACTGGGGTCAAGGAACCGCAGTCACCGTCTCCTCA |

BAP050 LC

| | | |
|---|---|---|
| SEQ ID NO: 10 (Kabat) | LCDR1 | SSSQDISNYLN |
| SEQ ID NO: 11 (Kabat) | LCDR2 | YTSTLHL |
| SEQ ID NO: 12 (Kabat) | LCDR3 | QQYYNLPWT |
| SEQ ID NO: 13 (Chothia) | LCDR1 | SQDISNY |
| SEQ ID NO: 14 (Chothia) | LCDR2 | YTS |
| SEQ ID NO: 15 (Chothia) | LCDR3 | YYNLPW |
| SEQ ID NO: 16 | VL | DIQMTQTTSSLSASLGDRVTISCSSSQDISNYLNWYQQKPDGTVKVLIYYTSTLHLGVPSRFSGSGSGTDYSLTISNLELEDIATYYCQQYYNLPWTFGGGTKLEIK |
| SEQ ID NO: 17 | DNA VL | GATATCCAGATGACACAGACTACATCCTCCCTGTCTGCCTCTCTGGGAGACAGAGTCACCATCAGTTGCAGTTCAAGTCAGGACATCAGCAATTATTTAAACTGGTATCAGCAGAAACCAGATGGAACTGTTAAAGTCCTGATCTATTACACATCAACCTTACACTTAGGAGTCCCATCAAGGTTCAGTGGCAGTGGGTCTGGGACAGATTATTCTCTCACCATCAGCAACCTGGAACTCGAAGATATTGCCACATACTATTGTCAGCAGTATTATAACCTTCCGTGGACGTTCGGTGGAGGCACCAAGTTGGAAATCAAA |

BAP050-chi HC

| | | |
|---|---|---|
| SEQ ID NO: 1 (Kabat) | HCDR1 | NYGMN |
| SEQ ID NO: 2 (Kabat) | HCDR2 | WINTDTGEPTYADDFKG |
| SEQ ID NO: 3 (Kabat) | HCDR3 | NPPYYYGTNNAEAMDY |
| SEQ ID NO: 4 (Chothia) | HCDR1 | GFTLTNY |
| SEQ ID NO: 5 (Chothia) | HCDR2 | NTDTGE |
| SEQ ID NO: 3 (Chothia) | HCDR3 | NPPYYYGTNNAEAMDY |
| SEQ ID NO: 20 | VH | QIQLVQSGPELKKPGETVKISCKASGFTLTNYGMNWVRQTPGKGLKWMGWINTDTGEPTYADDFKGRFAFSLETSASTASLQINNLKNADTATYFCARNPPYYYGTNNAEAMDYWGQGTTVTVSS |
| SEQ ID NO: 21 | DNA VH | CAGATCCAGTTGGTGCAGTCTGGACCTGAGCTGAAGAAGCCTGGAGAGACAGTCAAGATCTCCTGCAAGGCTTCTGGATTTACCCTCACAAACTATGGAATGAACTGGGTGAGGCAGACTCCAGGAAAGGGTTTAAAGTGGATGGGCTGGATAAACACCGACACTGGAGAGCCAACATATGCTGATGACTTCAAGGGACGGTTTGCCTTCTCTTTGGAGACCTCTGCCAGCACTGCCTCTTTGCAGATCAACAACCTCAAAAATGCGGACACGGCTACATATTTCTGTGCAAGAAACCCCCCTTATTACTACGGTACTAATAACGCGGAGGCTATGGACTACTGGGGCCAGGGCACCACCGTGACCGTGTCCTCC |
| SEQ ID NO: 22 | HC | QIQLVQSGPELKKPGETVKISCKASGFTLTNYGMNWVRQTPGKGLKWMGWINTDTGEPTYADDFKGRFAFSLETSASTASLQINNLKNADTATYFCARNPPYYYGTNNAEAMDYWGQGTTVTVSSASTKGPSVFPLAPCSRSTSESTAALGCLVKDYFPEPVTVSWNSGALTSGVHTFPAVLQSSGLYSLSSVVTVPSSSLGTKTYTCNVDHKPSNTKVDKRVESKYGPPCPPCPAPEFLGGPSVFLFPPKPKDTLMISRTPEVTCVVVDVSQEDPEVQFNWYVDGVEVHNAKTKPREEQFNSTYRVVSVLTVLHQDWLNGKEYKCKVSNKGLPSSIEKTISKAKGQPREPQVYTLPPSQEEMTKNQVSLTCLVKGFYPSDIAVEWESNGQPENNYKTTPPVLDSDGSFFLYSRLTVDKSRWQEGNVFSCSVMHEALHNHYTQKSLSLSLGK |
| SEQ ID NO: 23 | DNA HC | CAGATCCAGTTGGTGCAGTCTGGACCTGAGCTGAAGAAGCCTGGAGAGACAGTCAAGATCTCCTGCAAGGCTTCTGGATTTACCCTCACAAACTATGGAATGAACTGGGTGAGGCAGACTCCAGGAAAGGGTTTAAAGTGGATGGGCTGGATAAACACCGACACTGGAGAGCCAACATATGCTGATGACTTCAAGGGACGGTTTGCCTTCTCTTTGGAGACCTCTGCCAGCACTGCCTCTTTGCAGATCAACAACCTCAAAAATGCGGACACGGCTACATATTTCTGTGCAAGAAACCCCCCTTATTACTACGGTACTAATAACGCGGAGGCTATGGACTACTGGGGCCAGGGCACCACCGTGACCGTGTCCTCCGCTTCCACCAAGGGCCCATCCGTCTTCCCCCTGGCGCCCTGCTCCAGGAGCACCTCCGAGAGCACAGCCGCCCTGGGCTGCCTGGTCAAGGACTACTTCCCCGAACCGGTGACGGTGTCGTGGAACTCAGGCGCCCTGACCAGCGGCGTGCACACCTTCCCGGCTGTCCTACAGTCCTCAGGACTCTACTCCCTCAGCAGCGTGGTGACCGTGCCCTCCAGCAGCTTGGGCACGAAGACCTACACCTGCAACGTAGATCACAAGCCCAGCAACACCAAGGTGGACAAGAGAGTTGAGTCAAATATGGTCCCCATGCCCACCGTGCCCAGCACCTGAGTTCCTGGGGGGACCATCAGTCTTCCTGTTCCCCCCAAAACCCAAGGACACTCTCATGATCTCCCGGACCCCTGAGGTCACGTGCGTGGTGGTGGACGTGAGCCAGGAAGACCCCGAGGTCCAGTTCAACTGGTACGTGGATGGCGTGGAGGTGCATAATGCCAAGACAAAGCCGCGGGAGGAGCAGTTCAACAGCACGTACCGTGTGGTCAGCGTCCTCACCGTCCTGCACCAGGACTGGCTGAACGGCAAGGAGTACAAGTGCAAGGTCTCCAACAAAGGCCTCCCGTCCTCCATCGAGAAAACCATCTCCAAAGCCAAAGGGCAGCCCCGAGAGCCACAGGTGTACACCCTGCCCCCATCCCAGGAGGA |

TABLE 1-continued

Amino acid and nucleotide sequences for murine, chimeric and humanized antibody molecules. The antibody molecules include murine mAb BAP050, chimeric mAbs BAP050-chi, humanized mAbs BAP050-hum01 to BAP050-hum20, humanized mAbs BAP050-hum01-Ser to BAP050-hum15-Ser, BAP050-hum18-Ser to BAP050-hum20-Ser, and humanized mAbs BAP050-Clone-F to BAP050-Clone-J. The amino acid and nucleotide sequences of the heavy and light chain CDRs, the heavy and light chain variable regions, and the heavy and light chains are shown.

| | | |
|---|---|---|
| | | GATGACCAAGAACCAGGTCAGCCTGACCTGCCTGG<br>TCAAAGGCTTCTACCCCAGCGACATCGCCGTGGAG<br>TGGGAGAGCAATGGGCAGCCGGAGAACAACTACAA<br>GACCACGCCTCCCGTGCTGGACTCCGACGGCTCCT<br>TCTTCCTCTACAGCAGGCTAACCGTGGACAAGAGC<br>AGGTGGCAGGAGGGGAATGTCTTCTCATGCTCCGT<br>GATGCATGAGGCTCTGCACAACCACTACACACAGA<br>AGAGCCTCTCCCTGTCTCTGGGTAAA |
| | | BAP050-chi LC |
| SEQ ID<br>NO: 10<br>(Kabat) | LCDR1 | SSSQDISNYLN |
| SEQ ID<br>NO: 11<br>(Kabat) | LCDR2 | YTSTLHL |
| SEQ ID<br>NO: 12<br>(Kabat) | LCDR3 | QQYYNLPWT |
| SEQ ID<br>NO: 13<br>(Chothia) | LCDR1 | SQDISNY |
| SEQ ID<br>NO: 14<br>(Chothia) | LCDR2 | YTS |
| SEQ ID<br>NO: 15<br>(Chothia) | LCDR3 | YYNLPW |
| SEQ ID<br>NO: 24 | VL | DIQMTQTTSSLSASLGDRVTISCSSSQDISNYLNW<br>YQQKPDGTVKVLIYYTSTLHLGVPSRFSGSGSGTD<br>YSLTISNLELEDIATYYCQQYYNLPWTFGQGTKVE<br>IK |
| SEQ ID<br>NO: 25 | DNA<br>VL | GATATCCAGATGACACAGACTACATCCTCCCTGTC<br>TGCCTCTCTGGGAGACAGAGTCACCATCAGTTGCA<br>GTTCAAGTCAGGACATCAGCAATTATTTAAACTGG<br>TATCAGCAGAAACCAGATGGAACTGTTAAAGTCCT<br>GATCTATTACACATCAACCTTACACTTAGGAGTCC<br>CATCAAGGTTCAGTGGCAGTGGGTCTGGGACAGAT<br>TATTCTCTCACCATCAGCAACCTGGAACTGAAGA<br>TATTGCCACATACTATTGTCAGCAGTATTATAACC<br>TTCCGTGGACGTTCGGCCAAGGGACCAAGGTGGAA<br>ATCAAA |
| SEQ ID<br>NO: 26 | LC | DIQMTQTTSSLSASLGDRVTISCSSSQDISNYLNW<br>YQQKPDGTVKVLIYYTSTLHLGVPSRFSGSGSGTD<br>YSLTISNLELEDIATYYCQQYYNLPWTFGQGTKVE<br>IKRTVAAPSVFIFPPSDEQLKSGTASVVCLLNNFY<br>PREAKVQWKVDNALQSGNSQESVTEQDSKDSTYSL<br>SSTLTLSKADYEKHKVYACEVTHQGLSSPVTKSFN<br>RGEC |
| SEQ ID<br>NO: 27 | DNA<br>LC | GATATCCAGATGACACAGACTACATCCTCCCTGTC<br>TGCCTCTCTGGGAGACAGAGTCACCATCAGTTGCA<br>GTTCAAGTCAGGACATCAGCAATTATTTAAACTGG<br>TATCAGCAGAAACCAGATGGAACTGTTAAAGTCCT<br>GATCTATTACACATCAACCTTACACTTAGGAGTCC<br>CATCAAGGTTCAGTGGCAGTGGGTCTGGGACAGAT<br>TATTCTCTCACCATCAGCAACCTGGAACTGAAGA<br>TATTGCCACATACTATTGTCAGCAGTATTATAACC<br>TTCCGTGGACGTTCGGCCAAGGGACCAAGGTGGAA<br>ATCAAACGTACGGTGGCTGCACCATCTGTCTTCAT<br>CTTCCCGCCATCTGATGAGCAGTTGAAATCTGGAA<br>CTGCCTCTGTTGTGTGCCTGCTGAATAACTTCTAT<br>CCCAGAGAGGCCAAAGTACAGTGGAAGGTGGATAA<br>CGCCCTCCAATGGGTAACTCCCAGGAGAGTGTCA<br>CAGAGCAGGACAGCAAGGACAGCACCTACAGCCTC<br>AGCAGCACCCTGACGCTGAGCAAAGCAGACTACGA<br>GAAACACAAAGTCTACGCCTGCGAAGTCACCCATC<br>AGGGCCTGAGCTCGCCCGTCACAAAGAGCTTCAAC<br>AGGGGAGAGTGT |
| | | BAP050-hum01 HC |
| SEQ ID<br>NO: 1<br>(Kabat) | HCDR1 | NYGMN |
| SEQ ID<br>NO: 2<br>(Kabat) | HCDR2 | WINTDTGEPTYADDFKG |
| SEQ ID<br>NO: 3<br>(Kabat) | HCDR3 | NPPYYYGTNNAEAMDY |
| SEQ ID<br>NO: 4<br>(Chothia) | HCDR1 | GFTLTNY |
| SEQ ID<br>NO: 5<br>(Chothia) | HCDR2 | NTDTGE |
| SEQ ID<br>NO: 3<br>(Chothia) | HCDR3 | NPPYYYGTNNAEAMDY |
| SEQ ID<br>NO: 28 | VH | EVQLVQSGAEVKKPGATVKISCKVSGFTLTNYGMN<br>WVRQAPGQGLEWMGWINTDTGEPTYADDFKGRFVF<br>SLDTSVSTAYLQICSLKAEDTAVYYCARNPPYYYG<br>TNNAEAMDYWGQGTTVTVSS |
| SEQ ID<br>NO: 29 | DNA<br>VH | GAGGTCCAGCTGGTACAGTCTGGGGCTGAGGTGAA<br>GAAGCCTGGGGCTACAGTGAAAATCTCCTGCAAGG<br>TTTCTGGATTTACCCTCACAAACTATGGAATGAAC<br>TGGGTGCGACAGGCCCCTGGACAAGGGCTTGAGTG<br>GATGGGTTGGATAAACACCGACACTGGAGAGCCAA<br>CATATGCTGATGACTTCAAGGGAAGATTTGTCTTC<br>TCCTTGGACACCTCTGTCAGCACGGCATATCTGCA<br>GATCTGCAGCCTAAAGGCTGAGGACACTGCCGTGT<br>ATTACTGTGCAAGAAACCCTCCCTATTACTACGGT<br>ACTAATAACGCGGAGGCTATGGACTACTGGGGCCA<br>GGGCACCACCGTGACCGTGTCCTCC |
| SEQ ID<br>NO: 30 | HC | EVQLVQSGAEVKKPGATVKISCKVSGFTLTNYGMN<br>WVRQAPGQGLEWMGWINTDTGEPTYADDFKGRFVF<br>SLDTSVSTAYLQICSLKAEDTAVYYCARNPPYYYG<br>TNNAEAMDYWGQGTTVTVSSASTKGPSVFPLAPCS<br>RSTSESTAALGCLVKDYFPEPVTVSWNSGALTSGV<br>HTFPAVLQSSGLYSLSSVVTVPSSSLGTKTYTCNV<br>DHKPSNTKVDKRVESKYGPPCPPCPAPEFLGGPSV<br>FLFPPKPKDTLMISRTPEVTCVVVDVSQEDPEVQF<br>NWYVDGVEVHNAKTKPREEQFNSTYRVVSVLTVLH |

TABLE 1-continued

Amino acid and nucleotide sequences for murine, chimeric and humanized antibody molecules. The antibody molecules include murine mAb BAP050, chimeric mAbs BAP050-chi, humanized mAbs BAP050-hum01 to BAP050-hum20, humanized mAbs BAP050-hum01-Ser to BAP050-hum15-Ser, BAP050-hum18-Ser to BAP050-hum20-Ser, and humanized mAbs BAP050-Clone-F to BAP050-Clone-J. The amino acid and nucleotide sequences of the heavy and light chain CDRs, the heavy and light chain variable regions, and the heavy and light chains are shown.

| | | |
|---|---|---|
| | | QDWLNGKEYKCKVSNKGLPSSIEKTISKAKGQPRE PQVYTLPPSQEEMTKNQVSLTCLVKGFYPSDIAVE WESNGQPENNYKTTPPVLDSDGSFFLYSRLTVDKS RWQEGNVFSCSVMHEALHNHYTQKSLSLSLGK |
| SEQ ID NO: 31 | DNA HC | GAGGTCCAGCTGGTACAGTCTGGGGCTGAGGTGAA GAAGCCTGGGGCTACAGTGAAAATCTCCTGCAAGG TTTCTGGATTTACCCTCACAAACTATGGAATGAAC TGGGTGCGACAGGCCCCTGGACAAGGGCTTGAGTG GATGGGTTGGATAAACACCGACACTGGAGAGCCAA CATATGCTGATGACTTCAAGGGAAGATTTGTCTTC TCCTTGGACACCTCTGTCAGCACGGCATATCTGCA GATCTGCAGCCTAAAGGCTGAGGACACTGCCGTGT ATTACTGTGCAAGAAACCCTCCCTATTACTACGGT ACTAATAACGCGGAGGCTATGGACTACTGGGGCCA GGGCACCACCGTGACCGTGTCCTCCGCTTCCACCA AGGGCCCATCCGTCTTCCCCCTGGCGCCCTGCTCC AGGAGCACCTCCGAGAGCACAGCCGCCCTGGGCTG CCTGGTCAAGGACTACTTCCCCGAACCGGTGACGG TGTCGTGGAACTCAGGCGCCCTGACCAGCGGCGTG CACACCTTCCCGGCTGTCCTACAGTCCTCAGGACT CTACTCCCTCAGCAGCGTGGTGACCGTGCCCTCCA GCAGCTTGGGCACGAAGACCTACACCTGCAACGTA GATCACAAGCCCAGCAACACCAAGGTGGACAAGAG AGTTGAGTCCAAATATGGTCCCCCATGCCCACCGT GCCCAGCACCTGAGTTCCTGGGGGGACCATCAGTC TTCCTGTTCCCCCCAAAACCCAAGGACACTCTCAT GATCTCCCGGACCCCTGAGGTCACGTGCGTGGTGG TGGACGTGAGCCAGGAAGACCCCGAGGTCCAGTTC AACTGGTACGTGGATGGCGTGGAGGTGCATAATGC CAAGACAAAGCCGCGGGAGGAGCAGTTCAACAGCA CGTACCGTGTGGTCAGCGTCCTCACCGTCCTGCAC CAGGACTGGCTGAACGGCAAGGAGTACAAGTGCAA GGTGTCCAACAAAGGCCTCCCGTCCTCCATCGAGA AAACCATCTCCAAAGCCAAAGGGCAGCCCCGAGAG CCACAGGTGTACACCCTGCCCCCATCCCAGGAGGA GATGACCAAGAACCAGGTCAGCCTGACCTGCCTGG TCAAAGGCTTCTACCCCAGCGACATCGCCGTGGAG TGGGAGAGCAATGGGCAGCCGGAGAACAACTACAA GACCACGCCTCCCGTGCTGGACTCCGACGGCTCCT TCTTCCTCTACAGCAGGCTAACCGTGGACAAGAGC AGGTGGCAGGAGGGGAATGTCTTCTCATGCTCCGT GATGCATGAGGCTCTGCACAACCACTACACACAGA AGAGCCTCTCCCTGTCTCTGGGTAAA |

BAP050-hum01 LC

| | | |
|---|---|---|
| SEQ ID NO: 10 (Kabat) | LCDR1 | SSSQDISNYLN |
| SEQ ID NO: 11 (Kabat) | LCDR2 | YTSTLHL |
| SEQ ID NO: 12 (Kabat) | LCDR3 | QQYYNLPWT |
| SEQ ID NO: 13 (Chothia) | LCDR1 | SQDISNY |
| SEQ ID NO: 14 (Chothia) | LCDR2 | YTS |
| SEQ ID NO: 15 (Chothia) | LCDR3 | YYNLPW |
| SEQ ID NO: 32 | VL | DIQMTQSPSSLSASVGDRVTITCSSSQDISNYLNW YQQKPGKAPKLLIYYTSTLHLGVPSRFSGSGSGTD FTFTISSLEAEDAATYYCQQYYNLPWTFGQGTKVE IK |
| SEQ ID NO: 33 | DNA VL | GACATCCAGATGACCCAGTCTCCATCCTCCCTGTC TGCATCTGTAGGAGACAGAGTCACCATCACTTGCA GTTCAAGTCAGGACATCAGCAATTATTTAAACTGG TATCAGCAGAAACCAGGGAAAGCTCCTAAGCTCCT GATCTATTACACATCAACCTTACACTTAGGGGTCC CCTCGAGGTTCAGTGGCAGTGGATCTGGGACAGAT TTCACCTTTACCATCAGTAGCCTGGAAGCTGAAGA TGCTGCAACATATTACTGTCAGCAGTATTATAACC TTCCGTGGACGTTCGGCCAAGGGACCAAGGTGGAA ATCAAA |
| SEQ ID NO: 34 | LC | DIQMTQSPSSLSASVGDRVTITCSSSQDISNYLNW YQQKPGKAPKLLIYYTSTLHLGVPSRFSGSGSGTD FTFTISSLEAEDAATYYCQQYYNLPWTFGQGTKVE IKRTVAAPSVFIFPPSDEQLKSGTASVVCLLNNFY PREAKVQWKVDNALQSGNSQESVTEQDSKDSTYSL SSTLTLSKADYEKHKVYACEVTHQGLSSPVTKSFN RGEC |
| SEQ ID NO: 35 | DNA LC | GACATCCAGATGACCCAGTCTCCATCCTCCCTGTC TGCATCTGTAGGAGACAGAGTCACCATCACTTGCA GTTCAAGTCAGGACATCAGCAATTATTTAAACTGG TATCAGCAGAAACCAGGGAAAGCTCCTAAGCTCCT GATCTATTACACATCAACCTTACACTTAGGGGTCC CCTCGAGGTTCAGTGGCAGTGGATCTGGGACAGAT TTCACCTTTACCATCAGTAGCCTGGAAGCTGAAGA TGCTGCAACATATTACTGTCAGCAGTATTATAACC TTCCGTGGACGTTCGGCCAAGGGACCAAGGTGGAA ATCAAACGTACGGTGGCTGCACCATCTGTCTTCAT CTTCCCGCCATCTGATGAGCAGTTGAAATCTGGAA CTGCCTCTGTTGTGTGCCTGCTGAATAACTTCTAT CCCAGAGAGGCCAAAGTACAGTGGAAGGTGGATAA CGCCCTCCAATCGGGTAACTCCCAGGAGAGTGTCA CAGAGCAGGACAGCAAGGACAGCACCTACAGCCTC AGCAGCACCCTGACGCTGAGCAAAGCAGACTACGA GAAACACAAAGTCTACGCCTGCGAAGTCACCCATC AGGGCCTGAGCTCGCCCGTCACAAAGAGCTTCAAC AGGGGAGAGTGT |

BAP050-hum02 HC

| | | |
|---|---|---|
| SEQ ID NO: 1 (Kabat) | HCDR1 | NYGMN |
| SEQ ID NO: 2 (Kabat) | HCDR2 | WINTDTGEPTYADDFKG |
| SEQ ID NO: 3 (Kabat) | HCDR3 | NPPYYYGTNNAEAMDY |
| SEQ ID NO: 4 (Chothia) | HCDR1 | GFTLTNY |

TABLE 1-continued

Amino acid and nucleotide sequences for murine, chimeric and humanized antibody molecules. The antibody molecules include murine mAb BAP050, chimeric mAbs BAP050-chi, humanized mAbs BAP050-hum01 to BAP050-hum20, humanized mAbs BAP050-hum01-Ser to BAP050-hum15-Ser, BAP050-hum18-Ser to BAP050-hum20-Ser, and humanized mAbs BAP050-Clone-F to BAP050-Clone-J. The amino acid and nucleotide sequences of the heavy and light chain CDRs, the heavy and light chain variable regions, and the heavy and light chains are shown.

| | | |
|---|---|---|
| SEQ ID NO: 5 (Chothia) | HCDR2 | NTDTGE |
| SEQ ID NO: 3 (Chothia) | HCDR3 | NPPYYYGTNNAEAMDY |
| SEQ ID NO: 28 | VH | EVQLVQSGAEVKKPGATVKISCKVSGFTLTNYGMN WVRQAPGQGLEWMGWINTDTGEPTYADDFKGRFVF SLDTSVSTAYLQICSLKAEDTAVYYCARNPPYYYG TNNAEAMDYWGQGTTVTVSS |
| SEQ ID NO: 29 | DNA VH | GAGGTCCAGCTGGTACAGTCTGGGGCTGAGGTGAA GAAGCCTGGGGCTACAGTGAAAATCTCCTGCAAGG TTTCTGGATTTACCCTCACAAACTATGGAATGAAC TGGGTGCGACAGGCCCCTGGACAAGGGCTTGAGTG GATGGGTTGGATAAACACCGACACTGGAGAGCCAA CATATGCTGATGACTTCAAGGGAAGATTTGTCTTC TCCTTGGACACCTCTGTCAGCACGGCATATCTGCA GATCTGCAGCCTAAAGGCTGAGGACACTGCCGTGT ATTACTGTGCAAGAAACCCTCCCTATTACTACGGT ACTAATAACGCGGAGGCTATGGACTACTGGGGCCA GGGCACCACCGTGACCGTGTCCTCC |
| SEQ ID NO: 30 | HC | EVQLVQSGAEVKKPGATVKISCKVSGFTLTNYGMN WVRQAPGQGLEWMGWINTDTGEPTYADDFKGRFVF SLDTSVSTAYLQICSLKAEDTAVYYCARNPPYYYG TNNAEAMDYWGQGTTVTVSSASTKGPSVFPLAPCS RSTSESTAALGCLVKDYFPEPVTVSWNSGALTSGV HTFPAVLQSSGLYSLSSVVTVPSSSLGTKTYTCNV DHKPSNTKVDKRVESKYGPPCPPCPAPEFLGGPSV FLFPPKPKDTLMISRTPEVTCVVVDVSQEDPEVQF NWYVDGVEVHNAKTKPREEQFNSTYRVVSVLTVLH QDWLNGKEYKCKVSNKGLPSSIEKTISKAKGQPRE PQVYTLPPSQEEMTKNQVSLTCLVKGFYPSDIAVE WESNGQPENNYKTTPPVLDSDGSFFLYSRLTVDKS RWQEGNVFSCSVMHEALHNHYTQKSLSLSLGK |
| SEQ ID NO: 31 | DNA HC | GAGGTCCAGCTGGTACAGTCTGGGGCTGAGGTGAA GAAGCCTGGGGCTACAGTGAAAATCTCCTGCAAGG TTTCTGGATTTACCCTCACAAACTATGGAATGAAC TGGGTGCGACAGGCCCCTGGACAAGGGCTTGAGTG GATGGGTTGGATAAACACCGACACTGGAGAGCCAA CATATGCTGATGACTTCAAGGGAAGATTTGTCTTC TCCTTGGACACCTCTGTCAGCACGGCATATCTGCA GATCTGCAGCCTAAAGGCTGAGGACACTGCCGTGT ATTACTGTGCAAGAAACCCTCCCTATTACTACGGT ACTAATAACGCGGAGGCTATGGACTACTGGGGCCA GGGCACCACCGTGACCGTGTCCTCCGCTTCCACCA AGGGCCCATCCGTCTTCCCCCTGGCGCCCTGCTCC AGGAGCACCTCCGAGAGCACAGCCGCCCTGGGCTG CCTGGTCAAGGACTACTTCCCCGAACCGGTGACGG TGTCGTGGAACTCAGGCGCCCTGACCAGCGGCGTG CACACCTTCCCGGCTGTCCTACAGTCCTCAGGACT CTACTCCCTCAGCAGCGTGGTGACCGTGCCCTCCA GCAGCTTGGGCACGAAGACCTACACCTGCAACGTA GATCACAAGCCCAGCAACACCAAGGTGGACAAGAG AGTTGAGTCCAAATATGGTCCCCCATGCCCACCGT GCCCAGCACCTGAGTTCCTGGGGGGACCATCAGTC TTCCTGTTCCCCCCAAAACCCAAGGACACTCTCAT GATCTCCCGGACCCCTGAGGTCACGTGCGTGGTGG TGGACGTGAGCCAGGAAGACCCCGAGGTCCAGTTC AACTGGTACGTGGATGGCGTGGAGGTGCATAATGC CAAGACAAAGCCGCGGGAGGAGCAGTTCAACAGCA CGTACCGTGTGGTCAGCGTCCTCACCGTCCTGCAC CAGGACTGGCTGAACGGCAAGGAGTACAAGTGCAA |

| | | |
|---|---|---|
| | | GGTGTCCAACAAAGGCCTCCCGTCCTCCATCGAGA AAACCATCTCCAAAGCCAAAGGGCAGCCCCGAGAG CCACAGGTGTACACCCTGCCCCCATCCCAGGAGGA GATGACCAAGAACCAGGTCAGCCTGACCTGCCTGG TCAAAGGCTTCTACCCCAGCGACATCGCCGTGGAG TGGGAGAGCAATGGGCAGCCGGAGAACAACTACAA GACCACGCCTCCCGTGCTGGACTCCGACGGCTCCT TCTTCCTCTACAGCAGGCTAACCGTGGACAAGAGC AGGTGGCAGGAGGGGAATGTCTTCTCATGCTCCGT GATGCATGAGGCTCTGCACAACCACTACACACAGA AGAGCCTCTCCCTGTCTCTGGGTAAA |

BAP050-hum02 LC

| | | |
|---|---|---|
| SEQ ID NO: 10 (Kabat) | LCDR1 | SSSQDISNYLN |
| SEQ ID NO: 11 (Kabat) | LCDR2 | YTSTLHL |
| SEQ ID NO: 12 (Kabat) | LCDR3 | QQYYNLPWT |
| SEQ ID NO: 13 (Chothia) | LCDR1 | SQDISNY |
| SEQ ID NO: 14 (Chothia) | LCDR2 | YTS |
| SEQ ID NO: 15 (Chothia) | LCDR3 | YYNLPW |
| SEQ ID NO: 36 | VL | DIQMTQSPSSLSASVGDRVTITCSSSQDISNYLNW YQQKPGKAPKLLIYYTSTLHLGIPPRFSGSGYGTD FTLTINNIESEDAAYYFCQQYYNLPWTFGQGTKVE IK |
| SEQ ID NO: 37 | DNA VL | GACATCCAGATGACCCAGTCTCCATCCTCCCTGTC TGCATCTGTAGGAGACAGAGTCACCATCACTTGCA GTTCAAGTCAGGACATCAGCAATTATTTAAACTGG TATCAGCAGAAACCAGGGAAAGCTCCTAAGCTCCT GATCTATTACACATCAACCTTACACTTAGGGATCC CACCTCGATTCAGTGGCAGCGGGTATGGAACAGAT TTTACCCTCACAATTAATAACATAGAATCTGAGGA TGCTGCATATTACTTCTGTCAGCAGTATTATAACC TTCCGTGGACGTTCGGCCAAGGGACCAAGGTGGAA ATCAAA |
| SEQ ID NO: 38 | LC | DIQMTQSPSSLSASVGDRVTITCSSSQDISNYLNW YQQKPGKAPKLLIYYTSTLHLGIPPRFSGSGYGTD FTLTINNIESEDAAYYFCQQYYNLPWTFGQGTKVE IKRTVAAPSVFIFPPSDEQLKSGTASVVCLLNNFY PREAKVQWKVDNALQSGNSQESVTEQDSKDSTYSL SSTLTLSKADYEKHKVYACEVTHQGLSSPVTKSFN RGEC |
| SEQ ID NO: 39 | DNA LC | GACATCCAGATGACCCAGTCTCCATCCTCCCTGTC TGCATCTGTAGGAGACAGAGTCACCATCACTTGCA GTTCAAGTCAGGACATCAGCAATTATTTAAACTGG TATCAGCAGAAACCAGGGAAAGCTCCTAAGCTCCT GATCTATTACACATCAACCTTACACTTAGGGATCC |

TABLE 1-continued

Amino acid and nucleotide sequences for murine, chimeric and humanized antibody molecules. The antibody molecules include murine mAb BAP050, chimeric mAbs BAP050-chi, humanized mAbs BAP050-hum01 to BAP050-hum20, humanized mAbs BAP050-hum01-Ser to BAP050-hum15-Ser, BAP050-hum18-Ser to BAP050-hum20-Ser, and humanized mAbs BAP050-Clone-F to BAP050-Clone-J. The amino acid and nucleotide sequences of the heavy and light chain CDRs, the heavy and light chain variable regions, and the heavy and light chains are shown.

|  |  |  |
|---|---|---|
|  |  | CACCTCGATTCAGTGGCAGCGGGTATGGAACAGAT TTTACCCTCACAATTAATAACATAGAATCTGAGGA TGCTGCATATTACTTCTGTCAGCAGTATTATAACC TTCCGTGGACGTTCGGCCAAGGGACCAAGGTGAA ATCAAACGTACGGTGGCTGCACCATCTGTCTTCAT CTTCCCGCCATCTGATGAGCAGTTGAAATCTGAA CTGCCTCTGTTGTGTGCCTGCTGAATAACTTCTAT CCCAGAGAGGCCAAAGTACAGTGGAAGGTGGATAA CGCCCTCCAATCGGGTAACTCCCAGGAGAGTGTCA CAGAGCAGGACAGCAAGGACAGCACCTACAGCCTC AGCAGCACCCTGACGCTGAGCAAAGCAGACTACGA GAAACACAAAGTCTACGCCTGCGAAGTCACCCATC AGGGCCTGAGCTCGCCCGTCACAAAGAGCTTCAAC AGGGGAGAGTGT |
|  | BAP050-hum03 HC |  |
| SEQ ID NO: 1 (Kabat) | HCDR1 | NYGMN |
| SEQ ID NO: 2 (Kabat) | HCDR2 | WINTDTGEPTYADDFKG |
| SEQ ID NO: 3 (Kabat) | HCDR3 | NPPYYYGTNNAEAMDY |
| SEQ ID NO: 4 (Chothia) | HCDR1 | GFTLTNY |
| SEQ ID NO: 5 (Chothia) | HCDR2 | NTDTGE |
| SEQ ID NO: 3 (Chothia) | HCDR3 | NPPYYYGTNNAEAMDY |
| SEQ ID NO: 28 | VH | EVQLVQSGAEVKKPGATVKISCKVSGFTLTNYGMN WVRQAPGQGLEWMGWINTDTGEPTYADDFKGRFVF SLDTSVSTAYLQICSLKAEDTAVYYCARNPPYYYG TNNAEAMDYWGQGTTVTVSS |
| SEQ ID NO: 29 | DNA VH | GAGGTCCAGCTGGTACAGTCTGGGGCTGAGGTGAA GAAGCCTGGGGCTACAGTGAAAATCTCCTGCAAGG TTTCTGGATTTACCCTCACAAACTATGGAATGAAC TGGGTGCGACAGGCCCCTGGACAAGGGCTTGAGTG GATGGGTTGGATAAACACCGACACTGGAGAGCCAA CATATGCTGATGACTTCAAGGGAAGATTTGTCTTC TCCTTGGACACCTCTGTCAGCACGGCATATCTGCA GATCTGCAGCCTAAAGGCTGAGGACACTGCCGTGT ATTACTGTGCAAGAAACCCTCCCTATTACTACGGT ACTAATAACGCGGAGGCTATGGACTACTGGGGCCA GGGCACCACCGTGACCGTGTCCTCC |
| SEQ ID NO: 30 | HC | EVQLVQSGAEVKKPGATVKISCKVSGFTLTNYGMN WVRQAPGQGLEWMGWINTDTGEPTYADDFKGRFVF SLDTSVSTAYLQICSLKAEDTAVYYCARNPPYYYG TNNAEAMDYWGQGTTVTVSSASTKGPSVFPLAPCS RSTSESTAALGCLVKDYFPEPVTVSWNSGALTSGV HTFPAVLQSSGLYSLSSVVTVPSSSLGTKTYTCNV DHKPSNTKVDKRVESKYGPPCPPCPAPEFLGGPSV FLFPPKPKDTLMISRTPEVTCVVVDVSQEDPEVQF NWYVDGVEVHNAKTKPREEQFNSTYRVVSVLTVLH |

TABLE 1-continued

Amino acid and nucleotide sequences for murine, chimeric and humanized antibody molecules. The antibody molecules include murine mAb BAP050, chimeric mAbs BAP050-chi, humanized mAbs BAP050-hum01 to BAP050-hum20, humanized mAbs BAP050-hum01-Ser to BAP050-hum15-Ser, BAP050-hum18-Ser to BAP050-hum20-Ser, and humanized mAbs BAP050-Clone-F to BAP050-Clone-J. The amino acid and nucleotide sequences of the heavy and light chain CDRs, the heavy and light chain variable regions, and the heavy and light chains are shown.

|  |  |  |
|---|---|---|
|  |  | QDWLNGKEYKCKVSNKGLPSSIEKTISKAKGQPRE PQVYTLPPSQEEMTKNQVSLTCLVKGFYPSDIAVE WESNGQPENNYKTTPPVLDSDGSFFLYSRLTVDKS RWQEGNVFSCSVMHEALHNHYTQKSLSLSLGK |
| SEQ ID NO: 31 | DNA HC | GAGGTCCAGCTGGTACAGTCTGGGGCTGAGGTGAA GAAGCCTGGGGCTACAGTGAAAATCTCCTGCAAGG TTTCTGGATTTACCCTCACAAACTATGGAATGAAC TGGGTGCGACAGGCCCCTGGACAAGGGCTTGAGTG GATGGGTTGGATAAACACCGACACTGGAGAGCCAA CATATGCTGATGACTTCAAGGGAAGATTTGTCTTC TCCTTGGACACCTCTGTCAGCACGGCATATCTGCA GATCTGCAGCCTAAAGGCTGAGGACACTGCCGTGT ATTACTGTGCAAGAAACCCTCCCTATTACTACGGT ACTAATAACGCGGAGGCTATGGACTACTGGGGCCA GGGCACCACCGTGACCGTGTCCTCCGCTTCCACCA AGGGCCCATCCGTCTTCCCCCTGGCGCCCTGCTCC AGGAGCACCTCCGAGAGCACAGCCGCCCTGGGCTG CCTGGTCAAGGACTACTTCCCCGAACCGGTGACGG TGTCGTGGAACTCAGGCGCCCTGACCAGCGGCGTG CACACCTTCCCGGCTGTCCTACAGTCCTCAGGACT CTACTCCCTCAGCAGCGTGGTGACCGTGCCCTCCA GCAGCTTGGGCACGAAGACCTACACCTGCAACGTA GATCACAAGCCCAGCAACACCAAGGTGGACAAGAG AGTTGAGTCCAAATATGGTCCCCCATGCCCACCGT GCCCAGCACCTGAGTTCCTGGGGGGACCATCAGTC TTCCTGTTCCCCCCAAAACCCAAGGACACTCTCAT GATCTCCCGGACCCCTGAGGTCACGTGCGTGGTGG TGGACGTGAGCCAGGAAGACCCCGAGGTCCAGTTC AACTGGTACGTGGATGGCGTGGAGGTGCATAATGC CAAGACAAAGCCGCGGGAGGAGCAGTTCAACAGCA CGTACCGTGTGGTCAGCGTCCTCACCGTCCTGCAC CAGGACTGGCTGAACGGCAAGGAGTACAAGTGCAA GGTGTCCAACAAAGCCCTCCCGTCCTCCATCGAGA AAACCATCTCCAAAGCCAAAGGGCAGCCCCGAGAG CCACAGGTGTACACCCTGCCCCCATCCCAGGAGGA GATGACCAAGAACCAGGTCAGCCTGACCTGCCTGG TCAAAGGCTTCTACCCCAGCGACATCGCCGTGGAG TGGGAGAGCAATGGGCAGCCGGAGAACAACTACAA GACCACGCCTCCCGTGCTGGACTCCGACGGCTCCT TCTTCCTCTACAGCAGGCTAACCGTGGACAAGAGC AGGTGGCAGGAGGGGAATGTCTTCTCATGCTCCGT GATGCATGAGGCTCTGCACAACCACTACACAGA AGAGCCTCTCCCTGTCTCTGGGTAAA |
|  | BAP050-hum03 LC |  |
| SEQ ID NO: 10 (Kabat) | LCDR1 | SSQDISNYLN |
| SEQ ID NO: 11 (Kabat) | LCDR2 | YTSTLHL |
| SEQ ID NO: 12 (Kabat) | LCDR3 | QQYYNLPWT |
| SEQ ID NO: 13 (Chothia) | LCDR1 | SQDISNY |
| SEQ ID NO: 14 (Chothia) | LCDR2 | YTS |

TABLE 1-continued

Amino acid and nucleotide sequences for murine, chimeric and humanized antibody molecules. The antibody molecules include murine mAb BAP050, chimeric mAbs BAP050-chi, humanized mAbs BAP050-hum01 to BAP050-hum20, humanized mAbs BAP050-hum01-Ser to BAP050-hum15-Ser, BAP050-hum18-Ser to BAP050-hum20-Ser, and humanized mAbs BAP050-Clone-F to BAP050-Clone-J. The amino acid and nucleotide sequences of the heavy and light chain CDRs, the heavy and light chain variable regions, and the heavy and light chains are shown.

| SEQ ID NO: 15 (Chothia) | | LCDR3 YYNLPW |

| SEQ ID NO: 40 | VL | EIVLTQSPATLPVTLGQPASISCSSSQDISNYLNW YQQKPGQAPRLLIYYTSTLHLGVPSRFSGSGSGTD FTFTISSLEAEDAATYYCQQYYNLPWTFGQGTKVE IK |

| SEQ ID NO: 41 | DNA VL | GAAATTGTGTTGACACAGTCTCCAGCCACCCTGCC CGTCACCCTTGGACAGCCGGCCTCCATCTCCTGCA GTTCAAGTCAGGACATCAGCAATTATTTAAACTGG TACCAGCAGAAACCTGGCCAGGCTCCCAGGCTCCT CATCTATTACACATCAACCTTACACTTAGGGGTCC CCTCGAGGTTCAGTGGCAGTGGATCTGGGACAGAT TTCACCTTTACCATCAGTAGCCTGGAAGCTGAAGA TGCTGCAACATATTACTGTCAGCAGTATTATAACC TTCCGTGGACGTTCGGCCAAGGGACCAAGGTGGAA ATCAAA |

| SEQ ID NO: 42 | LC | EIVLTQSPATLPVTLGQPASISCSSSQDISNYLNW YQQKPGQAPRLLIYYTSTLHLGVPSRFSGSGSGTD FTFTISSLEAEDAATYYCQQYYNLPWTFGQGTKVE IKRTVAAPSVFIFPPSDEQLKSGTASVVCLLNNFY PREAKVQWKVDNALQSGNSQESVTEQDSKDSTYSL SSTLTLSKADYEKHKVYACEVTHQGLSSPVTKSFN RGEC |

| SEQ ID NO: 43 | DNA LC | GAAATTGTGTTGACACAGTCTCCAGCCACCCTGCC CGTCACCCTTGGACAGCCGGCCTCCATCTCCTGCA GTTCAAGTCAGGACATCAGCAATTATTTAAACTGG TACCAGCAGAAACCTGGCCAGGCTCCCAGGCTCCT CATCTATTACACATCAACCTTACACTTAGGGGTCC CCTCGAGGTTCAGTGGCAGTGGATCTGGGACAGAT TTCACCTTTACCATCAGTAGCCTGGAAGCTGAAGA TGCTGCAACATATTACTGTCAGCAGTATTATAACC TTCCGTGGACGTTCGGCCAAGGGACCAAGGTGGAA ATCAAACGTACGGTGGCTGCCACCATCTGTCTTCAT CTTCCCGCCATCTGATGAGCAGTTGAAATCTGGAA CTGCCTCTGTTGTGTGCCTGCTGAATAACTTCTAT CCCAGAGAGGCCAAAGTACAGTGGAAGGTGGATAA CGCCCTCCAATCGGGTAACTCCCAGGAGAGTGTCA CAGAGCAGGACAGCAAGGACAGCACCTACAGCCTC AGCAGCACCCTGACGCTGAGCAAAGCAGACTACGA GAAACACAAAGTCTACGCCTGCGAAGTCACCCATC AGGGCCTGAGCTCGCCCGTCACAAAGAGCTTCAAC AGGGGAGAGTGT |

BAP050-hum04 HC

| SEQ ID NO: 1 (Kabat) | | HCDR1 NYGMN |

| SEQ ID NO: 2 (Kabat) | | HCDR2 WINTDTGEPTYADDFKG |

| SEQ ID NO: 3 (Kabat) | | HCDR3 NPPYYYGTNNAEAMDY |

| SEQ ID NO: 4 (Chothia) | | HCDR1 GFTLTNY |

| SEQ ID NO: 5 (Chothia) | | HCDR2 NTDTGE |

| SEQ ID NO: 3 (Chothia) | | HCDR3 NPPYYYGTNNAEAMDY |

| SEQ ID NO: 28 | VH | EVQLVQSGAEVKKPGATVKISCKVSGFTLTNYGMN WVRQAPGQGLEWMGWINTDTGEPTYADDFKGRFVF SLDTSVSTAYLQICSLKAEDTAVYYCARNPPYYYG TNNAEAMDYWGQGTTVTVSS |

| SEQ ID NO: 29 | DNA VH | GAGGTCCAGCTGGTACAGTCTGGGGCTGAGGTGAA GAAGCCTGGGGCTACAGTGAAAATCTCCTGCAAGG TTTCTGGATTTACCCTCACAAACTATGGAATGAAC TGGGTGCGACAGGCCCCTGGACAAGGGCTTGAGTG GATGGGTTGGATAAACACCGACACTGGAGAGCCAA CATATGCTGATGACTTCAAGGGAAGATTTGTCTTC TCCTTGGACACCTCTGTCAGCACGGCATATCTGCA GATCTGCAGCCTAAAGGCTGAGGACACTGCCGTGT ATTACTGTGCAAGAAACCCTCCCTATTACTACGGT ACTAATAACGCGGAGGCTATGGACTACTGGGGCCA GGGCACCACCGTGACCGTGTCCTCC |

| SEQ ID NO: 30 | HC | EVQLVQSGAEVKKPGATVKISCKVSGFTLTNYGMN WVRQAPGQGLEWMGWINTDTGEPTYADDFKGRFVF SLDTSVSTAYLQICSLKAEDTAVYYCARNPPYYYG TNNAEAMDYWGQGTTVTVSSASTKGPSVFPLAPCS RSTSESTAALGCLVKDYFPEPVTVSWNSGALTSGV HTFPAVLQSSGLYSLSSVVTVPSSSLGTKTYTCNV DHKPSNTKVDKRVESKYGPPCPPCPAPEFLGGPSV FLFPPKPKDTLMISRTPEVTCVVVDVSQEDPEVQF NWYVDGVEVHNAKTKPREEQFNSTYRVVSVLTVLH QDWLNGKEYKCKVSNKGLPSSIEKTISKAKGQPRE PQVYTLPPSQEEMTKNQVSLTCLVKGFYPSDIAVE WESNGQPENNYKTTPPVLDSDGSFFLYSRLTVDKS RWQEGNVFSCSVMHEALHNHYTQKSLSLSLGK |

| SEQ ID NO: 31 | DNA HC | GAGGTCCAGCTGGTACAGTCTGGGGCTGAGGTGAA GAAGCCTGGGGCTACAGTGAAAATCTCCTGCAAGG TTTCTGGATTTACCCTCACAAACTATGGAATGAAC TGGGTGCGACAGGCCCCTGGACAAGGGCTTGAGTG GATGGGTTGGATAAACACCGACACTGGAGAGCCAA CATATGCTGATGACTTCAAGGGAAGATTTGTCTTC TCCTTGGACACCTCTGTCAGCACGGCATATCTGCA GATCTGCAGCCTAAAGGCTGAGGACACTGCCGTGT ATTACTGTGCAAGAAACCCTCCCTATTACTACGGT ACTAATAACGCGGAGGCTATGGACTACTGGGGCCA GGGCACCACCGTGACCGTGTCCTCCGCTTCCACCA AGGGCCCATCCGTCTTCCCCCTGGCGCCCTGCTCC AGGAGCACCTCCGAGAGCACAGCCGCCCTGGGCTG CCTGGTCAAGGACTACTTCCCCGAACCGGTGACGG TGTCGTGGAACTCAGGCGCCCTGACCAGCGGCGTG CACACCTTCCCGGCTGTCCTACAGTCCTCAGGACT CTACTCCCTCAGCAGCGTGGTGACCGTGCCCTCCA GCAGCTTGGGCACGAAGACCTACACCTGCAACGTA GATCACAAGCCCAGCAACACCAAGGTGGACAAGAG AGTTGAGTCCAAATATGGTCCCCCATGCCCACCGT GCCCAGCACCTGAGTTCCTGGGGGGACCATCAGTC TTCCTGTTCCCCCCAAAACCCAAGGACACTCTCAT GATCTCCCGGACCCCTGAGGTCACGTGCGTGGTGG TGGACGTGAGCCAGGAAGACCCCGAGGTCCAGTTC AACTGGTACGTGGATGGCGTGGAGGTGCATAATGC CAAGACAAAGCCGCGGGAGGAGCAGTTCAACAGCA CGTACCGTGTGGTCAGCGTCCTCACCGTCCTGCAC CAGGACTGGCTGAACGGCAAGGAGTACAAGTGCAA

TABLE 1-continued

Amino acid and nucleotide sequences for murine, chimeric and humanized antibody molecules. The antibody molecules include murine mAb BAP050, chimeric mAbs BAP050-chi, humanized mAbs BAP050-hum01 to BAP050-hum20, humanized mAbs BAP050-hum01-Ser to BAP050-hum15-Ser, BAP050-hum18-Ser to BAP050-hum20-Ser, and humanized mAbs BAP050-Clone-F to BAP050-Clone-J. The amino acid and nucleotide sequences of the heavy and light chain CDRs, the heavy and light chain variable regions, and the heavy and light chains are shown.

|  |  |  |
|---|---|---|
|  |  | GGTGTCCAACAAAGGCCTCCCGTCCTCCATCGAGA<br>AAACCATCTCCAAAGCCAAAGGGCAGCCCCGAGAG<br>CCACAGGTGTACACCCTGCCCCCATCCCAGGAGGA<br>GATGACCAAGAACCAGGTCAGCCTGACCTGCCTGG<br>TCAAAGGCTTCTACCCCAGCGACATCGCCGTGGAG<br>TGGGAGAGCAATGGGCAGCCGGAGAACAACTACAA<br>GACCACGCCTCCCGTGCTGGACTCCGACGGCTCCT<br>TCTTCCTCTACAGCAGGCTAACCGTGGACAAGAGC<br>AGGTGGCAGGAGGGGAATGTCTTCTCATGCTCCGT<br>GATGCATGAGGCTCTGCACAACCACTACACACAGA<br>AGAGCCTCTCCCTGTCTCTGGGTAAA |
| BAP050-hum04 LC |  |  |
| SEQ ID<br>NO: 10<br>(Kabat) | LCDR1 | SSSQDISNYLN |
| SEQ ID<br>NO: 11<br>(Kabat) | LCDR2 | YTSTLHL |
| SEQ ID<br>NO: 12<br>(Kabat) | LCDR3 | QQYYNLPWT |
| SEQ ID<br>NO: 13<br>(Chothia) | LCDR1 | SQDISNY |
| SEQ ID<br>NO: 14<br>(Chothia) | LCDR2 | YTS |
| SEQ ID<br>NO: 15<br>(Chothia) | LCDR3 | YYNLPW |
| SEQ ID<br>NO: 44 | VL | DIQMTQSPSSLSASVGDRVTITCSSSQDISNYLNW<br>YLQKPGQSPQLLIYYTSTLHLGIPDRFSGSGSGTD<br>FTLTISRLEPEDFAVYYCQQYYNLPWTFGQGTKVE<br>IK |
| SEQ ID<br>NO: 45 | DNA<br>VL | GACATCCAGATGACCCAGTCTCCATCCTCCCTGTC<br>TGCATCTGTAGGAGACAGAGTCACCATCACTTGCA<br>GTTCAAGTCAGGACATCAGCAATTATTTAAACTGG<br>TACCTGCAGAAGCCAGGGCAGTCTCCACAGCTCCT<br>GATCTATTACACATCAACCTTACACTTAGGGATCC<br>CAGACAGGTTCAGTGGCAGTGGGTCTGGGACAGAC<br>TTCACTCTCACCATCAGCAGACTGGAGCCTGAAGA<br>TTTTGCAGTGTATTACTGTCAGCAGTATTATAACC<br>TTCCGTGGACGTTCGGCCAAGGGACCAAGGTGGAA<br>ATCAAA |
| SEQ ID<br>NO: 46 | LC | DIQMTQSPSSLSASVGDRVTITCSSSQDISNYLNW<br>YLQKPGQSPQLLIYYTSTLHLGIPDRFSGSGSGTD<br>FTLTISRLEPEDFAVYYCQQYYNLPWTFGQGTKVE<br>IKRTVAAPSVFIFPPSDEQLKSGTASVVCLLNNFY<br>PREAKVQWKVDNALQSGNSQESVTEQDSKDSTYSL<br>SSTLTLSKADYEKHKVYACEVTHQGLSSPVTKSFN<br>RGEC |
| SEQ ID<br>NO: 47 | DNA<br>LC | GACATCCAGATGACCCAGTCTCCATCCTCCCTGTC<br>TGCATCTGTAGGAGACAGAGTCACCATCACTTGCA<br>GTTCAAGTCAGGACATCAGCAATTATTTAAACTGG<br>TACCTGCAGAAGCCAGGGCAGTCTCCACAGCTCCT<br>GATCTATTACACATCAACCTTACACTTAGGGATCC<br>CAGACAGGTTCAGTGGCAGTGGGTCTGGGACAGAC<br>TTCACTCTCACCATCAGCAGACTGGAGCCTGAAGA<br>TTTTGCAGTGTATTACTGTCAGCAGTATTATAACC<br>TTCCGTGGACGTTCGGCCAAGGGACCAAGGTGGAA<br>ATCAAACGTACGGTGGCTGCACCATCTGTCTTCAT<br>CTTCCCGCCATCTGATGAGCAGTTGAAATCTGGAA<br>CTGCCTCTGTTGTGTGCCTGCTGAATAACTTCTAT<br>CCCAGAGAGGCCAAAGTACAGTGGAAGGTGGATAA<br>CGCCCTCCAATCGGGTAACTCCCAGGAGAGTGTCA<br>CAGAGCAGGACAGCAAGGACAGCACCTACAGCCTC<br>AGCAGCACCCTGACGCTGAGCAAAGCAGACTACGA<br>GAAACACAAAGTCTACGCCTGCGAAGTCACCCATC<br>AGGGCCTGAGCTCGCCCGTCACAAAGAGCTTCAAC<br>AGGGGAGAGTGT |
| BAP050-hum05 HC |  |  |
| SEQ ID<br>NO: 1<br>(Kabat) | HCDR1 | NYGMN |
| SEQ ID<br>NO: 2<br>(Kabat) | HCDR2 | WINTDTGEPTYADDFKG |
| SEQ ID<br>NO: 3<br>(Kabat) | HCDR3 | NPPYYYGTNNAEAMDY |
| SEQ ID<br>NO: 4<br>(Chothia) | HCDR1 | GFTLTNY |
| SEQ ID<br>NO: 5<br>(Chothia) | HCDR2 | NTDTGE |
| SEQ ID<br>NO: 3<br>(Chothia) | HCDR3 | NPPYYYGTNNAEAMDY |
| SEQ ID<br>NO: 28 | VH | EVQLVQSGAEVKKPGATVKISCKVSGFTLTNYGMN<br>WVRQAPGQGLEWMGWINTDTGEPTYADDFKGRFVF<br>SLDTSVSTAYLQICSLKAEDTAVYYCARNPPYYYG<br>TNNAEAMDYWGQGTTVTVSS |
| SEQ ID<br>NO: 29 | DNA<br>VH | GAGGTCCAGCTGGTACAGTCTGGGGCTGAGGTGAA<br>GAAGCCTGGGGCTACAGTGAAAATCTCCTGCAAGG<br>TTTCTGGATTTACCCTCACAAACTATGGAATGAAC<br>TGGGTGCGACAGGCCCCTGGACAAGGGCTTGAGTG<br>GATGGGTTGGATAAACACCGACACTGGAGAGCCAA<br>CATATGCTGATGACTTCAAGGGAAGATTTGTCTTC<br>TCCTTGGACACCTCTGTCAGCACGGCATATCTGCA<br>GATCTGCAGCCTAAAGGCTGAGGACACTGCCGTGT<br>ATTACTGTGCAAGAAACCCTCCTATTACTACGGT<br>ACTAATAACGCGGAGGCTATGGACTACTGGGGCCA<br>GGGCACCACCGTGACCGTGTCCTCC |
| SEQ ID<br>NO: 30 | HC | EVQLVQSGAEVKKPGATVKISCKVSGFTLTNYGMN<br>WVRQAPGQGLEWMGWINTDTGEPTYADDFKGRFVF<br>SLDTSVSTAYLQICSLKAEDTAVYYCARNPPYYYG<br>TNNAEAMDYWGQGTTVTVSSASTKGPSVFPLAPCS<br>RSTSESTAALGCLVKDYFPEPVTVSWNSGALTSGV<br>HTFPAVLQSSGLYSLSSVVTVPSSSLGTKTYTCNV<br>DHKPSNTKVDKRVESKYGPPCPPCPAPEFLGGPSV<br>FLFPPKPKDTLMISRTPEVTCVVVDVSQEDPEVQF<br>NWYVDGVEVHNAKTKPREEQFNSTYRVVSVLTVLH |

TABLE 1-continued

Amino acid and nucleotide sequences for murine, chimeric and humanized antibody molecules. The antibody molecules include murine mAb BAP050, chimeric mAbs BAP050-chi, humanized mAbs BAP050-hum01 to BAP050-hum20, humanized mAbs BAP050-hum01-Ser to BAP050-hum15-Ser, BAP050-hum18-Ser to BAP050-hum20-Ser, and humanized mAbs BAP050-Clone-F to BAP050-Clone-J. The amino acid and nucleotide sequences of the heavy and light chain CDRs, the heavy and light chain variable regions, and the heavy and light chains are shown.

| | | |
|---|---|---|
| | | QDWLNGKEYKCKVSNKGLPSSIEKTISKAKGQPRE PQVYTLPPSQEEMTKNQVSLTCLVKGFYPSDIAVE WESNGQPENNYKTTPPVLDSDGSFFLYSRLTVDKS RWQEGNVFSCSVMHEALHNHYTQKSLSLSLGK |
| SEQ ID NO: 31 | DNA HC | GAGGTCCAGCTGGTACAGTCTGGGGCTGAGGTGAA GAAGCCTGGGGCTACAGTGAAAATCTCCTGCAAGG TTTCTGGATTTACCCTCACAAACTATGGAATGAAC TGGGTGCGACAGGCCCCTGGACAAGGGCTTGAGTG GATGGGTTGGATAAACACCGACACTGGAGAGCCAA CATATGCTGATGACTTCAAGGGAAGATTTGTCTTC TCCTTGGACACCTCTGTCAGCACGGCATATGTGCA GATCTGCAGCCTAAAGGCTGAGGACACTGCCGTGT ATTACTGTGCAAGAAACCCTCCCTATTACTACGGT ACTAATAACGCGGAGGCTATGGACTACTGGGGCCA GGGCACCACCGTGACCGTGTCCTCCGCTTCCACCA AGGGCCCATCCGTCTTCCCCCTGGCGCCCTGCTCC AGGAGCACCTCCGAGAGCACAGCCGCCCTGGGCTG CCTGGTCAAGGACTACTTCCCCGAACCGGTGACGG TGTCGTGGAACTCAGGCGCCCTGACCAGCGGCGTG CACACCTTCCCGGCTGTCCTACAGTCCTCAGGACT CTACTCCCTCAGCAGCGTGGTGACCGTGCCCTCCA GCAGCTTGGGCACGAAGACCTACACCTGCAACGTA GATCACAAGCCCAGCAACACCAAGGTGGACAAGAG AGTTGAGTCCAAATATGGTCCCCCATGCCCACCGT GCCCAGCACCTGAGTTCCTGGGGGGACCATCAGTC TTCCTGTTCCCCCCAAAACCCAAGGACACTCTCAT GATCTCCCGGACCCCTGAGGTCACGTGCGTGGTGG TGGACGTGAGCCAGGAAGACCCCGAGGTCCAGTTC AACTGGTACGTGGATGGCGTGGAGGTGCATAATGC CAAGACAAAGCCGCGGGAGGAGCAGTTCAACAGCA CGTACCGTGTGGTCAGCGTCCTCACCGTCCTGCAC CAGGACTGGCTGAACGGCAAGGAGTACAAGTGCAA GGTGTCCAACAAAGGCCTCCCGTCCTCCATCGAGA AAACCATCTCCAAAGCCAAAGGGCAGCCCCGAGAG CCACAGGTGTACACCCTGCCCCCATCCCAGGAGGA GATGACCAAGAACCAGGTCAGCCTGACCTGCCTGG TCAAAGGCTTCTACCCCAGCGACATCGCCGTGGAG TGGGAGAGCAATGGGCAGCCGGAGAACAACTACAA GACCACGCCTCCCGTGCTGGACTCCGACGGCTCCT TCTTCCTCTACAGCAGGCTAACCGTGGACAAGAGC AGGTGGCAGGAGGGGAATGTCTTCTCATGCTCCGT GATGCATGAGGCTCTGCACAACCACTACACACAGA AGAGCCTCTCCCTGTCTCTGGGTAAA |

BAP050-hum05 LC

| | |
|---|---|
| SEQ ID NO: 10 (Kabat) | LCDR1 SSSQDISNYLN |
| SEQ ID NO: 11 (Kabat) | LCDR2 YTSTLHL |
| SEQ ID NO: 12 (Kabat) | LCDR3 QQYYNLPWT |
| SEQ ID NO: 13 (Chothia) | LCDR1 SQDISNY |
| SEQ ID NO: 14 (Chothia) | LCDR2 YTS |
| SEQ ID NO: 15 (Chothia) | LCDR3 YYNLPW |
| SEQ ID NO: 48 | VL | EIVLTQSPATLSLSPGERATLSCSSSQDISNYLNW YQQKPGKAPKLLIYYTSTLHLGVPSRFSGSGSGTD FTFTISSLEAEDAATYYCQQYYNLPWTFGQGTKVE IK |
| SEQ ID NO: 49 | DNA VL | GAAATTGTTGACACAGTCTCCAGCCACCCTGTC TTTGTCTCCAGGGGAAAGAGCCACCCTCTCCTGCA GTTCAAGTCAGGACATCAGCAATTATTTAAACTGG TATCAGCAGAAACCAGGGAAAGCTCCTAAGCTCCT GATCTATTACACATCAACCTTACACTTAGGGGTCC CCTCGAGGTTCAGTGGCAGTGGATCTGGGACAGAT TTCACCTTTACCATCAGTAGCCTGGAAGCTGAAGA TGCTGCAACATATTACTGTCAGCAGTATTATAACC TTCCGTGGACGTTCGGCCAAGGGACCAAGGTGGAA ATCAAA |
| SEQ ID NO: 50 | LC | EIVLTQSPATLSLSPGERATLSCSSSQDISNYLNW YQQKPGKAPKLLIYYTSTLHLGVPSRFSGSGSGTD FTFTISSLEAEDAATYYCQQYYNLPWTFGQGTKVE IKRTVAAPSVFIFPPSDEQLKSGTASVVCLLNNFY PREAKVQWKVDNALQSGNSQESVTEQDSKDSTYSL SSTLTLSKADYEKHKVYACEVTHQGLSSPVTKSFN RGEC |
| SEQ ID NO: 51 | DNA LC | GAAATTGTTGACACAGTCTCCAGCCACCCTGTC TTTGTCTCCAGGGGAAAGAGCCACCCTCTCCTGCA GTTCAAGTCAGGACATCAGCAATTATTTAAACTGG TATCAGCAGAAACCAGGGAAAGCTCCTAAGCTCCT GATCTATTACACATCAACCTTACACTTAGGGGTCC CCTCGAGGTTCAGTGGCAGTGGATCTGGGACAGAT TTCACCTTTACCATCAGTAGCCTGGAAGCTGAAGA TGCTGCAACATATTACTGTCAGCAGTATTATAACC TTCCGTGGACGTTCGGCCAAGGGACCAAGGTGGAA ATCAAACGTACGGTGGCTGCACCATCTGTCTTCAT CTTCCCGCCATCTGATGAGCAGTTGAAATCTGGAA CTGCCTCTGTTGTGTGCCTGCTGAATAACTTCTAT CCCAGAGAGGCCAAAGTACAGTGGAAGGTGGATAA CGCCCTCCAATCGGGTAACTCCCAGGAGAGTGTCA CAGAGCAGGACAGCAAGGACAGCACCTACAGCCTC AGCAGCACCCTGACGCTGAGCAAAGCAGACTACGA GAAACACAAAGTCTACGCCTGCGAAGTCACCCATC AGGGCCTGAGCTCGCCCGTCACAAAGAGCTTCAAC AGGGGAGAGTGT |

BAP050-hum06 HC

| | |
|---|---|
| SEQ ID NO: 1 (Kabat) | HCDR1 NYGMN |
| SEQ ID NO: 2 (Kabat) | HCDR2 WINTDTGEPTYADDFKG |
| SEQ ID NO: 3 (Kabat) | HCDR3 NPPYYYGTNNAEAMDY |
| SEQ ID NO: 4 (Chothia) | HCDR1 GFTLTNY |

TABLE 1-continued

Amino acid and nucleotide sequences for murine, chimeric and humanized antibody molecules. The antibody molecules include murine mAb BAP050, chimeric mAbs BAP050-chi, humanized mAbs BAP050-hum01 to BAP050-hum20, humanized mAbs BAP050-hum01-Ser to BAP050-hum15-Ser, BAP050-hum18-Ser to BAP050-hum20-Ser, and humanized mAbs BAP050-Clone-F to BAP050-Clone-J. The amino acid and nucleotide sequences of the heavy and light chain CDRs, the heavy and light chain variable regions, and the heavy and light chains are shown.

| | | |
|---|---|---|
| SEQ ID NO: 5 (Chothia) | HCDR2 | NTDTGE |
| SEQ ID NO: 3 (Chothia) | HCDR3 | NPPYYYGTNNAEAMDY |
| SEQ ID NO: 28 | VH | EVQLVQSGAEVKKPGATVKISCKVSGFTLTNYGMN WVRQAPGQGLEWMGWINTDTGEPTYADDFKGRFVF SLDTSVSTAYLQICSLKAEDTAVYYCARNPPYYYG TNNAEAMDYWGQGTTVTVSS |
| SEQ ID NO: 29 | DNA VH | GAGGTCCAGCTGGTACAGTCTGGGGCTGAGGTGAA GAAGCCTGGGGCTACAGTGAAAATCTCCTGCAAGG TTTCTGGATTTACCCTCACAAACTATGGAATGAAC TGGGTGCGACAGGCCCCTGGACAAGGGCTTGAGTG GATGGGTTGGATAAACACCGACACTGGAGAGCCAA CATATGCTGATGACTTCAAGGGAAGATTTGTCTTC TCCTTGGACACCTCTGTCAGCACGGCATATCTGCA GATCTGCAGCCTAAAGGCTGAGGACACTGCCGTGT ATTACTGTGCAAGAAACCCTCCCTATTACTACGGT ACTAATAACGCGGAGGCTATGGACTACTGGGGCCA GGGCACCACCGTGACCGTGTCCTCC |
| SEQ ID NO: 30 | HC | EVQLVQSGAEVKKPGATVKISCKVSGFTLTNYGMN WVRQAPGQGLEWMGWINTDTGEPTYADDFKGRFVF SLDTSVSTAYLQICSLKAEDTAVYYCARNPPYYYG TNNAEAMDYWGQGTTVTVSSASTKGPSVFPLAPCS RSTSESTAALGCLVKDYFPEPVTVSWNSGALTSGV HTFPAVLQSSGLYSLSSVVTVPSSSLGTKTYTCNV DHKPSNTKVDKRVESKYGPPCPPCPAPEFLGGPSV FLFPPKPKDTLMISRTPEVTCVVVDVSQEDPEVQF NWYVDGVEVHNAKTKPREEQFNSTYRVVSVLTVLH QDWLNGKEYKCKVSNKGLPSSIEKTISKAKGQPRE PQVYTLPPSQEEMTKNQVSLTCLVKGFYPSDIAVE WESNGQPENNYKTTPPVLDSDGSFFLYSRLTVDKS RWQEGNVFSCSVMHEALHNHYTQKSLSLSLGK |
| SEQ ID NO: 31 | DNA HC | GAGGTCCAGCTGGTACAGTCTGGGGCTGAGGTGAA GAAGCCTGGGGCTACAGTGAAAATCTCCTGCAAGG TTTCTGGATTTACCCTCACAAACTATGGAATGAAC TGGGTGCGACAGGCCCCTGGACAAGGGCTTGAGTG GATGGGTTGGATAAACACCGACACTGGAGAGCCAA CATATGCTGATGACTTCAAGGGAAGATTTGTCTTC TCCTTGGACACCTCTGTCAGCACGGCATATCTGCA GATCTGCAGCCTAAAGGCTGAGGACACTGCCGTGT ATTACTGTGCAAGAAACCCTCCCTATTACTACGGT ACTAATAACGCGGAGGCTATGGACTACTGGGGCCA GGGCACCACCGTGACCGTGTCCTCCGCTTCCACCA AGGGCCCATCCGTCTTCCCCCTGGCGCCCTGCTCC AGGAGCACCTCCGAGAGCACAGCCGCCCTGGGCTG CCTGGTCAAGGACTACTTCCCCGAACCGGTGACGG TGTCGTGGAACTCAGGCGCCCTGACCAGCGGCGTG CACACCTTCCCGGCTGTCCTACAGTCCTCAGGACT CTACTCCCTCAGCAGCGTGGTGACCGTGCCCTCCA GCAGCTTGGGCACGAAGACCTACACCTGCAACGTA GATCACAAGCCCAGCAACACCAAGGTGGACAAGAG AGTTGAGTCCAAATATGGTCCCCCATGCCCACCGT GCCCAGCACCTGAGTTCCTGGGGGGACCATCAGTC TTCCTGTTCCCCCCAAAACCCAAGGACACTCTCAT GATCTCCCGGACCCCTGAGGTCACGTGCGTGGTGG TGGACGTGAGCCAGGAAGACCCCGAGGTCCAGTTC AACTGGTACGTGGATGGCGTGGAGGTGCATAATGC CAAGACAAAGCCGCGGGAGGAGCAGTTCAACAGCA CGTACCGTGTGGTCAGCGTCCTCACCGTCCTGCAC CAGGACTGGCTGAACGGCAAGGAGTACAAGTGCAA GGTGTCCAACAAAGGCCTCCCGTCCTCCATCGAGA AAACCATCTCCAAAGCCAAAGGGCAGCCCCGAGAG CCACAGGTGTACACCCTGCCCCCATCCCAGGAGGA GATGACCAAGAACCAGGTCAGCCTGACCTGCCTGG TCAAAGGCTTCTACCCCAGCGACATCGCCGTGGAG TGGGAGAGCAATGGGCAGCCGGAGAACAACTACAA GACCACGCCTCCCGTGCTGGACTCCGACGGCTCCT TCTTCCTCTACAGCAGGCTAACCGTGGACAAGAGC AGGTGGCAGGAGGGGAATGTCTTCTCATGCTCCGT GATGCATGAGGCTCTGCACAACCACTACACACAGA AGAGCCTCTCCCTGTCTCTGGGTAAA |

BAP050-hum06 LC

| | | |
|---|---|---|
| SEQ ID NO: 10 (Kabat) | LCDR1 | SSSQDISNYLN |
| SEQ ID NO: 11 (Kabat) | LCDR2 | YTSTLHL |
| SEQ ID NO: 12 (Kabat) | LCDR3 | QQYYNLPWT |
| SEQ ID NO: 13 (Chothia) | LCDR1 | SQDISNY |
| SEQ ID NO: 14 (Chothia) | LCDR2 | YTS |
| SEQ ID NO: 15 (Chothia) | LCDR3 | YYNLPW |
| SEQ ID NO: 52 | VL | DIVMTQTPLSLPVTPGEPASISCSSSQDISNYLNW YQQKPGQAPRLLIYYTSTLHLGVPSRFSGSGSGTE FTLTISSLQPDDFATYYCQQYYNLPWTFGQGTKVE IK |
| SEQ ID NO: 53 | DNA VL | GATATTGTGATGACCCAGACTCCACTCTCCCTGCC CGTCACCCCTGGAGAGCCGGCCTCCATCTCCTGCA GTTCAAGTCAGGACATCAGCAATTATTTAAACTGG TACCAGCAGAAACCTGGCCAGGCTCCCAGGCTCCT CATCTATTACACATCAACCTTACACTTAGGGGTCC CATCAAGGTTCAGCGGCAGTGGATCTGGGACAGAA TTCACTCTCACCATCAGCAGCCTGCAGCCTGATGA TTTTGCAACTTATTACTGTCAGCAGTATTATAACC TTCCGTGGACGTTCGGCCAAGGGACCAAGGTGGAA ATCAAA |
| SEQ ID NO: 54 | LC | DIVMTQTPLSLPVTPGEPASISCSSSQDISNYLNW YQQKPGQAPRLLIYYTSTLHLGVPSRFSGSGSGTE FTLTISSLQPDDFATYYCQQYYNLPWTFGQGTKVE IKRTVAAPSVFIFPPSDEQLKSGTASVVCLLNNFY PREAKVQWKVDNALQSGNSQESVTEQDSKDSTYSL SSTLTLSKADYEKHKVYACEVTHQGLSSPVTKSFN RGEC |
| SEQ ID NO: 55 | DNA LC | GATATTGTGATGACCCAGACTCCACTCTCCCTGCC CGTCACCCCTGGAGAGCCGGCCTCCATCTCCTGCA GTTCAAGTCAGGACATCAGCAATTATTTAAACTGG TACCAGCAGAAACCTGGCCAGGCTCCCAGGCTCCT CATCTATTACACATCAACCTTACACTTAGGGGTCC |

TABLE 1-continued

Amino acid and nucleotide sequences for murine, chimeric and humanized antibody molecules. The antibody molecules include murine mAb BAP050, chimeric mAbs BAP050-chi, humanized mAbs BAP050-hum01 to BAP050-hum20, humanized mAbs BAP050-hum01-Ser to BAP050-hum15-Ser, BAP050-hum18-Ser to BAP050-hum20-Ser, and humanized mAbs BAP050-Clone-F to BAP050-Clone-J. The amino acid and nucleotide sequences of the heavy and light chain CDRs, the heavy and light chain variable regions, and the heavy and light chains are shown.

|  |  |  |
|---|---|---|
|  |  | CATCAAGGTTCAGCGGCAGTGGATCTGGGACAGAA<br>TTCACTCTCACCATCAGCAGCCTGCAGCCTGATGA<br>TTTTGCAACTTATTACTGTCAGCAGTATTATAACC<br>TTCCGTGGACGTTCGGCCAAGGGACCAAGGTGGAA<br>ATCAAACGTACGGTGGCTGCACCATCTGTCTTCAT<br>CTTCCCGCCATCTGATGAGCAGTTGAAATCTGGAA<br>CTGCCTCTGTTGTGTGCCTGCTGAATAACTTCTAT<br>CCCAGAGAGGCCAAAGTACAGTGGAAGGTGGATAA<br>CGCCCTCCAATCGGGTAACTCCCAGGAGAGTCA<br>CAGAGCAGGACAGCAAGGACAGCACCTACAGCCTC<br>AGCAGCACCCTGACGCTGAGCAAAGCAGACTACGA<br>GAAACACAAAGTCTACGCCTGCGAAGTCACCCATC<br>AGGGCCTGAGCTCGCCCGTCACAAAGAGCTTCAAC<br>AGGGGAGAGTGT |
|  | BAP050-hum07 HC |  |
| SEQ ID<br>NO: 1<br>(Kabat) | HCDR1 | NYGMN |
| SEQ ID<br>NO: 2<br>(Kabat) | HCDR2 | WINTDTGEPTYADDFKG |
| SEQ ID<br>NO: 3<br>(Kabat) | HCDR3 | NPPYYYGTNNAEAMDY |
| SEQ ID<br>NO: 4<br>(Chothia) | HCDR1 | GFTLTNY |
| SEQ ID<br>NO: 5<br>(Chothia) | HCDR2 | NTDTGE |
| SEQ ID<br>NO: 3<br>(Chothia) | HCDR3 | NPPYYYGTNNAEAMDY |
| SEQ ID<br>NO: 28 | VH | EVQLVQSGAEVKKPGATVKISCKVSGFTLTNYGMN<br>WVRQAPGQGLEWMGWINTDTGEPTYADDFKGRFVF<br>SLDTSVSTAYLQICSLKAEDTAVYYCARNPPYYYG<br>TNNAEAMDYWGQGTTVTVSS |
| SEQ ID<br>NO: 29 | DNA<br>VH | GAGGTCCAGCTGGTACAGTCTGGGGCTGAGGTGAA<br>GAAGCCTGGGGCTACAGTGAAAATCTCCTGCAAGG<br>TTTCTGGATTTACCCTCACAAACTATGGAATGAAC<br>TGGGTGCGACAGGCCCCTGGACAAGGGCTTGAGTG<br>GATGGGTTGGATAAACACCGACACTGGAGAGCCAA<br>CATATGCTGATGACTTCAAGGGAAGATTTGTCTTC<br>TCCTTGGACACCTCTGTCAGCACGGCATATCTGCA<br>GATCTGCAGCCTAAAGGCTGAGGACACTGCCGTGT<br>ATTACTGTGCAAGAAACCCTCCCTATTACTACGGT<br>ACTAATAACGCGGAGGCTATGGACTACTGGGGCCA<br>GGGCACCACCGTGACCGTGTCCTCC |
| SEQ ID<br>NO: 30 | HC | EVQLVQSGAEVKKPGATVKISCKVSGFTLTNYGMN<br>WVRQAPGQGLEWMGWINTDTGEPTYADDFKGRFVF<br>SLDTSVSTAYLQICSLKAEDTAVYYCARNPPYYYG<br>TNNAEAMDYWGQGTTVTVSSASTKGPSVFPLAPCS<br>RSTSESTAALGCLVKDYFPEPVTVSWNSGALTSGV<br>HTFPAVLQSSGLYSLSSVVTVPSSSLGTKTYTCNV<br>DHKPSNTKVDKRVESKYGPPCPPCPAPEFLGGPSV<br>FLFPPKPKDTLMISRTPEVTCVVVDVSQEDPEVQF<br>NWYVDGVEVHNAKTKPREEQFNSTYRVVSVLTVLH |
|  |  | QDWLNGKEYKCKVSNKGLPSSIEKTISKAKGQPRE<br>PQVYTLPPSQEEMTKNQVSLTCLVKGFYPSDIAVE<br>WESNGQPENNYKTTPPVLDSDGSFFLYSRLTVDKS<br>RWQEGNVFSCSVMHEALHNHYTQKSLSLSLGK |
| SEQ ID<br>NO: 31 | DNA<br>HC | GAGGTCCAGCTGGTACAGTCTGGGGCTGAGGTGAA<br>GAAGCCTGGGGCTACAGTGAAAATCTCCTGCAAGG<br>TTTCTGGATTTACCCTCACAAACTATGGAATGAAC<br>TGGGTGCGACAGGCCCCTGGACAAGGGCTTGAGTG<br>GATGGGTTGGATAAACACCGACACTGGAGAGCCAA<br>CATATGCTGATGACTTCAAGGGAAGATTTGTCTTC<br>TCCTTGGACACCTCTGTCAGCACGGCATATCTGCA<br>GATCTGCAGCCTAAAGGCTGAGGACACTGCCGTGT<br>ATTACTGTGCAAGAAACCCTCCCTATTACTACGGT<br>ACTAATAACGCGGAGGCTATGGACTACTGGGGCCA<br>GGGCACCACCGTGACCGTGTCCTCCGGTTCCACCA<br>AGGGCCCATCCGTCTTCCCCCTGGCGCCCTGCTCC<br>AGGAGCACCTCCGAGAGCACAGCCGCCCTGGGCTG<br>CCTGGTCAAGGACTACTTCCCCGAACCGGTGACGG<br>TGTCGTGGAACTCAGGCGCCCTGACCAGCGGCGTG<br>CACACCTTCCCGGCTGTCCTACAGTCCTCAGGACT<br>CTACTCCCTCAGCAGCGTGGTGACCGTGCCCTCCA<br>GCAGCTTGGGCACGAAGACCTACACCTGCAACGTA<br>GATCACAAGCCCAGCAACACCAAGGTGGACAAGAG<br>AGTTGAGTCCAAATATGGTCCCCCATGCCCACCGT<br>GCCCAGCACCTGAGTTCCTGGGGGGACCATCAGTC<br>TTCCTGTTCCCCCCAAAACCCAAGGACACTCTCAT<br>GATCTCCCGGACCCCTGAGGTCACGTGCGTGGTGG<br>TGGACGTGAGCCAGGAAGACCCCGAGGTCCAGTTC<br>AACTGGTACGTGGATGGCGTGGAGGTGCATAATGC<br>CAAGACAAAGCCGCGGGAGGAGCAGTTCAACAGCA<br>CGTACCGTGTGGTCAGCGTCCTCACCGTCCTGCAC<br>CAGGACTGGCTGAACGGCAAGGAGTACAAGTGCAA<br>GGTCTCCAACAAAGCCCTCCCGTCCTCCATCGAGA<br>AAACCATCTCCAAAGCCAAAGGGCAGCCCCGAGAG<br>CCACAGGTGTACACCCTGCCCCCATCCCAGGAGGA<br>GATGACCAAGAACCAGGTCAGCCTGACCTGCCTGG<br>TCAAAGGCTTCTACCCCAGCGACATCGCCGTGGAG<br>TGGGAGAGCAATGGGCAGCCGGAGAACAACTACAA<br>GACCACGCCTCCCGTGCTGGACTCCGACGGCTCCT<br>TCTTCCTCTACAGCAGGCTAACCGTGGACAAGAGC<br>AGGTGGCAGGAGGGGAATGTCTTCTCATGCTCCGT<br>GATGCATGAGGCTCTGCACAACCACTACACAGA<br>AGAGCCTCTCCCTGTCTCTGGGTAAA |
|  | BAP050-hum07 LC |  |
| SEQ ID<br>NO: 10<br>(Kabat) | LCDR1 | SSQDISNYLN |
| SEQ ID<br>NO: 11<br>(Kabat) | LCDR2 | YTSTLHL |
| SEQ ID<br>NO: 12<br>(Kabat) | LCDR3 | QQYYNLPWT |
| SEQ ID<br>NO: 13<br>(Chothia) | LCDR1 | SQDISNY |
| SEQ ID<br>NO: 14<br>(Chothia) | LCDR2 | YTS |

TABLE 1-continued

Amino acid and nucleotide sequences for murine, chimeric and humanized antibody molecules. The antibody molecules include murine mAb BAP050, chimeric mAbs BAP050-chi, humanized mAbs BAP050-hum01 to BAP050-hum20, humanized mAbs BAP050-hum01-Ser to BAP050-hum15-Ser, BAP050-hum18-Ser to BAP050-hum20-Ser, and humanized mAbs BAP050-Clone-F to BAP050-Clone-J. The amino acid and nucleotide sequences of the heavy and light chain CDRs, the heavy and light chain variable regions, and the heavy and light chains are shown.

| SEQ ID NO: 15 (Chothia) | | LCDR3 YYNLPW |
|---|---|---|
| SEQ ID NO: 56 | VL | DIQMTQSPSSLSASVGDRVTITCSSSQDISNYLNW YLQKPGQSPQLLIYYTSTLHLGVPSRFSGSGSGTE FTLTISSLQPDDFATYYCQQYYNLPWTFGQGTKVE IK |
| SEQ ID NO: 57 | DNA VL | GACATCCAGATGACCCAGTCTCCATCCTCCCTGTC TGCATCTGTAGGAGACAGAGTCACTATCACTTGCA GTTCAAGTCAGGACATCAGCAATTATTTAAACTGG TACCTGCAGAAGCCAGGGCAGTCTCCACAGCTCCT GATCTATTACACATCAACCTTACACTTAGGGGTCC CATCAAGGTTCAGCGGCAGTGGATCTGGGACAGAA TTCACTCTCACCATCAGCAGCCTGCAGCCTGATGA TTTTGCAACTTATTACTGTCAGCAGTATTATAACC TTCCGTGGACGTTCGGCCAAGGGACCAAGGTGGAA ATCAAA |
| SEQ ID NO: 58 | LC | DIQMTQSPSSLSASVGDRVTITCSSSQDISNYLNW YLQKPGQSPQLLIYYTSTLHLGVPSRFSGSGSGTE FTLTISSLQPDDFATYYCQQYYNLPWTFGQGTKVE IKRTVAAPSVFIFPPSDEQLKSGTASVVCLLNNFY PREAKVQWKVDNALQSGNSQESVTEQDSKDSTYSL SSTLTLSKADYEKHKVYACEVTHQGLSSPVTKSFN RGEC |
| SEQ ID NO: 59 | DNA LC | GACATCCAGATGACCCAGTCTCCATCCTCCCTGTC TGCATCTGTAGGAGACAGAGTCACTATCACTTGCA GTTCAAGTCAGGACATCAGCAATTATTTAAACTGG TACCTGCAGAAGCCAGGGCAGTCTCCACAGCTCCT GATCTATTACACATCAACCTTACACTTAGGGGTCC CATCAAGGTTCAGCGGCAGTGGATCTGGGACAGAA TTCACTCTCACCATCAGCAGCCTGCAGCCTGATGA TTTTGCAACTTATTACTGTCAGCAGTATTATAACC TTCCGTGGACGTTCGGCCAAGGGACCAAGGTGGAA ATCAAACGTACGGTGGCTGCACCATCTGTCTTCAT CTTCCCGCCATCTGATGAGCAGTTGAAATCTGGAA CTGCCTCTGTTGTGTGCCTGCTGAATAACTTCTAT CCCAGAGAGGCCAAAGTACAGTGGAAGGTGGATAA CGCCCTCCAATCGGGTAACTCCCAGGAGAGTGTCA CAGAGCAGGACAGCAAGGACAGCACCTACAGCCTC AGCAGCACCCTGACGCTGAGCAAAGCAGACTACGA GAAACATAAAGTCTACGCCTGCGAAGTCACCCATC AGGGCCTGAGCTCGCCCGTCACAAAGAGCTTCAAC AGGGGAGAGTGT |

BAP050-hum08 HC

| SEQ ID NO: 1 (Kabat) | HCDR1 NYGMN |
|---|---|
| SEQ ID NO: 2 (Kabat) | HCDR2 WINTDTGEPTYADDFKG |
| SEQ ID NO: 3 (Kabat) | HCDR3 NPPYYYGTNNAEAMDY |
| SEQ ID NO: 4 (Chothia) | HCDR1 GFTLTNY |

TABLE 1-continued

Amino acid and nucleotide sequences for murine, chimeric and humanized antibody molecules. The antibody molecules include murine mAb BAP050, chimeric mAbs BAP050-chi, humanized mAbs BAP050-hum01 to BAP050-hum20, humanized mAbs BAP050-hum01-Ser to BAP050-hum15-Ser, BAP050-hum18-Ser to BAP050-hum20-Ser, and humanized mAbs BAP050-Clone-F to BAP050-Clone-J. The amino acid and nucleotide sequences of the heavy and light chain CDRs, the heavy and light chain variable regions, and the heavy and light chains are shown.

| SEQ ID NO: 5 (Chothia) | | HCDR2 NTDTGE |
|---|---|---|
| SEQ ID NO: 3 (Chothia) | | HCDR3 NPPYYYGTNNAEAMDY |
| SEQ ID NO: 28 | VH | EVQLVQSGAEVKKPGATVKISCKVSGFTLTNYGMN WVRQAPGQGLEWMGWINTDTGEPTYADDFKGRFVF SLDTSVSTAYLQICSLKAEDTAVYYCARNPPYYYG TNNAEAMDYWGQGTTVTVSS |
| SEQ ID NO: 29 | DNA VH | GAGGTCCAGCTGGTACAGTCTGGGGCTGAGGTGAA GAAGCCTGGGGCTACAGTGAAAATCTCCTGCAAGG TTTCTGGATTTACCCTCACAAACTATGGAATGAAC TGGGTGCGACAGGCCCCTGGACAAGGGCTTGAGTG GATGGGTTGGATAAACACCGACACTGGAGAGCCAA CATATGCTGATGACTTCAAGGGAAGATTTGTCTTC TCCTTGGACACCTCTGTCAGCACGGCATATCTGCA GATCTGCAGCCTAAAGGCTGAGGACACTGCCGTGT ATTACTGTGCAAGAAACCCTCCTATTACTACGGT ACTAATAACGCGGAGGCTATGGACTACTGGGGCCA GGGCACCACCGTGACCGTGTCCTCC |
| SEQ ID NO: 30 | HC | EVQLVQSGAEVKKPGATVKISCKVSGFTLTNYGMN WVRQAPGQGLEWMGWINTDTGEPTYADDFKGRFVF SLDTSVSTAYLQICSLKAEDTAVYYCARNPPYYYG TNNAEAMDYWGQGTTVTVSSASTKGPSVFPLAPCS RSTSESTAALGCLVKDYFPEPVTVSWNSGALTSGV HTFPAVLQSSGLYSLSSVVTVPSSSLGTKTYTCNV DHKPSNTKVDKRVESKYGPPCPPCPAPEFLGGPSV FLFPPKPKDTLMISRTPEVTCVVVDVSQEDPEVQF NWYVDGVEVHNAKTKPREEQFNSTYRVVSVLTVLH QDWLNGKEYKCKVSNKGLPSSIEKTISKAKGQPRE PQVYTLPPSQEEMTKNQVSLTCLVKGFYPSDIAVE WESNGQPENNYKTTPPVLDSDGSFFLYSRLTVDKS RWQEGNVFSCSVMHEALHNHYTQKSLSLSLGK |
| SEQ ID NO: 31 | DNA HC | GAGGTCCAGCTGGTACAGTCTGGGGCTGAGGTGAA GAAGCCTGGGGCTACAGTGAAAATCTCCTGCAAGG TTTCTGGATTTACCCTCACAAACTATGGAATGAAC TGGGTGCGACAGGCCCCTGGACAAGGGCTTGAGTG GATGGGTTGGATAAACACCGACACTGGAGAGCCAA CATATGCTGATGACTTCAAGGGAAGATTTGTCTTC TCCTTGGACACCTCTGTCAGCACGGCATATCTGCA GATCTGCAGCCTAAAGGCTGAGGACACTGCCGTGT ATTACTGTGCAAGAAACCCTCCTATTACTACGGT ACTAATAACGCGGAGGCTATGGACTACTGGGGCCA GGGCACCACCGTGACCGTGTCCTCCGCTTCCACCA AGGGCCCATCCGTCTTCCCCCTGGCGCCCTGCTCC AGGAGCACCTCCGAGAGCACAGCCGCCCTGGGCTG CCTGGTCAAGGACTACTTCCCCGAACCGGTGACGG TGTCGTGGAACTCAGGCGCCCTGACCAGCGGCGTG CACACCTTCCCGGCTGTCCTACAGTCCTCAGGACT CTACTCCCTCAGCAGCGTGGTGACCGTGCCCTCCA GCAGCTTGGGCACGAAGACCTACACCTGCAACGTA GATCACAAGCCCAGCAACACCAAGGTGGACAAGAG AGTTGAGTCCAAATATGGTCCCCCATGCCCACCGT GCCCAGCACCTGAGTTCCTGGGGGGACCATCAGTC TTCCTGTTCCCCCCAAAACCCAAGGACACTCTCAT GATCTCCCGGACCCCTGAGGTCACGTGCGTGGTGG TGGACGTGAGCCAGGAAGACCCCGAGGTCCAGTTC AACTGGTACGTGGATGGCGTGGAGGTGCATAATGC CAAGACAAAGCCGCGGGAGGAGCAGTTCAACAGCA CGTACCGTGTGGTCAGCGTCCTCACCGTCCTGCAC CAGGACTGGCTGAACGGCAAGGAGTACAAGTGCAA |

TABLE 1-continued

Amino acid and nucleotide sequences for murine, chimeric and humanized antibody molecules. The antibody molecules include murine mAb BAP050, chimeric mAbs BAP050-chi, humanized mAbs BAP050-hum01 to BAP050-hum20, humanized mAbs BAP050-hum01-Ser to BAP050-hum15-Ser, BAP050-hum18-Ser to BAP050-hum20-Ser, and humanized mAbs BAP050-Clone-F to BAP050-Clone-J. The amino acid and nucleotide sequences of the heavy and light chain CDRs, the heavy and light chain variable regions, and the heavy and light chains are shown.

```
GGTGTCCAACAAAGGCCTCCCGTCCTCCATCGAGA
AAACCATCTCCAAAGCCAAAGGGCAGCCCCGAGAG
CCACAGGTGTACACCCTGCCCCCATCCCAGGAGGA
GATGACCAAGAACCAGGTCAGCCTGACCTGCCTGG
TCAAAGGCTTCTACCCCAGCGACATCGCCGTGGAG
TGGGAGAGCAATGGGCAGCCGGAGAACAACTACAA
GACCACGCCTCCCGTGCTGGACTCCGACGGCTCCT
TCTTCCTCTACAGCAGGCTAACCGTGGACAAGAGC
AGGTGGCAGGAGGGGAATGTCTTCTCATGCTCCGT
GATGCATGAGGCTCTGCACAACCACTACACACAGA
AGAGCCTCTCCCTGTCTCTGGGTAAA
```

BAP050-hum08 LC

| SEQ ID NO: 10 (Kabat) | LCDR1 | SSSQDISNYLN |
|---|---|---|
| SEQ ID NO: 11 (Kabat) | LCDR2 | YTSTLHL |
| SEQ ID NO: 12 (Kabat) | LCDR3 | QQYYNLPWT |
| SEQ ID NO: 13 (Chothia) | LCDR1 | SQDISNY |
| SEQ ID NO: 14 (Chothia) | LCDR2 | YTS |
| SEQ ID NO: 15 (Chothia) | LCDR3 | YYNLPW |
| SEQ ID NO: 60 | VL | EIVLTQSPDFQSVTPKEKVTITCSSSQDISNYLNW YQQKPGQAPRLLIYYTSTLHLGVPSRFSGSGSGTD FTLTISSLQPEDFATYYCQQYYNLPWTFGQGTKVE IK |
| SEQ ID NO: 61 | DNA VL | GAAATTGTGCTGACTCAGTCTCCAGACTTTCAGTC TGTGACTCCAAAGGAGAAAGTCACCATCACCTGCA GTTCAAGTCAGGACATCAGCAATTATTTAAACTGG TACCAGCAGAAACCTGGCCAGGCTCCCAGGCTCCT CATCTATTACACATCAACCTTACACTTAGGGGTCC CATCAAGGTTCAGCGGCAGTGGATCTGGGACAGAT TTCACTCTCACCATCAGCAGCCTGCAGCCTGAAGA TTTTGCAACTTATTACTGTCAGCAGTATTATAACC TTCCGTGGACGTTCGGCCAAGGGACCAAGGTGGAA ATCAAA |
| SEQ ID NO: 62 | LC | EIVLTQSPDFQSVTPKEKVTITCSSSQDISNYLNW YQQKPGQAPRLLIYYTSTLHLGVPSRFSGSGSGTD FTLTISSLQPEDFATYYCQQYYNLPWTFGQGTKVE IKRTVAAPSVFIFPPSDEQLKSGTASVVCLLNNFY PREAKVQWKVDNALQSGNSQESVTEQDSKDSTYSL SSTLTLSKADYEKHKVYACEVTHQGLSSPVTKSFN RGEC |
| SEQ ID NO: 63 | DNA LC | GAAATTGTGCTGACTCAGTCTCCAGACTTTCAGTC TGTGACTCCAAAGGAGAAAGTCACCATCACCTGCA GTTCAAGTCAGGACATCAGCAATTATTTAAACTGG TACCAGCAGAAACCTGGCCAGGCTCCCAGGCTCCT CATCTATTACACATCAACCTTACACTTAGGGGTCC |

TABLE 1-continued

Amino acid and nucleotide sequences for murine, chimeric and humanized antibody molecules. The antibody molecules include murine mAb BAP050, chimeric mAbs BAP050-chi, humanized mAbs BAP050-hum01 to BAP050-hum20, humanized mAbs BAP050-hum01-Ser to BAP050-hum15-Ser, BAP050-hum18-Ser to BAP050-hum20-Ser, and humanized mAbs BAP050-Clone-F to BAP050-Clone-J. The amino acid and nucleotide sequences of the heavy and light chain CDRs, the heavy and light chain variable regions, and the heavy and light chains are shown.

```
CATCAAGGTTCAGCGGCAGTGGATCTGGGACAGAT
TTCACTCTCACCATCAGCAGCCTGCAGCCTGAAGA
TTTTGCAACTTATTACTGTCAGCAGTATTATAACC
TTCCGTGGACGTTCGGCCAAGGGACCAAGGTGGAA
ATCAAACGTACGGTGGCTGCACCATCTGTCTTCAT
CTTCCCGCCATCTGATGAGCAGTTGAAATCTGGAA
CTGCCTCTGTTGTGTGCCTGCTGAATAACTTCTAT
CCCAGAGAGGCCAAAGTACAGTGGAAGGTGGATAA
CGCCCTCCAATCGGGTAACTCCCAGGAGAGTGTCA
CAGAGCAGGACAGCAAGGACAGCACCTACAGCCTC
AGCAGCACCCTGACGCTGAGCAAAGCAGACTACGA
GAAACACAAAGTCTACGCCTGCGAAGTCACCCATC
AGGGCCTGAGCTCGCCCGTCACAAAGAGCTTCAAC
AGGGGAGAGTGT
```

BAP050-hum09 HC

| SEQ ID NO: 1 (Kabat) | HCDR1 | NYGMN |
|---|---|---|
| SEQ ID NO: 2 (Kabat) | HCDR2 | WINTDTGEPTYADDFKG |
| SEQ ID NO: 3 (Kabat) | HCDR3 | NPPYYYGTNNAEAMDY |
| SEQ ID NO: 4 (Chothia) | HCDR1 | GFTLTNY |
| SEQ ID NO: 5 (Chothia) | HCDR2 | NTDTGE |
| SEQ ID NO: 3 (Chothia) | HCDR3 | NPPYYYGTNNAEAMDY |
| SEQ ID NO: 64 | VH | QVQLVQSGAEVKKPGASVKVSCKASGFTLTNYGMN WVRQARGQRLEWIGWINTDTGEPTYADDFKGRFVF SLDTSVSTAYLQICSLKAEDTAVYYCARNPPYYYG TNNAEAMDYWGQGTTVTVSS |
| SEQ ID NO: 65 | DNA VH | CAGGTTCAGCTGGTGCAGTCTGGAGCTGAGGTGAA GAAGCCTGGGGCCTCAGTGAAGGTCTCCTGCAAGG CTTCTGGATTTACCCTCACAAACTATGGAATGAAC TGGGTGCGACAGGCTCGTGGACAACGCCTTGAGTG GATAGGTTGGATAAACACCGACACTGGAGAGCCAA CATATGCTGATGACTTCAAGGGAAGATTTGTCTTC TCCTTGGACACCTCTGTCAGCACGGCATATCTGCA GATCTGCAGCCTAAAGGCTGAGGACACTGCCGTGT ATTACTGTGCAAGAAACCCTCCCTATTACTACGGT ACTAATAACGCGGAGGCTATGGACTACTGGGGCCA GGGCACCACCGTGACCGTGTCCTCC |
| SEQ ID NO: 66 | HC | QVQLVQSGAEVKKPGASVKVSCKASGFTLTNYGMN WVRQARGQRLEWIGWINTDTGEPTYADDFKGRFVF SLDTSVSTAYLQICSLKAEDTAVYYCARNPPYYYG TNNAEAMDYWGQGTTVTVSSASTKGPSVFPLAPCS RSTSESTAALGCLVKDYFPEPVTVSWNSGALTSGV HTFPAVLQSSGLYSLSSVVTVPSSSLGTKTYTCNV DHKPSNTKVDKRVESKYGPPCPPCPAPEFLGGPSV FLFPPKPKDTLMISRTPEVTCVVVDVSQEDPEVQF NWYVDGVEVHNAKTKPREEQFNSTYRVVSVLTVLH |

TABLE 1-continued

Amino acid and nucleotide sequences for murine, chimeric and humanized antibody molecules. The antibody molecules include murine mAb BAP050, chimeric mAbs BAP050-chi, humanized mAbs BAP050-hum01 to BAP050-hum20, humanized mAbs BAP050-hum01-Ser to BAP050-hum15-Ser, BAP050-hum18-Ser to BAP050-hum20-Ser, and humanized mAbs BAP050-Clone-F to BAP050-Clone-J. The amino acid and nucleotide sequences of the heavy and light chain CDRs, the heavy and light chain variable regions, and the heavy and light chains are shown.

| | | |
|---|---|---|
| | | QDWLNGKEYKCKVSNKGLPSSIEKTISKAKGQPRE PQVYTLPPSQEEMTKNQVSLTCLVKGFYPSDIAVE WESNGQPENNYKTTPPVLDSDGSFFLYSRLTVDKS RWQEGNVFSCSVMHEALHNHYTQKSLSLSLGK |
| SEQ ID NO: 67 | DNA HC | CAGGTTCAGCTGGTGCAGTCTGGAGCTGAGGTGAA GAAGCCTGGGGCCTCAGTGAAGGTCTCCTGCAAGG CTTCTGGATTTACCCTCACAAACTATGGAATGAAC TGGGTGCGACAGGCTCGTGGACAACGCCTTGAGTG GATAGGTTGGATAAACACCGACACTGGAGAGCCAA CATATGCTGATGACTTCAAGGGAAGATTTGTCTTC TCCTTGGACACCTCTGTCAGCACGGCATATCTGCA GATCTGCAGCCTAAAGGCTGAGGACACTGCCGTGT ATTACTGTGCAAGAAACCCTCCCTATTACTACGGT ACTAATAACGCGGAGGCTATGGACTACTGGGGCCA GGGCACCACCGTGACCGTGTCCTCCGCTTCCACCA AGGGCCCATCCGTCTTCCCCCTGGCGCCCTGCTCC AGGAGCACCTCCGAGAGCACAGCCGCCCTGGGCTG CCTGGTCAAGGACTACTTCCCCGAACCGGTGACGG TGTCGTGGAACTCAGGCGCCCTGACCAGCGGCGTG CACACCTTCCCGGCTGTCCTACAGTCCTCAGGACT CTACTCCCTCAGCAGCGTGGTGACCGTGCCCTCCA GCAGCTTGGGCACGAAGACCTACACCTGCAACGTA GATCACAAGCCCAGCAACACCAAGGTGGACAAGAG AGTTGAGTCCAAATATGGTCCCCCATGCCCACCGT GCCCAGCACCTGAGTTCCTGGGGGGACCATCAGTC TTCCTGTTCCCCCCAAAACCCAAGGACACTCTCAT GATCTCCCGGACCCCTGAGGTCACGTGCGTGGTGG TGGACGTGAGCCAGGAAGACCCCGAGGTCCAGTTC AACTGGTACGTGGATGGCGTGGAGGTGCATAATGC CAAGACAAAGCCGCGGGAGGAGCAGTTCAACAGCA CGTACCGTGTGGTCAGCGTCCTCACCGTCCTGCAC CAGGACTGGCTGAACGGCAAGGAGTACAAGTGCAA GGTGTCCAACAAAGGCCTCCCGTCCTCCATCGAGA AAACCATCTCCAAAGCCAAAGGGCAGCCCCGAGAG CCACAGGTGTACACCCTGCCCCCATCCCAGGAGGA GATGACCAAGAACCAGGTCAGCCTGACCTGCCTGG TCAAAGGCTTCTACCCCAGCGACATCGCCGTGGAG TGGGAGAGCAATGGGCAGCCGGAGAACAACTACAA GACCACGCCTCCCGTGCTGGACTCCGACGGCTCCT TCTTCCTCTACAGCAGGCTAACCGTGGACAAGAGC AGGTGGCAGGAGGGGAATGTCTTCTCATGCTCCGT GATGCATGAGGCTCTGCACAACCACTACACACAGA AGAGCCTCTCCCTGTCTCTGGGTAAA |

BAP050-hum09 LC

| | | |
|---|---|---|
| SEQ ID NO: 10 (Kabat) | LCDR1 | SSSQDISNYLN |
| SEQ ID NO: 11 (Kabat) | LCDR2 | YTSTLHL |
| SEQ ID NO: 12 (Kabat) | LCDR3 | QQYYNLPWT |
| SEQ ID NO: 13 (Chothia) | LCDR1 | SQDISNY |
| SEQ ID NO: 14 (Chothia) | LCDR2 | YTS |
| SEQ ID NO: 15 (Chothia) | LCDR3 | YYNLPW |
| SEQ ID NO: 36 | VL | DIQMTQSPSSLSASVGDRVTITCSSSQDISNYLNW YQQKPGKAPKLLIYYTSTLHLGIPPRFSGSGYGTD FTLTINNIESEDAAYYFCQQYYNLPWTFGQGTKVE IK |
| SEQ ID NO: 37 | DNA VL | GACATCCAGATGACCCAGTCTCCATCCTCCCTGTC TGCATCTGTAGGAGACAGAGTCACCATCACTTGCA GTTCAAGTCAGGACATCAGCAATTATTTAAACTGG TATCAGCAGAAACCAGGGAAAGCTCCTAAGCTCCT GATCTATTACACATCAACCTTACACTTAGGGATCC CACCTCGATTCAGTGGCAGCGGGTATGGAACAGAT TTTACCCTCACAATTAATAACATAGAATCTGAGGA TGCTGCATATTACTTCTGTCAGCAGTATTATAACC TTCCGTGGACGTTCGGCCAAGGGACCAAGGTGGAA ATCAAA |
| SEQ ID NO: 38 | LC | DIQMTQSPSSLSASVGDRVTITCSSSQDISNYLNW YQQKPGKAPKLLIYYTSTLHLGIPPRFSGSGYGTD FTLTINNIESEDAAYYFCQQYYNLPWTFGQGTKVE IKRTVAAPSVFIFPPSDEQLKSGTASVVCLLNNFY PREAKVQWKVDNALQSGNSQESVTEQDSKDSTYSL SSTLTLSKADYEKHKVYACEVTHQGLSSPVTKSFN RGEC |
| SEQ ID NO: 39 | DNA LC | GACATCCAGATGACCCAGTCTCCATCCTCCCTGTC TGCATCTGTAGGAGACAGAGTCACCATCACTTGCA GTTCAAGTCAGGACATCAGCAATTATTTAAACTGG TATCAGCAGAAACCAGGGAAAGCTCCTAAGCTCCT GATCTATTACACATCAACCTTACACTTAGGGATCC CACCTCGATTCAGTGGCAGCGGGTATGGAACAGAT TTTACCCTCACAATTAATAACATAGAATCTGAGGA TGCTGCATATTACTTCTGTCAGCAGTATTATAACC TTCCGTGGACGTTCGGCCAAGGGACCAAGGTGGAA ATCAAACGTACGGTGGCTGCACCATCTGTCTTCAT CTTCCCGCCATCTGATGAGCAGTTGAAATCTGGAA CTGCCTCTGTTGTGTGCCTGCTGAATAACTTCTAT CCCAGAGAGGCCAAAGTACAGTGGAAGGTGGATAA CGCCCTCCAATCGGGTAACTCCCAGGAGAGTGTCA CAGAGCAGGACAGCAAGGACAGCACCTACAGCCTC AGCAGCACCCTGACGCTGAGCAAAGCAGACTACGA GAAACACAAAGTCTACGCCTGCGAAGTCACCCATC AGGGCCTGAGCTCGCCCGTCACAAAGAGCTTCAAC AGGGGAGAGTGT |

BAP050-hum10 HC

| | | |
|---|---|---|
| SEQ ID NO: 1 (Kabat) | HCDR1 | NYGMN |
| SEQ ID NO: 2 (Kabat) | HCDR2 | WINTDTGEPTYADDFKG |
| SEQ ID NO: 3 (Kabat) | HCDR3 | NPPYYYGTNNAEAMDY |
| SEQ ID NO: 4 (Chothia) | HCDR1 | GFTLTNY |

TABLE 1-continued

Amino acid and nucleotide sequences for murine, chimeric and humanized antibody molecules. The antibody molecules include murine mAb BAP050, chimeric mAbs BAP050-chi, humanized mAbs BAP050-hum01 to BAP050-hum20, humanized mAbs BAP050-hum01-Ser to BAP050-hum15-Ser, BAP050-hum18-Ser to BAP050-hum20-Ser, and humanized mAbs BAP050-Clone-F to BAP050-Clone-J. The amino acid and nucleotide sequences of the heavy and light chain CDRs, the heavy and light chain variable regions, and the heavy and light chains are shown.

| SEQ ID NO: 5 (Chothia) | | HCDR2 NTDTGE |
|---|---|---|
| SEQ ID NO: 3 (Chothia) | | HCDR3 NPPYYYGTNNAEAMDY |
| SEQ ID NO: 64 | VH | QVQLVQSGAEVKKPGASVKVSCKASGFTLTNYGMN WVRQARGQRLEWIGWINTDTGEPTYADDFKGRFVF SLDTSVSTAYLQICSLKAEDTAVYYCARNPPYYYG TNNAEAMDYWGQGTTVTVSS |
| SEQ ID NO: 65 | DNA VH | CAGGTTCAGCTGGTGCAGTCTGGAGCTGAGGTGAA GAAGCCTGGGGCCTCAGTGAAGGTCTCCTGCAAGG CTTCTGGATTTACCCTCACAAACTATGGAATGAAC TGGGTGCGACAGGCTCGTGGACAACGCCTTGAGTG GATAGGTTGGATAAACACCGACACTGGAGAGCCAA CATATGCTGATGACTTCAAGGGAAGATTTGTCTTC TCCTTGGACACCTCTGTCAGCACGGCATATCTGCA GATCTGCAGCCTAAAGGCTGAGGACACTGCCGTGT ATTACTGTGCAAGAAACCCTCCCTATTACTACGGT ACTAATAACGCGGAGGCTATGGACTACTGGGGCCA GGGCACCACCGTGACCGTGTCCTCC |
| SEQ ID NO: 66 | HC | QVQLVQSGAEVKKPGASVKVSCKASGFTLTNYGMN WVRQARGQRLEWIGWINTDTGEPTYADDFKGRFVF SLDTSVSTAYLQICSLKAEDTAVYYCARNPPYYYG TNNAEAMDYWGQGTTVTVSSASTKGPSVFPLAPCS RSTSESTAALGCLVKDYFPEPVTVSWNSGALTSGV HTFPAVLQSSGLYSLSSVVTVPSSSLGTKTYTCNV DHKPSNTKVDKRVESKYGPPCPPCPAPEFLGGPSV FLFPPKPKDTLMISRTPEVTCVVVDVSQEDPEVQF NWYVDGVEVHNAKTKPREEQFNSTYRVVSVLTVLH QDWLNGKEYKCKVSNKGLPSSIEKTISKAKGQPRE PQVYTLPPSQEEMTKNQVSLTCLVKGFYPSDIAVE WESNGQPENNYKTTPPVLDSDGSFFLYSRLTVDKS RWQEGNVFSCSVMHEALHNHYTQKSLSLSLGK |
| SEQ ID NO: 67 | DNA HC | CAGGTTCAGCTGGTGCAGTCTGGAGCTGAGGTGAA GAAGCCTGGGGCCTCAGTGAAGGTCTCCTGCAAGG CTTCTGGATTTACCCTCACAAACTATGGAATGAAC TGGGTGCGACAGGCTCGTGGACAACGCCTTGAGTG GATAGGTTGGATAAACACCGACACTGGAGAGCCAA CATATGCTGATGACTTCAAGGGAAGATTTGTCTTC TCCTTGGACACCTCTGTCAGCACGGCATATCTGCA GATCTGCAGCCTAAAGGCTGAGGACACTGCCGTGT ATTACTGTGCAAGAAACCCTCCCTATTACTACGGT ACTAATAACGCGGAGGCTATGGACTACTGGGGCCA GGGCACCACCGTGACCGTGTCCTCCACCA AGGGCCCATCCGTCTTCCCCCTGGCGCCCTGCTCC AGGAGCACCTCCGAGAGCACAGCCGCCCTGGGCTG CCTGGTCAAGGACTACTTCCCCGAACCGGTGACGG TGTCGTGGAACTCAGGCGCCCTGACCAGCGGCGTG CACACCTTCCCGGCTGTCCTACAGTCCTCAGGACT CTACTCCCTCAGCAGCGTGGTGACCGTGCCCTCCA GCAGCTTGGGCACGAAGACCTACACCTGCAACGTA GATCACAAGCCCAGCAACACCAAGGTGGACAAGAG AGTTGAGTCCAAATATGGTCCCCCATGCCCACCGT GCCCAGCACCTGAGTTCCTGGGGGGACCATCAGTC TTCCTGTTCCCCCCAAAACCCAAGGACACTCTCAT GATCTCCCGACCCCTGAGGTCACGTGCGTGGTGG TGGACGTGAGCCAGGAAGACCCCGAGGTCCAGTTC AACTGGTACGTGGATGGCGTGGAGGTGCATAATGC CAAGACAAAGCCGCGGGAGGAGCAGTTCAACAGCA CGTACCGTGTGGTCAGCGTCCTCACCGTCCTGCAC CAGGACTGGCTGAACGGCAAGGAGTACAAGTGCAA GGTGTCCAACAAAGGCCTCCCGTCCTCCATCGAGA AAACCATCTCCAAAGCCAAAGGGCAGCCCCGAGAG CCACAGGTGTACACCCTGCCCCCATCCCAGGAGGA GATGACCAAGAACCAGGTCAGCCTGACCTGCCTGG TCAAAGGCTTCTACCCCAGCGACATCGCCGTGGAG TGGGAGAGCAATGGGCAGCCGGAGAACAACTACAA GACCACGCCTCCCGTGCTGGACTCCGACGGCTCCT TCTTCCTCTACAGCAGGCTAACCGTGGACAAGAGC AGGTGGCAGGAGGGGAATGTCTTCTCATGCTCCGT GATGCATGAGGCTCTGCACAACCACTACACAGA AGAGCCTCTCCCTGTCTCTGGGTAAA |

BAP050-hum10 LC

| SEQ ID NO: 10 (Kabat) | | LCDR1 SSSQDISNYLN |
|---|---|---|
| SEQ ID NO: 11 (Kabat) | | LCDR2 YTSTLHL |
| SEQ ID NO: 12 (Kabat) | | LCDR3 QQYYNLPWT |
| SEQ ID NO: 13 (Chothia) | | LCDR1 SQDISNY |
| SEQ ID NO: 14 (Chothia) | | LCDR2 YTS |
| SEQ ID NO: 15 (Chothia) | | LCDR3 YYNLPW |
| SEQ ID NO: 40 | VL | EIVLTQSPATLPVTLGQPASISCSSSQDISNYLNW YQQKPGQAPRLLIYYTSTLHLGVPSRFSGSGSGTD FTFTISSLEAEDAATYYCQQYYNLPWTFGQGTKVE IK |
| SEQ ID NO: 41 | DNA VL | GAAATTGTGTTGACACAGTCTCCAGCCACCCTGCC CGTCACCCTTGGACAGCCGGCCTCCATCTCCTGCA GTTCAAGTCAGGACATCAGCAATTATTTAAACTGG TACCAGCAGAAACCTGGCCAGGCTCCCAGGCTCCT CATCTATTACACATCAACCTTACACTTAGGGGTCC CCTCGAGGTTCAGTGGCAGTGGATCTGGGACAGAT TTCACCTTTACCATCAGTAGCCTGGAAGCTGAAGA TGCTGCAACATATTACTGTCAGCAGTATTATAACC TTCCGTGGACGTTCGGCCAAGGGACCAAGGTGGAA ATCAAA |
| SEQ ID NO: 42 | LC | EIVLTQSPATLPVTLGQPASISCSSSQDISNYLNW YQQKPGQAPRLLIYYTSTLHLGVPSRFSGSGSGTD FTFTISSLEAEDAATYYCQQYYNLPWTFGQGTKVE IKRTVAAPSVFIFPPSDEQLKSGTASVVCLLNNFY PREAKVQWKVDNALQSGNSQESVTEQDSKDSTYSL SSTLTLSKADYEKHKVYACEVTHQGLSSPVTKSFN RGEC |
| SEQ ID NO: 43 | DNA LC | GAAATTGTGTTGACACAGTCTCCAGCCACCCTGCC CGTCACCCTTGGACAGCCGGCCTCCATCTCCTGCA GTTCAAGTCAGGACATCAGCAATTATTTAAACTGG TACCAGCAGAAACCTGGCCAGGCTCCCAGGCTCCT CATCTATTACACATCAACCTTACACTTAGGGGTCC |

TABLE 1-continued

Amino acid and nucleotide sequences for murine, chimeric and humanized antibody molecules. The antibody molecules include murine mAb BAP050, chimeric mAbs BAP050-chi, humanized mAbs BAP050-hum01 to BAP050-hum20, humanized mAbs BAP050-hum01-Ser to BAP050-hum15-Ser, BAP050-hum18-Ser to BAP050-hum20-Ser, and humanized mAbs BAP050-Clone-F to BAP050-Clone-J. The amino acid and nucleotide sequences of the heavy and light chain CDRs, the heavy and light chain variable regions, and the heavy and light chains are shown.

| | | |
|---|---|---|
| | | CCTCGAGGTTCAGTGGCAGTGGATCTGGGACAGAT<br>TTCACCTTTACCATCAGTAGCCTGGAAGCTGAAGA<br>TGCTGCAACATATTACTGTCAGCAGTATTATAACC<br>TTCCGTGGACGTTCGGCCAAGGGACCAAGGTGGAA<br>ATCAAACGTACGGTGGCTGCACCATCTGTCTTCAT<br>CTTCCCGCCATCTGATGAGCAGTTGAAATCTGGAA<br>CTGCCTCTGTTGTGTGCCTGCTGAATAACTTCTAT<br>CCCAGAGAGGCCAAAGTACAGTGGAAGGTGGATAA<br>CGCCCTCCAATCGGGTAACTCCCAGGAGAGTCA<br>CAGAGCAGGACAGCAAGGACAGCACCTACAGCCTC<br>AGCAGCACCCTGACGCTGAGCAAAGCAGACTACGA<br>GAAACAAAGTCTACGCCTGCGAAGTCACCCATC<br>AGGGCCTGAGCTCGCCCGTCACAAAGAGCTTCAAC<br>AGGGGAGAGTGT |
| | | BAP050-hum11 HC |
| SEQ ID NO: 1 (Kabat) | HCDR1 | NYGMN |
| SEQ ID NO: 2 (Kabat) | HCDR2 | WINTDTGEPTYADDFKG |
| SEQ ID NO: 3 (Kabat) | HCDR3 | NPPYYYGTNNAEAMDY |
| SEQ ID NO: 4 (Chothia) | HCDR1 | GFTLTNY |
| SEQ ID NO: 5 (Chothia) | HCDR2 | NTDTGE |
| SEQ ID NO: 3 (Chothia) | HCDR3 | NPPYYYGTNNAEAMDY |
| SEQ ID NO: 64 | VH | QVQLVQSGAEVKKPGASVKVSCKASGFTLTNYGMN<br>WVRQARGQRLEWIGWINTDTGEPTYADDFKGRFVF<br>SLDTSVSTAYLQICSLKAEDTAVYYCARNPPYYYG<br>TNNAEAMDYWGQGTTVTVSS |
| SEQ ID NO: 65 | DNA VH | CAGGTTCAGCTGGTGCAGTCTGGAGCTGAGGTGAA<br>GAAGCCTGGGGCCTCAGTGAAGGTCTCCTGCAAGG<br>CTTCTGGATTTACCCTCACAAACTATGGAATGAAC<br>TGGGTGCGACAGGCTCGTGGACAACGCCTTGAGTG<br>GATAGGTTGGATAAACACCGACACTGGAGAGCCAA<br>CATATGCTGATGACTTCAAGGGAAGATTTGTCTTC<br>TCCTTGGACACCTCTGTCAGCACGGCATATCTGCA<br>GATCTGCAGCCTAAAGGCTGAGGACACTGCCGTGT<br>ATTACTGTGCAAGAAACCCTCCCTATTACTACGGT<br>ACTAATAACGCGGAGGCTATGGACTACTGGGGCCA<br>GGGCACCACCGTGACCGTGTCCTCC |
| SEQ ID NO: 66 | HC | QVQLVQSGAEVKKPGASVKVSCKASGFTLTNYGMN<br>WVRQARGQRLEWIGWINTDTGEPTYADDFKGRFVF<br>SLDTSVSTAYLQICSLKAEDTAVYYCARNPPYYYG<br>TNNAEAMDYWGQGTTVTVSSASTKGPSVFPLAPCS<br>RSTSESTAALGCLVKDYFPEPVTVSWNSGALTSGV<br>HTFPAVLQSSGLYSLSSVVTVPSSSLGTKTYTCNV<br>DHKPSNTKVDKRVESKYGPPCPPCPAPEFLGGPSV<br>FLFPPKPKDTLMISRTPEVTCVVVDVSQEDPEVQF<br>NWYVDGVEVHNAKTKPREEQFNSTYRVVSVLTVLH |

TABLE 1-continued

Amino acid and nucleotide sequences for murine, chimeric and humanized antibody molecules. The antibody molecules include murine mAb BAP050, chimeric mAbs BAP050-chi, humanized mAbs BAP050-hum01 to BAP050-hum20, humanized mAbs BAP050-hum01-Ser to BAP050-hum15-Ser, BAP050-hum18-Ser to BAP050-hum20-Ser, and humanized mAbs BAP050-Clone-F to BAP050-Clone-J. The amino acid and nucleotide sequences of the heavy and light chain CDRs, the heavy and light chain variable regions, and the heavy and light chains are shown.

| | | |
|---|---|---|
| | | QDWLNGKEYKCKVSNKGLPSSIEKTISKAKGQPRE<br>PQVYTLPPSQEEMTKNQVSLTCLVKGFYPSDIAVE<br>WESNGQPENNYKTTPPVLDSDGSFFLYSRLTVDKS<br>RWQEGNVFSCSVMHEALHNHYTQKSLSLSLGK |
| SEQ ID NO: 67 | DNA HC | CAGGTTCAGCTGGTGCAGTCTGGAGCTGAGGTGAA<br>GAAGCCTGGGGCCTCAGTGAAGGTCTCCTGCAAGG<br>CTTCTGGATTTACCCTCACAAACTATGGAATGAAC<br>TGGGTGCGACAGGCTCGTGGACAACGCCTTGAGTG<br>GATAGGTTGGATAAACACCGACACTGGAGAGCCAA<br>CATATGCTGATGACTTCAAGGGAAGATTTGTCTTC<br>TCCTTGGACACCTCTGTCAGCACGGCATATCTGCA<br>GATCTGCAGCCTAAAGGCTGAGGACACTGCCGTGT<br>ATTACTGTGCAAGAAACCCTCCCTATTACTACGGT<br>ACTAATAACGCGGAGGCTATGGACTACTGGGGCCA<br>GGGCACCACCGTGACCGTGTCCTCCGCTTCCACCA<br>AGGGCCCATCCGTCTTCCCCCTGGCGCCCTGCTCC<br>AGGAGCACCTCCGAGAGCACAGCCGCCCTGGGCTG<br>CCTGGTCAAGGACTACTTCCCCGAACCGGTGACGG<br>TGTCGTGGAACTCAGGCGCCCTGACCAGCGGCGTG<br>CACACCTTCCCGGCTGTCCTACAGTCCTCAGGACT<br>CTACTCCCTCAGCAGCGTGGTGACCGTGCCCTCCA<br>GCAGCTTGGGCACGAAGACCTACACCTGCAACGTA<br>GATCACAAGCCCAGCAACACCAAGGTGGACAAGAG<br>AGTTGAGTCCAAATATGGTCCCCCATGCCCACCGT<br>GCCCAGCACCTGAGTTCCTGGGGGGACCATCAGTC<br>TTCCTGTTCCCCCCAAAACCCAAGGACACTCTCAT<br>GATCTCCCGGACCCCTGAGGTCACGTGCGTGGTGG<br>TGGACGTGAGCCAGGAAGACCCCGAGGTCCAGTTC<br>AACTGGTACGTGGATGGCGTGGAGGTGCATAATGC<br>CAAGACAAAGCCGCGGGAGGAGCAGTTCAACAGCA<br>CGTACCGTGTGGTCAGCGTCCTCACCGTCCTGCAC<br>CAGGACTGGCTGAACGGCAAGGAGTACAAGTGCAA<br>GGTGTCCAACAAAGCCCTCCCGTCCTCCATCGAGA<br>AAACCATCTCCAAAGCCAAAGGGCAGCCCCGAGAG<br>CCACAGGTGTACACCCTGCCCCCATCCCAGGAGGA<br>GATGACCAAGAACCAGGTCAGCCTGACCTGCCTGG<br>TCAAAGGCTTCTACCCCAGCGACATCGCCGTGGAG<br>TGGGAGAGCAATGGGCAGCCGGAGAACAACTACAA<br>GACCACGCCTCCCGTGCTGGACTCCGACGGCTCCT<br>TCTTCCTCTACAGCAGGCTAACCGTGGACAAGAGC<br>AGGTGGCAGGAGGGGAATGTCTTCTCATGCTCCGT<br>GATGCATGAGGCTCTGCACAACCACTACACAGA<br>AGAGCCTCTCCCTGTCTCTGGGTAAA |
| | | BAP050-hum11 LC |
| SEQ ID NO: 10 (Kabat) | LCDR1 | SSSQDISNYLN |
| SEQ ID NO: 11 (Kabat) | LCDR2 | YTSTLHL |
| SEQ ID NO: 12 (Kabat) | LCDR3 | QQYYNLPWT |
| SEQ ID NO: 13 (Chothia) | LCDR1 | SQDISNY |
| SEQ ID NO: 14 (Chothia) | LCDR2 | YTS |

TABLE 1-continued

Amino acid and nucleotide sequences for murine, chimeric and humanized antibody molecules. The antibody molecules include murine mAb BAP050, chimeric mAbs BAP050-chi, humanized mAbs BAP050-hum01 to BAP050-hum20, humanized mAbs BAP050-hum01-Ser to BAP050-hum15-Ser, BAP050-hum18-Ser to BAP050-hum20-Ser, and humanized mAbs BAP050-Clone-F to BAP050-Clone-J. The amino acid and nucleotide sequences of the heavy and light chain CDRs, the heavy and light chain variable regions, and the heavy and light chains are shown.

| SEQ ID NO: 15 (Chothia) | | LCDR3 YYNLPW |
|---|---|---|

| SEQ ID NO: 56 | VL | DIQMTQSPSSLSASVGDRVTITCSSSQDISNYLNW YLQKPGQSPQLLIYYTSTLHLGVPSRFSGSGSGTE FTLTISSLQPDDFATYYCQQYYNLPWTFGQGTKVE IK |
|---|---|---|

| SEQ ID NO: 57 | DNA VL | GACATCCAGATGACCCAGTCTCCATCCTCCCTGTC TGCATCTGTAGGAGACAGAGTCACTATCACTTGCA GTTCAAGTCAGGACATCAGCAATTATTTAAACTGG TACCTGCAGAAGCCAGGGCAGTCTCCACAGCTCCT GATCTATTACACATCAACCTTACACTTAGGGGTCC CATCAAGGTTCAGCGGCAGTGGATCTGGGACAGAA TTCACTCTCACCATCAGCAGCCTGCAGCCTGATGA TTTTGCAACTTATTACTGTCAGCAGTATTATAACC TTCCGTGGACGTTCGGCCAAGGGACCAAGGTGGAA ATCAAA |
|---|---|---|

| SEQ ID NO: 58 | LC | DIQMTQSPSSLSASVGDRVTITCSSSQDISNYLNW YLQKPGQSPQLLIYYTSTLHLGVPSRFSGSGSGTE FTLTISSLQPDDFATYYCQQYYNLPWTFGQGTKVE IKRTVAAPSVFIFPPSDEQLKSGTASVVCLLNNFY PREAKVQWKVDNALQSGNSQESVTEQDSKDSTYSL SSTLTLSKADYEKHKVYACEVTHQGLSSPVTKSFN RGEC |
|---|---|---|

| SEQ ID NO: 59 | DNA LC | GACATCCAGATGACCCAGTCTCCATCCTCCCTGTC TGCATCTGTAGGAGACAGAGTCACTATCACTTGCA GTTCAAGTCAGGACATCAGCAATTATTTAAACTGG TACCTGCAGAAGCCAGGGCAGTCTCCACAGCTCCT GATCTATTACACATCAACCTTACACTTAGGGGTCC CATCAAGGTTCAGCGGCAGTGGATCTGGGACAGAA TTCACTCTCACCATCAGCAGCCTGCAGCCTGATGA TTTTGCAACTTATTACTGTCAGCAGTATTATAACC TTCCGTGGACGTTCGGCCAAGGGACCAAGGTGGAA ATCAAACGTACGGTGGCTGCCACCATCTGTCTTCAT CTTCCCGCCATCTGATGAGCAGTTGAAATCTGGAA CTGCCTCTGTTGTGTGCCTGCTGAATAACTTCTAT CCCAGAGAGGCCAAAGTACAGTGGAAGGTGGATAA CGCCCTCCAATCGGGTAACTCCCAGGAGAGTGTCA CAGAGCAGGACAGCAAGGACAGCACCTACAGCCTC AGCAGCACCCTGACGCTGAGCAAAGCAGACTACGA GAAACACAAAGTCTACGCCTGCGAAGTCACCCATC AGGGCCTGAGCTCGCCCGTCACAAAGAGCTTCAAC AGGGGAGAGTGT |
|---|---|---|

BAP050-hum12 HC

| SEQ ID NO: 1 (Kabat) | | HCDR1 NYGMN |
|---|---|---|

| SEQ ID NO: 2 (Kabat) | | HCDR2 WINTDTGEPTYADDFKG |
|---|---|---|

| SEQ ID NO: 3 (Kabat) | | HCDR3 NPPYYYGTNNAEAMDY |
|---|---|---|

| SEQ ID NO: 4 (Chothia) | | HCDR1 GFTLTNY |
|---|---|---|

| SEQ ID NO: 5 (Chothia) | | HCDR2 NTDTGE |
|---|---|---|

| SEQ ID NO: 3 (Chothia) | | HCDR3 NPPYYYGTNNAEAMDY |
|---|---|---|

| SEQ ID NO: 64 | VH | QVQLVQSGAEVKKPGASVKVSCKASGFTLTNYGMN WVRQARGQRLEWIGWINTDTGEPTYADDFKGRFVF SLDTSVSTAYLQICSLKAEDTAVYYCARNPPYYYG TNNAEAMDYWGQGTTVTVSS |
|---|---|---|

| SEQ ID NO: 65 | DNA VH | CAGGTTCAGCTGGTGCAGTCTGGAGCTGAGGTGAA GAAGCCTGGGGCCTCAGTGAAGGTCTCCTGCAAGG CTTCTGGATTTACCCTCACAAACTATGGAATGAAC TGGGTGCGACAGGCTCGTGGACAACGCCTTGAGTG GATAGGTTGGATAAACACCGACACTGGAGAGCCAA CATATGCTGATGACTTCAAGGGAAGATTTGTCTTC TCCTTGGACACCTCTGTCAGCACGGCATATCTGCA GATCTGCAGCCTAAAGGCTGAGGACACTGCCGTGT ATTACTGTGCAAGAAACCCTCCTTATTACTACGGT ACTAATAACGCGGAGGCTATGGACTACTGGGGCCA GGGCACCACCGTGACCGTGTCCTCC |
|---|---|---|

| SEQ ID NO: 66 | HC | QVQLVQSGAEVKKPGASVKVSCKASGFTLTNYGMN WVRQARGQRLEWIGWINTDTGEPTYADDFKGRFVF SLDTSVSTAYLQICSLKAEDTAVYYCARNPPYYYG TNNAEAMDYWGQGTTVTVSSASTKGPSVFPLAPCS RSTSESTAALGCLVKDYFPEPVTVSWNSGALTSGV HTFPAVLQSSGLYSLSSVVTVPSSSLGTKTYTCNV DHKPSNTKVDKRVESKYGPPCPPCPAPEFLGGPSV FLFPPKPKDTLMISRTPEVTCVVVDVSQEDPEVQF NWYVDGVEVHNAKTKPREEQFNSTYRVVSVLTVLH QDWLNGKEYKCKVSNKGLPSSIEKTISKAKGQPRE PQVYTLPPSQEEMTKNQVSLTCLVKGFYPSDIAVE WESNGQPENNYKTTPPVLDSDGSFFLYSRLTVDKS RWQEGNVFSCSVMHEALHNHYTQKSLSLSLGK |
|---|---|---|

| SEQ ID NO: 67 | DNA HC | CAGGTTCAGCTGGTGCAGTCTGGAGCTGAGGTGAA GAAGCCTGGGGCCTCAGTGAAGGTCTCCTGCAAGG CTTCTGGATTTACCCTCACAAACTATGGAATGAAC TGGGTGCGACAGGCTCGTGGACAACGCCTTGAGTG GATAGGTTGGATAAACACCGACACTGGAGAGCCAA CATATGCTGATGACTTCAAGGGAAGATTTGTCTTC TCCTTGGACACCTCTGTCAGCACGGCATATCTGCA GATCTGCAGCCTAAAGGCTGAGGACACTGCCGTGT ATTACTGTGCAAGAAACCCTCCTTATTACTACGGT ACTAATAACGCGGAGGCTATGGACTACTGGGGCCA GGGCACCACCGTGACCGTGTCCTCCGCTTCCACCA AGGGCCCATCCGTCTTCCCCCTGGCGCCCTGCTCC AGGAGCACCTCCGAGAGCACAGCCGCCCTGGGCTG CCTGGTCAAGGACTACTTCCCCGAACCGGTGACGG TGTCGTGGAACTCAGGCGCCCTGACCAGCGGCGTG CACACCTTCCCGGCTGTCCTACAGTCCTCAGGACT CTACTCCCTCAGCAGCGTGGTGACCGTGCCCTCCA GCAGCTTGGGCACGAAGACCTACACCTGCAACGTA GATCACAAGCCCAGCAACACCAAGGTGGACAAGAG AGTTGAGTCCAAATATGGTCCCCCATGCCCACCGT GCCCAGCACCTGAGTTCCTGGGGGGACCATCAGTC TTCCTGTTCCCCCCAAAACCCAAGGACACTCTCAT GATCTCCCGGACCCCTGAGGTCACGTGCGTGGTGG TGGACGTGAGCCAGGAAGACCCCGAGGTCCAGTTC AACTGGTACGTGGATGGCGTGGAGGTGCATAATGC CAAGACAAAGCCGCGGGAGGAGCAGTTCAACAGCA CGTACCGTGTGGTCAGCGTCCTCACCGTCCTGCAC CAGGACTGGCTGAACGGCAAGGAGTACAAGTGCAA |
|---|---|---|

TABLE 1-continued

Amino acid and nucleotide sequences for murine, chimeric and humanized antibody molecules. The antibody molecules include murine mAb BAP050, chimeric mAbs BAP050-chi, humanized mAbs BAP050-hum01 to BAP050-hum20, humanized mAbs BAP050-hum01-Ser to BAP050-hum15-Ser, BAP050-hum18-Ser to BAP050-hum20-Ser, and humanized mAbs BAP050-Clone-F to BAP050-Clone-J. The amino acid and nucleotide sequences of the heavy and light chain CDRs, the heavy and light chain variable regions, and the heavy and light chains are shown.

|  |  |  |
|---|---|---|
|  |  | GGTGTCCAACAAAGGCCTCCCGTCCTCCATCGAGA AAACCATCTCCAAAGCCAAAGGGCAGCCCCGAGAG CCACAGGTGTACACCCTGCCCCCATCCCAGGAGGA GATGACCAAGAACCAGGTCAGCCTGACCTGCCTGG TCAAAGGCTTCTACCCCAGCGACATCGCCGTGGAG TGGGAGAGCAATGGGCAGCCGGAGAACAACTACAA GACCACGCCTCCCGTGCTGGACTCCGACGGCTCCT TCTTCCTCTACAGCAGGCTAACCGTGGACAAGAGC AGGTGGCAGGAGGGGAATGTCTTCTCATGCTCCGT GATGCATGAGGCTCTGCACAACCACTACACACAGA AGAGCCTCTCCCTGTCTCTGGGTAAA |

BAP050-hum12 LC

| SEQ ID NO: 10 (Kabat) | LCDR1 | SSSQDISNYLN |
|---|---|---|
| SEQ ID NO: 11 (Kabat) | LCDR2 | YTSTLHL |
| SEQ ID NO: 12 (Kabat) | LCDR3 | QQYYNLPWT |
| SEQ ID NO: 13 (Chothia) | LCDR1 | SQDISNY |
| SEQ ID NO: 14 (Chothia) | LCDR2 | YTS |
| SEQ ID NO: 15 (Chothia) | LCDR3 | YYNLPW |
| SEQ ID NO: 60 | VL | EIVLTQSPDFQSVTPKEKVTITCSSSQDISNYLNW YQQKPGQAPRLLIYYTSTLHLGVPSRFSGSGSGTD FTLTISSLQPEDFATYYCQQYYNLPWTFGQGTKVE IK |
| SEQ ID NO: 61 | DNA VL | GAAATTGTGCTGACTCAGTCTCCAGACTTTCAGTC TGTGACTCCAAAGGAGAAAGTCACCATCACCTGCA GTTCAAGTCAGGACATCAGCAATTATTTAAACTGG TACCAGCAGAAACCTGGCCAGGCTCCCAGGCTCCT CATCTATTACACATCAACCTTACACTTAGGGGTCC CATCAAGGTTCAGCGGCAGTGGATCTGGGACAGAT TTCACTCTCACCATCAGCAGCCTGCAGCCTGAAGA TTTTGCAACTTATTACTGTCAGCAGTATTATAACC TTCCGTGGACGTTCGGCCAAGGGACCAAGGTGGAA ATCAAA |
| SEQ ID NO: 62 | LC | EIVLTQSPDFQSVTPKEKVTITCSSSQDISNYLNW YQQKPGQAPRLLIYYTSTLHLGVPSRFSGSGSGTD FTLTISSLQPEDFATYYCQQYYNLPWTFGQGTKVE IKRTVAAPSVFIFPPSDEQLKSGTASVVCLLNNFY PREAKVQWKVDNALQSGNSQESVTEQDSKDSTYSL SSTLTLSKADYEKHKVYACEVTHQGLSSPVTKSFN RGEC |
| SEQ ID NO: 63 | DNA LC | GAAATTGTGCTGACTCAGTCTCCAGACTTTCAGTC TGTGACTCCAAAGGAGAAAGTCACCATCACCTGCA GTTCAAGTCAGGACATCAGCAATTATTTAAACTGG TACCAGCAGAAACCTGGCCAGGCTCCCAGGCTCCT CATCTATTACACATCAACCTTACACTTAGGGGTCC CATCAAGGTTCAGCGGCAGTGGATCTGGGACAGAT TTCACTCTCACCATCAGCAGCCTGCAGCCTGAAGA TTTTGCAACTTATTACTGTCAGCAGTATTATAACC TTCCGTGGACGTTCGGCCAAGGGACCAAGGTGGAA ATCAAACGTACGGTGGCTGCACCATCTGTCTTCAT CTTCCCGCCATCTGATGAGCAGTTGAAATCTGGAA CTGCCTCTGTTGTGTGCCTGCTGAATAACTTCTAT CCCAGAGAGGCCAAAGTACAGTGGAAGGTGGATAA CGCCCTCCAATCGGGTAACTCCCAGGAGAGTGTCA CAGAGCAGGACAGCAAGGACAGCACCTACAGCCTC AGCAGCACCCTGACGCTGAGCAAAGCAGACTACGA GAAACACAAAGTCTACGCCTGCGAAGTCACCCATC AGGGCCTGAGCTCGCCCGTCACAAAGAGCTTCAAC AGGGGAGAGTGT |

BAP050-hum13 HC

| SEQ ID NO: 1 (Kabat) | HCDR1 | NYGMN |
|---|---|---|
| SEQ ID NO: 2 (Kabat) | HCDR2 | WINTDTGEPTYADDFKG |
| SEQ ID NO: 3 (Kabat) | HCDR3 | NPPYYYGTNNAEAMDY |
| SEQ ID NO: 4 (Chothia) | HCDR1 | GFTLTNY |
| SEQ ID NO: 5 (Chothia) | HCDR2 | NTDTGE |
| SEQ ID NO: 3 (Chothia) | HCDR3 | NPPYYYGTNNAEAMDY |
| SEQ ID NO: 68 | VH | QVQLVQSGAEVKKPGASVKVSCKASGFTLTNYGMN WVRQAPGQGLEWMGWINTDTGEPTYADDFKGRFVF SLDTSVSTAYLQICSLKAEDTAVYYCARNPPYYYG TNNAEAMDYWGQGTTVTVSS |
| SEQ ID NO: 69 | DNA VH | CAGGTTCAGCTGGTGCAGTCCGGAGCTGAGGTGAA GAAGCCTGGGGCCTCAGTGAAGGTCTCCTGCAAGG CTTCTGGATTTACCCTCACAAACTATGGAATGAAC TGGGTGCGACAGGCCCCTGGACAAGGGCTTGAGTG GATGGGTTGGATAAACACCGACACTGGAGAGCCAA CATATGCTGATGACTTCAAGGGAAGATTTGTCTTC TCCTTGGACACCTCTGTCAGCACGGCATATCTGCA GATCTGCAGCCTAAAGGCTGAGGACACTGCCGTGT ATTACTGTGCAAGAAACCCTCCTTATTACTACGGT ACTAATAACGCGGAGGCTATGGACTACTGGGGCCA GGGCACCACCGTGACCGTGTCCTCC |
| SEQ ID NO: 70 | HC | QVQLVQSGAEVKKPGASVKVSCKASGFTLTNYGMN WVRQAPGQGLEWMGWINTDTGEPTYADDFKGRFVF SLDTSVSTAYLQICSLKAEDTAVYYCARNPPYYYG TNNAEAMDYWGQGTTVTVSSASTKGPSVFPLAPCS RSTSESTAALGCLVKDYFPEPVTVSWNSGALTSGV HTFPAVLQSSGLYSLSSVVTVPSSSLGTKTYTCNV DHKPSNTKVDKRVESKYGPPCPPCPAPEFLGGPSV FLFPPKPKDTLMISRTPEVTCVVVDVSQEDPEVQF NWYVDGVEVHNAKTKPREEQFNSTYRVVSVLTVLH |

TABLE 1-continued

Amino acid and nucleotide sequences for murine, chimeric and humanized antibody molecules. The antibody molecules include murine mAb BAP050, chimeric mAbs BAP050-chi, humanized mAbs BAP050-hum01 to BAP050-hum20, humanized mAbs BAP050-hum01-Ser to BAP050-hum15-Ser, BAP050-hum18-Ser to BAP050-hum20-Ser, and humanized mAbs BAP050-Clone-F to BAP050-Clone-J. The amino acid and nucleotide sequences of the heavy and light chain CDRs, the heavy and light chain variable regions, and the heavy and light chains are shown.

| | | |
|---|---|---|
| | | QDWLNGKEYKCKVSNKGLPSSIEKTISKAKGQPRE POVYTLPPSQEEMTKNQVSLTCLVKGFYPSDIAVE WESNGQPENNYKTTPPVLDSDGSFFLYSRLTVDKS RWQEGNVFSCSVMHEALHNHYTQKSLSLSLGK |
| SEQ ID NO: 71 | DNA HC | CAGGTTCAGCTGGTGCAGTCCGGAGCTGAGGTGAA GAAGCCTGGGGCCTCAGTGAAGGTCTCCTGCAAGG CTTCTGGATTTACCCTCACAAACTATGGAATGAAC TGGGTGCGACAGGCCCCTGGACAAGGGCTTGAGTG GATGGGTTGGATAAACACCGACACTGGAGAGCCAA CATATGCTGATGACTTCAAGGGAAGATTTGTCTTC TCCTTGGACACCTCTGTCAGCACGGCATATCTGCA GATCTGCAGCCTAAAGGCTGAGGACACTGCCGTGT ATTACTGTGCAAGAAACCCTCCCTATTACTACGGT ACTAATAACGCGGAGGCTATGGACTACTGGGGCCA GGGCACCACCGTGACCGTGTCCTCCGCTTCCACCA AGGGCCCATCCGTCTTCCCCCTGGCGCCCTGCTCC AGGAGCACCTCCGAGAGCACAGCCGCCCTGGGCTG CCTGGTCAAGGACTACTTCCCCGAACCGGTGACGG TGTCGTGGAACTCAGGCGCCCTGACCAGCGGCGTG CACACCTTCCCGGCTGTCCTACAGTCCTCAGGACT CTACTCCCTCAGCAGCGTGGTGACCGTGCCCTCCA GCAGCTTGGGCACGAAGACCTACACCTGCAACGTA GATCACAAGCCCAGCAACACCAAGGTGGACAAGAG AGTTGAGTCCAAATATGGTCCCCCATGCCCACCGT GCCCAGCACCTGAGTTCCTGGGGGGACCATCAGTC TTCCTGTTCCCCCCAAAACCCAAGGACACTCTCAT GATCTCCCGGACCCCTGAGGTCACGTGCGTGGTGG TGGACGTGAGCCAGGAAGACCCCGAGGTCCAGTTC AACTGGTACGTGGATGGCGTGGAGGTGCATAATGC CAAGACAAAGCCGCGGGAGGAGCAGTTCAACAGCA CGTACCGTGTGGTCAGCGTCCTCACCGTCCTGCAC CAGGACTGGCTGAACGGCAAGGAGTACAAGTGCAA GGTGTCCAACAAAGGCCTCCCGTCCTCCATCGAGA AAACCATCTCCAAAGCCAAAGGGCAGCCCCGAGAG CCACAGGTGTACACCCTGCCCCCATCCCAGGAGGA GATGACCAAGAACCAGGTCAGCCTGACCTGCCTGG TCAAAGGCTTCTACCCCAGCGACATCGCCGTGGAG TGGGAGAGCAATGGGCAGCCGGAGAACAACTACAA GACCACGCCTCCCGTGCTGGACTCCGACGGCTCCT TCTTCCTCTACAGCAGGCTAACCGTGGACAAGAGC AGGTGGCAGGAGGGGAATGTCTTCTCATGCTCCGT GATGCATGAGGCTCTGCACAACCACTACACACAGA AGAGCCTCTCCCTGTCTCTGGGTAAA |

BAP050-hum13 LC

| | | |
|---|---|---|
| SEQ ID NO: 10 (Kabat) | LCDR1 | SSSQDISNYLN |
| SEQ ID NO: 11 (Kabat) | LCDR2 | YTSTLHL |
| SEQ ID NO: 12 (Kabat) | LCDR3 | QQYYNLPWT |
| SEQ ID NO: 13 (Chothia) | LCDR1 | SQDISNY |
| SEQ ID NO: 14 (Chothia) | LCDR2 | YTS |
| SEQ ID NO: 15 (Chothia) | LCDR3 | YYNLPW |
| SEQ ID NO: 36 | VL | DIQMTQSPSSLSASVGDRVTITCSSSQDISNYLNW YQQKPGKAPKLLIYYTSTLHLGIPPRFSGSGYGTD FTLTINNIESEDAAYYFCQQYYNLPWTFGQGTKVE IK |
| SEQ ID NO: 37 | DNA VL | GACATCCAGATGACCCAGTCTCCATCCTCCCTGTC TGCATCTGTAGGAGACAGAGTCACCATCACTTGCA GTTCAAGTCAGGACATCAGCAATTATTTAAACTGG TATCAGCAGAAACCAGGGAAAGCTCCTAAGCTCCT GATCTATTACACATCAACCTTACACTTAGGGATCC CACCTCGATTCAGTGGCAGCGGGTATGGAACAGAT TTTACCCTCACAATTAATAACATAGAATCTGAGGA TGCTGCATATTACTTCTGTCAGCAGTATTATAACC TTCCGTGGACGTTCGGCCAAGGGACCAAGGTGGAA ATCAAA |
| SEQ ID NO: 38 | LC | DIQMTQSPSSLSASVGDRVTITCSSSQDISNYLNW YQQKPGKAPKLLIYYTSTLHLGIPPRESGSGYGTD FTLTINNIESEDAAYYFCQQYYNLPWTFGQGTKVE IKRTVAAPSVFIFPPSDEQLKSGTASVVCLLNNFY PREAKVQWKVDNALQSGNSQESVTEQDSKDSTYSL SSTLTLSKADYEKHKVYACEVTHQGLSSPVTKSFN RGEC |
| SEQ ID NO: 39 | DNA LC | GACATCCAGATGACCCAGTCTCCATCCTCCCTGTC TGCATCTGTAGGAGACAGAGTCACCATCACTTGCA GTTCAAGTCAGGACATCAGCAATTATTTAAACTGG TATCAGCAGAAACCAGGGAAAGCTCCTAAGCTCCT GATCTATTACACATCAACCTTACACTTAGGGATCC CACCTCGATTCAGTGGCAGCGGGTATGGAACAGAT TTTACCCTCACAATTAATAACATAGAATCTGAGGA TGCTGCATATTACTTCTGTCAGCAGTATTATAACC TTCCGTGGACGTTCGGCCAAGGGACCAAGGTGGAA ATCAAACGTACGGTGGCTGCACCATCTGTCTTCAT CTTCCCGCCATCTGATGAGCAGTTGAAATCTGGAA CTGCCTCTGTTGTGTGCCTGCTGAATAACTTCTAT CCCAGAGAGGCCAAAGTACAGTGGAAGGTGGATAA CGCCCTCCAATCGGGTAACTCCCAGGAGAGTGTCA CAGAGCAGGACAGCAAGGACAGCACCTACAGCCTC AGCAGCACCCTGACGCTGAGCAAAGCAGACTACGA GAAACACAAAGTCTACGCCTGCGAAGTCACCCATC AGGGCCTGAGCTCGCCCGTCACAAAGAGCTTCAAC AGGGGAGAGTGT |

BAP050-hum14 HC

| | | |
|---|---|---|
| SEQ ID NO: 1 (Kabat) | HCDR1 | NYGMN |
| SEQ ID NO: 2 (Kabat) | HCDR2 | WINTDTGEPTYADDFKG |
| SEQ ID NO: 3 (Kabat) | HCDR3 | NPPYYYGTNNAEAMDY |
| SEQ ID NO: 4 (Chothia) | HCDR1 | GFTLTNY |

TABLE 1-continued

Amino acid and nucleotide sequences for murine, chimeric and humanized antibody molecules. The antibody molecules include murine mAb BAP050, chimeric mAbs BAP050-chi, humanized mAbs BAP050-hum01 to BAP050-hum20, humanized mAbs BAP050-hum01-Ser to BAP050-hum15-Ser, BAP050-hum18-Ser to BAP050-hum20-Ser, and humanized mAbs BAP050-Clone-F to BAP050-Clone-J. The amino acid and nucleotide sequences of the heavy and light chain CDRs, the heavy and light chain variable regions, and the heavy and light chains are shown.

| | | |
|---|---|---|
| SEQ ID NO: 5 (Chothia) | HCDR2 | NTDTGE |
| SEQ ID NO: 3 (Chothia) | HCDR3 | NPPYYYGTNNAEAMDY |
| SEQ ID NO: 72 | VH | EVQLVQSGAEVKKPGATVKISCKVSGFTLTNYGMN WIRQSPSRGLEWLGWINTDTGEPTYADDFKGRFVF SLDTSVSTAYLQICSLKAEDTAVYYCARNPPYYYG TNNAEAMDYWGQGTTVTVSS |
| SEQ ID NO: 73 | DNA VH | GAGGTCCAGCTGGTACAGTCTGGGGCTGAGGTGAA GAAGCCTGGGGCTACAGTGAAAATCTCCTGCAAGG TTTCTGGATTTACCCTCACAAACTATGGAATGAAC TGGATCAGGCAGTCCCCATCGAGAGGCCTTGAGTG GCTGGGTTGGATAAACACCGACACTGGAGAGCCAA CATATGCTGATGACTTCAAGGGAAGATTTGTCTTC TCCTTGGACACCTCTGTCAGCACGGCATATCTGCA GATCTGCAGCCTAAAGGCTGAGGACACTGCCGTGT ATTACTGTGCAAGAAACCCTCCCTATTACTACGGT ACTAATAACGCGGAGGCTATGGACTACTGGGGCCA GGGCACCACCGTGACCGTGTCCTCC |
| SEQ ID NO: 74 | HC | EVQLVQSGAEVKKPGATVKISCKVSGFTLTNYGMN WIRQSPSRGLEWLGWINTDTGEPTYADDFKGRFVF SLDTSVSTAYLQICSLKAEDTAVYYCARNPPYYYG TNNAEAMDYWGQGTTVTVSSASTKGPSVFPLAPCS RSTSESTAALGCLVKDYFPEPVTVSWNSGALTSGV HTFPAVLQSSGLYSLSSVVTVPSSSLGTKTYTCNV DHKPSNTKVDKRVESKYGPPCPPCPAPEFLGGPSV FLFPPKPKDTLMISRTPEVTCVVVDVSQEDPEVQF NWYVDGVEVHNAKTKPREEQFNSTYRVVSVLTVLH QDWLNGKEYKCKVSNKGLPSSIEKTISKAKGQPRE PQVYTLPPSQEEMTKNQVSLTCLVKGFYPSDIAVE WESNGQPENNYKTTPPVLDSDGSFFLYSRLTVDKS RWQEGNVFSCSVMHEALHNHYTQKSLSLSLGK |
| SEQ ID NO: 75 | DNA HC | GAGGTCCAGCTGGTACAGTCTGGGGCTGAGGTGAA GAAGCCTGGGGCTACAGTGAAAATCTCCTGCAAGG TTTCTGGATTTACCCTCACAAACTATGGAATGAAC TGGATCAGGCAGTCCCCATCGAGAGGCCTTGAGTG GCTGGGTTGGATAAACACCGACACTGGAGAGCCAA CATATGCTGATGACTTCAAGGGAAGATTTGTCTTC TCCTTGGACACCTCTGTCAGCACGGCATATCTGCA GATCTGCAGCCTAAAGGCTGAGGACACTGCCGTGT ATTACTGTGCAAGAAACCCTCCCTATTACTACGGT ACTAATAACGCGGAGGCTATGGACTACTGGGGCCA GGGCACCACCGTGACCGTGTCCTCCTTCCACA AGGGCCCATCCGTCTTCCCCCTGGCGCCCTGCTCC AGGAGCACCTCCGAGAGCACAGCCGCCCTGGGCTG CCTGGTCAAGGACTACTTCCCCGAACCGGTGACGG TGTCGTGGAACTCAGGCGCCCTGACCAGCGGCGTG CACACCTTCCCGGCTGTCCTACAGTCCTCAGGACT CTACTCCCTCAGCAGCGTGGTGACCGTGCCCTCCA GCAGCTTGGGCACGAAGACCTACACCTGCAACGTA GATCACAAGCCCAGCAACACCAAGGTGGACAAGAG AGTTGAGTCCAAATATGGTCCCCCATGCCCACCGT GCCCAGCACCTGAGTTCCTGGGGGGACCATCAGTC TTCCTGTTCCCCCCAAAACCCAAGGACACTCTCAT GATCTCCCGGACCCCTGAGGTCACGTGCGTGGTGG TGGACGTGAGCCAGGAAGACCCCGAGGTCCAGTTC AACTGGTACGTGGATGGCGTGGAGGTGCATAATGC CAAGACAAAGCCGCGGGAGGAGCAGTTCAACAGCA CGTACCGTGTGGTCAGCGTCCTCACCGTCCTGCAC CAGGACTGGCTGAACGGCAAGGAGTACAAGTGCAA GGTGTCCAACAAAGGCCTCCCGTCCTCCATCGAGA AAACCATCTCCAAAGCCAAAGGGCAGCCCCGAGAG CCACAGGTGTACACCCTGCCCCCATCCCAGGAGGA GATGACCAAGAACCAGGTCAGCCTGACCTGCCTGG TCAAAGGCTTCTACCCCAGCGACATCGCCGTGGAG TGGGAGAGCAATGGGCAGCCGGAGAACAACTACAA GACCACGCCTCCCGTGCTGGACTCCGACGGCTCCT TCTTCCTCTACAGCAGGCTAACCGTGGACAAGAGC AGGTGGCAGGAGGGGAATGTCTTCTCATGCTCCGT GATGCATGAGGCTCTGCACAACCACTACACAGAGA AGAGCCTCTCCCTGTCTCTGGGTAAA |

BAP050-hum14 LC

| | | |
|---|---|---|
| SEQ ID NO: 10 (Kabat) | LCDR1 | SSSQDISNYLN |
| SEQ ID NO: 11 (Kabat) | LCDR2 | YTSTLHL |
| SEQ ID NO: 12 (Kabat) | LCDR3 | QQYYNLPWT |
| SEQ ID NO: 13 (Chothia) | LCDR1 | SQDISNY |
| SEQ ID NO: 14 (Chothia) | LCDR2 | YTS |
| SEQ ID NO: 15 (Chothia) | LCDR3 | YYNLPW |
| SEQ ID NO: 40 | VL | EIVLTQSPATLPVTLGQPASISCSSSQDISNYLNW YQQKPGQAPRLLIYYTSTLHLGVPSRFSGSGSGTD FTFTISSLEAEDAATYYCQQYYNLPWTFGQGTKVE IK |
| SEQ ID NO: 41 | DNA VL | GAAATTGTGTTGACACAGTCTCCAGCCACCCTGCC CGTCACCCTTGGACAGCCGGCCTCCATCTCCTGCA GTTCAAGTCAGGACATCAGCAATTATTTAAACTGG TACCAGCAGAAACCTGGCCAGGCTCCCAGGCTCCT CATCTATTACACATCAACCTTACACTTAGGGGTCC CCTCGAGGTTCAGTGGCAGTGGATCTGGGACAGAT TTCACCTTTACCATCAGTAGCCTGGAAGCTGAAGA TGCTGCAACATATTACTGTCAGCAGTATTATAACC TTCCGTGGACGTTCGGCCAAGGGACCAAGGTGGAA ATCAAA |
| SEQ ID NO: 42 | LC | EIVLTQSPATLPVTLGQPASISCSSSQDISNYLNW YQQKPGQAPRLLIYYTSTLHLGVPSRFSGSGSGTD FTFTISSLEAEDAATYYCQQYYNLPWTFGQGTKVE IKRTVAAPSVFIFPPSDEQLKSGTASVVCLLNNFY PREAKVQWKVDNALQSGNSQESVTEQDSKDSTYSL SSTLTLSKADYEKHKVYACEVTHQGLSSPVTKSFN RGEC |
| SEQ ID NO: 43 | DNA LC | GAAATTGTGTTGACACAGTCTCCAGCCACCCTGCC CGTCACCCTTGGACAGCCGGCCTCCATCTCCTGCA GTTCAAGTCAGGACATCAGCAATTATTTAAACTGG TACCAGCAGAAACCTGGCCAGGCTCCCAGGCTCCT CATCTATTACACATCAACCTTACACTTAGGGGTCC |

TABLE 1-continued

Amino acid and nucleotide sequences for murine, chimeric and humanized antibody molecules. The antibody molecules include murine mAb BAP050, chimeric mAbs BAP050-chi, humanized mAbs BAP050-hum01 to BAP050-hum20, humanized mAbs BAP050-hum01-Ser to BAP050-hum15-Ser, BAP050-hum18-Ser to BAP050-hum20-Ser, and humanized mAbs BAP050-Clone-F to BAP050-Clone-J. The amino acid and nucleotide sequences of the heavy and light chain CDRs, the heavy and light chain variable regions, and the heavy and light chains are shown.

|  |  |  |
|---|---|---|
|  |  | CCTCGAGGTTCAGTGGCAGTGGATCTGGGACAGAT<br>TTCACCTTTACCATCAGTAGCCTGGAAGCTGAAGA<br>TGCTGCAACATATTACTGTCAGCAGTATTATAACC<br>TTCCGTGGACGTTCGGCCAAGGGACCAAGGTGAA<br>ATCAAACGTACGGTGGCTGCACCATCTGTCTTCAT<br>CTTCCCGCCATCTGATGAGCAGTTGAAATCTGGAA<br>CTGCCTCTGTTGTGTGCCTGCTGAATAACTTCTAT<br>CCCAGAGAGGCCAAAGTACAGTGGAAGGTGGATAA<br>CGCCCTCCAATCGGGTAACTCCCAGGAGAGTCA<br>CAGAGCAGGACAGCAAGGACAGCACCTACAGCCTC<br>AGCAGCACCCTGACGCTGAGCAAAGCAGACTACGA<br>GAAACACAAAGTCTACGCCTGCGAAGTCACCCATC<br>AGGGCCTGAGCTCGCCCGTCACAAAGAGCTTCAAC<br>AGGGGAGAGTGT |
|  | BAP050-hum15 HC |  |
| SEQ ID NO: 1 (Kabat) | HCDR1 | NYGMN |
| SEQ ID NO: 2 (Kabat) | HCDR2 | WINTDTGEPTYADDFKG |
| SEQ ID NO: 3 (Kabat) | HCDR3 | NPPYYYGTNNAEAMDY |
| SEQ ID NO: 4 (Chothia) | HCDR1 | GFTLTNY |
| SEQ ID NO: 5 (Chothia) | HCDR2 | NTDTGE |
| SEQ ID NO: 3 (Chothia) | HCDR3 | NPPYYYGTNNAEAMDY |
| SEQ ID NO: 72 | VH | EVQLVQSGAEVKKPGATVKISCKVSGFTLTNYGMN<br>WIRQSPSRGLEWLGWINTDTGEPTYADDFKGRFVF<br>SLDTSVSTAYLQICSLKAEDTAVYYCARNPPYYYG<br>TNNAEAMDYWGQGTTVTVSS |
| SEQ ID NO: 73 | DNA VH | GAGGTCCAGCTGGTACAGTCTGGGGCTGAGGTGAA<br>GAAGCCTGGGGCTACAGTGAAAATCTCCTGCAAGG<br>TTTCTGGATTTACCCTCACAAACTATGGAATGAAC<br>TGGATCAGGCAGTCCCCATCGAGAGGCCTTGAGTG<br>GCTGGGTTGGATAAACACCGACACTGGAGAGCCAA<br>CATATGCTGATGACTTCAAGGGAAGATTTGTCTTC<br>TCCTTGGACACCTCTGTCAGCACGGCATATCTGCA<br>GATCTGCAGCCTAAAGGCTGAGGACACTGCCGTGT<br>ATTACTGTGCAAGAAACCCTCCCTATTACTACGGT<br>ACTAATAACGCGGAGGCTATGGACTACTGGGGCCA<br>GGGCACCACCGTGACCGTGTCCTCC |
| SEQ ID NO: 74 | HC | EVQLVQSGAEVKKPGATVKISCKVSGFTLTNYGMN<br>WIRQSPSRGLEWLGWINTDTGEPTYADDFKGRFVF<br>SLDTSVSTAYLQICSLKAEDTAVYYCARNPPYYYG<br>TNNAEAMDYWGQGTTVTVSSASTKGPSVFPLAPCS<br>RSTSESTAALGCLVKDYFPEPVTVSWNSGALTSGV<br>HTFPAVLQSSGLYSLSSVVTVPSSSLGTKTYTCNV<br>DHKPSNTKVDKRVESKYGPPCPPCPAPEFLGGPSV<br>FLFPPKPKDTLMISRTPEVTCVVVDVSQEDPEVQF<br>NWYVDGVEVHNAKTKPREEQFNSTYRVVSVLTVLH |

TABLE 1-continued

Amino acid and nucleotide sequences for murine, chimeric and humanized antibody molecules. The antibody molecules include murine mAb BAP050, chimeric mAbs BAP050-chi, humanized mAbs BAP050-hum01 to BAP050-hum20, humanized mAbs BAP050-hum01-Ser to BAP050-hum15-Ser, BAP050-hum18-Ser to BAP050-hum20-Ser, and humanized mAbs BAP050-Clone-F to BAP050-Clone-J. The amino acid and nucleotide sequences of the heavy and light chain CDRs, the heavy and light chain variable regions, and the heavy and light chains are shown.

|  |  |  |
|---|---|---|
|  |  | QDWLNGKEYKCKVSNKGLPSSIEKTISKAKGQPRE<br>PQVYTLPPSQEEMTKNQVSLTCLVKGFYPSDIAVE<br>WESNGQPENNYKTTPPVLDSDGSFFLYSRLTVDKS<br>RWQEGNVFSCSVMHEALHNHYTQKSLSLSLGK |
| SEQ ID NO: 75 | DNA HC | GAGGTCCAGCTGGTACAGTCTGGGGCTGAGGTGAA<br>GAAGCCTGGGGCTACAGTGAAAATCTCCTGCAAGG<br>TTTCTGGATTTACCCTCACAAACTATGGAATGAAC<br>TGGATCAGGCAGTCCCCATCGAGAGGCCTTGAGTG<br>GCTGGGTTGGATAAACACCGACACTGGAGAGCCAA<br>CATATGCTGATGACTTCAAGGGAAGATTTGTCTTC<br>TCCTTGGACACCTCTGTCAGCACGGCATATCTGCA<br>GATCTGCAGCCTAAAGGCTGAGGACACTGCCGTGT<br>ATTACTGTGCAAGAAACCCTCCCTATTACTACGGT<br>ACTAATAACGCGGAGGCTATGGACTACTGGGGCCA<br>GGGCACCACCGTGACCGTGTCCTCCGCTTCCACCA<br>AGGGCCCATCCGTCTTCCCCCTGGCGCCCTGCTCC<br>AGGAGCACCTCCGAGAGCACAGCCGCCCTGGGCTG<br>CCTGGTCAAGGACTACTTCCCCGAACCGGTGACGG<br>TGTCGTGGAACTCAGGCGCCCTGACCAGCGGCGTG<br>CACACCTTCCCGGCTGTCCTACAGTCCTCAGGACT<br>CTACTCCCTCAGCAGCGTGGTGACCGTGCCCTCCA<br>GCAGCTTGGGCACGAAGACCTACACCTGCAACGTA<br>GATCACAAGCCCAGCAACACCAAGGTGGACAAGAG<br>AGTTGAGTCCAAATATGGTCCCCCATGCCCACCGT<br>GCCCAGCACCTGAGTTCCTGGGGGGACCATCAGTC<br>TTCCTGTTCCCCCCAAAACCCAAGGACACTCTCAT<br>GATCTCCCGGACCCCTGAGGTCACGTGCGTGGTGG<br>TGGACGTGAGCCAGGAAGACCCCGAGGTCCAGTTC<br>AACTGGTACGTGGATGGCGTGGAGGTGCATAATGC<br>CAAGACAAAGCCGCGGGAGGAGCAGTTCAACAGCA<br>CGTACCGTGTGGTCAGCGTCCTCACCGTCCTGCAC<br>CAGGACTGGCTGAACGGCAAGGAGTACAAGTGCAA<br>GGTCTCCAACAAAGCCCTCCCGTCCTCCATCGAGA<br>AAACCATCTCCAAAGCCAAAGGGCAGCCCCGAGAG<br>CCACAGGTGTACACCCTGCCCCCATCCCAGGAGGA<br>GATGACCAAGAACCAGGTCAGCCTGACCTGCCTGG<br>TCAAAGGCTTCTACCCCAGCGACATCGCCGTGGAG<br>TGGGAGAGCAATGGGCAGCCGGAGAACAACTACAA<br>GACCACGCCTCCCGTGCTGGACTCCGACGGCTCCT<br>TCTTCCTCTACAGCAGGCTAACCGTGGACAAGAGC<br>AGGTGGCAGGAGGGGAATGTCTTCTCATGCTCCGT<br>GATGCATGAGGCTCTGCACAACCACTACACAGA<br>AGAGCCTCTCCCTGTCTCTGGGTAAA |
|  | BAP050-hum15 LC |  |
| SEQ ID NO: 10 (Kabat) | LCDR1 | SSSQDISNYLN |
| SEQ ID NO: 11 (Kabat) | LCDR2 | YTSTLHL |
| SEQ ID NO: 12 (Kabat) | LCDR3 | QQYYNLPWT |
| SEQ ID NO: 13 (Chothia) | LCDR1 | SQDISNY |
| SEQ ID NO: 14 (Chothia) | LCDR2 | YTS |

TABLE 1-continued

Amino acid and nucleotide sequences for murine, chimeric and humanized antibody molecules. The antibody molecules include murine mAb BAP050, chimeric mAbs BAP050-chi, humanized mAbs BAP050-hum01 to BAP050-hum20, humanized mAbs BAP050-hum01-Ser to BAP050-hum15-Ser, BAP050-hum18-Ser to BAP050-hum20-Ser, and humanized mAbs BAP050-Clone-F to BAP050-Clone-J. The amino acid and nucleotide sequences of the heavy and light chain CDRs, the heavy and light chain variable regions, and the heavy and light chains are shown.

| SEQ ID NO: 15 (Chothia) | | LCDR3 YYNLPW |
|---|---|---|

| SEQ ID NO: 60 | VL | EIVLTQSPDFQSVTPKEKVTITCSSSQDISNYLNW YQQKPGQAPRLLIYYTSTLHLGVPSRFSGSGSGTD FTLTISSLQPEDFATYYCQQYYNLPWTFGQGTKVE IK |

| SEQ ID NO: 61 | DNA VL | GAAATTGTGCTGACTCAGTCTCCAGACTTTCAGTC TGTGACTCCAAAGGAGAAAGTCACCATCACCTGCA GTTCAAGTCAGGACATCAGCAATTATTTAAACTGG TACCAGCAGAAACCTGGCCAGGCTCCCAGGCTCCT CATCTATTACACATCAACCTTACACTTAGGGGTCC CATCAAGGTTCAGCGGCAGTGGATCTGGGACAGAT TCACTCTCACCATCAGCAGCCTGCAGCCTGAAGA TTTTGCAACTTATTACTGTCAGCAGTATTATAACC TTCCGTGGACGTTCGGCCAAGGGACCAAGGTGGAA ATCAAA |

| SEQ ID NO: 62 | LC | EIVLTQSPDFQSVTPKEKVTITCSSSQDISNYLNW YQQKPGQAPRLLIYYTSTLHLGVPSRFSGSGSGTD FTLTISSLQPEDFATYYCQQYYNLPWTFGQGTKVE IKRTVAAPSVFIFPPSDEQLKSGTASVVCLLNNFY PREAKVQWKVDNALQSGNSQESVTEQDSKDSTYSL SSTLTLSKADYEKHKVYACEVTHQGLSSPVTKSFN RGEC |

| SEQ ID NO: 63 | DNA LC | GAAATTGTGCTGACTCAGTCTCCAGACTTTCAGTC TGTGACTCCAAAGGAGAAAGTCACCATCACCTGCA GTTCAAGTCAGGACATCAGCAATTATTTAAACTGG TACCAGCAGAAACCTGGCCAGGCTCCCAGGCTCCT CATCTATTACACATCAACCTTACACTTAGGGGTCC CATCAAGGTTCAGCGGCAGTGGATCTGGGACAGAT TCACTCTCACCATCAGCAGCCTGCAGCCTGAAGA TTTTGCAACTTATTACTGTCAGCAGTATTATAACC TTCCGTGGACGTTCGGCCAAGGGACCAAGGTGGAA ATCAAACGTACGGTGGCTGCCACCATCTGTCTTCAT CTTCCCGCCATCTGATGAGCAGTTGAAATCTGGAA CTGCCTCTGTTGTGTGCCTGCTGAATAACTTCTAT CCCAGAGAGGCCAAAGTACAGTGGAAGGTGGATAA CGCCCTCCAATCGGGTAACTCCCAGGAGAGTGTCA CAGAGCAGGACAGCAAGGACAGCACCTACAGCCTC AGCAGCACCCTGACGCTGAGCAAAGCAGACTACGA GAAACACAAAGTCTACGCCTGCGAAGTCACCCATC AGGGCCTGAGCTCGCCCGTCACAAAGAGCTTCAAC AGGGGAGAGTGT |

BAP050-hum16 HC

| SEQ ID NO: 1 (Kabat) | | HCDR1 NYGMN |
| SEQ ID NO: 2 (Kabat) | | HCDR2 WINTDTGEPTYADDFKG |
| SEQ ID NO: 3 (Kabat) | | HCDR3 NPPYYYGTNNAEAMDY |
| SEQ ID NO: 4 (Chothia) | | HCDR1 GFTLTNY |

| SEQ ID NO: 5 (Chothia) | | HCDR2 NTDTGE |
| SEQ ID NO: 3 (Chothia) | | HCDR3 NPPYYYGTNNAEAMDY |

| SEQ ID NO: 76 | VH | EVQLVQSGAEVKKPGESLRISCKGSGFTLTNYGMN WVRQATGQGLEWMGWINTDTGEPTYADDFKGRVTI SADKSISTAYLQWSSLKASDTAMYYCARNPPYYYG TNNAEAMDYWGQGTTVTVSS |

| SEQ ID NO: 77 | DNA VH | GAAGTGCAGCTGGTGCAGTCTGGAGCAGAGGTGAA AAAGCCCGGGGAGTCTCTGAGGATCTCCTGTAAGG GTTCTGGATTTACCCTCACAAACTATGGAATGAAC TGGGTGCGACAGGCCACTGGACAAGGGCTTGAGTG GATGGGTTGGATAAACACCGACACTGGAGAGCCAA CATATGCTGATGACTTCAAGGGAAGAGTCACCATC TCAGCCGACAAGTCCATCAGCACCGCCTACCTGCA GTGGAGCAGCCTGAAGGCCTCGGACACCGCCATGT ATTACTGTGCAAGAAACCCTCCCTATTACTACGGT ACTAATAACGCGGAGGCTATGGACTACTGGGGCCA GGGCACCACCGTGACCGTGTCCTCC |

| SEQ ID NO: 78 | HC | EVQLVQSGAEVKKPGESLRISCKGSGFTLTNYGMN WVRQATGQGLEWMGWINTDTGEPTYADDFKGRVTI SADKSISTAYLQWSSLKASDTAMYYCARNPPYYYG TNNAEAMDYWGQGTTVTVSSASTKGPSVFPLAPCS RSTSESTAALGCLVKDYFPEPVTVSWNSGALTSGV HTFPAVLQSSGLYSLSSVVTVPSSSLGTKTYTCNV DHKPSNTKVDKRVESKYGPPCPPCPAPEFLGGPSV FLFPPKPKDTLMISRTPEVTCVVVDVSQEDPEVQF NWYVDGVEVHNAKTKPREEQFNSTYRVVSVLTVLH QDWLNGKEYKCKVSNKGLPSSIEKTISKAKGQPRE PQVYTLPPSQEEMTKNQVSLTCLVKGFYPSDIAVE WESNGQPENNYKTTPPVLDSDGSFFLYSRLTVDKS RWQEGNVFSCSVMHEALHNHYTQKSLSLSLGK |

| SEQ ID NO: 79 | DNA HC | GAAGTGCAGCTGGTGCAGTCTGGAGCAGAGGTGAA AAAGCCCGGGGAGTCTCTGAGGATCTCCTGTAAGG GTTCTGGATTTACCCTCACAAACTATGGAATGAAC TGGGTGCGACAGGCCACTGGACAAGGGCTTGAGTG GATGGGTTGGATAAACACCGACACTGGAGAGCCAA CATATGCTGATGACTTCAAGGGAAGAGTCACCATC TCAGCCGACAAGTCCATCAGCACCGCCTACCTGCA GTGGAGCAGCCTGAAGGCCTCGGACACCGCCATGT ATTACTGTGCAAGAAACCCTCCCTATTACTACGGT ACTAATAACGCGGAGGCTATGGACTACTGGGGCCA GGGCACCACCGTGACCGTGTCCTCCGCTTCCACCA AGGGCCCATCCGTCTTCCCCCTGGCGCCCTGCTCC AGGAGCACCTCCGAGAGCACAGCCGCCCTGGGCTG CCTGGTCAAGGACTACTTCCCCGAACCGGTGACGG TGTCGTGGAACTCAGGCGCCCTGACCAGCGGCGTG CACACCTTCCCGGCTGTCCTACAGTCCTCAGGACT CTACTCCCTCAGCAGCGTGGTGACCGTGCCCTCCA GCAGCTTGGGCACGAAGACCTACACCTGCAACGTA GATCACAAGCCCAGCAACACCAAGGTGGACAAGAG AGTTGAGTCCAAATATGGTCCCCCATGCCCACCGT GCCCAGCACCTGAGTTCCTGGGGGGACCATCAGTC TTCCTGTTCCCCCCAAAACCCAAGGACACTCTCAT GATCTCCCGGACCCCTGAGGTCACGTGCGTGGTGG TGGACGTGAGCCAGGAAGACCCCGAGGTCCAGTTC AACTGGTACGTGGATGGCGTGGAGGTGCATAATGC CAAGACAAAGCCGCGGGAGGAGCAGTTCAACAGCA CGTACCGTGTGGTCAGCGTCCTCACCGTCCTGCAC CAGGACTGGCTGAACGGCAAGGAGTACAAGTGCAA |

TABLE 1-continued

Amino acid and nucleotide sequences for murine, chimeric and humanized antibody molecules. The antibody molecules include murine mAb BAP050, chimeric mAbs BAP050-chi, humanized mAbs BAP050-hum01 to BAP050-hum20, humanized mAbs BAP050-hum01-Ser to BAP050-hum15-Ser, BAP050-hum18-Ser to BAP050-hum20-Ser, and humanized mAbs BAP050-Clone-F to BAP050-Clone-J. The amino acid and nucleotide sequences of the heavy and light chain CDRs, the heavy and light chain variable regions, and the heavy and light chains are shown.

GGTGTCCAACAAAGGCCTCCCGTCCTCCATCGAGA
AAACCATCTCCAAAGCCAAAGGGCAGCCCCGAGAG
CCACAGGTGTACACCCTGCCCCCATCCCAGGAGGA
GATGACCAAGAACCAGGTCAGCCTGACCTGCCTGG
TCAAAGGCTTCTACCCCAGCGACATCGCCGTGGAG
TGGGAGAGCAATGGGCAGCCGGAGAACAACTACAA
GACCACGCCTCCCGTGCTGGACTCCGACGGCTCCT
TCTTCCTCTACAGCAGGCTAACCGTGGACAAGAGC
AGGTGGCAGGAGGGGAATGTCTTCTCATGCTCCGT
GATGCATGAGGCTCTGCACAACCACTACACACAGA
AGAGCCTCTCCCTGTCTCTGGGTAAA

BAP050-hum16 LC

| SEQ ID NO: 10 (Kabat) | LCDR1 | SSSQDISNYLN |
| SEQ ID NO: 11 (Kabat) | LCDR2 | YTSTLHL |
| SEQ ID NO: 12 (Kabat) | LCDR3 | QQYYNLPWT |
| SEQ ID NO: 13 (Chothia) | LCDR1 | SQDISNY |
| SEQ ID NO: 14 (Chothia) | LCDR2 | YTS |
| SEQ ID NO: 15 (Chothia) | LCDR3 | YYNLPW |
| SEQ ID NO: 60 | VL | EIVLTQSPDFQSVTPKEKVTITCSSSQDISNYLNW YQQKPGQAPRLLIYYTSTLHLGVPSRFSGSGSGTD FTLTISSLQPEDFATYYCQQYYNLPWTFGQGTKVE IK |
| SEQ ID NO: 61 | DNA VL | GAAATTGTGCTGACTCAGTCTCCAGACTTTCAGTC TGTGACTCCAAAGGAGAAAGTCACCATCACCTGCA GTTCAAGTCAGGACATCAGCAATTATTTAAACTGG TACCAGCAGAAACCTGGCCAGGCTCCCAGGCTCCT CATCTATTACACATCAACCTTACACTTAGGGGTCC CATCAAGGTTCAGCGGCAGTGGATCTGGGACAGAT TTCACTCTCACCATCAGCAGCCTGCAGCCTGAAGA TTTTGCAACTTATTACTGTCAGCAGTATTATAACC TTCCGTGGACGTTCGGCCAAGGGACCAAGGTGGAA ATCAAA |
| SEQ ID NO: 62 | LC | EIVLTQSPDFQSVTPKEKVTITCSSSQDISNYLNW YQQKPGQAPRLLIYYTSTLHLGVPSRFSGSGSGTD FTLTISSLQPEDFATYYCQQYYNLPWTFGQGTKVE IKRTVAAPSVFIFPPSDEQLKSGTASVVCLLNNFY PREAKVQWKVDNALQSGNSQESVTEQDSKDSTYSL SSTLTLSKADYEKHKVYACEVTHQGLSSPVTKSFN RGEC |
| SEQ ID NO: 63 | DNA LC | GAAATTGTGCTGACTCAGTCTCCAGACTTTCAGTC TGTGACTCCAAAGGAGAAAGTCACCATCACCTGCA GTTCAAGTCAGGACATCAGCAATTATTTAAACTGG TACCAGCAGAAACCTGGCCAGGCTCCCAGGCTCCT CATCTATTACACATCAACCTTACACTTAGGGGTCC CATCAAGGTTCAGCGGCAGTGGATCTGGGACAGAT TTCACTCTCACCATCAGCAGCCTGCAGCCTGAAGA TTTTGCAACTTATTACTGTCAGCAGTATTATAACC TTCCGTGGACGTTCGGCCAAGGGACCAAGGTGGAA ATCAAACGTACGGTGGCTGCACCATCTGTCTTCAT CTTCCCGCCATCTGATGAGCAGTTGAAATCTGGAA CTGCCTCTGTTGTGTGCCTGCTGAATAACTTCTAT CCCAGAGAGGCCAAAGTACAGTGGAAGGTGGATAA CGCCCTCCAATCGGGTAACTCCCAGGAGAGTGTCA CAGAGCAGGACAGCAAGGACAGCACCTACAGCCTC AGCAGCACCCTGACGCTGAGCAAAGCAGACTACGA GAAACACAAAGTCTACGCCTGCGAAGTCACCCATC AGGGCCTGAGCTCGCCCGTCACAAAGAGCTTCAAC AGGGGAGAGTGT |

BAP050-hum17 HC

| SEQ ID NO: 1 (Kabat) | HCDR1 | NYGMN |
| SEQ ID NO: 2 (Kabat) | HCDR2 | WINTDTGEPTYADDFKG |
| SEQ ID NO: 3 (Kabat) | HCDR3 | NPPYYYGTNNAEAMDY |
| SEQ ID NO: 4 (Chothia) | HCDR1 | GFTLTNY |
| SEQ ID NO: 5 (Chothia) | HCDR2 | NTDTGE |
| SEQ ID NO: 3 (Chothia) | HCDR3 | NPPYYYGTNNAEAMDY |
| SEQ ID NO: 80 | VH | QVQLVQSGSELKKPGASVKVSCKASGFTLTNYGMN WVRQAPGQGLEWMGWINTDTGEPTYADDFKGRFVF SLDTSVSTAYLQISTLKAEDTATYFCARNPPYYYG TNNAEAMDYWGQGTTVTVSS |
| SEQ ID NO: 81 | DNA VH | CAGGTGCAGCTGGTGCAATCTGGGTCTGAGTTGAA GAAGCCTGGGGCCTCAGTGAAGGTTTCCTGCAAGG CTTCTGGATTCACCCTGACTAACTATGGCATGAAT TGGGTGCGACAGGCCCCTGGACAAGGGCTTGAGTG GATGGGATGGATCAACACCGACACTGGGGAGCCAA CGTATGCCGATGACTTCAAGGGACGGTTTGTCTTC TCCTTGGACACCTCTGTCAGCACGGCATATCTGCA GATCAGCACGCTAAAGGCTGAGGACACTGCTACAT ATTTCTGTGCAAGAAACCCCCCTTATTACTACGGT ACTAATAACGCGGAGGCTATGGACTACTGGGGCCA GGGCACCACCGTGACCGTGTCCTCC |
| SEQ ID NO: 82 | HC | QVQLVQSGSELKKPGASVKVSCKASGFTLTNYGMN WVRQAPGQGLEWMGWINTDTGEPTYADDFKGRFVF SLDTSVSTAYLQISTLKAEDTATYFCARNPPYYYG TNNAEAMDYWGQGTTVTVSSASTKGPSVFPLAPCS RSTSESTAALGCLVKDYFPEPVTVSWNSGALTSGV HTFPAVLQSSGLYSLSSVVTVPSSSLGTKTYTCNV DHKPSNTKVDKRVESKYGPPCPPCPAPEFLGGPSV FLFPPKPKDTLMISRTPEVTCVVVDVSQEDPEVQF NWYVDGVEVHNAKTKPREEQFNSTYRVVSVLTVLH |

TABLE 1-continued

Amino acid and nucleotide sequences for murine, chimeric and humanized antibody molecules. The antibody molecules include murine mAb BAP050, chimeric mAbs BAP050-chi, humanized mAbs BAP050-hum01 to BAP050-hum20, humanized mAbs BAP050-hum01-Ser to BAP050-hum15-Ser, BAP050-hum18-Ser to BAP050-hum20-Ser, and humanized mAbs BAP050-Clone-F to BAP050-Clone-J. The amino acid and nucleotide sequences of the heavy and light chain CDRs, the heavy and light chain variable regions, and the heavy and light chains are shown.

| | | |
|---|---|---|
| | | QDWLNGKEYKCKVSNKGLPSSIEKTISKAKGQPRE PQVYTLPPSQEEMTKNQVSLTCLVKGFYPSDIAVE WESNGQPENNYKTTPPVLDSDGSFFLYSRLTVDKS RWQEGNVFSCSVMHEALHNHYTQKSLSLSLGK |
| SEQ ID NO: 83 | DNA HC | CAGGTGCAGCTGGTGCAATCTGGGTCTGAGTTGAA GAAGCCTGGGGCCTCAGTGAAGGTTTCCTGCAAGG CTTCTGGATTCACCCTGACTAACTATGGCATGAAT TGGGTGCGACAGGCCCCTGGACAAGGGCTTGAGTG GATGGGATGGATCAACACCGACACTGGGGAGCCAA CGTATGCCGATGACTTCAAGGGACGGTTTGTCTTC TCCTTGGACACCTCTGTCAGCACGGCATATCTGCA GATCAGCACGCTAAAGGCTGAGGACACTGCTACAT ATTTCTGTGCAAGAAACCCCCCTTATTACTACGGT ACTAATAACGCGGAGGCTATGGACTACTGGGGCCA GGGCACCACCGTGACCGTGTCCTCCGCTTCCACCA AGGGCCCATCCGTCTTCCCCCTGGCGCCCTGCTCC AGGAGCACCTCCGAGAGCACAGCCGCCCTGGGCTG CCTGGTCAAGGACTACTTCCCCGAACCGGTGACGG TGTCGTGGAACTCAGGCGCCCTGACCAGCGGCGTG CACACCTTCCCGGCTGTCCTACAGTCCTCAGGACT CTACTCCCTCAGCAGCGTGGTGACCGTGCCCTCCA GCAGCTTGGGCACGAAGACCTACACCTGCAACGTA GACCACAAGCCCAGCAACACCAAGGTGGACAAGAG AGTTGAGTCCAAATATGGTCCCCCATGCCCACCGT GCCCAGCACCTGAGTTCCTGGGGGGACCATCAGTC TTCCTGTTCCCCCCAAAACCCAAGGACACTCTCAT GATCTCCCGGACCCCTGAGGTCACGTGCGTGGTGG TGGACGTGAGCCAGGAAGACCCCGAGGTCCAGTTC AACTGGTACGTGGATGGCGTGGAGGTGCATAATGC CAAGACAAAGCCGCGGGAGGAGCAGTTCAACAGCA CGTACCGTGTGGTCAGCGTCCTCACCGTCCTGCAC CAGGACTGGCTGAACGGCAAGGAGTACAAGTGCAA GGTGTCCAACAAAGGCCTCCCGTCCTCCATCGAGA AAACCATCTCCAAAGCCAAAGGGCAGCCCCGAGAG CCACAGGTGTACACCCTGCCCCCATCCCAGGAGGA GATGACCAAGAACCAGGTCAGCCTGACCTGCCTGG TCAAAGGCTTCTACCCCAGCGACATCGCCGTGGAG TGGGAGAGCAATGGGCAGCCGGAGAACAACTACAA GACCACGCCTCCCGTGCTGGACTCCGACGGCTCCT TCTTCCTCTACAGCAGGCTAACCGTGGACAAGAGC AGGTGGCAGGAGGGGAATGTCTTCTCATGCTCCGT GATGCATGAGGCTCTGCACAACCACTACACACAGA AGAGCCTCTCCCTGTCTCTGGGTAAA |

BAP050-hum17 LC

| | | |
|---|---|---|
| SEQ ID NO: 10 (Kabat) | LCDR1 | SSSQDISNYLN |
| SEQ ID NO: 11 (Kabat) | LCDR2 | YTSTLHL |
| SEQ ID NO: 12 (Kabat) | LCDR3 | QQYYNLPWT |
| SEQ ID NO: 13 (Chothia) | LCDR1 | SQDISNY |
| SEQ ID NO: 14 (Chothia) | LCDR2 | YTS |
| SEQ ID NO: 15 (Chothia) | LCDR3 | YYNLPW |
| SEQ ID NO: 84 | VL | DIQMTQSPSSLSASVGDRVTITCSSSQDISNYLNW YQQKPGKAPKLLIYYTSTLHLGVPSRFSGSGSGTD FTFTISSLQPEDIATYYCQQYYNLPWTFGQGTKVE IK |
| SEQ ID NO: 85 | DNA VL | GACATCCAGATGACCCAGTCTCCATCCTCCCTGTC TGCATCTGTAGGAGACAGAGTCACCATCACTTGCT CCTCTAGTCAGGACATTAGCAACTATTTAAATTGG TATCAGCAGAAACCAGGGAAAGCCCCTAAGCTCCT GATCTACTATACATCCACTTTGCACCTGGGGGTCC CATCAAGGTTCAGTGGAAGTGGATCTGGGACAGAT TTTACTTTCACCATCAGCAGCCTGCAGCCTGAAGA TATTGCAACATATTACTGTCAACAGTATTATAATC TCCCTTGGACGTTCGGCCAAGGGACCAAGGTGGAA ATCAAA |
| SEQ ID NO: 86 | LC | DIQMTQSPSSLSASVGDRVTITCSSSQDISNYLNW YQQKPGKAPKLLIYYTSTLHLGVPSRFSGSGSGTD FTFTISSLQPEDIATYYCQQYYNLPWTFGQGTKVE IKRTVAAPSVFIFPPSDEQLKSGTASVVCLLNNFY PREAKVQWKVDNALQSGNSQESVTEQDSKDSTYSL SSTLTLSKADYEKHKVYACEVTHQGLSSPVTKSFN RGEC |
| SEQ ID NO: 87 | DNA LC | GACATCCAGATGACCCAGTCTCCATCCTCCCTGTC TGCATCTGTAGGAGACAGAGTCACCATCACTTGCT CCTCTAGTCAGGACATTAGCAACTATTTAAATTGG TATCAGCAGAAACCAGGGAAAGCCCCTAAGCTCCT GATCTACTATACATCCACTTTGCACCTGGGGGTCC CATCAAGGTTCAGTGGAAGTGGATCTGGGACAGAT TTTACTTTCACCATCAGCAGCCTGCAGCCTGAAGA TATTGCAACATATTACTGTCAACAGTATTATAATC TCCCTTGGACGTTCGGCCAAGGGACCAAGGTGGAA ATCAAACGTACGGTGGCTGCACCATCTGTCTTCAT CTTCCCGCCATCTGATGAGCAGTTGAAATCTGGAA CTGCCTCTGTTGTGTGCCTGCTGAATAACTTCTAT CCCAGAGAGGCCAAAGTACAGTGGAAGGTGGATAA CGCCCTCCAATCGGGTAACTCCCAGGAGAGTGTCA CAGAGCAGGACAGCAAGGACAGCACCTACAGCCTC AGCAGCACCCTGACGCTGAGCAAAGCAGACTACGA GAAACACAAAGTCTACGCCTGCGAAGTCACCCATC AGGGCCTGAGCTCGCCCGTCACAAAGAGCTTCAAC AGGGGAGAGTGT |

BAP050-hum18 HC

| | | |
|---|---|---|
| SEQ ID NO: 1 (Kabat) | HCDR1 | NYGMN |
| SEQ ID NO: 2 (Kabat) | HCDR2 | WINTDTGEPTYADDFKG |
| SEQ ID NO: 3 (Kabat) | HCDR3 | NPPYYYGTNNAEAMDY |
| SEQ ID NO: 4 (Chothia) | HCDR1 | GFTLTNY |

TABLE 1-continued

Amino acid and nucleotide sequences for murine, chimeric and humanized antibody molecules. The antibody molecules include murine mAb BAP050, chimeric mAbs BAP050-chi, humanized mAbs BAP050-hum01 to BAP050-hum20, humanized mAbs BAP050-hum01-Ser to BAP050-hum15-Ser, BAP050-hum18-Ser to BAP050-hum20-Ser, and humanized mAbs BAP050-Clone-F to BAP050-Clone-J. The amino acid and nucleotide sequences of the heavy and light chain CDRs, the heavy and light chain variable regions, and the heavy and light chains are shown.

| | | |
|---|---|---|
| SEQ ID NO: 5 (Chothia) | HCDR2 | NTDTGE |
| SEQ ID NO: 3 (Chothia) | HCDR3 | NPPYYYGTNNAEAMDY |
| SEQ ID NO: 28 | VH | EVQLVQSGAEVKKPGATVKISCKVSGFTLTNYGMN WVRQAPGQGLEWMGWINTDTGEPTYADDFKGRFVF SLDTSVSTAYLQICSLKAEDTAVYYCARNPPYYYG TNNAEAMDYWGQGTTVTVSS |
| SEQ ID NO: 29 | DNA VH | GAGGTCCAGCTGGTACAGTCTGGGGCTGAGGTGAA GAAGCCTGGGGCTACAGTGAAAATCTCCTGCAAGG TTTCTGGATTTACCCTCACAAACTATGGAATGAAC TGGGTGCGACAGGCCCCTGGACAAGGGCTTGAGTG GATGGGTTGGATAAACACCGACACTGGAGAGCCAA CATATGCTGATGACTTCAAGGGAAGATTTGTCTTC TCCTTGGACACCTCTGTCAGCACGGCATATCTGCA GATCTGCAGCCTAAAGGCTGAGGACACTGCCGTGT ATTACTGTGCAAGAAACCCTCCCTATTACTACGGT ACTAATAACGCGGAGGCTATGGACTACTGGGGCCA GGGCACCACCGTGACCGTGTCCTCC |
| SEQ ID NO: 30 | HC | EVQLVQSGAEVKKPGATVKISCKVSGFTLTNYGMN WVRQAPGQGLEWMGWINTDTGEPTYADDFKGRFVF SLDTSVSTAYLQICSLKAEDTAVYYCARNPPYYYG TNNAEAMDYWGQGTTVTVSSASTKGPSVFPLAPCS RSTSESTAALGCLVKDYFPEPVTVSWNSGALTSGV HTFPAVLQSSGLYSLSSVVTVPSSSLGTKTYTCNV DHKPSNTKVDKRVESKYGPPCPPCPAPEFLGGPSV FLFPPKPKDTLMISRTPEVTCVVVDVSQEDPEVQF NWYVDGVEVHNAKTKPREEQFNSTYRVVSVLTVLH QDWLNGKEYKCKVSNKGLPSSIEKTISKAKGQPRE PQVYTLPPSQEEMTKNQVSLTCLVKGFYPSDIAVE WESNGQPENNYKTTPPVLDSDGSFFLYSRLTVDKS RWQEGNVFSCSVMHEALHNHYTQKSLSLSLGK |
| SEQ ID NO: 31 | DNA HC | GAGGTCCAGCTGGTACAGTCTGGGGCTGAGGTGAA GAAGCCTGGGGCTACAGTGAAAATCTCCTGCAAGG TTTCTGGATTTACCCTCACAAACTATGGAATGAAC TGGGTGCGACAGGCCCCTGGACAAGGGCTTGAGTG GATGGGTTGGATAAACACCGACACTGGAGAGCCAA CATATGCTGATGACTTCAAGGGAAGATTTGTCTTC TCCTTGGACACCTCTGTCAGCACGGCATATCTGCA GATCTGCAGCCTAAAGGCTGAGGACACTGCCGTGT ATTACTGTGCAAGAAACCCTCCCTATTACTACGGT ACTAATAACGCGGAGGCTATGGACTACTGGGGCCA GGGCACCACCGTGACCGTGTCCTCCACCA AGGGCCCATCCGTCTTCCCCCTGGCGCCCTGCTCC AGGAGCACCTCCGAGAGCACAGCCGCCCTGGGCTG CCTGGTCAAGGACTACTTCCCCGAACCGGTGACGG TGTCGTGGAACTCAGGCGCCCTGACCAGCGGCGTG CACACCTTCCCGGCTGTCCTACAGTCCTCAGGACT CTACTCCCTCAGCAGCGTGGTGACCGTGCCCTCCA GCAGCTTGGGCACGAAGACCTACACCTGCAACGTA GATCACAAGCCCAGCAACACCAAGGTGGACAAGAG AGTTGAGTCCAAATATGGTCCCCCATGCCCACCGT GCCCAGCACCTGAGTTCCTGGGGGGACCATCAGTC TTCCTGTTCCCCCCAAAACCCAAGGACACTCTCAT GATCTCCCGGACCCCTGAGGTCACGTGCGTGGTGG TGGACGTGAGCCAGGAAGACCCCGAGGTCCAGTTC AACTGGTACGTGGATGGCGTGGAGGTGCATAATGC CAAGACAAAGCCGCGGGAGGAGCAGTTCAACAGCA CGTACCGTGTGGTCAGCGTCCTCACCGTCCTGCAC CAGGACTGGCTGAACGGCAAGGAGTACAAGTGCAA GGTGTCCAACAAAGGCCTCCCGTCCTCCATCGAGA AAACCATCTCCAAAGCCAAAGGGCAGCCCCGAGAG CCACAGGTGTACACCCTGCCCCCATCCCAGGAGGA GATGACCAAGAACCAGGTCAGCCTGACCTGCCTGG TCAAAGGCTTCTACCCCAGCGACATCGCCGTGGAG TGGGAGAGCAATGGGCAGCCGGAGAACAACTACAA GACCACGCCTCCCGTGCTGGACTCCGACGGCTCCT TCTTCCTCTACAGCAGGCTAACCGTGGACAAGAGC AGGTGGCAGGAGGGGAATGTCTTCTCATGCTCCGT GATGCATGAGGCTCTGCACAACCACTACACAGA AGAGCCTCTCCCTGTCTCTGGGTAAA |

BAP050-hum18 LC

| | | |
|---|---|---|
| SEQ ID NO: 10 (Kabat) | LCDR1 | SSSQDISNYLN |
| SEQ ID NO: 11 (Kabat) | LCDR2 | YTSTLHL |
| SEQ ID NO: 12 (Kabat) | LCDR3 | QQYYNLPWT |
| SEQ ID NO: 13 (Chothia) | LCDR1 | SQDISNY |
| SEQ ID NO: 14 (Chothia) | LCDR2 | YTS |
| SEQ ID NO: 15 (Chothia) | LCDR3 | YYNLPW |
| SEQ ID NO: 88 | VL | AIQLTQSPSSLSASVGDRVTITCSSSQDISNYLNW YQQKPGQAPRLLIYYTSTLHLGVPSRFSGSGSGTD FTLTISSLQPEDFATYYCQQYYNLPWTFGQGTKVE IK |
| SEQ ID NO: 89 | DNA VL | GCCATCCAGTTGACCCAGTCTCCATCCTCCCTGTC TGCATCTGTAGGAGACAGAGTCACCATCACTTGCA GTTCAAGTCAGGACATCAGCAATTATTTAAACTGG TACCAGCAGAAACCTGGCCAGGCTCCCAGGCTCCT CATCTATTACACATCAACCTTACACTTAGGGGTCC CATCAAGGTTCAGCGGCAGTGGATCTGGGACAGAT TTCACTCTCACCATCAGCAGCCTGCAGCCTGAAGA TTTTGCAACTTATTACTGTCAGCAGTATTATAACC TTCCGTGGACGTTCGGCCAAGGGACCAAGGTGGAA ATCAAA |
| SEQ ID NO: 90 | LC | AIQLTQSPSSLSASVGDRVTITCSSSQDISNYLNW YQQKPGQAPRLLIYYTSTLHLGVPSRFSGSGSGTD FTLTISSLQPEDFATYYCQQYYNLPWTFGQGTKVE IKRTVAAPSVFIFPPSDEQLKSGTASVVCLLNNFY PREAKVQWKVDNALQSGNSQESVTEQDSKDSTYSL SSTLTLSKADYEKHKVYACEVTHQGLSSPVTKSFN RGEC |
| SEQ ID NO: 91 | DNA LC | GCCATCCAGTTGACCCAGTCTCCATCCTCCCTGTC TGCATCTGTAGGAGACAGAGTCACCATCACTTGCA GTTCAAGTCAGGACATCAGCAATTATTTAAACTGG TACCAGCAGAAACCTGGCCAGGCTCCCAGGCTCCT CATCTATTACACATCAACCTTACACTTAGGGGTCC |

TABLE 1-continued

Amino acid and nucleotide sequences for murine, chimeric and humanized antibody molecules. The antibody molecules include murine mAb BAP050, chimeric mAbs BAP050-chi, humanized mAbs BAP050-hum01 to BAP050-hum20, humanized mAbs BAP050-hum01-Ser to BAP050-hum15-Ser, BAP050-hum18-Ser to BAP050-hum20-Ser, and humanized mAbs BAP050-Clone-F to BAP050-Clone-J. The amino acid and nucleotide sequences of the heavy and light chain CDRs, the heavy and light chain variable regions, and the heavy and light chains are shown.

| | | |
|---|---|---|
| | | CATCAAGGTTCAGCGGCAGTGGATCTGGGACAGAT<br>TTCACTCTCACCATCAGCAGCCTGCAGCCTGAAGA<br>TTTTGCAACTTATTACTGTCAGCAGTATTATAACC<br>TTCCGTGGACGTTCGGCCAAGGGACCAAGGTGGAA<br>ATCAAACGTACGGTGGCTGCACCATCTGTCTTCAT<br>CTTCCCGCCATCTGATGAGCAGTTGAAATCTGGAA<br>CTGCCTCTGTTGTGTGCCTGCTGAATAACTTCTAT<br>CCCAGAGAGGCCAAAGTACAGTGGAAGGTGGATAA<br>CGCCCTCCAATCGGGTAACTCCCAGGAGAGTGTCA<br>CAGAGCAGGACAGCAAGGACAGCACCTACAGCCTC<br>AGCAGCACCCTGACGCTGAGCAAAGCAGACTACGA<br>GAAACAAAGTCTACGCCTGCGAAGTCACCCATC<br>AGGGCCTGAGCTCGCCCGTCACAAAGAGCTTCAAC<br>AGGGGAGAGTGT |
| | | BAP050-hum19 HC |
| SEQ ID NO: 1 (Kabat) | HCDR1 | NYGMN |
| SEQ ID NO: 2 (Kabat) | HCDR2 | WINTDTGEPTYADDFKG |
| SEQ ID NO: 3 (Kabat) | HCDR3 | NPPYYYGTNNAEAMDY |
| SEQ ID NO: 4 (Chothia) | HCDR1 | GFTLTNY |
| SEQ ID NO: 5 (Chothia) | HCDR2 | NTDTGE |
| SEQ ID NO: 3 (Chothia) | HCDR3 | NPPYYYGTNNAEAMDY |
| SEQ ID NO: 28 | VH | EVQLVQSGAEVKKPGATVKISCKVSGFTLTNYGMN<br>WVRQAPGQGLEWMGWINTDTGEPTYADDFKGRFVF<br>SLDTSVSTAYLQICSLKAEDTAVYYCARNPPYYYG<br>TNNAEAMDYWGQGTTVTVSS |
| SEQ ID NO: 29 | DNA VH | GAGGTCCAGCTGGTACAGTCTGGGGCTGAGGTGAA<br>GAAGCCTGGGGCTACAGTGAAAATCTCCTGCAAGG<br>TTTCTGGATTTACCCTCACAAACTATGGAATGAAC<br>TGGGTGCGACAGGCCCCTGGACAAGGGCTTGAGTG<br>GATGGGTTGGATAAACACCGACACTGGAGAGCCAA<br>CATATGCTGATGACTTCAAGGGAAGATTTGTCTTC<br>TCCTTGGACACCTCTGTCAGCACGGCATATCTGCA<br>GATCTGCAGCCTAAAGGCTGAGGACACTGCCGTGT<br>ATTACTGTGCAAGAAACCCTCCCTATTACTACGGT<br>ACTAATAACGCGGAGGCTATGGACTACTGGGGCCA<br>GGGCACCACCGTGACCGTGTCCTCC |
| SEQ ID NO: 30 | HC | EVQLVQSGAEVKKPGATVKISCKVSGFTLTNYGMN<br>WVRQAPGQGLEWMGWINTDTGEPTYADDFKGRFVF<br>SLDTSVSTAYLQICSLKAEDTAVYYCARNPPYYYG<br>TNNAEAMDYWGQGTTVTVSSASTKGPSVFPLAPCS<br>RSTSESTAALGCLVKDYFPEPVTVSWNSGALTSGV<br>HTFPAVLQSSGLYSLSSVVTVPSSSLGTKTYTCNV<br>DHKPSNTKVDKRVESKYGPPCPPCPAPEFLGGPSV<br>FLFPPKPKDTLMISRTPEVTCVVVDVSQEDPEVQF<br>NWYVDGVEVHNAKTKPREEQFNSTYRVVSVLTVLH | |
| | | QDWLNGKEYKCKVSNKGLPSSIEKTISKAKGQPRE<br>PQVYTLPPSQEEMTKNQVSLTCLVKGFYPSDIAVE<br>WESNGQPENNYKTTPPVLDSDGSFFLYSRLTVDKS<br>RWQEGNVFSCSVMHEALHNHYTQKSLSLSLGK |
| SEQ ID NO: 31 | DNA HC | GAGGTCCAGCTGGTACAGTCTGGGGCTGAGGTGAA<br>GAAGCCTGGGGCTACAGTGAAAATCTCCTGCAAGG<br>TTTCTGGATTTACCCTCACAAACTATGGAATGAAC<br>TGGGTGCGACAGGCCCCTGGACAAGGGCTTGAGTG<br>GATGGGTTGGATAAACACCGACACTGGAGAGCCAA<br>CATATGCTGATGACTTCAAGGGAAGATTTGTCTTC<br>TCCTTGGACACCTCTGTCAGCACGGCATATCTGCA<br>GATCTGCAGCCTAAAGGCTGAGGACACTGCCGTGT<br>ATTACTGTGCAAGAAACCCTCCCTATTACTACGGT<br>ACTAATAACGCGGAGGCTATGGACTACTGGGGCCA<br>GGGCACCACCGTGACCGTGTCCTCCGGTTCCACCA<br>AGGGCCCATCCGTCTTCCCCCTGGCGCCCTGCTCC<br>AGGAGCACCTCCGAGAGCACAGCCGCCCTGGGCTG<br>CCTGGTCAAGGACTACTTCCCCGAACCGGTGACGG<br>TGTCGTGGAACTCAGGCGCCCTGACCAGCGGCGTG<br>CACACCTTCCCGGCTGTCCTACAGTCCTCAGGACT<br>CTACTCCCTCAGCAGCGTGGTGACCGTGCCCTCCA<br>GCAGCTTGGGCACGAAGACCTACACCTGCAACGTA<br>GATCACAAGCCCAGCAACACCAAGGTGGACAAGAG<br>AGTTGAGTCCAAATATGGTCCCCCATGCCCACCGT<br>GCCCAGCACCTGAGTTCCTGGGGGGACCATCAGTC<br>TTCCTGTTCCCCCCAAAACCCAAGGACACTCTCAT<br>GATCTCCCGGACCCCTGAGGTCACGTGCGTGGTGG<br>TGGACGTGAGCCAGGAAGACCCCGAGGTCCAGTTC<br>AACTGGTACGTGGATGGCGTGGAGGTGCATAATGC<br>CAAGACAAAGCCGCGGGAGGAGCAGTTCAACAGCA<br>CGTACCGTGTGGTCAGCGTCCTCACCGTCCTGCAC<br>CAGGACTGGCTGAACGGCAAGGAGTACAAGTGCAA<br>GGTGTCCAACAAAGGCCTCCCGTCCTCCATCGAGA<br>AAACCATCTCCAAAGCCAAAGGGCAGCCCCGAGAG<br>CCACAGGTGTACACCCTGCCCCCATCCCAGGAGGA<br>GATGACCAAGAACCAGGTCAGCCTGACCTGCCTGG<br>TCAAAGGCTTCTACCCCAGCGACATCGCCGTGGAG<br>TGGGAGAGCAATGGGCAGCCGGAGAACAACTACAA<br>GACCACGCCTCCCGTGCTGGACTCCGACGGCTCCT<br>TCTTCCTCTACAGCAGGCTAACCGTGGACAAGAGC<br>AGGTGGCAGGAGGGGAATGTCTTCTCATGCTCCGT<br>GATGCATGAGGCTCTGCACAACCACTACACAGA<br>AGAGCCTCTCCCTGTCTCTGGGTAAA |
| | | BAP050-hum19 LC |
| SEQ ID NO: 10 (Kabat) | LCDR1 | SSQDISNYLN |
| SEQ ID NO: 11 (Kabat) | LCDR2 | YTSTLHL |
| SEQ ID NO: 12 (Kabat) | LCDR3 | QQYYNLPWT |
| SEQ ID NO: 13 (Chothia) | LCDR1 | SQDISNY |
| SEQ ID NO: 14 (Chothia) | LCDR2 | YTS |

TABLE 1-continued

Amino acid and nucleotide sequences for murine, chimeric and humanized antibody molecules. The antibody molecules include murine mAb BAP050, chimeric mAbs BAP050-chi, humanized mAbs BAP050-hum01 to BAP050-hum20, humanized mAbs BAP050-hum01-Ser to BAP050-hum15-Ser, BAP050-hum18-Ser to BAP050-hum20-Ser, and humanized mAbs BAP050-Clone-F to BAP050-Clone-J. The amino acid and nucleotide sequences of the heavy and light chain CDRs, the heavy and light chain variable regions, and the heavy and light chains are shown.

| | | |
|---|---|---|
| SEQ ID NO: 15 (Chothia) | | LCDR3 YYNLPW |
| SEQ ID NO: 92 | VL | EIVLTQSPDFQSVTPKEKVTITCSSSQDISNYLNW YQQKPGQAPRLLIYYTSTLHLGVPSRFSGSGSGTD FTFTISSLEAEDAATYYCQQYYNLPWTFGQGTKVE IK |
| SEQ ID NO: 93 | DNA VL | GAAATTGTGCTGACTCAGTCTCCAGACTTTCAGTC TGTGACTCCAAAGGAGAAAGTCACCATCACCTGCA GTTCAAGTCAGGACATCAGCAATTATTTAAACTGG TACCAGCAGAAACCTGGCCAGGCTCCCAGGCTCCT CATCTATTACACATCAACCTTACACTTAGGGGTCC CCTCGAGGTTCAGTGGCAGTGGATCTGGGACAGAT TTCACCTTTACCATCAGTAGCCTGGAAGCTGAAGA TGCTGCAACATATTACTGTCAGCAGTATTATAACC TTCCGTGGACGTTCGGCCAAGGGACCAAGGTGGAA ATCAAA |
| SEQ ID NO: 94 | LC | EIVLTQSPDFQSVTPKEKVTITCSSSQDISNYLNW YQQKPGQAPRLLIYYTSTLHLGVPSRFSGSGSGTD FTFTISSLEAEDAATYYCQQYYNLPWTFGQGTKVE IKRTVAAPSVFIFPPSDEQLKSGTASVVCLLNNFY PREAKVQWKVDNALQSGNSQESVTEQDSKDSTYSL SSTLTLSKADYEKHKVYACEVTHQGLSSPVTKSFN RGEC |
| SEQ ID NO: 95 | DNA LC | GAAATTGTGCTGACTCAGTCTCCAGACTTTCAGTC TGTGACTCCAAAGGAGAAAGTCACCATCACCTGCA GTTCAAGTCAGGACATCAGCAATTATTTAAACTGG TACCAGCAGAAACCTGGCCAGGCTCCCAGGCTCCT CATCTATTACACATCAACCTTACACTTAGGGGTCC CCTCGAGGTTCAGTGGCAGTGGATCTGGGACAGAT TTCACCTTTACCATCAGTAGCCTGGAAGCTGAAGA TGCTGCAACATATTACTGTCAGCAGTATTATAACC TTCCGTGGACGTTCGGCCAAGGGACCAAGGTGGAA ATCAAACGTACGGTGGCTGCACCATCTGTCTTCAT CTTCCCGCCATCTGATGAGCAGTTGAAATCTGGAA CTGCCTCTGTTGTGTGCCTGCTGAATAACTTCTAT CCCAGAGAGGCCAAAGTACAGTGGAAGGTGGATAA CGCCCTCCAATCGGGTAACTCCCAGGAGAGTGTCA CAGAGCAGGACAGCAAGGACAGCACCTACAGCCTC AGCAGCACCCTGACGCTGAGCAAAGCAGACTACGA GAAACACAAAGTCTACGCCTGCGAAGTCACCCATC AGGGCCTGAGCTCGCCCGTCACAAAGAGCTTCAAC AGGGGAGAGTGT |

BAP050-hum20 HC

| | | |
|---|---|---|
| SEQ ID NO: 1 (Kabat) | | HCDR1 NYGMN |
| SEQ ID NO: 2 (Kabat) | | HCDR2 WINTDTGEPTYADDFKG |
| SEQ ID NO: 3 (Kabat) | | HCDR3 NPPYYYGTNNAEAMDY |
| SEQ ID NO: 4 (Chothia) | | HCDR1 GFTLTNY |
| SEQ ID NO: 5 (Chothia) | | HCDR2 NTDTGE |
| SEQ ID NO: 3 (Chothia) | | HCDR3 NPPYYYGTNNAEAMDY |
| SEQ ID NO: 64 | VH | QVQLVQSGAEVKKPGASVKVSCKASGFTLTNYGMN WVRQARGQRLEWIGWINTDTGEPTYADDFKGRFVF SLDTSVSTAYLQICSLKAEDTAVYYCARNPPYYYG TNNAEAMDYWGQGTTVTVSS |
| SEQ ID NO: 65 | DNA VH | CAGGTTCAGCTGGTGCAGTCTGGAGCTGAGGTGAA GAAGCCTGGGGCCTCAGTGAAGGTCTCCTGCAAGG CTTCTGGATTTACCCTCACAAACTATGGAATGAAC TGGGTGCGACAGGCTCGTGGACAACGCCTTGAGTG GATAGGTTGGATAAACACCGACACTGGAGAGCCAA CATATGCTGATGACTTCAAGGGAAGATTTGTCTTC TCCTTGGACACCTCTGTCAGCACGGCATATCTGCA GATCTGCAGCCTAAAGGCTGAGGACACTGCCGTGT ATTACTGTGCAAGAAACCCTCCTTATTACTACGGT ACTAATAACGCGGAGGCTATGGACTACTGGGGCCA GGGCACCACCGTGACCGTGTCCTCC |
| SEQ ID NO: 66 | HC | QVQLVQSGAEVKKPGASVKVSCKASGFTLTNYGMN WVRQARGQRLEWIGWINTDTGEPTYADDFKGRFVF SLDTSVSTAYLQICSLKAEDTAVYYCARNPPYYYG TNNAEAMDYWGQGTTVTVSSASTKGPSVFPLAPCS RSTSESTAALGCLVKDYFPEPVTVSWNSGALTSGV HTFPAVLQSSGLYSLSSVVTVPSSSLGTKTYTCNV DHKPSNTKVDKRVESKYGPPCPPCPAPEFLGGPSV FLFPPKPKDTLMISRTPEVTCVVVDVSQEDPEVQF NWYVDGVEVHNAKTKPREEQFNSTYRVVSVLTVLH QDWLNGKEYKCKVSNKGLPSSIEKTISKAKGQPRE PQVYTLPPSQEEMTKNQVSLTCLVKGFYPSDIAVE WESNGQPENNYKTTPPVLDSDGSFFLYSRLTVDKS RWQEGNVFSCSVMHEALHNHYTQKSLSLSLGK |
| SEQ ID NO: 67 | DNA HC | CAGGTTCAGCTGGTGCAGTCTGGAGCTGAGGTGAA GAAGCCTGGGGCCTCAGTGAAGGTCTCCTGCAAGG CTTCTGGATTTACCCTCACAAACTATGGAATGAAC TGGGTGCGACAGGCTCGTGGACAACGCCTTGAGTG GATAGGTTGGATAAACACCGACACTGGAGAGCCAA CATATGCTGATGACTTCAAGGGAAGATTTGTCTTC TCCTTGGACACCTCTGTCAGCACGGCATATCTGCA GATCTGCAGCCTAAAGGCTGAGGACACTGCCGTGT ATTACTGTGCAAGAAACCCTCCTTATTACTACGGT ACTAATAACGCGGAGGCTATGGACTACTGGGGCCA GGGCACCACCGTGACCGTGTCCTCCGCTTCCACCA AGGGCCCATCCGTCTTCCCCCTGGCGCCCTGCTCC AGGAGCACCTCCGAGAGCACAGCCGCCCTGGGCTG CCTGGTCAAGGACTACTTCCCCGAACCGGTGACGG TGTCGTGGAACTCAGGCGCCCTGACCAGCGGCGTG CACACCTTCCCGGCTGTCCTACAGTCCTCAGGACT CTACTCCCTCAGCAGCGTGGTGACCGTGCCCTCCA GCAGCTTGGGCACGAAGACCTACACCTGCAACGTA GATCACAAGCCCAGCAACACCAAGGTGGACAAGAG AGTTGAGTCCAAATATGGTCCCCCATGCCCACCGT GCCCAGCACCTGAGTTCCTGGGGGGACCATCAGTC TTCCTGTTCCCCCCAAAACCCAAGGACACTCTCAT GATCTCCCGGACCCCTGAGGTCACGTGCGTGGTGG TGGACGTGAGCCAGGAAGACCCCGAGGTCCAGTTC AACTGGTACGTGGATGGCGTGGAGGTGCATAATGC CAAGACAAAGCCGCGGGAGGAGCAGTTCAACAGCA CGTACCGTGTGGTCAGCGTCCTCACCGTCCTGCAC CAGGACTGGCTGAACGGCAAGGAGTACAAGTGCAA |

TABLE 1-continued

Amino acid and nucleotide sequences for murine, chimeric and humanized antibody molecules. The antibody molecules include murine mAb BAP050, chimeric mAbs BAP050-chi, humanized mAbs BAP050-hum01 to BAP050-hum20, humanized mAbs BAP050-hum01-Ser to BAP050-hum15-Ser, BAP050-hum18-Ser to BAP050-hum20-Ser, and humanized mAbs BAP050-Clone-F to BAP050-Clone-J. The amino acid and nucleotide sequences of the heavy and light chain CDRs, the heavy and light chain variable regions, and the heavy and light chains are shown.

```
                        GGTGTCCAACAAAGGCCTCCCGTCCTCCATCGAGA
                        AAACCATCTCCAAAGCCAAAGGGCAGCCCCGAGAG
                        CCACAGGTGTACACCCTGCCCCCATCCCAGGAGGA
                        GATGACCAAGAACCAGGTCAGCCTGACCTGCCTGG
                        TCAAAGGCTTCTACCCCAGCGACATCGCCGTGGAG
                        TGGGAGAGCAATGGGCAGCCGGAGAACAACTACAA
                        GACCACGCCTCCCGTGCTGGACTCCGACGGCTCCT
                        TCTTCCTCTACAGCAGGCTAACCGTGGACAAGAGC
                        AGGTGGCAGGAGGGGAATGTCTTCTCATGCTCCGT
                        GATGCATGAGGCTCTGCACAACCACTACACACAGA
                        AGAGCCTCTCCCTGTCTCTGGGTAAA
```

BAP050-hum20 LC

| | | |
|---|---|---|
| SEQ ID NO: 10 (Kabat) | LCDR1 | SSSQDISNYLN |
| SEQ ID NO: 11 (Kabat) | LCDR2 | YTSTLHL |
| SEQ ID NO: 12 (Kabat) | LCDR3 | QQYYNLPWT |
| SEQ ID NO: 13 (Chothia) | LCDR1 | SQDISNY |
| SEQ ID NO: 14 (Chothia) | LCDR2 | YTS |
| SEQ ID NO: 15 (Chothia) | LCDR3 | YYNLPW |
| SEQ ID NO: 96 | VL | DIVMTQTPLSLPVTPGEPASISCSSSQDISNYLNW YQQKPGQAPRLLIYYTSTLHLGIPDRFSGSGSGTD FTLTISRLEPEDFAVYYCQQYYNLPWTFGQGTKVE IK |
| SEQ ID NO: 97 | DNA VL | GATATTGTGATGACCCAGACTCCACTCTCCCTGCC CGTCACCCCTGGAGAGCCGGCCTCCATCTCCTGCA GTTCAAGTCAGGACATCAGCAATTATTTAAACTGG TACCAGCAGAAACCTGGCCAGGCTCCCAGGCTCCT CATCTATTACACATCAACCTTACACTTAGGGATCC CAGACAGGTTCAGTGGCAGTGGGTCTGGGACAGAC TTCACTCTCACCATCAGCAGACTGGAGCCTGAAGA TTTTGCAGTGTATTACTGTCAGCAGTATTATAACC TTCCGTGGACGTTCGGCCAAGGGACCAAGGTGGAA ATCAAA |
| SEQ ID NO: 98 | LC | DIVMTQTPLSLPVTPGEPASISCSSSQDISNYLNW YQQKPGQAPRLLIYYTSTLHLGIPDRFSGSGSGTD FTLTISRLEPEDFAVYYCQQYYNLPWTFGQGTKVE IKRTVAAPSVFIFPPSDEQLKSGTASVVCLLNNFY PREAKVQWKVDNALQSGNSQESVTEQDSKDSTYSL SSTLTLSKADYEKHKVYACEVTHQGLSSPVTKSFN RGEC |
| SEQ ID NO: 99 | DNA LC | GATATTGTGATGACCCAGACTCCACTCTCCCTGCC CGTCACCCCTGGAGAGCCGGCCTCCATCTCCTGCA GTTCAAGTCAGGACATCAGCAATTATTTAAACTGG TACCAGCAGAAACCTGGCCAGGCTCCCAGGCTCCT CATCTATTACACATCAACCTTACACTTAGGGATCC CAGACAGGTTCAGTGGCAGTGGGTCTGGGACAGAC TTCACTCTCACCATCAGCAGACTGGAGCCTGAAGA TTTTGCAGTGTATTACTGTCAGCAGTATTATAACC TTCCGTGGACGTTCGGCCAAGGGACCAAGGTGGAA ATCAAACGTACGGTGGCTGCACCATCTGTCTTCAT CTTCCCGCCATCTGATGAGCAGTTGAAATCTGGAA CTGCCTCTGTTGTGTGCCTGCTGAATAACTTCTAT CCCAGAGAGGCCAAAGTACAGTGGAAGGTGGATAA CGCCCTCCAATCGGGTAACTCCCAGGAGAGTGTCA CAGAGCAGGACAGCAAGGACAGCACCTACAGCCTC AGCAGCACCCTGACGCTGAGCAAAGCAGACTACGA GAAACACAAAGTCTACGCCTGCGAAGTCACCCATC AGGGCCTGAGCTCGCCCGTCACAAAGAGCTTCAAC AGGGGAGAGTGT |

BAP050-hum01-Ser HC

| | | |
|---|---|---|
| SEQ ID NO: 1 (Kabat) | HCDR1 | NYGMN |
| SEQ ID NO: 2 (Kabat) | HCDR2 | WINTDTGEPTYADDFKG |
| SEQ ID NO: 3 (Kabat) | HCDR3 | NPPYYYGTNNAEAMDY |
| SEQ ID NO: 4 (Chothia) | HCDR1 | GFTLTNY |
| SEQ ID NO: 5 (Chothia) | HCDR2 | NTDTGE |
| SEQ ID NO: 3 (Chothia) | HCDR3 | NPPYYYGTNNAEAMDY |
| SEQ ID NO: 100 | VH | EVQLVQSGAEVKKPGATVKISCKVSGFTLTNYGMN WVRQAPGQGLEWMGWINTDTGEPTYADDFKGRFVF SLDTSVSTAYLQISSLKAEDTAVYYCARNPPYYYG TNNAEAMDYWGQGTTVTVSS |
| SEQ ID NO: 101 | DNA VH | GAGGTCCAGCTGGTACAGTCTGGGGCTGAGGTGAA GAAGCCTGGGGCTACAGTGAAAATCTCCTGCAAGG TTTCTGGATTTACCCTCACAAACTATGGAATGAAC TGGGTGCGACAGGCCCCTGGACAAGGGCTTGAGTG GATGGGTTGGATAAACACCGACACTGGAGAGCCAA CATATGCTGATGACTTCAAGGGAAGATTTGTCTTC TCCTTGGACACCTCTGTCAGCACGGCATATCTGCA GATCAGCAGCCTAAAGGCTGAGGACACTGCCGTGT ATTACTGTGCAAGAAACCCTCCTTATTACTACGGT ACTAATAACGCGGAGGCTATGGACTACTGGGGCCA GGGCACCACCGTGACCGTGTCCTCC |
| SEQ ID NO: 102 | HC | EVQLVQSGAEVKKPGATVKISCKVSGFTLTNYGMN WVRQAPGQGLEWMGWINTDTGEPTYADDFKGRFVF SLDTSVSTAYLQISSLKAEDTAVYYCARNPPYYYG TNNAEAMDYWGQGTTVTVSSASTKGPSVFPLAPCS RSTSESTAALGCLVKDYFPEPVTVSWNSGALTSGV HTFPAVLQSSGLYSLSSVVTVPSSSLGTKTYTCNV DHKPSNTKVDKRVESKYGPPCPPCPAPEFLGGPSV FLFPPKPKDTLMISRTPEVTCVVVDVSQEDPEVQF NWYVDGVEVHNAKTKPREEQFNSTYRVVSVLTVLH |

TABLE 1-continued

Amino acid and nucleotide sequences for murine, chimeric and humanized antibody molecules. The antibody molecules include murine mAb BAP050, chimeric mAbs BAP050-chi, humanized mAbs BAP050-hum01 to BAP050-hum20, humanized mAbs BAP050-hum01-Ser to BAP050-hum15-Ser, BAP050-hum18-Ser to BAP050-hum20-Ser, and humanized mAbs BAP050-Clone-F to BAP050-Clone-J. The amino acid and nucleotide sequences of the heavy and light chain CDRs, the heavy and light chain variable regions, and the heavy and light chains are shown.

| | | |
|---|---|---|
| | | QDWLNGKEYKCKVSNKGLPSSIEKTISKAKGQPRE PQVYTLPPSQEEMTKNQVSLTCLVKGFYPSDIAVE WESNGQPENNYKTTPPVLDSDGSFFLYSRLTVDKS RWQEGNVFSCSVMHEALHNHYTQKSLSLSLGK |
| SEQ ID NO: 103 | DNA HC | GAGGTCCAGCTGGTACAGTCTGGGGCTGAGGTGAA GAAGCCTGGGGCTACAGTGAAAATCTCCTGCAAGG TTTCTGGATTTACCCTCACAAACTATGGAATGAAC TGGGTGCGACAGGCCCCTGGACAAGGGCTTGAGTG GATGGGTTGGATAAACACCGACACTGGAGAGCCAA CATATGCTGATGACTTCAAGGGAAGATTTGTCTTC TCCTTGGACACTCTGTCAGCACGGCATATCTGCA GATCAGCAGCCTAAAGGCTGAGGACACTGCCGTGT ATTACTGTGCAAGAAACCCTCCCTATTACTACGGT ACTAATAACGCGGAGGCTATGGACTACTGGGGCCA GGGCACCACCGTGACCGTGTCCTCCGCTTCCACCA AGGGCCCATCCGTCTTCCCCCTGGCGCCCTGCTCC AGGAGCACCTCCGAGAGCACAGCCGCCCTGGGCTG CCTGGTCAAGGACTACTTCCCCGAACCGGTGACGG TGTCGTGGAACTCAGGCGCCCTGACCAGCGGCGTG CACACCTTCCCGGCTGTCCTACAGTCCTCAGGACT CTACTCCCTCAGCAGCGTGGTGACCGTGCCCTCCA GCAGCTTGGGCACGAAGACCTACACCTGCAACGTA GATCACAAGCCCAGCAACACCAAGGTGGACAAGAG AGTTGAGTCCAAATATGGTCCCCCATGCCCACCGT GCCCAGCACCTGAGTTCCTGGGGGGACCATCAGTC TTCCTGTTCCCCCCAAAACCCAAGGACACTCTCAT GATCTCCCGGACCCCTGAGGTCACGTGCGTGGTGG TGGACGTGAGCCAGGAAGACCCCGAGGTCCAGTTC AACTGGTACGTGGATGGCGTGGAGGTGCATAATGC CAAGACAAAGCCGCGGGAGGAGCAGTTCAACAGCA CGTACCGTGTGGTCAGCGTCCTCACCGTCCTGCAC CAGGACTGGCTGAACGGCAAGGAGTACAAGTGCAA GGTGTCCAACAAAGGCCTCCCGTCCTCCATCGAGA AAACCATCTCCAAAGCCAAAGGGCAGCCCCGAGAG CCACAGGTGTACACCCTGCCCCCATCCCAGGAGGA GATGACCAAGAACCAGGTCAGCCTGACCTGCCTGG TCAAAGGCTTCTACCCCAGCGACATCGCCGTGGAG TGGGAGAGCAATGGGCAGCCGGAGAACAACTACAA GACCACGCCTCCCGTGCTGGACTCCGACGGCTCCT TCTTCCTCTACAGCAGGCTAACCGTGGACAAGAGC AGGTGGCAGGAGGGGAATGTCTTCTCATGCTCCGT GATGCATGAGGCTCTGCACAACCACTACACACAGA AGAGCCTCTCCCTGTCTCTGGGTAAA |

BAP050-hum01-Ser LC

| | | |
|---|---|---|
| SEQ ID NO: 10 (Kabat) | LCDR1 | SSSQDISNYLN |
| SEQ ID NO: 11 (Kabat) | LCDR2 | YTSTLHL |
| SEQ ID NO: 12 (Kabat) | LCDR3 | QQYYNLPWT |
| SEQ ID NO: 13 (Chothia) | LCDR1 | SQDISNY |
| SEQ ID NO: 14 (Chothia) | LCDR2 | YTS |

| | | |
|---|---|---|
| SEQ ID NO: 15 (Chothia) | LCDR3 | YYNLPW |
| SEQ ID NO: 32 | VL | DIQMTQSPSSLSASVGDRVTITCSSSQDISNYLNW YQQKPGKAPKLLIYYTSTLHLGVPSRFSGSGSGTD FTFTISSLEAEDAATYYCQQYYNLPWTFGQGTKVE IK |
| SEQ ID NO: 33 | DNA VL | GACATCCAGATGACCCAGTCTCCATCCTCCCTGTC TGCATCTGTAGGAGACAGAGTCACCATCACTTGCA GTTCAAGTCAGGACATCAGCAATTATTTAAACTGG TATCAGCAGAAACCAGGGAAAGCTCCTAAGCTCCT GATCTATTACACATCAACCTTACACTTAGGGGTCC CCTCGAGGTTCAGTGGCAGTGGATCTGGGACAGAT TTCACCTTTACCATCAGTAGCCTGGAAGCTGAAGA TGCTGCAACATATTACTGTCAGCAGTATTATAACC TTCCGTGGACGTTCGGCCAAGGGACCAAGGTGGAA ATCAAA |
| SEQ ID NO: 34 | LC | DIQMTQSPSSLSASVGDRVTITCSSSQDISNYLNW YQQKPGKAPKLLIYYTSTLHLGVPSRFSGSGSGTD FTFTISSLEAEDAATYYCQQYYNLPWTFGQGTKVE IKRTVAAPSVFIFPPSDEQLKSGTASVVCLLNNFY PREAKVQWKVDNALQSGNSQESVTEQDSKDSTYSL SSTLTLSKADYEKHKVYACEVTHQGLSSPVTKSFN RGEC |
| SEQ ID NO: 35 | DNA LC | GACATCCAGATGACCCAGTCTCCATCCTCCCTGTC TGCATCTGTAGGAGACAGAGTCACCATCACTTGCA GTTCAAGTCAGGACATCAGCAATTATTTAAACTGG TATCAGCAGAAACCAGGGAAAGCTCCTAAGCTCCT GATCTATTACACATCAACCTTACACTTAGGGGTCC CCTCGAGGTTCAGTGGCAGTGGATCTGGGACAGAT TTCACCTTTACCATCAGTAGCCTGGAAGCTGAAGA TGCTGCAACATATTACTGTCAGCAGTATTATAACC TTCCGTGGACGTTCGGCCAAGGGACCAAGGTGGAA ATCAAACGTACGGTGGCTGCACCATCTGTCTTCAT CTTCCCGCCATCTGATGAGCAGTTGAAATCTGGAA CTGCCTCTGTTGTGTGCCTGCTGAATAACTTCTAT CCCAGAGAGGCCAAAGTACAGTGGAAGGTGGATAA CGCCCTCCAATCGGGTAACTCCCAGGAGAGTGTCA CAGAGCAGGACAGCAAGGACAGCACCTACAGCCTC AGCAGCACCCTGACGCTGAGCAAAGCAGACTACGA GAAACACAAAGTCTACGCCTGCGAAGTCACCCATC AGGGCCTGAGCTCGCCCGTCACAAAGAGCTTCAAC AGGGGAGAGTGT |

BAP050-hum02-Ser HC

| | | |
|---|---|---|
| SEQ ID NO: 1 (Kabat) | HCDR1 | NYGMN |
| SEQ ID NO: 2 (Kabat) | HCDR2 | WINTDTGEPTYADDFKG |
| SEQ ID NO: 3 (Kabat) | HCDR3 | NPPYYYGTNNAEAMDY |
| SEQ ID NO: 4 (Chothia) | HCDR1 | GFTLTNY |

TABLE 1-continued

Amino acid and nucleotide sequences for murine, chimeric and humanized antibody molecules. The antibody molecules include murine mAb BAP050, chimeric mAbs BAP050-chi, humanized mAbs BAP050-hum01 to BAP050-hum20, humanized mAbs BAP050-hum01-Ser to BAP050-hum15-Ser, BAP050-hum18-Ser to BAP050-hum20-Ser, and humanized mAbs BAP050-Clone-F to BAP050-Clone-J. The amino acid and nucleotide sequences of the heavy and light chain CDRs, the heavy and light chain variable regions, and the heavy and light chains are shown.

| | | |
|---|---|---|
| SEQ ID NO: 5 (Chothia) | HCDR2 | NTDTGE |
| SEQ ID NO: 3 (Chothia) | HCDR3 | NPPYYYGTNNAEAMDY |
| SEQ ID NO: 100 | VH | EVQLVQSGAEVKKPGATVKISCKVSGFTLTNYGMN WVRQAPGQGLEWMGWINTDTGEPTYADDFKGRFVF SLDTSVSTAYLQISSLKAEDTAVYYCARNPPYYYG TNNAEAMDYWGQGTTVTVSS |
| SEQ ID NO: 101 | DNA VH | GAGGTCCAGCTGGTACAGTCTGGGGCTGAGGTGAA GAAGCCTGGGGCTACAGTGAAAATCTCCTGCAAGG TTTCTGGATTTACCCTCACAAACTATGGAATGAAC TGGGTGCGACAGGCCCCTGGACAAGGGCTTGAGTG GATGGGTTGGATAAACACCGACACTGGAGAGCCAA CATATGCTGATGACTTCAAGGGAAGATTTGTCTTC TCCTTGGACACCTCTGTCAGCACGGCATATCTGCA GATCAGCAGCCTAAAGGCTGAGGACACTGCCGTGT ATTACTGTGCAAGAAACCCTCCCTATTACTACGGT ACTAATAACGCGGAGGCTATGGACTACTGGGGCCA GGGCACCACCGTGACCGTGTCCTCC |
| SEQ ID NO: 102 | HC | EVQLVQSGAEVKKPGATVKISCKVSGFTLTNYGMN WVRQAPGQGLEWMGWINTDTGEPTYADDFKGRFVF SLDTSVSTAYLQISSLKAEDTAVYYCARNPPYYYG TNNAEAMDYWGQGTTVTVSSASTKGPSVFPLAPCS RSTSESTAALGCLVKDYFPEPVTVSWNSGALTSGV HTFPAVLQSSGLYSLSSVVTVPSSSLGTKTYTCNV DHKPSNTKVDKRVESKYGPPCPPCPAPEFLGGPSV FLFPPKPKDTLMISRTPEVTCVVVDVSQEDPEVQF NWYVDGVEVHNAKTKPREEQFNSTYRVVSVLTVLH QDWLNGKEYKCKVSNKGLPSSIEKTISKAKGQPRE PQVYTLPPSQEEMTKNQVSLTCLVKGFYPSDIAVE WESNGQPENNYKTTPPVLDSDGSFFLYSRLTVDKS RWQEGNVFSCSVMHEALHNHYTQKSLSLSLGK |
| SEQ ID NO: 103 | DNA HC | GAGGTCCAGCTGGTACAGTCTGGGGCTGAGGTGAA GAAGCCTGGGGCTACAGTGAAAATCTCCTGCAAGG TTTCTGGATTTACCCTCACAAACTATGGAATGAAC TGGGTGCGACAGGCCCCTGGACAAGGGCTTGAGTG GATGGGTTGGATAAACACCGACACTGGAGAGCCAA CATATGCTGATGACTTCAAGGGAAGATTTGTCTTC TCCTTGGACACCTCTGTCAGCACGGCATATCTGCA GATCAGCAGCCTAAAGGCTGAGGACACTGCCGTGT ATTACTGTGCAAGAAACCCTCCCTATTACTACGGT ACTAATAACGCGGAGGCTATGGACTACTGGGGCCA GGGCACCACCGTGACCGTGTCCTCCGCTTCCACCA AGGGCCCATCCGTCTTCCCCCTGGCGCCCTGCTCC AGGAGCACCTCCGAGAGCACAGCCGCCCTGGGCTG CCTGGTCAAGGACTACTTCCCCGAACCGGTGACGG TGTCGTGGAACTCAGGCGCCCTGACCAGCGGCGTG CACACCTTCCCGGCTGTCCTACAGTCCTCAGGACT CTACTCCCTCAGCAGCGTGGTGACCGTGCCCTCCA GCAGCTTGGGCACGAAGACCTACACCTGCAACGTA GATCACAAGCCCAGCAACACCAAGGTGGACAAGAG AGTTGAGTCCAAATATGGTCCCCCATGCCCACCGT GCCCAGCACCTGAGTTCCTGGGGGGACCATCAGTC TTCCTGTTCCCCCCAAAACCCAAGGACACTCTCAT GATCTCCCGGACCCCTGAGGTCACGTGCGTGGTGG TGGACGTGAGCCAGGAAGACCCCGAGGTCCAGTTC AACTGGTACGTGGATGGCGTGGAGGTGCATAATGC CAAGACAAAGCCGCGGGAGGAGCAGTTCAACAGCA CGTACCGTGTGGTCAGCGTCCTCACCGTCCTGCAC CAGGACTGGCTGAACGGCAAGGAGTACAAGTGCAA GGTGTCCAACAAAGGCCTCCCGTCCTCCATCGAGA AAACCATCTCCAAAGCCAAAGGGCAGCCCCGAGAG CCACAGGTGTACACCCTGCCCCCATCCCAGGAGGA GATGACCAAGAACCAGGTCAGCCTGACCTGCCTGG TCAAAGGCTTCTACCCCAGCGACATCGCCGTGGAG TGGGAGAGCAATGGGCAGCCGGAGAACAACTACAA GACCACGCCTCCCGTGCTGGACTCCGACGGCTCCT TCTTCCTCTACAGCAGGCTAACCGTGGACAAGAGC AGGTGGCAGGAGGGGAATGTCTTCTCATGCTCCGT GATGCATGAGGCTCTGCACAACCACTACACAGA AGAGCCTCTCCCTGTCTCTGGGTAAA |

BAP050-hum02-Ser LC

| | | |
|---|---|---|
| SEQ ID NO: 10 (Kabat) | LCDR1 | SSSQDISNYLN |
| SEQ ID NO: 11 (Kabat) | LCDR2 | YTSTLHL |
| SEQ ID NO: 12 (Kabat) | LCDR3 | QQYYNLPWT |
| SEQ ID NO: 13 (Chothia) | LCDR1 | SQDISNY |
| SEQ ID NO: 14 (Chothia) | LCDR2 | YTS |
| SEQ ID NO: 15 (Chothia) | LCDR3 | YYNLPW |
| SEQ ID NO: 36 | VL | DIQMTQSPSSLSASVGDRVTITCSSSQDISNYLNW YQQKPGKAPKLLIYYTSTLHLGIPPRFSGSGYGTD FTLTINNIESEDAAYYFCQQYYNLPWTFGQGTKVE IK |
| SEQ ID NO: 37 | DNA VL | GACATCCAGATGACCCAGTCTCCATCCTCCCTGTC TGCATCTGTAGGAGACAGAGTCACCATCACTTGCA GTTCAAGTCAGGACATCAGCAATTATTTAAACTGG TATCAGCAGAAACCAGGGAAAGCTCCTAAGCTCCT GATCTATTACACATCAACCTTACACTTAGGGATCC CACCTCGATTCAGTGGCAGCGGGTATGGAACAGAT TTTACCCTCACAATTAATAACATAGAATCTGAGGA TGCTGCATATTACTTCTGTCAGCAGTATTATAACC TTCCGTGGACGTTCGGCCAAGGGACCAAGGTGGAA ATCAAA |
| SEQ ID NO: 38 | LC | DIQMTQSPSSLSASVGDRVTITCSSSQDISNYLNW YQQKPGKAPKLLIYYTSTLHLGIPPRFSGSGYGTD FTLTINNIESEDAAYYFCQQYYNLPWTFGQGTKVE IKRTVAAPSVFIFPPSDEQLKSGTASVVCLLNNFY PREAKVQWKVDNALQSGNSQESVTEQDSKDSTYSL SSTLTLSKADYEKHKVYACEVTHQGLSSPVTKSFN RGEC |
| SEQ ID NO: 39 | DNA LC | GACATCCAGATGACCCAGTCTCCATCCTCCCTGTC TGCATCTGTAGGAGACAGAGTCACCATCACTTGCA GTTCAAGTCAGGACATCAGCAATTATTTAAACTGG TATCAGCAGAAACCAGGGAAAGCTCCTAAGCTCCT GATCTATTACACATCAACCTTACACTTAGGGATCC |

TABLE 1-continued

Amino acid and nucleotide sequences for murine, chimeric and humanized antibody molecules. The antibody molecules include murine mAb BAP050, chimeric mAbs BAP050-chi, humanized mAbs BAP050-hum01 to BAP050-hum20, humanized mAbs BAP050-hum01-Ser to BAP050-hum15-Ser, BAP050-hum18-Ser to BAP050-hum20-Ser, and humanized mAbs BAP050-Clone-F to BAP050-Clone-J. The amino acid and nucleotide sequences of the heavy and light chain CDRs, the heavy and light chain variable regions, and the heavy and light chains are shown.

| | | |
|---|---|---|
| | | CACCTCGATTCAGTGGCAGCGGGTATGGAACAGAT TTTTACCCTCACAATTAATAACATAGAATCTGAGGA TGCTGCATATTACTTCTGTCAGCAGTATTATAACC TTCCGTGGACGTTCGGCCAAGGGACCAAGGTGGAA ATCAAACGTACGGTGGCTGCACCATCTGTCTTCAT CTTCCCGCCATCTGATGAGCAGTTGAAATCTGGAA CTGCCTCTGTTGTGTGCCTGCTGAATAACTTCTAT CCCAGAGAGGCCAAAGTACAGTGGAAGGTGGATAA CGCCCTCCAATCGGGTAACTCCCAGGAGAGTCA CAGAGCAGGACAGCAAGGACAGCACCTACAGCCTC AGCAGCACCCTGACGCTGAGCAAAGCAGACTACGA GAAACAAAGTCTACGCCTGCGAAGTCACCCATC AGGGCCTGAGCTCGCCCGTCACAAAGAGCTTCAAC AGGGGAGAGTGT |
| | | BAP050-hum03-Ser HC |
| SEQ ID NO: 1 (Kabat) | HCDR1 | NYGMN |
| SEQ ID NO: 2 (Kabat) | HCDR2 | WINTDTGEPTYADDFKG |
| SEQ ID NO: 3 (Kabat) | HCDR3 | NPPYYYGTNNAEAMDY |
| SEQ ID NO: 4 (Chothia) | HCDR1 | GFTLTNY |
| SEQ ID NO: 5 (Chothia) | HCDR2 | NTDTGE |
| SEQ ID NO: 3 (Chothia) | HCDR3 | NPPYYYGTNNAEAMDY |
| SEQ ID NO: 100 | VH | EVQLVQSGAEVKKPGATVKISCKVSGFTLTNYGMN WVRQAPGQGLEWMGWINTDTGEPTYADDFKGRFVF SLDTSVSTAYLQISSLKAEDTAVYYCARNPPYYYG TNNAEAMDYWGQGTTVTVSS |
| SEQ ID NO: 101 | DNA VH | GAGGTCCAGCTGGTACAGTCTGGGGCTGAGGTGAA GAAGCCTGGGGCTACAGTGAAAATCTCCTGCAAGG TTTCTGGATTTACCCTCACAAACTATGGAATGAAC TGGGTGCGACAGGCCCCTGGACAAGGGCTTGAGTG GATGGGTTGGATAAACACCGACACTGGAGAGCCAA CATATGCTGATGACTTCAAGGGAAGATTTGTCTTC TCCTTGGACACCTCTGTCAGCACGGCATATCTGCA GATCAGCAGCCTAAAGGCTGAGGACACTGCCGTGT ATTACTGTGCAAGAAACCCTCCCTATTACTACGGT ACTAATAACGCGGAGGCTATGGACTACTGGGGCCA GGGCACCACCGTGACCGTGTCCTCC |
| SEQ ID NO: 102 | HC | EVQLVQSGAEVKKPGATVKISCKVSGFTLTNYGMN WVRQAPGQGLEWMGWINTDTGEPTYADDFKGRFVF SLDTSVSTAYLQISSLKAEDTAVYYCARNPPYYYG TNNAEAMDYWGQGTTVTVSSASTKGPSVFPLAPCS RSTSESTAALGCLVKDYFPEPVTVSWNSGALTSGV HTFPAVLQSSGLYSLSSVVTVPSSSLGTKTYTCNV DHKPSNTKVDKRVESKYGPPCPPCPAPEFLGGPSV FLFPPKPKDTLMISRTPEVTCVVVDVSQEDPEVQF NWYVDGVEVHNAKTKPREEQFNSTYRVVSVLTVLH QDWLNGKEYKCKVSNKGLPSSIEKTISKAKGQPRE PQVYTLPPSQEEMTKNQVSLTCLVKGFYPSDIAVE WESNGQPENNYKTTPPVLDSDGSFFLYSRLTVDKS RWQEGNVFSCSVMHEALHNHYTQKSLSLSLGK |
| SEQ ID NO: 103 | DNA HC | GAGGTCCAGCTGGTACAGTCTGGGGCTGAGGTGAA GAAGCCTGGGGCTACAGTGAAAATCTCCTGCAAGG TTTCTGGATTTACCCTCACAAACTATGGAATGAAC TGGGTGCGACAGGCCCCTGGACAAGGGCTTGAGTG GATGGGTTGGATAAACACCGACACTGGAGAGCCAA CATATGCTGATGACTTCAAGGGAAGATTTGTCTTC TCCTTGGACACCTCTGTCAGCACGGCATATCTGCA GATCAGCAGCCTAAAGGCTGAGGACACTGCCGTGT ATTACTGTGCAAGAAACCCTCCCTATTACTACGGT ACTAATAACGCGGAGGCTATGGACTACTGGGGCCA GGGCACCACCGTGACCGTGTCCTCCGCTTCCACCA AGGGCCCATCCGTCTTCCCCCTGGCGCCCTGCTCC AGGAGCACCTCCGAGAGCACAGCCGCCCTGGGCTG CCTGGTCAAGGACTACTTCCCCGAACCGGTGACGG TGTCGTGGAACTCAGGCGCCCTGACCAGCGGCGTG CACACCTTCCCGGCTGTCCTACAGTCCTCAGGACT CTACTCCCTCAGCAGCGTGGTGACCGTGCCCTCCA GCAGCTTGGGCACGAAGACCTACACCTGCAACGTA GATCACAAGCCCAGCAACACCAAGGTGGACAAGAG AGTTGAGTCCAAATATGGTCCCCCATGCCCACCGT GCCCAGCACCTGAGTTCCTGGGGGGACCATCAGTC TTCCTGTTCCCCCCAAAACCCAAGGACACTCTCAT GATCTCCCGGACCCCTGAGGTCACGTGCGTGGTGG TGGACGTGAGCCAGGAAGACCCCGAGGTCCAGTTC AACTGGTACGTGGATGGCGTGGAGGTGCATAATGC CAAGACAAAGCCGCGGGAGGAGCAGTTCAACAGCA CGTACCGTGTGGTCAGCGTCCTCACCGTCCTGCAC CAGGACTGGCTGAACGGCAAGGAGTACAAGTGCAA GGTCTCCAACAAAGGCCTCCCGTCCTCCATCGAGA AAACCATCTCCAAAGCCAAAGGGCAGCCCCGAGAG CCACAGGTGTACACCCTGCCCCCATCCCAGGAGGA GATGACCAAGAACCAGGTCAGCCTGACCTGCCTGG TCAAAGGCTTCTACCCCAGCGACATCGCCGTGGAG TGGGAGAGCAATGGGCAGCCGGAGAACAACTACAA GACCACGCCTCCCGTGCTGGACTCCGACGGCTCCT TCTTCCTCTACAGCAGGCTAACCGTGGACAAGAGC AGGTGGCAGGAGGGGAATGTCTTCTCATGCTCCGT GATGCATGAGGCTCTGCACAACCACTACACAGAA AGAGCCTCTCCCTGTCTCTGGGTAAA |
| | | BAP050-hum03-Ser LC |
| SEQ ID NO: 10 (Kabat) | LCDR1 | SSSQDISNYLN |
| SEQ ID NO: 11 (Kabat) | LCDR2 | YTSTLHL |
| SEQ ID NO: 12 (Kabat) | LCDR3 | QQYYNLPWT |
| SEQ ID NO: 13 (Chothia) | LCDR1 | SQDISNY |
| SEQ ID NO: 14 (Chothia) | LCDR2 | YTS |

TABLE 1-continued

Amino acid and nucleotide sequences for murine, chimeric and humanized antibody molecules. The antibody molecules include murine mAb BAP050, chimeric mAbs BAP050-chi, humanized mAbs BAP050-hum01 to BAP050-hum20, humanized mAbs BAP050-hum01-Ser to BAP050-hum15-Ser, BAP050-hum18-Ser to BAP050-hum20-Ser, and humanized mAbs BAP050-Clone-F to BAP050-Clone-J. The amino acid and nucleotide sequences of the heavy and light chain CDRs, the heavy and light chain variable regions, and the heavy and light chains are shown.

| SEQ ID NO: 15 (Chothia) | | LCDR3 YYNLPW |
|---|---|---|

| SEQ ID NO: 40 | VL | EIVLTQSPATLPVTLGQPASISCSSSQDISNYLNW YQQKPGQAPRLLIYYTSTLHLGVPSRFSGSGSGTD FTFTISSLEAEDAATYYCQQYYNLPWTFGQGTKVE IK |
|---|---|---|

| SEQ ID NO: 41 | DNA VL | GAAATTGTGTTGACACAGTCTCCAGCCACCCTGCC CGTCACCCTTGGACAGCCGGCCTCCATCTCCTGCA GTTCAAGTCAGGACATCAGCAATTATTTAAACTGG TACCAGCAGAAACCTGGCCAGGCTCCCAGGCTCCT CATCTATTACACATCAACCTTACACTTAGGGGTCC CCTCGAGGTTCAGTGGCAGTGGATCTGGGACAGAT TTCACCTTTACCATCAGTAGCCTGGAAGCTGAAGA TGCTGCAACATATTACTGTCAGCAGTATTATAACC TTCCGTGGACGTTCGGCCAAGGGACCAAGGTGGAA ATCAAA |
|---|---|---|

| SEQ ID NO: 42 | LC | EIVLTQSPATLPVTLGQPASISCSSSQDISNYLNW YQQKPGQAPRLLIYYTSTLHLGVPSRFSGSGSGTD FTFTISSLEAEDAATYYCQQYYNLPWTFGQGTKVE IKRTVAAPSVFIFPPSDEQLKSGTASVVCLLNNFY PREAKVQWKVDNALQSGNSQESVTEQDSKDSTYSL SSTLTLSKADYEKHKVYACEVTHQGLSSPVTKSFN RGEC |
|---|---|---|

| SEQ ID NO: 43 | DNA LC | GAAATTGTGTTGACACAGTCTCCAGCCACCCTGCC CGTCACCCTTGGACAGCCGGCCTCCATCTCCTGCA GTTCAAGTCAGGACATCAGCAATTATTTAAACTGG TACCAGCAGAAACCTGGCCAGGCTCCCAGGCTCCT CATCTATTACACATCAACCTTACACTTAGGGGTCC CCTCGAGGTTCAGTGGCAGTGGATCTGGGACAGAT TTCACCTTTACCATCAGTAGCCTGGAAGCTGAAGA TGCTGCAACATATTACTGTCAGCAGTATTATAACC TTCCGTGGACGTTCGGCCAAGGGACCAAGGTGGAA ATCAAACGTACGGTGGCTGCCACCATCTGTCTTCAT CTTCCCGCCATCTGATGAGCAGTTGAAATCTGGAA CTGCCTCTGTTGTGTGCCTGCTGAATAACTTCTAT CCCAGAGAGGCCAAAGTACAGTGGAAGGTGGATAA CGCCCTCCAATCGGGTAACTCCCAGGAGAGTGTCA CAGAGCAGGACAGCAAGGACAGCACCTACAGCCTC AGCAGCACCCTGACGCTGAGCAAAGCAGACTACGA GAAACACAAAGTCTACGCCTGCGAAGTCACCCATC AGGGCCTGAGCTCGCCCGTCACAAAGAGCTTCAAC AGGGGAGAGTGT |
|---|---|---|

BAP050-hum04-Ser HC

| SEQ ID NO: 1 (Kabat) | HCDR1 NYGMN |
|---|---|

| SEQ ID NO: 2 (Kabat) | HCDR2 WINTDTGEPTYADDFKG |
|---|---|

| SEQ ID NO: 3 (Kabat) | HCDR3 NPPYYYGTNNAEAMDY |
|---|---|

| SEQ ID NO: 4 (Chothia) | HCDR1 GFTLTNY |
|---|---|

| SEQ ID NO: 5 (Chothia) | HCDR2 NTDTGE |
|---|---|

| SEQ ID NO: 3 (Chothia) | HCDR3 NPPYYYGTNNAEAMDY |
|---|---|

| SEQ ID NO: 100 | VH | EVQLVQSGAEVKKPGATVKISCKVSGFTLTNYGMN WVRQAPGQGLEWMGWINTDTGEPTYADDFKGRFVF SLDTSVSTAYLQISSLKAEDTAVYYCARNPPYYYG TNNAEAMDYWGQGTTVTVSS |
|---|---|---|

| SEQ ID NO: 101 | DNA VH | GAGGTCCAGCTGGTACAGTCTGGGGCTGAGGTGAA GAAGCCTGGGGCTACAGTGAAAATCTCCTGCAAGG TTTCTGGATTTACCCTCACAAACTATGGAATGAAC TGGGTGCGACAGGCCCCTGGACAAGGGCTTGAGTG GATGGGTTGGATAAACACCGACACTGGAGAGCCAA CATATGCTGATGACTTCAAGGGAAGATTTGTCTTC TCCTTGGACACCTCTGTCAGCACGGCATATCTGCA GATCAGCAGCCTAAAGGCTGAGGACACTGCCGTGT ATTACTGTGCAAGAAACCCTCCTTATTACTACGGT ACTAATAACGCGGAGGCTATGGACTACTGGGGCCA GGGCACCACCGTGACCGTGTCCTCC |
|---|---|---|

| SEQ ID NO: 102 | HC | EVQLVQSGAEVKKPGATVKISCKVSGFTLTNYGMN WVRQAPGQGLEWMGWINTDTGEPTYADDFKGRFVF SLDTSVSTAYLQISSLKAEDTAVYYCARNPPYYYG TNNAEAMDYWGQGTTVTVSSASTKGPSVFPLAPCS RSTSESTAALGCLVKDYFPEPVTVSWNSGALTSGV HTFPAVLQSSGLYSLSSVVTVPSSSLGTKTYTCNV DHKPSNTKVDKRVESKYGPPCPPCPAPEFLGGPSV FLFPPKPKDTLMISRTPEVTCVVVDVSQEDPEVQF NWYVDGVEVHNAKTKPREEQFNSTYRVVSVLTVLH QDWLNGKEYKCKVSNKGLPSSIEKTISKAKGQPRE PQVYTLPPSQEEMTKNQVSLTCLVKGFYPSDIAVE WESNGQPENNYKTTPPVLDSDGSFFLYSRLTVDKS RWQEGNVFSCSVMHEALHNHYTQKSLSLSLGK |
|---|---|---|

| SEQ ID NO: 103 | DNA HC | GAGGTCCAGCTGGTACAGTCTGGGGCTGAGGTGAA GAAGCCTGGGGCTACAGTGAAAATCTCCTGCAAGG TTTCTGGATTTACCCTCACAAACTATGGAATGAAC TGGGTGCGACAGGCCCCTGGACAAGGGCTTGAGTG GATGGGTTGGATAAACACCGACACTGGAGAGCCAA CATATGCTGATGACTTCAAGGGAAGATTTGTCTTC TCCTTGGACACCTCTGTCAGCACGGCATATCTGCA GATCAGCAGCCTAAAGGCTGAGGACACTGCCGTGT ATTACTGTGCAAGAAACCCTCCTTATTACTACGGT ACTAATAACGCGGAGGCTATGGACTACTGGGGCCA GGGCACCACCGTGACCGTGTCCTCCGCTTCCACCA AGGGCCCATCCGTCTTCCCCCTGGCGCCCTGCTCC AGGAGCACCTCCGAGAGCACAGCCGCCCTGGGCTG CCTGGTCAAGGACTACTTCCCCGAACCGGTGACGG TGTCGTGGAACTCAGGCGCCCTGACCAGCGGCGTG CACACCTTCCCGGCTGTCCTACAGTCCTCAGGACT CTACTCCCTCAGCAGCGTGGTGACCGTGCCCTCCA GCAGCTTGGGCACGAAGACCTACACCTGCAACGTA GATCACAAGCCCAGCAACACCAAGGTGGACAAGAG AGTTGAGTCCAAATATGGTCCCCCATGCCCACCGT GCCCAGCACCTGAGTTCCTGGGGGGACCATCAGTC TTCCTGTTCCCCCCAAAACCCAAGGACACTCTCAT GATCTCCCGGACCCCTGAGGTCACGTGCGTGGTGG TGGACGTGAGCCAGGAAGACCCCGAGGTCCAGTTC AACTGGTACGTGGATGGCGTGGAGGTGCATAATGC CAAGACAAAGCCGCGGGAGGAGCAGTTCAACAGCA CGTACCGTGTGGTCAGCGTCCTCACCGTCCTGCAC CAGGACTGGCTGAACGGCAAGGAGTACAAGTGCAA

TABLE 1-continued

Amino acid and nucleotide sequences for murine, chimeric and humanized antibody molecules. The antibody molecules include murine mAb BAP050, chimeric mAbs BAP050-chi, humanized mAbs BAP050-hum01 to BAP050-hum20, humanized mAbs BAP050-hum01-Ser to BAP050-hum15-Ser, BAP050-hum18-Ser to BAP050-hum20-Ser, and humanized mAbs BAP050-Clone-F to BAP050-Clone-J. The amino acid and nucleotide sequences of the heavy and light chain CDRs, the heavy and light chain variable regions, and the heavy and light chains are shown.

```
GGTGTCCAACAAAGGCCTCCCGTCCTCCATCGAGA
AAACCATCTCCAAAGCCAAAGGGCAGCCCCGAGAG
CCACAGGTGTACACCCTGCCCCCATCCCAGGAGGA
GATGACCAAGAACCAGGTCAGCCTGACCTGCCTGG
TCAAAGGCTTCTACCCCAGCGACATCGCCGTGGAG
TGGGAGAGCAATGGGCAGCCGGAGAACAACTACAA
GACCACGCCTCCCGTGCTGGACTCCGACGGCTCCT
TCTTCCTCTACAGCAGGCTAACCGTGGACAAGAGC
AGGTGGCAGGAGGGGAATGTCTTCTCATGCTCCGT
GATGCATGAGGCTCTGCACAACCACTACACACAGA
AGAGCCTCTCCCTGTCTCTGGGTAAA
```

BAP050-hum04-Ser LC

| SEQ ID NO: 10 (Kabat) | LCDR1 | SSSQDISNYLN |
|---|---|---|
| SEQ ID NO: 11 (Kabat) | LCDR2 | YTSTLHL |
| SEQ ID NO: 12 (Kabat) | LCDR3 | QQYYNLPWT |
| SEQ ID NO: 13 (Chothia) | LCDR1 | SQDISNY |
| SEQ ID NO: 14 (Chothia) | LCDR2 | YTS |
| SEQ ID NO: 15 (Chothia) | LCDR3 | YYNLPW |
| SEQ ID NO: 44 | VL | DIQMTQSPSSLSASVGDRVTITCSSSQDISNYLNW YLQKPGQSPQLLIYYTSTLHLGIPDRFSGSGSGTD FTLTISRLEPEDFAVYYCQQYYNLPWTFGQGTKVE IK |
| SEQ ID NO: 45 | DNA VL | GACATCCAGATGACCCAGTCTCCATCCTCCCTGTC TGCATCTGTAGGAGACAGAGTCACCATCACTTGCA GTTCAAGTCAGGACATCAGCAATTATTTAAACTGG TACCTGCAGAAGCCAGGGCAGTCTCCACAGCTCCT GATCTATTACACATCAACCTTACACTTAGGGATCC CAGACAGGTTCAGTGGCAGTGGGTCTGGGACAGAC TTCACTCTCACCATCAGCAGACTGGAGCCTGAAGA TTTTGCAGTGTATTACTGTCAGCAGTATTATAACC TTCCGTGGACGTTCGGCCAAGGGACCAAGGTGGAA ATCAAA |
| SEQ ID NO: 46 | LC | DIQMTQSPSSLSASVGDRVTITCSSSQDISNYLNW YLQKPGQSPQLLIYYTSTLHLGIPDRFSGSGSGTD FTLTISRLEPEDFAVYYCQQYYNLPWTFGQGTKVE IKRTVAAPSVFIFPPSDEQLKSGTASVVCLLNNFY PREAKVQWKVDNALQSGNSQESVTEQDSKDSTYSL SSTLTLSKADYEKHKVYACEVTHQGLSSPVTKSFN RGEC |
| SEQ ID NO: 47 | DNA LC | GACATCCAGATGACCCAGTCTCCATCCTCCCTGTC TGCATCTGTAGGAGACAGAGTCACCATCACTTGCA GTTCAAGTCAGGACATCAGCAATTATTTAAACTGG TACCTGCAGAAGCCAGGGCAGTCTCCACAGCTCCT GATCTATTACACATCAACCTTACACTTAGGGATCC |

```
CAGACAGGTTCAGTGGCAGTGGGTCTGGGACAGAC
TTCACTCTCACCATCAGCAGACTGGAGCCTGAAGA
TTTTGCAGTGTATTACTGTCAGCAGTATTATAACC
TTCCGTGGACGTTCGGCCAAGGGACCAAGGTGGAA
ATCAAACGTACGGTGGCTGCACCATCTGTCTTCAT
CTTCCCGCCATCTGATGAGCAGTTGAAATCTGGAA
CTGCCTCTGTTGTGTGCCTGCTGAATAACTTCTAT
CCCAGAGAGGCCAAAGTACAGTGGAAGGTGGATAA
CGCCCTCCAATCGGGTAACTCCCAGGAGAGTGTCA
CAGAGCAGGACAGCAAGGACAGCACCTACAGCCTC
AGCAGCACCCTGACGCTGAGCAAAGCAGACTACGA
GAAACACAAAGTCTACGCCTGCGAAGTCACCCATC
AGGGCCTGAGCTCGCCCGTCACAAAGAGCTTCAAC
AGGGGAGAGTGT
```

BAP050-hum05-Ser HC

| SEQ ID NO: 1 (Kabat) | HCDR1 | NYGMN |
|---|---|---|
| SEQ ID NO: 2 (Kabat) | HCDR2 | WINTDTGEPTYADDFKG |
| SEQ ID NO: 3 (Kabat) | HCDR3 | NPPYYYGTNNAEAMDY |
| SEQ ID NO: 4 (Chothia) | HCDR1 | GFTLTNY |
| SEQ ID NO: 5 (Chothia) | HCDR2 | NTDTGE |
| SEQ ID NO: 3 (Chothia) | HCDR3 | NPPYYYGTNNAEAMDY |
| SEQ ID NO: 100 | VH | EVQLVQSGAEVKKPGATVKISCKVSGFTLTNYGMN WVRQAPGQGLEWMGWINTDTGEPTYADDFKGRFVF SLDTSVSTAYLQISSLKAEDTAVYYCARNPPYYYG TNNAEAMDYWGQGTTVTVSS |
| SEQ ID NO: 101 | DNA VH | GAGGTCCAGCTGGTACAGTCTGGGGCTGAGGTGAA GAAGCCTGGGGCTACAGTGAAAATCTCCTGCAAGG TTTCTGGATTTACCCTCACAAACTATGGAATGAAC TGGGTGCGACAGGCCCCTGGACAAGGGCTTGAGTG GATGGGTTGGATAAACACCGACACTGGAGAGCCAA CATATGCTGATGACTTCAAGGGAAGATTTGTCTTC TCCTTGGACACCTCTGTCAGCACGGCATATCTGCA GATCAGCAGCCTAAAGGCTGAGGACACTGCCGTGT ATTACTGTGCAAGAAACCCTCCCTATTACTACGGT ACTAATAACGCGGAGGCTATGGACTACTGGGGCCA GGGCACCACCGTGACCGTGTCCTCC |
| SEQ ID NO: 102 | HC | EVQLVQSGAEVKKPGATVKISCKVSGFTLTNYGMN WVRQAPGQGLEWMGWINTDTGEPTYADDFKGRFVF SLDTSVSTAYLQISSLKAEDTAVYYCARNPPYYYG TNNAEAMDYWGQGTTVTVSSASTKGPSVFPLAPCS RSTSESTAALGCLVKDYFPEPVTVSWNSGALTSGV HTFPAVLQSSGLYSLSSVVTVPSSSLGTKTYTCNV DHKPSNTKVDKRVESKYGPPCPPCPAPEFLGGPSV FLFPPKPKDTLMISRTPEVTCVVVDVSQEDPEVQF NWYVDGVEVHNAKTKPREEQFNSTYRVVSVLTVLH |

TABLE 1-continued

Amino acid and nucleotide sequences for murine, chimeric and humanized antibody molecules. The antibody molecules include murine mAb BAP050, chimeric mAbs BAP050-chi, humanized mAbs BAP050-hum01 to BAP050-hum20, humanized mAbs BAP050-hum01-Ser to BAP050-hum15-Ser, BAP050-hum18-Ser to BAP050-hum20-Ser, and humanized mAbs BAP050-Clone-F to BAP050-Clone-J. The amino acid and nucleotide sequences of the heavy and light chain CDRs, the heavy and light chain variable regions, and the heavy and light chains are shown.

| | | |
|---|---|---|
| | | QDWLNGKEYKCKVSNKGLPSSIEKTISKAKGQPRE PQVYTLPPSQEEMTKNQVSLTCLVKGFYPSDIAVE WESNGQPENNYKTTPPVLDSDGSFFLYSRLTVDKS RWQEGNVFSCSVMHEALHNHYTQKSLSLSLGK |
| SEQ ID NO: 103 | DNA HC | GAGGTCCAGCTGGTACAGTCTGGGGCTGAGGTGAA GAAGCCTGGGGCTACAGTGAAAATCTCCTGCAAGG TTTCTGGATTTACCCTCACAAACTATGGAATGAAC TGGGTGCGACAGGCCCCTGGACAAGGGCTTGAGTG GATGGGTTGGATAAACACCGACACTGGAGAGCCAA CATATGCTGATGACTTCAAGGGAAGATTTGTCTTC TCCTTGGACACCTCTGTCAGCACGGCATATCTGCA GATCAGCAGCCTAAAGGCTGAGGACACTGCCGTGT ATTACTGTGCAAGAAACCCTCCCTATTACTACGGT ACTAATAACGCGGAGGCTATGGACTACTGGGGCCA GGGCACCACCGTGACCGTGTCCTCCGCTTCCACCA AGGGCCCATCCGTCTTCCCCCTGGCGCCCTGCTCC AGGAGCACCTCCGAGAGCACAGCCGCCCTGGGCTG CCTGGTCAAGGACTACTTCCCCGAACCGGTGACGG TGTCGTGGAACTCAGGCGCCCTGACCAGCGGCGTG CACACCTTCCCGGCTGTCCTACAGTCCTCAGGACT CTACTCCCTCAGCAGCGTGGTGACCGTGCCCTCCA GCAGCTTGGGCACGAAGACCTACACCTGCAACGTA GATCACAAGCCCAGCAACACCAAGGTGGACAAGAG AGTTGAGTCCAAATATGGTCCCCCATGCCCACCGT GCCCAGCACCTGAGTTCCTGGGGGGACCATCAGTC TTCCTGTTCCCCCCAAAACCCAAGGACACTCTCAT GATCTCCCGGACCCCTGAGGTCACGTGCGTGGTGG TGGACGTGAGCCAGGAAGACCCCGAGGTCCAGTTC AACTGGTACGTGGATGGCGTGGAGGTGCATAATGC CAAGACAAAGCCGCGGGAGGAGCAGTTCAACAGCA CGTACCGTGTGGTCAGCGTCCTCACCGTCCTGCAC CAGGACTGGCTGAACGGCAAGGAGTACAAGTGCAA GGTGTCCAACAAAGGCCTCCCGTCCTCCATCGAGA AAACCATCTCCAAAGCCAAAGGGCAGCCCCGAGAG CCACAGGTGTACACCCTGCCCCCATCCCAGGAGGA GATGACCAAGAACCAGGTCAGCCTGACCTGCCTGG TCAAAGGCTTCTACCCCAGCGACATCGCCGTGGAG TGGGAGAGCAATGGGCAGCCGGAGAACAACTACAA GACCACGCCTCCCGTGCTGGACTCCGACGGCTCCT TCTTCCTCTACAGCAGGCTAACCGTGGACAAGAGC AGGTGGCAGGAGGGGAATGTCTTCTCATGCTCCGT GATGCATGAGGCTCTGCACAACCACTACACACAGA AGAGCCTCTCCCTGTCTCTGGGTAAA |

BAP050-hum05-Ser LC

| | | |
|---|---|---|
| SEQ ID NO: 10 (Kabat) | LCDR1 | SSSQDISNYLN |
| SEQ ID NO: 11 (Kabat) | LCDR2 | YTSTLHL |
| SEQ ID NO: 12 (Kabat) | LCDR3 | QQYYNLPWT |
| SEQ ID NO: 13 (Chothia) | LCDR1 | SQDISNY |
| SEQ ID NO: 14 (Chothia) | LCDR2 | YTS |
| SEQ ID NO: 15 (Chothia) | LCDR3 | YYNLPW |
| SEQ ID NO: 48 | VL | EIVLTQSPATLSLSPGERATLSCSSSQDISNYLNW YQQKPGKAPKLLIYYTSTLHLGVPSRFSGSGSGTD FTFTISSLEAEDAATYYCQQYYNLPWTFGQGTKVE IK |
| SEQ ID NO: 49 | DNA VL | GAAATTGTGTTGACACAGTCTCCAGCCACCCTGTC TTTGTCTCCAGGGGAAAGAGCCACCCTCTCCTGCA GTTCAAGTCAGGACATCAGCAATTATTTAAACTGG TATCAGCAGAAACCAGGGAAAGCTCCTAAGCTCCT GATCTATTACACATCAACCTTACACTTAGGGGTCC CCTCGAGGTTCAGTGGCAGTGGATCTGGGACAGAT TTCACCTTTACCATCAGTAGCCTGGAAGCTGAAGA TGCTGCAACATATTACTGTCAGCAGTATTATAACC TTCCGTGGACGTTCGGCCAAGGGACCAAGGTGGAA ATCAAA |
| SEQ ID NO: 50 | LC | EIVLTQSPATLSLSPGERATLSCSSSQDISNYLNW YQQKPGKAPKLLIYYTSTLHLGVPSRFSGSGSGTD FTFTISSLEAEDAATYYCQQYYNLPWTFGQGTKVE IKRTVAAPSVFIFPPSDEQLKSGTASVVCLLNNFY PREAKVQWKVDNALQSGNSQESVTEQDSKDSTYSL SSTLTLSKADYEKHKVYACEVTHQGLSSPVTKSFN RGEC |
| SEQ ID NO: 51 | DNA LC | GAAATTGTGTTGACACAGTCTCCAGCCACCCTGTC TTTGTCTCCAGGGGAAAGAGCCACCCTCTCCTGCA GTTCAAGTCAGGACATCAGCAATTATTTAAACTGG TATCAGCAGAAACCAGGGAAAGCTCCTAAGCTCCT GATCTATTACACATCAACCTTACACTTAGGGGTCC CCTCGAGGTTCAGTGGCAGTGGATCTGGGACAGAT TTCACCTTTACCATCAGTAGCCTGGAAGCTGAAGA TGCTGCAACATATTACTGTCAGCAGTATTATAACC TTCCGTGGACGTTCGGCCAAGGGACCAAGGTGGAA ATCAAACGTACGGTGGCTGCACCATCTGTCTTCAT CTTCCCGCCATCTGATGAGCAGTTGAAATCTGGAA CTGCCTCTGTTGTGTGCCTGCTGAATAACTTCTAT CCCAGAGAGGCCAAAGTACAGTGGAAGGTGGATAA CGCCCTCCAATCGGGTAACTCCCAGGAGAGTGTCA CAGAGCAGGACAGCAAGGACAGCACCTACAGCCTC AGCAGCACCCTGACGCTGAGCAAAGCAGACTACGA GAAACACAAAGTCTACGCCTGCGAAGTCACCCATC AGGGCCTGAGCTCGCCCGTCACAAAGAGCTTCAAC AGGGGAGAGTGT |

BAP050-hum06-Ser HC

| | | |
|---|---|---|
| SEQ ID NO: 1 (Kabat) | HCDR1 | NYGMN |
| SEQ ID NO: 2 (Kabat) | HCDR2 | WINTDTGEPTYADDFKG |
| SEQ ID NO: 3 (Kabat) | HCDR3 | NPPYYYGTNNAEAMDY |
| SEQ ID NO: 4 (Chothia) | HCDR1 | GFTLTNY |

TABLE 1-continued

Amino acid and nucleotide sequences for murine, chimeric and humanized antibody molecules. The antibody molecules include murine mAb BAP050, chimeric mAbs BAP050-chi, humanized mAbs BAP050-hum01 to BAP050-hum20, humanized mAbs BAP050-hum01-Ser to BAP050-hum15-Ser, BAP050-hum18-Ser to BAP050-hum20-Ser, and humanized mAbs BAP050-Clone-F to BAP050-Clone-J. The amino acid and nucleotide sequences of the heavy and light chain CDRs, the heavy and light chain variable regions, and the heavy and light chains are shown.

| | | |
|---|---|---|
| SEQ ID NO: 5 (Chothia) | | HCDR2 NTDTGE |
| SEQ ID NO: 3 (Chothia) | | HCDR3 NPPYYYGTNNAEAMDY |
| SEQ ID NO: 100 | VH | EVQLVQSGAEVKKPGATVKISCKVSGFTLTNYGMN WVRQAPGQGLEWMGWINTDTGEPTYADDFKGRFVF SLDTSVSTAYLQISSLKAEDTAVYYCARNPPYYYG TNNAEAMDYWGQGTTVTVSS |
| SEQ ID NO: 101 | DNA VH | GAGGTCCAGCTGGTACAGTCTGGGGCTGAGGTGAA GAAGCCTGGGGCTACAGTGAAAATCTCCTGCAAGG TTTCTGGATTTACCCTCACAAACTATGGAATGAAC TGGGTGCGACAGGCCCCTGGACAAGGGCTTGAGTG GATGGGTTGGATAAACACCGACACTGGAGAGCCAA CATATGCTGATGACTTCAAGGGAAGATTTGTCTTC TCCTTGGACACCTCTGTCAGCACGGCATATCTGCA GATCAGCAGCCTAAAGGCTGAGGACACTGCCGTGT ATTACTGTGCAAGAAACCCTCCCTATTACTACGGT ACTAATAACGCGGAGGCTATGGACTACTGGGGCCA GGGCACCACCGTGACCGTGTCCTCC |
| SEQ ID NO: 102 | HC | EVQLVQSGAEVKKPGATVKISCKVSGFTLTNYGMN WVRQAPGQGLEWMGWINTDTGEPTYADDFKGRFVF SLDTSVSTAYLQISSLKAEDTAVYYCARNPPYYYG TNNAEAMDYWGQGTTVTVSSASTKGPSVFPLAPCS RSTSESTAALGCLVKDYFPEPVTVSWNSGALTSGV HTFPAVLQSSGLYSLSSVVTVPSSSLGTKTYTCNV DHKPSNTKVDKRVESKYGPPCPPCPAPEFLGGPSV FLFPPKPKDTLMISRTPEVTCVVVDVSQEDPEVQF NWYVDGVEVHNAKTKPREEQFNSTYRVVSVLTVLH QDWLNGKEYKCKVSNKGLPSSIEKTISKAKGQPRE PQVYTLPPSQEEMTKNQVSLTCLVKGFYPSDIAVE WESNGQPENNYKTTPPVLDSDGSFFLYSRLTVDKS RWQEGNVFSCSVMHEALHNHYTQKSLSLSLGK |
| SEQ ID NO: 103 | DNA HC | GAGGTCCAGCTGGTACAGTCTGGGGCTGAGGTGAA GAAGCCTGGGGCTACAGTGAAAATCTCCTGCAAGG TTTCTGGATTTACCCTCACAAACTATGGAATGAAC TGGGTGCGACAGGCCCCTGGACAAGGGCTTGAGTG GATGGGTTGGATAAACACCGACACTGGAGAGCCAA CATATGCTGATGACTTCAAGGGAAGATTTGTCTTC TCCTTGGACACCTCTGTCAGCACGGCATATCTGCA GATCAGCAGCCTAAAGGCTGAGGACACTGCCGTGT ATTACTGTGCAAGAAACCCTCCCTATTACTACGGT ACTAATAACGCGGAGGCTATGGACTACTGGGGCCA GGGCACCACCGTGACCGTGTCCTCCACCA AGGGCCCATCCGTCTTCCCCCTGGCGCCCTGCTCC AGGAGCACCTCCGAGAGCACAGCCGCCCTGGGCTG CCTGGTCAAGGACTACTTCCCCGAACCGGTGACGG TGTCGTGGAACTCAGGCGCCCTGACCAGCGGCGTG CACACCTTCCCGGCTGTCCTACAGTCCTCAGGACT CTACTCCCTCAGCAGCGTGGTGACCGTGCCCTCCA GCAGCTTGGGCACGAAGACCTACACCTGCAACGTA GATCACAAGCCCAGCAACACCAAGGTGGACAAGAG AGTTGAGTCCAAATATGGTCCCCCATGCCCACCGT GCCCAGCACCTGAGTTCCTGGGGGGACCATCAGTC TTCCTGTTCCCCCCAAAACCCAAGGACACTCTCAT GATCTCCCGGACCCCTGAGGTCACGTGCGTGGTGG TGGACGTGAGCCAGGAAGACCCCGAGGTCCAGTTC AACTGGTACGTGGATGGCGTGGAGGTGCATAATGC CAAGACAAAGCCGCGGGAGGAGCAGTTCAACAGCA CGTACCGTGTGGTCAGCGTCCTCACCGTCCTGCAC CAGGACTGGCTGAACGGCAAGGAGTACAAGTGCAA |
| | | GGTGTCCAACAAAGGCCTCCCGTCCTCCATCGAGA AAACCATCTCCAAAGCCAAAGGGCAGCCCCGAGAG CCACAGGTGTACACCCTGCCCCCATCCCAGGAGGA GATGACCAAGAACCAGGTCAGCCTGACCTGCCTGG TCAAAGGCTTCTACCCCAGCGACATCGCCGTGGAG TGGGAGAGCAATGGGCAGCCGGAGAACAACTACAA GACCACGCCTCCCGTGCTGGACTCCGACGGCTCCT TCTTCCTCTACAGCAGGCTAACCGTGGACAAGAGC AGGTGGCAGGAGGGGAATGTCTTCTCATGCTCCGT GATGCATGAGGCTCTGCACAACCACTACACAGA AGAGCCTCTCCCTGTCTCTGGGTAAA |

BAP050-hum06-Ser LC

| | | |
|---|---|---|
| SEQ ID NO: 10 (Kabat) | | LCDR1 SSSQDISNYLN |
| SEQ ID NO: 11 (Kabat) | | LCDR2 YTSTLHL |
| SEQ ID NO: 12 (Kabat) | | LCDR3 QQYYNLPWT |
| SEQ ID NO: 13 (Chothia) | | LCDR1 SQDISNY |
| SEQ ID NO: 14 (Chothia) | | LCDR2 YTS |
| SEQ ID NO: 15 (Chothia) | | LCDR3 YYNLPW |
| SEQ ID NO: 52 | VL | DIVMTQTPLSLPVTPGEPASISCSSSQDISNYLNW YQQKPGQAPRLLIYYTSTLHLGVPSRFSGSGSGTE FTLTISSLQPDDFATYYCQQYYNLPWTFGQGTKVE IK |
| SEQ ID NO: 53 | DNA VL | GATATTGTGATGACCCAGACTCCACTCTCCCTGCC CGTCACCCCTGGAGAGCCGGCCTCCATCTCCTGCA GTTCAAGTCAGGACATCAGCAATTATTTAAACTGG TACCAGCAGAAACCTGGCCAGGCTCCCAGGCTCCT CATCTATTACACATCAACCTTACACTTAGGGGTCC CATCAAGGTTCAGCGGCAGTGGATCTGGGACAGAA TTCACTCTCACCATCAGCAGCCTGCAGCCTGATGA TTTTGCAACTTATTACTGTCAGCAGTATTATAACC TTCCGTGGACGTTCGGCCAAGGGACCAAGGTGGAA ATCAAA |
| SEQ ID NO: 54 | LC | DIVMTQTPLSLPVTPGEPASISCSSSQDISNYLNW YQQKPGQAPRLLIYYTSTLHLGVPSRFSGSGSGTE FTLTISSLQPDDFATYYCQQYYNLPWTFGQGTKVE IKRTVAAPSVFIFPPSDEQLKSGTASVVCLLNNFY PREAKVQWKVDNALQSGNSQESVTEQDSKDSTYSL SSTLTLSKADYEKHKVYACEVTHQGLSSPVTKSFN RGEC |
| SEQ ID NO: 55 | DNA LC | GATATTGTGATGACCCAGACTCCACTCTCCCTGCC CGTCACCCCTGGAGAGCCGGCCTCCATCTCCTGCA GTTCAAGTCAGGACATCAGCAATTATTTAAACTGG TACCAGCAGAAACCTGGCCAGGCTCCCAGGCTCCT CATCTATTACACATCAACCTTACACTTAGGGGTCC |

TABLE 1-continued

Amino acid and nucleotide sequences for murine, chimeric and humanized antibody molecules. The antibody molecules include murine mAb BAP050, chimeric mAbs BAP050-chi, humanized mAbs BAP050-hum01 to BAP050-hum20, humanized mAbs BAP050-hum01-Ser to BAP050-hum15-Ser, BAP050-hum18-Ser to BAP050-hum20-Ser, and humanized mAbs BAP050-Clone-F to BAP050-Clone-J. The amino acid and nucleotide sequences of the heavy and light chain CDRs, the heavy and light chain variable regions, and the heavy and light chains are shown.

|  |  |  |
|---|---|---|
|  |  | CATCAAGGTTCAGCGGCAGTGGATCTGGGACAGAA<br>TTCACTCTCACCATCAGCAGCCTGCAGCCTGATGA<br>TTTTGCAACTTATTACTGTCAGCAGTATTATAACC<br>TTCCGTGGACGTTCGGCCAAGGGACCAAGGTGGAA<br>ATCAAACGTACGGTGGCTGCACCATCTGTCTTCAT<br>CTTCCCGCCATCTGATGAGCAGTTGAAATCTGGAA<br>CTGCCTCTGTTGTGTGCCTGCTGAATAACTTCTAT<br>CCCAGAGAGGCCAAATACAGTGGAAGGTGGATAA<br>CGCCCTCCAATCGGGTAACTCCCAGGAGAGTCA<br>CAGAGCAGGACAGCAAGGACAGCACCTACAGCCTC<br>AGCAGCACCCTGACGCTGAGCAAAGCAGACTACGA<br>GAAACAAAGTCTACGCCTGCGAAGTCACCCATC<br>AGGGCCTGAGCTCGCCCGTCACAAAGAGCTTCAAC<br>AGGGGAGAGTGT |
|  |  | BAP050-hum07-Ser HC |
| SEQ ID NO: 1 (Kabat) | HCDR1 | NYGMN |
| SEQ ID NO: 2 (Kabat) | HCDR2 | WINTDTGEPTYADDFKG |
| SEQ ID NO: 3 (Kabat) | HCDR3 | NPPYYYGTNNAEAMDY |
| SEQ ID NO: 4 (Chothia) | HCDR1 | GFTLTNY |
| SEQ ID NO: 5 (Chothia) | HCDR2 | NTDTGE |
| SEQ ID NO: 3 (Chothia) | HCDR3 | NPPYYYGTNNAEAMDY |
| SEQ ID NO: 100 | VH | EVQLVQSGAEVKKPGATVKISCKVSGFTLTNYGMN<br>WVRQAPGQGLEWMGWINTDTGEPTYADDFKGRFVF<br>SLDTSVSTAYLQISSLKAEDTAVYYCARNPPYYYG<br>TNNAEAMDYWGQGTTVTVSS |
| SEQ ID NO: 101 | DNA VH | GAGGTCCAGCTGGTACAGTCTGGGGCTGAGGTGAA<br>GAAGCCTGGGGCTACAGTGAAAATCTCCTGCAAGG<br>TTTCTGGATTTACCCTCACAAACTATGGAATGAAC<br>TGGGTGCGACAGGCCCCTGGACAAGGGCTTGAGTG<br>GATGGGTTGGATAAACACCGACACTGGAGAGCCAA<br>CATATGCTGATGACTTCAAGGGAAGATTTGTCTTC<br>TCCTTGGACACCTCTGTCAGCACGGCATATCTGCA<br>GATCAGCAGCCTAAAGGCTGAGGACACTGCCGTGT<br>ATTACTGTGCAAGAAACCCTCCCTATTACTACGGT<br>ACTAATAACGCGGAGGCTATGGACTACTGGGGCCA<br>GGGCACCACCGTGACCGTGTCCTCC |
| SEQ ID NO: 102 | HC | EVQLVQSGAEVKKPGATVKISCKVSGFTLTNYGMN<br>WVRQAPGQGLEWMGWINTDTGEPTYADDFKGRFVF<br>SLDTSVSTAYLQISSLKAEDTAVYYCARNPPYYYG<br>TNNAEAMDYWGQGTTVTVSSASTKGPSVFPLAPCS<br>RSTSESTAALGCLVKDYFPEPVTVSWNSGALTSGV<br>HTFPAVLQSSGLYSLSSVVTVPSSSLGTKTYTCNV<br>DHKPSNTKVDKRVESKYGPPCPPCPAPEFLGGPSV<br>FLFPPKPKDTLMISRTPEVTCVVVDVSQEDPEVQF<br>NWYVDGVEVHNAKTKPREEQFNSTYRVVSVLTVLH |

TABLE 1-continued

Amino acid and nucleotide sequences for murine, chimeric and humanized antibody molecules. The antibody molecules include murine mAb BAP050, chimeric mAbs BAP050-chi, humanized mAbs BAP050-hum01 to BAP050-hum20, humanized mAbs BAP050-hum01-Ser to BAP050-hum15-Ser, BAP050-hum18-Ser to BAP050-hum20-Ser, and humanized mAbs BAP050-Clone-F to BAP050-Clone-J. The amino acid and nucleotide sequences of the heavy and light chain CDRs, the heavy and light chain variable regions, and the heavy and light chains are shown.

|  |  |  |
|---|---|---|
|  |  | QDWLNGKEYKCKVSNKGLPSSIEKTISKAKGQPRE<br>PQVYTLPPSQEEMTKNQVSLTCLVKGFYPSDIAVE<br>WESNGQPENNYKTTPPVLDSDGSFFLYSRLTVDKS<br>RWQEGNVFSCSVMHEALHNHYTQKSLSLSLGK |
| SEQ ID NO: 103 | DNA HC | GAGGTCCAGCTGGTACAGTCTGGGGCTGAGGTGAA<br>GAAGCCTGGGGCTACAGTGAAAATCTCCTGCAAGG<br>TTTCTGGATTTACCCTCACAAACTATGGAATGAAC<br>TGGGTGCGACAGGCCCCTGGACAAGGGCTTGAGTG<br>GATGGGTTGGATAAACACCGACACTGGAGAGCCAA<br>CATATGCTGATGACTTCAAGGGAAGATTTGTCTTC<br>TCCTTGGACACCTCTGTCAGCACGGCATATCTGCA<br>GATCAGCAGCCTAAAGGCTGAGGACACTGCCGTGT<br>ATTACTGTGCAAGAAACCCTCCCTATTACTACGGT<br>ACTAATAACGCGGAGGCTATGGACTACTGGGGCCA<br>GGGCACCACCGTGACCGTGTCCTCCGCTTCCACCA<br>AGGGCCCATCCGTCTTCCCCCTGGCGCCCTGCTCC<br>AGGAGCACCTCCGAGAGCACAGCCGCCCTGGGCTG<br>CCTGGTCAAGGACTACTTCCCCGAACCGGTGACGG<br>TGTCGTGGAACTCAGGCGCCCTGACCAGCGGCGTG<br>CACACCTTCCCGGCTGTCCTACAGTCCTCAGGACT<br>CTACTCCCTCAGCAGCGTGGTGACCGTGCCCTCCA<br>GCAGCTTGGGCACGAAGACCTACACCTGCAACGTA<br>GATCACAAGCCCAGCAACACCAAGGTGGACAAGAG<br>AGTTGAGTCCAAATATGGTCCCCCATGCCCACCGT<br>GCCCAGCACCTGAGTTCCTGGGGGGACCATCAGTC<br>TTCCTGTTCCCCCCAAAACCCAAGGACACTCTCAT<br>GATCTCCCGGACCCCTGAGGTCACGTGCGTGGTGG<br>TGGACGTGAGCCAGGAAGACCCCGAGGTCCAGTTC<br>AACTGGTACGTGGATGGCGTGGAGGTGCATAATGC<br>CAAGACAAAGCCGCGGGAGGAGCAGTTCAACAGCA<br>CGTACCGTGTGGTCAGCGTCCTCACCGTCCTGCAC<br>CAGGACTGGCTGAACGGCAAGGAGTACAAGTGCAA<br>GGTGTCCAACAAAGCCCTCCCGTCCTCCATCGAGA<br>AAACCATCTCCAAAGCCAAAGGGCAGCCCCGAGAG<br>CCACAGGTGTACACCCTGCCCCCATCCCAGGAGGA<br>GATGACCAAGAACCAGGTCAGCCTGACCTGCCTGG<br>TCAAAGGCTTCTACCCCAGCGACATCGCCGTGGAG<br>TGGGAGAGCAATGGGCAGCCGGAGAACAACTACAA<br>GACCACGCCTCCCGTGCTGGACTCCGACGGCTCCT<br>TCTTCCTCTACAGCAGGCTAACCGTGGACAAGAGC<br>AGGTGGCAGGAGGGGAATGTCTTCTCATGCTCCGT<br>GATGCATGAGGCTCTGCACAACCACTACACAGA<br>AGAGCCTCTCCCTGTCTCTGGGTAAA |
|  |  | BAP050-hum07-Ser LC |
| SEQ ID NO: 10 (Kabat) | LCDR1 | SSSQDISNYLN |
| SEQ ID NO: 11 (Kabat) | LCDR2 | YTSTLHL |
| SEQ ID NO: 12 (Kabat) | LCDR3 | QQYYNLPWT |
| SEQ ID NO: 13 (Chothia) | LCDR1 | SQDISNY |
| SEQ ID NO: 14 (Chothia) | LCDR2 | YTS |

TABLE 1-continued

Amino acid and nucleotide sequences for murine, chimeric and humanized antibody molecules. The antibody molecules include murine mAb BAP050, chimeric mAbs BAP050-chi, humanized mAbs BAP050-hum01 to BAP050-hum20, humanized mAbs BAP050-hum01-Ser to BAP050-hum15-Ser, BAP050-hum18-Ser to BAP050-hum20-Ser, and humanized mAbs BAP050-Clone-F to BAP050-Clone-J. The amino acid and nucleotide sequences of the heavy and light chain CDRs, the heavy and light chain variable regions, and the heavy and light chains are shown.

| | | |
|---|---|---|
| SEQ ID NO: 15 (Chothia) | LCDR3 | YYNLPW |
| SEQ ID NO: 56 | VL | DIQMTQSPSSLSASVGDRVTITCSSSQDISNYLNW YLQKPGQSPQLLIYYTSTLHLGVPSRFSGSGSGTE FTLTISSLQPDDFATYYCQQYYNLPWTFGQGTKVE IK |
| SEQ ID NO: 57 | DNA VL | GACATCCAGATGACCCAGTCTCCATCCTCCCTGTC TGCATCTGTAGGAGACAGAGTCACTATCACTTGCA GTTCAAGTCAGGACATCAGCAATTATTTAAACTGG TACCTGCAGAAGCCAGGGCAGTCTCCACAGCTCCT GATCTATTACACATCAACCTTACACTTAGGGGTCC CATCAAGGTTCAGCGGCAGTGGATCTGGGACAGAA TTCACTCTCACCATCAGCAGCCTGCAGCCTGATGA TTTTTGCAACTTATTACTGTCAGCAGTATTATAACC TTCCGTGGACGTTCGGCCAAGGGACCAAGGTGGAA ATCAAA |
| SEQ ID NO: 58 | LC | DIQMTQSPSSLSASVGDRVTITCSSSQDISNYLNW YLQKPGQSPQLLIYYTSTLHLGVPSRFSGSGSGTE FTLTISSLQPDDFATYYCQQYYNLPWTFGQGTKVE IKRTVAAPSVFIFPPSDEQLKSGTASVVCLLNNFY PREAKVQWKVDNALQSGNSQESVTEQDSKDSTYSL SSTLTLSKADYEKHKVYACEVTHQGLSSPVTKSFN RGEC |
| SEQ ID NO: 59 | DNA LC | GACATCCAGATGACCCAGTCTCCATCCTCCCTGTC TGCATCTGTAGGAGACAGAGTCACTATCACTTGCA GTTCAAGTCAGGACATCAGCAATTATTTAAACTGG TACCTGCAGAAGCCAGGGCAGTCTCCACAGCTCCT GATCTATTACACATCAACCTTACACTTAGGGGTCC CATCAAGGTTCAGCGGCAGTGGATCTGGGACAGAA TTCACTCTCACCATCAGCAGCCTGCAGCCTGATGA TTTTTGCAACTTATTACTGTCAGCAGTATTATAACC TTCCGTGGACGTTCGGCCAAGGGACCAAGGTGGAA ATCAAACGTACGGTGGCTGCACCATCTGTCTTCAT CTTCCCGCCATCTGATGAGCAGTTGAAATCTGGAA CTGCCTCTGTTGTGTGCCTGCTGAATAACTTCTAT CCCAGAGAGGCCAAAGTACAGTGGAAGGTGGATAA CGCCCTCCAATCGGGTAACTCCCAGGAGAGTGTCA CAGAGCAGGACAGCAAGGACAGCACCTACAGCCTC AGCAGCACCCTGACGCTGAGCAAAGCAGACTACGA GAAACACAAAGTCTACGCCTGCGAAGTCACCCATC AGGGCCTGAGCTCGCCCGTCACAAAGAGCTTCAAC AGGGGAGAGTGT |

BAP050-hum08-Ser HC

| | | |
|---|---|---|
| SEQ ID NO: 1 (Kabat) | HCDR1 | NYGMN |
| SEQ ID NO: 2 (Kabat) | HCDR2 | WINTDTGEPTYADDFKG |
| SEQ ID NO: 3 (Kabat) | HCDR3 | NPPYYYGTNNAEAMDY |
| SEQ ID NO: 4 (Chothia) eb;normal | HCDR1 | GFTLTNY |
| SEQ ID NO: | HCDR2 | NTDTGE |

| | | |
|---|---|---|
| NO: 5 (Chothia) | | |
| SEQ ID NO: 3 (Chothia) | HCDR3 | NPPYYYGTNNAEAMDY |
| SEQ ID NO: 100 | VH | EVQLVQSGAEVKKPGATVKISCKVSGFTLTNYGMN WVRQAPGQGLEWMGWINTDTGEPTYADDFKGRFVF SLDTSVSTAYLQISSLKAEDTAVYYCARNPPYYYG TNNAEAMDYWGQGTTVTVSS |
| SEQ ID NO: 101 | DNA VH | GAGGTCCAGCTGGTACAGTCTGGGGCTGAGGTGAA GAAGCCTGGGGCTACAGTGAAAATCTCCTGCAAGG TTTCTGGATTTACCCTCACAAACTATGGAATGAAC TGGGTGCGACAGGCCCCTGGACAAGGGCTTGAGTG GATGGGTTGGATAAACACCGACACTGGAGAGCCAA CATATGCTGATGACTTCAAGGGAAGATTTGTCTTC TCCTTGGACACCTCTGTCAGCACGGCATATCTGCA GATCAGCAGCCTAAAGGCTGAGGACACTGCCGTGT ATTACTGTGCAAGAAACCCTCCTTATTACTACGGT ACTAATAACGCGGAGGCTATGGACTACTGGGGCCA GGGCACCACCGTGACCGTGTCCTCC |
| SEQ ID NO: 102 | HC | EVQLVQSGAEVKKPGATVKISCKVSGFTLTNYGMN WVRQAPGQGLEWMGWINTDTGEPTYADDFKGRFVF SLDTSVSTAYLQISSLKAEDTAVYYCARNPPYYYG TNNAEAMDYWGQGTTVTVSSASTKGPSVFPLAPCS RSTSESTAALGCLVKDYFPEPVTVSWNSGALTSGV HTFPAVLQSSGLYSLSSVVTVPSSSLGTKTYTCNV DHKPSNTKVDKRVESKYGPPCPPCPAPEFLGGPSV FLFPPKPKDTLMISRTPEVTCVVVDVSQEDPEVQF NWYVDGVEVHNAKTKPREEQFNSTYRVVSVLTVLH QDWLNGKEYKCKVSNKGLPSSIEKTISKAKGQPRE PQVYTLPPSQEEMTKNQVSLTCLVKGFYPSDIAVE WESNGQPENNYKTTPPVLDSDGSFFLYSRLTVDKS RWQEGNVFSCSVMHEALHNHYTQKSLSLSLGK |
| SEQ ID NO: 103 | DNA HC | GAGGTCCAGCTGGTACAGTCTGGGGCTGAGGTGAA GAAGCCTGGGGCTACAGTGAAAATCTCCTGCAAGG TTTCTGGATTTACCCTCACAAACTATGGAATGAAC TGGGTGCGACAGGCCCCTGGACAAGGGCTTGAGTG GATGGGTTGGATAAACACCGACACTGGAGAGCCAA CATATGCTGATGACTTCAAGGGAAGATTTGTCTTC TCCTTGGACACCTCTGTCAGCACGGCATATCTGCA GATCAGCAGCCTAAAGGCTGAGGACACTGCCGTGT ATTACTGTGCAAGAAACCCTCCTTATTACTACGGT ACTAATAACGCGGAGGCTATGGACTACTGGGGCCA GGGCACCACCGTGACCGTGTCCTCCGCTTCCACCA AGGGCCCATCCGTCTTCCCCCTGGCGCCCTGCTCC AGGAGCACCTCCGAGAGCACAGCGGCCCTGGGCTG CCTGGTCAAGGACTACTTCCCCGAACCGGTGACGG TGTCGTGGAACTCAGGCGCCCTGACCAGCGGCGTG CACACCTTCCCGGCTGTCCTACAGTCCTCAGGACT CTACTCCCTCAGCAGCGTGGTGACCGTGCCCTCCA GCAGCTTGGGCACGAAGACCTACACCTGCAACGTA GATCACAAGCCCAGCAACACCAAGGTGGACAAGAG AGTTGAGTCCAAATATGGTCCCCCATGCCCACCGT GCCCAGCACCTGAGTTCCTGGGGGGACCATCAGTC TTCCTGTTCCCCCCAAAACCCAAGGACACTCTCAT GATCTCCCGGACCCCTGAGGTCACGTGCGTGGTGG TGGACGTGAGCCAGGAAGACCCCGAGGTCCAGTTC AACTGGTACGTGGATGGCGTGGAGGTGCATAATGC CAAGACAAAGCCGCGGGAGGAGCAGTTCAACAGCA CGTACCGTGTGGTCAGCGTCCTCACCGTCCTGCAC CAGGACTGGCTGAACGGCAAGGAGTACAAGTGCAA GGTGTCCAACAAAGGCCTCCCGTCCTCCATCGAGA |

TABLE 1-continued

Amino acid and nucleotide sequences for murine, chimeric and humanized antibody molecules. The antibody molecules include murine mAb BAP050, chimeric mAbs BAP050-chi, humanized mAbs BAP050-hum01 to BAP050-hum20, humanized mAbs BAP050-hum01-Ser to BAP050-hum15-Ser, BAP050-hum18-Ser to BAP050-hum20-Ser, and humanized mAbs BAP050-Clone-F to BAP050-Clone-J. The amino acid and nucleotide sequences of the heavy and light chain CDRs, the heavy and light chain variable regions, and the heavy and light chains are shown.

| | |
|---|---|
| | AAACCATCTCCAAAGCCAAAGGGCAGCCCCGAGAG<br>CCACAGGTGTACACCCTGCCCCCATCCCAGGAGGA<br>GATGACCAAGAACCAGGTCAGCCTGACCTGCCTGG<br>TCAAAGGCTTCTACCCCAGCGACATCGCCGTGGAG<br>TGGGAGAGCAATGGGCAGCCGGAGAACAACTACAA<br>GACCACGCCTCCCGTGCTGGACTCCGACGGCTCCT<br>TCTTCCTCTACAGCAGGCTAACCGTGGACAAGAGC<br>AGGTGGCAGGAGGGGAATGTCTTCTCATGCTCCGT<br>GATGCATGAGGCTCTGCACAACCACTACACACAGA<br>AGAGCCTCTCCCTGTCTCTGGGTAAA |

BAP050-hum08-Ser LC

| SEQ ID NO: 10 (Kabat) | LCDR1 SSSQDISNYLN |
|---|---|
| SEQ ID NO: 11 (Kabat) | LCDR2 YTSTLHL |
| SEQ ID NO: 12 (Kabat) | LCDR3 QQYYNLPWT |
| SEQ ID NO: 13 (Chothia) | LCDR1 SQDISNY |
| SEQ ID NO: 14 (Chothia) | LCDR2 YTS |
| SEQ ID NO: 15 (Chothia) | LCDR3 YYNLPW |
| SEQ ID NO: 60 | VL | EIVLTQSPDFQSVTPKEKVTITCSSSQDISNYLNW<br>YQQKPGQAPRLLIYYTSTLHLGVPSRFSGSGSGTD<br>FTLTISSLQPEDFATYYCQQYYNLPWTFGQGTKVE<br>IK |
| SEQ ID NO: 61 | DNA VL | GAAATTGTGCTGACTCAGTCTCCAGACTTTCAGTC<br>TGTGACTCCAAAGGAGAAAGTCACCATCACCTGCA<br>GTTCAAGTCAGGACATCAGCAATTATTTAAACTGG<br>TACCAGCAGAAACCTGGCCAGGCTCCCAGGCTCCT<br>CATCTATTACACATCAACCTTACACTTAGGGGTCC<br>CATCAAGGTTCAGCGGCAGTGGATCTGGGACAGAT<br>TTCACTCTCACCATCAGCAGCCTGCAGCCTGAAGA<br>TTTTGCAACTTATTACTGTCAGCAGTATTATAACC<br>TTCCGTGGACGTTCGGCCAAGGGACCAAGGTGGAA<br>ATCAAA |
| SEQ ID NO: 62 | LC | EIVLTQSPDFQSVTPKEKVTITCSSSQDISNYLNW<br>YQQKPGQAPRLLIYYTSTLHLGVPSRFSGSGSGTD<br>FTLTISSLQPEDFATYYCQQYYNLPWTFGQGTKVE<br>IKRTVAAPSVFIFPPSDEQLKSGTASVVCLLNNFY<br>PREAKVQWKVDNALQSGNSQESVTEQDSKDSTYSL<br>SSTLTLSKADYEKHKVYACEVTHQGLSSPVTKSFN<br>RGEC |
| SEQ ID NO: 63 | DNA LC | GAAATTGTGCTGACTCAGTCTCCAGACTTTCAGTC<br>TGTGACTCCAAAGGAGAAAGTCACCATCACCTGCA<br>GTTCAAGTCAGGACATCAGCAATTATTTAAACTGG<br>TACCAGCAGAAACCTGGCCAGGCTCCCAGGCTCCT<br>CATCTATTACACATCAACCTTACACTTAGGGGTCC<br>CATCAAGGTTCAGCGGCAGTGGATCTGGGACAGAT |

TABLE 1-continued

Amino acid and nucleotide sequences for murine, chimeric and humanized antibody molecules. The antibody molecules include murine mAb BAP050, chimeric mAbs BAP050-chi, humanized mAbs BAP050-hum01 to BAP050-hum20, humanized mAbs BAP050-hum01-Ser to BAP050-hum15-Ser, BAP050-hum18-Ser to BAP050-hum20-Ser, and humanized mAbs BAP050-Clone-F to BAP050-Clone-J. The amino acid and nucleotide sequences of the heavy and light chain CDRs, the heavy and light chain variable regions, and the heavy and light chains are shown.

| | |
|---|---|
| | TTCACTCTCACCATCAGCAGCCTGCAGCCTGAAGA<br>TTTTGCAACTTATTACTGTCAGCAGTATTATAACC<br>TTCCGTGGACGTTCGGCCAAGGGACCAAGGTGGAA<br>ATCAAACGTACGGTGGCTGCACCATCTGTCTTCAT<br>CTTCCCGCCATCTGATGAGCAGTTGAAATCTGGAA<br>CTGCCTCTGTTGTGTGCCTGCTGAATAACTTCTAT<br>CCCAGAGAGGCCAAAGTACAGTGGAAGGTGGATAA<br>CGCCCTCCAATCGGGTAACTCCCAGGAGAGTGTCA<br>CAGAGCAGGACAGCAAGGACAGCACCTACAGCCTC<br>AGCAGCACCCTGACGCTGAGCAAAGCAGACTACGA<br>GAAACACAAAGTCTACGCCTGCGAAGTCACCCATC<br>AGGGCCTGAGCTCGCCCGTCACAAAGAGCTTCAAC<br>AGGGGAGAGTGT |

BAP050-hum09-Ser HC

| SEQ ID NO: 1 (Kabat) | HCDR1 NYGMN |
|---|---|
| SEQ ID NO: 2 (Kabat) | HCDR2 WINTDTGEPTYADDFKG |
| SEQ ID NO: 3 (Kabat) | HCDR3 NPPYYYGTNNAEAMDY |
| SEQ ID NO: 4 (Chothia) | HCDR1 GFTLTNY |
| SEQ ID NO: 5 (Chothia) | HCDR2 NTDTGE |
| SEQ ID NO: 3 (Chothia) | HCDR3 NPPYYYGTNNAEAMDY |
| SEQ ID NO: 104 | VH | QVQLVQSGAEVKKPGASVKVSCKASGFTLTNYGMN<br>WVRQARGQRLEWIGWINTDTGEPTYADDFKGRFVF<br>SLDTSVSTAYLQISSLKAEDTAVYYCARNPPYYYG<br>TNNAEAMDYWGQGTTVTVSS |
| SEQ ID NO: 105 | DNA VH | CAGGTTCAGCTGGTGCAGTCTGGAGCTGAGGTGAA<br>GAAGCCTGGGGCCTCAGTGAAGGTCTCCTGCAAGG<br>CTTCTGGATTTACCCTCACAAACTATGGAATGAAC<br>TGGGTGCGACAGGCTCGTGGACAACGCCTTGAGTG<br>GATAGGTTGGATAAACACCGACACTGGAGAGCCAA<br>CATATGCTGATGACTTCAAGGGAAGATTTGTCTTC<br>TCCTTGGACACCTCTGTCAGCACGGCATATCTGCA<br>GATCAGCAGCCTAAAGGCTGAGGACACTGCCGTGT<br>ATTACTGTGCAAGAAACCCTCCCTATTACTACGGT<br>ACTAATAACGCGGAGGCTATGGACTACTGGGGCCA<br>GGGCACCACCGTGACCGTGTCCTCC |
| SEQ ID NO: 106 | HC | QVQLVQSGAEVKKPGASVKVSCKASGFTLTNYGMN<br>WVRQARGQRLEWIGWINTDTGEPTYADDFKGRFVF<br>SLDTSVSTAYLQISSLKAEDTAVYYCARNPPYYYG<br>TNNAEAMDYWGQGTTVTVSSASTKGPSVFPLAPCS<br>RSTSESTAALGCLVKDYFPEPVTVSWNSGALTSGV<br>HTFPAVLQSSGLYSLSSVVTVPSSSLGTKTYTCNV<br>DHKPSNTKVDKRVESKYGPPCPPCPAPEFLGGPSV<br>FLFPPKPKDTLMISRTPEVTCVVVDVSQEDPEVQF<br>NWYVDGVEVHNAKTKPREEQFNSTYRVVSVLTVLH<br>QDWLNGKEYKCKVSNKGLPSSIEKTISKAKGQPRE |

TABLE 1-continued

Amino acid and nucleotide sequences for murine, chimeric and humanized antibody molecules. The antibody molecules include murine mAb BAP050, chimeric mAbs BAP050-chi, humanized mAbs BAP050-hum01 to BAP050-hum20, humanized mAbs BAP050-hum01-Ser to BAP050-hum15-Ser, BAP050-hum18-Ser to BAP050-hum20-Ser, and humanized mAbs BAP050-Clone-F to BAP050-Clone-J. The amino acid and nucleotide sequences of the heavy and light chain CDRs, the heavy and light chain variable regions, and the heavy and light chains are shown.

| | | |
|---|---|---|
| | | PQVYTLPPSQEEMTKNQVSLTCLVKGFYPSDIAVE WESNGQPENNYKTTPPVLDSDGSFFLYSRLTVDKS RWQEGNVFSCSVMHEALHNHYTQKSLSLSLGK |
| SEQ ID NO: 107 | DNA HC | CAGGTTCAGCTGGTGCAGTCTGGAGCTGAGGTGAA GAAGCCTGGGGCCTCAGTGAAGGTCTCCTGCAAGG CTTCTGGATTTACCCTCACAAACTATGGAATGAAC TGGGTGCGACAGGCTCGTGGACAACGCCTTGAGTG GATAGGTTGGATAAACACCGACACTGGAGAGCCAA CATATGCTGATGACTTCAAGGGAAGATTTGTCTTC TCCTTGGACACCTCTGTCAGCACGGCATATCTGCA GATCAGCAGCCTAAAGGCTGAGGACACTGCCGTGT ATTACTGTGCAAGAAACCCTCCCTATTACTACGGT ACTAATAACGCGGAGGCTATGGACTACTGGGGCCA GGGCACCACCGTGACCGTGTCCTCCGCTTCCACCA AGGGCCCATCCGTCTTCCCCCTGGCGCCCTGCTCC AGGAGCACCTCCGAGAGCACAGCCGCCCTGGGCTG CCTGGTCAAGGACTACTTCCCCGAACCGGTGACGG TGTCGTGGAACTCAGGCGCCCTGACCAGCGGCGTG CACACCTTCCCGGCTGTCCTACAGTCCTCAGGACT CTACTCCCTCAGCAGCGTGGTGACCGTGCCCTCCA GCAGCTTGGGCACGAAGACCTACACCTGCAACGTA GATCACAAGCCCAGCAACACCAAGGTGGACAAGAG AGTTGAGTCCAAATATGGTCCCCCATGCCCACCGT GCCCAGCACCTGAGTTCCTCGGGGGACCATCAGTC TTCCTGTTCCCCCCAAAACCCAAGGACACTCTCAT GATCTCCCGGACCCCTGAGGTCACGTGCGTGGTGG TGGACGTGAGCCAGGAAGACCCCGAGGTCCAGTTC AACTGGTACGTGGATGGCGTGGAGGTGCATAATGC CAAGACAAAGCCGCGGGAGGAGCAGTTCAACAGCA CGTACCGTGTGGTCAGCGTCCTCACCGTCCTGCAC CAGGACTGGCTGAACGGCAAGGAGTACAAGTGCAA GGTGTCCAACAAAGGCCTCCCGTCCTCCATCGAGA AAACCATCTCCAAAGCCAAAGGGCAGCCCCGAGAG CCACAGGTGTACACCCTGCCCCCATCCCAGGAGGA GATGACCAAGAACCAGGTCAGCCTGACCTGCCTGG TCAAAGGCTTCTACCCCAGCGACATCGCCGTGGAG TGGGAGAGCAATGGGCAGCCGGAGAACAACTACAA GACCACGCCTCCCGTGCTGGACTCCGACGGCTCCT TCTTCCTCTACAGCAGGCTAACCGTGGACAAGAGC AGGTGGCAGGAGGGGAATGTCTTCTCATGCTCCGT GATGCATGAGGCTCTGCACAACCACTACACACAGA AGAGCCTCTCCCTGTCTCTGGGTAAA |

BAP050-hum09-Ser LC

| | |
|---|---|
| SEQ ID NO: 10 (Kabat) | LCDR1 SSSQDISNYLN |
| SEQ ID NO: 11 (Kabat) | LCDR2 YTSTLHL |
| SEQ ID NO: 12 (Kabat) | LCDR3 QQYYNLPWT |
| SEQ ID NO: 13 (Chothia) | LCDR1 SQDISNY |
| SEQ ID NO: 14 (Chothia) | LCDR2 YTS |

TABLE 1-continued

Amino acid and nucleotide sequences for murine, chimeric and humanized antibody molecules. The antibody molecules include murine mAb BAP050, chimeric mAbs BAP050-chi, humanized mAbs BAP050-hum01 to BAP050-hum20, humanized mAbs BAP050-hum01-Ser to BAP050-hum15-Ser, BAP050-hum18-Ser to BAP050-hum20-Ser, and humanized mAbs BAP050-Clone-F to BAP050-Clone-J. The amino acid and nucleotide sequences of the heavy and light chain CDRs, the heavy and light chain variable regions, and the heavy and light chains are shown.

| | | |
|---|---|---|
| SEQ ID NO: 15 (Chothia) | | LCDR3 YYNLPW |
| SEQ ID NO: 36 | VL | DIQMTQSPSSLSASVGDRVTITCSSSQDISNYLNW YQQKPGKAPKLLIYYTSTLHLGIPPRFSGSGYGTD FTLTINNIESEDAAYYFCQQYYNLPWTFGQGTKVE IK |
| SEQ ID NO: 37 | DNA VL | GACATCCAGATGACCCAGTCTCCATCCTCCCTGTC TGCATCTGTAGGAGACAGAGTCACCATCACTTGCA GTTCAAGTCAGGACATCAGCAATTATTTAAACTGG TATCAGCAGAAACCAGGGAAAGCTCCTAAGCTCCT GATCTATTACACATCAACCTTACACTTAGGGATCC CACCTCGATTCAGTGGCAGCGGGTATGGAACAGAT TTTACCCTCACAATTAATAACATAGAATCTGAGGA TGCTGCATATTACTTCTGTCAGCAGTATTATAACC TTCCGTGGACGTTCGGCCAAGGGACCAAGGTGGAA ATCAAA |
| SEQ ID NO: 38 | LC | DIQMTQSPSSLSASVGDRVTITCSSSQDISNYLNW YQQKPGKAPKLLIYYTSTLHLGIPPRFSGSGYGTD FTLTINNIESEDAAYYFCQQYYNLPWTFGQGTKVE IKRTVAAPSVFIFPPSDEQLKSGTASVVCLLNNFY PREAKVQWKVDNALQSGNSQESVTEQDSKDSTYSL SSTLTLSKADYEKHKVYACEVTHQGLSSPVTKSFN RGEC |
| SEQ ID NO: 39 | DNA LC | GACATCCAGATGACCCAGTCTCCATCCTCCCTGTC TGCATCTGTAGGAGACAGAGTCACCATCACTTGCA GTTCAAGTCAGGACATCAGCAATTATTTAAACTGG TATCAGCAGAAACCAGGGAAAGCTCCTAAGCTCCT GATCTATTACACATCAACCTTACACTTAGGGATCC CACCTCGATTCAGTGGCAGCGGGTATGGAACAGAT TTTACCCTCACAATTAATAACATAGAATCTGAGGA TGCTGCATATTACTTCTGTCAGCAGTATTATAACC TTCCGTGGACGTTCGGCCAAGGGACCAAGGTGGAA ATCAAACGTACGGTGGCTGCACCATCTGTCTTCAT CTTCCCGCCATCTGATGAGCAGTTGAAATCTGGAA CTGCCTCTGTTGTGTGCCTGCTGAATAACTTCTAT CCCAGAGAGGCCAAAGTACAGTGGAAGGTGGATAA CGCCCTCCAATCGGGTAACTCCCAGGAGAGTGTCA CAGAGCAGGACAGCAAGGACAGCACCTACAGCCTC AGCAGCACCCTGACGCTGAGCAAAGCAGACTACGA GAAACACAAAGTCTACGCCTGCGAAGTCACCCATC AGGGCCTGAGCTCGCCCGTCACAAAGAGCTTCAAC AGGGGAGAGTGT |

BAP050-hum10-Ser HC

| | |
|---|---|
| SEQ ID NO: 1 (Kabat) | HCDR1 NYGMN |
| SEQ ID NO: 2 (Kabat) | HCDR2 WINTDTGEPTYADDFKG |
| SEQ ID NO: 3 (Kabat) | HCDR3 NPPYYYGTNNAEAMDY |
| SEQ ID NO: 4 (Chothia) | HCDR1 GFTLTNY |

TABLE 1-continued

Amino acid and nucleotide sequences for murine, chimeric and humanized antibody molecules. The antibody molecules include murine mAb BAP050, chimeric mAbs BAP050-chi, humanized mAbs BAP050-hum01 to BAP050-hum20, humanized mAbs BAP050-hum01-Ser to BAP050-hum15-Ser, BAP050-hum18-Ser to BAP050-hum20-Ser, and humanized mAbs BAP050-Clone-F to BAP050-Clone-J. The amino acid and nucleotide sequences of the heavy and light chain CDRs, the heavy and light chain variable regions, and the heavy and light chains are shown.

| SEQ ID NO: 5 (Chothia) | | HCDR2 NTDTGE |
|---|---|---|
| SEQ ID NO: 3 (Chothia) | | HCDR3 NPPYYYGTNNAEAMDY |
| SEQ ID NO: 104 | VH | QVQLVQSGAEVKKPGASVKVSCKASGFTLTNYGMN WVRQARGQRLEWIGWINTDTGEPTYADDFKGRFVF SLDTSVSTAYLQISSLKAEDTAVYYCARNPPYYYG TNNAEAMDYWGQGTTVTVSS |
| SEQ ID NO: 105 | DNA VH | CAGGTTCAGCTGGTGCAGTCTGGAGCTGAGGTGAA GAAGCCTGGGGCCTCAGTGAAGGTCTCCTGCAAGG CTTCTGGATTTACCCTCACAAACTATGGAATGAAC TGGGTGCGACAGGCTCGTGGACAACGCCTTGAGTG GATAGGTTGGATAAACACCGACACTGGAGAGCCAA CATATGCTGATGACTTCAAGGGAAGATTTGTCTTC TCCTTGGACACCTCTGTCAGCACGGCATATCTGCA GATCAGCAGCCTAAAGGCTGAGGACACTGCCGTGT ATTACTGTGCAAGAAACCCTCCCTATTACTACGGT ACTAATAACGCGGAGGCTATGGACTACTGGGGCCA GGGCACCACCGTGACCGTGTCCTCC |
| SEQ ID NO: 106 | HC | QVQLVQSGAEVKKPGASVKVSCKASGFTLTNYGMN WVRQARGQRLEWIGWINTDTGEPTYADDFKGRFVF SLDTSVSTAYLQISSLKAEDTAVYYCARNPPYYYG TNNAEAMDYWGQGTTVTVSSASTKGPSVFPLAPCS RSTSESTAALGCLVKDYFPEPVTVSWNSGALTSGV HTFPAVLQSSGLYSLSSVVTVPSSSLGTKTYTCNV DHKPSNTKVDKRVESKYGPPCPPCPAPEFLGGPSV FLFPPKPKDTLMISRTPEVTCVVVDVSQEDPEVQF NWYVDGVEVHNAKTKPREEQFNSTYRVVSVLTVLH QDWLNGKEYKCKVSNKGLPSSIEKTISKAKGQPRE PQVYTLPPSQEEMTKNQVSLTCLVKGFYPSDIAVE WESNGQPENNYKTTPPVLDSDGSFFLYSRLTVDKS RWQEGNVFSCSVMHEALHNHYTQKSLSLSLGK |
| SEQ ID NO: 107 | DNA HC | CAGGTTCAGCTGGTGCAGTCTGGAGCTGAGGTGAA GAAGCCTGGGGCCTCAGTGAAGGTCTCCTGCAAGG CTTCTGGATTTACCCTCACAAACTATGGAATGAAC TGGGTGCGACAGGCTCGTGGACAACGCCTTGAGTG GATAGGTTGGATAAACACCGACACTGGAGAGCCAA CATATGCTGATGACTTCAAGGGAAGATTTGTCTTC TCCTTGGACACCTCTGTCAGCACGGCATATCTGCA GATCAGCAGCCTAAAGGCTGAGGACACTGCCGTGT ATTACTGTGCAAGAAACCCTCCCTATTACTACGGT ACTAATAACGCGGAGGCTATGGACTACTGGGGCCA GGGCACCACCGTGACCGTGTCCTCCGCTTCCACCA AGGGCCCATCCGTCTTCCCCCTGGCGCCCTGCTCC AGGAGCACCTCCGAGAGCACAGCCGCCCTGGGCTG CCTGGTCAAGGACTACTTCCCCGAACCGGTGACGG TGTCGTGGAACTCAGGCGCCCTGACCAGCGGCGTG CACACCTTCCCGGCTGTCCTACAGTCCTCAGGACT CTACTCCCTCAGCAGCGTGGTGACCGTGCCCTCCA GCAGCTTGGGCACGAAGACCTACACCTGCAACGTA GATCACAAGCCCAGCAACACCAAGGTGGACAAGAG AGTTGAGTCCAAATATGGTCCCCCATGCCCACCGT GCCCAGCACCTGAGTTCCTGGGGGGACCATCAGTC TTCCTGTTCCCCCCAAAACCCAAGGACACTCTCAT GATCTCCCGGACCCCTGAGGTCACGTGCGTGGTGG TGGACGTGAGCCAGGAAGACCCCGAGGTCCAGTTC AACTGGTACGTGGATGGCGTGGAGGTGCATAATGC CAAGACAAAGCCGCGGGAGGAGCAGTTCAACAGCA CGTACCGTGTGGTCAGCGTCCTCACCGTCCTGCAC CAGGACTGGCTGAACGGCAAGGAGTACAAGTGCAA | GGTGTCCAACAAAGGCCTCCCGTCCTCCATCGAGA AAACCATCTCCAAAGCCAAAGGGCAGCCCCGAGAG CCACAGGTGTACACCCTGCCCCCATCCCAGGAGGA GATGACCAAGAACCAGGTCAGCCTGACCTGCCTGG TCAAAGGCTTCTACCCCAGCGACATCGCCGTGGAG TGGGAGAGCAATGGGCAGCCGGAGAACAACTACAA GACCACGCCTCCCGTGCTGGACTCCGACGGCTCCT TCTTCCTCTACAGCAGGCTAACCGTGGACAAGAGC AGGTGGCAGGAGGGGAATGTCTTCTCATGCTCCGT GATGCATGAGGCTCTGCACAACCACTACACACAGA AGAGCCTCTCCCTGTCTCTGGGTAAA |

BAP050-hum10-Ser LC

| SEQ ID NO: 10 (Kabat) | | LCDR1 SSSQDISNYLN |
|---|---|---|
| SEQ ID NO: 11 (Kabat) | | LCDR2 YTSTLHL |
| SEQ ID NO: 12 (Kabat) | | LCDR3 QQYYNLPWT |
| SEQ ID NO: 13 (Chothia) | | LCDR1 SQDISNY |
| SEQ ID NO: 14 (Chothia) | | LCDR2 YTS |
| SEQ ID NO: 15 (Chothia) | | LCDR3 YYNLPW |
| SEQ ID NO: 40 | VL | EIVLTQSPATLPVTLGQPASISCSSSQDISNYLNW YQQKPGQAPRLLIYYTSTLHLGVPSRFSGSGSGTD FTFTISSLEAEDAATYYCQQYYNLPWTFGQGTKVE IK |
| SEQ ID NO: 41 | DNA VL | GAAATTGTGTTGACACAGTCTCCAGCCACCCTGCC CGTCACCCTTGGACAGCCGGCCTCCATCTCCTGCA GTTCAAGTCAGGACATCAGCAATTATTTAAACTGG TACCAGCAGAAACCTGGCCAGGCTCCCAGGCTCCT CATCTATTACACATCAACCTTACACTTAGGGGTCC CCTCGAGGTTCAGTGGCAGTGGATCTGGGACAGAT TTCACCTTTACCATCAGTAGCCTGGAAGCTGAAGA TGCTGCAACATATTACTGTCAGCAGTATTATAACC TTCCGTGGACGTTCGGCCAAGGGACCAAGGTGGAA ATCAAA |
| SEQ ID NO: 42 | LC | EIVLTQSPATLPVTLGQPASISCSSSQDISNYLNW YQQKPGQAPRLLIYYTSTLHLGVPSRFSGSGSGTD FTFTISSLEAEDAATYYCQQYYNLPWTFGQGTKVE IKRTVAAPSVFIFPPSDEQLKSGTASVVCLLNNFY PREAKVQWKVDNALQSGNSQESVTEQDSKDSTYSL SSTLTLSKADYEKHKVYACEVTHQGLSSPVTKSFN RGEC |
| SEQ ID NO: 43 | DNA LC | GAAATTGTGTTGACACAGTCTCCAGCCACCCTGCC CGTCACCCTTGGACAGCCGGCCTCCATCTCCTGCA GTTCAAGTCAGGACATCAGCAATTATTTAAACTGG TACCAGCAGAAACCTGGCCAGGCTCCCAGGCTCCT CATCTATTACACATCAACCTTACACTTAGGGGTCC |

TABLE 1-continued

Amino acid and nucleotide sequences for murine, chimeric and humanized antibody molecules. The antibody molecules include murine mAb BAP050, chimeric mAbs BAP050-chi, humanized mAbs BAP050-hum01 to BAP050-hum20, humanized mAbs BAP050-hum01-Ser to BAP050-hum15-Ser, BAP050-hum18-Ser to BAP050-hum20-Ser, and humanized mAbs BAP050-Clone-F to BAP050-Clone-J. The amino acid and nucleotide sequences of the heavy and light chain CDRs, the heavy and light chain variable regions, and the heavy and light chains are shown.

| | | |
|---|---|---|
| | | CCTCGAGGTTCAGTGGCAGTGGATCTGGGACAGAT<br>TTCACCTTTACCATCAGTAGCCTGGAAGCTGAAGA<br>TGCTGCAACATATTACTGTCAGCAGTATTATAACC<br>TTCCGTGGACGTTCGGCCAAGGGACCAAGGTGGAA<br>ATCAAACGTACGGTGGCTGCACCATCTGTCTTCAT<br>CTTCCCGCCATCTGATGAGCAGTTGAAATCTGGAA<br>CTGCCTCTGTTGTGTGCCTGCTGAATAACTTCTAT<br>CCCAGAGAGGCCAAAGTACAGTGGAAGGTGGATAA<br>CGCCCTCCAATCGGGTAACTCCCAGGAGAGTGTCA<br>CAGAGCAGGACAGCAAGGACAGCACCTACAGCCTC<br>AGCAGCACCCTGACGCTGAGCAAAGCAGACTACGA<br>GAAACAAAGTCTACGCCTGCGAAGTCACCCATC<br>AGGGCCTGAGCTCGCCCGTCACAAAGAGCTTCAAC<br>AGGGGAGAGTGT |
| | | BAP050-hum11-Ser HC |
| SEQ ID NO: (Kabat) | HCDR1 | NYGMN |
| SEQ ID NO: (Kabat) | HCDR2 | WINTDTGEPTYADDFKG |
| SEQ ID NO: (Kabat) | HCDR3 | NPPYYYGTNNAEAMDY |
| SEQ ID NO: (Chothia) | HCDR1 | GFTLTNY |
| SEQ ID NO: (Chothia) | HCDR2 | NTDTGE |
| SEQ ID NO: (Chothia) | HCDR3 | NPPYYYGTNNAEAMDY |
| SEQ ID NO: 104 | VH | QVQLVQSGAEVKKPGASVKVSCKASGFTLTNYGMN<br>WVRQARGQRLEWIGWINTDTGEPTYADDFKGRFVF<br>SLDTSVSTAYLQISSLKAEDTAVYYCARNPPYYYG<br>TNNAEAMDYWGQGTTVTVSS |
| SEQ ID NO: 105 | DNA<br>VH | CAGGTTCAGCTGGTGCAGTCTGGAGCTGAGGTGAA<br>GAAGCCTGGGGCCTCAGTGAAGGTCTCCTGCAAGG<br>CTTCTGGATTTACCCTCACAAACTATGGAATGAAC<br>TGGGTGCGACAGGCTCGTGGACAACGCCTTGAGTG<br>GATAGGTTGGATAAACACCGACACTGGAGAGCCAA<br>CATATGCTGATGACTTCAAGGGAAGATTTGTCTTC<br>TCCTTGGACACCTCTGTCAGCACGGCATATCTGCA<br>GATCAGCAGCCTAAAGGCTGAGGACACTGCCGTGT<br>ATTACTGTGCAAGAAACCCTCCCTATTACTACGGT<br>ACTAATAACGCGGAGGCTATGGACTACTGGGGCCA<br>GGGCACCACCGTGACCGTGTCCTCC |
| SEQ ID NO: 106 | HC | QVQLVQSGAEVKKPGASVKVSCKASGFTLTNYGMN<br>WVRQARGQRLEWIGWINTDTGEPTYADDFKGRFVF<br>SLDTSVSTAYLQISSLKAEDTAVYYCARNPPYYYG<br>TNNAEAMDYWGQGTTVTVSSASTKGPSVFPLAPCS<br>RSTSESTAALGCLVKDYFPEPVTVSWNSGALTSGV<br>HTFPAVLQSSGLYSLSSVVTVPSSSLGTKTYTCNV<br>DHKPSNTKVDKRVESKYGPPCPPCPAPEFLGGPSV<br>FLFPPKPKDTLMISRTPEVTCVVVDVSQEDPEVQF<br>NWYVDGVEVHNAKTKPREEQFNSTYRVVSVLTVLH |
| | | QDWLNGKEYKCKVSNKGLPSSIEKTISKAKGQPRE<br>PQVYTLPPSQEEMTKNQVSLTCLVKGFYPSDIAVE<br>WESNGQPENNYKTTPPVLDSDGSFFLYSRLTVDKS<br>RWQEGNVFSCSVMHEALHNHYTQKSLSLSLGK |
| SEQ ID NO: 107 | DNA<br>HC | CAGGTTCAGCTGGTGCAGTCTGGAGCTGAGGTGAA<br>GAAGCCTGGGGCCTCAGTGAAGGTCTCCTGCAAGG<br>CTTCTGGATTTACCCTCACAAACTATGGAATGAAC<br>TGGGTGCGACAGGCTCGTGGACAACGCCTTGAGTG<br>GATAGGTTGGATAAACACCGACACTGGAGAGCCAA<br>CATATGCTGATGACTTCAAGGGAAGATTTGTCTTC<br>TCCTTGGACACCTCTGTCAGCACGGCATATCTGCA<br>GATCAGCAGCCTAAAGGCTGAGGACACTGCCGTGT<br>ATTACTGTGCAAGAAACCCTCCCTATTACTACGGT<br>ACTAATAACGCGGAGGCTATGGACTACTGGGGCCA<br>GGGCACCACCGTGACCGTGTCCTCCGCTTCCACCA<br>AGGGCCCATCCGTCTTCCCCCTGGCGCCCTGCTCC<br>AGGAGCACCTCCGAGAGCACAGCCGCCCTGGGCTG<br>CCTGGTCAAGGACTACTTCCCCGAACCGGTGACGG<br>TGTCGTGGAACTCAGGCGCCCTGACCAGCGGCGTG<br>CACACCTTCCCGGCTGTCCTACAGTCCTCAGGACT<br>CTACTCCCTCAGCAGCGTGGTGACCGTGCCCTCCA<br>GCAGCTTGGGCACGAAGACCTACACCTGCAACGTA<br>GATCACAAGCCCAGCAACACCAAGGTGGACAAGAG<br>AGTTGAGTCCAAATATGGTCCCCCATGCCCACCGT<br>GCCCAGCACCTGAGTTCCTGGGGGGACCATCAGTC<br>TTCCTGTTCCCCCCAAAACCCAAGGACACTCTCAT<br>GATCTCCCGGACCCCTGAGGTCACGTGCGTGGTGG<br>TGGACGTGAGCCAGGAAGACCCCGAGGTCCAGTTC<br>AACTGGTACGTGGATGGCGTGGAGGTGCATAATGC<br>CAAGACAAAGCCGCGGGAGGAGCAGTTCAACAGCA<br>CGTACCGTGTGGTCAGCGTCCTCACCGTCCTGCAC<br>CAGGACTGGCTGAACGGCAAGGAGTACAAGTGCAA<br>GGTGTCCAACAAAGCCCTCCCGTCCTCCATCGAGA<br>AAACCATCTCCAAAGCCAAAGGGCAGCCCCGAGAG<br>CCACAGGTGTACACCCTGCCCCCATCCCAGGAGGA<br>GATGACCAAGAACCAGGTCAGCCTGACCTGCCTGG<br>TCAAAGGCTTCTACCCCAGCGACATCGCCGTGGAG<br>TGGGAGAGCAATGGGCAGCCGGAGAACAACTACAA<br>GACCACGCCTCCCGTGCTGGACTCCGACGGCTCCT<br>TCTTCCTCTACAGCAGGCTAACCGTGGACAAGAGC<br>AGGTGGCAGGAGGGGAATGTCTTCTCATGCTCCGT<br>GATGCATGAGGCTCTGCACAACCACTACACAGA<br>AGAGCCTCTCCCTGTCTCTGGGTAAA |
| | | BAP050-hum11-Ser LC |
| SEQ ID NO: 10 (Kabat) | LCDR1 | SSSQDISNYLN |
| SEQ ID NO: 11 (Kabat) | LCDR2 | YTSTLHL |
| SEQ ID NO: 12 (Kabat) | LCDR3 | QQYYNLPWT |
| SEQ ID NO: 13 (Chothia) | LCDR1 | SQDISNY |
| SEQ ID NO: 14 (Chothia) | LCDR2 | YTS |

TABLE 1-continued

Amino acid and nucleotide sequences for murine, chimeric and humanized antibody molecules. The antibody molecules include murine mAb BAP050, chimeric mAbs BAP050-chi, humanized mAbs BAP050-hum01 to BAP050-hum20, humanized mAbs BAP050-hum01-Ser to BAP050-hum15-Ser, BAP050-hum18-Ser to BAP050-hum20-Ser, and humanized mAbs BAP050-Clone-F to BAP050-Clone-J. The amino acid and nucleotide sequences of the heavy and light chain CDRs, the heavy and light chain variable regions, and the heavy and light chains are shown.

| SEQ ID NO: 15 (Chothia) | | LCDR3 YYNLPW |
|---|---|---|
| SEQ ID NO: 56 | VL | DIQMTQSPSSLSASVGDRVTITCSSSQDISNYLNW YLQKPGQSPQLLIYYTSTLHLGVPSRFSGSGSGTE FTLTISSLQPDDFATYYCQQYYNLPWTFGQGTKVE IK |
| SEQ ID NO: 57 | DNA VL | GACATCCAGATGACCCAGTCTCCATCCTCCCTGTC TGCATCTGTAGGAGACAGAGTCACTATCACTTGCA GTTCAAGTCAGGACATCAGCAATTATTTAAACTGG TACCTGCAGAAGCCAGGGCAGTCTCCACAGCTCCT GATCTATTACACATCAACCTTACACTTAGGGGTCC CATCAAGGTTCAGCGGCAGTGGATCTGGGACAGAA TTCACTCTCACCATCAGCAGCCTGCAGCCTGATGA TTTTTGCAACTTATTACTGTCAGCAGTATTATAACC TTCCGTGGACGTTCGGCCAAGGGACCAAGGTGGAA ATCAAA |
| SEQ ID NO: 58 | LC | DIQMTQSPSSLSASVGDRVTITCSSSQDISNYLNW YLQKPGQSPQLLIYYTSTLHLGVPSRFSGSGSGTE FTLTISSLQPDDFATYYCQQYYNLPWTFGQGTKVE IKRTVAAPSVFIFPPSDEQLKSGTASVVCLLNNFY PREAKVQWKVDNALQSGNSQESVTEQDSKDSTYSL SSTLTLSKADYEKHKVYACEVTHQGLSSPVTKSFN RGEC |
| SEQ ID NO: 59 | DNA LC | GACATCCAGATGACCCAGTCTCCATCCTCCCTGTC TGCATCTGTAGGAGACAGAGTCACTATCACTTGCA GTTCAAGTCAGGACATCAGCAATTATTTAAACTGG TACCTGCAGAAGCCAGGGCAGTCTCCACAGCTCCT GATCTATTACACATCAACCTTACACTTAGGGGTCC CATCAAGGTTCAGCGGCAGTGGATCTGGGACAGAA TTCACTCTCACCATCAGCAGCCTGCAGCCTGATGA TTTTTGCAACTTATTACTGTCAGCAGTATTATAACC TTCCGTGGACGTTCGGCCAAGGGACCAAGGTGGAA ATCAAACGTACGGTGGCTGCACCATCTGTCTTCAT CTTCCCGCCATCTGATGAGCAGTTGAAATCTGGAA CTGCCTCTGTTGTGTGCCTGCTGAATAACTTCTAT CCCAGAGAGGCCAAAGTACAGTGGAAGGTGGATAA CGCCCTCCAATCGGGTAACTCCCAGGAGAGTGTCA CAGAGCAGGACAGCAAGGACAGCACCTACAGCCTC AGCAGCACCCTGACGCTGAGCAAAGCAGACTACGA GAAACACAAAGTCTACGCCTGCGAAGTCACCCATC AGGGCCTGAGCTCGCCCGTCACAAAGAGCTTCAAC AGGGGAGAGTGT |

BAP050-hum12-Ser HC

| SEQ ID NO: 1 (Kabat) | HCDR1 NYGMN |
|---|---|
| SEQ ID NO: 2 (Kabat) | HCDR2 WINTDTGEPTYADDFKG |
| SEQ ID NO: 3 (Kabat) | HCDR3 NPPYYYGTNNAEAMDY |
| SEQ ID NO: 4 (Chothia) | HCDR1 GFTLTNY |

| SEQ ID NO: 5 (Chothia) | | HCDR2 NTDTGE |
|---|---|---|
| SEQ ID NO: 3 (Chothia) | | HCDR3 NPPYYYGTNNAEAMDY |
| SEQ ID NO: 104 | VH | QVQLVQSGAEVKKPGASVKVSCKASGFTLTNYGMN WVRQARGQRLEWIGWINTDTGEPTYADDFKGRFVF SLDTSVSTAYLQISSLKAEDTAVYYCARNPPYYYG TNNAEAMDYWGQGTTVTVSS |
| SEQ ID NO: 105 | DNA VH | CAGGTTCAGCTGGTGCAGTCTGGAGCTGAGGTGAA GAAGCCTGGGGCCTCAGTGAAGGTCTCCTGCAAGG CTTCTGGATTTACCCTCACAAACTATGGAATGAAC TGGGTGCGACAGGCTCGTGGACAACGCCTTGAGTG GATAGGTTGGATAAACACCGACACTGGAGAGCCAA CATATGCTGATGACTTCAAGGGAAGATTTGTCTTC TCCTTGGACACCTCTGTCAGCACGGCATATCTGCA GATCAGCAGCCTAAAGGCTGAGGACACTGCCGTGT ATTACTGTGCAAGAAACCCTCCTATTACTACGGT ACTAATAACGCGGAGGCTATGGACTACTGGGGCCA GGGCACCACCGTGACCGTGTCCTCC |
| SEQ ID NO: 106 | HC | QVQLVQSGAEVKKPGASVKVSCKASGFTLTNYGMN WVRQARGQRLEWIGWINTDTGEPTYADDFKGRFVF SLDTSVSTAYLQISSLKAEDTAVYYCARNPPYYYG TNNAEAMDYWGQGTTVTVSSASTKGPSVFPLAPCS RSTSESTAALGCLVKDYFPEPVTVSWNSGALTSGV HTFPAVLQSSGLYSLSSVVTVPSSSLGTKTYTCNV DHKPSNTKVDKRVESKYGPPCPPCPAPEFLGGPSV FLFPPKPKDTLMISRTPEVTCVVVDVSQEDPEVQF NWYVDGVEVHNAKTKPREEQFNSTYRVVSVLTVLH QDWLNGKEYKCKVSNKGLPSSIEKTISKAKGQPRE PQVYTLPPSQEEMTKNQVSLTCLVKGFYPSDIAVE WESNGQPENNYKTTPPVLDSDGSFFLYSRLTVDKS RWQEGNVFSCSVMHEALHNHYTQKSLSLSLGK |
| SEQ ID NO: 107 | DNA HC | CAGGTTCAGCTGGTGCAGTCTGGAGCTGAGGTGAA GAAGCCTGGGGCCTCAGTGAAGGTCTCCTGCAAGG CTTCTGGATTTACCCTCACAAACTATGGAATGAAC TGGGTGCGACAGGCTCGTGGACAACGCCTTGAGTG GATAGGTTGGATAAACACCGACACTGGAGAGCCAA CATATGCTGATGACTTCAAGGGAAGATTTGTCTTC TCCTTGGACACCTCTGTCAGCACGGCATATCTGCA GATCAGCAGCCTAAAGGCTGAGGACACTGCCGTGT ATTACTGTGCAAGAAACCCTCCTATTACTACGGT ACTAATAACGCGGAGGCTATGGACTACTGGGGCCA GGGCACCACCGTGACCGTGTCCTCCGCTTCCACCA AGGGCCCATCCGTCTTCCCCCTGGCGCCCTGCTCC AGGAGCACCTCCGAGAGCACAGCCGCCCTGGGCTG CCTGGTCAAGGACTACTTCCCCGAACCGGTGACGG TGTCGTGGAACTCAGGCGCCCTGACCAGCGGCGTG CACACCTTCCCGGCTGTCCTACAGTCCTCAGGACT CTACTCCCTCAGCAGCGTGGTGACCGTGCCCTCCA GCAGCTTGGGCACGAAGACCTACACCTGCAACGTA GATCACAAGCCCAGCAACACCAAGGTGGACAAGAG AGTTGAGTCCAAATATGGTCCCCCATGCCCACCGT GCCCAGCACCTGAGTTCCTGGGGGGACCATCAGTC TTCCTGTTCCCCCCAAAACCCAAGGACACTCTCAT GATCTCCCGGACCCCTGAGGTCACGTGCGTGGTGG TGGACGTGAGCCAGGAAGACCCCGAGGTCCAGTTC AACTGGTACGTGGATGGCGTGGAGGTGCATAATGC CAAGACAAAGCCGCGGGAGGAGCAGTTCAACAGCA CGTACCGTGTGGTCAGCGTCCTCACCGTCCTGCAC CAGGACTGGCTGAACGGCAAGGAGTACAAGTGCAA |

TABLE 1-continued

Amino acid and nucleotide sequences for murine, chimeric and humanized antibody molecules. The antibody molecules include murine mAb BAP050, chimeric mAbs BAP050-chi, humanized mAbs BAP050-hum01 to BAP050-hum20, humanized mAbs BAP050-hum01-Ser to BAP050-hum15-Ser, BAP050-hum18-Ser to BAP050-hum20-Ser, and humanized mAbs BAP050-Clone-F to BAP050-Clone-J. The amino acid and nucleotide sequences of the heavy and light chain CDRs, the heavy and light chain variable regions, and the heavy and light chains are shown.

|  |  |  |
|---|---|---|
|  |  | GGTGTCCAACAAAGGCCTCCCGTCCTCCATCGAGA<br>AAACCATCTCCAAAGCCAAAGGGCAGCCCCGAGAG<br>CCACAGGTGTACACCCTGCCCCCATCCCAGGAGGA<br>GATGACCAAGAACCAGGTCAGCCTGACCTGCCTGG<br>TCAAAGGCTTCTACCCCAGCGACATCGCCGTGGAG<br>TGGGAGAGCAATGGGCAGCCGGAGAACAACTACAA<br>GACCACGCCTCCCGTGCTGGACTCCGACGGCTCCT<br>TCTTCCTCTACAGCAGGCTAACCGTGGACAAGAGC<br>AGGTGGCAGGAGGGGAATGTCTTCTCATGCTCCGT<br>GATGCATGAGGCTCTGCACAACCACTACACACAGA<br>AGAGCCTCTCCCTGTCTCTGGGTAAA |
|  | BAP050-hum12-Ser LC |  |
| SEQ ID NO: 10 (Kabat) | LCDR1SSSQDISNYLN |  |
| SEQ ID NO: 11 (Kabat) | LCDR2YTSTLHL |  |
| SEQ ID NO: 12 (Kabat) | LCDR3QQYYNLPWT |  |
| SEQ ID NO: 13 (Chothia) | LCDR1SQDISNY |  |
| SEQ ID NO: 14 (Chothia) | LCDR2YTS |  |
| SEQ ID NO: 15 (Chothia) | LCDR3YYNLPW |  |
| SEQ ID NO: 60 | VL | EIVLTQSPDFQSVTPKEKVTITCSSSQDISNYLNW<br>YQQKPGQAPRLLIYYTSTLHLGVPSRFSGSGSGTD<br>FTLTISSLQPEDFATYYCQQYYNLPWTFGQGTKVE<br>IK |
| SEQ ID NO: 61 | DNA VL | GAAATTGTGCTGACTCAGTCTCCAGACTTTCAGTC<br>TGTGACTCCAAAGGAGAAAGTCACCATCACCTGCA<br>GTTCAAGTCAGGACATCAGCAATTATTTAAACTGG<br>TACCAGCAGAAACCTGGCCAGGCTCCCAGGCTCCT<br>CATCTATTACACATCAACCTTACACTTAGGGGTCC<br>CATCAAGGTTCAGCGGCAGTGGATCTGGGACAGAT<br>TTCACTCTCACCATCAGCAGCCTGCAGCCTGAAGA<br>TTTTGCAACTTATTACTGTCAGCAGTATTATAACC<br>TTCCGTGGACGTTCGGCCAAGGGACCAAGGTGGAA<br>ATCAAA |
| SEQ ID NO: 62 | LC | EIVLTQSPDFQSVTPKEKVTITCSSSQDISNYLNW<br>YQQKPGQAPRLLIYYTSTLHLGVPSRFSGSGSGTD<br>FTLTISSLQPEDFATYYCQQYYNLPWTFGQGTKVE<br>IKRTVAAPSVFIFPPSDEQLKSGTASVVCLLNNFY<br>PREAKVQWKVDNALQSGNSQESVTEQDSKDSTYSL<br>SSTLTLSKADYEKHKVYACEVTHQGLSSPVTKSFN<br>RGEC |
| SEQ ID NO: 63 | DNA LC | GAAATTGTGCTGACTCAGTCTCCAGACTTTCAGTC<br>TGTGACTCCAAAGGAGAAAGTCACCATCACCTGCA<br>GTTCAAGTCAGGACATCAGCAATTATTTAAACTGG<br>TACCAGCAGAAACCTGGCCAGGCTCCCAGGCTCCT<br>CATCTATTACACATCAACCTTACACTTAGGGGTCC |

|  |  |  |
|---|---|---|
|  |  | CATCAAGGTTCAGCGGCAGTGGATCTGGGACAGAT<br>TTCACTCTCACCATCAGCAGCCTGCAGCCTGAAGA<br>TTTTGCAACTTATTACTGTCAGCAGTATTATAACC<br>TTCCGTGGACGTTCGGCCAAGGGACCAAGGTGGAA<br>ATCAAACGTACGGTGGCTGCACCATCTGTCTTCAT<br>CTTCCCGCCATCTGATGAGCAGTTGAAATCTGGAA<br>CTGCCTCTGTTGTGTGCCTGCTGAATAACTTCTAT<br>CCCAGAGAGGCCAAAGTACAGTGGAAGGTGGATAA<br>CGCCCTCCAATCGGGTAACTCCCAGGAGAGTGTCA<br>CAGAGCAGGACAGCAAGGACAGCACCTACAGCCTC<br>AGCAGCACCCTGACGCTGAGCAAAGCAGACTACGA<br>GAAACACAAAGTCTACGCCTGCGAAGTCACCCATC<br>AGGGCCTGAGCTCGCCCGTCACAAAGAGCTTCAAC<br>AGGGGAGAGTGT |
|  | BAP050-hum13-Ser HC |  |
| SEQ ID NO: 1 (Kabat) | HCDR1NYGMN |  |
| SEQ ID NO: 2 (Kabat) | HCDR2WINTDTGEPTYADDFKG |  |
| SEQ ID NO: 3 (Kabat) | HCDR3NPPYYYGTNNAEAMDY |  |
| SEQ ID NO: 4 (Chothia) | HCDR1GFTLTNY |  |
| SEQ ID NO: 5 (Chothia) | HCDR2NTDTGE |  |
| SEQ ID NO: 3 (Chothia) | HCDR3NPPYYYGTNNAEAMDY |  |
| SEQ ID NO: 108 | VH | QVQLVQSGAEVKKPGASVKVSCKASGFTLTNYGMN<br>WVRQAPGQGLEWMGWINTDTGEPTYADDFKGRFVF<br>SLDTSVSTAYLQISSLKAEDTAVYYCARNPPYYYG<br>TNNAEAMDYWGQGTTVTVSS |
| SEQ ID NO: 109 | DNA VH | CAGGTTCAGCTGGTGCAGTCCGGAGCTGAGGTGAA<br>GAAGCCTGGGGCCTCAGTGAAGGTCTCCTGCAAGG<br>CTTCTGGATTTACCCTCACAAACTATGGAATGAAC<br>TGGGTGCGACAGGCCCCTGGACAAGGGCTTGAGTG<br>GATGGGTTGGATAAACACCGACACTGGAGAGCCAA<br>CATATGCTGATGACTTCAAGGGAAGATTTGTCTTC<br>TCCTTGGACACCTCTGTCAGCACGGCATATCTGCA<br>GATCAGCAGCCTAAAGGCTGAGGACACTGCCGTGT<br>ATTACTGTGCAAGAAACCCTCCCTATTACTACGGT<br>ACTAATAACGCGGAGGCTATGGACTACTGGGGCCA<br>GGGCACCACCGTGACCGTGTCCTCC |
| SEQ ID NO: 110 | HC | QVQLVQSGAEVKKPGASVKVSCKASGFTLTNYGMN<br>WVRQAPGQGLEWMGWINTDTGEPTYADDFKGRFVF<br>SLDTSVSTAYLQISSLKAEDTAVYYCARNPPYYYG<br>TNNAEAMDYWGQGTTVTVSSASTKGPSVFPLAPCS<br>RSTSESTAALGCLVKDYFPEPVTVSWNSGALTSGV<br>HTFPAVLQSSGLYSLSSVVTVPSSSLGTKTYTCNV<br>DHKPSNTKVDKRVESKYGPPCPPCPAPEFLGGPSV<br>FLFPPKPKDTLMISRTPEVTCVVVDVSQEDPEVQF<br>NWYVDGVEVHNAKTKPREEQFNSTYRVVSVLTVLH |

TABLE 1-continued

Amino acid and nucleotide sequences for murine, chimeric and humanized antibody molecules. The antibody molecules include murine mAb BAP050, chimeric mAbs BAP050-chi, humanized mAbs BAP050-hum01 to BAP050-hum20, humanized mAbs BAP050-hum01-Ser to BAP050-hum15-Ser, BAP050-hum18-Ser to BAP050-hum20-Ser, and humanized mAbs BAP050-Clone-F to BAP050-Clone-J. The amino acid and nucleotide sequences of the heavy and light chain CDRs, the heavy and light chain variable regions, and the heavy and light chains are shown.

| | | |
|---|---|---|
| | | QDWLNGKEYKCKVSNKGLPSSIEKTISKAKGQPRE<br>PQVYTLPPSQEEMTKNQVSLTCLVKGFYPSDIAVE<br>WESNGQPENNYKTTPPVLDSDGSFFLYSRLTVDKS<br>RWQEGNVFSCSVMHEALHNHYTQKSLSLSLGK |
| SEQ ID<br>NO: 111 | DNA<br>HC | CAGGTTCAGCTGGTGCAGTCCGGAGCTGAGGTGAA<br>GAAGCCTGGGGCCTCAGTGAAGGTCTCCTGCAAGG<br>CTTCTGGATTTACCCTCACAAACTATGGAATGAAC<br>TGGGTGCGACAGGCCCCTGGACAAGGGCTTGAGTG<br>GATGGGTTGGATAAACACCGACACTGGAGAGCCAA<br>CATATGCTGATGACTTCAAGGGAAGATTTGTCTTC<br>TCCTTGGACACCTCTGTCAGCACGGCATATCTGCA<br>GATCAGCAGCCTAAAGGCTGAGGACACTGCCGTGT<br>ATTACTGTGCAAGAAACCCTCCCTATTACTACGGT<br>ACTAATAACGCGGAGGCTATGGACTACTGGGGCCA<br>GGGCACCACCGTGACCGTGTCCTCCGCTTCCACCA<br>AGGGCCCATCCGTCTTCCCCCTGGCGCCCTGCTCC<br>AGGAGCACCTCCGAGAGCACAGCCGCCCTGGGCTG<br>CCTGGTCAAGGACTACTTCCCCGAACCGGTGACGG<br>TGTCGTGGAACTCAGGCGCCCTGACCAGCGGCGTG<br>CACACCTTCCCGGCTGTCCTACAGTCCTCAGGACT<br>CTACTCCCTCAGCAGCGTGGTGACCGTGCCCTCCA<br>GCAGCTTGGGCACGAAGACCTACACCTGCAACGTA<br>GATCACAAGCCCAGCAACACCAAGGTGGACAAGAG<br>AGTTGAGTCCAAATATGGTCCCCCATGCCCACCGT<br>GCCCAGCACCTGAGTTCCTGGGGGGACCATCAGTC<br>TTCCTGTTCCCCCCAAAACCCAAGGACACTCTCAT<br>GATCTCCCGGACCCCTGAGGTCACGTGCGTGGTGG<br>TGGACGTGAGCCAGGAAGACCCCGAGGTCCAGTTC<br>AACTGGTACGTGGATGGCGTGGAGGTGCATAATGC<br>CAAGACAAAGCCGCGGGAGGAGCAGTTCAACAGCA<br>CGTACCGTGTGGTCAGCGTCCTCACCGTCCTGCAC<br>CAGGACTGGCTGAACGGCAAGGAGTACAAGTGCAA<br>GGTGTCCAACAAAGGCCTCCCGTCCTCCATCGAGA<br>AAACCATCTCCAAAGCCAAAGGGCAGCCCCGAGAG<br>CCACAGGTGTACACCCTGCCCCCATCCCAGGAGGA<br>GATGACCAAGAACCAGGTCAGCCTGACCTGCCTGG<br>TCAAAGGCTTCTACCCCAGCGACATCGCCGTGGAG<br>TGGGAGAGCAATGGGCAGCCGGAGAACAACTACAA<br>GACCACGCCTCCCGTGCTGGACTCCGACGGCTCCT<br>TCTTCCTCTACAGCAGGCTAACCGTGGACAAGAGC<br>AGGTGGCAGGAGGGGAATGTCTTCTCATGCTCCGT<br>GATGCATGAGGCTCTGCACAACCACTACACACAGA<br>AGAGCCTCTCCCTGTCTCTGGGTAAA |

BAP050-hum13-Ser LC

| SEQ ID<br>NO: 10<br>(Kabat) | LCDR1 | SSSQDISNYLN |
|---|---|---|
| SEQ ID<br>NO: 11<br>(Kabat) | LCDR2 | YTSTLHL |
| SEQ ID<br>NO: 12<br>(Kabat) | LCDR3 | QQYYNLPWT |
| SEQ ID<br>NO: 13<br>(Chothia) | LCDR1 | SQDISNY |
| SEQ ID<br>NO: 14<br>(Chothia) | LCDR2 | YTS |

| SEQ ID<br>NO: 15<br>(Chothia) | LCDR3 | YYNLPW |
|---|---|---|
| SEQ ID<br>NO: 36 | VL | DIQMTQSPSSLSASVGDRVTITCSSSQDISNYLNW<br>YQQKPGKAPKLLIYYTSTLHLGIPPRFSGSGYGTD<br>FTLTINNIESEDAAYYFCQQYYNLPWTFGQGTKVE<br>IK |
| SEQ ID<br>NO: 37 | DNA<br>VL | GACATCCAGATGACCCAGTCTCCATCCTCCCTGTC<br>TGCATCTGTAGGAGACAGAGTCACCATCACTTGCA<br>GTTCAAGTCAGGACATCAGCAATTATTTAAACTGG<br>TATCAGCAGAAACCAGGGAAAGCTCCTAAGCTCCT<br>GATCTATTACACATCAACCTTACACTTAGGGATCC<br>CACCTCGATTCAGTGGCAGCGGGTATGGAACAGAT<br>TTTACCCTCACAATTAATAACATAGAATCTGAGGA<br>TGCTGCATATTACTTCTGTCAGCAGTATTATAACC<br>TTCCGTGGACGTTCGGCCAAGGGACCAAGGTGGAA<br>ATCAAA |
| SEQ ID<br>NO: 38 | LC | DIQMTQSPSSLSASVGDRVTITCSSSQDISNYLNW<br>YQQKPGKAPKLLIYYTSTLHLGIPPRESGSGYGTD<br>FTLTINNIESEDAAYYFCQQYYNLPWTFGQGTKVE<br>IKRTVAAPSVFIFPPSDEQLKSGTASVVCLLNNFY<br>PREAKVQWKVDNALQSGNSQESVTEQDSKDSTYSL<br>SSTLTLSKADYEKHKVYACEVTHQGLSSPVTKSFN<br>RGEC |
| SEQ ID<br>NO: 39 | DNA<br>LC | GACATCCAGATGACCCAGTCTCCATCCTCCCTGTC<br>TGCATCTGTAGGAGACAGAGTCACCATCACTTGCA<br>GTTCAAGTCAGGACATCAGCAATTATTTAAACTGG<br>TATCAGCAGAAACCAGGGAAAGCTCCTAAGCTCCT<br>GATCTATTACACATCAACCTTACACTTAGGGATCC<br>CACCTCGATTCAGTGGCAGCGGGTATGGAACAGAT<br>TTTACCCTCACAATTAATAACATAGAATCTGAGGA<br>TGCTGCATATTACTTCTGTCAGCAGTATTATAACC<br>TTCCGTGGACGTTCGGCCAAGGGACCAAGGTGGAA<br>ATCAAACGTACGGTGGCTGCACCATCTGTCTTCAT<br>CTTCCCGCCATCTGATGAGCAGTTGAAATCTGGAA<br>CTGCCTCTGTTGTGTGCCTGCTGAATAACTTCTAT<br>CCCAGAGAGGCCAAAGTACAGTGGAAGGTGGATAA<br>CGCCCTCCAATGGGTAACTCCCAGGAGAGTGTCA<br>CAGAGCAGGACAGCAAGGACAGCACCTACAGCCTC<br>AGCAGCACCCTGACGCTGAGCAAAGCAGACTACGA<br>GAAACACAAAGTCTACGCCTGCGAAGTCACCCATC<br>AGGGCCTGAGCTCGCCCGTCACAAAGAGCTTCAAC<br>AGGGGAGAGTGT |

BAP050-hum14-Ser HC

| SEQ ID<br>NO: 1<br>(Kabat) | HCDR1 | NYGMN |
|---|---|---|
| SEQ ID<br>NO: 2<br>(Kabat) | HCDR2 | WINTDTGEPTYADDFKG |
| SEQ ID<br>NO: 3<br>(Kabat) | HCDR3 | NPPYYYGTNNAEAMDY |
| SEQ ID<br>NO: 4<br>(Chothia) | HCDR1 | GFTLTNY |

TABLE 1-continued

Amino acid and nucleotide sequences for murine, chimeric and humanized antibody molecules. The antibody molecules include murine mAb BAP050, chimeric mAbs BAP050-chi, humanized mAbs BAP050-hum01 to BAP050-hum20, humanized mAbs BAP050-hum01-Ser to BAP050-hum15-Ser, BAP050-hum18-Ser to BAP050-hum20-Ser, and humanized mAbs BAP050-Clone-F to BAP050-Clone-J. The amino acid and nucleotide sequences of the heavy and light chain CDRs, the heavy and light chain variable regions, and the heavy and light chains are shown.

| SEQ ID NO: 5 (Chothia) | | HCDR2 NTDTGE |
|---|---|---|
| SEQ ID NO: 3 (Chothia) | | HCDR3 NPPYYYGTNNAEAMDY |
| SEQ ID NO: 8 | VH | EVQLVQSGAEVKKPGATVKISCKVSGFTLTNYGMN WIRQSPSRGLEWLGWINTDTGEPTYADDFKGRFVF SLDTSVSTAYLQISSLKAEDTAVYYCARNPPYYYG TNNAEAMDYWGQGTTVTVSS |
| SEQ ID NO: 9 | DNA VH | GAGGTCCAGCTGGTACAGTCTGGGGCTGAGGTGAA GAAGCCTGGGGCTACAGTGAAAATCTCCTGCAAGG TTTCTGGATTTACCCTCACAAACTATGGAATGAAC TGGATCAGGCAGTCCCCATCGAGAGGCCTTGAGTG GCTGGGTTGGATAAACACCGACACTGGAGAGCCAA CATATGCTGATGACTTCAAGGGAAGATTTGTCTTC TCCTTGGACACCTCTGTCAGCACGGCATATCTGCA GATCAGCAGCCTAAAGGCTGAGGACACTGCCGTGT ATTACTGTGCAAGAAACCCTCCCTATTACTACGGT ACTAATAACGCGGAGGCTATGGACTACTGGGGCCA GGGCACCACCGTGACCGTGTCCTCC |
| SEQ ID NO: 18 | HC | EVQLVQSGAEVKKPGATVKISCKVSGFTLTNYGMN WIRQSPSRGLEWLGWINTDTGEPTYADDFKGRFVF SLDTSVSTAYLQISSLKAEDTAVYYCARNPPYYYG TNNAEAMDYWGQGTTVTVSSASTKGPSVFPLAPCS RSTSESTAALGCLVKDYFPEPVTVSWNSGALTSGV HTFPAVLQSSGLYSLSSVVTVPSSSLGTKTYTCNV DHKPSNTKVDKRVESKYGPPCPPCPAPEFLGGPSV FLFPPKPKDTLMISRTPEVTCVVVDVSQEDPEVQF NWYVDGVEVHNAKTKPREEQFNSTYRVVSVLTVLH QDWLNGKEYKCKVSNKGLPSSIEKTISKAKGQPRE PQVYTLPPSQEEMTKNQVSLTCLVKGFYPSDIAVE WESNGQPENNYKTTPPVLDSDGSFFLYSRLTVDKS RWQEGNVFSCSVMHEALHNHYTQKSLSLSLGK |
| SEQ ID NO: 19 | DNA HC | GAGGTCCAGCTGGTACAGTCTGGGGCTGAGGTGAA GAAGCCTGGGGCTACAGTGAAAATCTCCTGCAAGG TTTCTGGATTTACCCTCACAAACTATGGAATGAAC TGGATCAGGCAGTCCCCATCGAGAGGCCTTGAGTG GCTGGGTTGGATAAACACCGACACTGGAGAGCCAA CATATGCTGATGACTTCAAGGGAAGATTTGTCTTC TCCTTGGACACCTCTGTCAGCACGGCATATCTGCA GATCAGCAGCCTAAAGGCTGAGGACACTGCCGTGT ATTACTGTGCAAGAAACCCTCCCTATTACTACGGT ACTAATAACGCGGAGGCTATGGACTACTGGGGCCA GGGCACCACCGTGACCGTGTCCTCCGCTTCCACCA AGGGCCCATCCGTCTTCCCCCTGGCGCCCTGCTCC AGGAGCACCTCCGAGAGCACAGCCGCCCTGGGCTG CCTGGTCAAGGACTACTTCCCCGAACCGGTGACGG TGTCGTGGAACTCAGGCGCCCTGACCAGCGGCGTG CACACCTTCCCGGCTGTCCTACAGTCCTCAGGACT CTACTCCCTCAGCAGCGTGGTGACCGTGCCCTCCA GCAGCTTGGGCACGAAGACCTACACCTGCAACGTA GATCACAAGCCCAGCAACACCAAGGTGGACAAGAG AGTTGAGTCCAAATATGGTCCCCCATGCCCACCGT GCCCAGCACCTGAGTTCCTGGGGGGACCATCAGTC TTCCTGTTCCCCCCAAAACCCAAGGACACTCTCAT GATCTCCCGGACCCCTGAGGTCACGTGCGTGGTGG TGGACGTGAGCCAGGAAGACCCCGAGGTCCAGTTC AACTGGTACGTGGATGGCGTGGAGGTGCATAATGC CAAGACAAAGCCGCGGGAGGAGCAGTTCAACAGCA CGTACCGTGTGGTCAGCGTCCTCACCGTCCTGCAC CAGGACTGGCTGAACGGCAAGGAGTACAAGTGCAA | |
| | | GGTGTCCAACAAAGGCCTCCCGTCCTCCATCGAGA AAACCATCTCCAAAGCCAAAGGGCAGCCCCGAGAG CCACAGGTGTACACCCTGCCCCCATCCCAGGAGGA GATGACCAAGAACCAGGTCAGCCTGACCTGCCTGG TCAAAGGCTTCTACCCCAGCGACATCGCCGTGGAG TGGGAGAGCAATGGGCAGCCGGAGAACAACTACAA GACCACGCCTCCCGTGCTGGACTCCGACGGCTCCT TCTTCCTCTACAGCAGGCTAACCGTGGACAAGAGC AGGTGGCAGGAGGGGAATGTCTTCTCATGCTCCGT GATGCATGAGGCTCTGCACAACCACTACACAGA AGAGCCTCTCCCTGTCTCTGGGTAAA |

BAP050-hum14-Ser LC

| SEQ ID NO: 10 (Kabat) | | LCDR1 SSSQDISNYLN |
|---|---|---|
| SEQ ID NO: 11 (Kabat) | | LCDR2 YTSTLHL |
| SEQ ID NO: 12 (Kabat) | | LCDR3 QQYYNLPWT |
| SEQ ID NO: 13 (Chothia) | | LCDR1 SQDISNY |
| SEQ ID NO: 14 (Chothia) | | LCDR2 YTS |
| SEQ ID NO: 15 (Chothia) | | LCDR3 YYNLPW |
| SEQ ID NO: 40 | VL | EIVLTQSPATLPVTLGQPASISCSSSQDISNYLNW YQQKPGQAPRLLIYYTSTLHLGVPSRFSGSGSGTD FTFTISSLEAEDAATYYCQQYYNLPWTFGQGTKVE IK |
| SEQ ID NO: 41 | DNA VL | GAAATTGTGTTGACACAGTCTCCAGCCACCCTGCC CGTCACCCTTGGACAGCCGGCCTCCATCTCCTGCA GTTCAAGTCAGGACATCAGCAATTATTTAAACTGG TACCAGCAGAAACCTGGCCAGGCTCCCAGGCTCCT CATCTATTACACATCAACCTTACATTAGGGGTCC CCTCGAGGTTCAGTGGCAGTGGATCTGGGACAGAT TTCACCTTTACCATCAGTAGCCTGGAAGCTGAAGA TGCTGCAACATATTACTGTCAGCAGTATTATAACC TTCCGTGGACGTTCGGCCAAGGGACCAAGGTGGAA ATCAAA |
| SEQ ID NO: 42 | LC | EIVLTQSPATLPVTLGQPASISCSSSQDISNYLNW YQQKPGQAPRLLIYYTSTLHLGVPSRFSGSGSGTD FTFTISSLEAEDAATYYCQQYYNLPWTFGQGTKVE IKRTVAAPSVFIFPPSDEQLKSGTASVVCLLNNFY PREAKVQWKVDNALQSGNSQESVTEQDSKDSTYSL SSTLTLSKADYEKHKVYACEVTHQGLSSPVTKSFN RGEC |
| SEQ ID NO: 43 | DNA LC | GAAATTGTGTTGACACAGTCTCCAGCCACCCTGCC CGTCACCCTTGGACAGCCGGCCTCCATCTCCTGCA GTTCAAGTCAGGACATCAGCAATTATTTAAACTGG TACCAGCAGAAACCTGGCCAGGCTCCCAGGCTCCT CATCTATTACACATCAACCTTACATTAGGGGTCC |

TABLE 1-continued

Amino acid and nucleotide sequences for murine, chimeric and humanized antibody molecules. The antibody molecules include murine mAb BAP050, chimeric mAbs BAP050-chi, humanized mAbs BAP050-hum01 to BAP050-hum20, humanized mAbs BAP050-hum01-Ser to BAP050-hum15-Ser, BAP050-hum18-Ser to BAP050-hum20-Ser, and humanized mAbs BAP050-Clone-F to BAP050-Clone-J. The amino acid and nucleotide sequences of the heavy and light chain CDRs, the heavy and light chain variable regions, and the heavy and light chains are shown.

| | | |
|---|---|---|
| | | CCTCGAGGTTCAGTGGCAGTGGATCTGGGACAGAT TTCACCTTTACCATCAGTAGCCTGGAAGCTGAAGA TGCTGCAACATATTACTGTCAGCAGTATTATAACC TTCCGTGGACGTTCGGCCAAGGGACCAAGGTGGAA ATCAAACGTACGGTGGCTGCACCATCTGTCTTCAT CTTCCCGCCATCTGATGAGCAGTTGAAATCTGGAA CTGCCTCTGTTGTGTGCCTGCTGAATAACTTCTAT CCCAGAGAGGCCAAAGTACAGTGGAAGGTGGATAA CGCCCTCCAATCGGGTAACTCCCAGGAGAGTGTCA CAGAGCAGGACAGCAAGGACAGCACCTACAGCCTC AGCAGCACCCTGACGCTGAGCAAAGCAGACTACGA GAAACAAAGTCTACGCCTGCGAAGTCACCCATC AGGGCCTGAGCTCGCCCGTCACAAAGAGCTTCAAC AGGGGAGAGTGT |
| | | BAP050-hum15-Ser HC |
| SEQ ID NO: 1 (Kabat) | HCDR1 | NYGMN |
| SEQ ID NO: 2 (Kabat) | HCDR2 | WINTDTGEPTYADDFKG |
| SEQ ID NO: 3 (Kabat) | HCDR3 | NPPYYYGTNNAEAMDY |
| SEQ ID NO: 4 (Chothia) | HCDR1 | GFTLTNY |
| SEQ ID NO: 5 (Chothia) | HCDR2 | NTDTGE |
| SEQ ID NO: 3 (Chothia) | HCDR3 | NPPYYYGTNNAEAMDY |
| SEQ ID NO: 8 | VH | EVQLVQSGAEVKKPGATVKISCKVSGFTLTNYGMN WIRQSPSRGLEWLGWINTDTGEPTYADDFKGRFVF SLDTSVSTAYLQISSLKAEDTAVYYCARNPPYYYG TNNAEAMDYWGQGTTVTVSS |
| SEQ ID NO: 9 | DNA VH | GAGGTCCAGCTGGTACAGTCTGGGGCTGAGGTGAA GAAGCCTGGGGCTACAGTGAAAATCTCCTGCAAGG TTTCTGGATTTACCCTCACAAACTATGGAATGAAC TGGATCAGGCAGTCCCCATCGAGAGGCCTTGAGTG GCTGGGTTGGATAAACACCGACACTGGAGAGCCAA CATATGCTGATGACTTCAAGGGAAGATTTGTCTTC TCCTTGGACACCTCTGTCAGCACGGCATATCTGCA GATCAGCAGCCTAAAGGCTGAGGACACTGCCGTGT ATTACTGTGCAAGAAACCCTCCCTATTACTACGGT ACTAATAACGCGGAGGCTATGGACTACTGGGGCCA GGGCACCACCGTGACCGTGTCCTCC |
| SEQ ID NO: 18 | HC | EVQLVQSGAEVKKPGATVKISCKVSGFTLTNYGMN WIRQSPSRGLEWLGWINTDTGEPTYADDFKGRFVF SLDTSVSTAYLQISSLKAEDTAVYYCARNPPYYYG TNNAEAMDYWGQGTTVTVSSASTKGPSVFPLAPCS RSTSESTAALGCLVKDYFPEPVTVSWNSGALTSGV HTFPAVLQSSGLYSLSSVVTVPSSSLGTKTYTCNV DHKPSNTKVDKRVESKYGPPCPPCPAPEFLGGPSV FLFPPKPKDTLMISRTPEVTCVVVDVSQEDPEVQF NWYVDGVEVHNAKTKPREEQFNSTYRVVSVLTVLH QDWLNGKEYKCKVSNKGLPSSIEKTISKAKGQPRE PQVYTLPPSQEEMTKNQVSLTCLVKGFYPSDIAVE WESNGQPENNYKTTPPVLDSDGSFFLYSRLTVDKS RWQEGNVFSCSVMHEALHNHYTQKSLSLSLGK |
| SEQ ID NO: 19 | DNA HC | GAGGTCCAGCTGGTACAGTCTGGGGCTGAGGTGAA GAAGCCTGGGGCTACAGTGAAAATCTCCTGCAAGG TTTCTGGATTTACCCTCACAAACTATGGAATGAAC TGGATCAGGCAGTCCCCATCGAGAGGCCTTGAGTG GCTGGGTTGGATAAACACCGACACTGGAGAGCCAA CATATGCTGATGACTTCAAGGGAAGATTTGTCTTC TCCTTGGACACCTCTGTCAGCACGGCATATCTGCA GATCAGCAGCCTAAAGGCTGAGGACACTGCCGTGT ATTACTGTGCAAGAAACCCTCCCTATTACTACGGT ACTAATAACGCGGAGGCTATGGACTACTGGGGCCA GGGCACCACCGTGACCGTGTCCTCCGCTTCCACCA AGGGCCCATCCGTCTTCCCCCTGGCGCCCTGCTCC AGGAGCACCTCCGAGAGCACAGCCGCCCTGGGCTG CCTGGTCAAGGACTACTTCCCCGAACCGGTGACGG TGTCGTGGAACTCAGGCGCCCTGACCAGCGGCGTG CACACCTTCCCGGCTGTCCTACAGTCCTCAGGACT CTACTCCCTCAGCAGCGTGGTGACCGTGCCCTCCA GCAGCTTGGGCACGAAGACCTACACCTGCAACGTA GATCACAAGCCCAGCAACACCAAGGTGGACAAGAG AGTTGAGTCCAAATATGGTCCCCCATGCCCACCGT GCCCAGCACCTGAGTTCCTGGGGGGACCATCAGTC TTCCTGTTCCCCCCAAAACCCAAGGACACTCTCAT GATCTCCCGGACCCCTGAGGTCACGTGCGTGGTGG TGGACGTGAGCCAGGAAGACCCCGAGGTCCAGTTC AACTGGTACGTGGATGGCGTGGAGGTGCATAATGC CAAGACAAAGCCGCGGGAGGAGCAGTTCAACAGCA CGTACCGTGTGGTCAGCGTCCTCACCGTCCTGCAC CAGGACTGGCTGAACGGCAAGGAGTACAAGTGCAA GGTGTCCAACAAAGCCCTCCCGTCCTCCATCGAGA AAACCATCTCCAAAGCCAAAGGGCAGCCCCGAGAG CCACAGGTGTACACCCTGCCCCCATCCCAGGAGGA GATGACCAAGAACCAGGTCAGCCTGACCTGCCTGG TCAAAGGCTTCTACCCCAGCGACATCGCCGTGGAG TGGGAGAGCAATGGGCAGCCGGAGAACAACTACAA GACCACGCCTCCCGTGCTGGACTCCGACGGCTCCT TCTTCCTCTACAGCAGGCTAACCGTGGACAAGAGC AGGTGGCAGGAGGGGAATGTCTTCTCATGCTCCGT GATGCATGAGGCTCTGCACAACCACTACACAGA AGAGCCTCTCCCTGTCTCTGGGTAAA |
| | | BAP050-hum15-Ser LC |
| SEQ ID NO: 10 (Kabat) | LCDR1 | SSSQDISNYLN |
| SEQ ID NO: 11 (Kabat) | LCDR2 | YTSTLHL |
| SEQ ID NO: 12 (Kabat) | LCDR3 | QQYYNLPWT |
| SEQ ID NO: 13 (Chothia) | LCDR1 | SQDISNY |
| SEQ ID NO: 14 (Chothia) | LCDR2 | YTS |

TABLE 1-continued

Amino acid and nucleotide sequences for murine, chimeric and humanized antibody molecules. The antibody molecules include murine mAb BAP050, chimeric mAbs BAP050-chi, humanized mAbs BAP050-hum01 to BAP050-hum20, humanized mAbs BAP050-hum01-Ser to BAP050-hum15-Ser, BAP050-hum18-Ser to BAP050-hum20-Ser, and humanized mAbs BAP050-Clone-F to BAP050-Clone-J. The amino acid and nucleotide sequences of the heavy and light chain CDRs, the heavy and light chain variable regions, and the heavy and light chains are shown.

| SEQ ID NO: 15 (Chothia) | | LCDR3 YYNLPW |
|---|---|---|
| SEQ ID NO: 60 | VL | EIVLTQSPDFQSVTPKEKVTITCSSSQDISNYLNW YQQKPGQAPRLLIYYTSTLHLGVPSRFSGSGSGTD FTLTISSLQPEDFATYYCQQYYNLPWTFGQGTKVE IK |
| SEQ ID NO: 61 | DNA VL | GAAATTGTGCTGACTCAGTCTCCAGACTTTCAGTC TGTGACTCCAAAGGAGAAAGTCACCATCACCTGCA GTTCAAGTCAGGACATCAGCAATTATTTAAACTGG TACCAGCAGAAACCTGGCCAGGCTCCCAGGCTCCT CATCTATTACACATCAACCTTACACTTAGGGGTCC CATCAAGGTTCAGCGGCAGTGGATCTGGGACAGAT TCACTCTCACCATCAGCAGCCTGCAGCCTGAAGA TTTTGCAACTTATTACTGTCAGCAGTATTATAACC TTCCGTGGACGTTCGGCCAAGGGACCAAGGTGGAA ATCAAA |
| SEQ ID NO: 62 | LC | EIVLTQSPDFQSVTPKEKVTITCSSSQDISNYLNW YQQKPGQAPRLLIYYTSTLHLGVPSRFSGSGSGTD FTLTISSLQPEDFATYYCQQYYNLPWTFGQGTKVE IKRTVAAPSVFIFPPSDEQLKSGTASVVCLLNNFY PREAKVQWKVDNALQSGNSQESVTEQDSKDSTYSL SSTLTLSKADYEKHKVYACEVTHQGLSSPVTKSFN RGEC |
| SEQ ID NO: 63 | DNA LC | GAAATTGTGCTGACTCAGTCTCCAGACTTTCAGTC TGTGACTCCAAAGGAGAAAGTCACCATCACCTGCA GTTCAAGTCAGGACATCAGCAATTATTTAAACTGG TACCAGCAGAAACCTGGCCAGGCTCCCAGGCTCCT CATCTATTACACATCAACCTTACACTTAGGGGTCC CATCAAGGTTCAGCGGCAGTGGATCTGGGACAGAT TCACTCTCACCATCAGCAGCCTGCAGCCTGAAGA TTTTGCAACTTATTACTGTCAGCAGTATTATAACC TTCCGTGGACGTTCGGCCAAGGGACCAAGGTGGAA ATCAAACGTACGGTGGCTGCCACCATCTGTCTTCAT CTTCCCGCCATCTGATGAGCAGTTGAAATCTGGAA CTGCCTCTGTTGTGTGCCTGCTGAATAACTTCTAT CCCAGAGAGGCCAAAGTACAGTGGAAGGTGGATAA CGCCCTCCAATCGGGTAACTCCCAGGAGAGTGTCA CAGAGCAGGACAGCAAGGACAGCACCTACAGCCTC AGCAGCACCCTGACGCTGAGCAAAGCAGACTACGA GAAACACAAAGTCTACGCCTGCGAAGTCACCCATC AGGGCCTGAGCTCGCCCGTCACAAAGAGCTTCAAC AGGGGAGAGTGT |

BAP050-hum18-Ser HC

| SEQ ID NO: 1 (Kabat) | HCDR1 NYGMN |
|---|---|
| SEQ ID NO: 2 (Kabat) | HCDR2 WINTDTGEPTYADDFKG |
| SEQ ID NO: 3 (Kabat) | HCDR3 NPPYYYGTNNAEAMDY |
| SEQ ID NO: 4 (Chothia) | HCDR1 GFTLTNY |

| SEQ ID NO: 5 (Chothia) | | HCDR2 NTDTGE |
|---|---|---|
| SEQ ID NO: 3 (Chothia) | | HCDR3 NPPYYYGTNNAEAMDY |
| SEQ ID NO: 100 | VH | EVQLVQSGAEVKKPGATVKISCKVSGFTLTNYGMN WVRQAPGQGLEWMGWINTDTGEPTYADDFKGRFVF SLDTSVSTAYLQISSLKAEDTAVYYCARNPPYYYG TNNAEAMDYWGQGTTVTVSS |
| SEQ ID NO: 101 | DNA VH | GAGGTCCAGCTGGTACAGTCTGGGGCTGAGGTGAA GAAGCCTGGGGCTACAGTGAAAATCTCCTGCAAGG TTTCTGGATTTACCCTCACAAACTATGGAATGAAC TGGGTGCGACAGGCCCCTGGACAAGGGCTTGAGTG GATGGGTTGGATAAACACCGACACTGGAGAGCCAA CATATGCTGATGACTTCAAGGGAAGATTTGTCTTC TCCTTGGACACCTCTGTCAGCACGGCATATCTGCA GATCAGCAGCCTAAAGGCTGAGGACACTGCCGTGT ATTACTGTGCAAGAAACCCTCCTATTACTACGGT ACTAATAACGCGGAGGCTATGGACTACTGGGGCCA GGGCACCACCGTGACCGTGTCCTCC |
| SEQ ID NO: 102 | HC | EVQLVQSGAEVKKPGATVKISCKVSGFTLTNYGMN WVRQAPGQGLEWMGWINTDTGEPTYADDFKGRFVF SLDTSVSTAYLQISSLKAEDTAVYYCARNPPYYYG TNNAEAMDYWGQGTTVTVSSASTKGPSVFPLAPCS RSTSESTAALGCLVKDYFPEPVTVSWNSGALTSGV HTFPAVLQSSGLYSLSSVVTVPSSSLGTKTYTCNV DHKPSNTKVDKRVESKYGPPCPPCPAPEFLGGPSV FLFPPKPKDTLMISRTPEVTCVVVDVSQEDPEVQF NWYVDGVEVHNAKTKPREEQFNSTYRVVSVLTVLH QDWLNGKEYKCKVSNKGLPSSIEKTISKAKGQPRE PQVYTLPPSQEEMTKNQVSLTCLVKGFYPSDIAVE WESNGQPENNYKTTPPVLDSDGSFFLYSRLTVDKS RWQEGNVFSCSVMHEALHNHYTQKSLSLSLGK |
| SEQ ID NO: 103 | DNA HC | GAGGTCCAGCTGGTACAGTCTGGGGCTGAGGTGAA GAAGCCTGGGGCTACAGTGAAAATCTCCTGCAAGG TTTCTGGATTTACCCTCACAAACTATGGAATGAAC TGGGTGCGACAGGCCCCTGGACAAGGGCTTGAGTG GATGGGTTGGATAAACACCGACACTGGAGAGCCAA CATATGCTGATGACTTCAAGGGAAGATTTGTCTTC TCCTTGGACACCTCTGTCAGCACGGCATATCTGCA GATCAGCAGCCTAAAGGCTGAGGACACTGCCGTGT ATTACTGTGCAAGAAACCCTCCTATTACTACGGT ACTAATAACGCGGAGGCTATGGACTACTGGGGCCA GGGCACCACCGTGACCGTGTCCTCCACCA AGGGCCCATCCGTCTTCCCCCTGGCGCCCTGCTCC AGGAGCACCTCCGAGAGCACAGCCGCCCTGGGCTG CCTGGTCAAGGACTACTTCCCCGAACCGGTGACGG TGTCGTGGAACTCAGGCGCCCTGACCAGCGGCGTG CACACCTTCCCGGCTGTCCTACAGTCCTCAGGACT CTACTCCCTCAGCAGCGTGGTGACCGTGCCCTCCA GCAGCTTGGGCACGAAGACCTACACCTGCAACGTA GATCACAAGCCCAGCAACACCAAGGTGGACAAGAG AGTTGAGTCCAAATATGGTCCCCCATGCCCACCGT GCCCAGCACCTGAGTTCCTGGGGGGACCATCAGTC TTCCTGTTCCCCCCAAAACCCAAGGACACTCTCAT GATCTCCCGGACCCCTGAGGTCACGTGCGTGGTGG TGGACGTGAGCCAGGAAGACCCCGAGGTCCAGTTC AACTGGTACGTGGATGGCGTGGAGGTGCATAATGC CAAGACAAAGCCGCGGGAGGAGCAGTTCAACAGCA CGTACCGTGTGGTCAGCGTCCTCACCGTCCTGCAC CAGGACTGGCTGAACGGCAAGGAGTACAAGTGCAA |

TABLE 1-continued

Amino acid and nucleotide sequences for murine, chimeric and humanized antibody molecules. The antibody molecules include murine mAb BAP050, chimeric mAbs BAP050-chi, humanized mAbs BAP050-hum01 to BAP050-hum20, humanized mAbs BAP050-hum01-Ser to BAP050-hum15-Ser, BAP050-hum18-Ser to BAP050-hum20-Ser, and humanized mAbs BAP050-Clone-F to BAP050-Clone-J. The amino acid and nucleotide sequences of the heavy and light chain CDRs, the heavy and light chain variable regions, and the heavy and light chains are shown.

|  |  |
|---|---|
|  | GGTGTCCAACAAAGGCCTCCCGTCCTCCATCGAGA<br>AAACCATCTCCAAAGCCAAAGGGCAGCCCCGAGAG<br>CCACAGGTGTACACCCTGCCCCCATCCCAGGAGGA<br>GATGACCAAGAACCAGGTCAGCCTGACCTGCCTGG<br>TCAAAGGCTTCTACCCCAGCGACATCGCCGTGGAG<br>TGGGAGAGCAATGGGCAGCCGGAGAACAACTACAA<br>GACCACGCCTCCCGTGCTGGACTCCGACGGCTCCT<br>TCTTCCTCTACAGCAGGCTAACCGTGGACAAGAGC<br>AGGTGGCAGGAGGGGAATGTCTTCTCATGCTCCGT<br>GATGCATGAGGCTCTGCACAACCACTACACACAGA<br>AGAGCCTCTCCCTGTCTCTGGGTAAA |
| | BAP050-hum18-Ser LC |

| SEQ ID NO: 10 (Kabat) | LCDR1 SSSQDISNYLN |
|---|---|
| SEQ ID NO: 11 (Kabat) | LCDR2 YTSTLHL |
| SEQ ID NO: 12 (Kabat) | LCDR3 QQYYNLPWT |
| SEQ ID NO: 13 (Chothia) | LCDR1 SQDISNY |
| SEQ ID NO: 14 (Chothia) | LCDR2 YTS |
| SEQ ID NO: 15 (Chothia) | LCDR3 YYNLPW |
| SEQ ID NO: 88 | VL AIQLTQSPSSLSASVGDRVTITCSSSQDISNYLNW<br>YQQKPGQAPRLLIYYTSTLHLGVPSRFSGSGSGTD<br>FTLTISSLQPEDFATYYCQQYYNLPWTFGQGTKVE<br>IK |
| SEQ ID NO: 89 | DNA VL GCCATCCAGTTGACCCAGTCTCCATCCTCCCTGTC<br>TGCATCTGTAGGAGACAGAGTCACCATCACTTGCA<br>GTTCAAGTCAGGACATCAGCAATTATTTAAACTGG<br>TACCAGCAGAAACCTGGCCAGGCTCCCAGGCTCCT<br>CATCTATTACACATCAACCTTACACTTAGGGGTCC<br>CATCAAGGTTCAGCGGCAGTGGATCTGGGACAGAT<br>TTCACTCTCACCATCAGCAGCCTGCAGCCTGAAGA<br>TTTTGCAACTTATTACTGTCAGCAGTATTATAACC<br>TTCCGTGGACGTTCGGCCAAGGGACCAAGGTGGAA<br>ATCAAA |
| SEQ ID NO: 90 | LC AIQLTQSPSSLSASVGDRVTITCSSSQDISNYLNW<br>YQQKPGQAPRLLIYYTSTLHLGVPSRFSGSGSGTD<br>FTLTISSLQPEDFATYYCQQYYNLPWTFGQGTKVE<br>IKRTVAAPSVFIFPPSDEQLKSGTASVVCLLNNFY<br>PREAKVQWKVDNALQSGNSQESVTEQDSKDSTYSL<br>SSTLTLSKADYEKHKVYACEVTHQGLSSPVTKSFN<br>RGEC |
| SEQ ID NO: 91 | DNA LC GCCATCCAGTTGACCCAGTCTCCATCCTCCCTGTC<br>TGCATCTGTAGGAGACAGAGTCACCATCACTTGCA<br>GTTCAAGTCAGGACATCAGCAATTATTTAAACTGG<br>TACCAGCAGAAACCTGGCCAGGCTCCCAGGCTCCT<br>CATCTATTACACATCAACCTTACACTTAGGGGTCC<br>CATCAAGGTTCAGCGGCAGTGGATCTGGGACAGAT<br>TTCACTCTCACCATCAGCAGCCTGCAGCCTGAAGA<br>TTTTGCAACTTATTACTGTCAGCAGTATTATAACC<br>TTCCGTGGACGTTCGGCCAAGGGACCAAGGTGGAA<br>ATCAAACGTACGGTGGCTGCACCATCTGTCTTCAT<br>CTTCCCGCCATCTGATGAGCAGTTGAAATCTGGAA<br>CTGCCTCTGTTGTGTGCCTGCTGAATAACTTCTAT<br>CCCAGAGAGGCCAAAGTACAGTGGAAGGTGGATAA<br>CGCCCTCCAATCGGGTAACTCCCAGGAGAGTGTCA<br>CAGAGCAGGACAGCAAGGACAGCACCTACAGCCTC<br>AGCAGCACCCTGACGCTGAGCAAAGCAGACTACGA<br>GAAACACAAAGTCTACGCCTGCGAAGTCACCCATC<br>AGGGCCTGAGCTCGCCCGTCACAAAGAGCTTCAAC<br>AGGGGAGAGTGT |
| | BAP050-hum19-Ser HC |

| SEQ ID NO: 1 (Kabat) | HCDR1 NYGMN |
|---|---|
| SEQ ID NO: 2 (Kabat) | HCDR2 WINTDTGEPTYADDFKG |
| SEQ ID NO: 3 (Kabat) | HCDR3 NPPYYYGTNNAEAMDY |
| SEQ ID NO: 4 (Chothia) | HCDR1 GFTLTNY |
| SEQ ID NO: 5 (Chothia) | HCDR2 NTDTGE |
| SEQ ID NO: 3 (Chothia) | HCDR3 NPPYYYGTNNAEAMDY |
| SEQ ID NO: 100 | VH EVQLVQSGAEVKKPGATVKISCKVSGFTLTNYGMN<br>WVRQAPGQGLEWMGWINTDTGEPTYADDFKGRFVF<br>SLDTSVSTAYLQISSLKAEDTAVYYCARNPPYYYG<br>TNNAEAMDYWGQGTTVTVSS |
| SEQ ID NO: 101 | DNA VH GAGGTCCAGCTGGTACAGTCTGGGGCTGAGGTGAA<br>GAAGCCTGGGGCTACAGTGAAAATCTCCTGCAAGG<br>TTTCTGGATTTACCCTCACAAACTATGGAATGAAC<br>TGGGTGCGACAGGCCCCTGGACAAGGGCTTGAGTG<br>GATGGGTTGGATAAACACCGACACTGGAGAGCCAA<br>CATATGCTGATGACTTCAAGGGAAGATTTGTCTTC<br>TCCTTGGACACCTCTGTCAGCACGGCATATCTGCA<br>GATCAGCAGCCTAAAGGCTGAGGACACTGCCGTGT<br>ATTACTGTGCAAGAAACCCTCCCTATTACTACGGT<br>ACTAATAACGCGGAGGCTATGGACTACTGGGGCCA<br>GGGCACCACCGTGACCGTGTCCTCC |
| SEQ ID NO: 102 | HC EVQLVQSGAEVKKPGATVKISCKVSGFTLTNYGMN<br>WVRQAPGQGLEWMGWINTDTGEPTYADDFKGRFVF<br>SLDTSVSTAYLQISSLKAEDTAVYYCARNPPYYYG<br>TNNAEAMDYWGQGTTVTVSSASTKGPSVFPLAPCS<br>RSTSESTAALGCLVKDYFPEPVTVSWNSGALTSGV<br>HTFPAVLQSSGLYSLSSVVTVPSSSLGTKTYTCNV<br>DHKPSNTKVDKRVESKYGPPCPPCPAPEFLGGPSV<br>FLFPPKPKDTLMISRTPEVTCVVVDVSQEDPEVQF<br>NWYVDGVEVHNAKTKPREEQFNSTYRVVSVLTVLH |

TABLE 1-continued

Amino acid and nucleotide sequences for murine, chimeric and humanized antibody molecules. The antibody molecules include murine mAb BAP050, chimeric mAbs BAP050-chi, humanized mAbs BAP050-hum01 to BAP050-hum20, humanized mAbs BAP050-hum01-Ser to BAP050-hum15-Ser, BAP050-hum18-Ser to BAP050-hum20-Ser, and humanized mAbs BAP050-Clone-F to BAP050-Clone-J. The amino acid and nucleotide sequences of the heavy and light chain CDRs, the heavy and light chain variable regions, and the heavy and light chains are shown.

| | | |
|---|---|---|
| | | QDWLNGKEYKCKVSNKGLPSSIEKTISKAKGQPRE PQVYTLPPSQEEMTKNQVSLTCLVKGFYPSDIAVE WESNGQPENNYKTTPPVLDSDGSFFLYSRLTVDKS RWQEGNVFSCSVMHEALHNHYTQKSLSLSLGK |
| SEQ ID NO: 103 | DNA HC | GAGGTCCAGCTGGTACAGTCTGGGGCTGAGGTGAA GAAGCCTGGGGCTACAGTGAAAATCTCCTGCAAGG TTTCTGGATTTACCCTCACAAACTATGGAATGAAC TGGGTGCGACAGGCCCCTGGACAAGGGCTTGAGTG GATGGGTTGGATAAACACCGACACTGGAGAGCCAA CATATGCTGATGACTTCAAGGGAAGATTTGTCTTC TCCTTGGACACCTCTGTCAGCACGGCATATCTGCA GATCAGCAGCCTAAAGGCTGAGGACACTGCCGTGT ATTACTGTGCAAGAAACCCTCCCTATTACTACGGT ACTAATAACGCGGAGGCTATGGACTACTGGGGCCA GGGCACCACCGTGACCGTGTCCTCCGCTTCCACCA AGGGCCCATCCGTCTTCCCCCTGGCGCCCTGCTCC AGGAGCACCTCCGAGAGCACAGCCGCCCTGGGCTG CCTGGTCAAGGACTACTTCCCCGAACCGGTGACGG TGTCGTGGAACTCAGGCGCCCTGACCAGCGGCGTG CACACCTTCCCGGCTGTCCTACAGTCCTCAGGACT CTACTCCCTCAGCAGCGTGGTGACCGTGCCCTCCA GCAGCTTGGGCACGAAGACCTACACCTGCAACGTA GATCACAAGCCCAGCAACACCAAGGTGGACAAGAG AGTTGAGTCCAAATATGGTCCCCCATGCCCACCGT GCCCAGCACCTGAGTTCCTGGGGGGACCATCAGTC TTCCTGTTCCCCCCAAAACCCAAGGACACTCTCAT GATCTCCCGGACCCCTGAGGTCACGTGCGTGGTGG TGGACGTGAGCCAGGAAGACCCCGAGGTCCAGTTC AACTGGTACGTGGATGGCGTGGAGGTGCATAATGC CAAGACAAAGCCGCGGGAGGAGCAGTTCAACAGCA CGTACCGTGTGGTCAGCGTCCTCACCGTCCTGCAC CAGGACTGGCTGAACGGCAAGGAGTACAAGTGCAA GGTGTCCAACAAAGGCCTCCCGTCCTCCATCGAGA AAACCATCTCCAAAGCCAAAGGGCAGCCCCGAGAG CCACAGGTGTACACCCTGCCCCCATCCCAGGAGGA GATGACCAAGAACCAGGTCAGCCTGACCTGCCTGG TCAAAGGCTTCTACCCCAGCGACATCGCCGTGGAG TGGGAGAGCAATGGGCAGCCGGAGAACAACTACAA GACCACGCCTCCCGTGCTGGACTCCGACGGCTCCT TCTTCCTCTACAGCAGGCTAACCGTGGACAAGAGC AGGTGGCAGGAGGGGAATGTCTTCTCATGCTCCGT GATGCATGAGGCTCTGCACAACCACTACACACAGA AGAGCCTCTCCCTGTCTCTGGGTAAA |

BAP050-hum19-Ser LC

| | |
|---|---|
| SEQ ID NO: 10 (Kabat) | LCDR1 SSSQDISNYLN |
| SEQ ID NO: 11 (Kabat) | LCDR2 YTSTLHL |
| SEQ ID NO: 12 (Kabat) | LCDR3 QQYYNLPWT |
| SEQ ID NO: 13 (Chothia) | LCDR1 SQDISNY |
| SEQ ID NO: 14 (Chothia) | LCDR2 YTS |

TABLE 1-continued

Amino acid and nucleotide sequences for murine, chimeric and humanized antibody molecules. The antibody molecules include murine mAb BAP050, chimeric mAbs BAP050-chi, humanized mAbs BAP050-hum01 to BAP050-hum20, humanized mAbs BAP050-hum01-Ser to BAP050-hum15-Ser, BAP050-hum18-Ser to BAP050-hum20-Ser, and humanized mAbs BAP050-Clone-F to BAP050-Clone-J. The amino acid and nucleotide sequences of the heavy and light chain CDRs, the heavy and light chain variable regions, and the heavy and light chains are shown.

| | | |
|---|---|---|
| SEQ ID NO: 15 (Chothia) | LCDR3 | YYNLPW |
| SEQ ID NO: 92 | VL | EIVLTQSPDFQSVTPKEKVTITCSSSQDISNYLNW YQQKPGQAPRLLIYYTSTLHLGVPSRFSGSGSGTD FTFTISSLEAEDAATYYCQQYYNLPWTFGQGTKVE IK |
| SEQ ID NO: 93 | DNA VL | GAAATTGTGCTGACTCAGTCTCCAGACTTTCAGTC TGTGACTCCAAAGGAGAAAGTCACCATCACCTGCA GTTCAAGTCAGGACATCAGCAATTATTTAAACTGG TACCAGCAGAAACCTGGCCAGGCTCCCAGGCTCCT CATCTATTACACATCAACCTTACACTTAGGGGTCC CCTCGAGGTTCAGTGGCAGTGGATCTGGGACAGAT TTCACCTTTACCATCAGTAGCCTGGAAGCTGAAGA TGCTGCAACATATTACTGTCAGCAGTATTATAACC TTCCGTGGACGTTCGGCCAAGGGACCAAGGTGGAA ATCAAA |
| SEQ ID NO: 94 | LC | EIVLTQSPDFQSVTPKEKVTITCSSSQDISNYLNW YQQKPGQAPRLLIYYTSTLHLGVPSRFSGSGSGTD FTFTISSLEAEDAATYYCQQYYNLPWTFGQGTKVE IKRTVAAPSVFIFPPSDEQLKSGTASVVCLLNNFY PREAKVQWKVDNALQSGNSQESVTEQDSKDSTYSL SSTLTLSKADYEKHKVYACEVTHQGLSSPVTKSFN RGEC |
| SEQ ID NO: 95 | DNA LC | GAAATTGTGCTGACTCAGTCTCCAGACTTTCAGTC TGTGACTCCAAAGGAGAAAGTCACCATCACCTGCA GTTCAAGTCAGGACATCAGCAATTATTTAAACTGG TACCAGCAGAAACCTGGCCAGGCTCCCAGGCTCCT CATCTATTACACATCAACCTTACACTTAGGGGTCC CCTCGAGGTTCAGTGGCAGTGGATCTGGGACAGAT TTCACCTTTACCATCAGTAGCCTGGAAGCTGAAGA TGCTGCAACATATTACTGTCAGCAGTATTATAACC TTCCGTGGACGTTCGGCCAAGGGACCAAGGTGGAA ATCAAACGTACGGTGGCTGCACCATCTGTCTTCAT CTTCCCGCCATCTGATGAGCAGTTGAAATCTGGAA CTGCCTCTGTTGTGTGCCTGCTGAATAACTTCTAT CCCAGAGAGGCCAAAGTACAGTGGAAGGTGGATAA CGCCCTCCAATCGGGTAACTCCCAGGAGAGTGTCA CAGAGCAGGACAGCAAGGACAGCACCTACAGCCTC AGCAGCACCCTGACGCTGAGCAAAGCAGACTACGA GAAACACAAAGTCTACGCCTGCGAAGTCACCCATC AGGGCCTGAGCTCGCCCGTCACAAAGAGCTTCAAC AGGGGAGAGTGT |

BAP050-hum20-Ser HC

| | |
|---|---|
| SEQ ID NO: 1 (Kabat) | HCDR1 NYGMN |
| SEQ ID NO: 2 (Kabat) | HCDR2 WINTDTGEPTYADDFKG |
| SEQ ID NO: 3 (Kabat) | HCDR3 NPPYYYGTNNAEAMDY |
| SEQ ID NO: 4 (Chothia) | HCDR1 GFTLTNY |

TABLE 1-continued

Amino acid and nucleotide sequences for murine, chimeric and humanized antibody molecules. The antibody molecules include murine mAb BAP050, chimeric mAbs BAP050-chi, humanized mAbs BAP050-hum01 to BAP050-hum20, humanized mAbs BAP050-hum01-Ser to BAP050-hum15-Ser, BAP050-hum18-Ser to BAP050-hum20-Ser, and humanized mAbs BAP050-Clone-F to BAP050-Clone-J. The amino acid and nucleotide sequences of the heavy and light chain CDRs, the heavy and light chain variable regions, and the heavy and light chains are shown.

| SEQ ID NO: 5 (Chothia) | HCDR2 | NTDTGE |
|---|---|---|
| SEQ ID NO: 3 (Chothia) | HCDR3 | NPPYYYGTNNAEAMDY |
| SEQ ID NO: 104 | VH | QVQLVQSGAEVKKPGASVKVSCKASGFTLTNYGMN WVRQARGQRLEWIGWINTDTGEPTYADDFKGRFVF SLDTSVSTAYLQISSLKAEDTAVYYCARNPPYYYG TNNAEAMDYWGQGTTVTVSS |
| SEQ ID NO: 105 | DNA VH | CAGGTTCAGCTGGTGCAGTCTGGAGCTGAGGTGAA GAAGCCTGGGGCCTCAGTGAAGGTCTCCTGCAAGG CTTCTGGATTTACCCTCACAAACTATGGAATGAAC TGGGTGCGACAGGCTCGTGGACAACGCCTTGAGTG GATAGGTTGGATAAACACCGACACTGGAGAGCCAA CATATGCTGATGACTTCAAGGGAAGATTTGTCTTC TCCTTGGACACCTCTGTCAGCACGGCATATCTGCA GATCAGCAGCCTAAAGGCTGAGGACACTGCCGTGT ATTACTGTGCAAGAAACCCTCCCTATTACTACGGT ACTAATAACGCGGAGGCTATGGACTACTGGGGCCA GGGCACCACCGTGACCGTGTCCTCC |
| SEQ ID NO: 106 | HC | QVQLVQSGAEVKKPGASVKVSCKASGFTLTNYGMN WVRQARGQRLEWIGWINTDTGEPTYADDFKGRFVF SLDTSVSTAYLQISSLKAEDTAVYYCARNPPYYYG TNNAEAMDYWGQGTTVTVSSASTKGPSVFPLAPCS RSTSESTAALGCLVKDYFPEPVTVSWNSGALTSGV HTFPAVLQSSGLYSLSSVVTVPSSSLGTKTYTCNV DHKPSNTKVDKRVESKYGPPCPPCPAPEFLGGPSV FLFPPKPKDTLMISRTPEVTCVVVDVSQEDPEVQF NWYVDGVEVHNAKTKPREEQFNSTYRVVSVLTVLH QDWLNGKEYKCKVSNKGLPSSIEKTISKAKGQPRE PQVYTLPPSQEEMTKNQVSLTCLVKGFYPSDIAVE WESNGQPENNYKTTPPVLDSDGSFFLYSRLTVDKS RWQEGNVFSCSVMHEALHNHYTQKSLSLSLGK |
| SEQ ID NO: 107 | DNA HC | CAGGTTCAGCTGGTGCAGTCTGGAGCTGAGGTGAA GAAGCCTGGGGCCTCAGTGAAGGTCTCCTGCAAGG CTTCTGGATTTACCCTCACAAACTATGGAATGAAC TGGGTGCGACAGGCTCGTGGACAACGCCTTGAGTG GATAGGTTGGATAAACACCGACACTGGAGAGCCAA CATATGCTGATGACTTCAAGGGAAGATTTGTCTTC TCCTTGGACACCTCTGTCAGCACGGCATATCTGCA GATCAGCAGCCTAAAGGCTGAGGACACTGCCGTGT ATTACTGTGCAAGAAACCCTCCCTATTACTACGGT ACTAATAACGCGGAGGCTATGGACTACTGGGGCCA GGGCACCACCGTGACCGTGTCCTCCGCCTCCACCA AGGGCCCATCCGTCTTCCCCCTGGCGCCCTGCTCC AGGAGCACCTCCGAGAGCACAGCCGCCCTGGGCTG CCTGGTCAAGGACTACTTCCCCGAACCGGTGACGG TGTCGTGGAACTCAGGCGCCCTGACCAGCGGCGTG CACACCTTCCCGGCTGTCCTACAGTCCTCAGGACT CTACTCCCTCAGCAGCGTGGTGACCGTGCCCTCCA GCAGCTTGGGCACGAAGACCTACACCTGCAACGTA GATCACAAGCCCAGCAACACCAAGGTGGACAAGAG AGTTGAGTCCAAATATGGTCCCCCATGCCCACCGT GCCCAGCACCTGAGTTCCTGGGGGGACCATCAGTC TTCCTGTTCCCCCCAAAACCCAAGGACACTCTCAT GATCTCCCGGACCCCTGAGGTCACGTGCGTGGTGG TGGACGTGAGCCAGGAAGACCCCGAGGTCCAGTTC AACTGGTACGTGGATGGCGTGGAGGTGCATAATGC CAAGACAAAGCCGCGGGAGGAGCAGTTCAACAGCA CGTACCGTGTGGTCAGCGTCCTCACCGTCCTGCAC CAGGACTGGCTGAACGGCAAGGAGTACAAGTGCAA GGTGTCCAACAAAGGCCTCCCGTCCTCCATCGAGA AAACCATCTCCAAAGCCAAAGGGCAGCCCCGAGAG CCACAGGTGTACACCCTGCCCCCATCCCAGGAGGA GATGACCAAGAACCAGGTCAGCCTGACCTGCCTGG TCAAAGGCTTCTACCCCAGCGACATCGCCGTGGAG TGGGAGAGCAATGGGCAGCCGGAGAACAACTACAA GACCACGCCTCCCGTGCTGGACTCCGACGGCTCCT TCTTCCTCTACAGCAGGCTAACCGTGGACAAGAGC AGGTGGCAGGAGGGGAATGTCTTCTCATGCTCCGT GATGCATGAGGCTCTGCACAACCACTACACAGAGA AGAGCCTCTCCCTGTCTCTGGGTAAA |

BAP050-hum20-Ser LC

| SEQ ID NO: 10 (Kabat) | LCDR1 | SSSQDISNYLN |
|---|---|---|
| SEQ ID NO: 11 (Kabat) | LCDR2 | YTSTLHL |
| SEQ ID NO: 12 (Kabat) | LCDR3 | QQYYNLPWT |
| SEQ ID NO: 13 (Chothia) | LCDR1 | SQDISNY |
| SEQ ID NO: 14 (Chothia) | LCDR2 | YTS |
| SEQ ID NO: 15 (Chothia) | LCDR3 | YYNLPW |
| SEQ ID NO: 96 | VL | DIVMTQTPLSLPVTPGEPASISCSSSQDISNYLNW YQQKPGQAPRLLIYYTSTLHLGIPDRFSGSGSGTD FTLTISRLEPEDFAVYYCQQYYNLPWTFGQGTKVE IK |
| SEQ ID NO: 97 | DNA VL | GATATTGTGATGACCCAGACTCCACTCTCCCTGCC CGTCACCCCTGGAGAGCCGGCCTCCATCTCCTGCA GTTCAAGTCAGGACATCAGCAATTATTTAAACTGG TACCAGCAGAAACCTGGCCAGGCTCCCAGGCTCCT CATCTATTACACATCAACCTTACACTTAGGGATCC CAGACAGGTTCAGTGGCAGTGGGTCTGGGACAGAC TTCACTCTCACCATCAGCAGACTGGAGCCTGAAGA TTTTGCAGTGTATTACTGTCAGCAGTATTATAACC TTCCGTGGACGTTCGGCCAAGGGACCAAGGTGGAA ATCAAA |
| SEQ ID NO: 98 | LC | DIVMTQTPLSLPVTPGEPASISCSSSQDISNYLNW YQQKPGQAPRLLIYYTSTLHLGIPDRFSGSGSGTD FTLTISRLEPEDFAVYYCQQYYNLPWTFGQGTKVE IKRTVAAPSVFIFPPSDEQLKSGTASVVCLLNNFY PREAKVQWKVDNALQSGNSQESVTEQDSKDSTYSL SSTLTLSKADYEKHKVYACEVTHQGLSSPVTKSFN RGEC |
| SEQ ID NO: 99 | DNA LC | GATATTGTGATGACCCAGACTCCACTCTCCCTGCC CGTCACCCCTGGAGAGCCGGCCTCCATCTCCTGCA GTTCAAGTCAGGACATCAGCAATTATTTAAACTGG TACCAGCAGAAACCTGGCCAGGCTCCCAGGCTCCT CATCTATTACACATCAACCTTACACTTAGGGATCC |

TABLE 1-continued

Amino acid and nucleotide sequences for murine, chimeric and humanized antibody molecules. The antibody molecules include murine mAb BAP050, chimeric mAbs BAP050-chi, humanized mAbs BAP050-hum01 to BAP050-hum20, humanized mAbs BAP050-hum01-Ser to BAP050-hum15-Ser, BAP050-hum18-Ser to BAP050-hum20-Ser, and humanized mAbs BAP050-Clone-F to BAP050-Clone-J. The amino acid and nucleotide sequences of the heavy and light chain CDRs, the heavy and light chain variable regions, and the heavy and light chains are shown.

| | | |
|---|---|---|
| | | CAGACAGGTTCAGTGGCAGTGGGTCTGGGACAGAC<br>TTCACTCTCACCATCAGCAGACTGGAGCCTGAAGA<br>TTTTGCAGTGTATTACTGTCAGCAGTATTATAACC<br>TTCCGTGGACGTTCGGCCAAGGGACCAAGGTGAA<br>ATCAAACGTACGGTGGCTGCACCATCTGTCTTCAT<br>CTTCCCGCCATCTGATGAGCAGTTGAAATCTGGAA<br>CTGCCTCTGTTGTGTGCCTGCTGAATAACTTCTAT<br>CCCAGAGAGGCCAAAGTACAGTGGAAGGTGGATAA<br>CGCCCTCCAATCGGGTAACTCCCAGGAGAGTGTCA<br>CAGAGCAGGACAGCAAGGACAGCACCTACAGCCTC<br>AGCAGCACCCTGACGCTGAGCAAAGCAGACTACGA<br>GAAACAAAGTCTACGCCTGCGAAGTCACCCATC<br>AGGGCCTGAGCTCGCCCGTCACAAAGAGCTTCAAC<br>AGGGGAGAGTGT |

| | | BAP050-Clone-F HC |
|---|---|---|
| SEQ ID NO: 1 (Kabat) | HCDR1 | NYGMN |
| SEQ ID NO: 2 (Kabat) | HCDR2 | WINTDTGEPTYADDFKG |
| SEQ ID NO: 3 (Kabat) | HCDR3 | NPPYYYGTNNAEAMDY |
| SEQ ID NO: 4 (Chothia) | HCDR1 | GFTLTNY |
| SEQ ID NO: 5 (Chothia) | HCDR2 | NTDTGE |
| SEQ ID NO: 3 (Chothia) | HCDR3 | NPPYYYGTNNAEAMDY |
| SEQ ID NO: 100 | VH | EVQLVQSGAEVKKPGATVKISCKVSGFTLTNYGMN<br>WVRQAPGQGLEWMGWINTDTGEPTYADDFKGRFVF<br>SLDTSVSTAYLQISSLKAEDTAVYYCARNPPYYYG<br>TNNAEAMDYWGQGTTVTVSS |
| SEQ ID NO: 112 | DNA VH | GAAGTGCAGCTGGTGCAGTCTGGCGCCGAAGTGAA<br>GAAACCCGGCGCTACCGTGAAGATCTCCTGCAAGG<br>TGTCCGGCTTCACCCTGACCAACTACGGCATGAAC<br>TGGGTGCGACAGGCCCCTGGACAGGGCCTGGAATG<br>GATGGGCTGGATCAACACCGACACCGGCGAGCCTA<br>CCTACGCCGACGACTTCAAGGGCAGATTCGTGTTC<br>TCCCTGGACACCTCCGTGTCCACCGCCTACCTGCA<br>GATCTCCAGCCTGAAGGCCGAGGATACCGCCGTGT<br>ACTACTGCGCCCGGAACCCCCCTTACTACTACGGC<br>ACCAACAACGCCGAGGCCATGGACTATTGGGGCCA<br>GGGCACCACCGTGACCGTGTCCTCT |
| SEQ ID NO: 113 | HC | EVQLVQSGAEVKKPGATVKISCKVSGFTLTNYGMN<br>WVRQAPGQGLEWMGWINTDTGEPTYADDFKGRFVF<br>SLDTSVSTAYLQISSLKAEDTAVYYCARNPPYYYG<br>TNNAEAMDYWGQGTTVTVSSASTKGPSVFPLAPCS<br>RSTSESTAALGCLVKDYFPEPVTVSWNSGALTSGV<br>HTFPAVLQSSGLYSLSSVVTVPSSSLGTKTYTCNV<br>DHKPSNTKVDKRVESKYGPPCPPCPAPEFLGGPSV<br>FLFPPKPKDTLMISRTPEVTCVVVDVSQEDPEVQF<br>NWYVDGVEVHNAKTKPREEQFNSTYRVVSVLTVLH |
| | | QDWLNGKEYKCKVSNKGLPSSIEKTISKAKGQPRE<br>PQVYTLPPSQEEMTKNQVSLTCLVKGFYPSDIAVE<br>WESNGQPENNYKTTPPVLDSDGSFFLYSRLTVDKS<br>RWQEGNVFSCSVMHEALHNHYTQKSLSLSLG |
| SEQ ID NO: 114 | DNA HC | GAAGTGCAGCTGGTGCAGTCTGGCGCCGAAGTGAA<br>GAAACCCGGCGCTACCGTGAAGATCTCCTGCAAGG<br>TGTCCGGCTTCACCCTGACCAACTACGGCATGAAC<br>TGGGTGCGACAGGCCCCTGGACAGGGCCTGGAATG<br>GATGGGCTGGATCAACACCGACACCGGCGAGCCTA<br>CCTACGCCGACGACTTCAAGGGCAGATTCGTGTTC<br>TCCCTGGACACCTCCGTGTCCACCGCCTACCTGCA<br>GATCTCCAGCCTGAAGGCCGAGGATACCGCCGTGT<br>ACTACTGCGCCCGGAACCCCCCTTACTACTACGGC<br>ACCAACAACGCCGAGGCCATGGACTATTGGGGCCA<br>GGGCACCACCGTGACCGTGTCCTCTGCTTCTACCA<br>AGGGGCCCAGCGTGTTCCCCCTGGCCCCCTGCTCC<br>AGAAGCACCAGCGAGAGCACAGCCGCCCTGGGCTG<br>CCTGGTGAAGGACTACTTCCCCGAGCCCGTGACCG<br>TGTCCTGGAACAGCGGAGCCCTGACCAGCGGCGTG<br>CACACCTTCCCCGCCGTGCTGCAGAGCAGCGGCCT<br>GTACAGCCTGAGCAGCGTGGTGACCGTGCCCAGCA<br>GCAGCCTGGGCACCAAGACCTACACCTGTAACGTG<br>GACCACAAGCCCAGCAACACCAAGGTGGACAAGAG<br>GGTGGAGAGCAAGTACGGCCCACCCTGCCCCCCCT<br>GCCCAGCCCCCGAGTTCCTGGGCGGACCCAGCGTG<br>TTCCTGTTCCCCCCCAAGCCCAAGGACACCCTGAT<br>GATCAGCAGAACCCCCGAGGTGACCTGTGTGGTGG<br>TGGACGTGTCCCAGGAGGACCCCGAGGTCCAGTTC<br>AACTGGTACGTGGACGGCGTGGAGGTGCACAACGC<br>CAAGACCAAGCCCAGAGAGGAGCAGTTTAACAGCA<br>CCTACCGGGTGGTGTCCGTGCTGACCGTGCTGCAC<br>CAGGACTGGCTGAACGGCAAAGAGTACAAGTGTAA<br>GGTCTCCAACAAGGGCCTGCCAAGCAGCATCGAAA<br>AGACCATCAGCAAGGCCAAGGGCCAGCCTAGAGAG<br>CCCCAGGTCTACACCCTGCCACCCAGCCAAGAGGA<br>GATGACCAAGAACCAGGTGTCCCTGACCTGTCTGG<br>TGAAGGGCTTCTACCCAAGCGACATCGCCGTGGAG<br>TGGGAGAGCAACGGCCAGCCCGAGAACAACTACAA<br>GACCACCCCCCCAGTGCTGGACAGCGACGGCAGCT<br>TCTTCCTGTACAGCAGGCTGACCGTGGACAAGTCC<br>AGATGGCAGGAGGGCAACGTCTTTAGCTGCTCCGT<br>GATGCACGAGGCCCTGCACAACCACTACACCCAGA<br>AGAGCCTGAGCCTGTCCCTGGGC |

| | | BAP050-Clone-F LC |
|---|---|---|
| SEQ ID NO: 10 (Kabat) | LCDR1 | SSSQDISNYLN |
| SEQ ID NO: 11 (Kabat) | LCDR2 | YTSTLHL |
| SEQ ID NO: 12 (Kabat) | LCDR3 | QQYYNLPWT |
| SEQ ID NO: 13 (Chothia) | LCDR1 | SQDISNY |
| SEQ ID NO: 14 (Chothia) | LCDR2 | YTS |

TABLE 1-continued

Amino acid and nucleotide sequences for murine, chimeric and humanized antibody molecules. The antibody molecules include murine mAb BAP050, chimeric mAbs BAP050-chi, humanized mAbs BAP050-hum01 to BAP050-hum20, humanized mAbs BAP050-hum01-Ser to BAP050-hum15-Ser, BAP050-hum18-Ser to BAP050-hum20-Ser, and humanized mAbs BAP050-Clone-F to BAP050-Clone-J. The amino acid and nucleotide sequences of the heavy and light chain CDRs, the heavy and light chain variable regions, and the heavy and light chains are shown.

| SEQ ID NO: 15 (Chothia) | | LCDR3 YYNLPW |
|---|---|---|
| SEQ ID NO: 32 | VL | DIQMTQSPSSLSASVGDRVTITCSSSQDISNYLNW YQQKPGKAPKLLIYYTSTLHLGVPSRFSGSGSGTD FTFTISSLEAEDAATYYCQQYYNLPWTFGQGTKVE IK |
| SEQ ID NO: 115 | DNA VL | GACATCCAGATGACCCAGTCCCCCTCCAGCCTGTC TGCTTCCGTGGGCGACAGAGTGACCATCACCTGTT CCTCCAGCCAGGACATCTCCAACTACCTGAACTGG TATCAGCAGAAGCCCGGCAAGGCCCCCAAGCTGCT GATCTACTACACCTCCACCCTGCACCTGGGCGTGC CCTCCAGATTTTCCGGCTCTGGCTCTGGCACCGAC TTTACCTTCACCATCAGCTCCCTGGAAGCCGAGGA CGCCGCCACCTACTACTGCCAGCAGTACTACAACC TGCCCTGGACCTTCGGCCAGGGCACCAAGGTGGAA ATCAAG |
| SEQ ID NO: 34 | LC | DIQMTQSPSSLSASVGDRVTITCSSSQDISNYLNW YQQKPGKAPKLLIYYTSTLHLGVPSRFSGSGSGTD FTFTISSLEAEDAATYYCQQYYNLPWTFGQGTKVE IKRTVAAPSVFIFPPSDEQLKSGTASVVCLLNNFY PREAKVQWKVDNALQSGNSQESVTEQDSKDSTYSL SSTLTLSKADYEKHKVYACEVTHQGLSSPVTKSFN RGEC |
| SEQ ID NO: 117 | DNA LC | GACATCCAGATGACCCAGTCCCCCTCCAGCCTGTC TGCTTCCGTGGGCGACAGAGTGACCATCACCTGTT CCTCCAGCCAGGACATCTCCAACTACCTGAACTGG TATCAGCAGAAGCCCGGCAAGGCCCCCAAGCTGCT GATCTACTACACCTCCACCCTGCACCTGGGCGTGC CCTCCAGATTTTCCGGCTCTGGCTCTGGCACCGAC TTTACCTTCACCATCAGCTCCCTGGAAGCCGAGGA CGCCGCCACCTACTACTGCCAGCAGTACTACAACC TGCCCTGGACCTTCGGCCAGGGCACCAAGGTGGAA ATCAAGCGTACGGTGGCCGCTCCCAGCGTGTTCAT CTTCCCCCCAAGCGACGAGCAGCTGAAGAGCGGCA CCGCCAGCGTGGTGTGTCTGCTGAACAACTTCTAC CCCAGGGAGGCCAAGGTGCAGTGGAAGGTGGACAA CGCCCTGCAGAGCGGCAACAGCCAGGAGAGCGTCA CCGAGCAGGACAGCAAGGACTCCACCTACAGCCTG AGCAGCACCCTGACCCTGAGCAAGGCCGACTACGA GAAGCACAAGGTGTACGCCTGTGAGGTGACCCACC AGGGCCTGTCCAGCCCCGTGACCAAGAGCTTCAAC AGGGGCGAGTGC |

BAP050-Clone-G HC

| SEQ ID NO: 1 (Kabat) | HCDR1 NYGMN |
|---|---|
| SEQ ID NO: 2 (Kabat) | HCDR2 WINTDTGEPTYADDFKG |
| SEQ ID NO: 3 (Kabat) | HCDR3 NPPYYYGTNNAEAMDY |
| SEQ ID NO: 4 (Chothia) | HCDR1 GFTLTNY |

TABLE 1-continued

Amino acid and nucleotide sequences for murine, chimeric and humanized antibody molecules. The antibody molecules include murine mAb BAP050, chimeric mAbs BAP050-chi, humanized mAbs BAP050-hum01 to BAP050-hum20, humanized mAbs BAP050-hum01-Ser to BAP050-hum15-Ser, BAP050-hum18-Ser to BAP050-hum20-Ser, and humanized mAbs BAP050-Clone-F to BAP050-Clone-J. The amino acid and nucleotide sequences of the heavy and light chain CDRs, the heavy and light chain variable regions, and the heavy and light chains are shown.

| SEQ ID NO: 5 (Chothia) | | HCDR2 NTDTGE |
|---|---|---|
| SEQ ID NO: 3 (Chothia) | | HCDR3 NPPYYYGTNNAEAMDY |
| SEQ ID NO: 100 | VH | EVQLVQSGAEVKKPGATVKISCKVSGFTLTNYGMN WVRQAPGQGLEWMGWINTDTGEPTYADDFKGRFVF SLDTSVSTAYLQISSLKAEDTAVYYCARNPPYYYG TNNAEAMDYWGQGTTVTVSS |
| SEQ ID NO: 112 | DNA VH | GAAGTGCAGCTGGTGCAGTCTGGCGCCGAAGTGAA GAAACCCGGCGCTACCGTGAAGATCTCCTGCAAGG TGTCCGGCTTCACCCTGACCAACTACGGCATGAAC TGGGTGCGACAGGCCCCTGGACAGGGCCTGGAATG GATGGGCTGGATCAACACCGACACCGGCGAGCCTA CCTACGCCGACGACTTCAAGGGCAGATTCGTGTTC TCCCTGGACACCTCCGTGTCCACCGCCTACCTGCA GATCTCCAGCCTGAAGGCCGAGGATACCGCCGTGT ACTACTGCGCCCGGAACCCCCCTTACTACTACGGC ACCAACAACGCCGAGGCCATGGACTATTGGGGCCA GGGCACCACCGTGACCGTGTCCTCT |
| SEQ ID NO: 113 | HC | EVQLVQSGAEVKKPGATVKISCKVSGFTLTNYGMN WVRQAPGQGLEWMGWINTDTGEPTYADDFKGRFVF SLDTSVSTAYLQISSLKAEDTAVYYCARNPPYYYG TNNAEAMDYWGQGTTVTVSSASTKGPSVFPLAPCS RSTSESTAALGCLVKDYFPEPVTVSWNSGALTSGV HTFPAVLQSSGLYSLSSVVTVPSSSLGTKTYTCNV DHKPSNTKVDKRVESKYGPPCPPCPAPEFLGGPSV FLFPPKPKDTLMISRTPEVTCVVVDVSQEDPEVQF NWYVDGVEVHNAKTKPREEQFNSTYRVVSVLTVLH QDWLNGKEYKCKVSNKGLPSSIEKTISKAKGQPRE PQVYTLPPSQEEMTKNQVSLTCLVKGFYPSDIAVE WESNGQPENNYKTTPPVLDSDGSFFLYSRLTVDKS RWQEGNVFSCSVMHEALHNHYTQKSLSLSLG |
| SEQ ID NO: 114 | DNA HC | GAAGTGCAGCTGGTGCAGTCTGGCGCCGAAGTGAA GAAACCCGGCGCTACCGTGAAGATCTCCTGCAAGG TGTCCGGCTTCACCCTGACCAACTACGGCATGAAC TGGGTGCGACAGGCCCCTGGACAGGGCCTGGAATG GATGGGCTGGATCAACACCGACACCGGCGAGCCTA CCTACGCCGACGACTTCAAGGGCAGATTCGTGTTC TCCCTGGACACCTCCGTGTCCACCGCCTACCTGCA GATCTCCAGCCTGAAGGCCGAGGATACCGCCGTGT ACTACTGCGCCCGGAACCCCCCTTACTACTACGGC ACCAACAACGCCGAGGCCATGGACTATTGGGGCCA GGGCACCACCGTGACCGTGTCCTCTGCTTCTACCA AGGGGCCCAGCGTGTTCCCCCTGGCCCCCTGCTCC AGAAGCACCAGCGAGAGCACAGCCGCCCTGGGCTG CCTGGTGAAGGACTACTTCCCCGAGCCCGTGACCG TGTCCTGGAACAGCGGAGCCCTGACCAGCGGCGTG CACACCTTCCCCGCCGTGCTGCAGAGCAGCGGCCT GTACAGCCTGAGCAGCGTGGTGACCGTGCCCAGCA GCAGCCTGGGCACCAAGACCTACACCTGTAACGTG GACCACAAGCCCAGCAACACCAAGGTGGACAAGAG GGTGGAGAGCAAGTACGGCCCACCCTGCCCCCCCT GCCCAGCCCCCGAGTTCCTGGGCGGACCCAGCGTG TTCCTGTTCCCCCCCAAGCCCAAGGACACCCTGAT GATCAGCAGAACCCCCGAGGTGACCTGTGTGGTGG TGGACGTGTCCCAGGAGGACCCCGAGGTCCAGTTC AACTGGTACGTGGACGGCGTGGAGGTGCACAACGC CAAGACCAAGCCCAGAGAGGAGCAGTTTAACAGCA CCTACCGGGTGGTGTCCGTGCTGACCGTGCTGCAC CAGGACTGGCTGAACGGCAAGGAGTACAAGTGTAA |

TABLE 1-continued

Amino acid and nucleotide sequences for murine, chimeric and humanized antibody molecules. The antibody molecules include murine mAb BAP050, chimeric mAbs BAP050-chi, humanized mAbs BAP050-hum01 to BAP050-hum20, humanized mAbs BAP050-hum01-Ser to BAP050-hum15-Ser, BAP050-hum18-Ser to BAP050-hum20-Ser, and humanized mAbs BAP050-Clone-F to BAP050-Clone-J. The amino acid and nucleotide sequences of the heavy and light chain CDRs, the heavy and light chain variable regions, and the heavy and light chains are shown.

|  |  |
|---|---|
|  | GGTCTCCAACAAGGGCCTGCCAAGCAGCATCGAAA<br>AGACCATCAGCAAGGCCAAGGGCCAGCCTAGAGAG<br>CCCCAGGTCTACACCCTGCCACCCAGCCAAGAGGA<br>GATGACCAAGAACCAGGTGTCCCTGACCTGTCTGG<br>TGAAGGGCTTCTACCCAAGCGACATCGCCGTGGAG<br>TGGGAGAGCAACGGCCAGCCGAGAACAACTACAA<br>GACCACCCCCCCAGTGCTGGACAGCGACGGCAGCT<br>TCTTCCTGTACAGCAGGCTGACCGTGGACAAGTCC<br>AGATGGCAGGAGGGCAACGTCTTTAGCTGCTCCGT<br>GATGCACGAGGCCCTGCACAACCACTACACCCAGA<br>AGAGCCTGAGCCTGTCCCTGGGC |
|  | BAP050-Clone-G LC |

| SEQ ID NO: 10 (Kabat) | LCDR1 SSSQDISNYLN |
|---|---|
| SEQ ID NO: 11 (Kabat) | LCDR2 YTSTLHL |
| SEQ ID NO: 12 (Kabat) | LCDR3 QQYYNLPWT |
| SEQ ID NO: 13 (Chothia) | LCDR1 SQDISNY |
| SEQ ID NO: 14 (Chothia) | LCDR2 YTS |
| SEQ ID NO: 15 (Chothia) | LCDR3 YYNLPW |
| SEQ ID NO: 36 | VL DIQMTQSPSSLSASVGDRVTITCSSSQDISNYLNW YQQKPGKAPKLLIYYTSTLHLGIPPRFSGSGYGTD FTLTINNIESEDAAYYFCQQYYNLPWTFGQGTKVE IK |
| SEQ ID NO: 118 | DNA VL GACATCCAGATGACCCAGTCCCCCTCCAGCCTGTC TGCTTCCGTGGGCGACAGAGTGACCATCACCTGTT CCTCCAGCCAGGACATCTCCAACTACCTGAACTGG TATCAGCAGAAGCCCGGCAAGGCCCCCAAGCTGCT GATCTACTACACCTCCACCCTGCACCTGGGCATCC CCCCTAGATTCTCCGGCTCTGGCTACGGCACCGAC TTCACCCTGACCATCAACAACATCGAGTCCGAGGA CGCCGCCTACTACTTCTGCCAGCAGTACTACAACC TGCCCTGGACCTTCGGCCAGGGCACCAAGGTGGAA ATCAAG |
| SEQ ID NO: 38 | LC DIQMTQSPSSLSASVGDRVTITCSSSQDISNYLNW YQQKPGKAPKLLIYYTSTLHLGIPPRFSGSGYGTD FTLTINNIESEDAAYYFCQQYYNLPWTFGQGTKVE IKRTVAAPSVFIFPPSDEQLKSGTASVVCLLNNFY PREAKVQWKVDNALQSGNSQESVTEQDSKDSTYSL SSTLTLSKADYEKHKVYACEVTHQGLSSPVTKSFN RGEC |
| SEQ ID NO: 120 | DNA LC GACATCCAGATGACCCAGTCCCCCTCCAGCCTGTC TGCTTCCGTGGGCGACAGAGTGACCATCACCTGTT CCTCCAGCCAGGACATCTCCAACTACCTGAACTGG TATCAGCAGAAGCCCGGCAAGGCCCCCAAGCTGCT GATCTACTACACCTCCACCCTGCACCTGGGCATCC CCCCTAGATTCTCCGGCTCTGGCTACGGCACCGAC TTCACCCTGACCATCAACAACATCGAGTCCGAGGA CGCCGCCTACTACTTCTGCCAGCAGTACTACAACC TGCCCTGGACCTTCGGCCAGGGCACCAAGGTGGAA ATCAAGCGTACGGTGGCCGCTCCCAGCGTGTTCAT CTTCCCCCCAAGCGACGAGCAGCTGAAGAGCGGCA CCGCCAGCGTGGTGTGTCTGCTGAACAACTTCTAC CCCAGGGAGGCCAAGGTGCAGTGGAAGGTGGACAA CGCCCTGCAGAGCGGCAACAGCCAGGAGAGCGTCA CCGAGCAGGACAGCAAGGACTCCACCTACAGCCTG AGCAGCACCCTGACCCTGAGCAAGGCCGACTACGA GAAGCACAAGGTGTACGCCTGTGAGGTGACCCACC AGGGCCTGTCCAGCCCCGTGACCAAGAGCTTCAAC AGGGGCGAGTGCTGATGAATTC |
|  | BAP050-Clone-H HC |

| SEQ ID NO: 1 (Kabat) | HCDR1 NYGMN |
|---|---|
| SEQ ID NO: 2 (Kabat) | HCDR2 WINTDTGEPTYADDFKG |
| SEQ ID NO: 3 (Kabat) | HCDR3 NPPYYYGTNNAEAMDY |
| SEQ ID NO: 4 (Chothia) | HCDR1 GFTLTNY |
| SEQ ID NO: 5 (Chothia) | HCDR2 NTDTGE |
| SEQ ID NO: 3 (Chothia) | HCDR3 NPPYYYGTNNAEAMDY |
| SEQ ID NO: 104 | VH QVQLVQSGAEVKKPGASVKVSCKASGFTLTNYGMN WVRQARGQRLEWIGWINTDTGEPTYADDFKGRFVF SLDTSVSTAYLQISSLKAEDTAVYYCARNPPYYYG TNNAEAMDYWGQGTTVTVSS |
| SEQ ID NO: 121 | DNA VH CAGGTGCAGCTGGTGCAGTCTGGCGCCGAAGTGAA GAAACCTGGCGCCTCCGTGAAGGTGTCCTGCAAGG CCTCTGGCTTCACCCTGACCAACTACGGCATGAAC TGGGTGCGACAGGCCAGGGCCCAGCGGCTGGAATG GATCGGCTGGATCAACACCGACACCGGCGAGCCTA CCTACGCCGACGACTTCAAGGGCAGATTCGTGTTC TCCCTGGACACCTCCGTGTCCACCGCCTACCTGCA GATCTCCAGCCTGAAGGCCGAGGATACCGCCGTGT ACTACTGCGCCCGGAACCCCCCTTACTACTACGGC ACCAACAACGCCGAGGCCATGGACTATTGGGGCCA GGGCACCACCGTGACCGTGTCCTCT |
| SEQ ID NO: 122 | HC QVQLVQSGAEVKKPGASVKVSCKASGFTLTNYGMN WVRQARGQRLEWIGWINTDTGEPTYADDFKGRFVF SLDTSVSTAYLQISSLKAEDTAVYYCARNPPYYYG TNNAEAMDYWGQGTTVTVSSASTKGPSVFPLAPCS RSTSESTAALGCLVKDYFPEPVTVSWNSGALTSGV HTFPAVLQSSGLYSLSSVVTVPSSSLGTKTYTCNV DHKPSNTKVDKRVESKYGPPCPPCPAPEFLGGPSV FLFPPKPKDTLMISRTPEVTCVVVDVSQEDPEVQF NWYVDGVEVHNAKTKPREEQFNSTYRVVSVLTVLH |

TABLE 1-continued

Amino acid and nucleotide sequences for murine, chimeric and humanized antibody molecules. The antibody molecules include murine mAb BAP050, chimeric mAbs BAP050-chi, humanized mAbs BAP050-hum01 to BAP050-hum20, humanized mAbs BAP050-hum01-Ser to BAP050-hum15-Ser, BAP050-hum18-Ser to BAP050-hum20-Ser, and humanized mAbs BAP050-Clone-F to BAP050-Clone-J. The amino acid and nucleotide sequences of the heavy and light chain CDRs, the heavy and light chain variable regions, and the heavy and light chains are shown.

| | | |
|---|---|---|
| | | QDWLNGKEYKCKVSNKGLPSSIEKTISKAKGQPRE PQVYTLPPSQEEMTKNQVSLTCLVKGFYPSDIAVE WESNGQPENNYKTTPPVLDSDGSFFLYSRLTVDKS RWQEGNVFSCSVMHEALHNHYTQKSLSLSLG |
| SEQ ID NO: 123 | DNA HC | CAGGTGCAGCTGGTGCAGTCTGGCGCCGAAGTGAA GAAACCTGGCGCCTCCGTGAAGGTGTCCTGCAAGG CCTCTGGCTTCACCCTGACCAACTACGGCATGAAC TGGGTGCGACAGGCCAGGGGCCAGCGGCTGGAATG GATCGGCTGGATCAACACCGACACCGGCGAGCCTA CCTACGCCGACGACTTCAAGGGCAGATTCGTGTTC TCCCTGGACACCTCCGTGTCCACCGCCTACCTGCA GATCTCCAGCCTGAAGGCCGAGGATACCGCCGTGT ACTACTGCGCCCGGAACCCCCCTTACTACTACGGC ACCAACAACGCCGAGGCCATGGACTATTGGGGCCA GGGCACCACCGTGACCGTGTCCTGCTTCTACCA AGGGGCCCAGCGTGTTCCCCCTGGCCCCCTGCTCC AGAAGCACCAGCGAGAGCACAGCCGCCCTGGGCTG CCTGGTGAAGGACTACTTCCCCGAGCCCGTGACCG TGTCCTGGAACAGCGGAGCCCTGACCAGCGGCGTG CACACCTTCCCCGCCGTGCTGCAGAGCAGCGGCCT GTACAGCCTGAGCAGCGTGGTGACCGTGCCCAGCA GCAGCCTGGGCACCAAGACCTACACCTGTAACGTG GACCACAAGCCCAGCAACACCAAGGTGGACAAGAG GGTGGAGCCAAGTACGGCCCAGCTCTCCCCCCT GCCCAGCCCCGAGTTCCTGGGCGGACCCAGCGTG TTCCTGTTCCCCCCCAAGCCCAAGGACACCCTGAT GATCAGCAGAACCCCCGAGGTGACCTGTGTGGTGG TGGACGTGTCCAGGAGGACCCCGAGGTCCAGTTC AACTGGTACGTGGACGGCGTGGAGGTGCACAACGC CAAGACCAAGCCCAGAGAGGAGCAGTTTAACAGCA CCTACCGGGTGGTGTCCGTGCTGACCGTGCTGCAC CAGGACTGGCTGAACGGCAAAGAGTACAAGTGTAA GGTCTCCAACAAGGGCCTGCCAAGCAGCATCGAAA AGACCATCTCCAAGGCCAAGGGCCAGCCTAGAGAG CCCCAGGTCTACACCCTGCCACCCAGCCAAGAGGA GATGACCAAGAACCAGGTGTCCCTGACCTGTCTGG TGAAGGGCTTCTACCCCAAGCGACATCGCCGTGGAG TGGGAGAGCAACGGCCAGCCCGAGAACAACTACAA GACCACCCCCCCAGTGCTGGACAGCGACGGCAGCT TCTTCCTGTACAGCAGGCTGACCGTGGACAAGTCC AGATGGCAGGAGGGCAACGTCTTTAGCTGCTCCGT GATGCACGAGGCCCTGCACAACCACTACACCCAGA AGAGCCTGAGCCTGTCCCTGGGC |

BAP050-Clone-H LC

| | | |
|---|---|---|
| SEQ ID NO: 10 (Kabat) | LCDR1 | SSSQDISNYLN |
| SEQ ID NO: 11 (Kabat) | LCDR2 | YTSTLHL |
| SEQ ID NO: 12 (Kabat) | LCDR3 | QQYYNLPWT |
| SEQ ID NO: 13 (Chothia) | LCDR1 | SQDISNY |
| SEQ ID NO: 14 (Chothia) | LCDR2 | YTS |
| SEQ ID NO: 15 (Chothia) | LCDR3 | YYNLPW |
| SEQ ID NO: 36 | VL | DIQMTQSPSSLSASVGDRVTITCSSSQDISNYLNW YQQKPGKAPKLLIYYTSTLHLGIPPRFSGSGYGTD FTLTINNIESEDAAYYFCQQYYNLPWTFGQGTKVE IK |
| SEQ ID NO: 118 | DNA VL | GACATCCAGATGACCCAGTCCCCCTCCAGCCTGTC TGCTTCCGTGGGCGACAGAGTGACCATCACCTGTT CCTCCAGCCAGGACATCTCCAACTACCTGAACTGG TATCAGCAGAAGCCCGGCAAGGCCCCCAAGCTGCT GATCTACTACACCTCCACCCTGCACCTGGGCATCC CCCCTAGATTCTCCGGCTCTGGCTACGGCACCGAC TTCACCCTGACCATCAACAACATCGAGTCCGAGGA CGCCGCCTACTACTTCTGCCAGCAGTACTACAACC TGCCCTGGACCTTCGGCCAGGGCACCAAGGTGGAA ATCAAG |
| SEQ ID NO: 38 | LC | DIQMTQSPSSLSASVGDRVTITCSSSQDISNYLNW YQQKPGKAPKLLIYYTSTLHLGIPPRFSGSGYGTD FTLTINNIESEDAAYYFCQQYYNLPWTFGQGTKVE IKRTVAAPSVFIFPPSDEQLKSGTASVVCLLNNFY PREAKVQWKVDNALQSGNSQESVTEQDSKDSTYSL SSTLTLSKADYEKHKVYACEVTHQGLSSPVTKSFN RGEC |
| SEQ ID NO: 120 | DNA LC | GACATCCAGATGACCCAGTCCCCCTCCAGCCTGTC TGCTTCCGTGGGCGACAGAGTGACCATCACCTGTT CCTCCAGCCAGGACATCTCCAACTACCTGAACTGG TATCAGCAGAAGCCCGGCAAGGCCCCCAAGCTGCT GATCTACTACACCTCCACCCTGCACCTGGGCATCC CCCCTAGATTCTCCGGCTCTGGCTACGGCACCGAC TTCACCCTGACCATCAACAACATCGAGTCCGAGGA CGCCGCCTACTACTTCTGCCAGCAGTACTACAACC TGCCCTGGACCTTCGGCCAGGGCACCAAGGTGGAA ATCAAGCGTACGGTGGCCGCTCCCAGCGTGTTCAT CTTCCCCCCAAGCGACGAGCAGCTGAAGAGCGGCA CCGCCAGCGTGGTGTGTCTGCTGAACAACTTCTAC CCCAGGGAGGCCAAGGTGCAGTGGAAGGTGGACAA CGCCCTGCAGAGCGGCAACAGCCAGGAGAGCGTCA CCGAGCAGGACAGCAAGGACTCCACCTACAGCCTG AGCAGCACCCTGACCCTGAGCAAGGCCGACTACGA GAAGCACAAGGTGTACGCCTGTGAGGTGACCCACC AGGGGCTGTCCAGCCCCGTGACCAAGAGCTTCAAC AGGGGCGAGTGC |

BAP050-Clone-I HC

| | | |
|---|---|---|
| SEQ ID NO: 1 (Kabat) | HCDR1 | NYGMN |
| SEQ ID NO: 2 (Kabat) | HCDR2 | WINTDTGEPTYADDFKG |
| SEQ ID NO: 3 (Kabat) | HCDR3 | NPPYYYGTNNAEAMDY |
| SEQ ID NO: 4 (Chothia) | HCDR1 | GFTLTNY |

TABLE 1-continued

Amino acid and nucleotide sequences for murine, chimeric and humanized antibody molecules. The antibody molecules include murine mAb BAP050, chimeric mAbs BAP050-chi, humanized mAbs BAP050-hum01 to BAP050-hum20, humanized mAbs BAP050-hum01-Ser to BAP050-hum15-Ser, BAP050-hum18-Ser to BAP050-hum20-Ser, and humanized mAbs BAP050-Clone-F to BAP050-Clone-J. The amino acid and nucleotide sequences of the heavy and light chain CDRs, the heavy and light chain variable regions, and the heavy and light chains are shown.

| SEQ ID NO: 5 (Chothia) | | HCDR2 NTDTGE |
|---|---|---|
| SEQ ID NO: 3 (Chothia) | | HCDR3 NPPYYYGTNNAEAMDY |
| SEQ ID NO: 104 | VH | QVQLVQSGAEVKKPGASVKVSCKASGFTLTNYGMN WVRQARGQRLEWIGWINTDTGEPTYADDFKGRFVF SLDTSVSTAYLQISSLKAEDTAVYYCARNPPYYYG TNNAEAMDYWGQGTTVTVSS |
| SEQ ID NO: 124 | DNA VH | CAAGTGCAGCTGGTGCAGTCGGGAGCCGAAGTGAA GAAGCCTGGAGCCTCGGTGAAGGTGTCGTGCAAGG CATCCGGATTCACCCTCACCAATTACGGGATGAAC TGGGTCAGACAGGCCCGGGGTCAACGGCTGGAGTG GATCGGATGGATTAACACCGACACCGGGGAGCCTA CCTACGCGGACGATTTCAAGGGACGGTTCGTGTTC TCCCTCGACACCTCCGTGTCCACCGCCTACCTCCA AATCTCCTCACTGAAAGCGGAGGACACCGCCGTGT ACTATTGCGCGAGGAACCCCGCCCTACTACTACGGA ACCAACAACGCCGAAGCCATGGACTACTGGGGCCA GGGCACCACTGTGACTGTGTCCAGC |
| SEQ ID NO: 125 | DNA VH | CAGGTGCAGCTGGTGCAGTCTGGCGCCGAAGTGAA GAAACCTGGCGCCTCCGTGAAGGTGTCCTGCAAGG CCTCTGGCTTCACCCTGACCAACTACGGCATGAAC TGGGTGCGACAGGCCAGGGGCCAGCGGCTGGAATG GATCGGCTGGATCAACACCGACACCGGCGAGCCTA CCTACGCCGACGACTTCAAGGGCAGATTCGTGTTC TCCCTGGACACCTCCGTGTCCACCGCCTACCTGCA GATCTCCAGCCTGAAGGCCGAGGATACCGCCGTGT ACTACTGCGCCCGGAACCCCCCTTACTACTACGGC ACCAACAACGCCGAGGCCATGGACTATTGGGGCCA GGGCACCACCGTGACCGTGTCCTCT |
| SEQ ID NO: 122 | HC | QVQLVQSGAEVKKPGASVKVSCKASGFTLTNYGMN WVRQARGQRLEWIGWINTDTGEPTYADDFKGRFVF SLDTSVSTAYLQISSLKAEDTAVYYCARNPPYYYG TNNAEAMDYWGQGTTVTVSSASTKGPSVFPLAPCS RSTSESTAALGCLVKDYFPEPVTVSWNSGALTSGV HTFPAVLQSSGLYSLSSVVTVPSSSLGTKTYTCNV DHKPSNTKVDKRVESKYGPPCPPCPAPEFLGGPSV FLFPPKPKDTLMISRTPEVTCVVVDVSQEDPEVQF NWYVDGVEVHNAKTKPREEQFNSTYRVVSVLTVLH QDWLNGKEYKCKVSNKGLPSSIEKTISKAKGQPRE PQVYTLPPSQEEMTKNQVSLTCLVKGFYPSDIAVE WESNGQPENNYKTTPPVLDSDGSFFLYSRLTVDKS RWQEGNVFSCSVMHEALHNHYTQKSLSLSLG |
| SEQ ID NO: 126 | DNA HC | CAAGTGCAGCTGGTGCAGTCGGGAGCCGAAGTGAA GAAGCCTGGAGCCTCGGTGAAGGTGTCGTGCAAGG CATCCGGATTCACCCTCACCAATTACGGGATGAAC TGGGTCAGACAGGCCCGGGGTCAACGGCTGGAGTG GATCGGATGGATTAACACCGACACCGGGGAGCCTA CCTACGCGGACGATTTCAAGGGACGGTTCGTGTTC TCCCTCGACACCTCCGTGTCCACCGCCTACCTCCA AATCTCCTCACTGAAAGCGGAGGACACCGCCGTGT ACTATTGCGCGAGGAACCCCGCCCTACTACTACGGA ACCAACAACGCCGAAGCCATGGACTACTGGGGCCA GGGCACCACTGTGACTGTGTCAGCGCGTCCACTA AGGGCCCGTCCGTGTTCCCCCTGGCACCTTGTAGC CGGAGCACTAGCGAATCCACCGCTGCCCTCGGCTG CCTGGTCAAGGATTACTTCCCGGAGCCCGTGACCG TGTCCTGGAACAGCGGAGCCCTGACCTCCGGAGTG CACACCTTCCCCGCTGTGCTGCAGAGCTCCGGGCT GTACTCGCTGTCGTCGGTGGTCACGGTGCCTTCAT CTAGCCTGGGTACCAAGACCTACACTTGCAACGTG GACCACAAGCCTTCCAACACTAAGGTGGACAAGCG CGTCGAATCGAAGTACGGCCCACCGTGCCCGCCTT GTCCCGCGCCGGAGTTCCTCGGCGGTCCCTCGGTC TTTCTGTTCCCACCGAAGCCCAAGGACACTTTGAT GATTTCCCGCACCCCTGAAGTGACATGCGTGGTCG TGGACGTGTCACAGGAAGATCCGGAGGTGCAGTTC AATTGGTACGTGGATGGCGTCGAGGTGCACAACGC CAAAACCAAGCCGAGGGAGGAGCAGTTCAACTCCA CTTACCGCGTCGTGTCCGTGCTGACGGTGCTGCAT CAGGACTGGCTGAACGGGAAGGAGTACAAGTGCAA AGTGTCCAACAAGGGACTTCCTAGCTCAATCGAAA AGACCATCTCGAAAGCCAAGGGACAGCCCCGGGAA CCCCAAGTGTATACCCTGCCACCGAGCCAGGAAGA AATGACTAAGAACCAAGTCTCATTGACTTGCCTTG TGAAGGGCTTCTACCCATCGGATATCGCCGTGGAA TGGGAGTCCAACGGCCAGCGGAAAACAACTACAA GACCACCCCTCCGGTGCTGGACTCAGACGGATCCT TCTTCCTCTACTCGCGGCTGACCGTGGATAAGAGC AGATGGCAGGAGGGAAATGTGTTCAGCTGTTCTGT GATGCATGAAGCCCTGCACAACCACTACACTCAGA AGTCCCTGTCCCTCTCCCTGGGA |
| SEQ ID NO: 127 | DNA HC | CAGGTGCAGCTGGTGCAGTCTGGCGCCGAAGTGAA GAAACCTGGCGCCTCCGTGAAGGTGTCCTGCAAGG CCTCTGGCTTCACCCTGACCAACTACGGCATGAAC TGGGTGCGACAGGCCAGGGGCCAGCGGCTGGAATG GATCGGCTGGATCAACACCGACACCGGCGAGCCTA CCTACGCCGACGACTTCAAGGGCAGATTCGTGTTC TCCCTGGACACCTCCGTGTCCACCGCCTACCTGCA GATCTCCAGCCTGAAGGCCGAGGATACCGCCGTGT ACTACTGCGCCCGGAACCCCCCTTACTACTACGGC ACCAACAACGCCGAGGCCATGGACTATTGGGGCCA GGGCACCACCGTGACCGTGTCCTCTGCTTCTACCA AGGGGCCCAGCGTGTTCCCCCTGGCCCCCTGCTCC AGAAGCACCAGCGAGAGCACAGCCGCCCTGGGCTG CCTGGTGAAGGACTACTTCCCCGAGCCCGTGACCG TGTCCTGGAACAGCGGAGCCCTGACCAGCGGCGTG CACACCTTCCCCGCCGTGCTGCAGAGCAGCGGCCT GTACAGCCTGAGCAGCGTGGTGACCGTGCCCAGCA GCAGCCTGGGCACCAAGACCTACACCTGTAACGTG GACCACAAGCCCAGCAACACCAAGGTGGACAAGAG GGTGGAGAGCAAGTACGGCCCACCGTGCCCCCCT GCCCAGCCCCGAGTTCCTGGGCGGACCCAGCGTG TTCCTGTTCCCCCCAAGCCCAAGGACACCCTGAT GATCAGCAGAACCCCCGAGGTGACCTGTGTGGTGG TGGACGTGTCCCAGGAGGACCCCGAGGTCCAGTTC AACTGGTACGTGGACGGCGTGGAGGTGCACAACGC CAAGACCAAGCCCAGAGAGGAGCAGTTTAACAGCA CCTACCGGGTGGTGTCCGTGCTGACCGTGCTGCAC CAGGACTGGCTGAACGGCAAAGAGTACAAGTGTAA GGTCTCCAACAAGGGCCTGCCAAGCAGCATCGAAA AGACCATCAGCAAGGCCAAGGGCCAGCCTAGAGAG CCCCAGGTCTACACCCTGCCACCCAGCCAAGAGGA GATGACCAAGAACCAGGTGTCCCTGACCTGTCTGG TGAAGGGCTTCTACCCAAGCGACATCGCCGTGGAG TGGGAGAGCAACGGCCAGCCCGAGAACAACTACAA |

TABLE 1-continued

Amino acid and nucleotide sequences for murine, chimeric and humanized antibody molecules. The antibody molecules include murine mAb BAP050, chimeric mAbs BAP050-chi, humanized mAbs BAP050-hum01 to BAP050-hum20, humanized mAbs BAP050-hum01-Ser to BAP050-hum15-Ser, BAP050-hum18-Ser to BAP050-hum20-Ser, and humanized mAbs BAP050-Clone-F to BAP050-Clone-J. The amino acid and nucleotide sequences of the heavy and light chain CDRs, the heavy and light chain variable regions, and the heavy and light chains are shown.

|  |  |  |
|---|---|---|
|  |  | GACCACCCCCCAGTGCTGGACAGCGACGGCAGCT TCTTCCTGTACAGCAGGCTGACCGTGGACAAGTCC AGATGGCAGGAGGGCAACGTCTTTAGCTGCTCCGT GATGCACGAGGCCCTGCACAACCACTACACCCAGA AGAGCCTGAGCCTGTCCCTGGGC |

BAP050-Clone-I LC

| SEQ ID NO: 10 (Kabat) | LCDR1 | SSSQDISNYLN |
|---|---|---|
| SEQ ID NO: 11 (Kabat) | LCDR2 | YTSTLHL |
| SEQ ID NO: 12 (Kabat) | LCDR3 | QQYYNLPWT |
| SEQ ID NO: 13 (Chothia) | LCDR1 | SQDISNY |
| SEQ ID NO: 14 (Chothia) | LCDR2 | YTS |
| SEQ ID NO: 15 (Chothia) | LCDR3 | YYNLPW |
| SEQ ID NO: 56 | VL | DIQMTQSPSSLSASVGDRVTITCSSSQDISNYLNW YLQKPGQSPQLLIYYTSTLHLGVPSRFSGSGSGTE FTLTISSLQPDDFATYYCQQYYNLPWTFGQGTKVE IK |
| SEQ ID NO: 128 | DNA VL | GATATTCAGATGACTCAGTCACCTAGTAGCCTGAG CGCTAGTGTGGGCGATAGAGTGACTATCACCTGTA GCTCTAGTCAGGATATCTCTAACTACCTGAACTGG TATCTGCAGAAGCCCGGTCAATCACCTCAGCTGCT GATCTACTACACTAGCACCCTGCACCTGGGCGTGC CCTCTAGGTTTAGCGGTAGCGGTAGTGGCACCGAG TTCACCCTGACTATCTCTAGCCTGCAGCCCGACGA CTTCGCTACCTACTACTGTCAGCAGTACTATAACC TGCCCTGGACCTTCGGTCAAGGCACTAAGGTCGAG ATTAAG |
| SEQ ID NO: 129 | DNA VL | GACATCCAGATGACCCAGTCCCCCTCCAGCCTGTC TGCTTCCGTGGGCGACAGAGTGACCATCACCTGTT CCTCCAGCCAGGACATCTCCAACTACCTGAACTGG TATCTGCAGAAGCCCGGCCAGTCCCCTCAGCTGCT GATCTACTACACCTCCACCCTGCACCTGGGCGTGC CCTCCAGATTTTCCGGCTCTGGCTCTGGCACCGAG TTTACCCTGACCATCAGCTCCCTGCAGCCCGACGA CTTCGCCACCTACTACTGCCAGCAGTACTACAACC TGCCCTGGACCTTCGGCCAGGGCACCAAGGTGGAA ATCAAG |
| SEQ ID NO: 58 | LC | DIQMTQSPSSLSASVGDRVTITCSSSQDISNYLNW YLQKPGQSPQLLIYYTSTLHLGVPSRFSGSGSGTE FTLTISSLQPDDFATYYCQQYYNLPWTFGQGTKVE IKRTVAAPSVFIFPPSDEQLKSGTASVVCLLNNFY PREAKVQWKVDNALQSGNSQESVTEQDSKDSTYSL SSTLTLSKADYEKHKVYACEVTHQGLSSPVTKSFN RGEC |
| SEQ ID NO: 130 | DNA LC | GATATTCAGATGACTCAGTCACCTAGTAGCCTGAG CGCTAGTGTGGGCGATAGAGTGACTATCACCTGTA GCTCTAGTCAGGATATCTCTAACTACCTGAACTGG TATCTGCAGAAGCCCGGTCAATCACCTCAGCTGCT GATCTACTACACTAGCACCCTGCACCTGGGCGTGC CCTCTAGGTTTAGCGGTAGCGGTAGTGGCACCGAG TTCACCCTGACTATCTCTAGCCTGCAGCCCGACGA CTTCGCTACCTACTACTGTCAGCAGTACTATAACC TGCCCTGGACCTTCGGTCAAGGCACTAAGGTCGAG ATTAAGCGTACGGTGGCCGCTCCCAGCGTGTTCAT CTTCCCCCCAGCGACGAGCAGCTGAAGAGCGGCA CCGCCAGCGTGGTGTGCCTGCTGAACAACTTCTAC CCCCGGGAGGCCAAGGTGCAGTGGAAGGTGGACAA CGCCCTGCAGAGCGGCAACAGCCAGGAGAGCGTCA CCGAGCAGGACAGCAAGGACTCCACCTACAGCCTG AGCAGCACCCTGACCCTGAGCAAGGCCGACTACGA GAAGCATAAGGTGTACGCCTGCGAGGTGACCCACC AGGGCCTGTCCAGCCCCGTGACCAAGAGCTTCAAC AGGGGCGAGTGC |
| SEQ ID NO: 131 | DNA LC | GACATCCAGATGACCCAGTCCCCCTCCAGCCTGTC TGCTTCCGTGGGCGACAGAGTGACCATCACCTGTT CCTCCAGCCAGGACATCTCCAACTACCTGAACTGG TATCTGCAGAAGCCCGGCCAGTCCCCTCAGCTGCT GATCTACTACACCTCCACCCTGCACCTGGGCGTGC CCTCCAGATTTTCCGGCTCTGGCTCTGGCACCGAG TTTACCCTGACCATCAGCTCCCTGCAGCCCGACGA CTTCGCCACCTACTACTGCCAGCAGTACTACAACC TGCCCTGGACCTTCGGCCAGGGCACCAAGGTGGAA ATCAAGCGTACGGTGGCCGCTCCCAGCGTGTTCAT CTTCCCCCCAAGCGACGAGCAGCTGAAGAGCGGCA CCGCCAGCGTGGTGTGTCTGCTGAACAACTTCTAC CCCAGGGAGGCCAAGGTGCAGTGGAAGGTGGACAA CGCCCTGCAGAGCGGCAACAGCCAGGAGAGCGTCA CCGAGCAGGACAGCAAGGACTCCACCTACAGCCTG AGCAGCACCCTGACCCTGAGCAAGGCCGACTACGA GAAGCACAAGGTGTACGCCTGTGAGGTGACCCACC AGGGCCTGTCCAGCCCCGTGACCAAGAGCTTCAAC AGGGGCGAGTGC |

BAP050-Clone-J HC

| SEQ ID NO: 1 (Kabat) | HCDR1 | NYGMN |
|---|---|---|
| SEQ ID NO: 2 (Kabat) | HCDR2 | WINTDTGEPTYADDFKG |
| SEQ ID NO: 3 (Kabat) | HCDR3 | NPPYYYGTNNAEAMDY |
| SEQ ID NO: 4 (Chothia) | HCDR1 | GFTLTNY |
| SEQ ID NO: 5 (Chothia) | HCDR2 | NTDTGE |
| SEQ ID NO: 3 (Chothia) | HCDR3 | NPPYYYGTNNAEAMDY |

TABLE 1-continued

Amino acid and nucleotide sequences for murine, chimeric and humanized antibody molecules. The antibody molecules include murine mAb BAP050, chimeric mAbs BAP050-chi, humanized mAbs BAP050-hum01 to BAP050-hum20, humanized mAbs BAP050-hum01-Ser to BAP050-hum15-Ser, BAP050-hum18-Ser to BAP050-hum20-Ser, and humanized mAbs BAP050-Clone-F to BAP050-Clone-J. The amino acid and nucleotide sequences of the heavy and light chain CDRs, the heavy and light chain variable regions, and the heavy and light chains are shown.

| | | |
|---|---|---|
| SEQ ID NO: 108 | VH | QVQLVQSGAEVKKPGASVKVSCKASGFTLTNYGMN WVRQAPGQGLEWMGWINTDTGEPTYADDFKGRFVF SLDTSVSTAYLQISSLKAEDTAVYYCARNPPYYYG TNNAEAMDYWGQGTTVTVSS |
| SEQ ID NO: 132 | DNA VH | CAGGTGCAGCTGGTGCAGTCAGGCGCCGAAGTGAA GAAACCCGGCGCTAGTGTGAAAGTCAGCTGTAAAG CTAGTGGCTTCACCCTGACTAACTACGGGATGAAC TGGGTCCGCCAGGCCCCAGGTCAAGGCCTCGAGTG GATGGGCTGGATTAACACCGACACCGGCGAGCCTA CCTACGCCGACGACTTTAAGGGCAGATTCGTGTTT AGCCTGGACACTAGTGTGTCTACCGCCTACCTGCA GATCTCTAGCCTGAAGGCCGAGGACACCGCCGTCT ACTACTGCGCTAGAAACCCCCCTACTACTACGGC ACTAACAACGCCGAGGCTATGGACTACTGGGGTCA AGGCACTACCGTGACCGTGTCTAGC |
| SEQ ID NO: 133 | DNA VH | CAGGTGCAGCTGGTGCAGTCTGGCGCCGAAGTGAA GAAACCTGGCGCCTCCGTGAAGGTGTCCTGCAAGG CCTCTGGCTTCACCCTGACCAACTACGGCATGAAC TGGGTGCGACAGGCCCCTGGACAGGGCCTGGAATG GATGGGCTGGATCAACACCGACACCGGCGAGCCTA CCTACGCCGACGACTTCAAGGGCAGATTCGTGTTC TCCCTGGACACCTCCGTGTCCACCGCCTACCTGCA GATCTCCAGCCTGAAGGCCGAGGATACCGCCGTGT ACTACTGCGCCCGGAACCCCCCTTACTACTACGGC ACCAACAACGCCGAGGCCATGGACTATTGGGGCCA GGGCACCACCGTGACCGTGTCCTCT |
| SEQ ID NO: 134 | HC | QVQLVQSGAEVKKPGASVKVSCKASGFTLTNYGMN WVRQAPGQGLEWMGWINTDTGEPTYADDFKGRFVF SLDTSVSTAYLQISSLKAEDTAVYYCARNPPYYYG TNNAEAMDYWGQGTTVTVSSASTKGPSVFPLAPCS RSTSESTAALGCLVKDYFPEPVTVSWNSGALTSGV HTFPAVLQSSGLYSLSSVVTVPSSSLGTKTYTCNV DHKPSNTKVDKRVESKYGPPCPPCPAPEFLGGPSV FLFPPKPKDTLMISRTPEVTCVVVDVSQEDPEVQF NWYVDGVEVHNAKTKPREEQFNSTYRVVSVLTVLH QDWLNGKEYKCKVSNKGLPSSIEKTISKAKGQPRE PQVYTLPPSQEEMTKNQVSLTCLVKGFYPSDIAVE WESNGQPENNYKTTPPVLDSDGSFFLYSRLTVDKS RWQEGNVFSCSVMHEALHNHYTQKSLSLSLG |
| SEQ ID NO: 135 | DNA HC | CAGGTGCAGCTGGTGCAGTCAGGCGCCGAAGTGAA GAAACCCGGCGCTAGTGTGAAAGTCAGCTGTAAAG CTAGTGGCTTCACCCTGACTAACTACGGGATGAAC TGGGTCCGCCAGGCCCCAGGTCAAGGCCTCGAGTG GATGGGCTGGATTAACACCGACACCGGCGAGCCTA CCTACGCCGACGACTTTAAGGGCAGATTCGTGTTT AGCCTGGACACTAGTGTGTCTACCGCCTACCTGCA GATCTCTAGCCTGAAGGCCGAGGACACCGCCGTCT ACTACTGCGCTAGAAACCCCCCTACTACTACGGC ACTAACAACGCCGAGGCTATGGACTACTGGGGTCA AGGCACTACCGTGACCGTGTCTAGCGCTACTA AGGGCCCGTCCGTGTTCCCCTGGCACCTTGTAGC CGGAGCACTAGCGAATCCACCGCTGCCCTCGGCTG CCTGGTCAAGGATTACTTCCCGGAGCCCGTGACCG TGTCCTGGAACAGCGGAGCCTGACCAGCGGCGTG CACACCTTCCCGCTGTGCTGCAGAGCTCCGGGCT GTACTCGCTGTCGTCGGTGGTCACGGTGCCTTCAT CTAGCCTGGGTACCAAGACCTACACTTGCAACGTG GACCACAAGCCTTCCAACACTAAGGTGACAAGCG CGTGGAATCGAAGTACGGCCCACCGTGCCCGCCTT GTCCCGCGCCGGAGTTCCTCGGCGGTCCTCGGTC TTTCTGTTCCCACCGAAGCCCAAGGACACTTTGAT GATTTCCCGCACCCCTGAAGTGACATGCGTGGTCG TGGACGTGTCACAGGAAGATCCGGAGGTGCAGTTC AATTGGTACGTGGATGGCGTCGAGGTGCACAACGC CAAAACCAAGCCGAGGGAGGAGCAGTTCAACTCCA CTTACCGCGTCGTGTCCGTGCTGACGGTGCTGCAT CAGGACTGGCTGAACGGGAAGGAGTACAAGTGCAA AGTGTCCAACAAGGGACTTCCTAGCTCAATCGAAA AGACCATCTCGAAAGCCAAGGGACAGCCCCGGGAA CCCCAAGTGTATACCCTGCCACCGAGCCAGGAAGA AATGACTAAGAACCAAGTCTCATTGACTTGCCTTG TGAAGGGCTTCTACCCATCGGATATCGCCGTGGAA TGGGAGTCCAACGGCCAGCCGGAAAACAACTACAA GACCACCCCTCCGGTGCTGGACTCAGACGGATCCT TCTTCCTCTACTCGCGGCTGACCGTGGATAAGAGC AGATGGCAGGAGGGAAATGTGTTCAGCTGTTCTGT GATGCATGAAGCCCTGCACAACCACTACACTCAGA AGTCCCTGTCCCTCTCCCTGGGA |
| SEQ ID NO: 136 | DNA HC | CAGGTGCAGCTGGTGCAGTCTGGCGCCGAAGTGAA GAAACCTGGCGCCTCCGTGAAGGTGTCCTGCAAGG CCTCTGGCTTCACCCTGACCAACTACGGCATGAAC TGGGTGCGACAGGCCCCTGGACAGGGCCTGGAATG GATGGGCTGGATCAACACCGACACCGGCGAGCCTA CCTACGCCGACGACTTCAAGGGCAGATTCGTGTTC TCCCTGGACACCTCCGTGTCCACCGCCTACCTGCA GATCTCCAGCCTGAAGGCCGAGGATACCGCCGTGT ACTACTGCGCCCGGAACCCCCCTTACTACTACGGC ACCAACAACGCCGAGGCCATGGACTATTGGGGCCA GGGCACCACCGTGACCGTGTCCTCTGCTTCTACCA AGGGGCCCAGCGTGTTCCCCCTGGCCCCCTGCTCC AGAAGCACCAGCGAGAGCACAGCCGCCCTGGGCTG CCTGGTGAAGGACTACTTCCCCGAGCCCGTGACCG TGTCCTGGAACAGCGGAGCCCTGACCAGCGGCGTG CACACCTTCCCCGCCGTGCTGCAGAGCAGCGGCCT GTACAGCCTGAGCAGCGTGGTGACCGTGCCCAGCA GCAGCCTGGGCACCAAGACCTACACCTGTAACGTG GACCACAAGCCCAGCAACACCAAGGTGGACAAGAG GGTGGAGAGCAAGTACGGCCCCACCTGCCCCCCCT GCCCAGCCCCCGAGTTCCTGGGCGGACCCAGCGTG TTCCTGTTCCCCCCCAAGCCCAAGGACACCCTGAT GATCAGCAGAACCCCCGAGGTGACCTGTGTGGTGG TGGACGTGTCCCAGGAGGACCCCGAGGTCCAGTTC AACTGGTACGTGGACGGCGTGGAGGTGCACAACGC CAAGACCAAGCCCAGAGAGGAGCAGTTTAACAGCA CCTACCGGGTGGTGTCCGTGCTGACCGTGCTGCAC CAGGACTGGCTGAACGGCAAAGAGTACAAGTGTAA GGTCTCCAACAAGGGCCTGCCAAGCAGCATCGAAA AGACCATCAGCAAGGCCAAGGGCCAGCCTAGAGAG CCCCAGGTCTACACCCTGCCACCCAGCCAAGGAGGA GATGACCAAGAACCAGGTGTCCCTGACCTGTCTGG TGAAGGGCTTCTACCCAAGCGACATCGCCGTGGAG TGGGAGAGCAACGGCCAGCCCGAGAACAACTACAA GACCACCCCCCAGTGCTGGACAGCGACGGCAGCT TCTTCCTGTACAGCAGGCTGACCGTGGACAAGTCC AGATGGCAGGAGGGCAACGTCTTTAGCTGCTCCGT GATGCACGAGGCCCTGCACAACCACTACACCCAGA AGAGCCTGAGCCTGTCCCTGGGC |

BAP050-Clone-J LC

| | | |
|---|---|---|
| SEQ ID NO: 10 (Kabat) | LCDR1 | SSQDISNYLN |
| SEQ ID NO: 11 (Kabat) | LCDR2 | YTSTLHL |

TABLE 1-continued

Amino acid and nucleotide sequences for murine, chimeric and humanized antibody molecules. The antibody molecules include murine mAb BAP050, chimeric mAbs BAP050-chi, humanized mAbs BAP050-hum01 to BAP050-hum20, humanized mAbs BAP050-hum01-Ser to BAP050-hum15-Ser, BAP050-hum18-Ser to BAP050-hum20-Ser, and humanized mAbs BAP050-Clone-F to BAP050-Clone-J. The amino acid and nucleotide sequences of the heavy and light chain CDRs, the heavy and light chain variable regions, and the heavy and light chains are shown.

| | | |
|---|---|---|
| SEQ ID NO: 12 (Kabat) | LCDR3 | QQYYNLPWT |
| SEQ ID NO: 13 (Chothia) | LCDR1 | SQDISNY |
| SEQ ID NO: 14 (Chothia) | LCDR2 | YTS |
| SEQ ID NO: 15 (Chothia) | LCDR3 | YYNLPW |
| SEQ ID NO: 36 | VL | DIQMTQSPSSLSASVGDRVTITCSSSQDISNYLNW YQQKPGKAPKLLIYYTSTLHLGIPPRFSGSGYGTD FTLTINNIESEDAAYYFCQQYYNLPWTFGQGTKVE IK |
| SEQ ID NO: 137 | DNA VL | GATATTCAGATGACTCAGTCACCTAGTAGCCTGAG CGCTAGTGTGGGCGATAGAGTGACTATCACCTGTA GCTCTAGTCAGGATATCTCTAACTACCTGAACTGG TATCAGCAGAAGCCCGGTAAAGCCCCTAAGCTGCT GATCTACTACACTAGCACCCTGCACCTGGGAATCC CCCCTAGGTTTAGCGGTAGCGGCTACGGCACCGAC TTCACCCTGACTATTAACAATATCGAGTCAGAGGA CGCCGCCTACTACTTCTGTCAGCAGTACTATAACC TGCCCTGGACCTTCGGTCAAGGCACTAAGGTCGAG ATTAAG |
| SEQ ID NO: 118 | DNA VL | GACATCCAGATGACCCAGTCCCCCTCCAGCCTGTC TGCTTCCGTGGGCGACAGAGTGACCATCACCTGTT CCTCCAGCCAGGACATCTCCAACTACCTGAACTGG TATCAGCAGAAGCCCGGCAAGGCCCCCAAGCTGCT GATCTACTACACCTCCACCCTGCACCTGGGCATCC CCCCTAGATTCTCCGGCTCTGGCTACGGCACCGAC TTCACCCTGACCATCAACAACATCGAGTCCGAGGA CGCCGCCTACTACTTCTGCCAGCAGTACTACAACC TGCCCTGGACCTTCGGCCAGGGCACCAAGGTGGAA ATCAAG |
| SEQ ID NO: 38 | LC | DIQMTQSPSSLSASVGDRVTITCSSSQDISNYLNW YQQKPGKAPKLLIYYTSTLHLGIPPRFSGSGYGTD FTLTINNIESEDAAYYFCQQYYNLPWTFGQGTKVE IKRTVAAPSVFIFPPSDEQLKSGTASVVCLLNNFY PREAKVQWKVDNALQSGNSQESVTEQDSKDSTYSL SSTLTLSKADYEKHKVYACEVTHQGLSSPVTKSFN RGEC |
| SEQ ID NO: 138 | DNA LC | GATATTCAGATGACTCAGTCACCTAGTAGCCTGAG CGCTAGTGTGGGCGATAGAGTGACTATCACCTGTA GCTCTAGTCAGGATATCTCTAACTACCTGAACTGG TATCAGCAGAAGCCCGGTAAAGCCCCTAAGCTGCT GATCTACTACACTAGCACCCTGCACCTGGGAATCC CCCCTAGGTTTAGCGGTAGCGGCTACGGCACCGAC TTCACCCTGACTATTAACAATATCGAGTCAGAGGA CGCCGCCTACTACTTCTGTCAGCAGTACTATAACC TGCCCTGGACCTTCGGTCAAGGCACTAAGGTCGAG ATTAAGCGTACGGTGGCCGCTCCCAGCGTGTTCAT CTTCCCCCCAAGCGACGAGCAGCTGAAGAGCGGCA CCGCCAGCGTGGTGTGCCTGCTGAACAACTTCTAC CCCGGGAGGCCAAGGTGCAGTGGAAGGTGGACAA CGCCCTGCAGAGCGGCAACAGCCAGGAGAGCGTCA CCGAGCAGGACAGCAAGGACTCCACCTACAGCCTG AGCAGCACCCTGACCCTGAGCAAGGCCGACTACGA |

TABLE 1-continued

Amino acid and nucleotide sequences for murine, chimeric and humanized antibody molecules. The antibody molecules include murine mAb BAP050, chimeric mAbs BAP050-chi, humanized mAbs BAP050-hum01 to BAP050-hum20, humanized mAbs BAP050-hum01-Ser to BAP050-hum15-Ser, BAP050-hum18-Ser to BAP050-hum20-Ser, and humanized mAbs BAP050-Clone-F to BAP050-Clone-J. The amino acid and nucleotide sequences of the heavy and light chain CDRs, the heavy and light chain variable regions, and the heavy and light chains are shown.

| | | |
|---|---|---|
| | | GAAGCATAAGGTGTACGCCTGCGAGGTGACCCACC AGGGCCTGTCCAGCCCCGTGACCAAGAGCTTCAAC AGGGGCGAGTGC |
| SEQ ID NO: 139 | DNA LC | GACATCCAGATGACCCAGTCCCCCTCCAGCCTGTC TGCTTCCGTGGGCGACAGAGTGACCATCACCTGTT CCTCCAGCCAGGACATCTCCAACTACCTGAACTGG TATCAGCAGAAGCCCGGCAAGGCCCCCAAGCTGCT GATCTACTACACCTCCACCCTGCACCTGGGCATCC CCCCTAGATTCTCCGGCTCTGGCTACGGCACCGAC TTCACCCTGACCATCAACAACATCGAGTCCGAGGA CGCCGCCTACTACTTCTGCCAGCAGTACTACAACC TGCCCTGGACCTTCGGCCAGGGCACCAAGGTGGAA ATCAAGCGTACGGTGGCCGCTCCCAGCGTGTTCAT CTTCCCCCCAAGCGACGAGCAGCTGAAGAGCGGCA CCGCCAGCGTGGTGTGTCTGCTGAACAACTTCTAC CCCAGGGAGGCCAAGGTGCAGTGGAAGGTGGACAA CGCCCTGCAGAGCGGCAACAGCCAGGAGAGCGTCA CCGAGCAGGACAGCAAGGACTCCACCTACAGCCTG AGCAGCACCCTGACCCTGAGCAAGGCCGACTACGA GAAGCACAAGGTGTACGCCTGTGAGGTGACCCACC AGGGCCTGTCCAGCCCCGTGACCAAGAGCTTCAAC AGGGGCGAGTGC |

BAP050 HC

| | | |
|---|---|---|
| SEQ ID NO: 140 (Kabat) | HCDR1 | AACTATGGAATGAAC |
| SEQ ID NO: 141 (Kabat) | HCDR2 | TGGATAAACACCGACACTGGAGAGCCAACATATGC TGATGACTTCAAGGGA |
| SEQ ID NO: 142 (Kabat) | HCDR3 | AACCCCCCTTATTACTACGGTACTAATAACGCGGA GGCTATGGACTAC |
| SEQ ID NO: 143 (Chothia) | HCDR1 | GGATTTACCCTCACAAACTAT |
| SEQ ID NO: 144 (Chothia) | HCDR2 | AACACCGACACTGGAGAG |
| SEQ ID NO: 142 (Chothia) | HCDR3 | AACCCCCCTTATTACTACGGTACTAATAACGCGGA GGCTATGGACTAC |

BAP050 LC

| | | |
|---|---|---|
| SEQ ID NO: 145 (Kabat) | LCDR1 | AGTTCAAGTCAGGACATCAGCAATTATTTAAAC |
| SEQ ID NO: 146 (Kabat) | LCDR2 | TACACATCAACCTTACACTTA |
| SEQ ID NO: 147 (Kabat) | LCDR3 | CAGCAGTATTATAACCTTCCGTGGACG |
| SEQ ID NO: 148 (Chothia) | LCDR1 | AGTCAGGACATCAGCAATTAT |

TABLE 1-continued

Amino acid and nucleotide sequences for murine, chimeric and humanized antibody molecules. The antibody molecules include murine mAb BAP050, chimeric mAbs BAP050-chi, humanized mAbs BAP050-hum01 to BAP050-hum20, humanized mAbs BAP050-hum01-Ser to BAP050-hum15-Ser, BAP050-hum18-Ser to BAP050-hum20-Ser, and humanized mAbs BAP050-Clone-F to BAP050-Clone-J. The amino acid and nucleotide sequences of the heavy and light chain CDRs, the heavy and light chain variable regions, and the heavy and light chains are shown.

| SEQ ID NO: 149 (Chothia) | LCDR2TACACATCA |
| SEQ ID NO: 150 (Chothia) | LCDR3TATTATAACCTTCCGTGG |

BAP050-chi HC

| SEQ ID NO: 140 (Kabat) | HCDR1AACTATGGAATGAAC |
| SEQ ID NO: 141 (Kabat) | HCDR2TGGATAAACACCGACACTGGAGAGCCAACATATGCTGATGACTTCAAGGGA |
| SEQ ID NO: 142 (Kabat) | HCDR3AACCCCCCTTATTACTACGGTACTAATAACGCGGAGGCTATGGACTAC |
| SEQ ID NO: 143 (Chothia) | HCDR1GGATTTACCCTCACAAACTAT |
| SEQ ID NO: 144 (Chothia) | HCDR2AACACCGACACTGGAGAG |
| SEQ ID NO: 142 (Chothia) | HCDR3AACCCCCCTTATTACTACGGTACTAATAACGCGGAGGCTATGGACTAC |

BAP050-chi LC

| SEQ ID NO: 145 (Kabat) | LCDR1AGTTCAAGTCAGGACATCAGCAATTATTTAAAC |
| SEQ ID NO: 146 (Kabat) | LCDR2TACACATCAACCTTACACTTA |
| SEQ ID NO: 147 (Kabat) | LCDR3CAGCAGTATTATAACCTTCCGTGGACG |
| SEQ ID NO: 148 (Chothia) | LCDR1AGTCAGGACATCAGCAATTAT |
| SEQ ID NO: 149 (Chothia) | LCDR2TACACATCA |
| SEQ ID NO: 150 (Chothia) | LCDR3TATTATAACCTTCCGTGG |

BAP050-hum01 HC

| SEQ ID NO: 140 (Kabat) | HCDR1AACTATGGAATGAAC |
| SEQ ID NO: 141 (Kabat) | HCDR2TGGATAAACACCGACACTGGAGAGCCAACATATGCTGATGACTTCAAGGGA |
| SEQ ID NO: 151 (Kabat) | HCDR3AACCCTCCCTATTACTACGGTACTAATAACGCGGAGGCTATGGACTAC |
| SEQ ID NO: 143 (Chothia) | HCDR1GGATTTACCCTCACAAACTAT |
| SEQ ID NO: 144 (Chothia) | HCDR2AACACCGACACTGGAGAG |
| SEQ ID NO: 151 (Chothia) | HCDR3AACCCTCCCTATTACTACGGTACTAATAACGCGGAGGCTATGGACTAC |

BAP050-hum01 LC

| SEQ ID NO: 145 (Kabat) | LCDR1AGTTCAAGTCAGGACATCAGCAATTATTTAAAC |
| SEQ ID NO: 146 (Kabat) | LCDR2TACACATCAACCTTACACTTA |
| SEQ ID NO: 147 (Kabat) | LCDR3CAGCAGTATTATAACCTTCCGTGGACG |
| SEQ ID NO: 148 (Chothia) | LCDR1AGTCAGGACATCAGCAATTAT |
| SEQ ID NO: 149 (Chothia) | LCDR2TACACATCA |
| SEQ ID NO: 150 (Chothia) | LCDR3TATTATAACCTTCCGTGG |

BAP050-hum02 HC

| SEQ ID NO: 140 (Kabat) | HCDR1AACTATGGAATGAAC |
| SEQ ID NO: 141 (Kabat) | HCDR2TGGATAAACACCGACACTGGAGAGCCAACATATGCTGATGACTTCAAGGGA |
| SEQ ID NO: 151 (Kabat) | HCDR3AACCCTCCCTATTACTACGGTACTAATAACGCGGAGGCTATGGACTAC |
| SEQ ID NO: 143 (Chothia) | HCDR1GGATTTACCCTCACAAACTAT |
| SEQ ID NO: 144 (Chothia) | HCDR2AACACCGACACTGGAGAG |
| SEQ ID NO: 151 (Chothia) | HCDR3AACCCTCCCTATTACTACGGTACTAATAACGCGGAGGCTATGGACTAC |

BAP050-hum02 LC

| SEQ ID NO: 145 (Kabat) | LCDR1AGTTCAAGTCAGGACATCAGCAATTATTTAAAC |
| SEQ ID NO: 146 (Kabat) | LCDR2TACACATCAACCTTACACTTA |
| SEQ ID NO: 147 (Kabat) | LCDR3CAGCAGTATTATAACCTTCCGTGGACG |
| SEQ ID NO: 148 (Chothia) | LCDR1AGTCAGGACATCAGCAATTAT |
| SEQ ID NO: 149 (Chothia) | LCDR2TACACATCA |
| SEQ ID NO: 150 (Chothia) | LCDR3TATTATAACCTTCCGTGG |

TABLE 1-continued

Amino acid and nucleotide sequences for murine, chimeric and humanized antibody molecules. The antibody molecules include murine mAb BAP050, chimeric mAbs BAP050-chi, humanized mAbs BAP050-hum01 to BAP050-hum20, humanized mAbs BAP050-hum01-Ser to BAP050-hum15-Ser, BAP050-hum18-Ser to BAP050-hum20-Ser, and humanized mAbs BAP050-Clone-F to BAP050-Clone-J. The amino acid and nucleotide sequences of the heavy and light chain CDRs, the heavy and light chain variable regions, and the heavy and light chains are shown.

BAP050-hum03 HC

| | |
|---|---|
| SEQ ID NO: 140 (Kabat) | HCDR1AACTATGGAATGAAC |
| SEQ ID NO: 141 (Kabat) | HCDR2TGGATAAACACCGACACTGGAGAGCCAACATATGCTGATGACTTCAAGGGA |
| SEQ ID NO: 151 (Kabat) | HCDR3AACCCTCCCTATTACTACGGTACTAATAACGCGGAGGCTATGGACTAC |
| SEQ ID NO: 143 (Chothia) | HCDR1GGATTTACCCTCACAAACTAT |
| SEQ ID NO: 144 (Chothia) | HCDR2AACACCGACACTGGAGAG |
| SEQ ID NO: 151 (Chothia) | HCDR3AACCCTCCCTATTACTACGGTACTAATAACGCGGAGGCTATGGACTAC |

BAP050-hum03 LC

| | |
|---|---|
| SEQ ID NO: 145 (Kabat) | LCDR1AGTTCAAGTCAGGACATCAGCAATTATTTAAAC |
| SEQ ID NO: 146 (Kabat) | LCDR2TACACATCAACCTTACACTTA |
| SEQ ID NO: 147 (Kabat) | LCDR3CAGCAGTATTATAACCTTCCGTGGACG |
| SEQ ID NO: 148 (Chothia) | LCDR1AGTCAGGACATCAGCAATTAT |
| SEQ ID NO: 149 (Chothia) | LCDR2TACACATCA |
| SEQ ID NO: 150 (Chothia) | LCDR3TATTATAACCTTCCGTGG |

BAP050-hum04 HC

| | |
|---|---|
| SEQ ID NO: 140 (Kabat) | HCDR1AACTATGGAATGAAC |
| SEQ ID NO: 141 (Kabat) | HCDR2TGGATAAACACCGACACTGGAGAGCCAACATATGCTGATGACTTCAAGGGA |
| SEQ ID NO: 151 (Kabat) | HCDR3AACCCTCCCTATTACTACGGTACTAATAACGCGGAGGCTATGGACTAC |
| SEQ ID NO: 143 (Chothia) | HCDR1GGATTTACCCTCACAAACTAT |
| SEQ ID NO: 144 (Chothia) | HCDR2AACACCGACACTGGAGAG |
| SEQ ID NO: 151 (Chothia) | HCDR3AACCCTCCCTATTACTACGGTACTAATAACGCGGAGGCTATGGACTAC |

BAP050-hum04 LC

| | |
|---|---|
| SEQ ID NO: 145 (Kabat) | LCDR1AGTTCAAGTCAGGACATCAGCAATTATTTAAAC |
| SEQ ID NO: 146 (Kabat) | LCDR2TACACATCAACCTTACACTTA |
| SEQ ID NO: 147 (Kabat) | LCDR3CAGCAGTATTATAACCTTCCGTGGACG |
| SEQ ID NO: 148 (Chothia) | LCDR1AGTCAGGACATCAGCAATTAT |
| SEQ ID NO: 149 (Chothia) | LCDR2TACACATCA |
| SEQ ID NO: 150 (Chothia) | LCDR3TATTATAACCTTCCGTGG |

BAP050-hum05 HC

| | |
|---|---|
| SEQ ID NO: 140 (Kabat) | HCDR1AACTATGGAATGAAC |
| SEQ ID NO: 141 (Kabat) | HCDR2TGGATAAACACCGACACTGGAGAGCCAACATATGCTGATGACTTCAAGGGA |
| SEQ ID NO: 151 (Kabat) | HCDR3AACCCTCCCTATTACTACGGTACTAATAACGCGGAGGCTATGGACTAC |
| SEQ ID NO: 143 (Chothia) | HCDR1GGATTTACCCTCACAAACTAT |
| SEQ ID NO: 144 (Chothia) | HCDR2AACACCGACACTGGAGAG |
| SEQ ID NO: 151 (Chothia) | HCDR3AACCCTCCCTATTACTACGGTACTAATAACGCGGAGGCTATGGACTAC |

BAP050-hum05 LC

| | |
|---|---|
| SEQ ID NO: 145 (Kabat) | LCDR1AGTTCAAGTCAGGACATCAGCAATTATTTAAAC |
| SEQ ID NO: 146 (Kabat) | LCDR2TACACATCAACCTTACACTTA |
| SEQ ID NO: 147 (Kabat) | LCDR3CAGCAGTATTATAACCTTCCGTGGACG |
| SEQ ID NO: 148 (Chothia) | LCDR1AGTCAGGACATCAGCAATTAT |
| SEQ ID NO: 149 (Chothia) | LCDR2TACACATCA |
| SEQ ID NO: 150 (Chothia) | LCDR3TATTATAACCTTCCGTGG |

TABLE 1-continued

Amino acid and nucleotide sequences for murine, chimeric and humanized antibody molecules. The antibody molecules include murine mAb BAP050, chimeric mAbs BAP050-chi, humanized mAbs BAP050-hum01 to BAP050-hum20, humanized mAbs BAP050-hum01-Ser to BAP050-hum15-Ser, BAP050-hum18-Ser to BAP050-hum20-Ser, and humanized mAbs BAP050-Clone-F to BAP050-Clone-J. The amino acid and nucleotide sequences of the heavy and light chain CDRs, the heavy and light chain variable regions, and the heavy and light chains are shown.

BAP050-hum06 HC

| | | |
|---|---|---|
| SEQ ID NO: 140 (Kabat) | HCDR1 | AACTATGGAATGAAC |
| SEQ ID NO: 141 (Kabat) | HCDR2 | TGGATAAACACCGACACTGGAGAGCCAACATATGCTGATGACTTCAAGGGA |
| SEQ ID NO: 151 (Kabat) | HCDR3 | AACCCTCCCTATTACTACGGTACTAATAACGCGGAGGCTATGGACTAC |
| SEQ ID NO: 143 (Chothia) | HCDR1 | GGATTTACCCTCACAAACTAT |
| SEQ ID NO: 144 (Chothia) | HCDR2 | AACACCGACACTGGAGAG |
| SEQ ID NO: 151 (Chothia) | HCDR3 | AACCCTCCCTATTACTACGGTACTAATAACGCGGAGGCTATGGACTAC |

BAP050-hum06 LC

| | | |
|---|---|---|
| SEQ ID NO: 145 (Kabat) | LCDR1 | AGTTCAAGTCAGGACATCAGCAATTATTTAAAC |
| SEQ ID NO: 146 (Kabat) | LCDR2 | TACACATCAACCTTACACTTA |
| SEQ ID NO: 147 (Kabat) | LCDR3 | CAGCAGTATTATAACCTTCCGTGGACG |
| SEQ ID NO: 148 (Chothia) | LCDR1 | AGTCAGGACATCAGCAATTAT |
| SEQ ID NO: 149 (Chothia) | LCDR2 | TACACATCA |
| SEQ ID NO: 150 (Chothia) | LCDR3 | TATTATAACCTTCCGTGG |

BAP050-hum07 HC

| | | |
|---|---|---|
| SEQ ID NO: 140 (Kabat) | HCDR1 | AACTATGGAATGAAC |
| SEQ ID NO: 141 (Kabat) | HCDR2 | TGGATAAACACCGACACTGGAGAGCCAACATATGCTGATGACTTCAAGGGA |
| SEQ ID NO: 151 (Kabat) | HCDR3 | AACCCTCCCTATTACTACGGTACTAATAACGCGGAGGCTATGGACTAC |
| SEQ ID NO: 143 (Chothia) | HCDR1 | GGATTTACCCTCACAAACTAT |
| SEQ ID NO: 144 (Chothia) | HCDR2 | AACACCGACACTGGAGAG |
| SEQ ID NO: 151 (Chothia) | HCDR3 | AACCCTCCCTATTACTACGGTACTAATAACGCGGAGGCTATGGACTAC |

BAP050-hum07 LC

| | | |
|---|---|---|
| SEQ ID NO: 145 (Kabat) | LCDR1 | AGTTCAAGTCAGGACATCAGCAATTATTTAAAC |
| SEQ ID NO: 146 (Kabat) | LCDR2 | TACACATCAACCTTACACTTA |
| SEQ ID NO: 147 (Kabat) | LCDR3 | CAGCAGTATTATAACCTTCCGTGGACG |
| SEQ ID NO: 148 (Chothia) | LCDR1 | AGTCAGGACATCAGCAATTAT |
| SEQ ID NO: 149 (Chothia) | LCDR2 | TACACATCA |
| SEQ ID NO: 150 (Chothia) | LCDR3 | TATTATAACCTTCCGTGG |

BAP050-hum08 HC

| | | |
|---|---|---|
| SEQ ID NO: 140 (Kabat) | HCDR1 | AACTATGGAATGAAC |
| SEQ ID NO: 141 (Kabat) | HCDR2 | TGGATAAACACCGACACTGGAGAGCCAACATATGCTGATGACTTCAAGGGA |
| SEQ ID NO: 151 (Kabat) | HCDR3 | AACCCTCCCTATTACTACGGTACTAATAACGCGGAGGCTATGGACTAC |
| SEQ ID NO: 143 (Chothia) | HCDR1 | GGATTTACCCTCACAAACTAT |
| SEQ ID NO: 144 (Chothia) | HCDR2 | AACACCGACACTGGAGAG |
| SEQ ID NO: 151 (Chothia) | HCDR3 | AACCCTCCCTATTACTACGGTACTAATAACGCGGAGGCTATGGACTAC |

BAP050-hum08 LC

| | | |
|---|---|---|
| SEQ ID NO: 145 (Kabat) | LCDR1 | AGTTCAAGTCAGGACATCAGCAATTATTTAAAC |
| SEQ ID NO: 146 (Kabat) | LCDR2 | TACACATCAACCTTACACTTA |
| SEQ ID NO: 147 (Kabat) | LCDR3 | CAGCAGTATTATAACCTTCCGTGGACG |
| SEQ ID NO: 148 (Chothia) | LCDR1 | AGTCAGGACATCAGCAATTAT |
| SEQ ID NO: 149 (Chothia) | LCDR2 | TACACATCA |
| SEQ ID NO: 150 (Chothia) | LCDR3 | TATTATAACCTTCCGTGG |

TABLE 1-continued

Amino acid and nucleotide sequences for murine, chimeric and humanized antibody molecules. The antibody molecules include murine mAb BAP050, chimeric mAbs BAP050-chi, humanized mAbs BAP050-hum01 to BAP050-hum20, humanized mAbs BAP050-hum01-Ser to BAP050-hum15-Ser, BAP050-hum18-Ser to BAP050-hum20-Ser, and humanized mAbs BAP050-Clone-F to BAP050-Clone-J. The amino acid and nucleotide sequences of the heavy and light chain CDRs, the heavy and light chain variable regions, and the heavy and light chains are shown.

BAP050-hum09 HC

| | |
|---|---|
| SEQ ID NO: 140 (Kabat) | HCDR1 AACTATGGAATGAAC |
| SEQ ID NO: 141 (Kabat) | HCDR2 TGGATAAACACCGACACTGGAGAGCCAACATATGC TGATGACTTCAAGGGA |
| SEQ ID NO: 151 (Kabat) | HCDR3 AACCCTCCCTATTACTACGGTACTAATAACGCGGA GGCTATGGACTAC |
| SEQ ID NO: 143 (Chothia) | HCDR1 GGATTTACCCTCACAAACTAT |
| SEQ ID NO: 144 (Chothia) | HCDR2 AACACCGACACTGGAGAG |
| SEQ ID NO: 151 (Chothia) | HCDR3 AACCCTCCCTATTACTACGGTACTAATAACGCGGA GGCTATGGACTAC |

BAP050-hum09 LC

| | |
|---|---|
| SEQ ID NO: 145 (Kabat) | LCDR1 AGTTCAAGTCAGGACATCAGCAATTATTTAAAC |
| SEQ ID NO: 146 (Kabat) | LCDR2 TACACATCAACCTTACACTTA |
| SEQ ID NO: 147 (Kabat) | LCDR3 CAGCAGTATTATAACCTTCCGTGGACG |
| SEQ ID NO: 148 (Chothia) | LCDR1 AGTCAGGACATCAGCAATTAT |
| SEQ ID NO: 149 (Chothia) | LCDR2 TACACATCA |
| SEQ ID NO: 150 (Chothia) | LCDR3 TATTATAACCTTCCGTGG |

BAP050-hum10 HC

| | |
|---|---|
| SEQ ID NO: 140 (Kabat) | HCDR1 AACTATGGAATGAAC |
| SEQ ID NO: 141 (Kabat) | HCDR2 TGGATAAACACCGACACTGGAGAGCCAACATATGC TGATGACTTCAAGGGA |
| SEQ ID NO: 151 (Kabat) | HCDR3 AACCCTCCCTATTACTACGGTACTAATAACGCGGA GGCTATGGACTAC |
| SEQ ID NO: 143 (Chothia) | HCDR1 GGATTTACCCTCACAAACTAT |
| SEQ ID NO: 144 (Chothia) | HCDR2 AACACCGACACTGGAGAG |
| SEQ ID NO: 151 (Chothia) | HCDR3 AACCCTCCCTATTACTACGGTACTAATAACGCGGA GGCTATGGACTAC |

BAP050-hum10 LC

| | |
|---|---|
| SEQ ID NO: 145 (Kabat) | LCDR1 AGTTCAAGTCAGGACATCAGCAATTATTTAAAC |
| SEQ ID NO: 146 (Kabat) | LCDR2 TACACATCAACCTTACACTTA |
| SEQ ID NO: 147 (Kabat) | LCDR3 CAGCAGTATTATAACCTTCCGTGGACG |
| SEQ ID NO: 148 (Chothia) | LCDR1 AGTCAGGACATCAGCAATTAT |
| SEQ ID NO: 149 (Chothia) | LCDR2 TACACATCA |
| SEQ ID NO: 150 (Chothia) | LCDR3 TATTATAACCTTCCGTGG |

BAP050-hum11 HC

| | |
|---|---|
| SEQ ID NO: 140 (Kabat) | HCDR1 AACTATGGAATGAAC |
| SEQ ID NO: 141 (Kabat) | HCDR2 TGGATAAACACCGACACTGGAGAGCCAACATATGC TGATGACTTCAAGGGA |
| SEQ ID NO: 151 (Kabat) | HCDR3 AACCCTCCCTATTACTACGGTACTAATAACGCGGA GGCTATGGACTAC |
| SEQ ID NO: 143 (Chothia) | HCDR1 GGATTTACCCTCACAAACTAT |
| SEQ ID NO: 144 (Chothia) | HCDR2 AACACCGACACTGGAGAG |
| SEQ ID NO: 151 (Chothia) | HCDR3 AACCCTCCCTATTACTACGGTACTAATAACGCGGA GGCTATGGACTAC |

BAP050-hum11 LC

| | |
|---|---|
| SEQ ID NO: 145 (Kabat) | LCDR1 AGTTCAAGTCAGGACATCAGCAATTATTTAAAC |
| SEQ ID NO: 146 (Kabat) | LCDR2 TACACATCAACCTTACACTTA |
| SEQ ID NO: 147 (Kabat) | LCDR3 CAGCAGTATTATAACCTTCCGTGGACG |
| SEQ ID NO: 148 (Chothia) | LCDR1 AGTCAGGACATCAGCAATTAT |
| SEQ ID NO: 149 (Chothia) | LCDR2 TACACATCA |
| SEQ ID NO: 150 (Chothia) | LCDR3 TATTATAACCTTCCGTGG |

TABLE 1-continued

Amino acid and nucleotide sequences for murine, chimeric and humanized antibody molecules. The antibody molecules include murine mAb BAP050, chimeric mAbs BAP050-chi, humanized mAbs BAP050-hum01 to BAP050-hum20, humanized mAbs BAP050-hum01-Ser to BAP050-hum15-Ser, BAP050-hum18-Ser to BAP050-hum20-Ser, and humanized mAbs BAP050-Clone-F to BAP050-Clone-J. The amino acid and nucleotide sequences of the heavy and light chain CDRs, the heavy and light chain variable regions, and the heavy and light chains are shown.

BAP050-hum12 HC

| | |
|---|---|
| SEQ ID NO: 140 (Kabat) | HCDR1 AACTATGGAATGAAC |
| SEQ ID NO: 141 (Kabat) | HCDR2 TGGATAAACACCGACACTGGAGAGCCAACATATGC TGATGACTTCAAGGGA |
| SEQ ID NO: 151 (Kabat) | HCDR3 AACCCTCCCTATTACTACGGTACTAATAACGCGGA GGCTATGGACTAC |
| SEQ ID NO: 143 (Chothia) | HCDR1 GGATTTACCCTCACAAACTAT |
| SEQ ID NO: 144 (Chothia) | HCDR2 AACACCGACACTGGAGAG |
| SEQ ID NO: 151 (Chothia) | HCDR3 AACCCTCCCTATTACTACGGTACTAATAACGCGGA GGCTATGGACTAC |

BAP050-hum12 LC

| | |
|---|---|
| SEQ ID NO: 145 (Kabat) | LCDR1 AGTTCAAGTCAGGACATCAGCAATTATTTAAAC |
| SEQ ID NO: 146 (Kabat) | LCDR2 TACACATCAACCTTACACTTA |
| SEQ ID NO: 147 (Kabat) | LCDR3 CAGCAGTATTATAACCTTCCGTGGACG |
| SEQ ID NO: 148 (Chothia) | LCDR1 AGTCAGGACATCAGCAATTAT |
| SEQ ID NO: 149 (Chothia) | LCDR2 TACACATCA |
| SEQ ID NO: 150 (Chothia) | LCDR3 TATTATAACCTTCCGTGG |

BAP050-hum13 HC

| | |
|---|---|
| SEQ ID NO: 140 (Kabat) | HCDR1 AACTATGGAATGAAC |
| SEQ ID NO: 141 (Kabat) | HCDR2 TGGATAAACACCGACACTGGAGAGCCAACATATGC TGATGACTTCAAGGGA |
| SEQ ID NO: 151 (Kabat) | HCDR3 AACCCTCCCTATTACTACGGTACTAATAACGCGGA GGCTATGGACTAC |
| SEQ ID NO: 143 (Chothia) | HCDR1 GGATTTACCCTCACAAACTAT |
| SEQ ID NO: 144 (Chothia) | HCDR2 AACACCGACACTGGAGAG |
| SEQ ID NO: 151 (Chothia) | HCDR3 AACCCTCCCTATTACTACGGTACTAATAACGCGGA GGCTATGGACTAC |

BAP050-hum13 LC

| | |
|---|---|
| SEQ ID NO: 145 (Kabat) | LCDR1 AGTTCAAGTCAGGACATCAGCAATTATTTAAAC |
| SEQ ID NO: 146 (Kabat) | LCDR2 TACACATCAACCTTACACTTA |
| SEQ ID NO: 147 (Kabat) | LCDR3 CAGCAGTATTATAACCTTCCGTGGACG |
| SEQ ID NO: 148 (Chothia) | LCDR1 AGTCAGGACATCAGCAATTAT |
| SEQ ID NO: 149 (Chothia) | LCDR2 TACACATCA |
| SEQ ID NO: 150 (Chothia) | LCDR3 TATTATAACCTTCCGTGG |

BAP050-hum14 HC

| | |
|---|---|
| SEQ ID NO: 140 (Kabat) | HCDR1 AACTATGGAATGAAC |
| SEQ ID NO: 141 (Kabat) | HCDR2 TGGATAAACACCGACACTGGAGAGCCAACATATGC TGATGACTTCAAGGGA |
| SEQ ID NO: 151 (Kabat) | HCDR3 AACCCTCCCTATTACTACGGTACTAATAACGCGGA GGCTATGGACTAC |
| SEQ ID NO: 143 (Chothia) | HCDR1 GGATTTACCCTCACAAACTAT |
| SEQ ID NO: 144 (Chothia) | HCDR2 AACACCGACACTGGAGAG |
| SEQ ID NO: 151 (Chothia) | HCDR3 AACCCTCCCTATTACTACGGTACTAATAACGCGGA GGCTATGGACTAC |

BAP050-hum14 LC

| | |
|---|---|
| SEQ ID NO: 145 (Kabat) | LCDR1 AGTTCAAGTCAGGACATCAGCAATTATTTAAAC |
| SEQ ID NO: 146 (Kabat) | LCDR2 TACACATCAACCTTACACTTA |
| SEQ ID NO: 147 (Kabat) | LCDR3 CAGCAGTATTATAACCTTCCGTGGACG |
| SEQ ID NO: 148 (Chothia) | LCDR1 AGTCAGGACATCAGCAATTAT |
| SEQ ID NO: 149 (Chothia) | LCDR2 TACACATCA |
| SEQ ID NO: 150 (Chothia) | LCDR3 TATTATAACCTTCCGTGG |

TABLE 1-continued

Amino acid and nucleotide sequences for murine, chimeric and humanized antibody molecules. The antibody molecules include murine mAb BAP050, chimeric mAbs BAP050-chi, humanized mAbs BAP050-hum01 to BAP050-hum20, humanized mAbs BAP050-hum01-Ser to BAP050-hum15-Ser, BAP050-hum18-Ser to BAP050-hum20-Ser, and humanized mAbs BAP050-Clone-F to BAP050-Clone-J. The amino acid and nucleotide sequences of the heavy and light chain CDRs, the heavy and light chain variable regions, and the heavy and light chains are shown.

BAP050-hum15 HC

| | |
|---|---|
| SEQ ID NO: 140 (Kabat) | HCDR1 AACTATGGAATGAAC |
| SEQ ID NO: 141 (Kabat) | HCDR2 TGGATAAACACCGACACTGGAGAGCCAACATATGC TGATGACTTCAAGGGA |
| SEQ ID NO: 151 (Kabat) | HCDR3 AACCCTCCCTATTACTACGGTACTAATAACGCGGA GGCTATGGACTAC |
| SEQ ID NO: 143 (Chothia) | HCDR1 GGATTTACCCTCACAAACTAT |
| SEQ ID NO: 144 (Chothia) | HCDR2 AACACCGACACTGGAGAG |
| SEQ ID NO: 151 (Chothia) | HCDR3 AACCCTCCCTATTACTACGGTACTAATAACGCGGA GGCTATGGACTAC |

BAP050-hum15 LC

| | |
|---|---|
| SEQ ID NO: 145 (Kabat) | LCDR1 AGTTCAAGTCAGGACATCAGCAATTATTTAAAC |
| SEQ ID NO: 146 (Kabat) | LCDR2 TACACATCAACCTTACACTTA |
| SEQ ID NO: 147 (Kabat) | LCDR3 CAGCAGTATTATAACCTTCCGTGGACG |
| SEQ ID NO: 148 (Chothia) | LCDR1 AGTCAGGACATCAGCAATTAT |
| SEQ ID NO: 149 (Chothia) | LCDR2 TACACATCA |
| SEQ ID NO: 150 (Chothia) | LCDR3 TATTATAACCTTCCGTGG |

BAP050-hum16 HC

| | |
|---|---|
| SEQ ID NO: 140 (Kabat) | HCDR1 AACTATGGAATGAAC |
| SEQ ID NO: 141 (Kabat) | HCDR2 TGGATAAACACCGACACTGGAGAGCCAACATATGC TGATGACTTCAAGGGA |
| SEQ ID NO: 151 (Kabat) | HCDR3 AACCCTCCCTATTACTACGGTACTAATAACGCGGA GGCTATGGACTAC |
| SEQ ID NO: 143 (Chothia) | HCDR1 GGATTTACCCTCACAAACTAT |
| SEQ ID NO: 144 (Chothia) | HCDR2 AACACCGACACTGGAGAG |
| SEQ ID NO: 151 (Chothia) | HCDR3 AACCCTCCCTATTACTACGGTACTAATAACGCGGA GGCTATGGACTAC |

BAP050-hum16 LC

| | |
|---|---|
| SEQ ID NO: 145 (Kabat) | LCDR1 AGTTCAAGTCAGGACATCAGCAATTATTTAAAC |
| SEQ ID NO: 146 (Kabat) | LCDR2 TACACATCAACCTTACACTTA |
| SEQ ID NO: 147 (Kabat) | LCDR3 CAGCAGTATTATAACCTTCCGTGGACG |
| SEQ ID NO: 148 (Chothia) | LCDR1 AGTCAGGACATCAGCAATTAT |
| SEQ ID NO: 149 (Chothia) | LCDR2 TACACATCA |
| SEQ ID NO: 150 (Chothia) | LCDR3 TATTATAACCTTCCGTGG |

BAP050-hum17 HC

| | |
|---|---|
| SEQ ID NO: 152 (Kabat) | HCDR1 AACTATGGCATGAAT |
| SEQ ID NO: 153 (Kabat) | HCDR2 TGGATCAACACCGACACTGGGGAGCCAACGTATGC CGATGACTTCAAGGGA |
| SEQ ID NO: 142 (Kabat) | HCDR3 AACCCCCCTTATTACTACGGTACTAATAACGCGGA GGCTATGGACTAC |
| SEQ ID NO: 154 (Chothia) | HCDR1 GGATTCACCCTGACTAACTAT |
| SEQ ID NO: 155 (Chothia) | HCDR2 AACACCGACACTGGGGAG |
| SEQ ID NO: 142 (Chothia) | HCDR3 AACCCCCCTTATTACTACGGTACTAATAACGCGGA GGCTATGGACTAC |

BAP050-hum17 LC

| | |
|---|---|
| SEQ ID NO: 156 (Kabat) | LCDR1 TCCTCTAGTCAGGACATTAGCAACTATTTAAAT |
| SEQ ID NO: 157 (Kabat) | LCDR2 TATACATCCACTTTGCACCTG |
| SEQ ID NO: 158 (Kabat) | LCDR3 CAACAGTATTATAATCTCCCTTGGACG |
| SEQ ID NO: 159 (Chothia) | LCDR1 AGTCAGGACATTAGCAACTAT |
| SEQ ID NO: 160 (Chothia) | LCDR2 TATACATCC |
| SEQ ID NO: 161 (Chothia) | LCDR3 TATTATAATCTCCCTTGG |

TABLE 1-continued

Amino acid and nucleotide sequences for murine, chimeric and humanized antibody molecules. The antibody molecules include murine mAb BAP050, chimeric mAbs BAP050-chi, humanized mAbs BAP050-hum01 to BAP050-hum20, humanized mAbs BAP050-hum01-Ser to BAP050-hum15-Ser, BAP050-hum18-Ser to BAP050-hum20-Ser, and humanized mAbs BAP050-Clone-F to BAP050-Clone-J. The amino acid and nucleotide sequences of the heavy and light chain CDRs, the heavy and light chain variable regions, and the heavy and light chains are shown.

BAP050-hum18 HC

| | |
|---|---|
| SEQ ID NO: 140 (Kabat) | HCDR1 AACTATGGAATGAAC |
| SEQ ID NO: 141 (Kabat) | HCDR2 TGGATAAACACCGACACTGGAGAGCCAACATATGC TGATGACTTCAAGGGA |
| SEQ ID NO: 151 (Kabat) | HCDR3 AACCCTCCCTATTACTACGGTACTAATAACGCGGA GGCTATGGACTAC |
| SEQ ID NO: 143 (Chothia) | HCDR1 GGATTTACCCTCACAAACTAT |
| SEQ ID NO: 144 (Chothia) | HCDR2 AACACCGACACTGGAGAG |
| SEQ ID NO: 151 (Chothia) | HCDR3 AACCCTCCCTATTACTACGGTACTAATAACGCGGA GGCTATGGACTAC |

BAP050-hum18 LC

| | |
|---|---|
| SEQ ID NO: 145 (Kabat) | LCDR1 AGTTCAAGTCAGGACATCAGCAATTATTTAAAC |
| SEQ ID NO: 146 (Kabat) | LCDR2 TACACATCAACCTTACACTTA |
| SEQ ID NO: 147 (Kabat) | LCDR3 CAGCAGTATTATAACCTTCCGTGGACG |
| SEQ ID NO: 148 (Chothia) | LCDR1 AGTCAGGACATCAGCAATTAT |
| SEQ ID NO: 149 (Chothia) | LCDR2 TACACATCA |
| SEQ ID NO: 150 (Chothia) | LCDR3 TATTATAACCTTCCGTGG |

BAP050-hum19 HC

| | |
|---|---|
| SEQ ID NO: 140 (Kabat) | HCDR1 AACTATGGAATGAAC |
| SEQ ID NO: 141 (Kabat) | HCDR2 TGGATAAACACCGACACTGGAGAGCCAACATATGC TGATGACTTCAAGGGA |
| SEQ ID NO: 151 (Kabat) | HCDR3 AACCCTCCCTATTACTACGGTACTAATAACGCGGA GGCTATGGACTAC |
| SEQ ID NO: 143 (Chothia) | HCDR1 GGATTTACCCTCACAAACTAT |
| SEQ ID NO: 144 (Chothia) | HCDR2 AACACCGACACTGGAGAG |
| SEQ ID NO: 151 (Chothia) | HCDR3 AACCCTCCCTATTACTACGGTACTAATAACGCGGA GGCTATGGACTAC |

BAP050-hum19 LC

| | |
|---|---|
| SEQ ID NO: 145 (Kabat) | LCDR1 AGTTCAAGTCAGGACATCAGCAATTATTTAAAC |
| SEQ ID NO: 146 (Kabat) | LCDR2 TACACATCAACCTTACACTTA |
| SEQ ID NO: 147 (Kabat) | LCDR3 CAGCAGTATTATAACCTTCCGTGGACG |
| SEQ ID NO: 148 (Chothia) | LCDR1 AGTCAGGACATCAGCAATTAT |
| SEQ ID NO: 149 (Chothia) | LCDR2 TACACATCA |
| SEQ ID NO: 150 (Chothia) | LCDR3 TATTATAACCTTCCGTGG |

BAP050-hum20 HC

| | |
|---|---|
| SEQ ID NO: 140 (Kabat) | HCDR1 AACTATGGAATGAAC |
| SEQ ID NO: 141 (Kabat) | HCDR2 TGGATAAACACCGACACTGGAGAGCCAACATATGC TGATGACTTCAAGGGA |
| SEQ ID NO: 151 (Kabat) | HCDR3 AACCCTCCCTATTACTACGGTACTAATAACGCGGA GGCTATGGACTAC |
| SEQ ID NO: 143 (Chothia) | HCDR1 GGATTTACCCTCACAAACTAT |
| SEQ ID NO: 144 (Chothia) | HCDR2 AACACCGACACTGGAGAG |
| SEQ ID NO: 151 (Chothia) | HCDR3 AACCCTCCCTATTACTACGGTACTAATAACGCGGA GGCTATGGACTAC |

BAP050-hum20 LC

| | |
|---|---|
| SEQ ID NO: 145 (Kabat) | LCDR1 AGTTCAAGTCAGGACATCAGCAATTATTTAAAC |
| SEQ ID NO: 146 (Kabat) | LCDR2 TACACATCAACCTTACACTTA |
| SEQ ID NO: 147 (Kabat) | LCDR3 CAGCAGTATTATAACCTTCCGTGGACG |
| SEQ ID NO: 148 (Chothia) | LCDR1 AGTCAGGACATCAGCAATTAT |
| SEQ ID NO: 149 (Chothia) | LCDR2 TACACATCA |
| SEQ ID NO: 150 (Chothia) | LCDR3 TATTATAACCTTCCGTGG |

TABLE 1-continued

Amino acid and nucleotide sequences for murine, chimeric and humanized antibody molecules. The antibody molecules include murine mAb BAP050, chimeric mAbs BAP050-chi, humanized mAbs BAP050-hum01 to BAP050-hum20, humanized mAbs BAP050-hum01-Ser to BAP050-hum15-Ser, BAP050-hum18-Ser to BAP050-hum20-Ser, and humanized mAbs BAP050-Clone-F to BAP050-Clone-J. The amino acid and nucleotide sequences of the heavy and light chain CDRs, the heavy and light chain variable regions, and the heavy and light chains are shown.

BAP050-hum01-Ser HC

| | |
|---|---|
| SEQ ID NO: 140 (Kabat) | HCDR1AACTATGGAATGAAC |
| SEQ ID NO: 141 (Kabat) | HCDR2TGGATAAACACCGACACTGGAGAGCCAACATATGCTGATGACTTCAAGGGA |
| SEQ ID NO: 151 (Kabat) | HCDR3AACCCTCCCTATTACTACGGTACTAATAACGCGGAGGCTATGGACTAC |
| SEQ ID NO: 143 (Chothia) | HCDR1GGATTTACCCTCACAAACTAT |
| SEQ ID NO: 144 (Chothia) | HCDR2AACACCGACACTGGAGAG |
| SEQ ID NO: 151 (Chothia) | HCDR3AACCCTCCCTATTACTACGGTACTAATAACGCGGAGGCTATGGACTAC |

BAP050-hum01-Ser LC

| | |
|---|---|
| SEQ ID NO: 145 (Kabat) | LCDR1AGTTCAAGTCAGGACATCAGCAATTATTTAAAC |
| SEQ ID NO: 146 (Kabat) | LCDR2TACACATCAACCTTACACTTA |
| SEQ ID NO: 147 (Kabat) | LCDR3CAGCAGTATTATAACCTTCCGTGGACG |
| SEQ ID NO: 148 (Chothia) | LCDR1AGTCAGGACATCAGCAATTAT |
| SEQ ID NO: 149 (Chothia) | LCDR2TACACATCA |
| SEQ ID NO: 150 (Chothia) | LCDR3TATTATAACCTTCCGTGG |

BAP050-hum02-Ser HC

| | |
|---|---|
| SEQ ID NO: 140 (Kabat) | HCDR1AACTATGGAATGAAC |
| SEQ ID NO: 141 (Kabat) | HCDR2TGGATAAACACCGACACTGGAGAGCCAACATATGCTGATGACTTCAAGGGA |
| SEQ ID NO: 151 (Kabat) | HCDR3AACCCTCCCTATTACTACGGTACTAATAACGCGGAGGCTATGGACTAC |
| SEQ ID NO: 143 (Chothia) | HCDR1GGATTTACCCTCACAAACTAT |
| SEQ ID NO: 144 (Chothia) | HCDR2AACACCGACACTGGAGAG |
| SEQ ID NO: 151 (Chothia) | HCDR3AACCCTCCCTATTACTACGGTACTAATAACGCGGAGGCTATGGACTAC |

BAP050-hum02-Ser LC

| | |
|---|---|
| SEQ ID NO: 145 (Kabat) | LCDR1AGTTCAAGTCAGGACATCAGCAATTATTTAAAC |
| SEQ ID NO: 146 (Kabat) | LCDR2TACACATCAACCTTACACTTA |
| SEQ ID NO: 147 (Kabat) | LCDR3CAGCAGTATTATAACCTTCCGTGGACG |
| SEQ ID NO: 148 (Chothia) | LCDR1AGTCAGGACATCAGCAATTAT |
| SEQ ID NO: 149 (Chothia) | LCDR2TACACATCA |
| SEQ ID NO: 150 (Chothia) | LCDR3TATTATAACCTTCCGTGG |

BAP050-hum03-Ser HC

| | |
|---|---|
| SEQ ID NO: 140 (Kabat) | HCDR1AACTATGGAATGAAC |
| SEQ ID NO: 141 (Kabat) | HCDR2TGGATAAACACCGACACTGGAGAGCCAACATATGCTGATGACTTCAAGGGA |
| SEQ ID NO: 151 (Kabat) | HCDR3AACCCTCCCTATTACTACGGTACTAATAACGCGGAGGCTATGGACTAC |
| SEQ ID NO: 143 (Chothia) | HCDR1GGATTTACCCTCACAAACTAT |
| SEQ ID NO: 144 (Chothia) | HCDR2AACACCGACACTGGAGAG |
| SEQ ID NO: 151 (Chothia) | HCDR3AACCCTCCCTATTACTACGGTACTAATAACGCGGAGGCTATGGACTAC |

BAP050-hum03-Ser LC

| | |
|---|---|
| SEQ ID NO: 145 (Kabat) | LCDR1AGTTCAAGTCAGGACATCAGCAATTATTTAAAC |
| SEQ ID NO: 146 (Kabat) | LCDR2TACACATCAACCTTACACTTA |
| SEQ ID NO: 147 (Kabat) | LCDR3CAGCAGTATTATAACCTTCCGTGGACG |
| SEQ ID NO: 148 (Chothia) | LCDR1AGTCAGGACATCAGCAATTAT |
| SEQ ID NO: 149 (Chothia) | LCDR2TACACATCA |
| SEQ ID NO: 150 (Chothia) | LCDR3TATTATAACCTTCCGTGG |

TABLE 1-continued

Amino acid and nucleotide sequences for murine, chimeric and humanized antibody molecules. The antibody molecules include murine mAb BAP050, chimeric mAbs BAP050-chi, humanized mAbs BAP050-hum01 to BAP050-hum20, humanized mAbs BAP050-hum01-Ser to BAP050-hum15-Ser, BAP050-hum18-Ser to BAP050-hum20-Ser, and humanized mAbs BAP050-Clone-F to BAP050-Clone-J. The amino acid and nucleotide sequences of the heavy and light chain CDRs, the heavy and light chain variable regions, and the heavy and light chains are shown.

BAP050-hum04-Ser HC

| | |
|---|---|
| SEQ ID NO: 140 (Kabat) | HCDR1 AACTATGGAATGAAC |
| SEQ ID NO: 141 (Kabat) | HCDR2 TGGATAAACACCGACACTGGAGAGCCAACATATGCTGATGACTTCAAGGGA |
| SEQ ID NO: 151 (Kabat) | HCDR3 AACCCTCCCTATTACTACGGTACTAATAACGCGGAGGCTATGGACTAC |
| SEQ ID NO: 143 (Chothia) | HCDR1 GGATTTACCCTCACAAACTAT |
| SEQ ID NO: 144 (Chothia) | HCDR2 AACACCGACACTGGAGAG |
| SEQ ID NO: 151 (Chothia) | HCDR3 AACCCTCCCTATTACTACGGTACTAATAACGCGGAGGCTATGGACTAC |

BAP050-hum04-Ser LC

| | |
|---|---|
| SEQ ID NO: 145 (Kabat) | LCDR1 AGTTCAAGTCAGGACATCAGCAATTATTTAAAC |
| SEQ ID NO: 146 (Kabat) | LCDR2 TACACATCAACCTTACACTTA |
| SEQ ID NO: 147 (Kabat) | LCDR3 CAGCAGTATTATAACCTTCCGTGGACG |
| SEQ ID NO: 148 (Chothia) | LCDR1 AGTCAGGACATCAGCAATTAT |
| SEQ ID NO: 149 (Chothia) | LCDR2 TACACATCA |
| SEQ ID NO: 150 (Chothia) | LCDR3 TATTATAACCTTCCGTGG |

BAP050-hum05-Ser HC

| | |
|---|---|
| SEQ ID NO: 140 (Kabat) | HCDR1 AACTATGGAATGAAC |
| SEQ ID NO: 141 (Kabat) | HCDR2 TGGATAAACACCGACACTGGAGAGCCAACATATGCTGATGACTTCAAGGGA |
| SEQ ID NO: 151 (Kabat) | HCDR3 AACCCTCCCTATTACTACGGTACTAATAACGCGGAGGCTATGGACTAC |
| SEQ ID NO: 143 (Chothia) | HCDR1 GGATTTACCCTCACAAACTAT |
| SEQ ID NO: 144 (Chothia) | HCDR2 AACACCGACACTGGAGAG |
| SEQ ID NO: 151 (Chothia) | HCDR3 AACCCTCCCTATTACTACGGTACTAATAACGCGGAGGCTATGGACTAC |

BAP050-hum05-Ser LC

| | |
|---|---|
| SEQ ID NO: 145 (Kabat) | LCDR1 AGTTCAAGTCAGGACATCAGCAATTATTTAAAC |
| SEQ ID NO: 146 (Kabat) | LCDR2 TACACATCAACCTTACACTTA |
| SEQ ID NO: 147 (Kabat) | LCDR3 CAGCAGTATTATAACCTTCCGTGGACG |
| SEQ ID NO: 148 (Chothia) | LCDR1 AGTCAGGACATCAGCAATTAT |
| SEQ ID NO: 149 (Chothia) | LCDR2 TACACATCA |
| SEQ ID NO: 150 (Chothia) | LCDR3 TATTATAACCTTCCGTGG |

BAP050-hum06-Ser HC

| | |
|---|---|
| SEQ ID NO: 140 (Kabat) | HCDR1 AACTATGGAATGAAC |
| SEQ ID NO: 141 (Kabat) | HCDR2 TGGATAAACACCGACACTGGAGAGCCAACATATGCTGATGACTTCAAGGGA |
| SEQ ID NO: 151 (Kabat) | HCDR3 AACCCTCCCTATTACTACGGTACTAATAACGCGGAGGCTATGGACTAC |
| SEQ ID NO: 143 (Chothia) | HCDR1 GGATTTACCCTCACAAACTAT |
| SEQ ID NO: 144 (Chothia) | HCDR2 AACACCGACACTGGAGAG |
| SEQ ID NO: 151 (Chothia) | HCDR3 AACCCTCCCTATTACTACGGTACTAATAACGCGGAGGCTATGGACTAC |

BAP050-hum06-Ser LC

| | |
|---|---|
| SEQ ID NO: 145 (Kabat) | LCDR1 AGTTCAAGTCAGGACATCAGCAATTATTTAAAC |
| SEQ ID NO: 146 (Kabat) | LCDR2 TACACATCAACCTTACACTTA |
| SEQ ID NO: 147 (Kabat) | LCDR3 CAGCAGTATTATAACCTTCCGTGGACG |
| SEQ ID NO: 148 (Chothia) | LCDR1 AGTCAGGACATCAGCAATTAT |
| SEQ ID NO: 149 (Chothia) | LCDR2 TACACATCA |
| SEQ ID NO: 150 (Chothia) | LCDR3 TATTATAACCTTCCGTGG |

TABLE 1-continued

Amino acid and nucleotide sequences for murine, chimeric and humanized antibody molecules. The antibody molecules include murine mAb BAP050, chimeric mAbs BAP050-chi, humanized mAbs BAP050-hum01 to BAP050-hum20, humanized mAbs BAP050-hum01-Ser to BAP050-hum15-Ser, BAP050-hum18-Ser to BAP050-hum20-Ser, and humanized mAbs BAP050-Clone-F to BAP050-Clone-J. The amino acid and nucleotide sequences of the heavy and light chain CDRs, the heavy and light chain variable regions, and the heavy and light chains are shown.

BAP050-hum07-Ser HC

| SEQ ID NO: 140 (Kabat) | HCDR1 AACTATGGAATGAAC |
| --- | --- |
| SEQ ID NO: 141 (Kabat) | HCDR2 TGGATAAACACCGACACTGGAGAGCCAACATATGCTGATGACTTCAAGGGA |
| SEQ ID NO: 151 (Kabat) | HCDR3 AACCCTCCCTATTACTACGGTACTAATAACGCGGAGGCTATGGACTAC |
| SEQ ID NO: 143 (Chothia) | HCDR1 GGATTTACCCTCACAAACTAT |
| SEQ ID NO: 144 (Chothia) | HCDR2 AACACCGACACTGGAGAG |
| SEQ ID NO: 151 (Chothia) | HCDR3 AACCCTCCCTATTACTACGGTACTAATAACGCGGAGGCTATGGACTAC |

BAP050-hum07-Ser LC

| SEQ ID NO: 145 (Kabat) | LCDR1 AGTTCAAGTCAGGACATCAGCAATTATTTAAAC |
| --- | --- |
| SEQ ID NO: 146 (Kabat) | LCDR2 TACACATCAACCTTACACTTA |
| SEQ ID NO: 147 (Kabat) | LCDR3 CAGCAGTATTATAACCTTCCGTGGACG |
| SEQ ID NO: 148 (Chothia) | LCDR1 AGTCAGGACATCAGCAATTAT |
| SEQ ID NO: 149 (Chothia) | LCDR2 TACACATCA |
| SEQ ID NO: 150 (Chothia) | LCDR3 TATTATAACCTTCCGTGG |

BAP050-hum08-Ser HC

| SEQ ID NO: 140 (Kabat) | HCDR1 AACTATGGAATGAAC |
| --- | --- |
| SEQ ID NO: 141 (Kabat) | HCDR2 TGGATAAACACCGACACTGGAGAGCCAACATATGCTGATGACTTCAAGGGA |
| SEQ ID NO: 151 (Kabat) | HCDR3 AACCCTCCCTATTACTACGGTACTAATAACGCGGAGGCTATGGACTAC |
| SEQ ID NO: 143 (Chothia) | HCDR1 GGATTTACCCTCACAAACTAT |
| SEQ ID NO: 144 (Chothia) | HCDR2 AACACCGACACTGGAGAG |
| SEQ ID NO: 151 (Chothia) | HCDR3 AACCCTCCCTATTACTACGGTACTAATAACGCGGAGGCTATGGACTAC |

BAP050-hum08-Ser LC

| SEQ ID NO: 145 (Kabat) | LCDR1 AGTTCAAGTCAGGACATCAGCAATTATTTAAAC |
| --- | --- |
| SEQ ID NO: 146 (Kabat) | LCDR2 TACACATCAACCTTACACTTA |
| SEQ ID NO: 147 (Kabat) | LCDR3 CAGCAGTATTATAACCTTCCGTGGACG |
| SEQ ID NO: 148 (Chothia) | LCDR1 AGTCAGGACATCAGCAATTAT |
| SEQ ID NO: 149 (Chothia) | LCDR2 TACACATCA |
| SEQ ID NO: 150 (Chothia) | LCDR3 TATTATAACCTTCCGTGG |

BAP050-hum09-Ser HC

| SEQ ID NO: 140 (Kabat) | HCDR1 AACTATGGAATGAAC |
| --- | --- |
| SEQ ID NO: 141 (Kabat) | HCDR2 TGGATAAACACCGACACTGGAGAGCCAACATATGCTGATGACTTCAAGGGA |
| SEQ ID NO: 151 (Kabat) | HCDR3 AACCCTCCCTATTACTACGGTACTAATAACGCGGAGGCTATGGACTAC |
| SEQ ID NO: 143 (Chothia) | HCDR1 GGATTTACCCTCACAAACTAT |
| SEQ ID NO: 144 (Chothia) | HCDR2 AACACCGACACTGGAGAG |
| SEQ ID NO: 151 (Chothia) | HCDR3 AACCCTCCCTATTACTACGGTACTAATAACGCGGAGGCTATGGACTAC |

BAP050-hum09-Ser LC

| SEQ ID NO: 145 (Kabat) | LCDR1 AGTTCAAGTCAGGACATCAGCAATTATTTAAAC |
| --- | --- |
| SEQ ID NO: 146 (Kabat) | LCDR2 TACACATCAACCTTACACTTA |
| SEQ ID NO: 147 (Kabat) | LCDR3 CAGCAGTATTATAACCTTCCGTGGACG |
| SEQ ID NO: 148 (Chothia) | LCDR1 AGTCAGGACATCAGCAATTAT |
| SEQ ID NO: 149 (Chothia) | LCDR2 TACACATCA |
| SEQ ID NO: 150 (Chothia) | LCDR3 TATTATAACCTTCCGTGG |

TABLE 1-continued

Amino acid and nucleotide sequences for murine, chimeric and humanized antibody molecules. The antibody molecules include murine mAb BAP050, chimeric mAbs BAP050-chi, humanized mAbs BAP050-hum01 to BAP050-hum20, humanized mAbs BAP050-hum01-Ser to BAP050-hum15-Ser, BAP050-hum18-Ser to BAP050-hum20-Ser, and humanized mAbs BAP050-Clone-F to BAP050-Clone-J. The amino acid and nucleotide sequences of the heavy and light chain CDRs, the heavy and light chain variable regions, and the heavy and light chains are shown.

---

BAP050-hum10-Ser HC

| | | |
|---|---|---|
| SEQ ID NO: 140 (Kabat) | HCDR1 | AACTATGGAATGAAC |
| SEQ ID NO: 141 (Kabat) | HCDR2 | TGGATAAACACCGACACTGGAGAGCCAACATATGCTGATGACTTCAAGGGA |
| SEQ ID NO: 151 (Kabat) | HCDR3 | AACCCTCCCTATTACTACGGTACTAATAACGCGGAGGCTATGGACTAC |
| SEQ ID NO: 143 (Chothia) | HCDR1 | GGATTTACCCTCACAAACTAT |
| SEQ ID NO: 144 (Chothia) | HCDR2 | AACACCGACACTGGAGAG |
| SEQ ID NO: 151 (Chothia) | HCDR3 | AACCCTCCCTATTACTACGGTACTAATAACGCGGAGGCTATGGACTAC |

BAP050-hum10-Ser LC

| | | |
|---|---|---|
| SEQ ID NO: 145 (Kabat) | LCDR1 | AGTTCAAGTCAGGACATCAGCAATTATTTAAAC |
| SEQ ID NO: 146 (Kabat) | LCDR2 | TACACATCAACCTTACACTTA |
| SEQ ID NO: 147 (Kabat) | LCDR3 | CAGCAGTATTATAACCTTCCGTGGACG |
| SEQ ID NO: 148 (Chothia) | LCDR1 | AGTCAGGACATCAGCAATTAT |
| SEQ ID NO: 149 (Chothia) | LCDR2 | TACACATCA |
| SEQ ID NO: 150 (Chothia) | LCDR3 | TATTATAACCTTCCGTGG |

BAP050-hum11-Ser HC

| | | |
|---|---|---|
| SEQ ID NO: 140 (Kabat) | HCDR1 | AACTATGGAATGAAC |
| SEQ ID NO: 141 (Kabat) | HCDR2 | TGGATAAACACCGACACTGGAGAGCCAACATATGCTGATGACTTCAAGGGA |
| SEQ ID NO: 151 (Kabat) | HCDR3 | AACCCTCCCTATTACTACGGTACTAATAACGCGGAGGCTATGGACTAC |
| SEQ ID NO: 143 (Chothia) | HCDR1 | GGATTTACCCTCACAAACTAT |
| SEQ ID NO: 144 (Chothia) | HCDR2 | AACACCGACACTGGAGAG |
| SEQ ID NO: 151 (Chothia) | HCDR3 | AACCCTCCCTATTACTACGGTACTAATAACGCGGAGGCTATGGACTAC |

BAP050-hum11-Ser LC

| | | |
|---|---|---|
| SEQ ID NO: 145 (Kabat) | LCDR1 | AGTTCAAGTCAGGACATCAGCAATTATTTAAAC |
| SEQ ID NO: 146 (Kabat) | LCDR2 | TACACATCAACCTTACACTTA |
| SEQ ID NO: 147 (Kabat) | LCDR3 | CAGCAGTATTATAACCTTCCGTGGACG |
| SEQ ID NO: 148 (Chothia) | LCDR1 | AGTCAGGACATCAGCAATTAT |
| SEQ ID NO: 149 (Chothia) | LCDR2 | TACACATCA |
| SEQ ID NO: 150 (Chothia) | LCDR3 | TATTATAACCTTCCGTGG |

BAP050-hum12-Ser HC

| | | |
|---|---|---|
| SEQ ID NO: 140 (Kabat) | HCDR1 | AACTATGGAATGAAC |
| SEQ ID NO: 141 (Kabat) | HCDR2 | TGGATAAACACCGACACTGGAGAGCCAACATATGCTGATGACTTCAAGGGA |
| SEQ ID NO: 151 (Kabat) | HCDR3 | AACCCTCCCTATTACTACGGTACTAATAACGCGGAGGCTATGGACTAC |
| SEQ ID NO: 143 (Chothia) | HCDR1 | GGATTTACCCTCACAAACTAT |
| SEQ ID NO: 144 (Chothia) | HCDR2 | AACACCGACACTGGAGAG |
| SEQ ID NO: 151 (Chothia) | HCDR3 | AACCCTCCCTATTACTACGGTACTAATAACGCGGAGGCTATGGACTAC |

BAP050-hum12-Ser LC

| | | |
|---|---|---|
| SEQ ID NO: 145 (Kabat) | LCDR1 | AGTTCAAGTCAGGACATCAGCAATTATTTAAAC |
| SEQ ID NO: 146 (Kabat) | LCDR2 | TACACATCAACCTTACACTTA |
| SEQ ID NO: 147 (Kabat) | LCDR3 | CAGCAGTATTATAACCTTCCGTGGACG |
| SEQ ID NO: 148 (Chothia) | LCDR1 | AGTCAGGACATCAGCAATTAT |
| SEQ ID NO: 149 (Chothia) | LCDR2 | TACACATCA |
| SEQ ID NO: 150 (Chothia) | LCDR3 | TATTATAACCTTCCGTGG |

TABLE 1-continued

Amino acid and nucleotide sequences for murine, chimeric and humanized antibody molecules. The antibody molecules include murine mAb BAP050, chimeric mAbs BAP050-chi, humanized mAbs BAP050-hum01 to BAP050-hum20, humanized mAbs BAP050-hum01-Ser to BAP050-hum15-Ser, BAP050-hum18-Ser to BAP050-hum20-Ser, and humanized mAbs BAP050-Clone-F to BAP050-Clone-J. The amino acid and nucleotide sequences of the heavy and light chain CDRs, the heavy and light chain variable regions, and the heavy and light chains are shown.

BAP050-hum13-Ser HC

| | |
|---|---|
| SEQ ID NO: 140 (Kabat) | HCDR1AACTATGGAATGAAC |
| SEQ ID NO: 141 (Kabat) | HCDR2TGGATAAACACCGACACTGGAGAGCCAACATATGCTGATGACTTCAAGGGA |
| SEQ ID NO: 151 (Kabat) | HCDR3AACCCTCCCTATTACTACGGTACTAATAACGCGGAGGCTATGGACTAC |
| SEQ ID NO: 143 (Chothia) | HCDR1GGATTTACCCTCACAAACTAT |
| SEQ ID NO: 144 (Chothia) | HCDR2AACACCGACACTGGAGAG |
| SEQ ID NO: 151 (Chothia) | HCDR3AACCCTCCCTATTACTACGGTACTAATAACGCGGAGGCTATGGACTAC |

BAP050-hum13-Ser LC

| | |
|---|---|
| SEQ ID NO: 145 (Kabat) | LCDR1AGTTCAAGTCAGGACATCAGCAATTATTTAAAC |
| SEQ ID NO: 146 (Kabat) | LCDR2TACACATCAACCTTACACTTA |
| SEQ ID NO: 147 (Kabat) | LCDR3CAGCAGTATTATAACCTTCCGTGGACG |
| SEQ ID NO: 148 (Chothia) | LCDR1AGTCAGGACATCAGCAATTAT |
| SEQ ID NO: 149 (Chothia) | LCDR2TACACATCA |
| SEQ ID NO: 150 (Chothia) | LCDR3TATTATAACCTTCCGTGG |

BAP050-hum14-Ser HC

| | |
|---|---|
| SEQ ID NO: 140 (Kabat) | HCDR1AACTATGGAATGAAC |
| SEQ ID NO: 141 (Kabat) | HCDR2TGGATAAACACCGACACTGGAGAGCCAACATATGCTGATGACTTCAAGGGA |
| SEQ ID NO: 151 (Kabat) | HCDR3AACCCTCCCTATTACTACGGTACTAATAACGCGGAGGCTATGGACTAC |
| SEQ ID NO: 143 (Chothia) | HCDR1GGATTTACCCTCACAAACTAT |
| SEQ ID NO: 144 (Chothia) | HCDR2AACACCGACACTGGAGAG |
| SEQ ID NO: 151 (Chothia) | HCDR3AACCCTCCCTATTACTACGGTACTAATAACGCGGAGGCTATGGACTAC |

BAP050-hum14-Ser LC

| | |
|---|---|
| SEQ ID NO: 145 (Kabat) | LCDR1AGTTCAAGTCAGGACATCAGCAATTATTTAAAC |
| SEQ ID NO: 146 (Kabat) | LCDR2TACACATCAACCTTACACTTA |
| SEQ ID NO: 147 (Kabat) | LCDR3CAGCAGTATTATAACCTTCCGTGGACG |
| SEQ ID NO: 148 (Chothia) | LCDR1AGTCAGGACATCAGCAATTAT |
| SEQ ID NO: 149 (Chothia) | LCDR2TACACATCA |
| SEQ ID NO: 150 (Chothia) | LCDR3TATTATAACCTTCCGTGG |

BAP050-hum15-Ser HC

| | |
|---|---|
| SEQ ID NO: 140 (Kabat) | HCDR1AACTATGGAATGAAC |
| SEQ ID NO: 141 (Kabat) | HCDR2TGGATAAACACCGACACTGGAGAGCCAACATATGCTGATGACTTCAAGGGA |
| SEQ ID NO: 151 (Kabat) | HCDR3AACCCTCCCTATTACTACGGTACTAATAACGCGGAGGCTATGGACTAC |
| SEQ ID NO: 143 (Chothia) | HCDR1GGATTTACCCTCACAAACTAT |
| SEQ ID NO: 144 (Chothia) | HCDR2AACACCGACACTGGAGAG |
| SEQ ID NO: 151 (Chothia) | HCDR3AACCCTCCCTATTACTACGGTACTAATAACGCGGAGGCTATGGACTAC |

BAP050-hum15-Ser LC

| | |
|---|---|
| SEQ ID NO: 145 (Kabat) | LCDR1AGTTCAAGTCAGGACATCAGCAATTATTTAAAC |
| SEQ ID NO: 146 (Kabat) | LCDR2TACACATCAACCTTACACTTA |
| SEQ ID NO: 147 (Kabat) | LCDR3CAGCAGTATTATAACCTTCCGTGGACG |
| SEQ ID NO: 148 (Chothia) | LCDR1AGTCAGGACATCAGCAATTAT |
| SEQ ID NO: 149 (Chothia) | LCDR2TACACATCA |

TABLE 1-continued

Amino acid and nucleotide sequences for murine, chimeric and humanized antibody molecules. The antibody molecules include murine mAb BAP050, chimeric mAbs BAP050-chi, humanized mAbs BAP050-hum01 to BAP050-hum20, humanized mAbs BAP050-hum01-Ser to BAP050-hum15-Ser, BAP050-hum18-Ser to BAP050-hum20-Ser, and humanized mAbs BAP050-Clone-F to BAP050-Clone-J. The amino acid and nucleotide sequences of the heavy and light chain CDRs, the heavy and light chain variable regions, and the heavy and light chains are shown.

| SEQ ID NO: 150 (Chothia) | LCDR3 TATTATAACCTTCCGTGG |
|---|---|

BAP050-hum18-Ser HC

| SEQ ID NO: 140 (Kabat) | HCDR1 AACTATGGAATGAAC |
|---|---|
| SEQ ID NO: 141 (Kabat) | HCDR2 TGGATAAACACCGACACTGGAGAGCCAACATATGCTGATGACTTCAAGGGA |
| SEQ ID NO: 151 (Kabat) | HCDR3 AACCCTCCCTATTACTACGGTACTAATAACGCGGAGGCTATGGACTAC |
| SEQ ID NO: 143 (Chothia) | HCDR1 GGATTTACCCTCACAAACTAT |
| SEQ ID NO: 144 (Chothia) | HCDR2 AACACCGACACTGGAGAG |
| SEQ ID NO: 151 (Chothia) | HCDR3 AACCCTCCCTATTACTACGGTACTAATAACGCGGAGGCTATGGACTAC |

BAP050-hum18-Ser LC

| SEQ ID NO: 145 (Kabat) | LCDR1 AGTTCAAGTCAGGACATCAGCAATTATTTAAAC |
|---|---|
| SEQ ID NO: 146 (Kabat) | LCDR2 TACACATCAACCTTACACTTA |
| SEQ ID NO: 147 (Kabat) | LCDR3 CAGCAGTATTATAACCTTCCGTGGACG |
| SEQ ID NO: 148 (Chothia) | LCDR1 AGTCAGGACATCAGCAATTAT |
| SEQ ID NO: 149 (Chothia) | LCDR2 TACACATCA |
| SEQ ID NO: 150 (Chothia) | LCDR3 TATTATAACCTTCCGTGG |

BAP050-hum19-Ser HC

| SEQ ID NO: 140 (Kabat) | HCDR1 AACTATGGAATGAAC |
|---|---|
| SEQ ID NO: 141 (Kabat) | HCDR2 TGGATAAACACCGACACTGGAGAGCCAACATATGCTGATGACTTCAAGGGA |
| SEQ ID NO: 151 (Kabat) | HCDR3 AACCCTCCCTATTACTACGGTACTAATAACGCGGAGGCTATGGACTAC |
| SEQ ID NO: 143 (Chothia) | HCDR1 GGATTTACCCTCACAAACTAT |
| SEQ ID NO: 144 (Chothia) | HCDR2 AACACCGACACTGGAGAG |
| SEQ ID NO: 151 (Chothia) | HCDR3 AACCCTCCCTATTACTACGGTACTAATAACGCGGAGGCTATGGACTAC |

BAP050-hum19-Ser LC

| SEQ ID NO: 145 (Kabat) | LCDR1 AGTTCAAGTCAGGACATCAGCAATTATTTAAAC |
|---|---|
| SEQ ID NO: 146 (Kabat) | LCDR2 TACACATCAACCTTACACTTA |
| SEQ ID NO: 147 (Kabat) | LCDR3 CAGCAGTATTATAACCTTCCGTGGACG |
| SEQ ID NO: 148 (Chothia) | LCDR1 AGTCAGGACATCAGCAATTAT |
| SEQ ID NO: 149 (Chothia) | LCDR2 TACACATCA |
| SEQ ID NO: 150 (Chothia) | LCDR3 TATTATAACCTTCCGTGG |

BAP050-hum20-Ser HC

| SEQ ID NO: 140 (Kabat) | HCDR1 AACTATGGAATGAAC |
|---|---|
| SEQ ID NO: 141 (Kabat) | HCDR2 TGGATAAACACCGACACTGGAGAGCCAACATATGCTGATGACTTCAAGGGA |
| SEQ ID NO: 151 (Kabat) | HCDR3 AACCCTCCCTATTACTACGGTACTAATAACGCGGAGGCTATGGACTAC |
| SEQ ID NO: 143 (Chothia) | HCDR1 GGATTTACCCTCACAAACTAT |
| SEQ ID NO: 144 (Chothia) | HCDR2 AACACCGACACTGGAGAG |
| SEQ ID NO: 151 (Chothia) | HCDR3 AACCCTCCCTATTACTACGGTACTAATAACGCGGAGGCTATGGACTAC |

BAP050-hum20-Ser LC

| SEQ ID NO: 145 (Kabat) | LCDR1 AGTTCAAGTCAGGACATCAGCAATTATTTAAAC |
|---|---|
| SEQ ID NO: 146 (Kabat) | LCDR2 TACACATCAACCTTACACTTA |
| SEQ ID NO: 147 (Kabat) | LCDR3 CAGCAGTATTATAACCTTCCGTGGACG |
| SEQ ID NO: 148 (Chothia) | LCDR1 AGTCAGGACATCAGCAATTAT |
| SEQ ID NO: 149 (Chothia) | LCDR2 TACACATCA |
| SEQ ID NO: 150 (Chothia) | LCDR3 TATTATAACCTTCCGTGG |

TABLE 1-continued

Amino acid and nucleotide sequences for murine, chimeric and humanized antibody molecules. The antibody molecules include murine mAb BAP050, chimeric mAbs BAP050-chi, humanized mAbs BAP050-hum01 to BAP050-hum20, humanized mAbs BAP050-hum01-Ser to BAP050-hum15-Ser, BAP050-hum18-Ser to BAP050-hum20-Ser, and humanized mAbs BAP050-Clone-F to BAP050-Clone-J. The amino acid and nucleotide sequences of the heavy and light chain CDRs, the heavy and light chain variable regions, and the heavy and light chains are shown.

BAP050-Clone-F HC

| | | |
|---|---|---|
| SEQ ID NO: 162 (Kabat) | HCDR1 | AACTACGGCATGAAC |
| SEQ ID NO: 163 (Kabat) | HCDR2 | TGGATCAACACCGACACCGGCGAGCCTACCTACGCCGACGACTTCAAGGGC |
| SEQ ID NO: 164 (Kabat) | HCDR3 | AACCCCCCTTACTACTACGGCACCAACAACGCCGAGGCCATGGACTAT |
| SEQ ID NO: 165 (Chothia) | HCDR1 | GGCTTCACCCTGACCAACTAC |
| SEQ ID NO: 166 (Chothia) | HCDR2 | AACACCGACACCGGCGAG |
| SEQ ID NO: 164 (Chothia) | HCDR3 | AACCCCCCTTACTACTACGGCACCAACAACGCCGAGGCCATGGACTAT |

BAP050-Clone-F LC

| | | |
|---|---|---|
| SEQ ID NO: 167 (Kabat) | LCDR1 | TCCTCCAGCCAGGACATCTCCAACTACCTGAAC |
| SEQ ID NO: 168 (Kabat) | LCDR2 | TACACCTCCACCCTGCACCTG |
| SEQ ID NO: 169 (Kabat) | LCDR3 | CAGCAGTACTACAACCTGCCCTGGACC |
| SEQ ID NO: 170 (Chothia) | LCDR1 | AGCCAGGACATCTCCAACTAC |
| SEQ ID NO: 171 (Chothia) | LCDR2 | TACACCTCC |
| SEQ ID NO: 172 (Chothia) | LCDR3 | TACTACAACCTGCCCTGG |

BAP050-Clone-G HC

| | | |
|---|---|---|
| SEQ ID NO: 162 (Kabat) | HCDR1 | AACTACGGCATGAAC |
| SEQ ID NO: 163 (Kabat) | HCDR2 | TGGATCAACACCGACACCGGCGAGCCTACCTACGCCGACGACTTCAAGGGC |
| SEQ ID NO: 164 (Kabat) | HCDR3 | AACCCCCCTTACTACTACGGCACCAACAACGCCGAGGCCATGGACTAT |
| SEQ ID NO: 165 (Chothia) | HCDR1 | GGCTTCACCCTGACCAACTAC |
| SEQ ID NO: 166 (Chothia) | HCDR2 | AACACCGACACCGGCGAG |
| SEQ ID NO: 164 (Chothia) | HCDR3 | AACCCCCCTTACTACTACGGCACCAACAACGCCGAGGCCATGGACTAT |

BAP050-Clone-G LC

| | | |
|---|---|---|
| SEQ ID NO: 167 (Kabat) | LCDR1 | TCCTCCAGCCAGGACATCTCCAACTACCTGAAC |
| SEQ ID NO: 168 (Kabat) | LCDR2 | TACACCTCCACCCTGCACCTG |
| SEQ ID NO: 169 (Kabat) | LCDR3 | CAGCAGTACTACAACCTGCCCTGGACC |
| SEQ ID NO: 170 (Chothia) | LCDR1 | AGCCAGGACATCTCCAACTAC |
| SEQ ID NO: 171 (Chothia) | LCDR2 | TACACCTCC |
| SEQ ID NO: 172 (Chothia) | LCDR3 | TACTACAACCTGCCCTGG |

BAP050-Clone-H HC

| | | |
|---|---|---|
| SEQ ID NO: 162 (Kabat) | HCDR1 | AACTACGGCATGAAC |
| SEQ ID NO: 163 (Kabat) | HCDR2 | TGGATCAACACCGACACCGGCGAGCCTACCTACGCCGACGACTTCAAGGGC |
| SEQ ID NO: 164 (Kabat) | HCDR3 | AACCCCCCTTACTACTACGGCACCAACAACGCCGAGGCCATGGACTAT |
| SEQ ID NO: 165 (Chothia) | HCDR1 | GGCTTCACCCTGACCAACTAC |
| SEQ ID NO: 166 (Chothia) | HCDR2 | AACACCGACACCGGCGAG |
| SEQ ID NO: 164 (Chothia) | HCDR3 | AACCCCCCTTACTACTACGGCACCAACAACGCCGAGGCCATGGACTAT |

BAP050-Clone-H LC

| | | |
|---|---|---|
| SEQ ID NO: 167 (Kabat) | LCDR1 | TCCTCCAGCCAGGACATCTCCAACTACCTGAAC |
| SEQ ID NO: 168 (Kabat) | LCDR2 | TACACCTCCACCCTGCACCTG |
| SEQ ID NO: 169 (Kabat) | LCDR3 | CAGCAGTACTACAACCTGCCCTGGACC |
| SEQ ID NO: 170 (Chothia) | LCDR1 | AGCCAGGACATCTCCAACTAC |
| SEQ ID NO: 171 (Chothia) | LCDR2 | TACACCTCC |
| SEQ ID NO: 172 (Chothia) | LCDR3 | TACTACAACCTGCCCTGG |

TABLE 1-continued

Amino acid and nucleotide sequences for murine, chimeric and humanized antibody molecules. The antibody molecules include murine mAb BAP050, chimeric mAbs BAP050-chi, humanized mAbs BAP050-hum01 to BAP050-hum20, humanized mAbs BAP050-hum01-Ser to BAP050-hum15-Ser, BAP050-hum18-Ser to BAP050-hum20-Ser, and humanized mAbs BAP050-Clone-F to BAP050-Clone-J. The amino acid and nucleotide sequences of the heavy and light chain CDRs, the heavy and light chain variable regions, and the heavy and light chains are shown.

BAP050-Clone-I HC

| SEQ ID NO: 173 (Kabat) | HCDR1 AATTACGGGATGAAC |
| --- | --- |
| SEQ ID NO: 162 (Kabat) | HCDR1 AACTACGGCATGAAC |
| SEQ ID NO: 174 (Kabat) | HCDR2 TGGATTAACACCGACACCGGGGAGCCTACCTACGC GGACGATTTCAAGGGA |
| SEQ ID NO: 163 (Kabat) | HCDR2 TGGATCAACACCGACACCGGCGAGCCTACCTACGC CGACGACTTCAAGGGC |
| SEQ ID NO: 175 (Kabat) | HCDR3 AACCCGCCCTACTACTACGGAACCAACAACGCCGA AGCCATGGACTAC |
| SEQ ID NO: 164 (Kabat) | HCDR3 AACCCCCCTTACTACTACGGCACCAACAACGCCGA GGCCATGGACTAT |
| SEQ ID NO: 176 (Chothia) | HCDR1 GGATTCACCCTCACCAATTAC |
| SEQ ID NO: 165 (Chothia) | HCDR1 GGCTTCACCCTGACCAACTAC |
| SEQ ID NO: 177 (Chothia) | HCDR2 AACACCGACACCGGGGAG |
| SEQ ID NO: 166 (Chothia) | HCDR2 AACACCGACACCGGCGAG |
| SEQ ID NO: 175 (Chothia) | HCDR3 AACCCGCCCTACTACTACGGAACCAACAACGCCGA AGCCATGGACTAC |
| SEQ ID NO: 164 (Chothia) | HCDR3 AACCCCCCTTACTACTACGGCACCAACAACGCCGA GGCCATGGACTAT |

BAP050-Clone-I LC

| SEQ ID NO: 178 (Kabat) | LCDR1 AGCTCTAGTCAGGATATCTCTAACTACCTGAAC |
| --- | --- |
| SEQ ID NO: 167 (Kabat) | LCDR1 TCCTCCAGCCAGGACATCTCCAACTACCTGAAC |
| SEQ ID NO: 179 (Kabat) | LCDR2 TACACTAGCACCCTGCACCTG |
| SEQ ID NO: 168 (Kabat) | LCDR2 TACACCTCCACCCTGCACCTG |
| SEQ ID NO: 180 (Kabat) | LCDR3 CAGCAGTACTATAACCTGCCCTGGACC |
| SEQ ID NO: 169 (Kabat) | LCDR3 CAGCAGTACTACAACCTGCCCTGGACC |
| SEQ ID NO: 181 (Chothia) | LCDR1 AGTCAGGATATCTCTAACTAC |
| SEQ ID NO: 170 (Chothia) | LCDR1 AGCCAGGACATCTCCAACTAC |
| SEQ ID NO: 182 (Chothia) | LCDR2 TACACTAGC |
| SEQ ID NO: 171 (Chothia) | LCDR2 TACACCTCC |
| SEQ ID NO: 183 (Chothia) | LCDR3 TACTATAACCTGCCCTGG |
| SEQ ID NO: 172 (Chothia) | LCDR3 TACTACAACCTGCCCTGG |

BAP050-Clone-J HC

| SEQ ID NO: 184 (Kabat) | HCDR1 AACTACGGGATGAAC |
| --- | --- |
| SEQ ID NO: 162 (Kabat) | HCDR1 AACTACGGCATGAAC |
| SEQ ID NO: 185 (Kabat) | HCDR2 TGGATTAACACCGACACCGGCGAGCCTACCTACGC CGACGACTTTAAGGGC |
| SEQ ID NO: 163 (Kabat) | HCDR2 TGGATCAACACCGACACCGGCGAGCCTACCTACGC CGACGACTTCAAGGGC |
| SEQ ID NO: 186 (Kabat) | HCDR3 AACCCCCCCTACTACTACGGCACTAACAACGCCGA GGCTATGGACTAC |
| SEQ ID NO: 164 (Kabat) | HCDR3 AACCCCCCTTACTACTACGGCACCAACAACGCCGA GGCCATGGACTAT |
| SEQ ID NO: 287 (Chothia) | HCDR1 GGCTTCACCCTGACTAACTAC |
| SEQ ID NO: 165 (Chothia) | HCDR1 GGCTTCACCCTGACCAACTAC |
| SEQ ID NO: 177 (Chothia) | HCDR2 AACACCGACACCGGGGAG |
| SEQ ID NO: 166 (Chothia) | HCDR2 AACACCGACACCGGCGAG |
| SEQ ID NO: 186 (Chothia) | HCDR3 AACCCCCCCTACTACTACGGCACTAACAACGCCGA GGCTATGGACTAC |
| SEQ ID NO: 164 (Chothia) | HCDR3 AACCCCCCTTACTACTACGGCACCAACAACGCCGA GGCCATGGACTAT |

BAP050-Clone-J LC

| SEQ ID NO: 178 (Kabat) | LCDR1 AGCTCTAGTCAGGATATCTCTAACTACCTGAAC |
| --- | --- |
| SEQ ID NO: 167 (Kabat) | LCDR1 TCCTCCAGCCAGGACATCTCCAACTACCTGAAC |
| SEQ ID NO: 179 (Kabat) | LCDR2 TACACTAGCACCCTGCACCTG |
| SEQ ID NO: 168 (Kabat) | LCDR2 TACACCTCCACCCTGCACCTG |

TABLE 1-continued

Amino acid and nucleotide sequences for murine, chimeric and humanized antibody molecules. The antibody molecules include murine mAb BAP050, chimeric mAbs BAP050-chi, humanized mAbs BAP050-hum01 to BAP050-hum20, humanized mAbs BAP050-hum01-Ser to BAP050-hum15-Ser, BAP050-hum18-Ser to BAP050-hum20-Ser, and humanized mAbs BAP050-Clone-F to BAP050-Clone-J. The amino acid and nucleotide sequences of the heavy and light chain CDRs, the heavy and light chain variable regions, and the heavy and light chains are shown.

| | |
|---|---|
| SEQ ID NO: 180 (Kabat) | LCDR3CAGCAGTACTATAACCTGCCCTGGACC |
| SEQ ID NO: 169 (Kabat) | LCDR3CAGCAGTACTACAACCTGCCCTGGACC |
| SEQ ID NO: 181 (Chothia) | LCDR1AGTCAGGATATCTCTAACTAC |
| SEQ ID NO: 170 (Chothia) | LCDR1AGCCAGGACATCTCCAACTAC |
| SEQ ID NO: 182 (Chothia) | LCDR2TACACTAGC |
| SEQ ID NO: 171 (Chothia) | LCDR2TACACCTCC |
| SEQ ID NO: 183 (Chothia) | LCDR3TACTATAACCTGCCCTGG |
| SEQ ID NO: 172 (Chothia) | LCDR3TACTACAACCTGCCCTGG |

TABLE 2

Amino acid and nucleotide sequences of the heavy and light chain framework regions for humanized mAbs BAP050-hum01 to BAP050-hum20, BAP050-hum01-Ser to BAP050-hum15-Ser, BAP050-hum18-Ser to BAP050-hum20-Ser, and BAP050-Clone-F to BAP050-Clone-J

| | Amino Acid Sequence | Nucleotide Sequence |
|---|---|---|
| VHFW1 (type a) | EVQLVQSGAEVKKPGATVKISCKVS (SEQ ID NO: 187) | GAAGTGCAGCTGGTGCAGTCTGGCGCCGAAGTGAA GAAACCCGGCGCTACCGTGAAGATCTCCTGCAAGG TGTCC (SEQ ID NO: 188) |
| | | GAGGTCCAGCTGGTACAGTCTGGGGCTGAGGTGAA GAAGCCTGGGGCTACAGTGAAAATCTCCTGCAAGG TTTCT (SEQ ID NO: 189) |
| VHFW1 (type b) | QVQLVQSGAEVKKPGASVKVSCKAS (SEQ ID NO: 190) | CAAGTGCAGCTGGTGCAGTCGGGAGCCGAAGTGAA GAAGCCTGGAGCCTCGGTGAAGGTGTCGTGCAAGG CATCC (SEQ ID NO: 191) |
| | | CAGGTGCAGCTGGTGCAGTCTGGCGCCGAAGTGAA GAAACCTGGCGCCTCCGTGAAGGTGTCCTGCAAGG CCTCT (SEQ ID NO: 192) |
| | | CAGGTTCAGCTGGTGCAGTCCGGAGCTGAGGTGAA GAAGCCTGGGGCCTCAGTGAAGGTCTCCTGCAAGG CTTCT (SEQ ID NO: 193) |
| VHFW1 (type c) | EVQLVQSGAEVKKPGESLRISCKGS (SEQ ID NO: 194) | GAAGTGCAGCTGGTGCAGTCTGGAGCAGAGGTGAA AAAGCCCGGGGAGTCTCTGAGGATCTCCTGTAAGG GTTCT (SEQ ID NO: 195) |
| VHFW1 (type d) | QVQLVQSGSELKKPGASVKVSCKAS (SEQ ID NO: 196) | CAGGTGCAGCTGGTGCAATCTGGGTCTGAGTTGAA GAAGCCTGGGGCCTCAGTGAAGGTTTCCTGCAAGG CTTCT (SEQ ID NO: 197) |
| VHFW2 (type a) | WVRQAPGQGLEWMG (SEQ ID NO: 198) | TGGGTCCGCCAGGCCCCAGGTCAAGGCCTCGAGTG GATGGGC (SEQ ID NO: 199) |
| | | TGGGTGCGACAGGCCCCTGGACAGGGCCTGGAATG GATGGGC (SEQ ID NO: 200) |
| | | TGGGTGCGACAGGCCCCTGGACAAGGGCTTGAGTG GATGGGT (SEQ ID NO: 201) |

TABLE 2-continued

Amino acid and nucleotide sequences of the heavy and light chain framework regions for humanized mAbs BAP050-hum01 to BAP050-hum20, BAP050-hum01-Ser to BAP050-hum15-Ser, BAP050-hum18-Ser to BAP050-hum20-Ser, and BAP050-Clone-F to BAP050-Clone-J

| | Amino Acid Sequence | Nucleotide Sequence |
|---|---|---|
| VHFW2 (type b) | WVRQARGQRLEWIG (SEQ ID NO: 202) | TGGGTCAGACAGGCCCGGGGTCAACGGCTGGAGTGGATCGGA (SEQ ID NO: 203) |
| | | TGGGTGCGACAGGCCAGGGGCCAGCGGCTGGAATGGATCGGC (SEQ ID NO: 204) |
| | | TGGGTGCGACAGGCTCGTGGACAACGCCTTGAGTGGATAGGT (SEQ ID NO: 205) |
| VHFW2 (type c) | WIRQSPSRGLEWLG (SEQ ID NO: 206) | TGGATCAGGCAGTCCCCATCGAGAGGCCTTGAGTGGCTGGGT (SEQ ID NO: 207) |
| VHFW2 (type d) | WVRQATGQGLEWMG (SEQ ID NO: 208) | TGGGTGCGACAGGCCACTGGACAAGGGCTTGAGTGGATGGGT (SEQ ID NO: 209) |
| VHFW3 (type a) | RFVFSLDTSVSTAYLQICSLKAEDTAVYYCAR (SEQ ID NO: 210) | AGATTTGTCTTCTCCTTGGACACCTCTGTCAGCACGGCATATCTGCAGATCTGCAGCCTAAAGGCTGAGGACACTGCCGTGTATTACTGTGCAAGA (SEQ ID NO: 211) |
| VHFW3 (type a-Ser) | RFVFSLDTSVSTAYLQISSLKAEDTAVYYCAR (SEQ ID NO: 212) | TCGGTTCGTGTTCTCCCTCGACACCTCCGTGTCCACCGCCTACCTCCAAATCTCCTCACTGAAAGCGGAGGACACCGCCGTGTACTATTGCGCGAGG SEQ ID NO: 213) |
| | | AGATTCGTGTTTAGCCTGGACACTAGTGTGTCTACCGCCTACCTGCAGATCTCTAGCCTGAAGGCCGAGGACACCGCCGTCTACTACTGCGCGTAGA SEQ ID NO: 214 |
| | | AGATTCGTGTTCTCCCTGGACACCTCCGTGTCCACCGCCTACCTGCAGATCTCCAGCCTGAAGGCCGAGGATACCGCCGTGTACTACTGCGCCCGG (SEQ ID NO: 215) |
| | | AGATTTGTCTTCTCCTTGGACACCTCTGTCAGCACGGCATATCTGCAGATCAGCAGCCTAAAGGCTGAGGACACTGCCGTGTATTACTGTGCAAGA (SEQ ID NO: 216) |
| VHFW3 (type b) | RVTISADKSISTAYLQWSSLKASDTAMYYCAR (SEQ ID NO: 217) | TAGAGTCACCATCTCAGCCGACAAGTCCATCAGCACCGCCTACCTGCAGTGGAGCAGCCTGAAGGCCTCGGACACCGCCATGTATTACTGTGCAAGA (SEQ ID NO: 218) |
| VHFW3 (type c) | RFVFSLDTSVSTAYLQISTLKAEDTATYFCAR (SEQ ID NO: 219) | TCGGTTTGTCTTCTCCTTGGACACCTCTGTCAGCACGGCATATCTGCAGATCAGCACGCTAAAGGCTGAGGACACTGCTACATATTTCTGTGCAAGA (SEQ ID NO: 220) |
| VHFW4 | WGQGTTVTVSS (SEQ ID NO: 221) | TGGGGCCAGGGCACCACTGTGACTGTGTCCAGC (SEQ ID NO: 222) |
| | | TGGGGTCAAGGCACTACCGTGACCGTGTCTAGC (SEQ ID NO: 223) |
| | | TGGGGCCAGGGCACCACCGTGACCGTGTCCTCT (SEQ ID NO: 224) |
| | | TGGGGCCAGGGCACCACCGTGACCGTGTCCTCC (SEQ ID NO: 225) |
| VLFW1 (type a) | DIQMTQSPSSLSASVGDRVTITC (SEQ ID NO: 226) | GATATTCAGATGACTCAGTCACCTAGTAGCCTGAGCGCTAGTGTGGGCGATAGAGTGACTATCACCTGT (SEQ ID NO: 227) |
| | | GACATCCAGATGACCCAGTCCCCCTCCAGCCTGTCTGCTTCCGTGGGCGACAGAGTGACCATCACCTGT (SEQ ID NO: 228) |

TABLE 2-continued

Amino acid and nucleotide sequences of the heavy and light chain framework regions for humanized mAbs BAP050-hum01 to BAP050-hum20, BAP050-hum01-Ser to BAP050-hum15-Ser, BAP050-hum18-Ser to BAP050-hum20-Ser, and BAP050-Clone-F to BAP050-Clone-J

| | Amino Acid Sequence | Nucleotide Sequence |
|---|---|---|
| | | GACATCCAGATGACCCAGTCTCCATCCTCCCTGTC TGCATCTGTAGGAGACAGAGTCACCATCACTTGC (SEQ ID NO: 229) |
| VLFW1 (type b) | EIVLTQSPATLPVTLGQPASISC (SEQ ID NO: 230) | GAAATTGTGTTGACACAGTCTCCAGCCACCCTGCC CGTCACCCTTGGACAGCCGGCCTCCATCTCCTGC (SEQ ID NO: 231) |
| VLFW1 (type c) | EIVLTQSPATLSLSPGERATLSC (SEQ ID NO: 232) | GAAATTGTGTTGACACAGTCTCCAGCCACCCTGTC TTTGTCTCCAGGGGAAAGAGCCACCCTCTCCTGC (SEQ ID NO: 233) |
| VLFW1 (type d) | DIVMTQTPLSLPVTPGEPASISC (SEQ ID NO: 234) | GATATTGTGATGACCCAGACTCCACTCTCCCTGCC CGTCACCCCTGGAGAGCCGGCCTCCATCTCCTGC (SEQ ID NO: 235) |
| VLFW1 (type e) | EIVLTQSPDFQSVTPKEKVTITC (SEQ ID NO: 236) | GAAATTGTGCTGACTCAGTCTCCAGACTTTCAGTC TGTGACTCCAAAGGAGAAAGTCACCATCACCTGC (SEQ ID NO: 237) |
| VLFW1 (type f) | AIQLTQSPSSLSASVGDRVTITC (SEQ ID NO: 238) | GCCATCCAGTTGACCCAGTCTCCATCCTCCCTGTC TGCATCTGTAGGAGACAGAGTCACCATCACTTGC (SEQ ID NO: 239) |
| VLFW2 (type a) | WYQQKPGKAPKLLIY (SEQ ID NO: 240) | TGGTATCAGCAGAAGCCCGGTAAAGCCCCTAAGCT GCTGATCTAC (SEQ ID NO: 241) |
| | | TGGTATCAGCAGAAGCCCGGCAAGGCCCCCAAGCT GCTGATCTAC (SEQ ID NO: 242) |
| | | TGGTATCAGCAGAAACCAGGGAAAGCTCCTAAGCT CCTGATCTAT (SEQ ID NO: 243) |
| VLFW2 (type b) | WYQQKPGQAPRLLIY (SEQ ID NO: 244) | TGGTACCAGCAGAAACCTGGCCAGGCTCCCAGGCT CCTCATCTAT (SEQ ID NO: 245) |
| VLFW2 (type c) | WYLQKPGQSPQLLIY (SEQ ID NO: 246) | TGGTACCTGCAGAAGCCAGGGCAGTCTCCACAGCT CCTGATCTAT (SEQ ID NO: 247) |
| VLFW2 (type d) | WYLQKPGQSPQLLIY (SEQ ID NO: 248) | TGGTATCTGCAGAAGCCCGGTCAATCACCTCAGCT GCTGATCTAC (SEQ ID NO: 249) |
| | | TGGTATCTGCAGAAGCCCGGCCAGTCCCCTCAGCT GCTGATCTAC (SEQ ID NO: 250) |
| | | TGGTACCTGCAGAAGCCAGGGCAGTCTCCACAGCT CCTGATCTAT (SEQ ID NO: 251) |
| VLFW3 (type a) | GVPSRFSGSGSGTDFTFTISSLEAEDAATYYC (SEQ ID NO: 252) | GGCGTGCCCTCCAGATTTTCCGGCTCTGGCTCTGG CACCGACTTTACCTTCACCATCAGCTCCCTGGAAG CCGAGGACGCCGCCACCTACTACTGC (SEQ ID NO: 253) |
| | | GGGGTCCCCTCGAGGTTCAGTGGCAGTGGATCTGG GACAGATTTCACCTTTACCATCAGTAGCCTGGAAG CTGAAGATGCTGCAACATATTACTGT (SEQ ID NO: 254) |
| VLFW3 (type b) | GIPPRFSGSGYGTDFTLTINNIESDAAYYFC (SEQ ID NO: 255) | EGGAATCCCCCCTAGGTTTAGCGGTAGCGGCTACGG CACCGACTTCACCCTGACTATTAACAATATCGAGT CAGAGGACGCCGCCTACTACTTCTGT (SEQ ID NO: 256) |
| | | GGCATCCCCCCTAGATTCTCCGGCTCTGGCTACGG CACCGACTTCACCCTGACCATCAACAACATCGAGT CCGAGGACGCCGCCTACTACTTCTGC (SEQ ID NO: 257) |
| | | GGGATCCCACCTCGATTCAGTGGCAGCGGGTATGG AACAGATTTTACCCTCACAATTAATAACATAGAAT CTGAGGATGCTGCATATTACTTCTGT (SEQ ID NO: 258) |

TABLE 2-continued

Amino acid and nucleotide sequences of the heavy and light chain framework regions for humanized mAbs BAP050-hum01 to BAP050-hum20, BAP050-hum01-Ser to BAP050-hum15-Ser, BAP050-hum18-Ser to BAP050-hum20-Ser, and BAP050-Clone-F to BAP050-Clone-J

| Amino Acid Sequence | Nucleotide Sequence |
|---|---|
| VLFW3 (type c) GIPDRFSGSGSGTDFTLTISRLEPEGGGATCCCAGACAGGTTCAGTGGCAGTGGGTCTGG DFAVYYC (SEQ ID NO: 259) | GACAGACTTCACTCTCACCATCAGCAGACTGGAGC CTGAAGATTTTGCAGTGTATTACTGT (SEQ ID NO: 260) |
| VLFW3 (type d) GVPSRFSGSGSGTEFTLTISSLQPDGGCGTGCCCTCTAGGTTTAGCGGTAGCGGTAGTGG DFATYYC (SEQ ID NO: 261) | CACCGAGTTCACCCTGACTATCTCTAGCCTGCAGC CCGACGACTTCGCTACCTACTACTGT (SEQ ID NO: 262) |
| | GGCGTGCCCTCCAGATTTTCCGGCTCTGGCTCTGG CACCGAGTTTACCCTGACCATCAGCTCCCTGCAGC CCGACGACTTCGCCACCTACTACTGC (SEQ ID NO: 263) |
| | GGGGTCCCATCAAGGTTCAGCGGCAGTGGATCTGG GACAGAATTCACTCTCACCATCAGCAGCCTGCAGC CTGATGATTTTGCAACTTATTACTGT (SEQ ID NO: 264) |
| VLFW3 (type e) GVPSRFSGSGSGTDFTLTISSLQPEGGGGTCCCATCAAGGTTCAGCGGCAGTGGATCTGG DFATYYC (SEQ ID NO: 265) | GACAGATTTCACTCTCACCATCAGCAGCCTGCAGC CTGAAGATTTTGCAACTTATTACTGT (SEQ ID NO: 266) |
| VLFW3 (type f) GVPSRFSGSGSGTDFTFTISSLQPEGGGGTCCCATCAAGGTTCAGTGGAAGTGGATCTGG DIATYYC (SEQ ID NO: 267) | GACAGATTTTACTTTCACCATCAGCAGCCTGCAGC CTGAAGATATTGCAACATATTACTGT (SEQ ID NO: 268) |
| VLFW3 (type g) GIPDRFSGSGSGTDFTLTISRLEPEGGGATCCCAGACAGGTTCAGTGGCAGTGGGTCTGG DFAVYYC (SEQ ID NO: 269) | GACAGACTTCACTCTCACCATCAGCAGACTGGAGC CTGAAGATTTTGCAGTGTATTACTGT (SEQ ID NO: 270) |
| VLFW4 FGQGTKVEIK (SEQ ID NO: 271) | TTCGGTCAAGGCACTAAGGTCGAGATTAAG (SEQ ID NO: 272) |
| | TTCGGCCAGGGCACCAAGGTGGAAATCAAG (SEQ ID NO: 273) |
| | TTCGGCCAAGGGACCAAGGTGGAAATCAAA (SEQ ID NO: 274) |

TABLE 3

Constant region amino acid sequences of human IgG heavy chains and human kappa light chain HC    IgG4 (S228P) mutant constant region amino acid sequence (EU Numbering)

ASTKGPSVFP LAPCSRSTSE STAALGCLVK DYFPEPVTVS
WNSGALTSGV HTFPAVLQSS GLYSLSSVVT VPSSSLGTKT
YTCNVDHKPS NTKVDKRVES KYGPPCPPCP APEFLGGPSV
FLFPPKPKDT LMISRTPEVT CVVVDVSQED PEVQFNWYVD
GVEVHNAKTK PREEQFNSTY RVVSVLTVLH QDWLNGKEYK
CKVSNKGLPS SIEKTISKAK GQPREPQVYT LPPSQEEMTK
NQVSLTCLVK GFYPSDIAVE WESNGQPENN YKTTPPVLDS
DGSFFLYSRL TVDKSRWQEG NVFSCSVMHE ALHNHYTQKS
LSLSLGK (SEQ ID NO: 275)

TABLE 3-continued

Constant region amino acid sequences of human IgG heavy chains and human kappa light chain LC    Human kappa constant region amino acid sequence RTVAAPSVFI FPPSDEQLKS GTASVVCLLN NFYPREAKVQ
WKVDNALQSG NSQESVTEQD SKDSTYSLSS TLTLSKADYE
KHKVYACEVT HQGLSSPVTK SFNRGEC
(SEQ ID NO: 276)

HC    IgG4 (S228P) mutant constant region amino acid sequence lacking the C-terminal Lysine (K) (EU Numbering)

ASTKGPSVFP LAPCSRSTSE STAALGCLVK DYFPEPVTVS
WNSGALTSGV HTFPAVLQSS GLYSLSSVVT VPSSSLGTKT
YTCNVDHKPS NTKVDKRVES KYGPPCPPCP APEFLGGPSV
FLFPPKPKDT LMISRTPEVT CVVVDVSQED PEVQFNWYVD
GVEVHNAKTK PREEQFNSTY RVVSVLTVLH QDWLNGKEYK

TABLE 3-continued

Constant region amino acid sequences of human IgG heavy chains and human kappa light chain

|    |                                                                                                                                                                                                                                                                                                                                                                                                                                                                                |
|----|------------------------------------------------------------------------------------------------------------------------------------------------------------------------------------------------------------------------------------------------------------------------------------------------------------------------------------------------------------------------------------------------------------------------------------------------------------------------------|
|    | CKVSNKGLPS SIEKTISKAK GQPREPQVYT LPPSQEEMTK NQVSLTCLVK GFYPSDIAVE WESNGQPENN YKTTPPVLDS DGSFFLYSRL TVDKSRWQEG NVFSCSVMHE ALHNHYTQKS LSLSLG (SEQ ID NO: 277) |
| HC | IgG1 wild type |
|    | ASTKGPSVFP LAPSSKSTSG GTAALGCLVK DYFPEPVTVS WNSGALTSGV HTFPAVLQSS GLYSLSSVVT VPSSSLGTQT YICNVNHKPS NTKVDKRVEP KSCDKTHTCP PCPAPELLGG PSVFLFPPKP KDTLMISRTP EVTCVVVDVS HEDPEVKFNW YVDGVEVHNA KTKPREEQYN STYRVVSVLT VLHQDWLNGK EYKCKVSNKA LPAPIEKTIS KAKGQPREPQ VYTLPPSREE MTKNQVSLTC LVKGFYPSDI AVEWESNGQP ENNYKTTPPV LDSDGSFFLY SKLTVDKSRW QQGNVFSCSV MHEALHNHYT QKSLSLSPGK (SEQ ID NO: 278) |
| HC | IgG1 (N297A) mutant constant region amino acid sequence (EU Numbering) |
|    | ASTKGPSVFP LAPSSKSTSG GTAALGCLVK DYFPEPVTVS WNSGALTSGV HTFPAVLQSS GLYSLSSVVT VPSSSLGTQT YICNVNHKPS NTKVDKRVEP KSCDKTHTCP PCPAPELLGG PSVFLFPPKP KDTLMISRTP EVTCVVVDVS HEDPEVKFNW YVDGVEVHNA KTKPREEQYA STYRVVSVLT VLHQDWLNGK EYKCKVSNKA LPAPIEKTIS KAKGQPREPQ VYTLPPSREE MTKNQVSLTC LVKGFYPSDI AVEWESNGQP ENNYKTTPPV LDSDGSFFLY SKLTVDKSRW QQGNVFSCSV MHEALHNHYT QKSLSLSPGK (SEQ ID NO: 279) |
| HC | IgG1 (D265A, P329A) mutant constant region amino acid sequence (EU Numbering) |
|    | ASTKGPSVFP LAPSSKSTSG GTAALGCLVK DYFPEPVTVS WNSGALTSGV HTFPAVLQSS GLYSLSSVVT VPSSSLGTQT YICNVNHKPS NTKVDKRVEP KSCDKTHTCP PCPAPELLGG PSVFLFPPKP KDTLMISRTP EVTCVVVAVS HEDPEVKFNW YVDGVEVHNA KTKPREEQYN STYRVVSVLT VLHQDWLNGK EYKCKVSNKA LAAPIEKTIS KAKGQPREPQ VYTLPPSREE MTKNQVSLTC LVKGFYPSDI AVEWESNGQP ENNYKTTPPV LDSDGSFFLY SKLTVDKSRW QQGNVFSCSV MHEALHNHYT QKSLSLSPGK (SEQ ID NO: 280) |
| HC | IgG1 (L234A, L235A) mutant constant region amino acid sequence (EU Numbering) |
|    | ASTKGPSVFP LAPSSKSTSG GTAALGCLVK DYFPEPVTVS WNSGALTSGV HTFPAVLQSS GLYSLSSVVT VPSSSLGTQT YICNVNHKPS NTKVDKRVEP KSCDKTHTCP PCPAPEAAGG PSVFLFPPKP KDTLMISRTP EVTCVVVDVS HEDPEVKFNW YVDGVEVHNA KTKPREEQYN STYRVVSVLT VLHQDWLNGK EYKCKVSNKA LPAPIEKTIS KAKGQPREPQ VYTLPPSREE MTKNQVSLTC LVKGFYPSDI AVEWESNGQP ENNYKTTPPV |

TABLE 3-continued

Constant region amino acid sequences of human IgG heavy chains and human kappa light chain

|   |                                                                                                              |
|---|--------------------------------------------------------------------------------------------------------------|
|   | LDSDGSFFLY SKLTVDKSRW QQGNVFSCSV MHEALHNHYT QKSLSLSPGK (SEQ ID NO: 281) |

TABLE 4

Amino acid sequences of the heavy and light chain leader sequences for humanized mAbs BAP050-Clone-F to BAP050-Clone-J

| BAP050-Clone-F | HC | MEWSWVFLFFLSVTTGVHS (SEQ ID NO: 282) |
|---|---|---|
| BAP050-Clone-F | LC | MSVPTQVLGLLLLWLTDARC (SEQ ID NO: 283) |
| BAP050-Clone-G | HC | MEWSWVFLFFLSVTTGVHS (SEQ ID NO: 282) |
| BAP050-Clone-G | LC | MSVPTQVLGLLLLWLTDARC (SEQ ID NO: 283) |
| BAP050-Clone-H | HC | MEWSWVFLFFLSVTTGVHS (SEQ ID NO: 282) |
| BAP050-Clone-H | LC | MSVPTQVLGLLLLWLTDARC (SEQ ID NO: 283) |
| BAP050-Clone-I | HC | MAWVWTLPFLMAAAQSVQA (SEQ ID NO: 284) |
|  |  | MEWSWVFLFFLSVTTGVHS (SEQ ID NO: 282) |
| BAP050-Clone-I | LC | MSVLTQVLALLLLWLTGTRC (SEQ ID NO: 285) |
|  |  | MSVPTQVLGLLLLWLTDARC (SEQ ID NO: 283) |
| BAP050-Clone-J | HC | MAWVWTLPFLMAAAQSVQA (SEQ ID NO: 284) |
|  |  | MEWSWVFLFFLSVTTGVHS (SEQ ID NO: 282) |
| BAP050-Clone-J | LC | MSVLTQVLALLLLWLTGTRC (SEQ ID NO: 285) |
|  |  | MSVPTQVLGLLLLWLTDARC (SEQ ID NO: 283) |

Table 5. See Examples.
Table 6. See Examples.

TABLE 7

Selected therapeutic agents that can be administered in combination with the anti-LAG-3 antibody molecules, e.g., as a single agent or in combination with other immunomodulators described herein. Each publication listed in this Table is herein incorporated by reference in its entirety, including all structural formulae therein.

| Compound No. | Generic Name Tradename | Compound Structure | Patents/Patent Application Publications |
|---|---|---|---|
| A1 | Sotrastaurin | 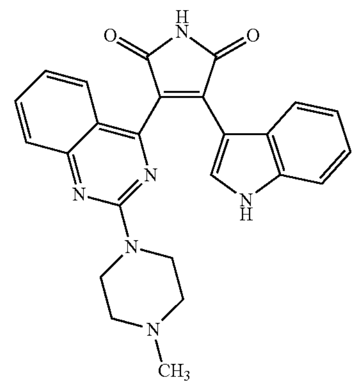 [SMILES: CN1CCN(c2nc(C3=C(c4c[nH]c5ccccc45)C(=O)NC3=O)c3ccccc3n2)CC1] | EP 1682103<br>U.S. 2007/142401<br>WO 2005/039549 |
| A2 | Nilotinib HCl monohydrate TASIGNA ® | HCl·H$_2$O | WO 2004/005281<br>U.S. Pat. No. 7,169,791 |
| A3 | | 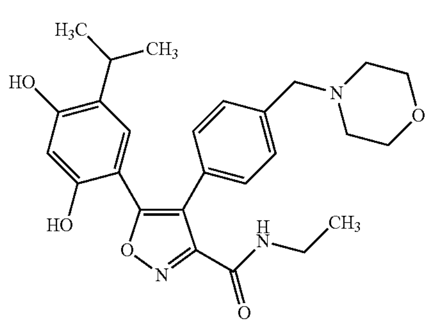 [SMILES: CCNC(=O)c1noc(-c2cc(C(C)C)c(O)cc2O)c1-c1ccc(CN2CCOCC2)cc1] | WO 2010/060937<br>WO 2004/072051<br>EP 1611112<br>U.S. Pat. No. 8,450,310 |

TABLE 7-continued

Selected therapeutic agents that can be administered in combination with the anti-LAG-3 antibody molecules, e.g., as a single agent or in combination with other immunomodulators described herein. Each publication listed in this Table is herein incorporated by reference in its entirety, including all structural formulae therein.

| Compound No. | Generic Name Tradename | Compound Structure | Patents/Patent Application Publications |
|---|---|---|---|
| A4 | Dactolisib | 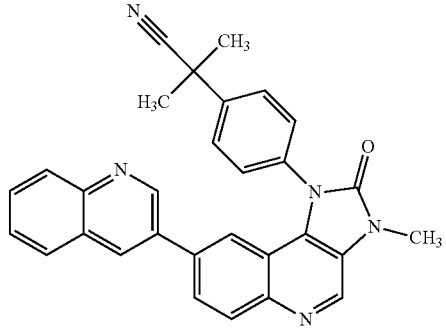 [SMILES: Cn1c(=O)n(-c2ccc(C(C)(C)C#N)cc2)c2c3cc(-c4cnc5ccccc5c4)ccc3ncc21] | WO 2006/122806 |
| A5 | | 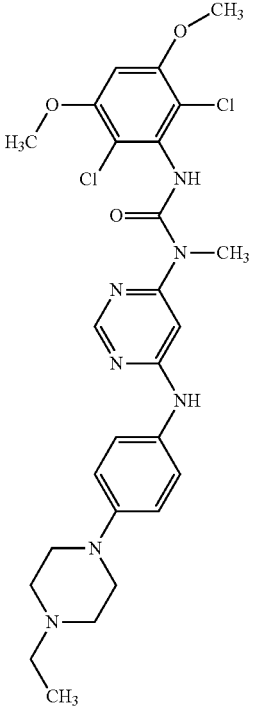 [SMILES: CCN1CCN(c2ccc(Nc3cc(N(C)C(=O)Nc4c(Cl)c(OC)cc(OC)c4Cl)ncn3)cc2)CC1] | U.S. Pat. No. 8,552,002 |
| A6 | Buparlisib | 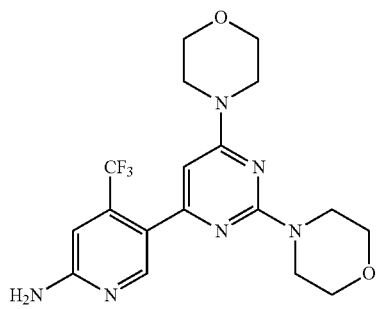 [SMILES: Nc1cc(C(F)(F)F)c(-c2cc(N3CCOCC3)nc(N3CCOCC3)n2)cn1] | WO 2007/084786 |

TABLE 7-continued

Selected therapeutic agents that can be administered in combination with the anti-LAG-3 antibody molecules, e.g., as a single agent or in combination with other immunomodulators described herein. Each publication listed in this Table is herein incorporated by reference in its entirety, including all structural formulae therein.

| Compound No. | Generic Name Tradename | Compound Structure | Patents/Patent Application Publications |
|---|---|---|---|
| A7 | | 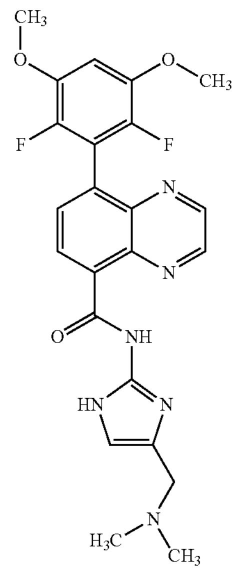 [SMILES: COc1cc(OC)c(F)c(-c2ccc(C(=O)Nc3nc(CN(C)C)c[nH]3)c3nccnc23)c1F] | WO 2009/141386 U.S. 2010/0105667 |
| A8 | | 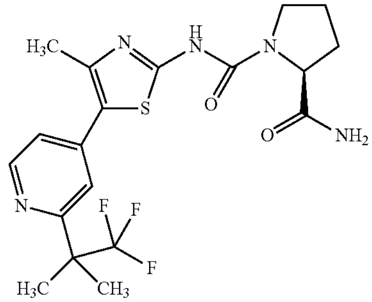 [SMILES: Cc1nc(NC(=O)N2CCC[C@H]2C(N)=O)sc1-c1ccnc(C(C)(C)C(F)(F)F)c1] | WO 2010/029082 |
| A9 | | CYP17 inhibitor | WO 2010/149755 U.S. Pat. No. 8,263,635 B2 EP 2445903 B1 |
| A10 | | 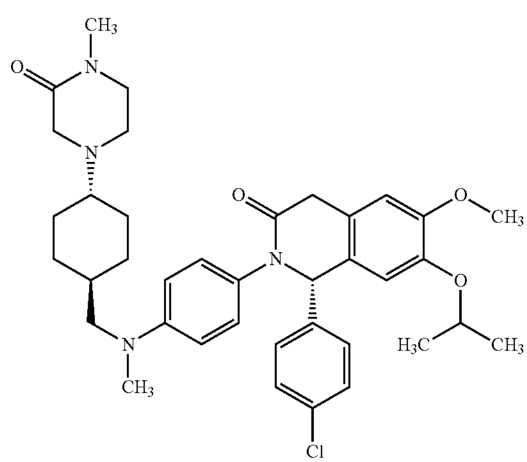 [SMILES: COc1cc2c(cc1OC(C)C)[C@H](c1ccc(Cl)cc1)N(c1ccc(N(C)C[C@H]3CC[C@H](N4CCN(C)C(=O)C4)CC3)cc1)C(=O)C2] | WO 2011/076786 |

TABLE 7-continued

Selected therapeutic agents that can be administered in combination with the anti-LAG-3 antibody molecules, e.g., as a single agent or in combination with other immunomodulators described herein. Each publication listed in this Table is herein incorporated by reference in its entirety, including all structural formulae therein.

| Compound No. | Generic Name Tradename | Compound Structure | Patents/Patent Application Publications |
|---|---|---|---|
| A11 | Deferasirox EXJADE ® | 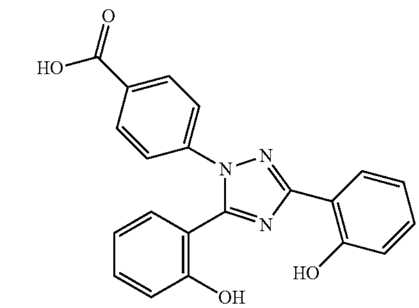 [SMILES: O=C(O)c1ccc(-n2nc(-c3ccccc3O)nc2-c2ccccc2O)cc1] | WO 1997/049395 |
| A12 | Letrozole FEMARA ® | 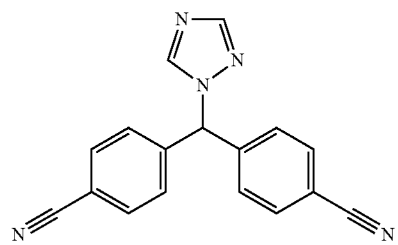 [SMILES: N#Cc1ccc(C(c2ccc(C#N)cc2)n2cncn2)cc1] | U.S. Pat. No. 4,978,672 |
| A13 | | 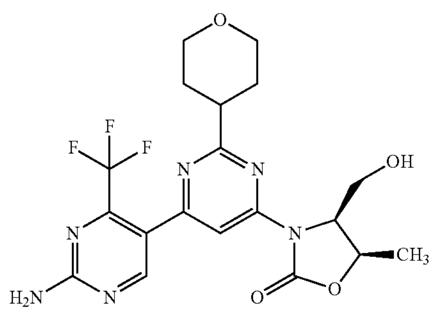 [SMILES: C[C@H]1OC(=O)N(c2cc(-c3cnc(N)nc3C(F)(F)F)nc(C3CCOCC3)n2)[C@H]1CO] | WO 2013/124826 U.S. 2013/0225574 |
| A14 | | 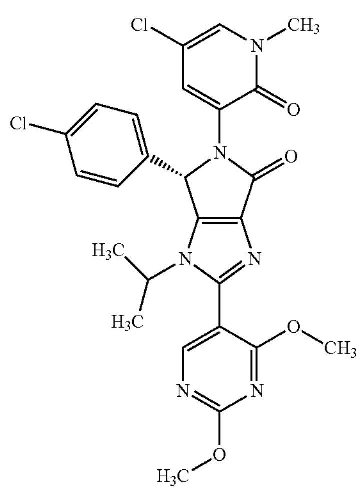 [SMILES: COc1ncc(-c2nc3c(n2C(C)C)[C@H](c2ccc(Cl)cc2)N(c2cc(Cl)cn(C)c2=O)C3=O)c(OC)n1] | WO 2013/111105 |

TABLE 7-continued

Selected therapeutic agents that can be administered in combination with the anti-LAG-3 antibody molecules, e.g., as a single agent or in combination with other immunomodulators described herein. Each publication listed in this Table is herein incorporated by reference in its entirety, including all structural formulae therein.

| Compound No. | Generic Name Tradename | Compound Structure | Patents/Patent Application Publications |
|---|---|---|---|
| A15 | | 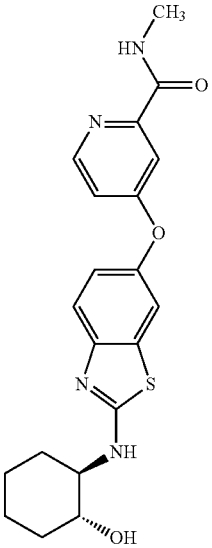 [SMILES: CNC(=O)c1cc(Oc2ccc3nc(N[C@@H]4CCCC[C@H]4O)sc3c2)ccn1] | WO 2005/073224 |
| A16 | Imatinib mesylate GLEEVEC ® | 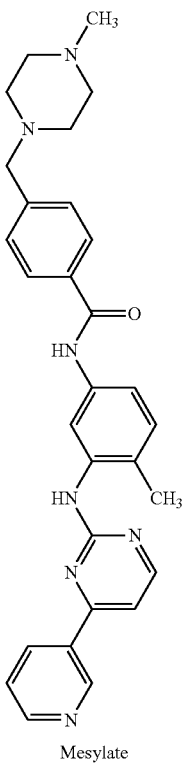 [SMILES: Cc1ccc(NC(=O)c2ccc(CN3CCN(C)CC3)cc2)cc1Nc1nccc(-c2cccnc2)n1]<br>Mesylate | WO 1999/003854 |

TABLE 7-continued

Selected therapeutic agents that can be administered in combination with the anti-LAG-3 antibody molecules, e.g., as a single agent or in combination with other immunomodulators described herein. Each publication listed in this Table is herein incorporated by reference in its entirety, including all structural formulae therein.

| Compound No. | Generic Name Tradename | Compound Structure | Patents/Patent Application Publications |
|---|---|---|---|
| A17 | | Dihydrochloric salt | EP 2099447<br>U.S. Pat. No. 7,767,675<br>U.S. Pat. No. 8,420,645 |
| A18 | Ruxolitinib Phosphate JAKAFI® | $H_3PO_4$ | WO 2007/070514<br>EP 2474545<br>U.S. Pat. No. 7,598,257<br>WO 2014/018632 |
| A19 | Panobinostat | 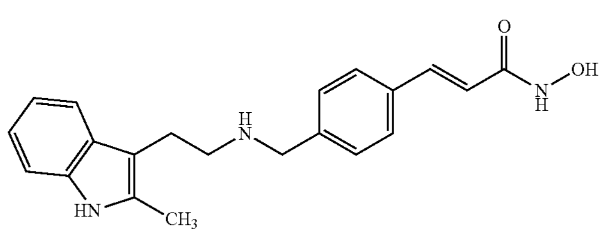 [SMILES: Cc1[nH]c2ccccc2c1CCNCc1ccc(/C=C/C(=O)NO)cc1] | WO 2014/072493<br>WO 2002/022577<br>EP 1870399 |
| A20 | Osilodrostat | 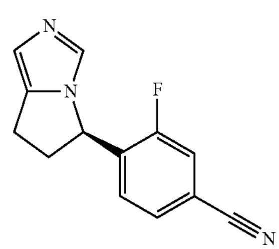 [SMILES: N#Cc1ccc([C@H]2CCc3cncn32)c(F)c1] | WO 2007/024945 |

TABLE 7-continued

Selected therapeutic agents that can be administered in combination with the anti-LAG-3 antibody molecules, e.g., as a single agent or in combination with other immunomodulators described herein. Each publication listed in this Table is herein incorporated by reference in its entirety, including all structural formulae therein.

| Compound No. | Generic Name Tradename | Compound Structure | Patents/Patent Application Publications |
|---|---|---|---|
| A21 | | 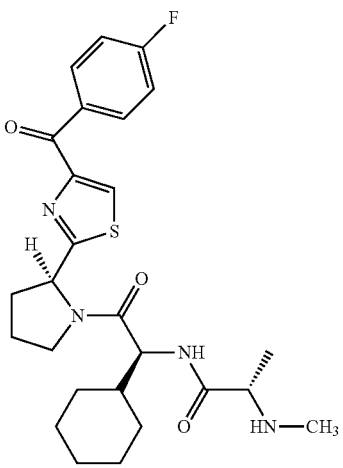 [SMILES: CN[C@@H](C)C(=O)N[C@H](C(=O)N1CCC[C@H]1c1nc(C(=O)c2ccc(F)cc2)cs1)C1CCCCC1] | WO 2008/016893<br>EP 2051990<br>U.S. Pat. No. 8,546,336 |
| A22 | Sonidegib phosphate | 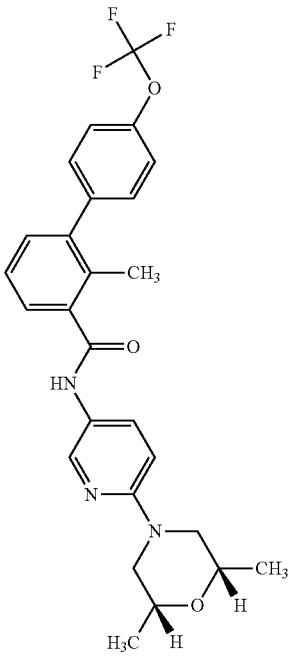 [SMILES: Cc1c(C(=O)Nc2ccc(N3C[C@@H](C)O[C@@H](C)C3)nc2)cccc1-c1ccc(OC(F)(F)F)cc1] | WO 2007/131201<br>EP 2021328<br>U.S. Pat. No. 8,178,563 |
| A23 | ceritinib ZYKADIA ™ | 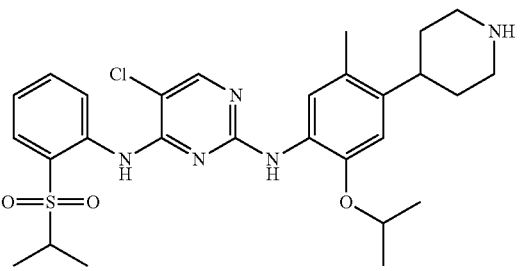 [SMILES: Cc1cc(Nc2ncc(Cl)c(Nc3ccccc3S(=O)(=O)C(C)C)n2)c(OC(C)C)cc1C1CCNCC1] | WO 2008/073687<br>U.S. Pat. No. 8,039,479 |

TABLE 7-continued

Selected therapeutic agents that can be administered in combination with the anti-LAG-3 antibody molecules, e.g., as a single agent or in combination with other immunomodulators described herein. Each publication listed in this Table is herein incorporated by reference in its entirety, including all structural formulae therein.

| Compound No. | Generic Name Tradename | Compound Structure | Patents/Patent Application Publications |
|---|---|---|---|
| A24 | | 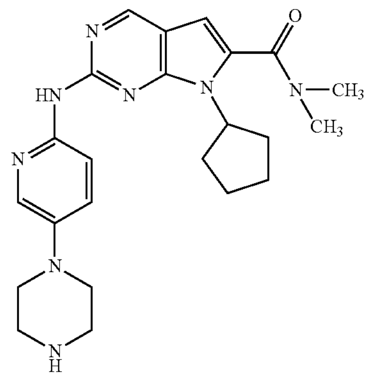 [SMILES: CN(C)C(=O)c1cc2cnc(Nc3ccc(N4CCNCC4)cn3)nc2n1C1CCCC1] | U.S. Pat. No. 8,415,355<br>U.S. Pat. No. 8,685,980 |
| A25 | | 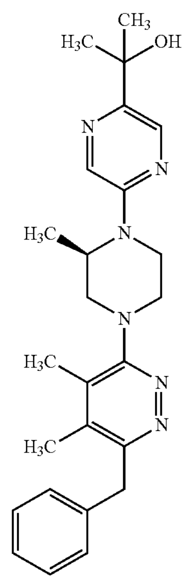 [SMILES: Cc1c(Cc2ccccc2)nnc(N2CCN(c3cnc(C(C)(C)O)cn3)[C@H](C)C2)c1C] | WO 2010/007120 |
| A26 | | Human monoclonal antibody to PRLR | U.S. Pat. No. 7,867,493 |
| A27 | | 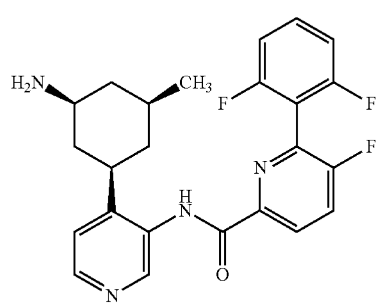 [SMILES: C[C@@H]1C[C@H](N)C[C@H](c2ccncc2NC(=O)c2ccc(F)c(-c3c(F)cccc3F)n2)C1] | WO 2010/026124<br>EP 2344474<br>U.S. 2010/0056576<br>WO2008/106692 |

TABLE 7-continued

Selected therapeutic agents that can be administered in combination with the anti-LAG-3 antibody molecules, e.g., as a single agent or in combination with other immunomodulators described herein. Each publication listed in this Table is herein incorporated by reference in its entirety, including all structural formulae therein.

| Compound No. | Generic Name Tradename | Compound Structure | Patents/Patent Application Publications |
|---|---|---|---|
| A28 | | 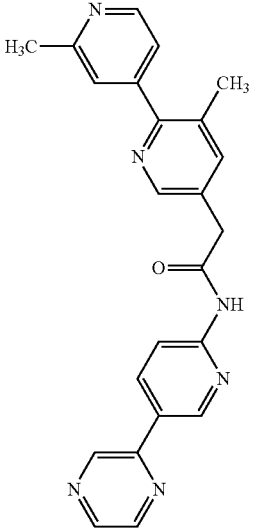 | WO 2010/101849 |
| A29 | Encorafenib | 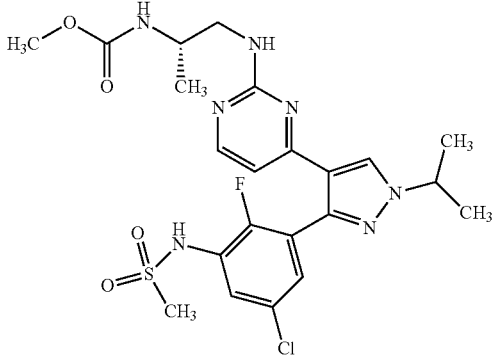 [SMILES: COC(=O)N[C@@H](C)CNc1nccc(-c2cn(C(C)C)nc2-c2cc(Cl)cc(NS(C)(=O)=O)c2F)n1] | WO 2011/025927 |
| A30 | | 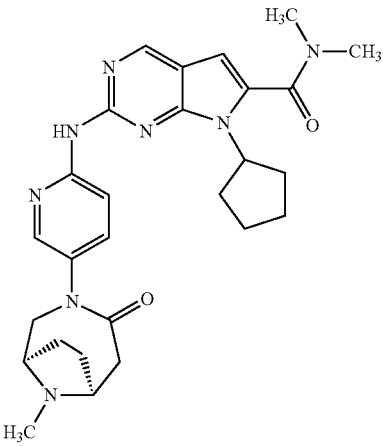 [SMILES: CN(C)C(=O)c1cc2cnc(Nc3ccc(N4C[C@H]5CC[C@@H](CC4=O)N5C)cn3)nc2n1C1CCCC1] | WO 2011/101409 |

TABLE 7-continued

Selected therapeutic agents that can be administered in combination with the anti-LAG-3 antibody molecules, e.g., as a single agent or in combination with other immunomodulators described herein. Each publication listed in this Table is herein incorporated by reference in its entirety, including all structural formulae therein.

| Compound No. | Generic Name Tradename | Compound Structure | Patents/Patent Application Publications |
|---|---|---|---|
| A31 | | Human monoclonal antibody to HER3 | WO 2012/022814<br>EP 2606070<br>U.S. Pat. No. 8,735,551 |
| A32 | | Antibody Drug Conjugate (ADC) | WO 2014/160160<br>Ab: 12425 (see Table 1, paragraph [00191])<br>Linker: SMCC (see paragraph [00117]<br>Payload: DM1 (see paragraph [00111]<br>See also Claim 29 |
| A33 | | Monoclonal antibody or Fab to M-CSF | WO 2004/045532 |
| A34 | Binimetinib | 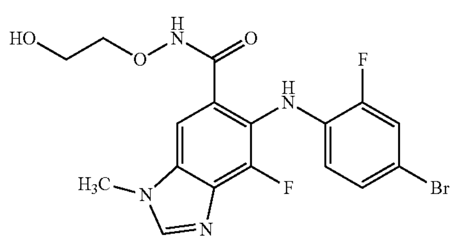 [SMILES: Cn1cnc2c(F)c(Nc3ccc(Br)cc3F)c(C(=O)NOCCO)cc21] | WO 2003/077914 |
| A35 | Midostarurin | 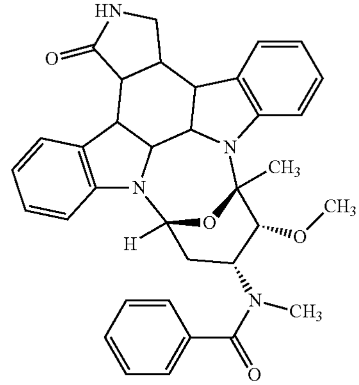 [SMILES: CO[C@@H]1[C@H](N(C)C(=O)c2ccccc2)C[C@H]2O[C@]1(C)N1c3ccccc3C3C4CNC(=O)C4C4c5ccccc5N2C4C31] | WO 2003/037347<br>EP 1441737<br>U.S. 2012/252785 |

TABLE 7-continued

Selected therapeutic agents that can be administered in combination with the anti-LAG-3 antibody molecules, e.g., as a single agent or in combination with other immunomodulators described herein. Each publication listed in this Table is herein incorporated by reference in its entirety, including all structural formulae therein.

| Compound No. | Generic Name Tradename | Compound Structure | Patents/Patent Application Publications |
|---|---|---|---|
| A36 | Everolimus AFINITOR ® | 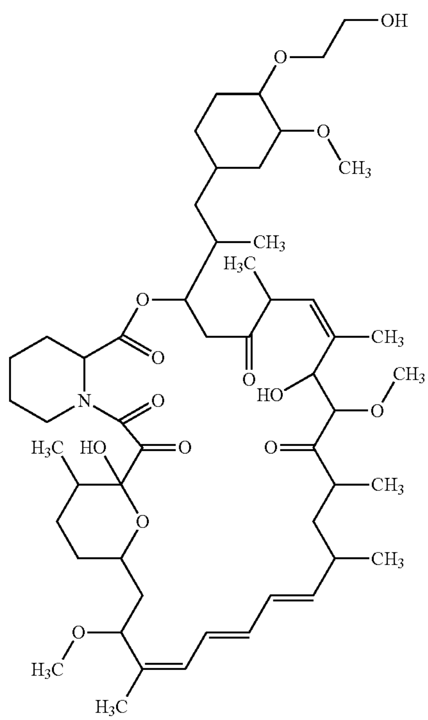 [SMILES: COC1CC2CCC(C)C(O)(O2)C(=O)C(=O)N2CCCCC2C(=O)OC(C(C)CC2CCC(OCCO)C(OC)C2)CC(=O)C(C)/C=C(/C)C(O)C(OC)C(=O)C(C)CC(C)/C=C/C=C/C=C\1C] | WO 2014/085318 |
| A37 | | 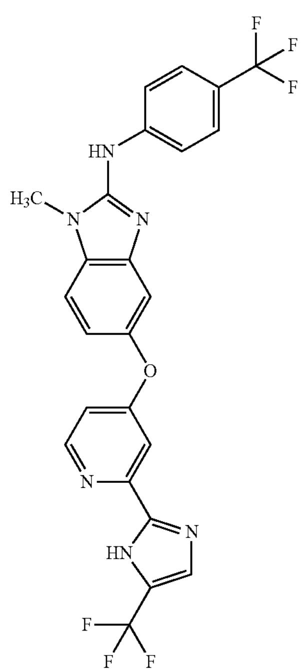 [SMILES: Cn1c(Nc2ccc(C(F)(F)F)cc2)nc2cc(Oc3ccnc(-c4ncc(C(F)(F)F)[nH]4)c3)ccc21] | WO 2007/030377 U.S. Pat. No. 7,482,367 |

TABLE 7-continued

Selected therapeutic agents that can be administered in combination with the anti-LAG-3 antibody molecules, e.g., as a single agent or in combination with other immunomodulators described herein. Each publication listed in this Table is herein incorporated by reference in its entirety, including all structural formulae therein.

| Compound No. | Generic Name Tradename | Compound Structure | Patents/Patent Application Publications |
|---|---|---|---|
| A38 | Pasireotide diaspartate SIGNIFOR® | 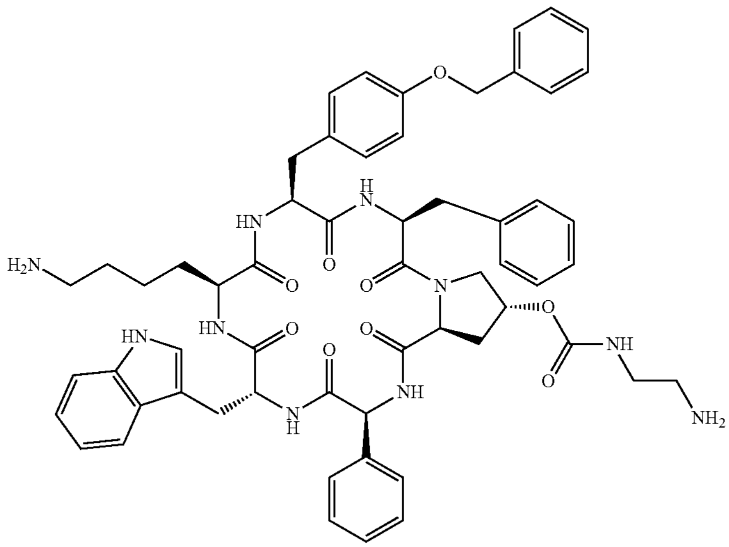 [SMILES: NCCCC[C@@H]1NC(=O)[C@@H](Cc2c[nH]c3ccccc23)NC(=O)[C@H](c2ccccc2)NC(=O)[C@@H]2C[C@@H](OC(=O)NCCN)CN2C(=O)[C@H](Cc2ccccc2)NC(=O)[C@H](Cc2ccc(OCc3ccccc3)cc2)NC1=O] | WO2002/010192 U.S. Pat. No. 7,473,761 |
| A39 | Dovitinib | 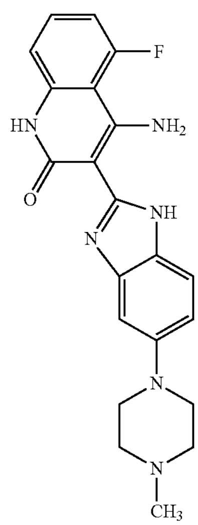 [SMILES: CN1CCN(c2ccc3[nH]c(-c4c(N)c5c(F)cccc5[nH]c4=O)nc3c2)CC1] | WO 2009/115562 U.S. Pat. No. 8,563,556 |
| A40 | | 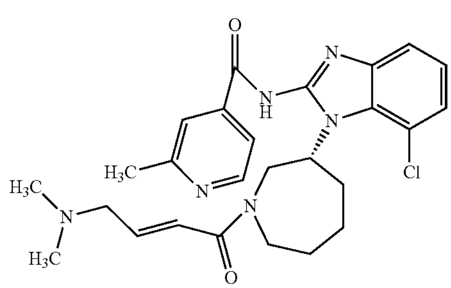 [SMILES: Cc1cc(C(=O)Nc2nc3cccc(Cl)c3n2[C@@H]2CCCCN(C(=O)/C=C/CN(C)C)C2)ccn1] | WO 2013/184757 |

TABLE 7-continued

Selected therapeutic agents that can be administered in combination with the anti-LAG-3 antibody molecules, e.g., as a single agent or in combination with other immunomodulators described herein. Each publication listed in this Table is herein incorporated by reference in its entirety, including all structural formulae therein.

| Compound No. | Generic Name Tradename | Compound Structure | Patents/Patent Application Publications |
|---|---|---|---|
| A41 | | 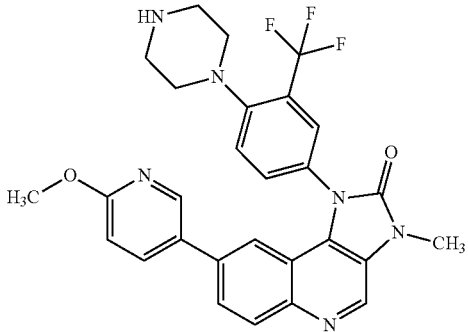 | WO 2006/122806 |
| A42 | | 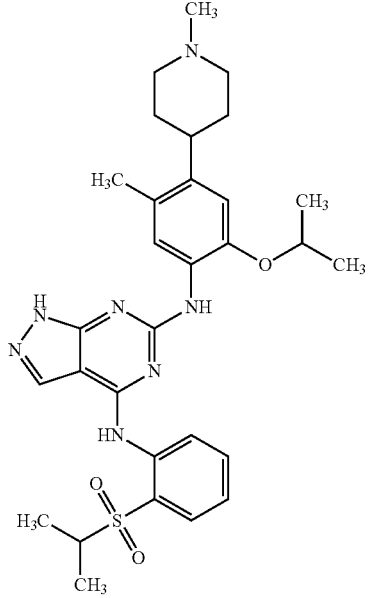 [SMILES: Cc1cc(Nc2nc(Nc3ccccc3S(=O)(=O)C(C)C)c3cn[nH]c3n2)c(OC(C)C)cc1C1CCN(C)CC1] | WO 2008/073687<br>U.S. Pat. No. 8,372,858 |

TABLE 7-continued

Selected therapeutic agents that can be administered in combination with the anti-LAG-3 antibody molecules, e.g., as a single agent or in combination with other immunomodulators described herein. Each publication listed in this Table is herein incorporated by reference in its entirety, including all structural formulae therein.

| Compound No. | Generic Name Tradename | Compound Structure | Patents/Patent Application Publications |
|---|---|---|---|
| A43 | | 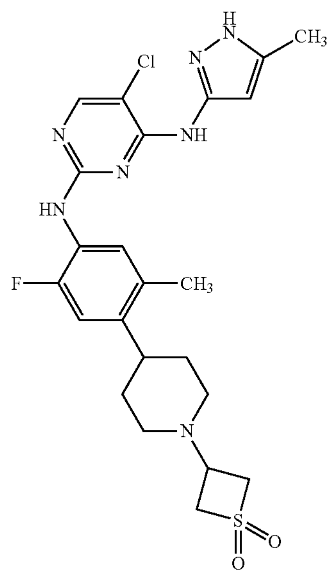 [SMILES: Cc1cc(Nc2nc(Nc3cc(C)c(C4CCN(C5CS(=O)(=O)C5)CC4)cc3F)ncc2Cl)n[nH]1] | WO 2010/002655<br>U.S. Pat. No. 8,519,129 |
| A44 | | 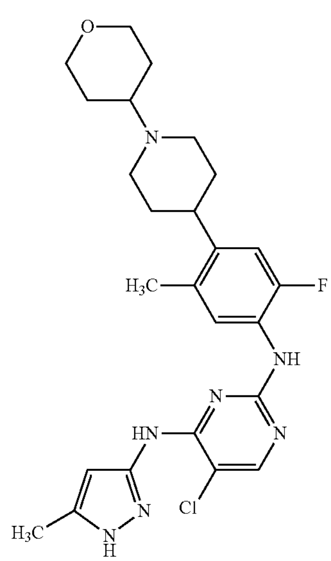 [SMILES: Cc1cc(Nc2nc(Nc3cc(C)c(C4CCN(C5CCOCC5)CC4)cc3F)ncc2Cl)n[nH]1] | WO 2010/002655<br>U.S. Pat. No. 8,519,129 |

TABLE 7-continued

Selected therapeutic agents that can be administered in combination with the anti-LAG-3 antibody molecules, e.g., as a single agent or in combination with other immunomodulators described herein. Each publication listed in this Table is herein incorporated by reference in its entirety, including all structural formulae therein.

| Compound No. | Generic Name Tradename | Compound Structure | Patents/Patent Application Publications |
|---|---|---|---|
| A45 | | 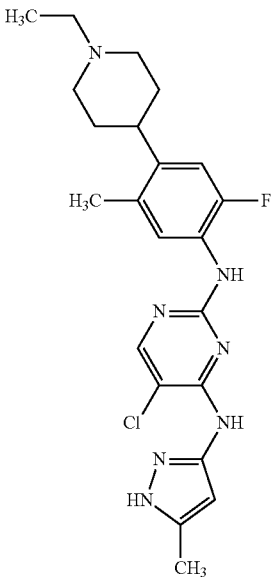 [SMILES: CCN1CCC(c2cc(F)c(Nc3ncc(Cl)c(Nc4cc(C)[nH]n4)n3)cc2C)CC1] | WO 2010/002655 |
| A46 | Valspodar AMDRAY ™ | 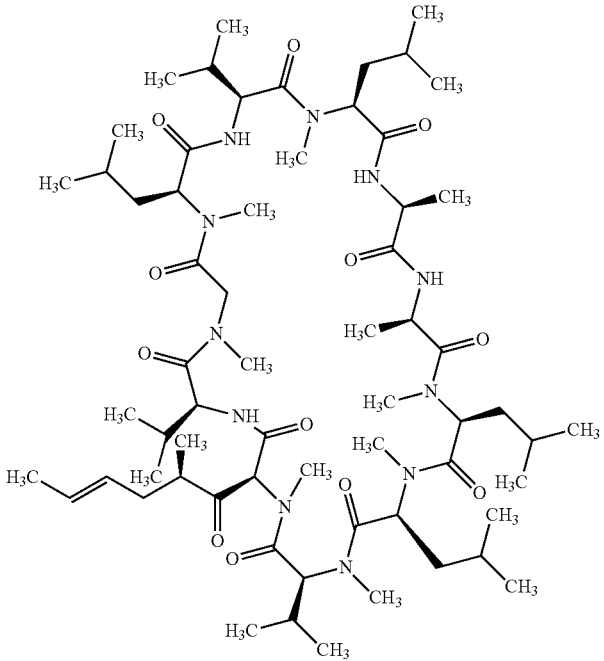 [SMILES: C/C=C/C[C@@H](C)C(=O)[C@H]1C(=O)N[C@@H](C(C)C)C(=O)N(C)CC(=O)N(C)[C@@H](CC(C)C)C(=O)N[C@@H](C(C)C)C(=O)N(C)[C@@H](CC(C)C)C(=O)N[C@@H](C)C(=O)N[C@H](C)C(=O)N(C)[C@@H](CC(C)C)C(=O)N(C)[C@@H](CC(C)C)C(=O)N(C)[C@@H](C(C)C)C(=O)N1C] | EP 296122 |

TABLE 7-continued

Selected therapeutic agents that can be administered in combination with the anti-LAG-3 antibody molecules, e.g., as a single agent or in combination with other immunomodulators described herein. Each publication listed in this Table is herein incorporated by reference in its entirety, including all structural formulae therein.

| Compound No. | Generic Name Tradename | Compound Structure | Patents/Patent Application Publications |
|---|---|---|---|
| A47 | Vatalanib succinate | (structure) succinate | WO 98/35958 |
| A48 | | IDH inhibitor | WO2014/141104 |
| A49 | | BCR-ABL inhibitor | WO2013/171639 |
| | | | WO2013/171640 |
| | | | WO2013/171641 |
| | | | WO2013/171642 |
| A50 | | cRAF inhibitor | WO2014/151616 |
| A51 | | ERK1/2 ATP competitive inhibitor | PCT/U.S.2014/062913 |

EXAMPLES

The Examples below are set forth to aid in the understanding of the inventions but are not intended to, and should not be construed to, limit its scope in any way.

Example 1: Humanization of Anti-LAG-3 Antibody, BAP050

A murine anti-LAG-3 monoclonal antibody, BAP050, was humanized. The sequences and test samples of twenty humanized BAP050 clones with unique variable region sequences were obtained. These clones were further analyzed for their biological functions (e.g., antigen binding and ligand blocking), structural features, and transient expression in CHO cells.

Example 1.1: Humanization Technology and Process

Humanization of BAP050 was performed using a combinatorial library of human germ line variable region frameworks (FWs). The technology entails transferring the murine CDRs in frame to a library of human variable regions (VRs) that had been constructed by randomly combining human germ line FW1, FW2 and FW3 sequences. Only one FW4 sequence is used, which is WGQGTTVTVSS (SEQ ID NO: 221) for the heavy chain (HC) (Kabat human HC subgroup I. No. 21) and FGQGTKVEIK (SEQ ID NO: 271) for the light chain (LC) (Kabat human κ subgroup I, No. 5). The library of VR sequences is fused to human constant region (CR) sequences, human IgG4 (S228P) of HC and human κ CR of LC, and the resulting library of whole IgG is expressed in CHO cells for screening. Screening was performed with tissue culture supernatants measuring binding avidity on antigen-expressing cells in a whole cell ELISA format or on FACS.

The humanization process was performed in a stepwise manner starting with the construction and expression of the appropriate chimeric mAb (murine VR, IgG4 (S228P), human κ), which can serve as a comparator for the screening of the humanized clones. The constant region amino acid sequences for human IgG4 (S228P) heavy chain and human kappa light chain are shown in Table 6.

Humanization of the VR of LC and HC were performed in two independent steps. The library of humanized LC (huLC) was paired with the chimeric HC (murine VR, IgG4 (S228P)) and the resulting "half-humanized" mAbs were screened for binding activity by ELISA. The huLC of clones with adequate binding activity (≥binding of chimeric mAb) were selected. Analogously, the library of humanized HC (huHC) was paired with the chimeric LC (murine VR, human κ) and screened for binding activity by ELISA. The huHC of clones with appropriate binding activity (≥binding of chimeric mAb) were selected.

The variable regions of the selected huLC and huHC were then sequenced to identify the huLC and huHC with unique sequences (some clones from the initial selection process may share the same LC or HC). The unique huLC and huHC were then randomly combined to form a small library of humAbs, which was expressed in CHO cells and screened on antigen-expressing cells in an ELISA and FACS format. Clones with binding activities that were equal or better than the binding of the chimeric comparator mAb are the final product of the humanization process.

Example 1.2: Sequence of Murine mAb BAP050

The LC and HC variable region sequences of the murine anti-LAG-3 mAb were determined. The sequences obtained from two independent analyses were identical and are shown in FIG. 1.

Germline analysis was performed and part of the result is shown in FIG. 2 as an amino acid sequence alignment. For the light chain, the V-gene is 96.88% identical to mIGkV10-94*01F (279/288 nts) and the J-gene is 97.30% identical to mIGkJ1*01F (36/37 nts). For the heavy chain, the V-gene is 96.88% identical to mIGHV9-3-1*01F (279/288 nts), the J-gene is 86.79% identical to mIGHJ4*01F, and the D-gene is mIGHD1-1*01F.

Example 1.3: Humanized Antibody Clones

As shown in FIG. 3, the process of humanization yielded twenty humanized clones with binding affinities comparable to that of the chimeric antibody. In addition to binding data, for each clone, the VR sequences were provided along with a sample of the mAb. The samples had been prepared by transient transfections of CHO cells and were concentrated tissue culture supernatants. The mAb concentrations in the solutions had been determined by an IgG4-specific ELISA.

As shown in FIG. 4, the twenty unique clones are combinations of six unique HC and twelve unique LC. The amino acid and nucleotide sequences of the heavy and light chain variable domains for the humanized BAP050 clones are shown in Table 1. The amino acid and nucleotide sequences of the heavy and light chain CDRs of the humanized BAP050 clones are shown in Table 1.

Limited diversity was obtained for the HC FW3 region with eighteen clones having the same FWH3, which is from the human germ line IGHV7-4 and has an exposed Cys residue at position 84 of the humanized clones. Closely related VHFW3 sequences typically have a Ser or Ala residue in this position. Therefore, Cys84 was replaced by Ser in selected humanized clones.

FIG. 4 indicates that the samples varied in the concentration of the mAb, ranging from 3.2 µg/mL to 35.8 µg/mL. These numbers were representative of several transient expression experiments.

Example 1.4: Analysis of the Humanized Clones

Figure 5A:
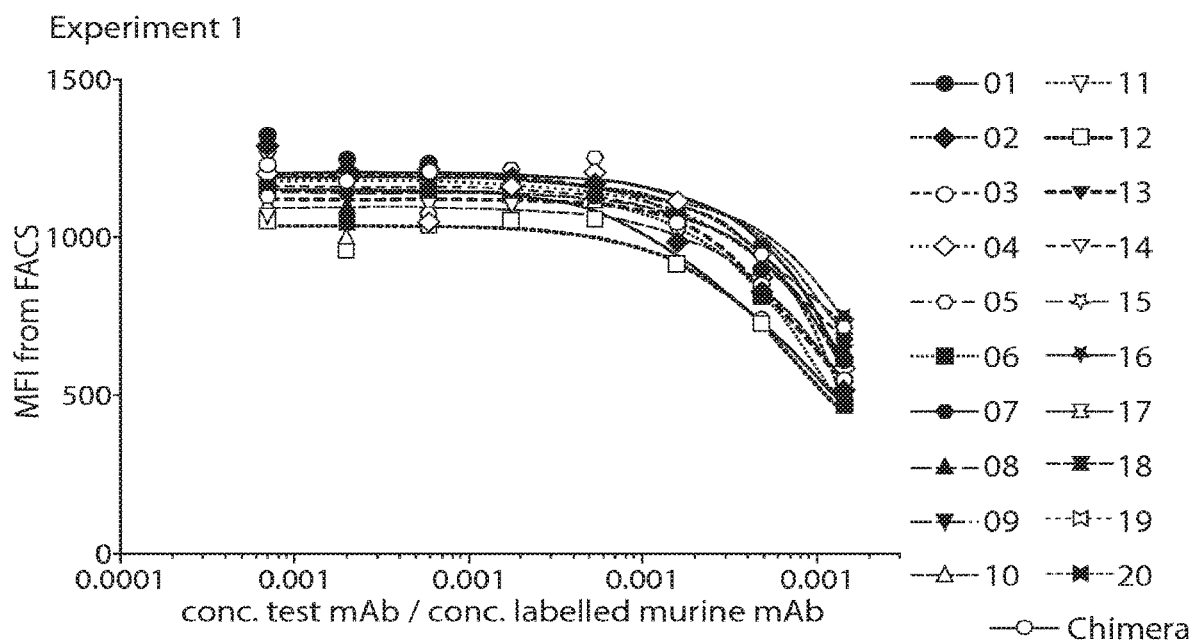
FIG. 5A-5B depicts the binding affinity and specificity of humanized mAbs measured in a competition binding assay using a constant concentration of FITC-labeled murine mAb, serial dilutions of the test antibodies, and LAG-3-expressing CHO cells. Experiment was performed twice, and the results are shown in FIGS. 5A and 5B, respectively.
Figure 5B:
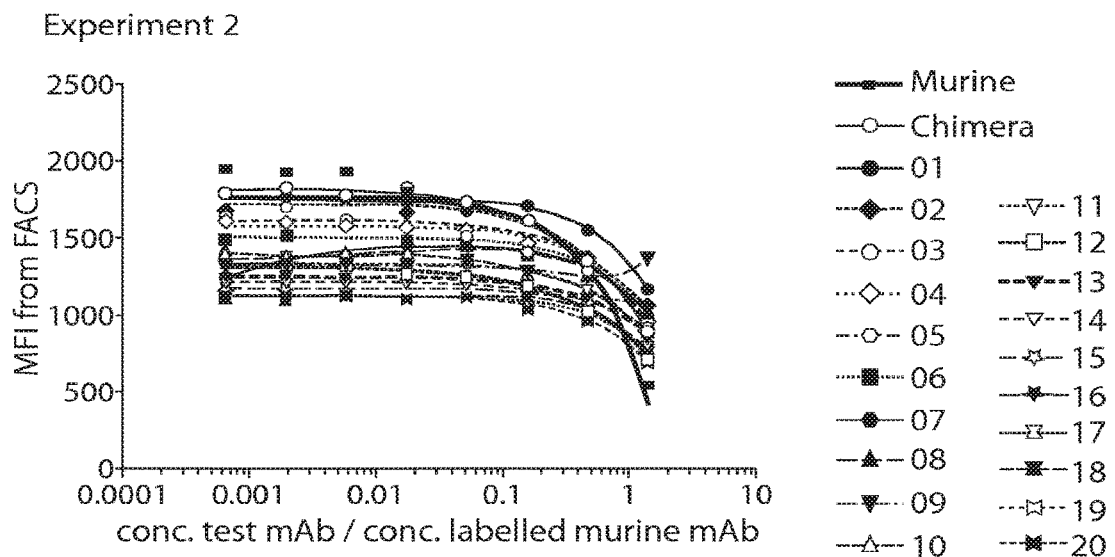

Example 1.4.1: Analysis of Binding Activity and Binding Specificity of Humanized Clones The binding activity and specificity was measured in a competition binding assay using a constant concentration of FITC-labeled murine mAb, serial dilutions of the test mAbs, and LAG-3-expressing CHO cells. Incubations with the mAb mixtures having different concentration ratios of test mAb to labeled mAb was at 4° C. for 30 min. Bound labeled murine mAb was then quantified using a FACS machine. The experiment was performed twice. The results are shown in FIGS. 5A-5B.

Within the accuracy of the experiment, all humanized clones show similar activity for competing with binding of labeled murine mAb. The activity is also comparable to the activity of the parent murine mAb and chimeric mAb. MAbs were ranked relative to each other. For example, it can be a weaker competitor if in both experiments the curve of a certain clone is to the right of the chimeric mAb curve or it can be a better competitor if the curve of a certain clone is to the left of the chimeric mAb curve. Such a ranking system was used in FIG. 6.

Example 1.4.2: Sequence Analysis of Humanized Clones

Based on structural features, the twenty humanized mAbs were divided into six groups and ranked them from A to F. The results are shown in FIG. 6.

Example 1.4.3: Selection of Humunized Clones and Generation of New Versions with the C84S Mutation FIG. 6 summarizes the data which was considered for the selection of humanized clones. Expression data ($2^{nd}$ column), the diversity in the composition of the variable regions ($3^{rd}$ column), relative rankings in binding studies ($4^{th}$ and $5^{th}$ columns), and structural analysis ($6^{th}$ column), were considered. Certain characteristics that lead to the selection of individual clones are marked with grey fields.

Certain clones were mutated at position 84 of VHFW3 from Cys to Ser (see Example 1.3 above). The new versions are called clones Nos. 1S, 2S, 5S, 9S, 11S, 12S, and 13S, and together huBAP050 (Ser) clones.

Figure 7:
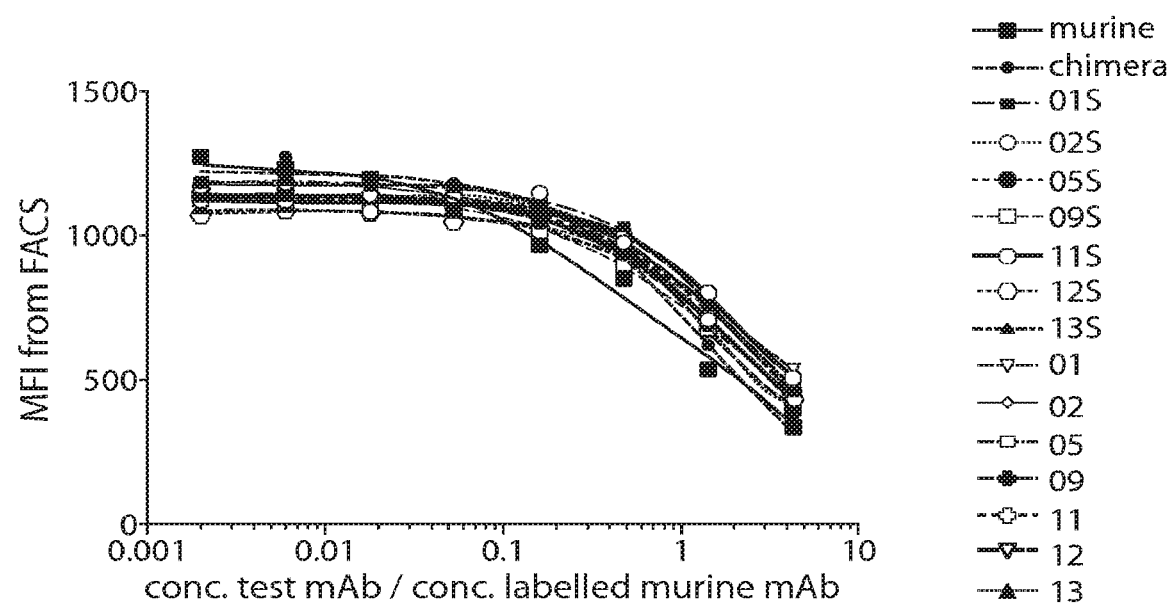
FIG. 7 depicts the binding affinity and specificity of huBAP050 (Ser) clones measured in a competition binding assay using a constant concentration of FITC-labeled murine mAb, serial dilutions of the test antibodies, and LAG-3-expressing CHO cells. HuBAP050 (Ser) clones, such as, BAP050-hum01-Ser, BAP050-hum02-Ser, BAP050-hum05-Ser, BAP050-hum09-Ser, BAP050-hum11-Ser, BAP050-hum 12-Ser, and BAP050-hum13-Ser, were evaluated. Murine mAb BAP050, chimeric mAb BAP050-chi, and humanized BAP050-hum01, BAP050-hum02, BAP050-hum05, BAP050-hum09, BAP050-hum11, BAP050-hum12, and BAP050-hum13 were also included in the analyses.

Example 1.4.4: Analysis of Binding Activity and Binding Specificity of huBAP050 (Ser) Clones The new versions of the selected clones with the C84S mutation in VHFW3 were subject to an analogous competition binding assay as described under Example 1.4.1. The experiment included the original humanized clones with the Cys84 residue, the new humanized clones with the Ser84 residue, chimeric mAb and the parent murine mAb. The results are shown in FIG. 7.

All tested variants were comparable to the murine parent mAb in blocking the binding of labeled murine mAb to LAG-3-expressing CHO cells. It follows that the behavior of the new humanized clones with the Ser84 residue was not different from the behavior of the original humanized clones with the Cys84 residue.

Figure 8:
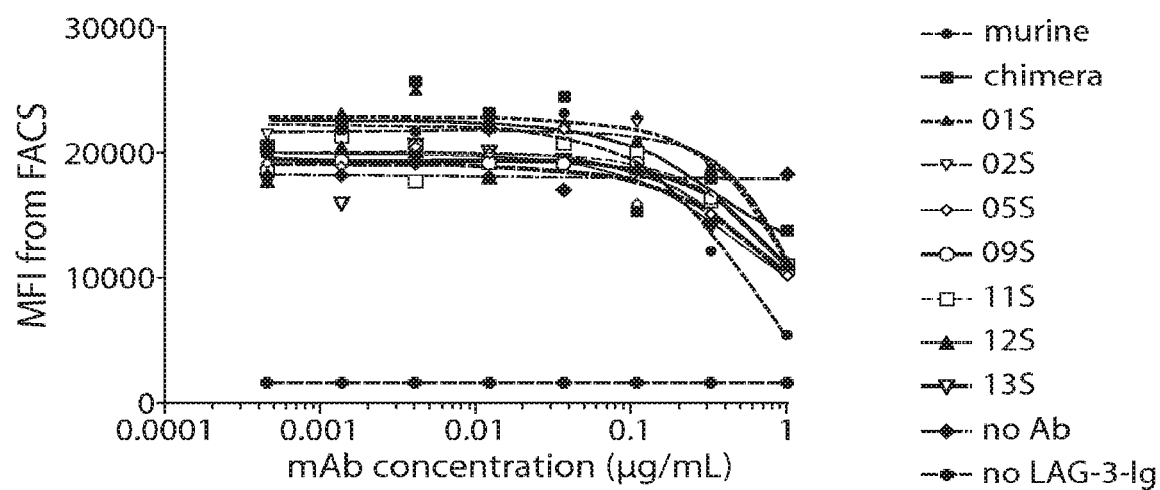
FIG. 8 depicts blocking of binding of LAG-3-Ig to Daudi cells by huBAP050 (Ser) clones. HuBAP050 (Ser) clones, such as, BAP050-hum01-Ser, BAP050-hum02-Ser, BAP050-hum05-Ser, BAP050-hum09-Ser, BAP050-hum11-Ser, BAP050-hum12-Ser, and BAP050-hum13-Ser, were evaluated. Murine mAb BAP050 and chimeric mAb BAP050-chi were also included in the analyses.

Example 1.4.5: Blocking of Binding of LAG-3-Ig to MHC Class II on Daudi Cells LAG-3 binds to MHC class II, therefore the selected huBAP050 (Ser) clones were tested for their ability to block the binding of soluble LAG-3-Ig to Daudi cells (a Burkitt's lymphoma cell line) that express MHC class II. The blocking capacity of the mAbs was evaluated in a competition binding assay using a constant concentration of LAG-3-huIgG1 Fc fusion protein (2 µg/mL), serial dilutions of the mAbs to be tested, and Daudi cells. Incubation was at 4° C. for 30 min. Bound ligand fusion protein was detected with PE-conjugated F(ab')2 fragment of goat anti-human IgG which doesn't recognize IgG4 mAbs (Southern Biotech 2043-09), and flow cytometry. The results are shown in FIG. 8.

Within the accuracy of the experiments, the seven huBAP050 (Ser) clones, chimeric mAb and murine parent mAb demonstrated comparable blocking activity for LAG-3-Ig.

Example 1.4.6: T Cell Epitope Analysis

Humanized mAbs were analyzed for T cell epitopes using Epibase™. The algorithm analyzes each possible peptide (each 10-mer along the protein advancing by one amino acid) for binding to HLA class II. It estimates free energy of binding ($\Delta G_{bind}$) for each peptide and calculates a putative KD ($\Delta G_{bind}$=RT $lnK_D$). Then peptides are labeled S, M, or N for strong, medium, and non-binders. Threshold values used for this classification are different for each allotype.

The data was normalized to a risk score. The overall "risk score" is the sum of all potential epitopes to all tested alleles, weighted by the affinities of the respective peptides but leaving out all potential epitopes in germ line sequences (lower value therefor is "better")

There are roughly three categories of mAbs, derived from a large set of mAbs of different composition as described below.

Risk score of around 500: fully human mAbs generated from humans, "humanized" mice, and phage libraries ("values below 500 are really good even for fully human antibodies"). Humanized mAbs specifically engineered (even the CDRs) to have a low score are typically in the 500-700 risk category.

Risk score around 900: typical CDR-grafted antibodies, which have fully murine CDRs with or without changes in the FW region ("Gary Queen technology"); approved CDR-grafted mAbs are basically all in this category.

Risk score around 1500: chimeric mAbs.

The results for selected humanized BAP050 mAbs are:

TABLE 9

| Clone No. | Risk score |
|---|---|
| 01 | 999 |
| 02 | 1006 |
| 05 | 967 |
| 09 | 998 |
| 11 | 1042 |
| 12 | 1042 |
| 13 | 950 |

The risk scores of the seven selected humanized clones are in the typical CDR-grafted mAb category. For example, the human mAb, adalimumab (Humira®), has a score of 654, which is relatively high for human mAbs (at the upper end of the Gaussian curve) but low in comparison to a typical CDR-grafted mAb.

The scores come from the murine CDRs, specifically the Y residues. These are acceptable scores for antibodies for cancer treatment. Changing the score would mean engineering the murine CDRs, specifically removing Y residues.

Summary and Conclusions

Murine anti-LAG-3 monoclonal antibody, BAP050, was humanized. The technology entails the cloning of the murine CDRs in-frame into an ordered library of human germ line variable region frameworks, expressing the library of cloned variable regions as intact IgG4 (S228P) humanized mAbs in CHO cells, and selecting clones that bind with comparable or higher affinity to the target as the parent mAb. Therefore, the murine CDRs were asked to select the best human germ line framework sequences that preserve their conformations and thus the binding affinity and specificity of the parent murine mAb. The sequences and test samples of twenty humanized versions with unique variable region sequences were obtained, which had also passed a binding test with LAG-3-transfected CHO cells. Eighteen clones contained the same HC FW3 germ line sequence, which has a rare Cys at position 84. In seven selected clones, Cys was replaced by Ser creating new mAbs labeled huBAP050 (Ser) clones. These clones were further analyzed for their biological functions (e.g., antigen binding and ligand blocking), structural features, and transcient expression in CHO cells.

Example 2: Expression of Humanized Anti-LAG-3 Antibody, BAP050

Five humanized clones described in Example 1 were selected for evaluation of expression in Chinese Hamster Ovary (CHO) cells.

Single gene vectors (SGVs) were constructed using Lonza's GS XCEED™ vectors (IgG4proΔk for heavy chain and Kappa for light chain). The SGVs were amplified and transiently co-transfected into CHOKISV GS-KO™ cells for expression at a volume of 2.8 L.

Expression cultures were harvested Day 6 post-transfection and clarified by centrifugation and sterile filtration. The clarified cell culture supernatant was purified using one-step Protein A chromatography. Product quality analysis in the form of SE-HPLC, SDS-PAGE, IEF, and LAL was carried out using purified material at a concentration of 1 mg/ml including an antibody as a control sample.

Example 2.1: Vector Construction

The sequences of the light and heavy chain variable domain encoding regions were synthesised by GeneArt AG. Light chain variable domain encoding regions were sub-cloned into pXC-Kappa and heavy chain variable domain encoding regions into pXC-IgG4pro ΔK vectors respectively using the N-terminal restriction site Hind III and the C-terminal restriction sites BsiWI (light chain) and ApaI (heavy chain). Positive clones were screened by PCR amplification (primers 1053: GCTGACAGACTAACA-GACTGTTCC (SEQ ID NO: 288) and 1072: CAAATGTGGTATGGCTGA (SEQ ID NO: 289)) and verified by restriction digest (using a double digest of EcoRI-HF and HindIII-HF) and nucleotide sequencing of the gene of interest.

Example 2.2: DNA Amplification

A single bacterial colony was picked into 15 ml Luria Bertani (LB) medium (LB Broth, Sigma-Aldrich, L7275) containing 50 μg/ml ampicillin and incubated at 37° C. overnight with shaking at 220 rpm. The resulting starter culture was used to inoculate 1 L Luria Bertani (LB) medium containing 50 μg/ml ampicillin and incubated at 37° C. overnight with shaking at 220 rpm. Vector DNA was isolated using the QIAGEN™ Plasmid Plus Gigaprep system (QIAGEN™, 12991). In all instances, DNA concentration was measured using a NANODROP™ 1000 spectrophotometer (Thermo-Scientific) and adjusted to 1 mg/ml with EB buffer (10 mM Tris-Cl, pH 8.5). DNA quality for the single gene vectors was assessed by measuring the absorbance ratio A260/A280. This was found to be between 1.88 and 1.90.

Example 2.3: Culture of CHOKISV GS-KO Cells™

CHOK1SV GS-KO™ cells were cultured in CD-CHO media (INVITROGEN™, 10743-029) supplemented with 6 mM glutamine (INVITROGEN™, 25030-123). Cells were incubated in a shaking incubator at 36.5° C., 5% $CO_2$, 85% humidity, 140 rpm. Cells were routinely sub-cultured every 3-4 days, seeding at $2\times10^5$ cells/ml and were propagated in order to have sufficient cells available for transfection. Cells were discarded by passage 20.

Example 2.4: Transient Transfections of CHOKISV GS-KO Cells™

Transient transfections were performed using CHOKISV GS-KO™ cells which had been in culture a minimum two weeks. Cells were sub-cultured 24 h prior to transfection and cell viability was >99% at the time of transfection.

All transfections were carried out via electroporation using a Gene Pulse MXCELL™ (Bio-Rad), a plate based system for electroporation. For each transfection, viable cells were resuspended in pre-warmed media to $2.86 \times 10^7$ cells/ml. 80 μg DNA (1:1 ratio of heavy and light chain SGVs) and 700 μl cell suspension were aliquotted into each cuvette/well. Cells were electroporated at 300 V, 1300 μF. Transfected cells were transferred to pre-warmed media in Erlenmeyer flasks and the cuvette/wells rinsed twice with pre-warmed media which was also transferred to the flasks. Transfected cell cultures were incubated in a shaking incubator at 36.5° C., 5% $CO_2$, 85% humidity, 140 rpm for 6 days. Cell viability and viable cell concentrations were measured at the time of harvest using a CEDEX™ HiRes automated cell counter (Roche).

Example 2.5: Protein A Affinity Chromatography

Cell culture supernatant was harvested and clarified by centrifugation at 2000 rpm for 10 min, then filtered through a 0.22 μm PES membrane filter. Clarified supernatant was purified using a pre-packed 5 ml HITRAP™ MABSELECT SURE™ column (GE Healthcare, 11-0034-94) on an AKTA purifier (10 ml/min). The column was equilibrated with 50 mM sodium phosphate, 125 mM sodium chloride, pH 7.0 (equilibration buffer) for 5 column volumes (CVs). After sample loading, the column was washed with 2 CVs of equilibration buffer followed by 3 CVs of 50 mM sodium phosphate, 1 M sodium chloride pH 7.0 and a repeat wash of 2 CVs of equilibration buffer. The Product was then eluted with 10 mM sodium formate, pH 3.5 over 5 CVs. Protein containing, eluted fractions were immediately pH adjusted to pH 7.2 and filtered through a 0.2 μm filter.

A single protein-containing peak was observed during the elution phase. This peak was shown to contain the mAb, when analyzed by SE-HPLC and SDS-PAGE. Recovered protein yield is shown in Table 5. The clones expressed transiently in a range from 21.9 to 29.4 mg/L.

TABLE 5

Summary of yield, titre, monomer content and endotoxin levels

| Product | Yield* (mg) | Titre* (mg/L) | Monomer Content (%) | Endotoxin levels (EU/mg) |
|---|---|---|---|---|
| Clone F | 79.1 | 28.25 | 95.63 | 0.22 |
| Clone G | 61.3 | 21.88 | 95.31 | 0.15 |
| Clone H | 76.0 | 27.13 | 97.07 | 0.20 |
| Clone I | 82.3 | 29.38 | 97.82 | 0.05 |
| Clone J | 64.0 | 24.63‡ | 96.97 | 0.27 |

*Post Protein A purification;
‡from a 2.6 L expression culture

Example 2.6: SE-HPLC Analysis

Samples of Protein A purified antibodies were analyzed in duplicate by SE-HPLC on an Agilent 1200 series HPLC system, using a ZORBAX™ GF-250 4 μm 9.4 mm ID×250 mm column (Agilent). Aliquots of sample at a concentration of 1 mg/ml were filtered through a 0.2 μm filter prior to injection. 80 μl aliquots were injected respectively and run at 1 ml/min for 15 minutes. Soluble aggregate levels were analysed using Chemstation (Agilent) software.

Chromatography profiles with retention time showing the percentage of the overall detected peak areas were obtained for the tested antibodies and a control IgG4 antibody. The products show a single protein peak at approximately 8.59 to 8.61 min comparable to the human IgG4 antibody control (about 8.64 min) and consistent with a monomeric antibody. Small amounts (up to about 3-4%) of higher molecular weight impurities, consistent with soluble aggregates, were detected at retention times around 7.90 min.

Example 2.7: SDS-PAGE Analysis

Reduced samples were prepared for analysis by mixing with NUPAGE™ 4× LDS sample buffer (INVITROGEN™, NP0007) and NUPAGE™ 10× sample reducing agent (INVITROGEN™, NP0009), and incubated at 70° C., 10 min. For non-reduced samples, the reducing agent and heat incubation were omitted. Samples were electrophoresed on 1.5 mm NUPAGE™ 4-12% Bis-Tris NOVEX™ pre-cast gels (INVITROGEN™, NP0335PK2) with NUPAGE™ MES SDS running buffer under denaturing conditions. 10 μl aliquots of SEEBLUE™ Plus 2 pre-stained molecular weight standard (INVITROGEN™, LC5925) and a control IgG4 antibody at 1 mg/ml were included on the gel. 1 μl of each sample at 1 mg/ml were loaded onto the gel. Once electrophoresed, gels were stained with INSTANTBLUE™ (TripleRed, ISB01L) for 30 min at room temperature. Images of the stained gels were analysed on a BIOSPECTRUM™ Imaging System (UVP).

The analysis confirmed the presence of the antibody products and good levels of purity. Under non-reducing conditions, a predominant protein band close to 98 kDa was observed comparable with the control IgG4 antibody. The control IgG4 antibody and one tested clone display an additional fainter band corresponding to a heavy plus light chain half-antibody at approximately 70 kDa under non-reducing conditions. This is expected for the control antibody. Two bands were observed under reducing conditions consistent with the size of heavy (close to the position of the 49 kDa marker) and light chains (close to the position of the 28 kDa marker) and comparable with the bands found for the control IgG4 antibody.

Example 2.8: Iso-Electric Focusing (IEF) Analysis

Non-reduced samples of Protein A purified antibody were electrophoresed as described below.

5 μg of Protein A purified samples were electrophoresed on a 1.0 mm NOVEX™ pH 3-10 gradient gel (INVITROGEN™, EC66552BOX) using manufacturers recommended running conditions. A 10 μl aliquot of IEF pH 3-10 markers (INVITROGEN™, 39212-01) was included on the gel. Once electrophoresed, gels were fixed with 10% TCA solution for 30 min and then stained with INSTANTBLUE™ (TripleRed, ISB01L) over night at room temperature. Images of the stained gels were analysed on a BIOSPECTRUM™ Imaging System (UVP).

As shown in Table 6, the tested clones display charge isoforms between pH 6.0 and 7.45. The detected charge isoforms are comparable to the theoretically calculated pIs for these antibodies which were predicted to be between 6.35 and 6.82. Clones F and G both have a predicted pI of 6.35 and show comparable charge isoforms, which is also consistent with the theoretically calculated pI being the same for both (6.35). The control IgG4 antibody behaved as expected.

TABLE 6

Charge isoforms as detected by NOVEX ™ IEF analysis

| Product | pI of predominant charge isoform* | Acidic charge isoforms* | Basic charge isoforms* |
|---|---|---|---|
| Clone F | 6.2 | 2x; 6.0 to 6.1 | 6.3 |
| Clone G | 6.2 | 2x; 6.0 to 6.1 | 6.3 |
| Clone H | 7.4 | 2x; 6.9 to 7.3 | 7.45 |
| Clone I | 7.0 | 2x; 6.7 to 6.9 | 7.3 |
| Clone J | 6.5 | 2x; 6.0 to 6.4 | 6.8 |

*pI readings are estimated from the staining positions correlated against the IEF 3-10 marker.

Example 2.9: Endotoxin Analysis

Endotoxin levels of purified proteins were measured at final concentrations (up to 3.44 mg/ml) using an ENDOSAFE™-PTS instrument, a cartridge based method based on the LAL assay (Charles River).

As shown in Table 8, the endotoxin content was found to range from 0.05 to 0.27 EU/mg.

Conclusion

GS single gene expression vectors for selected humanized anti-LAG-3 mAbs were constructed and used to transiently transfect CHOK1SV GS-KO™ cells. 2.6 to 2.8 litres of expression culture were incubated under standard conditions for 6 days and the resulting cell culture supernatant purified using Protein A chromatography. Post-purification titres are indicated in Table 8 and were found to be ranging from 21.88 to 29.38 mg/L. The recovered yields range from 61.3 to 82.3 mg.

SDS-PAGE and SE-HPLC analysis indicated the presence of a small amount (up to 4.69%) of soluble aggregates present in the products being predominantly consistent with dimeric antibody for the mAb. The mAbs also showed higher molecular weight impurities at retention times consistent with that of trimeric antibodies.

Iso-electric focusing detected a number of charge isoforms for all mAbs. The mAbs showed isoforms generally more basic when based on theoretically calculated pI for these molecules indicating some level of post translation modification. The mAbs were found to be comparable to their theoretically calculated pI values.

The endotoxin levels for all samples were measured prior to provision of samples and found to be below 0.63 EU/mg.

Example 3: Characterization of Murine and Humanized Anti-LAG-3 Antibodies

Example 3.1: Characterization of Murine Anti-LAG-3 Antibody

The binding affinity of murine anti-LAG-3 antibody BAP050 to LAG-3 was investigated. As shown by FACS analyses, the murine anti-LAG-3 antibody binds to human LAG-3 transfected CHO cells with a $K_D$ of 0.2 nM, to human T cells with a $K_D$ of 0.26 nM, and to human LAG-3 transfected 300.19 cells with a $K_D$ of 13.6 nM.

The blocking activity of murine anti-LAG-3 antibody BAP050 was examined by competition binding assays. The murine anti-LAG-3 antibody blocked LAG-3-Ig binding to MHC class II molecules on Raji cells with an IC50 of 2.3 nM.

The effect of murine anti-LAG-3 antibody BAP050 on interferon gamma (IFN-γ) expression was tested. The murine anti-LAG-3 antibody resulted in 3.0±2.1 fold increase in IFN-γ expression on cells stimulated with anti-CD3 (0.1 µg/mL), 1.6±0.4 fold increase on cells stimulated with Staphylococcal enterotoxin B (SEB) (3 pg/mL), and 1.4±0.3 fold increase on cells stimulated with CMV peptides.

The regions in LAG-3 that may bind murine anti-LAG-3 antibody BAP050 were examined. As shown by ELISA, the murine anti-LAG-3 antibody binds a LAG-3 Ig fusion protein (sLAG-3 D1-D4Ig) that contains all four extracellular Ig-like domains (D1-D4), as well as a LAG-3 Ig fusion protein (sLAG-3 D1-D2Ig) that only contains Domain 1 (D1) to Domain 2 (D2). Further analysis shows that the anti-LAG-3 antibody binds CHO cells that express full length LAG-3, LAG-3 with D2 deletion (CHO-LAG-3ΔD2), and LAG-3 with partial deletion of D1 extra loop (CHO-LAG-3ΔP48A60). Thus, the anti-LAG-3 antibody binds D1 of LAG-3.

The murine anti-LAG-3 antibody BAP050 was also found to increase IFN-γ secretion in CD3-stimulated PBMCs compared to mouse IgG1 control and no antibody control. The fold of increase ranges from 1.4 to 2.9-fold among four donors.

Example 3.2: Characterization of Humanized Anti-LAG-3 Antibody

Binding Affinity and Specificity

The binding of an exemplary humanized anti-LAG-3 antibody on human LAG-3 protein was measured using BIACORE™ method. The results are: Ka=6.41×10⁵ M⁻¹s⁻¹; Kd=7.00×10⁵ s⁻¹; $K_D$=0.109±0.008 nM. The anti-LAG-3 antibody also binds cynomolgus LAG-3 as measured by BIACORE™ method.

The binding of the same humanized anti-LAG-3 antibody on human LAG-3-expressing CHO cells and cynomologous monkey LAG-3 expressing HEK 209 cells. was measured using FACS analysis. The result shows that the anti-LAG-3 antibody (human IgG4) binds with high affinity to human LAG-3 compared to a human IgG4 isotype control. The anti-LAG-3 antibody binds human LAG-3-expressing cells with a $K_D$ of 1.92 nM and binds cynomologous monkey LAG-3-expressing cells with a $K_D$ of 2.3 nM.

The binding of the anti-LAG-3 antibody on rhesus LAG-3-expressing 300.19 cells was also measured. The results show that the anti-LAG-3 antibody binds rhesus LAG-3 with a $K_D$ of 8.03 nM.

Additional binding analyses show that the exemplary humanized anti-LAG-3 antibody is not cross-reactive with mouse LAG-3 or cross-reactive with parental cell line.

Blocking of Interactions Between LAG-3 and its Ligands

The ability of the exemplary humanized anti-LAG-3 antibody to block the interactions between LAG-3 and both of its known ligand, MHC class II molecules, was examined. The results show that the anti-LAG-3 antibody blocked the interaction between LAG-3 and MHC class II molecules on Daudi cells with an IC50 of 5.5 nM, compared to a human IgG4 isotype control.

LAG-3 Stimulation of Cytokine Release In Vitro in the Absence of T Cell Receptor Engagement Anti-LAG-3 antibody is not expected to stimulate detectable cytokine responses without specific stimulation by the T cell receptor. Anti-LAG-3 antibody was immobilized and highly crosslinked by air-drying on a tissue culture plate and tested for its ability to stimulate cytokine production using a method derived from Stebbings R., et al. (*J Immunol.* 2007 179 (5): 3325-3331). No IL-2 or IFN-γ production was induced by anti-LAG-3 antibody or control IgG in the absence of staphylococcal enterotoxin B (SEB) stimulation of whole blood.

Example 4: Patient Selection Based on PD-L1/CD8/IFN-γ Status

Figure 11:
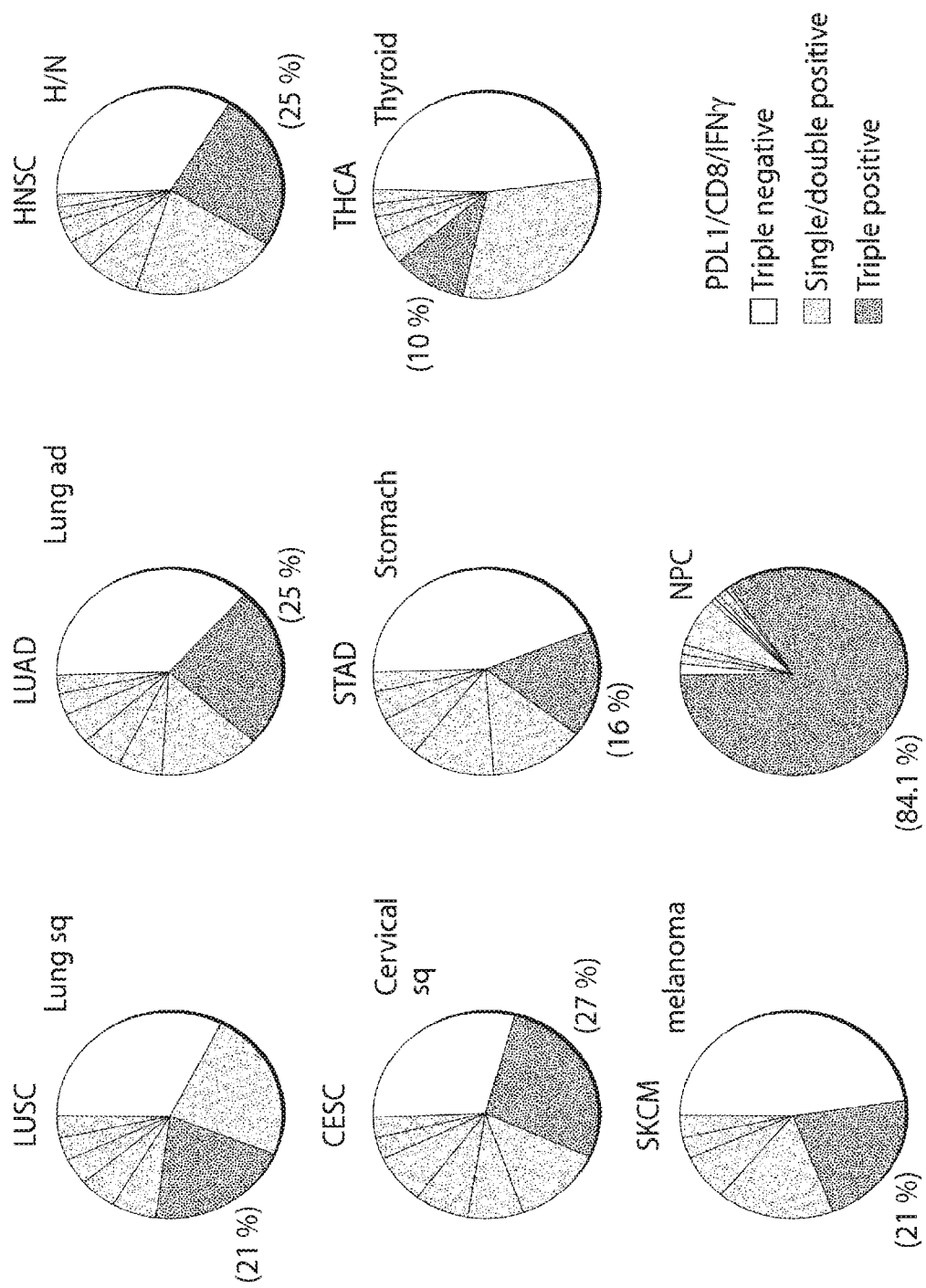
FIG. 11 shows exemplary cancers having relatively high proportions of patients that are triple-positive for PD-L1/CD8/IFN-γ.

For each of several types of cancer, samples from multiple patients were tested for PD-L1/CD8/IFN-γ status. Each sample was classified as: triple-negative for PD-L1/CD8/IFN-γ, single or double positive for these markers, or triple-positive for these markers. FIG. 11 shows that in this experiment, within a population of patients, the following types of cancer are frequently triple-positive for PD-L1/CD8/IFN-γ: Lung cancer (squamous), lung cancer (adenocarcinoma), head and neck cancer, cervical cancer (squamous), stomach cancer, thyroid cancer, melanoma, and nasopharyngeal cancer. Patients having these types of cancer are good candidates for therapy with anti PD-1 antibodies in combination therapies as described herein, e.g., anti-LAG-3 antibodies. The likelihood of successful treatment can be further boosted by determining which patients are triple-positive for PD-L1/CD8/IFN-γ, and treating the triple-positive patients with anti-PD-1 or anti-PD-L1 antibodies and combination therapies as described herein, e.g., anti-LAG-3 antibodies.

Figure 12:
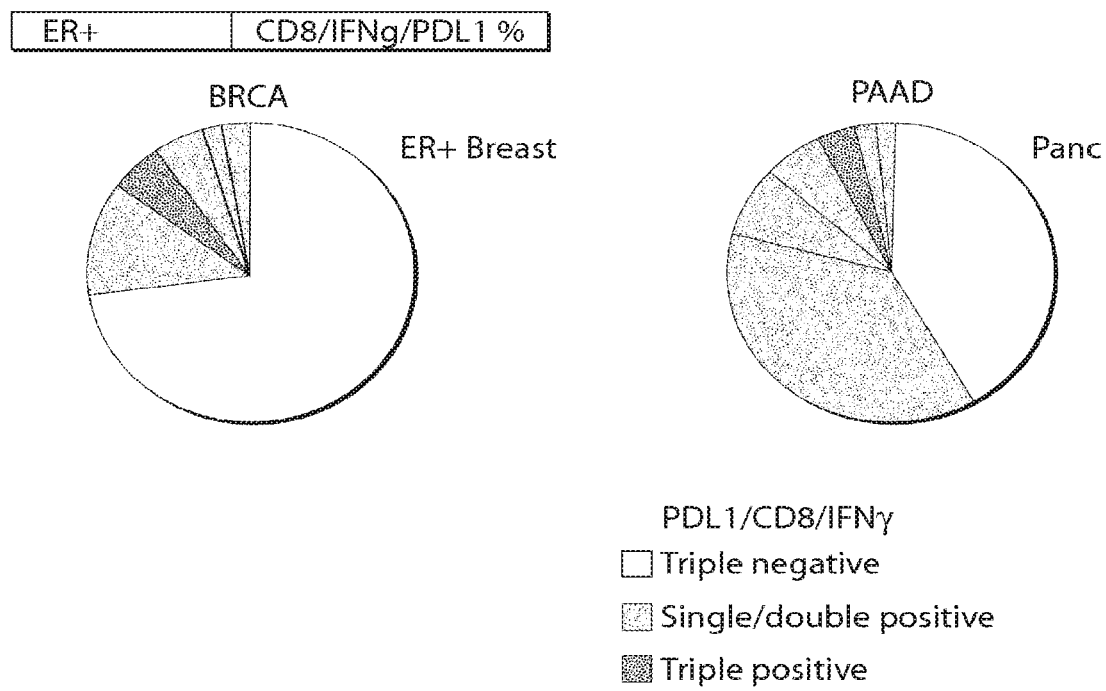
FIG. 12 shows exemplary ER+ breast cancer and pancreatic cancer having relatively low proportions for patients that are triple positive for PD-L1/CD8/IFN-γ.

FIG. 12 shows that within a population of patients, the following types of cancer are rarely triple positive for PD-L1/CD8/IFN-γ: ER+ breast cancer and pancreatic cancer. Notably, even in cancers that are generally not positive for PD-L1/CD8/IFN-γ, one can increase the likelihood of successful treatment by determining which patients are triple-positive for PD-L1/CD8/IFN-γ, and treating the triple-positive patients with anti-PD-1 or anti-PD-L1 antibodies and combination therapies as described herein, e.g., anti-LAG-3 antibodies.

Figure 13:
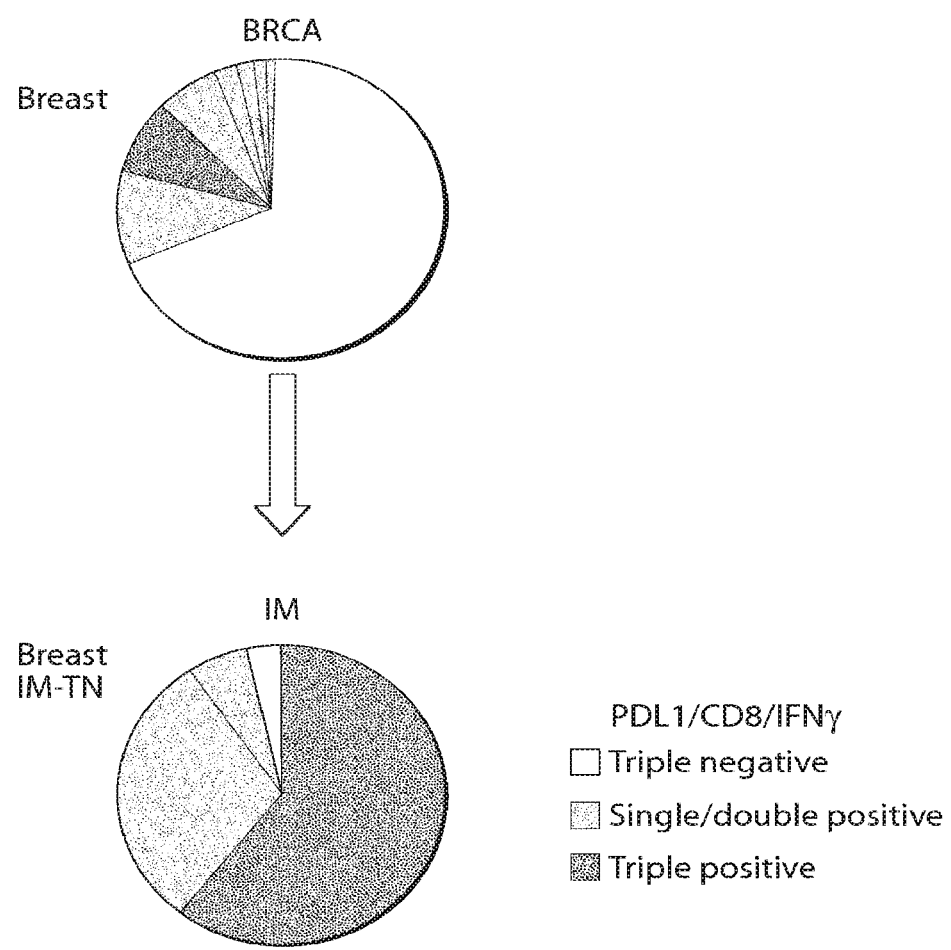
FIG. 13 shows the proportion of exemplary breast cancer patients that are triple positive for PD-L1/CD8/IFN-γ.

FIG. 13 shows the proportion of breast cancer patients that are triple positive for PDL1/CD8/IFN-γ. Considering breast cancer in general, the proportion of triple-positives is somewhat low. However, when one focuses only on IM-TN breast cancer, it can be seen that a much larger percentage of patients is triple positive for PD-L1/CD8/IFN-γ. IM-TN breast cancer is particularly difficult to treat with conventional therapies. The discovery that IM-TN breast cancer is often triple-positive for PD-L1/CD8/IFN-γ opens up new avenues of therapy for this cancer with anti-PD-1 or anti-PD-L1 antibodies and combination therapies as described herein, e.g., anti-LAG-3 antibodies.

Figure 14:
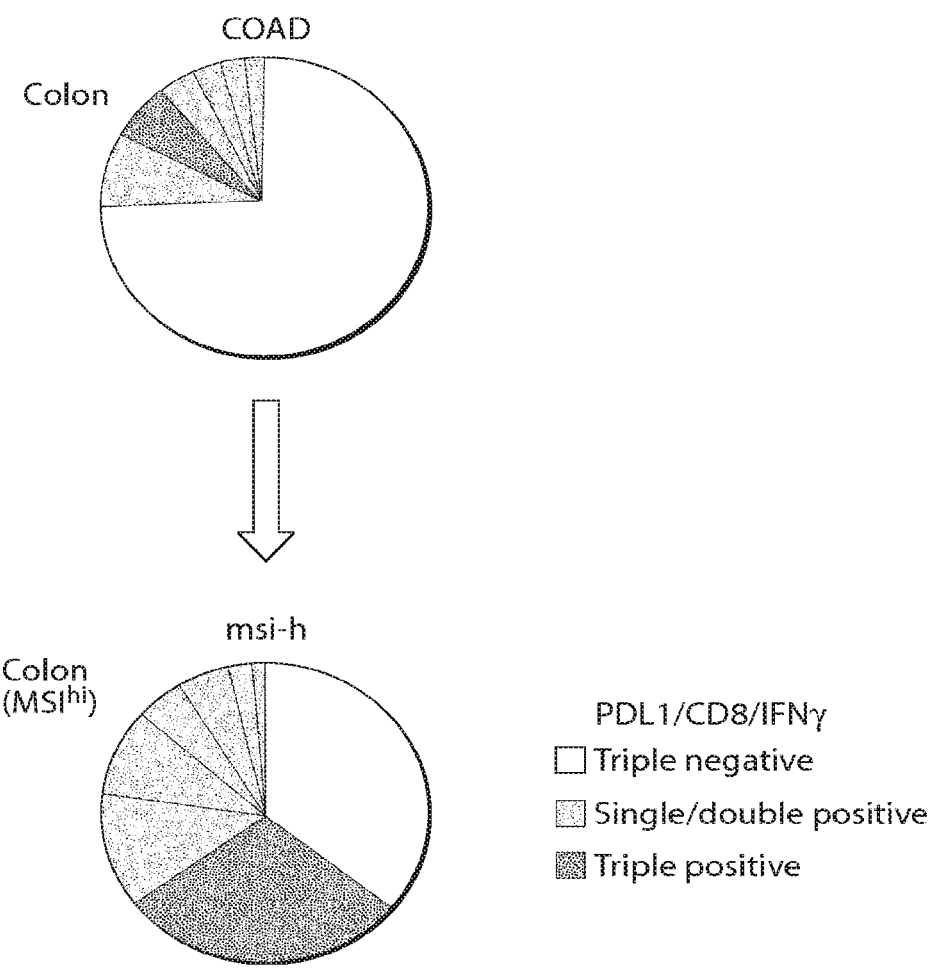
FIG. 14 shows the proportion of exemplary colon cancer patients that are triple positive for PD-L1/CD8/IFN-γ.

FIG. 14 shows the proportion of colon cancer patients that are triple positive for PD-L1/CD8/IFN-γ. Considering colon cancer in general, the proportion of triple-positive is somewhat low. However, when one focuses only on MSI-high (high microsatellite instability) breast cancer, it can be seen that a much larger percentage of patients is triple positive for PD-L1/CD8/IFN-γ. MSI levels can be assayed using, e.g., commercially available PCR-based methods.

Gastric cancer samples were tested for levels of PD-L1/CD8/IFN-γ (data not shown). It was found that in MSI-high or EBV+ gastric cancers, about 49% were positive for PD-L1, and a high proportion of the PD-L1-positive cells were triple positive for PD-L1/CD8/IFN-γ. It was also found that a proportion of PD-L1-positive cells and PD-L1/CD8/IFN-γ positive cells were also positive for PIK3CA. This finding suggests that these cancers may be treated with a PD-1 or an anti-PD-L1 antibody, e.g., in combination with an anti-LAG-3 antibody, optionally in combination with a PIK3 therapeutic.

MSI-high CRC samples were tested for a combination of markers (data not shown). It was found that in MSI-high CRC samples, a high proportion of the PD-L1/CD8/IFN-γ samples are also positive for LAG-3, PD-1 (also called PDCD1), RNF43, and BRAF. This finding suggests that these cancers may be treated with a LAG-3 antibody, optionally in combination with a therapeutic that targets one or more of PD-1, PD-L1, PDCD1, RNF43, and BRAF.

Squamous cell lung cancers were tested for a combination of markers (data not shown). It was found that in squamous cell lung cancer samples, a high proportion of the PD-L1/CD8/IFN-γ samples are also positive for LAG-3. This finding suggests that these cancers may be treated with a LAG-3 antibody, optionally in combination with a therapeutic that targets PD-1 or PD-L1, e.g., an anti-PD-1 antibody or an anti-PD-L1 antibody.

Papillary thyroid cancers were tested for a combination of markers including the BRAF V600E mutation (data not shown). It was found that a high proportion of thyroid cancer samples that are positive for PD-L1 are also positive for BRAF V600E. This finding suggests that these cancers may be treated with an anti-PD-1 antibody or an anti-PD-L1 antibody, e.g., in combination with an anti-LAG-3 antibody, optionally in combination with a therapeutic that targets BRAF.

Example 5: Patient Selection Based on PD-L1 Status

To enable broad examination of cancer indications for immunomodulator (e.g., LAG-3 alone or in combination with PD1/PD-L1) based therapies, PD-L1 expression was evaluated at both the protein and mRNA levels in human cancers including both lung and hepatic tumors.

PD-L1 protein expression was evaluated in a set of formalin-fixed paraffin-embedded non-small cell lung (NSCLC) adenocarcinoma (ACA), NSCLC squamous cell carcinoma (SCC), and hepatocellular carcinoma (HCC) tumors by immunohistochemistry (IHC). PD-L1 expression was scored semi-quantitatively by a manual histo-score (H-score) methodology based on staining intensity and percentage of positive tumor cells. In our IHC analysis, PD-L1 positivity (PD-L1+) was defined as an H-score ≥20. In parallel, PD-L1 mRNA expression data was examined from The Cancer Genome Atlas (TCGA) in these same indications (503 NSCLC ACA, 489 NSCLC SCC, and 191 HCC) and analyzed by comparing the expression in matched normal tissues from TCGA.

With RNAseq analysis, data was calculated as log 2 (RPKM+0.1) after RSEM normalization, utilizing OmicSoft RNASeq pipelines across TCGA tumor indications. The expression of PD-L1 is elevated in NSCLC ACA and SCC, relative to that in HCC. By overlaying the distributions and comparing the expression levels across all indications in TCGA, we ranked overexpression profiles for PD-L1 and found the TCGA HCC cohort to have much reduced PD-L1 mRNA levels, with a median level of −0.8 compared to 1.3 for ACA and 1.5 for SCC, which amounts to more than a 2-fold change of median level expression. With RNAseq, our analysis defines 50% of NSCLC adenocarcinoma, 54% of NSCLC squamous cell carcinoma, and 6% of HCC as high expressers for PD-L1.

Tumor cell PD-L1 protein expression was measured in 45 lung adenocarcinoma (ACA) samples, 47 lung squamous cell carcinoma (SCC) samples, and 36 hepatocellular carcinoma (HCC) samples. 16/45 (35.6%) lung ACA, 21/47 (44.7%) lung SCC were PD-L1 positive. In contrast, PD-L1 positivity was seen in only 2/36 (5.6%) HCC samples.

In summary, with IHC and RNAseq analysis in large and independent human NSCLC and HCC sample sets, PD-L1 expression was found to be more enriched in NSCLC than in HCC. Within NSCLC, there are comparable findings between adenocarcinoma and squamous cell carcinomas. Importantly, amongst the large number of samples (128 for IHC and 1183 for RNAseq) in the 3 indications, very good concordance is observed between protein- and mRNA-based analyses. This finding thus establishes the basis for large scale mRNA-based data mining in TCGA for indications and patient segments that may be enriched for responses to immunomodulator (e.g., PD-1/PD-L1, e.g., in combination with LAG-3) based immune therapies.

INCORPORATION BY REFERENCE

All publications, patents, and Accession numbers mentioned herein are hereby incorporated by reference in their entirety as if each individual publication or patent was specifically and individually indicated to be incorporated by reference.

EQUIVALENTS

While specific embodiments of the subject invention have been discussed, the above specification is illustrative and not restrictive. Many variations of the invention will become apparent to those skilled in the art upon review of this specification and the claims below. The full scope of the invention should be determined by reference to the claims, along with their full scope of equivalents, and the specification, along with such variations.

What is claimed is:

1. A bispecific antibody molecule having a first binding specificity for LAG-3 and a second binding specificity for one of the following antigens: PD-1, TIM-3, CEACAM-1, CEACAM-5, PD-L1, or PD-L2, wherein the bispecific antibody molecule comprises a LAG-3 binding domain comprising:
(a) a heavy chain variable region (VH) comprising a VHCDR1 amino acid sequence of SEQ ID NO: 4, a VHCDR2 amino acid sequence of SEQ ID NO: 5, and a VHCDR3 amino acid sequence of SEQ ID NO: 3; and a light chain variable region (VL) comprising a VLCDR1 amino acid sequence of SEQ ID NO: 13, a VLCDR2 amino acid sequence of SEQ ID NO: 14, and a VLCDR3 amino acid sequence of SEQ ID NO: 15;
(b) a VH comprising a VHCDR1 amino acid sequence of SEQ ID NO: 1; a VHCDR2 amino acid sequence of SEQ ID NO: 2; and a VHCDR3 amino acid sequence of SEQ ID NO: 3; and a VL comprising a VLCDR1 amino acid sequence of SEQ ID NO: 10, a VLCDR2 amino acid sequence of SEQ ID NO: 11, and a VLCDR3 amino acid sequence of SEQ ID NO: 12;
(c) a VH comprising a VHCDR1 amino acid sequence of SEQ ID NO: 286, a VHCDR2 amino acid sequence of SEQ ID NO: 5, and a VHCDR3 amino acid sequence of SEQ ID NO: 3; and a VL comprising a VLCDR1 amino acid sequence of SEQ ID NO: 13, a VLCDR2 amino acid sequence of SEQ ID NO: 14, and a VLCDR3 amino acid sequence of SEQ ID NO: 15; or
(d) a VH comprising a VHCDR1 amino acid sequence of SEQ ID NO: 286; a VHCDR2 amino acid sequence of SEQ ID NO: 2; and a VHCDR3 amino acid sequence of SEQ ID NO: 3; and a VL comprising a VLCDR1 amino acid sequence of SEQ ID NO: 10, a VLCDR2 amino acid sequence of SEQ ID NO: 11, and a VLCDR3 amino acid sequence of SEQ ID NO: 12.

2. An isolated nucleic acid molecule comprising a first nucleotide sequence that encodes a VH, or a second nucleotide sequence that encodes a VL, or both, of a bispecific antibody molecule having a first binding specificity for LAG-3 and a second binding specificity for one of the following antigens: PD-1, TIM-3, CEACAM-1, CEACAM-5, PD-L1, or PD-L2, wherein the bispecific antibody molecule comprises a LAG-3 binding domain comprising:
(a) a heavy chain variable region (VH) comprising a VHCDR1 amino acid sequence of SEQ ID NO: 4, a VHCDR2 amino acid sequence of SEQ ID NO: 5, and a VHCDR3 amino acid sequence of SEQ ID NO: 3; and a light chain variable region (VL) comprising a VLCDR1 amino acid sequence of SEQ ID NO: 13, a VLCDR2 amino acid sequence of SEQ ID NO: 14, and a VLCDR3 amino acid sequence of SEQ ID NO: 15;
(b) a VH comprising a VHCDR1 amino acid sequence of SEQ ID NO: 1; a VHCDR2 amino acid sequence of SEQ ID NO: 2; and a VHCDR3 amino acid sequence of SEQ ID NO: 3; and a VL comprising a VLCDR1 amino acid sequence of SEQ ID NO: 10, a VLCDR2 amino acid sequence of SEQ ID NO: 11, and a VLCDR3 amino acid sequence of SEQ ID NO: 12;
(c) a VH comprising a VHCDR1 amino acid sequence of SEQ ID NO: 286, a VHCDR2 amino acid sequence of SEQ ID NO: 5, and a VHCDR3 amino acid sequence of SEQ ID NO: 3; and a VL comprising a VLCDR1 amino acid sequence of SEQ ID NO: 13, a VLCDR2 amino acid sequence of SEQ ID NO: 14, and a VLCDR3 amino acid sequence of SEQ ID NO: 15; or
(d) a VH comprising a VHCDR1 amino acid sequence of SEQ ID NO: 286; a VHCDR2 amino acid sequence of SEQ ID NO: 2; and a VHCDR3 amino acid sequence of SEQ ID NO: 3; and a VL comprising a VLCDR1 amino acid sequence of SEQ ID NO: 10, a VLCDR2 amino acid sequence of SEQ ID NO: 11, and a VLCDR3 amino acid sequence of SEQ ID NO: 12.

3. The bispecific antibody molecule of claim 1, wherein the LAG-3 binding domain comprises:
(a) a VH comprising the amino acid sequence of SEQ ID NO: 28 or SEQ ID NO: 100; and a VL comprising the amino acid sequence of SEQ ID NO: 32;
(b) a VH comprising the amino acid sequence of SEQ ID NO: 28 or SEQ ID NO: 100; and a VL comprising the amino acid sequence of SEQ ID NO: 36;
(c) a VH comprising the amino acid sequence of SEQ ID NO: 28 or SEQ ID NO: 100; and a VL comprising the amino acid sequence of SEQ ID NO: 40;
(d) a VH comprising the amino acid sequence of SEQ ID NO: 28 or SEQ ID NO: 100; and a VL comprising the amino acid sequence of SEQ ID NO: 44;
(e) a VH comprising the amino acid sequence of SEQ ID NO: 28 or SEQ ID NO: 100; and a VL comprising the amino acid sequence of SEQ ID NO: 48;
(f) a VH comprising the amino acid sequence of SEQ ID NO: 28 or SEQ ID NO: 100; and a VL comprising the amino acid sequence of SEQ ID NO: 52;
(g) a VH comprising the amino acid sequence of SEQ ID NO: 28 or SEQ ID NO: 100; and a VL comprising the amino acid sequence of SEQ ID NO: 56;
(h) a VH comprising the amino acid sequence of SEQ ID NO: 28 or SEQ ID NO: 100; and a VL comprising the amino acid sequence of SEQ ID NO: 60;
(i) a VH comprising the amino acid sequence of SEQ ID NO: 64 or SEQ ID NO: 104; and a VL comprising the amino acid sequence of SEQ ID NO: 36;
(j) a VH comprising the amino acid sequence of SEQ ID NO: 64 or SEQ ID NO: 104; and a VL comprising the amino acid sequence of SEQ ID NO: 40;
(k) a VH comprising the amino acid sequence of SEQ ID NO: 64 or SEQ ID NO: 104; and a VL comprising the amino acid sequence of SEQ ID NO: 56;
(l) a VH comprising the amino acid sequence of SEQ ID NO: 64 or SEQ ID NO: 104; and a VL comprising the amino acid sequence of SEQ ID NO: 60;
(m) a VH comprising the amino acid sequence of SEQ ID NO: 68 or SEQ ID NO: 108; and a VL comprising the amino acid sequence of SEQ ID NO: 36;
(n) a VH comprising the amino acid sequence of SEQ ID NO: 72 or SEQ ID NO: 8; and a VL comprising the amino acid sequence of SEQ ID NO: 40;
(o) a VH comprising the amino acid sequence of SEQ ID NO: 72 or SEQ ID NO: 8; and a VL comprising the amino acid sequence of SEQ ID NO: 60;
(p) a VH comprising the amino acid sequence of SEQ ID NO: 76 and a VL comprising the amino acid sequence of SEQ ID NO: 60;
(q) a VH comprising the amino acid sequence of SEQ ID NO: 80 and a VL comprising the amino acid sequence of SEQ ID NO: 84;
(r) a VH comprising the amino acid sequence of SEQ ID NO: 28 or SEQ ID NO: 100; and a VL comprising the amino acid sequence of SEQ ID NO: 88;
(s) a VH comprising the amino acid sequence of SEQ ID NO: 28 or SEQ ID NO: 100; and a VL comprising the amino acid sequence of SEQ ID NO: 92; or
(t) a VH comprising the amino acid sequence of SEQ ID NO: 64 or SEQ ID NO: 104; and a VL comprising the amino acid sequence of SEQ ID NO: 96.

4. The bispecific antibody molecule of claim 1, wherein the LAG-3 binding domain comprises:
(a) a heavy chain comprising the amino acid sequence of SEQ ID NO: 30 or SEQ ID NO: 102; and a light chain comprising the amino acid sequence of SEQ ID NO: 34;
(b) a heavy chain comprising the amino acid sequence of SEQ ID NO: 30 or SEQ ID NO: 102; and a light chain comprising the amino acid sequence of SEQ ID NO: 38;
(c) a heavy chain comprising the amino acid sequence of SEQ ID NO: 30 or SEQ ID NO: 102; and a light chain comprising the amino acid sequence of SEQ ID NO: 42;
(d) a heavy chain comprising the amino acid sequence of SEQ ID NO: 30 or SEQ ID NO: 102; and a light chain comprising the amino acid sequence of SEQ ID NO: 46;
(e) a heavy chain comprising the amino acid sequence of SEQ ID NO: 30 or SEQ ID NO: 102; and a light chain comprising the amino acid sequence of SEQ ID NO: 50;

(f) a heavy chain comprising the amino acid sequence of SEQ ID NO: 30 or SEQ ID NO: 102; and a light chain comprising the amino acid sequence of SEQ ID NO: 54;

(g) a heavy chain comprising the amino acid sequence of SEQ ID NO: 30 or SEQ ID NO: 102; and a light chain comprising the amino acid sequence of SEQ ID NO: 58;

(h) a heavy chain comprising the amino acid sequence of SEQ ID NO: 30 or SEQ ID NO: 102; and a light chain comprising the amino acid sequence of SEQ ID NO: 62;

(i) a heavy chain comprising the amino acid sequence of SEQ ID NO: 66 or SEQ ID NO: 106; and a light chain comprising the amino acid sequence of SEQ ID NO: 38;

(j) a heavy chain comprising the amino acid sequence of SEQ ID NO: 66 or SEQ ID NO: 106; and a light chain comprising the amino acid sequence of SEQ ID NO: 42;

(k) a heavy chain comprising the amino acid sequence of SEQ ID NO: 66 or SEQ ID NO: 106; and a light chain comprising the amino acid sequence of SEQ ID NO: 58;

(l) a heavy chain comprising the amino acid sequence of SEQ ID NO: 66 or SEQ ID NO: 106; and a light chain comprising the amino acid sequence of SEQ ID NO: 62;

(m) a heavy chain comprising the amino acid sequence of SEQ ID NO: 70 or SEQ ID NO: 110; and a light chain comprising the amino acid sequence of SEQ ID NO: 38;

(n) a heavy chain comprising the amino acid sequence of SEQ ID NO: 74 or SEQ ID NO: 18; and a light chain comprising the amino acid sequence of SEQ ID NO: 42;

(o) a heavy chain comprising the amino acid sequence of SEQ ID NO: 74 or SEQ ID NO: 18; and a light chain comprising the amino acid sequence of SEQ ID NO: 62;

(p) a heavy chain comprising the amino acid sequence of SEQ ID NO: 78 and a light chain comprising the amino acid sequence of SEQ ID NO: 62;

(q) a heavy chain comprising the amino acid sequence of SEQ ID NO: 82 and a light chain comprising the amino acid sequence of SEQ ID NO: 86;

(r) a heavy chain comprising the amino acid sequence of SEQ ID NO: 30 or SEQ ID NO: 102; and a light chain comprising the amino acid sequence of SEQ ID NO: 94;

(s) a heavy chain comprising the amino acid sequence of SEQ ID NO: 66 or SEQ ID NO: 106; and a light chain comprising the amino acid sequence of SEQ ID NO: 98;

(t) a heavy chain comprising the amino acid sequence of SEQ ID NO: 113 and a light chain comprising the amino acid sequence of SEQ ID NO: 34;

(u) a heavy chain comprising the amino acid sequence of SEQ ID NO: 113 and a light chain comprising the amino acid sequence of SEQ ID NO: 38;

(v) a heavy chain comprising the amino acid sequence of SEQ ID NO: 122 and a light chain comprising the amino acid sequence of SEQ ID NO: 38;

(w) a heavy chain comprising the amino acid sequence of SEQ ID NO: 122 and a light chain comprising the amino acid sequence of SEQ ID NO: 58; or (x) a heavy chain comprising the amino acid sequence of SEQ ID NO: 134 and a light chain comprising the amino acid sequence of SEQ ID NO: 38.

5. The bispecific antibody molecule of claim 1, wherein the LAG-3 binding domain comprises a VH comprising the amino acid sequence of SEQ ID NO: 104 and a VL comprising the amino acid sequence of SEQ ID NO: 56.

6. The bispecific antibody molecule of claim 1, wherein the LAG-3 binding domain comprises a heavy chain comprising the amino acid sequence of SEQ ID NO: 122 and a light chain comprising the amino acid sequence of SEQ ID NO: 58.

7. An expression vector comprising the nucleic acid molecule of claim 2.

8. An isolated host cell comprising the nucleic acid molecule of claim 2.

9. A method of producing a bispecific antibody molecule, comprising culturing the host cell of claim 8 under conditions suitable for gene expression, wherein upon gene expression the bispecific antibody molecule is produced.

10. The method of claim 9, further comprising isolating the bispecific antibody molecule.

* * * * *